US009730939B2

United States Patent
Li et al.

(10) Patent No.: US 9,730,939 B2
(45) Date of Patent: *Aug. 15, 2017

(54) HETEROCYCLYLAMINES AS PI3K INHIBITORS

(71) Applicants: Incyte Corporation, Wilmington, DE (US); Incyte Holdings Corporation, Wilmington, DE (US)

(72) Inventors: Yun-Long Li, Chadds Ford, PA (US); Wenqing Yao, Chadds Ford, PA (US); Andrew P. Combs, Kennett Square, PA (US); Eddy W. Yue, Landenberg, PA (US); Song Mei, Wilmington, DE (US); Wenyu Zhu, Media, PA (US); Joseph Glenn, Mount Royal, NJ (US); Thomas P. Maduskuie, Jr., Wilmington, DE (US); Richard B. Sparks, Wilmington, DE (US); Brent Douty, Fallowfield, PA (US); Chunhong He, Chadds Ford, PA (US)

(73) Assignees: Incyte Holdings Corporation, Wilmington, DE (US); Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/872,881

(22) Filed: Oct. 1, 2015

(65) Prior Publication Data

US 2016/0024117 A1    Jan. 28, 2016

Related U.S. Application Data

(63) Continuation of application No. 13/601,349, filed on Aug. 31, 2012, now Pat. No. 9,199,982.

(60) Provisional application No. 61/677,445, filed on Jul. 30, 2012, provisional application No. 61/594,882, filed on Feb. 3, 2012, provisional application No. 61/530,866, filed on Sep. 2, 2011.

(51) Int. Cl.
| | | |
|---|---|---|
| *C07D 471/04* | (2006.01) | |
| *C07D 487/04* | (2006.01) | |
| *A61K 31/519* | (2006.01) | |
| *C07D 519/00* | (2006.01) | |

(52) U.S. Cl.
CPC .......... *A61K 31/519* (2013.01); *C07D 471/04* (2013.01); *C07D 487/04* (2013.01); *C07D 519/00* (2013.01)

(58) Field of Classification Search
None
See application file for complete search history.

(56) References Cited

U.S. PATENT DOCUMENTS

| | | |
|---|---|---|
| 3,037,980 A | 6/1962 | Hitchings et al. |
| 3,169,967 A | 2/1965 | Schittler |
| 3,506,643 A | 4/1970 | Thiel et al. |
| 3,862,189 A | 1/1975 | Schwender et al. |
| 3,936,454 A | 2/1976 | Schwender et al. |
| 3,962,443 A | 6/1976 | Minami et al. |
| 4,482,629 A | 11/1984 | Nakagawa et al. |
| 4,840,951 A | 6/1989 | Iwasaki et al. |
| 4,845,020 A | 7/1989 | Itoh et al. |
| 4,861,701 A | 8/1989 | Burns et al. |
| 5,124,331 A | 6/1992 | Arita et al. |
| 5,208,250 A | 5/1993 | Cetenko et al. |
| 5,252,580 A | 10/1993 | Takahashi et al. |
| 5,294,620 A | 3/1994 | Ratcliffe et al. |
| 5,314,883 A | 5/1994 | Tanikawa et al. |
| 5,459,132 A | 10/1995 | Bru-Magniez et al. |
| 5,521,184 A | 5/1996 | Zimmermann |
| 5,646,153 A | 7/1997 | Spada et al. |
| 5,811,439 A | 9/1998 | Ogawa et al. |
| 5,866,702 A | 2/1999 | Mackman et al. |

(Continued)

FOREIGN PATENT DOCUMENTS

| | | |
|---|---|---|
| AT | 388372 | 6/1989 |
| CA | 1066701 | 11/1979 |

(Continued)

OTHER PUBLICATIONS

"A to Z List of Cancers," National Cancer Institute (http://www.cancer.gov/) (Downloaded May 29, 2014), 22 pages.

(Continued)

*Primary Examiner* — Bong-Sook Baek
(74) *Attorney, Agent, or Firm* — Fish & Richardson P.C.

(57) ABSTRACT

The present invention provides heterocyclylamine derivatives of Formula I:

wherein the variables are defined herein, that modulate the activity of phosphoinositide 3-kinases (PI3Ks) and are useful in the treatment of diseases related to the activity of PI3Ks including, for example, inflammatory disorders, immune-based disorders, cancer, and other diseases.

7 Claims, 1 Drawing Sheet

(56) References Cited

U.S. PATENT DOCUMENTS

| | | |
|---|---|---|
| 6,028,076 A | 2/2000 | Hirota et al. |
| 6,342,501 B1 | 1/2002 | Townsend et al. |
| 6,376,501 B1 | 4/2002 | Isobe et al. |
| 6,392,047 B1 | 5/2002 | Geissler et al. |
| 6,479,487 B1 | 11/2002 | Dumont et al. |
| 6,630,496 B1 | 10/2003 | Seehra et al. |
| 6,734,187 B1 | 5/2004 | Tanaka et al. |
| 6,828,344 B1 | 12/2004 | Seehra et al. |
| 7,129,264 B2 | 10/2006 | Smallheer et al. |
| 7,494,987 B2 | 2/2009 | Akada et al. |
| 7,495,002 B2 | 2/2009 | Langkopf et al. |
| 7,528,143 B2 | 5/2009 | Noronha et al. |
| 7,598,257 B2 | 10/2009 | Rodgers et al. |
| 7,612,114 B2 | 11/2009 | Hamaoka et al. |
| 8,680,108 B2 | 3/2014 | Li et al. |
| 8,759,359 B2 | 6/2014 | Combs et al. |
| 8,940,752 B2 | 1/2015 | Li et al. |
| 9,249,087 B2 | 2/2016 | Kozikowski et al. |
| 9,434,746 B2 | 9/2016 | Li et al. |
| 2003/0008898 A1 | 1/2003 | Mahboobi et al. |
| 2003/0157052 A1 | 8/2003 | Choe et al. |
| 2004/0058930 A1 | 3/2004 | Belema et al. |
| 2004/0063658 A1 | 4/2004 | Roberts et al. |
| 2004/0067964 A1 | 4/2004 | Matsuoka et al. |
| 2004/0142941 A1 | 7/2004 | Gudmundsson et al. |
| 2004/0209866 A1 | 10/2004 | Wang et al. |
| 2004/0242615 A1 | 12/2004 | Yamamori et al. |
| 2005/0043328 A1 | 2/2005 | Dolezal |
| 2005/0059677 A1 | 3/2005 | Alberti et al. |
| 2005/0107343 A1 | 5/2005 | Kasibhatla et al. |
| 2005/0165030 A1 | 7/2005 | Liu et al. |
| 2005/0261317 A1 | 11/2005 | Sadhu et al. |
| 2005/0267110 A1 | 12/2005 | Hirano et al. |
| 2005/0282831 A1 | 12/2005 | Beauglehole et al. |
| 2006/0025383 A1 | 2/2006 | Wishart et al. |
| 2006/0052403 A1 | 3/2006 | Isobe et al. |
| 2006/0074102 A1 | 4/2006 | Cusack et al. |
| 2006/0084687 A1 | 4/2006 | Boyce et al. |
| 2006/0166925 A1 | 7/2006 | Dolezal et al. |
| 2006/0247245 A1 | 11/2006 | Xu |
| 2006/0293334 A1 | 12/2006 | Fuji et al. |
| 2007/0060577 A1 | 3/2007 | Player et al. |
| 2007/0066624 A1 | 3/2007 | Zhou et al. |
| 2007/0167443 A1 | 7/2007 | Melikan et al. |
| 2007/0191395 A1 | 8/2007 | Kawakami et al. |
| 2007/0225303 A1 | 9/2007 | Ogita et al. |
| 2007/0275984 A1 | 11/2007 | Imogai et al. |
| 2008/0004269 A1 | 1/2008 | Xu et al. |
| 2008/0009508 A1 | 1/2008 | Szucova et al. |
| 2008/0014227 A1 | 1/2008 | Popa et al. |
| 2008/0114007 A1 | 5/2008 | Player |
| 2008/0161332 A1 | 7/2008 | Bissantz et al. |
| 2008/0194616 A1 | 8/2008 | Liu et al. |
| 2008/0249155 A1 | 10/2008 | Gong et al. |
| 2008/0287469 A1 | 11/2008 | Diacovo et al. |
| 2008/0293739 A1 | 11/2008 | Trede |
| 2008/0306093 A1 | 12/2008 | Servant et al. |
| 2009/0023729 A1 | 1/2009 | Nakamura et al. |
| 2009/0047249 A1 | 2/2009 | Graupe et al. |
| 2009/0053192 A1 | 2/2009 | Millan et al. |
| 2009/0074884 A1 | 3/2009 | Chesney et al. |
| 2009/0118263 A1 | 5/2009 | Hashimoto |
| 2009/0137581 A1 | 5/2009 | Chen et al. |
| 2009/0163545 A1 | 6/2009 | Goldfarb |
| 2009/0170879 A1 | 7/2009 | Szucova et al. |
| 2009/0253717 A1 | 10/2009 | Brown et al. |
| 2009/0325930 A1 | 12/2009 | Hamaoka et al. |
| 2010/0010059 A1 | 1/2010 | Yeh et al. |
| 2010/0035756 A1 | 2/2010 | Luthy et al. |
| 2010/0105683 A1 | 4/2010 | Keegan et al. |
| 2010/0190819 A1 | 7/2010 | Kanner |
| 2010/0240537 A1 | 9/2010 | Spichal et al. |
| 2010/0256118 A1 | 10/2010 | Isobe et al. |
| 2010/0298334 A1 | 11/2010 | Rodgers et al. |
| 2010/0298351 A1 | 11/2010 | Konakanchi et al. |
| 2011/0015212 A1 | 1/2011 | Li et al. |
| 2011/0028715 A1 | 2/2011 | Isobe et al. |
| 2011/0059951 A1 | 3/2011 | Rodgers et al. |
| 2011/0098248 A1 | 4/2011 | Halcomb et al. |
| 2011/0105508 A1 | 5/2011 | Allen et al. |
| 2011/0183985 A1 | 7/2011 | Li et al. |
| 2011/0190319 A1 | 8/2011 | Combs |
| 2011/0224155 A1 | 9/2011 | Tachdjian et al. |
| 2011/0224190 A1 | 9/2011 | Huang et al. |
| 2011/0281884 A1 | 11/2011 | Combs et al. |
| 2011/0312979 A1 | 12/2011 | Li et al. |
| 2012/0149681 A1 | 6/2012 | Rodgers et al. |
| 2012/0149682 A1 | 6/2012 | Rodgers et al. |
| 2012/0157430 A1 | 6/2012 | Li et al. |
| 2013/0018034 A1 | 1/2013 | Yao et al. |
| 2013/0029982 A1 | 1/2013 | Castro et al. |
| 2013/0045963 A1 | 2/2013 | Rodgers et al. |
| 2013/0059835 A1 | 3/2013 | Li et al. |
| 2013/0261101 A1 | 10/2013 | Combs et al. |
| 2014/0005166 A1 | 1/2014 | Rodgers et al. |
| 2014/0031355 A1 | 1/2014 | Fisher et al. |
| 2014/0057912 A1 | 2/2014 | Combs et al. |
| 2014/0066448 A1 | 3/2014 | Combs et al. |
| 2014/0121198 A1 | 5/2014 | Li et al. |
| 2014/0121222 A1 | 5/2014 | Li et al. |
| 2014/0275127 A1 | 9/2014 | Combs et al. |
| 2014/0343030 A1 | 11/2014 | Li et al. |
| 2015/0284390 A1 | 10/2015 | Li et al. |
| 2015/0361094 A1 | 12/2015 | Li et al. |
| 2016/0022685 A1 | 1/2016 | Li et al. |
| 2016/0257689 A1 | 9/2016 | Qiao et al. |
| 2016/0264580 A1 | 9/2016 | Combs et al. |
| 2016/0362424 A1 | 12/2016 | Li et al. |
| 2016/0362425 A1 | 12/2016 | Li et al. |
| 2016/0362426 A1 | 12/2016 | Zhou et al. |

FOREIGN PATENT DOCUMENTS

| | | |
|---|---|---|
| DE | 1770420 | 11/1971 |
| DE | 2139107 | 2/1973 |
| EP | 255085 | 2/1988 |
| EP | 464612 | 1/1992 |
| EP | 481614 | 4/1992 |
| EP | 1138328 | 11/2001 |
| EP | 1109805 | 12/2003 |
| EP | 1783114 | 5/2007 |
| EP | 1972631 | 9/2008 |
| EP | 2031037 | 3/2009 |
| EP | 2050749 | 4/2009 |
| EP | 934307 | 4/2011 |
| GB | 1440478 | 6/1976 |
| GB | 1472342 | 5/1977 |
| JP | 50111080 | 9/1975 |
| JP | 53059663 | 5/1978 |
| JP | 53092767 | 8/1978 |
| JP | 56025234 | 6/1981 |
| JP | 56123981 | 9/1981 |
| JP | 58083698 | 5/1983 |
| JP | 62103640 | 5/1987 |
| JP | 62245252 | 10/1987 |
| JP | 1250316 | 10/1989 |
| JP | 4190232 | 7/1992 |
| JP | 9087282 | 3/1997 |
| JP | 9176116 | 7/1997 |
| JP | 10025294 | 1/1998 |
| JP | 10231297 | 9/1998 |
| JP | 2000080295 | 3/2000 |
| JP | 2000281654 | 10/2000 |
| JP | 2001151771 | 6/2001 |
| JP | 2005035924 | 2/2005 |
| JP | 2009080233 | 4/2009 |
| JP | 2009120686 | 6/2009 |
| JP | 2011511761 | 4/2011 |
| JP | 2011136925 | 7/2011 |
| RU | 2233842 | 8/2004 |
| SU | 1712359 | 2/1992 |
| WO | WO 93/16076 | 8/1993 |
| WO | WO 93/22291 | 11/1993 |
| WO | WO 93/25524 | 12/1993 |

(56) References Cited

FOREIGN PATENT DOCUMENTS

| | | |
|---|---|---|
| WO | WO 99/43651 | 9/1999 |
| WO | WO 99/43672 | 9/1999 |
| WO | WO 00/09495 | 2/2000 |
| WO | WO 00/44750 | 8/2000 |
| WO | WO 00/53595 | 9/2000 |
| WO | WO 01/14402 | 3/2001 |
| WO | WO 01/64639 | 9/2001 |
| WO | WO 01/64655 | 9/2001 |
| WO | WO 01/72709 | 10/2001 |
| WO | WO 02/00196 | 1/2002 |
| WO | WO 02/06477 | 1/2002 |
| WO | WO 02/24685 | 3/2002 |
| WO | WO 02/064599 | 8/2002 |
| WO | WO 02/066478 | 8/2002 |
| WO | WO 02/078701 | 10/2002 |
| WO | WO 03/020721 | 3/2003 |
| WO | WO 03/024967 | 3/2003 |
| WO | WO 03/029209 | 4/2003 |
| WO | WO 03/037347 | 5/2003 |
| WO | WO 03/044014 | 5/2003 |
| WO | WO 03/049678 | 6/2003 |
| WO | WO 03/050064 | 6/2003 |
| WO | WO 03/068750 | 8/2003 |
| WO | WO 03/074497 | 9/2003 |
| WO | WO 03/099771 | 12/2003 |
| WO | WO 2004/005281 | 1/2004 |
| WO | WO 2004/024693 | 3/2004 |
| WO | WO 2004/046120 | 6/2004 |
| WO | WO 2004/048365 | 6/2004 |
| WO | WO 2004/056786 | 7/2004 |
| WO | WO 2004/069256 | 8/2004 |
| WO | WO 2004/076455 | 9/2004 |
| WO | WO 2004/080980 | 9/2004 |
| WO | WO 2004/087704 | 10/2004 |
| WO | WO 2004/107863 | 12/2004 |
| WO | WO 2004/113335 | 12/2004 |
| WO | WO 2005/000309 | 1/2005 |
| WO | WO 2005/016528 | 2/2005 |
| WO | WO 2005/028444 | 3/2005 |
| WO | WO 2005/046578 | 5/2005 |
| WO | WO 2005/091857 | 10/2005 |
| WO | WO 2005/113556 | 12/2005 |
| WO | WO 2006/008523 | 1/2006 |
| WO | WO 2006/030031 | 3/2006 |
| WO | WO 2006/056399 | 6/2006 |
| WO | WO 2006/068760 | 6/2006 |
| WO | WO 2006/089106 | 8/2006 |
| WO | WO 2007/002701 | 1/2007 |
| WO | WO 2007/012724 | 2/2007 |
| WO | WO 2007/042806 | 4/2007 |
| WO | WO 2007/076092 | 7/2007 |
| WO | WO 2007/087548 | 8/2007 |
| WO | WO 2007/095588 | 8/2007 |
| WO | WO 2007/102392 | 9/2007 |
| WO | WO 2007/114926 | 10/2007 |
| WO | WO 2007/126841 | 11/2007 |
| WO | WO 2008/002490 | 1/2008 |
| WO | WO 2008/005303 | 1/2008 |
| WO | WO 2008/025821 | 3/2008 |
| WO | WO 2008/032033 | 3/2008 |
| WO | WO 2008/064018 | 5/2008 |
| WO | WO 2008/064157 | 5/2008 |
| WO | WO 2008/082490 | 7/2008 |
| WO | WO 2008/097991 | 8/2008 |
| WO | WO 2008/100867 | 8/2008 |
| WO | WO 2008/116129 | 9/2008 |
| WO | WO 2008/118454 | 10/2008 |
| WO | WO 2008/118468 | 10/2008 |
| WO | WO 2009/026701 | 3/2009 |
| WO | WO 2009/034386 | 3/2009 |
| WO | WO 2009/062118 | 5/2009 |
| WO | WO 2009/063235 | 5/2009 |
| WO | WO 2009/081105 | 7/2009 |
| WO | WO 2009/085230 | 7/2009 |
| WO | WO 2009/086123 | 7/2009 |
| WO | WO 2009/097446 | 8/2009 |
| WO | WO 2009/128520 | 10/2009 |
| WO | WO 2009/130560 | 10/2009 |
| WO | WO 2009/140215 | 11/2009 |
| WO | WO 2009/151972 | 12/2009 |
| WO | WO 2010/006234 | 1/2010 |
| WO | WO 2010/008739 | 1/2010 |
| WO | WO 2010/018458 | 2/2010 |
| WO | WO 2010/036380 | 4/2010 |
| WO | WO 2010/057048 | 5/2010 |
| WO | WO 2010/074588 | 7/2010 |
| WO | WO 2010/075068 | 7/2010 |
| WO | WO 2010/092340 | 8/2010 |
| WO | WO 2010/114900 | 10/2010 |
| WO | WO 2010/118367 | 10/2010 |
| WO | WO 2010/123931 | 10/2010 |
| WO | WO 2010/127208 | 11/2010 |
| WO | WO 2010/129816 | 11/2010 |
| WO | WO 2010/151735 | 12/2010 |
| WO | WO 2010/151740 | 12/2010 |
| WO | WO 2011/001052 | 1/2011 |
| WO | WO 2011/002708 | 1/2011 |
| WO | WO 2011/002817 | 1/2011 |
| WO | WO 2011/008302 | 1/2011 |
| WO | WO 2011/008487 | 1/2011 |
| WO | WO 2011/011550 | 1/2011 |
| WO | WO 2011/025889 | 3/2011 |
| WO | WO 2011/048082 | 4/2011 |
| WO | WO 2011/055215 | 5/2011 |
| WO | WO 2011/058111 | 5/2011 |
| WO | WO 2011/058113 | 5/2011 |
| WO | WO 2011/058474 | 5/2011 |
| WO | WO 2011/069294 | 6/2011 |
| WO | WO 2011/075628 | 6/2011 |
| WO | WO 2011/075630 | 6/2011 |
| WO | WO 2011/075643 | 6/2011 |
| WO | WO 2011/092198 | 8/2011 |
| WO | WO 2011/117711 | 9/2011 |
| WO | WO 2011/123751 | 10/2011 |
| WO | WO 2011/130342 | 10/2011 |
| WO | WO 2011/146882 | 11/2011 |
| WO | WO 2011/156759 | 12/2011 |
| WO | WO 2011/163195 | 12/2011 |
| WO | WO 2012/003262 | 1/2012 |
| WO | WO 2012/003271 | 1/2012 |
| WO | WO 2012/003274 | 1/2012 |
| WO | WO 2012/040634 | 3/2012 |
| WO | WO 2012/061696 | 5/2012 |
| WO | WO 2012/064973 | 5/2012 |
| WO | WO 2012/068343 | 5/2012 |
| WO | WO 2012/080729 | 6/2012 |
| WO | WO 2012/087784 | 6/2012 |
| WO | WO 2012/087881 | 6/2012 |
| WO | WO 2012/097000 | 7/2012 |
| WO | WO 2012/125629 | 9/2012 |
| WO | WO 2012/135009 | 10/2012 |
| WO | WO 2013/033569 | 3/2013 |
| WO | WO 2013/052699 | 4/2013 |
| WO | WO 2013/151930 | 10/2013 |

OTHER PUBLICATIONS

"Angiogenesis" Merriam-Webster.com. Merriam-Webster, n.d. Web Jun. 16, 2014, www.merriam-webster.com/dictionary/angiogenesis, 3 pages.

"Arthritis: MedlinePlus Medical Encyclopedica," 2014, p. 1-5, accessed online Oct. 7, 2014; http://www.nlm.nih.gove/medlineplus/ency/article/001243.htm.

"Autoimmune disorders: MedlinePlus Medical Encyclopedia," 2013, p. 1-4, accessed online Oct. 7, 2014; http://www.nlm.nih.gov/medlineplus/ency/article/000816.htm.

"Adult Acute Myeloid Leukemia Treatment (PDQ®)—Patient Version, Last Modified Jul. 30, 2012," National Cancer Institute, [retrieved from the internet on Nov. 26, 2012] at http://www.cancer.gov/cancertopics/pdq/treatment/adultAML/Patient/page1, 5 pgs.

Ali, et al., "Essential role for the p110δ phosphoinositide 3-kinase in the allergic response," Nature. 2004, 431(7011):1007-11.

(56) References Cited

OTHER PUBLICATIONS

Allen, et al., "Synthesis of C-6 substituted pyrazolo[1,5-a]pyridines with potent activity against herpesviruses," *Bioorganic & Medicinal Chemistry* (2006), 14(4), 944-954.

Apsel et al., "Targeted polypharmacology: discovery of dual inhibitors of tyrosine and phosphoinositide kinases," Nat. Chem. Biol., 2008, 4(11): 691-699.

Bader, et al., "Cancer-specific mutations in PIK3CA are oncogenic in vivo," Proc Natl Acad Sci U S A. 2006, 103(5):1475-9.

Baek et al., "Complete remission induced by rituximab in refractory, seronegative, muscle-specific, kinase-positive myasthenia gravis," J Neurol Neurosurg Psychiatry, 2007, 78(7):771.

Ball, "PI3K inhibitors as potential therapeutics for autoimmune disease," Drug Discovery Today, 2014, pp. 1195-119.

Barber, et al., "PI3Kγ inhibition blocks glomerulonephritis and extends lifespan in a mouse model of systemic lupus," Nat Med. 2005, 11(9):933-5.

Barragan et al., "Protein Kinases in the Regulation of Apoptosis in B-cell Chronic Lymphocytic Leukemia," *Leukemia and Lymphoma*, 2003, 44(11):1865-1870.

Belema, et al., "Synthesis and structure-activity relationship of imidazo(1,2-a)thieno(3,2-e)pyrazines as IKK-β inhibitors," *Bioorganic & Medicinal Chemistry Letters* (2007), 17(15), 4284-4289.

Bendell, J.C., "Phase I, dose-escalation study of BKM120, an oral pan-Class I PI3K inhibitor, in patients with advanced solid tumors," Journal of Clincial Oncology (2011): JCO-2011.

Benistant, et al., "A specific function for phosphatidylinositol 3-kinase α(p85α-p110α) in cell survival and for phosphatidylinositol 3-kinase β(p85α-p110β) in de novo DNA synthesis of human colon carcinoma cells," Oncogene, 2000, 19(44):5083-90.

Bennasar, et al., "Generation and Intermolecular Reactions of 2-Indolylacyl Radicals," *Organic Letters* (2001), 3(11), 1697-1700, CODEN: ORLEF7; ISSN: 1523-7060.

Berge et al., "Pharmaceutical Salts," J Pharma Sci, 1977, 66(1):1-19.

Bergman, et al., "Synthesis of indolocarbazole quinones; potent aryl hydrocarbon receptor ligands," *Tetrahedron* (2002), 58(7), 1443-1452.

Bhatia and Rose, "Autoimmunity and autoimmune disease," Principles of Med Biol., 1996, 6:239-263, 244.

Bhovi, et al., "1,3-dipolar cycloaddition reaction: Synthesis and antimicrobial activity of some new3-ethoxycarbonyl-5-methoxy-6-bromo-2-triazolylmethylindoles," *Indian Journal of Heterocyclic Chemistry* (2004), 14(1), 15-18 CODEN: IJCHEI; ISSN: 0971-1627.

Billottet, et al., "A selective inhibitor of the p110δ isoform of PI 3-kinase inhibits AML cell proliferation and survival and increases the cytotoic effects of VP16," Oncogene. 2006, 25(50):6648-59.

Biswas, et al., "Synthesis of a trifluoromethylindolocarbazole, novel cyclic 27- and 36-membered N-benzyltri- and -tetraindoles, and an N-benzyltetraindolyltrimethane," *Monatshefte fuer Chemie* (1999), 130(10), 1227-1239, CODEN: MOCMB7; ISSN: 0026-9247.

Blom et al., Preparative LC-MS Purification: Improved Compound Specific Method Optimization, J. Combi. Chem. 2004, 6(6), 874-883.

Boger, et al., "First and Second Generation Total Synthesis of the Teicoplanin Aglycon," JACS, 123(9), 1862-1871, 2001.

Brachmann et al., "PI3K and mTOR inhibitors—a new generation of targeted anticancer agents," Current Opinion Cell Biol., 2009, 21:194-198.

Bringmann, et al., "Novel concepts in directed biaryl synthesis. Part 65. Synthesis and structure of a novel twofold lactone-bridged ternaphthyl," *Tetrahedron Letters* (1998), 39(12), 1545-1548 CODEN: TELEAY; ISSN: 0040-4039.

Brock et al., "Roles of Gβγ in membrane recruitment and activation of p110γ/p101 phosphoinositide 3-kinaseγ," J Cell Biol., 2003, 160(1):89-99.

Brown, et al., "Small molecule inhibitors of IgE synthesis," *Bioorganic & Medicinal Chemistry Letters* (2006), 16(17), 4697-4699.

Camps, et al., "Blockade of PI3Kγ suppresses joint inflammation and damage in mouse models of rheumatoid arthritis," Nat Med. 2005, 11(9):936-43.

Cannon, Burger's Medicinal Chemistry and Drug Discovery, Fifth Edition, vol. 1 Principles and Practice, Wiley-Interscience 1995, Ch. 19, pp. 783-803, 784.

Cantley, "The Phosphoinositide 3-Kinase Pathway," Science, (2002) 296 (5573):1655-7.

Castillo-Trivino, et al., "Rituximab in relapsing and progressive forms of multiple sclerosis: a systematic review," The PLoS One. Jul. 2013; 8(7):e66308. doi: 10.1371/journal.pone.0066308. Print 2013.

Chai, et al., "Synthesis and in vitro anti-hepatitis B virus activities of some ethyl 6-bromo-5-hydroxy-1H-indole-3-carboxylates," *Bioorganic & Medicinal Chemistry* (2006), 14(4), 911-917.

Chang, K-Y., "Novel phosphoinositide 3-kinase/mTOR dual inhibitor, NVP-BGT226, displays potent growth-inhibitory activity against human head and neck cancer cells in vitro and in vivo," Clinical Cancer Research 17.22 (2011): 7116-7126.

Chen, X., "Targeting oxidative stress in embryonal rhabdomyosarcoma," Cancer cell 24.6 (2013): 710-724.

Clayton, et al., "A Crucial Role for the p110δ Subunit of Phosphatidylinositol 3-Kinase in B Cell Development and Activation," J Exp Med. 2002, 196(6):753-63.

Collins et al., "Rituximab treatment of fibrillary glomerulonephritis," Am J Kidney Dis., 2008, 52(6):1158-62.

Coughlin et al., Approaches and limitations of phosphatidylinositol-3-kinase pathway activation status as a predictive biomarker in the clinical development of targeted theraphy, Breast Cancer Res Treatment, 2010, 124:1-11.

Courtney et al., "The PI3K Pathway as Drug Target in Human Cancer," J Clinc Oncol., 2010, 29:1075-1083.

Crabbe, "The PI3K inhibitor arsenal: choose your weapon!" Trends Biochem Sci., 2007, 32(10):450-56.

Dagia et al., A preferential p110α/γ PI3K inhibitor attenuates experimental infalmmation by suppressing the production of proinflammatory mediators in a NF-κB-dependent manner, Am J Physiol—Cell Physiol., 2010, 298:929-941.

DeBerardinis et al., "The Biology of Cancer: Metabolic Reprogramming Fuels Cell Growth and Proliferation," Cell Metabolism, Jan. 2008, 7:11-20.

Delmas and Meunier, "The Management of Paget's Disease of Bone," N Engl J Med., 1997, 336:558-566.

Devauchelle-Pensec, "Treatment of Primary Sjogren Syndrome with Rituximab," Annal Internal Med., 2014, 160:233-242.

Dolezal et al., "Preparation and biological activity of 6-benzylaminopurine derivatives in plants and human cancer cells," *Bioorganic & Medicinal Chemistry* (2006), 14(3), 875-884.

Dolezal et al., "Preparation, biological activity and endogenous occurrence of N6-benzyladenosines," *Bioorganic & Medicinal Chemistry* (2007), 15(11), 3737-3747.

Dorokhov, et al., "Synthesis of functionalized pyrimidine-4-thiones and pyrido[2,3-d]pyrimidin-5-one derivatives from aminals of monoacylketenes", Izvestiya Akademii Nauk, Seriya Khimicheskaya (1993), (11), 1932-7.

Doukas et al., "Aerosolized Phosphoinositide 3-Kinase γ/δ Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease," The Journal of Pharmacology and Experimental Therapeutics, 328(3):758-765, 2009.

Dushianthan et al., "Acute respiratory distress syndrome and acute lung injury," Post Graduate Med J., 2011, 87:612-622.

Engelman, "Targeting PI3K signalling in cancer: opportunities, challenges and limitations," Nature Rev: Cancer, 2009, 9:550-562.

Fadeyeva, et al , "Inhibitors of early virus-cell interaction stages among 3-ethoxycarbonyl-5-hydroxy-bromoindole derivatives," Khimiko-Farmatsevticheskii Zhurnal (1992), 26(9-10), 17-20 (with English abstract).

Fine et al., "Neoplasms of the Central Nervous System," Cancer Principles Practice Oncol., 2005, 2:1834-1887.

(56) References Cited

OTHER PUBLICATIONS

Flinn et al., "Preliminary evidence of clinical activity in a phase I study of CAL-101, a selective inhibitor of the p110δ isoform of phosphatidylinositol 3-kinase (PI3K), in patients with select hematologic malignancies," Journal of Clinical Oncology, (abstract), 27(15S):3543, 2009.

Floberg et al., "Extractive alkylation of 6-mercaptopurine and determination in plasma by gas chromatography-mass spectrometry," *Journal of Chromatography, Biomedical Applications*, (1981), 225(1), 73-81.

Fruman and Bismuth, "Fine Tuning the Immune Response with PI3K," *Immunological Revs.*, 2006, 228:253-272.

Gati et al., "(125I)Iodohydroxynitrobenzylthioinosine: a new high-affinity nucleoside transporter probe," *Biochemistry and Cell Biology* (1987), 65(5), 467-73.

Geng, et al., "Exploring 9-benzyl purines as inhibitors of glutamate racemase (MurI) in Gram-positive bacteria", Bioorganic & Medicinal Chemistry Letters (2008),18(15), 4368-4372.

Ghigo et al., "PI3K inhibition in inflammation: Toward tailored therapies for specific diseases," BioEssays, 2010, 32:185-196.

Golantsov, et al., "Chirally N-substituted indole-2-carbaldehydes. Preparation and use in asymmetric synthesis," *Chemistry of Heterocyclic Compounds* (New York, NY, United States) (2005), 41(10), 1290-1299.

Granik, "Acetals of lactams and amides of acids. 40. Synthesis and hydrolytic splitting of mono- and bicyclic derivatives of 4-pyrimidinone", Khimiya Geterotsiklicheskikh Soedinenii (1984), (4),532-7 (with English abstract).

Greene and P. G. M. Wuts, Protective Groups in Organic Synthesis, 3rd Ed., Wiley & Sons, Inc., New York (1999).

Harley, "Medical Management of Actue Renal Failure," Renal Failure Replacement Therapies, 2008, pp. 26-32.

Harris et al., "Alkyl 4-Chlorobenzoyloxycarbamates as Highly Effective Nitrogen Source Reagents for the Base-Free, Intermolecular Aminohydroxylation Reaction," J. Org. Chem., 76, 358-372, 2011.

Hauser et al., "B-Cell Depletion with Rituximab in Relapsing—Remitting Multiple Sclerosis," The New England Journal of Medicine, 358(7):676-688, 2008.

Hayter and Cook, "Updated assessment of the prevalence, spectrum and case definition of autoimmune disease," Autoimmunity Reviews, 2012, 11:754-765.

Hickey, et al., "BCR-ABL Regulates Phosphatidylinositol 3-Kinase-p110γ Transcription and Activation and is Required for Proliferation and Drug Resistance," J Biol Chem. 2006, 281(5):2441-50.

Hirose, et al., "Pyridone-carboxylic acids as antibacterial agents. I. Synthesis and antibacterial activity of 1-alkyl-1,4-dihydro-4-oxo-1,8-and-1,6-naphthyridine-3-carboxylic acids", Chemical & Pharmaceutical Bulletin (1982), 30(7), 2399-409.

Hirota, "Efficient synthesis of 2,9-disubstituted 8-hydroxyadenine derivatives", Organic & Biomolecular Chemistry (2003), 1(8), 1354-1365.

Hirsch et al., "Taming the PI3K team to hold inflammation and cancer at bay," Pharmacology & Therapeutics, 2008, 118: 192-205.

Hosalkar et al., "Skeletal Trauma and Common Orthopedic Problems," Chpt 10, Khurana (ed.) Bone Pathology, 2009, 93 pages.

Huang et al., "Design and synthesis of a pyrido[2,3-d]pyrimidin-5-one class of anti-inflammatory FMS inhibitors,", *Bioorganic & Medicinal Chemistry Letters* (2008), 18(7), 2355-2361.

Huang et al., "Synthesis and bioassay of a fluorine-containing cytokinin, N6-pentafluoro-benzyladenosine," *Youji Huaxue* (1988), 8(2), 147-8 (with English abstract).

Ihle et al , "Inhibitors of phosphatidylinositol-3-kinase in cancer therapy", Molecular Aspects of Medicine, 31(2):135-144, 2010.

Irie, et al., "Discovery of selective and nonpeptidic cathepsin Sinhibitors," *Bioorganic & Medicinal Chemistry Letters* (2008), 18(14), 3959-3962.

Isobe, et al., "Synthesis and Biological Evaluation of Novel 9-Substituted-8-Hydroxyadenine Derivatives as Potent Interferon Inducers", Journal of Medicinal Chemistry (2006), 49(6),2088-2095.

Itaya, et al., "Syntheses of the marine ascidian purine aplidiamine and its 9-β-D-ribofuranoside," *Tetrahedron Letters* (1998), 39(26), 4695-4696.

Itaya, et al., "Synthesis and structure of the marine ascidian 8-oxoadenine aplidiamine," *Chemical & Pharmaceutical Bulletin* (1999), 47(9), 1297-1300.

Jager et al., "Molecular recognition. II Discrimination of specific and non-specific intermolecular interactions by means of magnetic resonance spectroscopy," *Magnetic Resonance in Chemistry* (1998), 36(3), 205-210, CODEN: MRCHEG; ISSN: 0749-1581.

Jager, et al., "Molecular recognition analyzed by EPR, ENDOR, and NMR spectroscopy," *Angewandte Chemie*, International Edition in English (1996), 35(16), 1815-1818.

Japanese Office Action in Japanese Application No. 2014-528654, dated Mar. 29, 2016, 5 pages (English Translation) (20443-0245JP1).

Jimenez, et al, "The p85 Regulator Subunit Controls Sequential Activation of Phosphoinositide 3- Kinase by Tyr Kinases and Ras," J Biol Chem., 2002, 277(44):41556-62.

Jou, et al., "Essential, Nonredundant Role for the Phosphoinositide 3-Kinase p110δ in Signaling by the B-Cell Receptor Complex," Mol Cell Biol. 2002, 22(24):8580-91.

Kang et al., "Aplidiamine, a unique zwitterionic benzyl hydroxyadenine from the Western Australian marine ascidian *Aplidiopsis* sp.," *Tetrahedron Letters* (1997), 38(6), 941-944.

Kang, et al., "Phosphtidylinositol 3-kinase mutations identified in human cancer are oncogenic," Proc Natl Acad Sci U S A. 2005, 102(3):802-7.

Karpouzas, et al., "Rituximab Therapy Induces Durable Remissions in Hispanic and African American Patients with Refractory Systemic Lupus Erythematosus (SLE)," Presented at 73th Annual Scientific Meeting of the American College of Rheumatology, Oct. 2009; Philadelphia, PA.

Kasibhatla, "Rationally Designed High-Affinity 2-Amino-6-halopurine Heat Shock Protein 90 Inhibitors That Exhibit Potent Antitumor Activity", Journal of Medicinal Chemistry (2007), 50(12),2767-2778.

Katritzky, et al., "Facile Synthesis of 2-Substituted Indoles and Indolo[3,2-b]carbazoles from 2-(Benzotriazol-1-ylmethyl)indole," *Journal of Organic Chemistry* (1995), 60(11), 3401-4.

Kim et al., "A signaling network in Phenylephrine-Induced Benign Prostatic Hyperplasia," Endocrinology, 2009, 150:3576-3583.

Kim, et al., "A new structural class of S-adenosylhomocysteine hydrolase inhibitors", Bioorganic & Medicinal Chemistry (2009), 17(18), 6707-6714.

Kim, et al., "Synthesis and evaluation of antitumor activity of novel 1,4-naphthoquinone derivatives," *Archives of Pharmacal Research* (2006), 29(2), 123-130 CODEN: APHRDQ; ISSN: 0253-6269.

Knobbe, et al., "Genetic alteration and expression of the phosphoinositol-3-kinase/Akt pathway genes *PIK3CA* and *PIKE* in human glioblastomas," Neuropathol Appl Neurobiol. 2005, 31(5):486-90.

Kolasa, et al., "Synthesis of indolylalkoxyiminoalkylcarboxylates as leukotriene biosynthesis inhibitors," *Bioorganic & Medicinal Chemistry* (1997), 5(3), 507-514.

Kolliputi and Waxman, "IL-6 cytoprotection in hyperoxic acute lung injury occurs via PI3K/Akt-mediated Bax phosphorylation," Am J Physiol Lung Cellular Mole Physiol., 2009, 297:L6-L16.

Kong and Yamori, "Phosphatidylinositol 3-kinase inhibitors: promising drug candidates for cancer theraphy," Cancer Sci., 2008, 9:1734-1740.

Kong and Yamori, "Advances in Development of Phosphatidylinositol 3-Kinase Inhibitors," Current Medicinal Chemistry, 16:2839-2854, 2009.

Kuduk et al., "Heterocyclic fused pyridone carboxylic acid M1 positive allosteric modulators," *Bioorganic & Medicinal Chemistry Letters* (2010), 20(8), 2533-2537.

Kung et al., "Characterization of a Murine Model of Allergic Pulmonary Inflammation," Int. Arch. Allergy Immunol., (abstract), 105(1):83-90, 1994.

(56) References Cited

OTHER PUBLICATIONS

Kurimoto, et al., "Synthesis and Biological Evaluation of 8-0xoadenine Derivatives as Toll-like Receptor 7 Agonists Introducing the Antedrug Concept", *Journal of Medicinal Chemistry* (2010), 53(7),2964-2972.

Kuster (ed), Kinase Inhibitors: Methods and Protocols Methods in Molecular Biology, 2012, 795:1-44.

Kutney, et al., "Dihydropyridines in synthesis and biosynthesis. IV. Dehydrosecodine, in vitro precursor of indole alkaloids," *Canadian Journal of Chemistry* (1982), 60(11), 1269-78.

Lee, et al , "Inhibition of phosphoinositide 3-kinase δ attenuates allergic airway inflammation and hyperresponsiveness in murine asthma model," FASEB J. 2006, 20(3):455-65.

Li et al., "Design, synthesis and antitumor activities of novel 4-anilino-5H-pyridazino [4,5-b]indoles," *Zhongnan Yaoxue* (2008), 6(2), 144-148, CODEN: ZYHAC6; ISSN: 1672-2981, Publisher: Zhongnan Yaoxue Zazhishe (with English abstract within the article).

Li et al., "Synthesis and antitumor activities of novel 1-anilino 5H-pyridazino[4,5-b]indoles," *Zhongguo Yaowu Huaxue Zazhi* (2007), 17(6), 339-343, CODEN: ZYHZEF; ISSN: 1005-0108 (with English abstract within the article).

Li, et al., "Optimization of the heterocyclic core of the quinazolinone-derived CXCR3 antagonists," *Bioorganic & Medicinal Chemistry Letters* (2008), 18(2), 688-693.

Li, et al., "Synthesis and anti-tumor activities of a novel series of tricyclic 1-anilino-5H-pyridazino[4,5-b]indoles," *Archiv der Pharmazie* (Weinheim, Germany) (2007), 340(8), 424-428, CODEN: ARPMAS; ISSN: 0365-6233.

Lindsay, et al., "SmI2-Promoted Radical Addition Reactions with N-(2-Indolylacyl)oxazolidinones: Synthesis of Bisindole Compounds," *Journal of Organic Chemistry* (2007), 72(11), 4181-4188, CODEN: JOCEAH; ISSN: 0022-3263.

Link, J. T., "The intramolecular Heck reaction," *Organic Reactions* (Hoboken, NJ, United States) (2002), 60, No pp. given CODEN: ORHNBA URL: http://www3.interscience.wiley.com/cgi-bin/mrwhome/107610747/HOME.

Lipsky, "Systemic lupus erythematosus: an autoimmune disease of B cell hyperactivity," Nat Immunol., 2001, 2(9):764-6.

Liu et al , "Inhibition of the mitotic kinesin Eg5 up-regulates Hsp70 through the phosphatidylinositol 3-kinase/Akt pathway in multiple myeloma cells," J Biol Chem., 2006, 281(26):18090-18097.

Liu et al., "mTOR mediated anti-cancer drug discovery," Drug Discovery Today: Therapeutic Strategies, 2009, 6:47-55.

Lucas, et al., "Rauwolfia alkaloids. XXXI. The synthesis and activity of some reserpine analogs," *Journal of the American Chemical Society* (1959), 81, 1928-32.

Luo et al., "Principles of Cancer Therapy: Oncogene and Non-oncogene Addiction," Cell, 2009, 36:823-837.

Ma, et al., "Bromophenols Coupled with Nucleoside Bases and Brominated Tetrahydroisoquinolines from the Red Alga Rhodomela confervoides", Journal of Natural Products (2007), 70(3), 337-341.

Ma, et al., "Two new constituents from Artemisia capillaris Thunb", Molecules (2008), 13(2), 267-271.

Mahboobi, et al., "Bis(1H-2-indolyl)methanones as a Novel Class of Inhibitors of the Platelet-Derived Growth Factor Receptor Kinase," Journal of Medicinal Chemistry (2002), 45(5):1002-1018.

Martelli et al., "Targeting the PI3K/AKT/mTOR signaling network in acute myelogenous leukemia," Expert Opin Investig Drugs. Sep. 2009;18(9):1333-49.

Matsumoto, et al., "Pyrido[2,3-d]pyrimidine antibacterial agents. 3. 8-Alkyl-and 8-vinyl-5,8-dihydro-5-oxo-2-(1-piperazinyl)pyrido[2,3-d]pyrimidine-6-carboxylic acids and their derivatives", *J Medicinal Chem* (1975), 18(1), 74-9.

McDermott and Settleman, "Personalized Cancer Theraphy with Selective Kinase Inhibitors: An Emerging Paradigm in Medical Oncology," J Clinical Oncol., 2009, 27:5650-5659.

McLean, et al., "Discovery of covalent inhibitors for MIF tautomerase via cocrystal structures with phantom hits from virtual screening," *Bioorganic & Medicinal Chemistry Letters* (2009), 19(23), 6717-6720.

McMahon, G., "VEGF Receptor Signaling in Tumor Angiogenesis," The Oncologist, 5(1):3-10, 2000.

Meade, et al., "Anxiolytic activity of analogs of 4-benzylamino-2-methyl-7H-pyrrolo[2,3-d]pyrimidines," *European Journal of Medicinal Chemistry* (1998), 33(5), 363-374.

MedicineNet.com' [online]. "Definition of Cancer," Sep. 18, 2004, retrieved on Sep. 16, 2005. Retrieved from the Internet: http://www.medterms.com, 1 page.

Medpagetoday.com' [online] "Current Role of Rituximab in Systematic Lupus," Jan. 2015, [retrieved Apr. 23, 2015]. Retrieved from the Internet: URL <http://www.medpagetoday.com/Rheumatology/Lupus/49398#./49398?&_suid=14297429843880910545130428968$4>$. 10 pages.

Meijer et al., "Treatment of primary Sjögren syndrome with rituximab: extended follow-up, safety and efficacy of retreatment," Ann. Rheum. Dis., 68(2):284-285, 2009.

Merrill, "Efficacy and safety of rituximab in moderately-to-severely active systemic lupus erythematosus: The randomized, double-blind, phase ii/iii systemic lupus erythematosus evaluation of rituximab trial," Arthritis & Rheumatism, 2010, 61(1):222-233.

Miki, et al., "Reaction of 1-benzylindole-2,3-dicarboxylic anhydride with 3-bromo-4-lithiopyridine: formal synthesis of ellipticine," *Heterocycles* (1998), 48(8), 1593-1597.

Miki, et al., "Reaction of indole-2,3-dicarboxylic anhydride with (3-bromo-4-pyridyl)triisopropoxytitanium: synthesis of ellipticine," *Tetrahedron Letters* (1996), 37(43), 7753-7754.

Miki, et al., "Synthesis of caulersin and its isomers by reaction of indole-2,3-dicarboxylic anhydrides with methyl indoleacetates," *Tetrahedron Letters* (2006), 47(29), 5215-5218, CODEN: TELEAY; ISSN: 0040-4039.

Miki, et al., "Synthesis of ellipticine by reaction of 1-(4-methoxybenzyl)indole-2,3-dicarboxylic anhydride with (3-bromo-4-pyridyl)triisopropoxytitanium," *Journal of the Chemical Society, Perkin Transactions 1* (2001), (18), 2213-2216.

Mishra et al., "Decanuclear Copper Framework Supported by a Tripodal Adenine Ligand," *Inorganic Chemistry* (Washington, DC, United States), (2010), 49(8), 3691-3693.

Mizoguchi, et al., "Genetic Alterations of Phosphoinositide 3-kinase Subunit Genes in Human Glioblastomas," Brain Pathol. 2004, 14(4):372-7.

Moffett, "Antiulcer agents. p-Aminobenzamido aromatic compounds", Journal of Medicinal Chemistry (1971), 14(10), 963-8.

Mohammadizadeh, et al., "A novel and expedient synthesis of 7-pyrimidinylpyrimido[4,5-d]pyrimidinones," *Helvetica Chimica Acta* (2010), 93(1), 153-157.

Morrison, et al., "Pyrimido[4,5-c]pyridazines. 1. Cyclizations with α-keto esters", *Journal of Organic Chemistry* (1978), 43(25), 4844-9.

Mukhopadhyay, et al., "An ionic liquid {[secbmim]+Br-} as a "dual reagent catalyst" for the multicomponent synthesis of (quinolinyl- and isoquinolinyl-amino) alkylnaphthols, their bis-analogs and a facile route to naphthoxazines," ARKIVOC (Gainesville, FL, United States) (2010), (10), 291-304.

Musmuca, et al., "Small-Molecule Interferon Inducers. Toward the Comprehension of the Molecular Determinants through Ligand-Based Approaches", Journal of Chemical Information and Modeling (2009),49(7), 1777-1786.

Najiwara, et al., "Behavior of naphthoyloxyl and methoxynaphthoyloxyl radicals generated from the photocleavage of dinaphthoyl peroxides and 1-(naphthoyloxy)-2-pyridones," *Bulletin of the Chemical Society of Japan* (2003), 76(3), 575-585.

Najiwara, et al., Generation and behavior of naphthoyloxyl radicals in photocleavage of 1-(naphthoyloxy)-2-pyridones, *Chemistry Letters* (2001), (10), 1064-1065.

Nettekoven, M., "A combinatorial approach towards 2-acyl-3-amino-indole derivatives," *Tetrahedron Letters* (2000), 41(43), 8251-8254.

(56) References Cited

OTHER PUBLICATIONS

Norman, P., "Selective PI3Kδ inhibitors, a review of the patent literature", Expert Opinion on Therapeutic Patents, Informa Healthcare, 21(11):1773-1790, 2011.
Oki, et al., "Reactivities of Stable Rotamers. XLII. Generation and Fates of Rotameric [1-(9Fluorenyl)-2-naphthyl]methyl Radicals," Bulletin of the Chemical Society of Japan (1999), 72(10), 2327-2336.
Okkenhaug, et al., "Impaired B and T Cell Antigen Receptor Signaling in p110δ PI 3-Kinase Mutant Mice," Science, 2002, 297(5583):1031-4).
Park et al., "Phosphoinositide 3-kinase δ inhibitor as a novel therapeutic agent in asthma," Respirology, 13:764-771, 2008.
Phillips, et al., "The reaction of anils with 8-quinolinol," Journal of Organic Chemistry (1954), 19, 907-9 CODEN: JOCEAH; ISSN: 0022-3263.
Pinedo and Slamon, "Translational Research: The Role of VEGF in Tumor Angiogenesis," The Oncologist, 5(1):1-2, 2000.
Platts, et al., "A concise synthesis of HIV integrase inhibitors bearing the dipyridone acid motif," Tetrahedron Letters (2011), 52(4), 512-514.
Portnaya, et al., "Azomethine dyes. IV. Indoaniline dyes derived from heterocyclic N-substituted 1-hydroxy-2-naphthamides," Ts. Vses. Nauchn.-Issled. Kinofotoinst. (1960), (No. 40), 106-18 (with English abstract).
Prezent, et al., STN Abstract, Accession No. 2004:358794, "Boron chelates as intermediates in the synthesis of new functionalized pyridines and pyrimidines from α,α-dioxoketene aminals," Boron Chemistry at the Beginning of the 21st Century, [Proceedings of the International Conference on the Chemistry of Boron], 11th, Moscow, Russian Federation, Jul. 28-Aug. 1, 2002 (2003), Meeting Date 2002, 91-93. Editor(s): Bubnov, Yu. N. A. N. Nesmeyanov Institute of Organoelement Compounds, Russian Academy of Sciences: Moscow, Russia.
Puri and Gold, "Selective inhibitors of phosphoinositide 3-kinase delta: modulators of B-cell function with potential for treating autoimmune inflammatory diseases and B-cell malignancies," Frontiers in Immunology, 3(256):1-16, 2012.
Ramos-Casals et al., "Rituximab in systemic lupus erythematosus; A systematic review of off-label use in 188 cases," Lupus, 18:767-776, 2009.
Randis, et al., "Role of PI3Kδ and PI3Kγ in inflammatory arthritis and tissue localization of neutrophils," Eur. J. Immunol., 2008, 38(5):1215-24.
Reich, et al., "Preparation of a,b-unsaturated carbonyl compounds and nitriles by selenoxide elimination ," Organic Reactions (Hoboken, NJ, United States) (1993), 44, No pp. given.
Remington's Pharmaceutical Sciences, 17th ed., Mack Publishing Company, Easton, PA., 1985, p. 1418.
Ringshausen et al., "Constitutively Actived phosphatidylinositol-3-kinase (PI-3K) is involved in the defect of apoptosis is B-CLL: assocaite with protein kinase C delta," Blood, 2002, 100:3741-3748.
Roxas-Duncan, et al., "Identification and biochemical characterization of small-molecule inhibitors of Clostridium botulinum neurotoxin serotype A," Antimicrobial Agents and Chemotherapy (2009), 53(8), 3478-3486.
Sahoo, et al., "Antispasmodic compounds. IV," Journal of the Indian Chemical Society (1959), 36, 421-4.
Sako, M., "Product class 19: pyridopyrimidines," Science of Synthesis (2004), 16, 1155-1267.
Samuels and Ericson, "Oncogenic PI3K and its role in cancer," Curr Opin Oncol., 2006, 18(1):77-82.
Samuels, et al., "High Frequency of Mutations of the PIK3CA Gene in Human Cancers," Science, 2004, 304(5670):554.
Sasaki, et al., "Function of PI3Kγ in Thymocyte Development, T Cell Activation, and Neutrophil Migration," Science, 2000, 287(5455):1040-6.
Sawyers, "The cancer biomarker problem," Nature, 2008, 452:548-552.
Saxena, et al., "Pharmacophore-based virtual screening and docking studies on Hsp90 inhibitors", SAR and QSAR in Environmental Research (2010), 21(5-6), 445-462.
Schafer and Kolkhof, "Failure is an option: learning from unsuccessful proof-of-concept trials," Drug Discovery Today, Nov. 2008, 13(21/22):913-916.
Schell, et al., "Versatile Solid-Phase Synthesis of Trisubstituted 1H-Pyrido[2,3-d]pyrimidin-4-ones and Related Heterocycles," Journal of Combinatorial Chemistry (2005), 7(1), 96-98.
Segarra et al., "Successful treatment of membranous glomerulonephritis with rituximab in calcineurin inhibitor-dependent patients," Clin J Am Soc Nephrol., 2009, 4(6):1083-8.
Sen, et al., "Reaction of aldehydes and amines with 8-hydroxyquinaldine and 8-quinolinol. II," Journal of the Indian Chemical Society (1960), 37, 640-2.
Shi, et al., "Synthesis and preliminary cytotoxic evaluation of substituted indoles as potential anticancer agents," Chinese Chemical Letters (2007), 18(8), 899-901, CODEN: CCLEE7; ISSN: 1001-8417.
Shuttleworth et al., "Progress in the Preclinical Discovery and Clinical Development of Class 1 and Dual Class I/IV Phosphoinositide 3-Kinase (PI3K) Inhibitors", Current Medicinal Chemistry, 18(1):2686-2714, 2011.
Silverman, R. B., "The organic Chemistry of Drugs Design and Drug Action." Elselvier. Northwestern University. Second Edition. Evanstons Illinois. 2004. p. 29 and table 2.2.
Singh et al., "Application of Nazarov cyclization to access [6-5-6] and [6-5-5]tricyclic core embedded new heterocycles: an easy entry to structures related to Taiwaniaquinoids," Organic & Biomolecular Chemistry (2009), 7(9), 1858-1867, CODEN: OBCRAK; ISSN: 1477-0520.
Steliou, et al., "Does diatomic sulfur(S2) react as a free species?", Journal of the American Chemical Society (1992), 114(4), 1456-62.
Strive et al., "Long-term B-Lymphocyte Depletion With Rituximab in Patients With Relapsing-Remitting Multiple Sclerosis," Arch. Neurol., 66(2):259-261, 2009.
Sujobert, et al al., "Essential role for the p110δ isoform in phosphoinositide 3-kinase activation and cell proliferation in acute myeloid leukemia," Blood, 2005, 106(3):1063-6.
Szuecova, et al., "Synthesis, characterization and biological activity of ring-substituted 6-benzylamino-9-tetrahydropyran-2-yl and 9-tetrahydrofuran-2-ylpurine derivatives," Bioorganic & Medicinal Chemistry (2009), 17(5), 1938-1947.
Terrier, et al., "Tolerance and Efficacy of Rituximab (RTX) in Systemic Lupus Erythematosus (SLE): Data of 104 Patients From the AIR (Auto-immunity and Rituximab) Registry," Presented at 73th Annual Scientific Meeting of the American College of Rheumatology, Oct. 2009; Philadelphia, PA.
Thomas, et al., "Airway inflammation: chemokine-induced neutrophilia and the class I phosphoinositide 3-kinases," Eur J Immunol. 2005, 35(4):1283-91.
Travnickek, et al., "2-Chloro-6-[(4-hydroxy-3,5-dimethoxybenzyl)amino]-9-isopropylpurine," Acta Crystallographica, Section E: Structure Reports Online (2007), E63(2), o728-o730 CODEN: ACSEBH; ISSN: 1600-5368 URL: http://journals.iucr.org/e/issues/2007/02/00/1h2285/1h2285.pdf.
Umar, A., "Future directions in cancer prevention," Nature Reviews Cancer, 12.12 (2012): 835-848.
Uddin et al., "Role of phosphatidylinositol 3'-kinase/AKT pathway in diffuse large B-cell lymphomas survival," Blood, 2006, 108:4178-4186.
Vanhaesebroeck et al., "Signalling by PI3K isoforms: insights from gene-targeted mice," Trends Biochem Sci., 2005, 30(4):194-204.
Vasil'ev, et al, "Chelate synthesis of 1-alkyl-5-(trifluoromethyl)-1,6-naphthyridin-4(1H)-ones", Izvestiya Akademii Nauk, Seriya Khimicheskaya (1994),(8), 1510-11 (with English abstract).
Venet et al., "Lymphocytes in the Development of Lung Inflammation: A role of Regulatory CD4+ T Cells in Indirect Pulmonary Lung Injury," J Immunol., 2009, 183:6472-3480.
Wallin, J. J., "GDC-0980 is a novel class I PI3K/mTOR kinase inhibitor with robust activity in cancer models driven by the PI3K pathway," Molecular cancer therapeutics 10.12 (2011): 2426-2436.

(56) References Cited

OTHER PUBLICATIONS

WebMD. Arthritis Health Center: What is Inflammation? Jul. 6, 2012, www.webmd.com/arthritis/about-inflammation?page=2, 4 pages.
WebMD. Bladder Cancer Health Center: Bladder Cancer-Prevention, Apr. 30, 2013, www.webmd.com/cancer/bladder-cancer/bladder-cancer-prevention, 1 page.
WebMD. Lung Disease & Respiratory Health Center: ARDS, May 21, 2014, www.webmd.com/lung/ards-acute-respiratory-distress-syndrome?page=2, 4 pages.
WebMD. Lung Disease & Respiratory Health Center: Lung Disease Overview, May 23, 2014, www.webmd.com/lung/lung-diseases-overview, 3 pages.
WebMD. Osteoarthritis Health Center: Osteoarthritis-prevention, Apr. 9, 2013, www.webmd.com/osteoarthritis/tc/osteoarthritis-prevention, 2 pages.
WebMD. Psoriasis Health Center: Psoriasis-prevention, Jan. 9, 2012, www.webmd.com/skin-problems-and-treatments/psoriasis/psoriasis-prevention, 1 page.
Xu et al., "Activation of the PI3K/AKT/mTOR pathway in diffuse large B cell lymphoma: clinical significance and inhibitory effect of rituximab," Ann Hematol., 2013, 92:1351-1358.
Yaguchi et al., "Antitumor Activity of ZSTK474, a new Phosphatidylinositol 3-Kinase Inhibitor," *J Natl. Cancer Inst.*, 2006, 98(8):545-556.
Yahay-Zadeh, "Synthesis of 9-Aryl-6-aminopurines from 5-Amino-1-aryl-1H-imidazole-4-carbonitriles", Russian Journal of Organic Chemistry (Translation of Zhurnal Organicheskoi Khimii) (2003), 39(11),1649-1651.
Yahyazadeh, et al., "Synthesis of 9-benzyl-6-aminopurines from 5-amino-1-benzyl-4-cyanoimidazoles", Bulletin of the Korean Chemical Society (2003), 24(12), 1723-1724.
Yamada et al., "Alpha-1 Adrenoceptors in Human Prostate: Characterization and Alteration in Benign Prostatic Hypertrophy," J Pharmacol Experimental Therapeutics, 1987, 242(1):326-330.
Yanni, A. S., "Synthesis of some new 5-iodo-7-substituted-aminomethyl-8-hydroxyquinoline," *Revue Roumaine de Chimie* (1994), 39(7), 833-6 CODEN: RRCHAX; ISSN: 0035-3930.
Yanni, et al., "Synthesis and biological activity of some 7-substituted aminomethyl-8-hydroxyquinoline-5-sulfonic acids," *Indian Journal of Chemistry, Section B: Organic Chemistry Including Medicinal Chemistry* (1982), 21B(7), 705-6.
Yoo, et al., "Synthesis and evaluation of antitumor activity of novel 2-[N-methyl-N-(4-methyl-1,3-benzothiazol-2-yl)aminomethyl]-5,8-diacyloxy-1,4-naphthoquinones," *Archives of Pharmacal Research* (2008), 31(2), 142-147 CODEN: APHRDQ; ISSN: 0253-6269.
Yoon et al., "Impact of fluoroquinolones on the diagnosis of pulmonary tuberculosis initially treated as bacterial pneumonia," Int'l J Tuberculosis and Lung Dis, 2005, 9:1215-1219.
Yoshida, et al., "MexAB-OprM specific efflux pump inhibitors in Pseudomonas aeruginosa. Part 5: Carbon-substituted analogues at the C-2 position," *Bioorganic & Medicinal Chemistry* (2006), 14(6), 1993-2004.
Yuan, T.L., "PI3K pathway alterations in cancer: variations on a theme," Oncogene, 2008, 27.41: 5497-551.
Zhang et al., "Advances in preclinical small molecules for the treatment of NSCLC", Expert Opinion on Therapeutic Patents, 19(6):731-751, 2009.
Zhao and Vogt, "Class I PI3K in oncogenic cellular transformation," Oncogene, 2008, 27:5486-5496.
Zhao, et al "Synthesis and in vitro anti-hepatitis B virus activities of some ethyl 5-hydroxy-1H-indole-3-carboxylates," *Bioorganic & Medicinal Chemistry* (2006), 14(8), 2552-2558.
International Preliminary Report on Patentability dated Dec. 28, 2012 for International Appln. No. PCT/US2011/041202 (8 pgs.).
International Preliminary Report on Patentability dated Jul. 4, 2013 for International Appln. No. PCT/US2011/065743 (8 pgs).
International Preliminary Report on Patentability dated Jun. 19, 2012 for International Appln. No. PCT/US2010/061023 (6 pgs.).

International Preliminary Report on Patentability dated Jun. 19, 2012 for International Appln. No. PCT/US2010/060980 (8 pgs.).
International Preliminary Report on Patentability dated Oct. 16, 2012 for International Appln. No. PCT/US2011/032213 (6 pgs.).
International Preliminary Report on Patentability for PCT/US2010/040150 dated Jul. 5, 2011 (24pgs.).
International Preliminary Report on Patentability for PCT/US2012/030310 dated Oct. 1, 2013 (7pgs.).
International Preliminary Report on Patentability for PCT/US2012/028915 dated Sep. 17, 2013 (6pgs.).
International Preliminary Report on Patentability for PCT/US2012/053398, issued Mar. 4, 2014 (6 pgs.).
International Search Report dated Jul. 11, 2013 for International Appln. No. PCT/US2013/034803 (15 pgs.).
International Search Report dated Dec. 21, 2012 for International Appln. No. PCT/US2012/053398 (11 pgs.).
International Search Report dated Feb. 28, 2012 for International Appln. No. PCT/US2011/065743 (13 pgs.).
International Search Report dated May 11, 2012 for International Appln. No. PCT/US2012/030310 (11 pgs.).
International Search Report dated May 31, 2012 for International Appln. No. PCT/US2012/028915 (11 pgs.).
International Search Report dated Sep. 23, 2011 for International Appln. No. PCT/US2011/041202 (12 pgs.).
International Search Report for PCT/US2010/040150 dated Nov. 8, 2010 (19 pgs.).
International Search Report for PCT/US2010/060980 dated Mar. 15, 2011 (12 pgs.).
International Search Report for PCT/US2010/061023 dated Feb. 16, 2011 (10 pgs.).
International Search Report for PCT/US2011/032213 dated Jun. 14, 2011 (11 pgs.).
STN Search Report, conducted Dec. 1, 2010, 132 pages.
STN Search Report, conducted Dec. 16, 2009, 72 pages.
STN Search Report, conducted prior to Jun. 21, 2011, 224 pages.
STN Search Report, conducted Apr. 5, 2010, 513 pages.
STN Search Report, conducted Apr. 24, 2009, 43 pages.
STN Search Report, conducted Dec. 7, 2010, 213 pages.
STN Search Report, conducted Aug. 29, 2011, 181 pages.
STN Search Report, conducted May 27, 2009, 2 pages.
STN Search Report, conducted May 28, 2009, 81 pages.
STN Search Report, conducted Apr. 2, 2010, 141 pages.
STN Search Report, conducted Aug. 30, 2011, 61 pages.
Office Action in CO Application No. 11-179.464, received on Mar. 14, 2014, 17 pages.
Office Action in JP Application No. 2012-518563, dated Jul. 8, 2014, 6 pages (with English translation).
Office Action in JP Application No. 2013-546274, dated Sep. 15, 2015, 7 pages (with English Translation).
Office Action in JP Application No. 2014-223540, dated Jul. 21, 2015, 5 pages (with English Translation).
Blom et al., "Two-Pump at Column Dilution Configuration for Preparative LC-MS," 2002, 4: 295.
Blom et al., "Optimizing Preparative LC-MS Configurations and Methods for Parallel Synthesis Purification," 2003, 5: 670.
Cacoub et al., "Anti-CD20 monoclonal antibody (rituximab) treatment for cryoglobulinemic vasculitis: where do we stand?," Ann Rheum Dis, Mar. 2008, 67: 283-287.
Garvey, "Rituximab in the treatment of autoimmune haematolgoical disorders," British Journal of Haematology, 2008, 141: 149-169.
Godeau et al., "Rituximab efficacy and safety in adult splenectomy candidates with chronic immune thrombocytopenic purpura: results of a prospective multicenter phase 2 study," Blood, 2008, 112(4): 999-1004.
Wuts and Greene, Protective Groups in Organic Synthesis, 4th ed., John Wiley & Sons: New Jersey, pp. 696-887,2007.
Lovric et al., "Rituximab as rescue therapy in anti-neutrophil cytoplasmic antibody-associated vasculitis: a single-center experience with 15 patients," Nephrol Dial Transplant, 2009, 24: 179-185.
Medeot et al., "Rituximab therapy in adult patients with relapsed or refractory immune thrombocytopenic purpura: long-term follow-up results," European Journal of Haematology, 2008, 81: 165-169.
Park et al., Analytical Biochemistry 1999, 269, 94-104.

(56) References Cited

OTHER PUBLICATIONS

Selig et al., "The application of Stille cross-coupling reactions with multiple nitrogen containing heterocycles," Tetrahedron, Sep. 2011, 67(47): 9204-9213.
Walsh and Jayne, "Rituximab in the treatment of anti-neutrophil cytoplasm antibody associated vasculitis and systemic lupus erythematosis: past, present and future," Kidney International, 2007, 72: 676-682.
International Search Report and Written Opinion in International Application No. PCT/US2016/031606, dated Jun. 20, 2016, 10 pages.
International Search Report and Written Opinion in International Application No. PCT/US2016/031611, dated Jun. 20, 2016, 10 pages.
International Search Report and Written Opinion in International Application No. PCT/US2016/031603, dated Jun. 22, 2016, 11 pages.
International Search Report and Written Opinion in International Application No. PCT/US2015/035046, dated Aug. 27, 2015, 9 pages.
International Search Report and Written Opinion in International Application No. PCT/US2016/019741, dated Aug. 2, 2016, 16 pages.
International Preliminary Report on Patentability in International Application No. PCT/US2015/035046, dated Dec. 22, 2016, 7 pages.

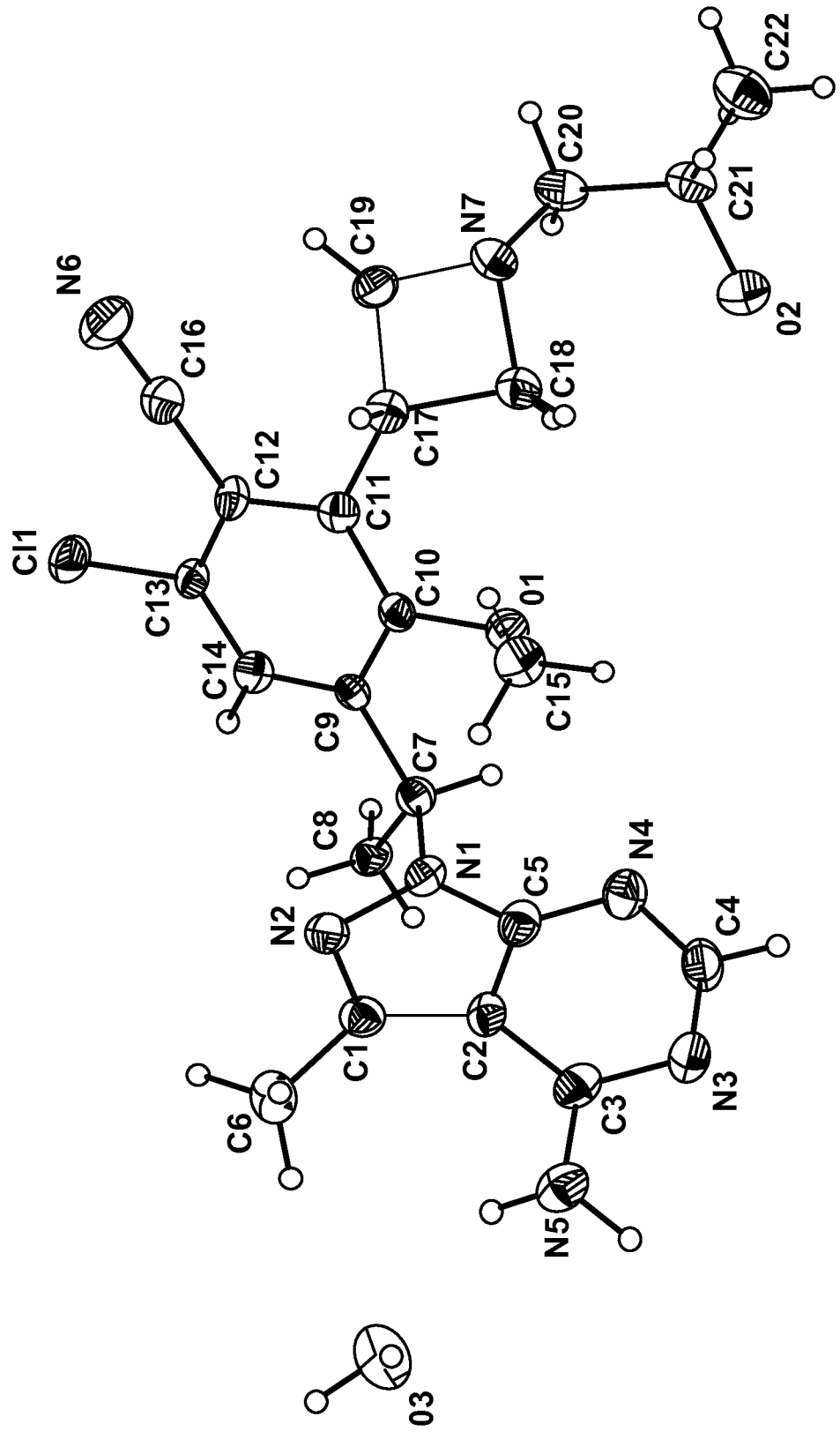

HETEROCYCLYLAMINES AS PI3K INHIBITORS

This application is a continuation of U.S. Ser. No. 13/601,349, filed Aug. 31, 2012, which claims the benefit of U.S. Prov. Appl. No. 61/530,866, filed Sep. 2, 2011, U.S. Prov. Appl. No. 61/594,882, filed Feb. 3, 2012, and U.S. Prov. Appl. No. 61/677,445, filed Jul. 30, 2012, each of which is incorporated herein by reference in its entirety.

FIELD OF THE INVENTION

The present invention provides heterocyclylamine derivatives, for example, pyrazolopyrimidines, that modulate the activity of phosphoinositide 3-kinases (PI3Ks) and are useful in the treatment of diseases related to the activity of PI3Ks including, for example, inflammatory disorders, immune-based disorders, cancer, and other diseases.

BACKGROUND OF THE INVENTION

The phosphoinositide 3-kinases (PI3Ks) belong to a large family of lipid signaling kinases that phosphorylate phosphoinositides at the D3 position of the inositol ring (Cantley, Science, 2002, 296(5573):1655-7). PI3Ks are divided into three classes (class I, II, and III) according to their structure, regulation and substrate specificity. Class I PI3Ks, which include PI3Kα, PI3Kβ, PI3Kγ, and PI3Kδ, are a family of dual specificity lipid and protein kinases that catalyze the phosphorylation of phosphatidylinosito-4,5-bisphosphate (PIP2) giving rise to phosphatidylinosito-3,4,5-trisphosphate (PIP3). PIP3 functions as a second messenger that controls a number of cellular processes, including growth, survival, adhesion and migration. All four class I PI3K isoforms exist as heterodimers composed of a catalytic subunit (p110) and a tightly associated regulatory subunit that controls their expression, activation, and subcellular localization. PI3Kα, PI3Kβ, and PI3Kδ associate with a regulatory subunit known as p85 and are activated by growth factors and cytokines through a tyrosine kinase-dependent mechanism (Jimenez, et al., J Biol Chem., 2002, 277(44):41556-62) whereas PI3Kγ associates with two regulatory subunits (p101 and p84) and its activation is driven by the activation of G-protein-coupled receptors (Brock, et al., J Cell Biol., 2003, 160(1):89-99). PI3Kα and PI3Kβ are ubiquitously expressed. In contrast, PI3Kγ and PI3Kδ are predominantly expressed in leukocytes (Vanhaesebroeck, et al., Trends Biochem Sci., 2005, 30(4):194-204).

The differential tissue distribution of the PI3K isoforms factors in their distinct biological functions. Genetic ablation of either PI3Kα or PI3Kβ results in embryonic lethality, indicating that PI3Kα and PI3Kβ have essential and non-redundant functions, at least during development (Vanhaesebroeck, et al., 2005). In contrast, mice which lack PI3Kγ and PI3Kδ are viable, fertile and have a normal life span although they show an altered immune system. PI3Kγ deficiency leads to impaired recruitment of macrophages and neutrophils to sites of inflammation as well as impaired T cell activation (Sasaki, et al., Science, 2000, 287(5455):1040-6). PI3Kδ-mutant mice have specific defects in B cell signaling that lead to impaired B cell development and reduced antibody responses after antigen stimulation (Clayton, et al., J Exp Med. 2002, 196(6):753-63; Jou, et al., Mol Cell Biol. 2002, 22(24):8580-91; Okkenhaug, et al., Science, 2002, 297(5583):1031-4).

The phenotypes of the PI3Kγ and PI3Kδ-mutant mice suggest that these enzymes may play a role in inflammation and other immune-based diseases and this is borne out in preclinical models. PI3Kγ-mutant mice are largely protected from disease in mouse models of rheumatoid arthritis (RA) and asthma (Camps, et al., Nat Med. 2005, 11(9):936-43; Thomas, et al., Eur J Immunol. 2005, 35(4):1283-91). In addition, treatment of wild-type mice with a selective inhibitor of PI3Kγ was shown to reduce glomerulonephritis and prolong survival in the MRL-lpr model of systemic lupus nephritis (SLE) and to suppress joint inflammation and damage in models of RA (Barber, et al., Nat Med. 2005, 11(9):933-5; Camps, et al., 2005) Similarly, both PI3Kδ-mutant mice and wild-type mice treated with a selective inhibitor of PI3Kδ have been shown to have attenuated allergic airway inflammation and hyper-responsiveness in a mouse model of asthma (Ali, et al., Nature. 2004, 431(7011):1007-11; Lee, et al., FASEB J. 2006, 20(3):455-65) and to have attenuated disease in a model of RA (Randis, et al., Eur. J. Immunol., 2008, 38(5):1215-24).

In addition to their potential role in inflammatory diseases, all four class I PI3K isoforms may play a role in cancer. The gene encoding p110α is mutated frequently in common cancers, including breast, prostate, colon and endometrial (Samuels, et al., Science, 2004, 304(5670):554; Samuels, et al., Curr Opin Oncol. 2006, 18(1):77-82). Eighty percent of these mutations are represented by one of three amino acid substitutions in the helical or kinase domains of the enzyme and lead to a significant upregulation of kinase activity resulting in oncogenic transformation in cell culture and in animal models (Kang, et al., Proc Natl Acad Sci USA. 2005, 102(3):802-7; Bader, et al., Proc Natl Acad Sci USA. 2006, 103(5):1475-9). No such mutations have been identified in the other PI3K isoforms although there is evidence that they can contribute to the development and progression of malignancies. Consistent overexpression of PI3Kδ is observed in acute myeloblastic leukemia (Sujobert, et al., Blood, 2005, 106(3):1063-6) and inhibitors of PI3Kδ can prevent the growth of leukemic cells (Billottet, et al., Oncogene. 2006, 25(50):6648-59). Elevated expression of PI3Kγ is seen in chronic myeloid leukemia (Hickey, et al., J Biol Chem. 2006, 281(5):2441-50). Alterations in expression of PI3Kβ, PI3Kγ and PI3Kδ have also been observed in cancers of the brain, colon and bladder (Benistant, et al., Oncogene, 2000, 19(44):5083-90; Mizoguchi, et al., Brain Pathol. 2004, 14(4):372-7; Knobbe, et al., Neuropathol Appl Neurobiol. 2005, 31(5):486-90). Further, these isoforms have all been shown to be oncogenic in cell culture (Kang, et al., 2006).

Thus, new or improved agents which inhibit kinases such as PI3K are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases (e.g., multiple sclerosis, rheumatoid arthritis, asthma, type I diabetes, inflammatory bowel disease, Crohn's disease, autoimmune thyroid disorders, Alzheimer's disease, nephritis), diseases involving a hyperactive inflammatory response (e.g., eczema), allergies, lung diseases, cancer (e.g., prostate, breast, leukemia, multiple myeloma), and some immune reactions (e.g., skin rash or contact dermatitis or diarrhea) caused by other therapeutics. The compounds, compositions, and methods described herein are directed toward these needs and others.

SUMMARY

The present invention provides, inter alia, a compound of Formula I:

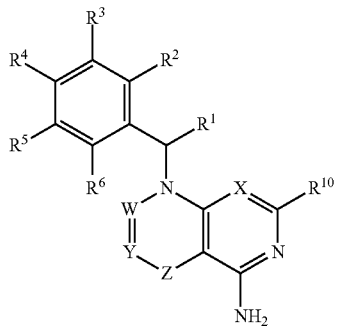

or a pharmaceutically acceptable salt thereof, wherein the variables are defined infra.

The present invention further provides compositions comprising a compound of the invention, or a pharmaceutically acceptable salt thereof, and at least one pharmaceutically acceptable carrier.

The present invention also provides methods of modulating an activity of a PI3K kinase, comprising contacting the kinase with a compound of the invention, or a pharmaceutically acceptable salt thereof.

The present invention further provides methods of treating a disease in a patient, wherein said disease is associated with abnormal expression or activity of a PI3K kinase, comprising administering to said patient a therapeutically effective amount of a compound of the invention, or a pharmaceutically acceptable salt thereof.

The present invention further provides methods of treating an immune-based disease in a patient, comprising administering to said patient a therapeutically effective amount of a compound of the invention, or a pharmaceutically acceptable salt thereof.

The present invention also provides methods of treating a cancer in a patient, comprising administering to said patient a therapeutically effective amount of a compound of the invention, or a pharmaceutically acceptable salt thereof.

The present invention further provides methods of treating a lung disease in a patient, comprising administering to said patient a therapeutically effective amount of a compound of the invention, or a pharmaceutically acceptable salt thereof.

The present invention also provides a compound of the invention, or a pharmaceutically acceptable salt thereof, for use in any of the methods described herein.

The present invention further provides use of a compound, or a pharmaceutically acceptable salt thereof, for the manufacture of a medicament for use in any of the methods described herein.

BRIEF DESCRIPTION OF THE FIGURES

FIG. 1 depicts the crystal structure of the compound of Example 269.

DETAILED DESCRIPTION

The present invention provides, inter alia, a compound of Formula I:

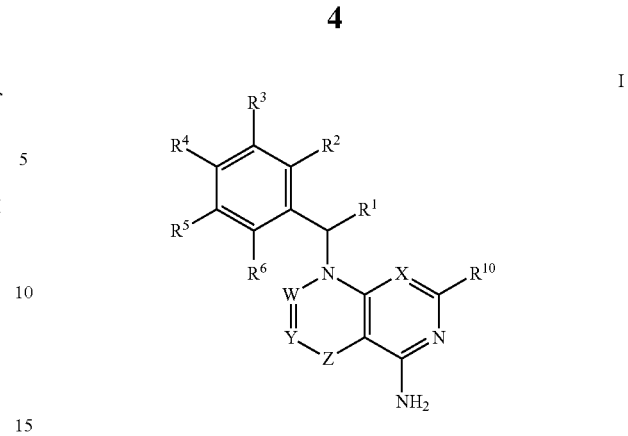

or a pharmaceutically acceptable salt thereof, wherein:
X is $CR^9$ or N;
W is $CR^7$ or N;
Y is $CR^8$, $CR^{8a}$, or N;
Z is a bond or $C(=O)$;
provided that —W=Y—Z— is $-CR^7=CR^8-$, $-N=CR^8-$, $-CR^7=CR^{8a}-C(=O)-$, $-N=CR^{8a}-C(=O)-$, or $-CR^7=N-C(=O)-$;
$R^1$ is $C_{1-3}$ alkyl;
$R^2$ is halo, $C_{1-6}$ alkyl, $C_{1-6}$ alkoxy, $C_{1-6}$ haloalkyl, $C_{1-6}$ haloalkoxy, phenyl, or 5-6 membered heteroaryl; wherein said phenyl and 5-6 membered heteroaryl are each optionally substituted by 1, 2, 3, or 4 substituents independently selected from halo, OH, CN, $C_{1-4}$ alkyl, $C_{1-4}$ alkoxy, and $C_{1-4}$ haloalkoxy;
$R^3$ is Cy, —($C_{1-3}$ alkylene)-Cy, halo, CN, $NO_2$, $C_{1-6}$ alkyl, $C_{2-6}$ alkenyl, $C_{2-6}$ alkynyl, $C_{1-6}$ haloalkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$; wherein said $C_{1-6}$ alkyl, $C_{2-6}$ alkenyl, and $C_{2-6}$ alkynyl are each optionally substituted by 1, 2, 3, or 4 independently selected $R^{3a}$ groups;
$R^4$ is H, halo, OH, CN, $C_{1-4}$ alkyl, $C_{1-4}$ haloalkyl, $C_{1-4}$ alkoxy, or $C_{1-4}$ haloalkoxy;
$R^5$ is halo, OH, CN, $C_{1-4}$ alkyl, $C_{1-4}$ haloalkyl, $C_{1-4}$ alkoxy, $C_{1-4}$ haloalkoxy, or cyclopropyl;
$R^6$ is H, halo, OH, CN, $C_{1-4}$ alkyl, $C_{1-4}$ haloalkyl, $C_{1-4}$ alkoxy, or $C_{1-4}$ haloalkoxy;
$R^7$ is H or $C_{1-4}$ alkyl;
$R^8$ is H, halo, —OH, —CN, $C_{1-6}$ alkyl, $C_{2-6}$ alkenyl, $C_{2-6}$ alkynyl, $C_{1-6}$ haloalkyl, $Cy^2$, —($C_{1-3}$ alkylene)-$Cy^2$, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=O)NR^{c2}R^{d2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $C(=NR^e)R^{b2}$, $C(=NR^e)NR^{c2}R^{d2}$, $NR^{c2}C(=NR^e)NR^{c2}R^{d2}$, $NR^{c2}S(=O)R^{b2}$, $NR^{c2}S(=O)_2NR^{c2}R^{d2}$, $S(=O)R^{b2}$, or $S(=O)_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;
$R^{8a}$ is H, halo, —CN, $C_{1-6}$alkyl, $C_{2-6}$ alkenyl, $C_{2-6}$ alkynyl, $C_{1-6}$haloalkyl, $Cy^2$, —($C_{1-3}$ alkylene)-$Cy^2$, $C(=O)R^{b2}$, $C(=O)NR^{c2}R^{d2}$, $C(=O)OR^{a2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $NR^{c2}S(=O)R^{b2}$, $NR^{c2}S(=O)_2NR^{c2}R^{d2}$, $S(=O)R^{b2}$, or $S(=O)_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;
$R^9$ is H, halo, OH, CN, $C_{1-4}$ alkyl, $C_{1-4}$ haloalkyl, $C_{1-4}$ alkoxy, or $C_{1-4}$ haloalkoxy;

$R^{10}$ is H or $C_{1-4}$ alkyl;

each $R^a$, $R^b$, $R^c$, and $R^d$ is independently selected from H, $C_{1-6}$ alkyl, $C_{1-6}$ haloalkyl, $C_{2-6}$ alkenyl, $C_{2-6}$ alkynyl, and Cy; wherein said $C_{1-6}$ alkyl, $C_{2-6}$ alkenyl, and $C_{2-6}$ alkynyl are each optionally substituted with 1, 2, or 3 independently selected $R^{3a}$ groups;

or $R^c$ and $R^d$ together with the N atom to which they are attached form a 4-, 5-, 6-, or 7 membered heterocycloalkyl group, which is optionally substituted with —OH or $C_{1-3}$ alkyl;

each $R^e$ is independently selected from H, CN, OH, $C_{1-4}$ alkyl, and $C_{1-4}$ alkoxy;

each Cy is independently selected from $C_{3-7}$ cycloalkyl, 4-10 membered heterocycloalkyl, phenyl, naphthyl, and 5-10 membered heteroaryl, each of which is optionally substituted with 1, 2, 3, or 4 independently selected $R^{3b}$ groups;

each $R^{3a}$ is independently selected from halo, CN, NO$_2$, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{a1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)R^{b1}$, $NR^{c1}S(=O)_2NR^{c1}R^{d1}$, $S(=O)_2R^{b1}$, and $S(=O)_2NR^{c1}R^{d1}$; wherein said $C_{1-6}$ alkyl, $C_{2-6}$ alkenyl, $C_{2-6}$ alkynyl are each optionally substituted with 1, 2, or 3 independently selected $R^{11}$ groups;

each $R^{3b}$ is independently selected from $Cy^1$, —($C_{1-3}$ alkylene)-$Cy^1$, halo, CN, NO$_2$, $C_{1-6}$ alkyl, $C_{2-6}$ alkenyl, $C_{2-6}$ alkynyl, $C_{1-6}$ haloalkyl, $OR^{a1}$, $SR^{a1}$, $C(=O)R^{b1}$, $C(=O)NR^{c1}R^{d1}$, $C(=O)OR^{a1}$, $OC(=O)R^{b1}$, $OC(=O)NR^{c1}R^{d1}$, $NR^{c1}R^{d1}$, $NR^{c1}C(=O)R^{b1}$, $NR^{c1}C(=O)OR^{b1}$, $NR^{c1}C(=O)NR^{c1}R^{d1}$, $C(=NR^e)R^{b1}$, $C(=NR^e)NR^{c1}R^{d1}$, $NR^{c1}C(=NR^e)NR^{c1}R^{d1}$, $NR^{c1}S(=O)R^{b1}$, $NR^{c1}S(=O)_2NR^{c1}R^{d1}$, $S(=O)R^{b1}$, and $S(=O)_2NR^{c1}R^{d1}$; wherein said $C_{1-6}$ alkyl, $C_{2-6}$ alkenyl, $C_{2-6}$ alkynyl are each optionally substituted with 1, 2, or 3 independently selected $R^{11}$ groups;

each $Cy^1$ is independently selected from $C_{3-7}$ cycloalkyl, 4-7 membered heterocycloalkyl, phenyl, and 5-6 membered heteroaryl, each of which is optionally substituted with 1, 2, 3, or 4 independently selected $R^{11}$ groups;

each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups;

or $R^{c1}$ and $R^{d1}$ together with the N atom to which they are attached form a 4-, 5-, 6-, or 7 membered heterocycloalkyl group, which is optionally substituted with —OH or $C_{1-3}$ alkyl;

each $Cy^2$ is independently selected from $C_{3-7}$ cycloalkyl, 4-7 membered heterocycloalkyl, phenyl, and 5-6 membered heteroaryl, each of which is optionally substituted with 1, 2, 3, or 4 independently selected $R^{11}$ groups;

each $R^{a2}$, $R^{b2}$, $R^{c2}$ and $R^{d2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups;

or $R^{c2}$ and $R^{d2}$ together with the N atom to which they are attached form a 4-, 5-, 6-, or 7 membered heterocycloalkyl group, which is optionally substituted with —OH or $C_{1-3}$ alkyl; and each $R^{11}$ is independently selected from OH, NO$_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-3}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

The present invention also provides, a compound of Formula I:

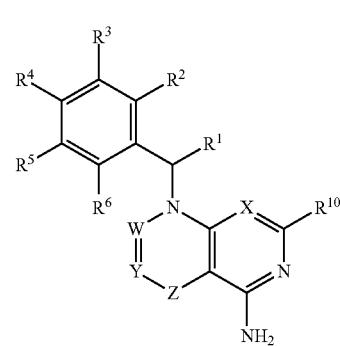

I or a pharmaceutically acceptable salt thereof, wherein:
X is $CR^9$ or N;
W is $CR^7$ or N;
Y is $CR^8$, $CR^{8a}$, or N;
Z is a bond or $C(=O)$;
provided that —W=Y—Z— is —$CR^7$=$CR^8$—, —N=$CR^8$—, —$CR^7$=$CR^{8a}$—C(=O)—, —N=$CR^{8a}$—C(=O)—, or —$CR^7$=N—C(=O)—;
$R^1$ is $C_{1-3}$ alkyl;
$R^2$ is halo, $C_{1-6}$ alkyl, $C_{1-6}$ alkoxy, $C_{1-6}$ haloalkyl, $C_{1-6}$ haloalkoxy, phenyl, or 5-6 membered heteroaryl; wherein said phenyl and 5-6 membered heteroaryl are each optionally substituted by 1, 2, 3, or 4 substituents independently selected from halo, OH, CN, $C_{1-4}$ alkyl, $C_{1-4}$ alkoxy, and $C_{1-4}$ haloalkoxy;
$R^3$ is Cy, —($C_{1-3}$ alkylene)-Cy, halo, CN, NO$_2$, $C_{1-6}$ alkyl, $C_{2-6}$ alkenyl, $C_{2-6}$ alkynyl, $C_{1-6}$ haloalkyl, $OR^a$, $SR^a$, $C(=O)R^b$, $C(=O)NR^cR^d$, $C(=O)OR^a$, $OC(=O)R^b$, $OC(=O)NR^cR^d$, $NR^cR^d$, $NR^cC(=O)R^b$, $NR^cC(=O)OR^b$, $NR^cC(=O)NR^cR^d$, $C(=NR^e)R^b$, $C(=NR^e)NR^cR^d$, $NR^cC(=NR^e)NR^cR^d$, $NR^cS(=O)_2R^b$, $NR^cS(=O)_2NR^cR^d$, $S(=O)_2R^b$, or $S(=O)_2NR^cR^d$; wherein said $C_{1-6}$ alkyl, $C_{2-6}$ alkenyl, and $C_{2-6}$ alkynyl are each optionally substituted by 1, 2, 3, or 4 independently selected $R^{3a}$ groups;
$R^4$ is H, halo, OH, CN, $C_{1-4}$ alkyl, $C_{1-4}$ haloalkyl, $C_{1-4}$ alkoxy, or $C_{1-4}$ haloalkoxy;
$R^5$ is halo, OH, CN, $C_{1-4}$ alkyl, $C_{1-4}$ haloalkyl, $C_{1-4}$ alkoxy, $C_{1-4}$ haloalkoxy, or cyclopropyl;
$R^6$ is H, halo, OH, CN, $C_{1-4}$ alkyl, $C_{1-4}$ haloalkyl, $C_{1-4}$ alkoxy, or $C_{1-4}$ haloalkoxy;
$R^7$ is H or $C_{1-4}$ alkyl;

R$^8$ is H, halo, —OH, —CN, C$_{1-6}$ alkyl, C$_{2-6}$ alkenyl, C$_{2-6}$ alkynyl, C$_{1-6}$ haloalkyl, Cy$^2$, —(C$_{1-3}$ alkylene)-Cy$^2$, OR$^{a2}$, SR$^{a2}$, C(=O)R$^{b2}$, C(=O)NR$^{c2}$R$^{d2}$, C(=O)OR$^{a2}$, OC(=O)R$^{b2}$, OC(=O)NR$^{c2}$R$^{d2}$, NR$^{c2}$R$^{d2}$, NR$^{c2}$C(=O)R$^{b2}$, NR$^{c2}$C(=O)OR$^{b2}$, NR$^{c2}$C(=O)NR$^{c2}$R$^{d2}$, C(=NR$^e$)R$^{b2}$, C(=NR$^e$)NR$^{c2}$R$^{d2}$, NR$^{c2}$C(=NR$^e$)NR$^{c2}$R$^{d2}$, NR$^{c2}$S(=O)R$^{b2}$, NR$^{c2}$S(=O)$_2$NR$^{c2}$R$^{d2}$, S(=O)R$^{b2}$, S(=O)$_2$R$^{b2}$, or S(=O)$_2$NR$^{c2}$R$^{d2}$; wherein said C$_{1-6}$ alkyl, C$_{2-6}$ alkenyl, C$_{2-6}$ alkynyl are each optionally substituted by 1, 2, 3, or 4 independently selected R$^{11}$ groups;

R$^{8a}$ is H, halo, —CN, C$_{1-6}$alkyl, C$_{2-6}$ alkenyl, C$_{2-6}$ alkynyl, C$_{1-6}$haloalkyl, Cy$^2$, —(C$_{1-3}$ alkylene)-Cy$^2$, C(=O)R$^{b2}$, C(=O)NR$^{c2}$R$^{d2}$, C(=O)OR$^{a2}$, NR$^{c2}$R$^{d2}$, NR$^{c2}$C(=O)R$^{b2}$, NR$^{c2}$C(=O)OR$^{b2}$, NR$^{c2}$C(=O)NR$^{c2}$R$^{d2}$, NR$^{c2}$S(=O)R$^{b2}$, NR$^{c2}$S(=O)$_2$NR$^{c2}$R$^{d2}$, S(=O)R$^{b2}$, S(=O)$_2$R$^{b2}$, or S(=O)$_2$NR$^{c2}$R$^{d2}$; wherein said C$_{1-6}$ alkyl, C$_{2-6}$ alkenyl, C$_{2-6}$ alkynyl are each optionally substituted by 1, 2, 3, or 4 independently selected R$^{11}$ groups;

R$^9$ is H, halo, OH, CN, C$_{1-4}$ alkyl, C$_{1-4}$ haloalkyl, C$_{1-4}$ alkoxy, or C$_{1-4}$ haloalkoxy;

R$^{10}$ is H or C$_{1-4}$ alkyl;

each R$^a$, R$^b$, R$^c$, and R$^d$ is independently selected from H, C$_{1-6}$ alkyl, C$_{1-6}$ haloalkyl, C$_{2-6}$ alkenyl, C$_{2-6}$ alkynyl, and Cy; wherein said C$_{1-6}$ alkyl, C$_{2-6}$ alkenyl, and C$_{2-6}$ alkynyl are each optionally substituted with 1, 2, or 3 independently selected R$^{3b}$ groups;

or R$^c$ and R$^d$ together with the N atom to which they are attached form a 4-, 5-, 6-, or 7 membered heterocycloalkyl group, which is optionally substituted with —OH or C$_{1-3}$ alkyl;

each R$^e$ is independently selected from H, CN, OH, C$_{1-4}$ alkyl, and C$_{1-4}$ alkoxy;

each Cy is independently selected from C$_{3-7}$ cycloalkyl, 4-10 membered heterocycloalkyl, phenyl, naphthyl, and 5-10 membered heteroaryl, each of which is optionally substituted with 1, 2, 3, or 4 independently selected R$^{3b}$ groups;

each R$^{3a}$ is independently selected from halo, CN, NO$_2$, C$_{1-6}$ alkyl, C$_{2-6}$ alkenyl, C$_{2-6}$ alkynyl, C$_{1-6}$ haloalkyl, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, NR$^{c1}$R$^{d1}$, NR$^{c1}$C(=O)R$^{b1}$, NR$^{c1}$C(=O)OR$^{b1}$, NR$^{c1}$C(=O)NR$^{c1}$R$^{d1}$, C(=NR$^e$)R$^{b1}$, C(=NR$^e$)NR$^{c1}$R$^{d1}$, NR$^{c1}$C(=NR$^e$)NR$^{c1}$R$^{d1}$, NR$^{c1}$S(=O)R$^{b1}$, NR$^{c1}$S(=O)$_2$NR$^{c1}$R$^{d1}$, S(=O)R$^{b1}$, and S(=O)$_2$NR$^{c1}$R$^{d1}$; wherein said C$_{1-6}$ alkyl, C$_{2-6}$ alkenyl, C$_{2-6}$ alkynyl are each optionally substituted with 1, 2, or 3 independently selected R$^{11}$ groups;

each R$^{3b}$ is independently selected from Cy$^1$, —(C$_{1-3}$ alkylene)-Cy$^1$, halo, CN, NO$_2$, C$_{1-6}$ alkyl, C$_{2-6}$ alkenyl, C$_{2-6}$ alkynyl, C$_{1-6}$ haloalkyl, OR$^{a1}$, SR$^{a1}$, C(=O)R$^{b1}$, C(=O)NR$^{c1}$R$^{d1}$, C(=O)OR$^{a1}$, OC(=O)R$^{b1}$, OC(=O)NR$^{c1}$R$^{d1}$, NR$^{c1}$R$^{d1}$, NR$^{c1}$C(=O)R$^{b1}$, NR$^{c1}$C(=O)OR$^{b1}$, NR$^{c1}$C(=O)NR$^{c1}$R$^{d1}$, C(=NR$^e$)R$^{b1}$, C(=NR$^e$)NR$^{c1}$R$^{d1}$, NR$^{c1}$C(=NR$^e$)NR$^{c1}$R$^{d1}$, NR$^{c1}$S(=O)R$^{b1}$, NR$^{c1}$S(=O)$_2$NR$^{c1}$R$^{d1}$, S(=O)R$^{b1}$, S(=O)$_2$R$^{b1}$, and S(=O)$_2$NR$^{c1}$R$^{d1}$; wherein said C$_{1-6}$ alkyl, C$_{2-6}$ alkenyl, C$_{2-6}$ alkynyl are each optionally substituted with 1, 2, or 3 independently selected R$^{11}$ groups;

each Cy$^1$ is independently selected from C$_{3-7}$ cycloalkyl, 4-7 membered heterocycloalkyl, phenyl, and 5-6 membered heteroaryl, each of which is optionally substituted with 1, 2, 3, or 4 independently selected R$^{11}$ groups;

each R$^{a1}$, R$^{b1}$, R$^{c1}$, and R$^{d1}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, 4-7 membered heterocycloalkyl, phenyl, and 5-6 membered heteroaryl; wherein said C$_{1-6}$ alkyl, C$_{2-6}$ alkenyl, C$_{2-6}$ alkynyl, C$_{3-7}$ cycloalkyl, 4-7 membered heterocycloalkyl, phenyl and 5-6 membered heteroaryl are each optionally substituted with 1, 2, or 3 independently selected R$^{11}$ groups;

or R$^{c1}$ and R$^{d1}$ together with the N atom to which they are attached form a 4-, 5-, 6-, or 7 membered heterocycloalkyl group, which is optionally substituted with —OH or C$_{1-3}$ alkyl;

each Cy$^2$ is independently selected from C$_{3-7}$ cycloalkyl, 4-7 membered heterocycloalkyl, phenyl, 5-6 membered heteroaryl, or 9-10-membered bicyclic heteroaryl, each of which is optionally substituted with 1, 2, 3, or 4 independently selected R$^{11}$ groups;

each R$^{a2}$, R$^{b2}$, R$^{c2}$, and R$^{d2}$ is independently selected from H, C$_{1-6}$ alkyl, C$_{1-6}$ haloalkyl, C$_{2-6}$ alkenyl, C$_{2-6}$ alkynyl, C$_{3-7}$ cycloalkyl, 4-7 membered heterocycloalkyl, phenyl, and 5-6 membered heteroaryl; wherein said C$_{1-6}$ alkyl, C$_{2-6}$ alkenyl, C$_{2-6}$ alkynyl, C$_{3-7}$ cycloalkyl, 4-7 membered heterocycloalkyl, phenyl and 5-6 membered heteroaryl are each optionally substituted with 1, 2, or 3 independently selected R$^{11}$ groups;

or R$^{c2}$ and R$^{d2}$ together with the N atom to which they are attached form a 4-, 5-, 6-, or 7 membered heterocycloalkyl group, which is optionally substituted with —OH or C$_{1-3}$ alkyl; and each R$^{11}$ is independently selected from OH, NO$_2$, CN, halo, C$_{1-3}$ alkyl, C$_{2-3}$ alkenyl, C$_{2-3}$ alkynyl, C$_{1-3}$ haloalkyl, cyano-C$_{1-3}$ alkyl, HO—C$_{1-3}$ alkyl, C$_{1-3}$ alkoxy-C$_{1-3}$ alkyl, C$_{3-7}$ cycloalkyl, C$_{1-3}$ alkoxy, C$_{1-3}$ haloalkoxy, amino, C$_{1-3}$ alkylamino, di(C$_{1-3}$ alkyl)amino, thio, C$_{1-3}$ alkylthio, C$_{1-3}$ alkylsulfinyl, C$_{1-3}$ alkylsulfonyl, carbamyl, C$_{1-3}$ alkylcarbamyl, di(C$_{1-3}$ alkyl)carbamyl, carboxy, C$_{1-3}$ alkylcarbonyl, C$_{1-4}$ alkoxycarbonyl, C$_{1-3}$ alkylcarbonylamino, C$_{1-3}$ alkylsulfonylamino, aminosulfonyl, C$_{1-3}$ alkylaminosulfonyl, di(C$_{1-3}$ alkyl)aminosulfonyl, aminosulfonylamino, C$_{1-3}$ alkylaminosulfonylamino, di(C$_{1-3}$ alkyl)aminosulfonylamino, aminocarbonylamino, C$_{1-3}$ alkylaminocarbonylamino, and di(C$_{1-3}$ alkyl)aminocarbonylamino.

In an embodiment of either of the preceding embodiments, Cy is not

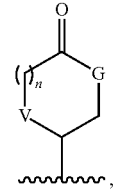

wherein:
G is NH, n is 1, and V is O; or
G is NH, n is 0, and V is O or CH$_2$; or
G is O, n is 0 and V is NH.

In an embodiments of the preceding embodiments, R$^3$ is

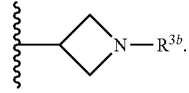

In an embodiment of the preceding embodiments, R$^3$ is Cy, wherein each Cy is independently selected from an azetidine ring, a pyrazole ring, a pyridine ring, a pyrimidine ring, and a phenyl ring, each of which is optionally substituted with 1, 2, 3, or 4 independently selected R3b groups.

In some embodiments: the

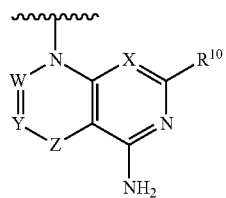

moiety is:

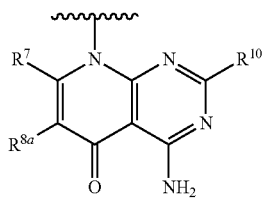

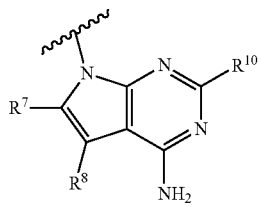

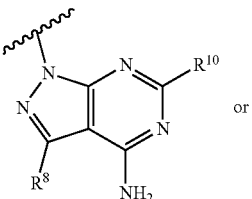 or

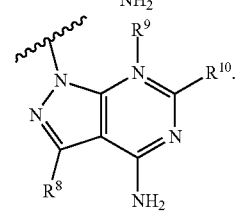

In some embodiments: the

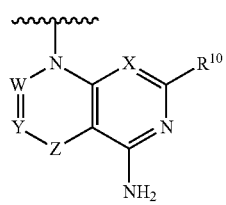

moiety is

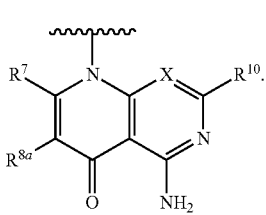

In some embodiments: the

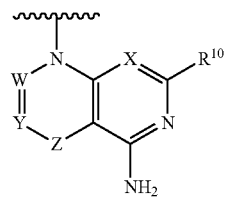

moiety is

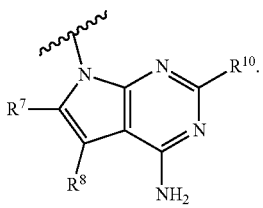

In some embodiments: the

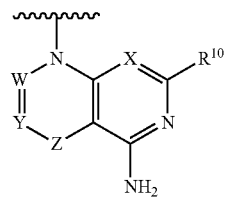

moiety is

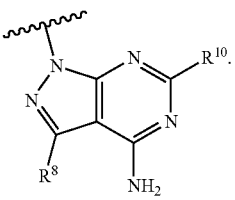

In some embodiments: the

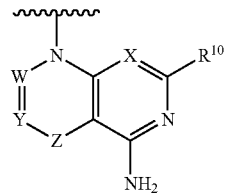

moiety is

In some embodiments, $R^1$ is methyl.

In some embodiments, $R^2$ is $C_{1-6}$ alkyl, $C_{1-3}$ alkoxy, or phenyl; wherein said phenyl is optionally substituted by 1, 2, 3, or 4 substituents independently selected from halo.

In some embodiments, each $R^a$, $R^b$, $R^c$, and $R^d$ is independently selected from H, $C_{1-6}$ alkyl, and $C_{1-6}$ haloalkyl.

In some embodiments, $R^3$ is Cy or $C(=O)NR^cR^d$; wherein each $R^c$ and $R^d$ is independently selected from $C_{1-6}$ alkyl.

In some embodiments, $R^3$ is Cy.

In some embodiments, $R^3$ is $C(=O)NR^cR^d$; wherein each $R^c$ and $R^d$ is independently selected from $C_{1-6}$ alkyl.

In some embodiments, each Cy is independently selected from $C_{3-7}$ cycloalkyl, 4-7 membered heterocycloalkyl, phenyl, and 5-6 membered heteroaryl, each of which is optionally substituted with 1, 2, 3, or 4 independently selected $R^{3b}$ groups.

In some embodiments, each Cy is independently selected from an azetidine ring, a pyrazole ring, a pyridine ring, a pyrimidine ring, and a phenyl ring, each of which is optionally substituted with 1, 2, 3, or 4 independently selected $R^{3b}$ groups.

In some embodiments:

each Cy is independently selected from $C_{3-7}$ cycloalkyl, 4-7 membered heterocycloalkyl, phenyl, and 5-6 membered heteroaryl, each of which is optionally substituted with 1 or 2 $R^{3b}$ independently selected from $Cy^1$, —($C_{1-3}$ alkylene)-$Cy^1$, halo, CN, OH, $C_{1-6}$ alkyl, $C_{1-6}$ alkoxy, $C_{1-6}$ haloalkyl, $C(=O)R^{b1}$, $C(=O)NR^{c1}R^{d1}$, $S(=O)R^{b1}$, and $S(=O)_2NR^{c1}R^{d1}$; wherein said $C_{1-6}$ alkyl is optionally substituted with 1, 2, or 3 independently selected $R^{11}$ groups;

$Cy^1$ is $C_{3-6}$ cycloalkyl or 4-7 membered heterocycloalkyl;

each $R^{a1}$, $R^{b1}$, $R^{c1}$, and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups; and each $R^{11}$ is independently OH or $C_{1-3}$ alkoxy.

In some embodiments:

each Cy is independently selected from an azetidine ring, a pyrazole ring, a pyridine ring, a pyrimidine ring, a phenyl ring, each of which is optionally substituted with one $R^{3b}$ selected from $Cy^1$, —($C_{1-3}$ alkylene)-$Cy^1$, halo, CN, OH, $C_{1-6}$ alkyl, $C_{1-6}$ alkoxy, $C_{1-6}$ haloalkyl, $C(=O)R^{b1}$, $C(=O)NR^{c1}R^{d1}$, $S(=O)R^{b1}$, and $S(=O)_2NR^{c1}R^{d1}$; wherein said $C_{1-6}$ alkyl is optionally substituted with 1, 2, or 3 independently selected $R^{11}$ groups;

$Cy^1$ is $C_{3-6}$ cycloalkyl or 4-7 membered heterocycloalkyl;

each $R^{a1}$, $R^{b1}$, $R^{c1}$, and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups; and each $R^{11}$ is independently OH or $C_{1-3}$ alkoxy.

In some embodiments:

each Cy is independently selected from $C_{3-7}$ cycloalkyl, 4-7 membered heterocycloalkyl, phenyl, and 5-6 membered heteroaryl, each of which is optionally substituted with 1 or 2 $R^{3b}$ independently selected from $Cy^1$, —($C_{1-3}$ alkylene)-$Cy^1$, halo, CN, OH, $C_{1-6}$ alkyl, $C_{1-6}$ alkoxy, $C_{1-6}$ haloalkyl, $C(=O)R^{b1}$, $C(=O)NR^{c1}R^{d1}$, $S(=O)R^{b1}$, and $S(=O)_2NR^{c1}R^{d1}$; wherein said $C_{1-6}$ alkyl is optionally substituted with 1, 2, or 3 independently selected $R^{11}$ groups;

$Cy^1$ is $C_{3-6}$ cycloalkyl or 4-7 membered heterocycloalkyl;

each $R^{a1}$, $R^{b1}$, $R^{c1}$ and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups; and each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl)carbamyl.

In some embodiments:

each Cy is independently selected from an azetidine ring, a pyrazole ring, a pyridine ring, a pyrimidine ring, a phenyl ring, each of which is optionally substituted with one $R^{3b}$ selected from $Cy^1$, —($C_{1-3}$ alkylene)-$Cy^1$, halo, CN, OH, $C_{1-6}$ alkyl, $C_{1-6}$ alkoxy, $C_{1-6}$ haloalkyl, $C(=O)R^{b1}$, $C(=O)NR^{c1}R^{d1}$, $S(=O)R^{b1}$, and $S(=O)_2NR^{c1}R^{d1}$; wherein said $C_{1-6}$ alkyl is optionally substituted with 1, 2, or 3 independently selected $R^{11}$ groups;

$Cy^1$ is $C_{3-6}$ cycloalkyl or 4-7 membered heterocycloalkyl;

each $R^{a1}$, $R^{b1}$, $R^{c1}$, and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups; and each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl)carbamyl.

In some embodiments, $R^4$ is halo, CN, or $C_{1-4}$ alkyl.

In some embodiments, $R^4$ is F, Cl, CN, or methyl.

In some embodiments, $R^4$ is F.

In some embodiments, $R^4$ is Cl.

In some embodiments, $R^4$ is CN.

In some embodiments, $R^4$ is methyl

In some embodiments, $R^5$ is halo or CN.

In some embodiments, $R^5$ is Cl.

In some embodiments, $R^6$ is H.

In some embodiments, $R^7$ is H.

In some embodiments, $R^8$ is H, halo, CN, $C_{1-6}$ alkyl, or $Cy^2$; wherein $Cy^2$ is selected from $C_{3-6}$ cycloalkyl, phenyl, 5-6 membered heteroaryl, and 4-7 membered heterocycloalkyl, each of which is optionally substituted by 1 or 2 independently selected $R^{11}$ groups.

In some embodiments, $R^8$ is H, halo, CN, $C_{1-6}$ alkyl, or $Cy^2$; wherein $Cy^2$ is selected from $C_{3-6}$ cycloalkyl, phenyl, 5-6 membered heteroaryl, or 4-7 membered heterocycloalkyl each of which is optionally substituted by 1 $R^{11}$ selected from OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, and di($C_{1-3}$ alkyl)carbamyl.

In some embodiments, $R^8$ is H, halo, CN, methyl, or $Cy^2$; wherein $Cy^2$ is selected from cyclopropyl, phenyl, a pyrazole ring, a pyridine ring, or a pyrimidine ring, each of which is optionally substituted by 1 $R^{11}$ selected from OH, CN, fluoro, methyl, 2-hydroxyethyl, dimethylcarbamyl, amino, methylcarbamyl, and dimethylcarbamyl.

In some embodiments, $R^8$ is H, methyl, F, Cl, or I.

In some embodiments, $R^8$ is methyl.

In some embodiments, $R^8$ is H.

In some embodiments, $R^8$ is F.

In some embodiments, $R^8$ is Cl.

In some embodiments, $R^8$ is I.

In some embodiments, each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl)carbamyl.

In some embodiments, $R^{8a}$ is H, halo, —CN, $C_{1-6}$alkyl, $C_{2-6}$ alkenyl, $C_{2-6}$ alkynyl, $C_{1-6}$haloalkyl, or $Cy^2$.

In some embodiments, $R^{8a}$ is H or halo.

In some embodiments, $R^{8a}$ is H.

In some embodiments, $R^9$ is H.

In some embodiments, $R^{10}$ is H.

In some embodiments:
the

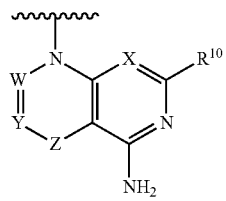

moiety is:

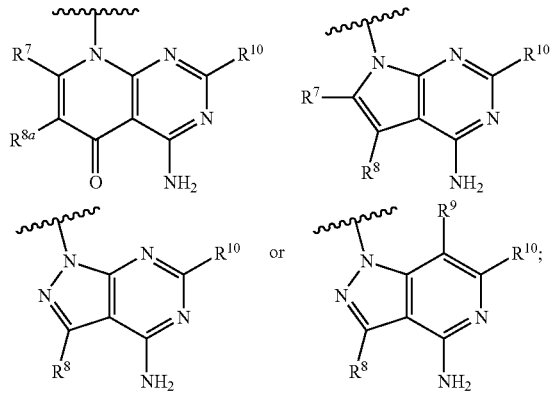

$R^1$ is methyl;

$R^2$ is $C_{1-6}$ alkyl, $C_{1-3}$ alkoxy, or phenyl; wherein said phenyl is optionally substituted by 1, 2, 3, or 4 substituents independently selected from halo;

$R^3$ is Cy or C(=O)NR$^c$R$^d$; wherein each R$^c$ and R$^d$ is independently selected from $C_{1-6}$ alkyl;

Cy is selected from $C_{3-7}$ cycloalkyl, 4-7 membered heterocycloalkyl, phenyl, and 5-6 membered heteroaryl, each of which is optionally substituted with 1, 2, 3, or 4 independently selected $R^{3b}$ groups;

$R^4$ is halo, CN, or $C_{1-4}$ alkyl;

$R^5$ is halo or CN;

$R^6$, $R^7$, $R^9$, and $R^{10}$ are each H;

$R^8$ is H, halo, CN, $C_{1-6}$ alkyl, or Cy$^2$; wherein Cy$^2$ is selected from $C_{3-6}$ cycloalkyl, phenyl, 5-6 membered heteroaryl, and 4-7 membered heterocycloalkyl, each of which is optionally substituted by 1 or 2 independently selected $R^{11}$ groups;

$R^{8a}$ is H or halo; and each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl) carbamyl.

In some embodiments:
the

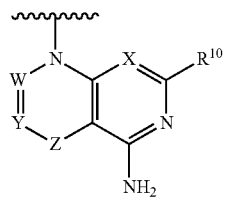

moiety is:

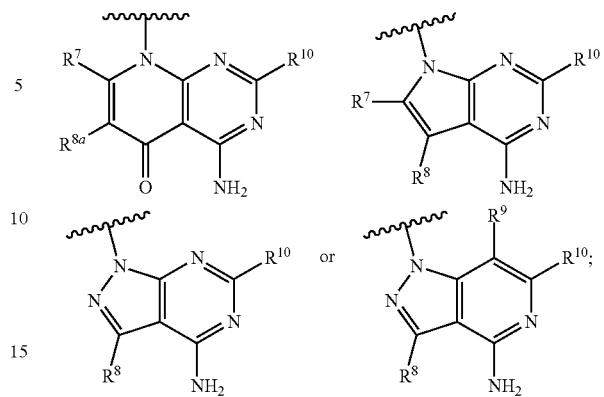

$R^1$ is methyl;

$R^2$ is $C_{1-6}$ alkyl, $C_{1-3}$ alkoxy, or phenyl; wherein said phenyl is optionally substituted by 1, 2, 3, or 4 substituents independently selected from halo;

$R^3$ is Cy or C(=O)NR$^c$R$^d$; wherein each R$^c$ and R$^d$ is independently selected from $C_{1-6}$alkyl;

Cy is selected from $C_{3-7}$ cycloalkyl, 4-7 membered heterocycloalkyl, phenyl, and 5-6 membered heteroaryl, each of which is optionally substituted with 1 or 2 $R^{3b}$ independently selected from Cy$^1$, —($C_{1-3}$ alkylene)-Cy$^1$, halo, CN, OH, $C_{1-6}$ alkyl, $C_{1-6}$ alkoxy, $C_{1-6}$ haloalkyl, C(=O)R$^{b1}$, C(=O)NR$^{c1}$R$^{d1}$, S(=O)R$^{b1}$, and S(=O)$_2$NR$^{c1}$R$^{d1}$; wherein said $C_{1-6}$ alkyl is optionally substituted with 1, 2, or 3 independently selected $R^{11}$ groups;

Cy$^1$ is $C_{3-6}$ cycloalkyl or 4-7 membered heterocycloalkyl;

each $R^{a1}$, $R^{b1}$, $R^{c1}$, and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups;

$R^4$ is halo, CN, or $C_{1-4}$ alkyl;

$R^5$ is halo or CN;

$R^6$, $R^7$, $R^9$, and $R^{10}$ are each H;

$R^8$ is H, halo, CN, $C_{1-6}$ alkyl, or Cy$^2$; wherein Cy$^2$ is selected from $C_{3-6}$ cycloalkyl, phenyl, 5-6 membered heteroaryl, and 4-7 membered heterocycloalkyl, each of which is optionally substituted by 1 $R^{11}$ group;

$R^{8a}$ is H or halo; and each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl) carbamyl.

In some embodiments:
the

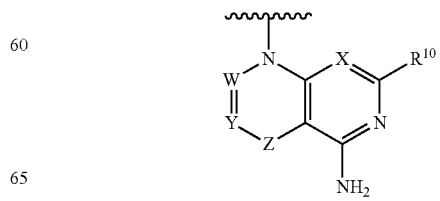

moiety is:

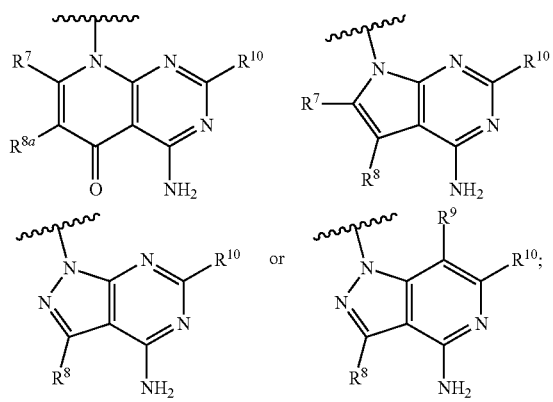

R$^1$ is methyl;
R$^2$ is C$_{1-3}$ alkoxy;
R$^3$ is Cy;
Cy is selected from C$_{3-7}$ cycloalkyl, 4-7 membered heterocycloalkyl, phenyl, and 5-6 membered heteroaryl, each of which is optionally substituted with 1, 2, 3, or 4 independently selected R$^{3b}$ groups;
R$^4$ is halo, CN, or C$_{1-4}$ alkyl;
R$^5$ is halo or CN;
R$^6$, R$^7$, R$^9$, and R$^{10}$ are each H;
R$^8$ is H, halo, CN, C$_{1-6}$ alkyl, or Cy$^2$; wherein Cy$^2$ is selected from C$_{3-6}$ cycloalkyl, phenyl, 5-6 membered heteroaryl, and 4-7 membered heterocycloalkyl, each of which is optionally substituted by 1 or 2 independently selected R$^{11}$ groups;
R$^{8a}$ is H or halo; and
each R$^{11}$ is independently OH, CN, halo, C$_{1-3}$ alkyl, C$_{1-3}$ haloalkyl, HO—C$_{1-3}$ alkyl, C$_{1-3}$ alkoxy-C$_{1-3}$ alkyl, C$_{1-3}$ alkoxy, C$_{1-3}$ haloalkoxy, amino, C$_{1-3}$ alkylamino, di(C$_{1-3}$ alkyl)amino, carbamyl, C$_{1-3}$ alkylcarbamyl, or di(C$_{1-3}$ alkyl) carbamyl.

In some embodiments:
the

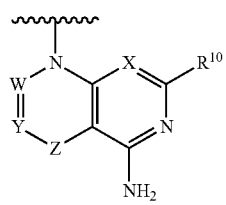

moiety is:

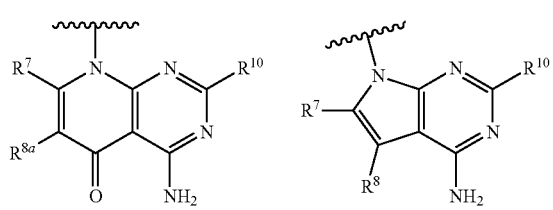

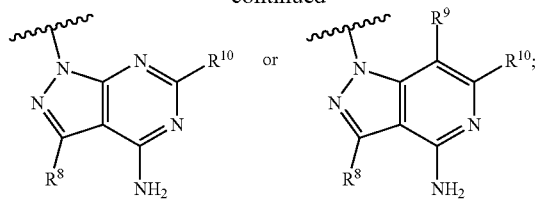

R$^1$ is methyl;
R$^2$ is phenyl; wherein said phenyl is optionally substituted by 1, 2, 3, or 4 substituents independently selected from halo;
R$^3$ is C(=O)NR$^c$R$^d$; wherein each R$^c$ and R$^d$ is independently selected from C$_{1-6}$alkyl; Cy is selected from C$_{3-7}$ cycloalkyl, 4-7 membered heterocycloalkyl, phenyl, and 5-6 membered heteroaryl, each of which is optionally substituted with 1, 2, 3, or 4 independently selected R$^{3b}$ groups;
R$^4$ is halo, CN, or C$_{1-4}$ alkyl;
R$^5$ is halo or CN;
R$^6$, R$^7$, R$^9$, and R$^{10}$ are each H;
R$^8$ is H, halo, CN, C$_{1-6}$ alkyl, or Cy$^2$; wherein Cy$^2$ is selected from C$_{3-6}$ cycloalkyl, phenyl, 5-6 membered heteroaryl, and 4-7 membered heterocycloalkyl, each of which is optionally substituted by 1 or 2 independently selected R$^{11}$ groups;
R$^{8a}$ is H or halo; and
each R$^{11}$ is independently OH, CN, halo, C$_{1-3}$ alkyl, C$_{1-3}$ haloalkyl, HO—C$_{1-3}$ alkyl, C$_{1-3}$ alkoxy-C$_{1-3}$ alkyl, C$_{1-3}$ alkoxy, C$_{1-3}$ haloalkoxy, amino, C$_{1-3}$ alkylamino, di(C$_{1-3}$ alkyl)amino, carbamyl, C$_{1-3}$ alkylcarbamyl, or di(C$_{1-3}$ alkyl) carbamyl.

In some embodiments:
the

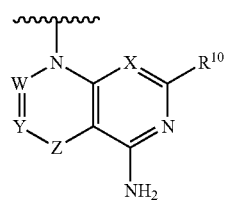

moiety is:

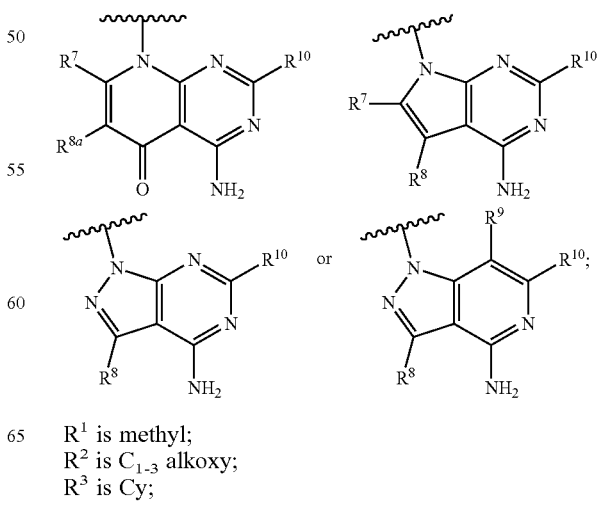

R$^1$ is methyl;
R$^2$ is C$_{1-3}$ alkoxy;
R$^3$ is Cy;

Cy is selected from $C_{3-7}$ cycloalkyl, 4-7 membered heterocycloalkyl, phenyl, and 5-6 membered heteroaryl, each of which is optionally substituted with 1 or 2 $R^{3b}$ independently selected from $Cy^1$, —($C_{1-3}$ alkylene)-$Cy^1$, halo, CN, OH, $C_{1-6}$ alkyl, $C_{1-6}$ alkoxy, $C_{1-6}$ haloalkyl, $C(=O)R^{b1}$, $C(=O)NR^{c1}R^{d1}$, $S(=O)R^{b1}$, and $S(=O)_2NR^{c1}R^{d1}$; wherein said $C_{1-6}$ alkyl is optionally substituted with 1, 2, or 3 independently selected $R^{11}$ groups;

$Cy^1$ is $C_{3-6}$ cycloalkyl or 4-7 membered heterocycloalkyl;

each $R^{a1}$, $R^{b1}$, $R^{c1}$, and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups;

$R^4$ is halo, CN, or $C_{1-4}$ alkyl;

$R^5$ is halo or CN;

$R^6$, $R^7$, $R^9$, and $R^{10}$ are each H;

$R^8$ is H, halo, CN, $C_{1-6}$ alkyl, or $Cy^2$; wherein $Cy^2$ is selected from $C_{3-6}$ cycloalkyl, phenyl, 5-6 membered heteroaryl, and 4-7 membered heterocycloalkyl, each of which is optionally substituted by 1 $R^{11}$ group;

$R^{8a}$ is H or halo; and each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl) carbamyl.

In some embodiments:
the

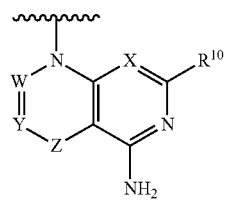

moiety is:

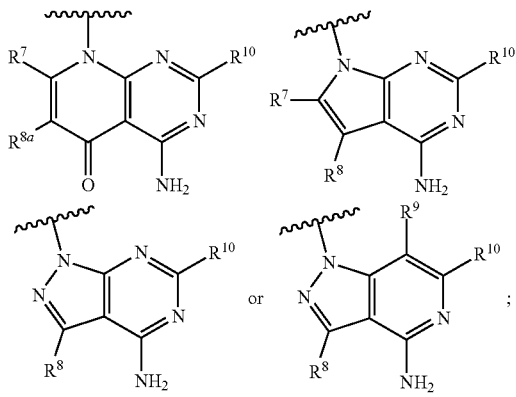

$R^1$ is methyl;

$R^2$ is phenyl; wherein said phenyl is optionally substituted by 1, 2, 3, or 4 substituents independently selected from halo;

$R^3$ is $C(=O)NR^cR^d$; wherein each $R^c$ and $R^d$ is independently selected from $C_{1-6}$alkyl; Cy is selected from $C_{3-7}$ cycloalkyl, 4-7 membered heterocycloalkyl, phenyl, and 5-6 membered heteroaryl, each of which is optionally substituted with 1 or 2 $R^{3b}$ independently selected from $Cy^1$, —($C_{1-3}$ alkylene)-$Cy^1$, halo, CN, OH, $C_{1-6}$ alkyl, $C_{1-6}$ alkoxy, $C_{1-6}$ haloalkyl, $C(=O)R^{b1}$, $C(=O)NR^{c1}R^{d1}$, $S(=O)R^{b1}$, and $S(=O)_2NR^{c1}R^{d1}$; wherein said $C_{1-6}$ alkyl is optionally substituted with 1, 2, or 3 independently selected $R^{11}$ groups;

$Cy^1$ is $C_{3-6}$ cycloalkyl or 4-7 membered heterocycloalkyl;

each $R^{a1}$, $R^{b1}$, $R^{c1}$, and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups;

$R^4$ is halo, CN, or $C_{1-4}$ alkyl;

$R^5$ is halo or CN;

$R^6$, $R^7$, $R^9$, and $R^{10}$ are each H;

$R^8$ is H, halo, CN, $C_{1-6}$ alkyl, or $Cy^2$; wherein $Cy^2$ is selected from $C_{3-6}$ cycloalkyl, phenyl, 5-6 membered heteroaryl, and 4-7 membered heterocycloalkyl, each of which is optionally substituted by 1 $R^{11}$ group;

$R^{8a}$ is H or halo; and each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl) carbamyl.

In some embodiments, the compound is a compound of Formula II:

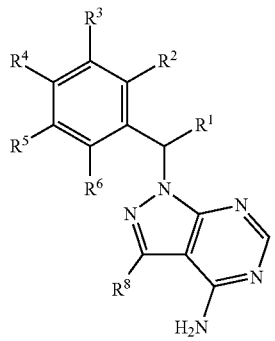

or a pharmaceutically acceptable salt thereof.

In some embodiments, the compound is a compound of Formula III:

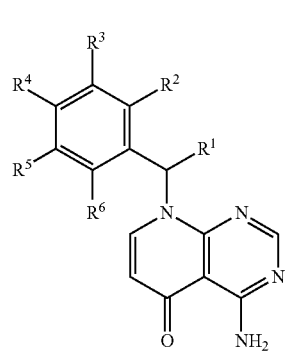

or a pharmaceutically acceptable salt thereof.

In some embodiments, the compound is a compound of Formula IV:

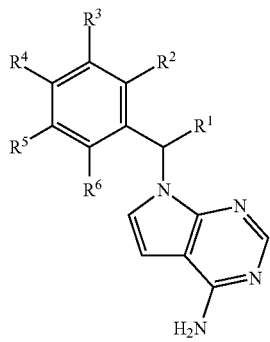

or a pharmaceutically acceptable salt thereof.

In some embodiments, the compound is a compound of Formula V:

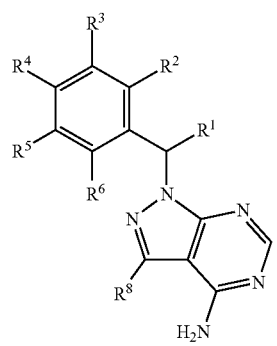

or a pharmaceutically acceptable salt thereof.

In some embodiments, the compound is a compound of Formula VIa:

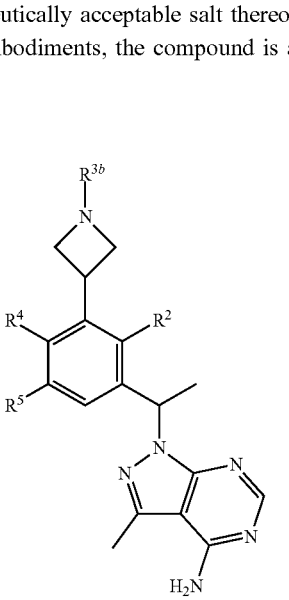

or a pharmaceutically acceptable salt thereof.

In some embodiments, the compound is a compound of Formula VIb:

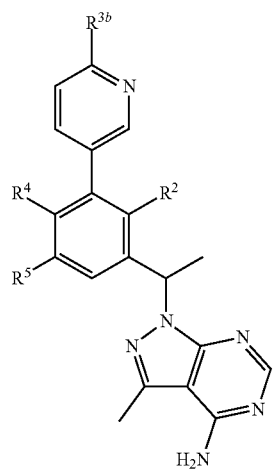

or a pharmaceutically acceptable salt thereof.

In some embodiments, the compound is a compound of Formula VIa:

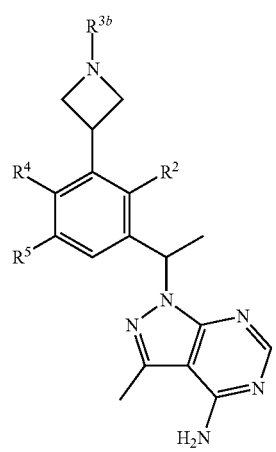

or a pharmaceutically acceptable salt thereof; wherein:
$R^2$ is methoxy or ethoxy;
$R^{3b}$ is $C_{1-6}$ alkyl, optionally substituted by 1 or 2 groups independently selected from F, OH, and $C_{1-3}$ alkoxy groups;
$R^4$ is F, CN, methyl or ethyl; and
$R^5$ is F, Cl, methyl or ethyl.

In some embodiments, the compound is a compound of Formula VIb:

VIb

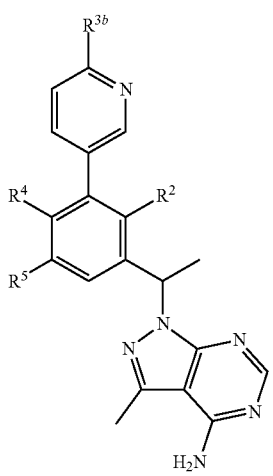

or a pharmaceutically acceptable salt thereof; wherein:
$R^2$ is methoxy or ethoxy;
$R^{3b}$ is C(=O)NR$^{c1}$R$^{d1}$;
$R^4$ is F, CN, methyl or ethyl; and
$R^5$ is F, Cl, methyl or ethyl.

In some embodiments, the compound is a compound of Formula IIa:

IIa

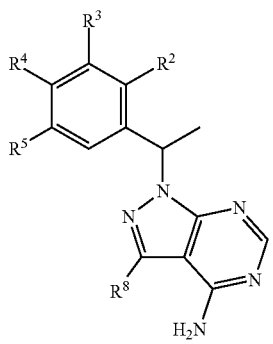

or a pharmaceutically acceptable salt thereof; wherein:
$R^2$ is $C_{1-6}$ alkyl, $C_{1-3}$ alkoxy, or phenyl; wherein said phenyl is optionally substituted by 1, 2, 3, or 4 substituents independently selected from halo;
$R^3$ is Cy or C(=O)NR$^c$R$^d$; wherein each R$^c$ and R$^d$ is independently selected from $C_{1-6}$ alkyl; Cy is selected from $C_{3-7}$ cycloalkyl, 4-7 membered heterocycloalkyl, phenyl, and 5-6 membered heteroaryl, each of which is optionally substituted with 1 or 2 R$^{3b}$ independently selected from Cy$^1$, —($C_{1-3}$ alkylene)-Cy$^1$, halo, CN, OH, $C_{1-6}$ alkyl, $C_{1-6}$ alkoxy, $C_{1-6}$ haloalkyl, C(=O)R$^{b1}$, C(=O)NR$^{c1}$R$^{d1}$, S(=O)R$^{b1}$, and S(=O)$_2$NR$^{c1}$R$^{d1}$; wherein said $C_{1-6}$ alkyl is optionally substituted with 1, 2, or 3 independently selected R$^{11}$ groups;
Cy$^1$ is $C_{3-6}$ cycloalkyl or 4-7 membered heterocycloalkyl;
each R$^{a1}$, R$^{b1}$, R$^{c1}$, and R$^{d1}$ is independently selected from H, $C_{1-6}$ alkyl, and $C_{1-6}$ haloalkyl; wherein said $C_{1-6}$ alkyl is optionally substituted with 1, 2, or 3 independently selected R$^{11}$ groups;
$R^4$ is halo, CN, or $C_{1-4}$ alkyl;
$R^5$ is halo or CN;
$R^8$ is H, halo, CN, $C_{1-6}$ alkyl, or Cy$^2$; wherein Cy$^2$ is selected from $C_{3-6}$ cycloalkyl, phenyl, 5-6 membered heteroaryl, and 4-7 membered heterocycloalkyl, each of which is optionally substituted by 1 R$^{11}$ group; and each R$^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl) carbamyl.

In some embodiments, the compound is a compound of IIIa:

IIIa

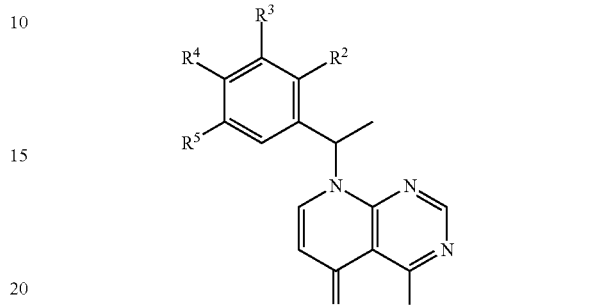

or a pharmaceutically acceptable salt thereof; wherein:
$R^2$ is $C_{1-6}$ alkyl, $C_{1-3}$ alkoxy, or phenyl; wherein said phenyl is optionally substituted by 1, 2, 3, or 4 substituents independently selected from halo;
$R^3$ is Cy or C(=O)NR$^c$R$^d$; wherein each R$^c$ and R$^d$ is independently selected from $C_{1-6}$ alkyl;
Cy is selected from $C_{3-7}$ cycloalkyl, 4-7 membered heterocycloalkyl, phenyl, and 5-6 membered heteroaryl, each of which is optionally substituted with 1 or 2 R$^{3b}$ independently selected from Cy$^1$, —($C_{1-3}$ alkylene)-Cy$^1$, halo, CN, OH, $C_{1-6}$ alkyl, $C_{1-6}$ alkoxy, $C_{1-6}$ haloalkyl, C(=O)R$^{b1}$, C(=O)NR$^{c1}$R$^{d1}$, S(=O)R$^{b1}$, and S(=O)$_2$NR$^{c1}$R$^{d1}$;
wherein said $C_{1-6}$ alkyl is optionally substituted with 1, 2, or 3 independently selected R$^{11}$ groups;
Cy$^1$ is $C_{3-6}$ cycloalkyl or 4-7 membered heterocycloalkyl;
each R$^{a1}$, R$^{b1}$, R$^{c1}$, and R$^{d1}$ is independently selected from H, $C_{1-6}$ alkyl, and $C_{1-6}$ haloalkyl; wherein said $C_{1-6}$ alkyl is optionally substituted with 1, 2, or 3 independently selected R$^{11}$ groups;
$R^4$ is halo, CN, or $C_{1-4}$ alkyl;
$R^5$ is halo or CN; and
each R$^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl) carbamyl.

In some embodiments, the compound is a compound of Formula IVa:

IVa

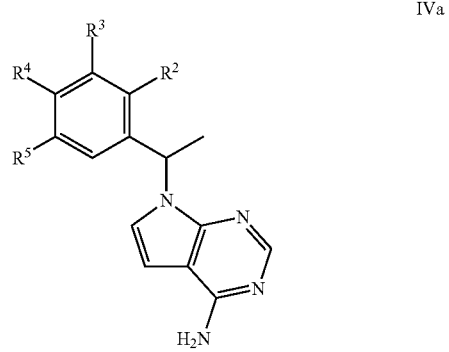

or a pharmaceutically acceptable salt thereof; wherein:

$R^2$ is $C_{1-6}$ alkyl, $C_{1-3}$ alkoxy, or phenyl; wherein said phenyl is optionally substituted by 1, 2, 3, or 4 substituents independently selected from halo;

$R^3$ is Cy or $C(=O)NR^cR^d$; wherein each $R^c$ and $R^d$ is independently selected from $C_{1-6}$alkyl; Cy is selected from $C_{3-7}$ cycloalkyl, 4-7 membered heterocycloalkyl, phenyl, and 5-6 membered heteroaryl, each of which is optionally substituted with 1 or 2 $R^{3b}$ independently selected from $Cy^1$, —$(C_{1-3}$ alkylene)-$Cy^1$, halo, CN, OH, $C_{1-6}$ alkyl, $C_{1-6}$ alkoxy, $C_{1-6}$ haloalkyl, $C(=O)R^{b1}$, $C(=O)NR^{c1}R^{d1}$, $S(=O)R^{b1}$, and $S(=O)_2NR^{c1}R^{d1}$; wherein said $C_{1-6}$ alkyl is optionally substituted with 1, 2, or 3 independently selected $R^{11}$ groups;

$Cy^1$ is $C_{3-6}$ cycloalkyl or 4-7 membered heterocycloalkyl;

each $R^{a1}$, $R^{b1}$, $R^{c1}$, and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups;

$R^4$ is halo, CN, or $C_{1-4}$ alkyl;

$R^5$ is halo or CN; and each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl)carbamyl.

In some embodiments, the compound is a compound of Formula Va:

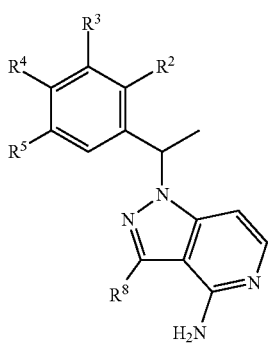

Va or a pharmaceutically acceptable salt thereof; wherein:

$R^2$ is $C_{1-6}$ alkyl, $C_{1-3}$ alkoxy, or phenyl; wherein said phenyl is optionally substituted by 1, 2, 3, or 4 substituents independently selected from halo;

$R^3$ is Cy or $C(=O)NR^cR^d$; wherein each $R^c$ and $R^d$ is independently selected from $C_{1-6}$alkyl;

Cy is selected from $C_{3-7}$ cycloalkyl, 4-7 membered heterocycloalkyl, phenyl, and 5-6 membered heteroaryl, each of which is optionally substituted with 1 or 2 $R^{3b}$ independently selected from $Cy^1$, —$(C_{1-3}$ alkylene)-$Cy^1$, halo, CN, OH, $C_{1-6}$ alkyl, $C_{1-6}$ alkoxy, $C_{1-6}$ haloalkyl, $C(=O)R^{b1}$, $C(=O)NR^{c1}R^{d1}$, $S(=O)R^{b1}$, and $S(=O)_2NR^{c1}R^{d1}$; wherein said $C_{1-6}$ alkyl is optionally substituted with 1, 2, or 3 independently selected $R^{11}$ groups;

$Cy^1$ is $C_{3-6}$ cycloalkyl or 4-7 membered heterocycloalkyl;

each $R^{a1}$, $R^{b1}$, $R^{c1}$, and $R^{d1}$ is independently selected from H, $C_{1-6}$ alkyl, and $C_{1-6}$ haloalkyl; wherein said $C_{1-6}$ alkyl is optionally substituted with 1, 2, or 3 independently selected $R^{11}$ groups;

$R^4$ is halo, CN, or $C_{1-4}$ alkyl;

$R^5$ is halo or CN;

$R^8$ is H, halo, CN, $C_{1-6}$ alkyl, or $Cy^2$; wherein $Cy^2$ is selected from $C_{3-6}$ cycloalkyl, phenyl, 5-6 membered heteroaryl, and 4-7 membered heterocycloalkyl, each of which is optionally substituted by 1 $R^{11}$ group; and each $R^{11}$ is independently OH, CN, halo, $C_{1-3}$ alkyl, $C_{1-3}$ haloalkyl, HO—$C_{1-3}$ alkyl, $C_{1-3}$ alkoxy-$C_{1-3}$ alkyl, $C_{1-3}$ alkoxy, $C_{1-3}$ haloalkoxy, amino, $C_{1-3}$ alkylamino, di($C_{1-3}$ alkyl)amino, carbamyl, $C_{1-3}$ alkylcarbamyl, or di($C_{1-3}$ alkyl)carbamyl.

In the embodiments above for Formula IIa, IIIa, Iva or Va, $R^2$ is $C_{1-3}$ alkoxy; and $R^3$ is Cy.

In the embodiments above for Formula IIa, IIIa, Iva or Va, $R^2$ is phenyl; wherein said phenyl is optionally substituted by 1, 2, 3, or 4 substituents independently selected from halo; and $R^3$ is $C(=O)NR^cR^d$; wherein each $R^c$ and $R^d$ is independently selected from $C_{1-6}$alkyl.

In any of the aforementioned embodiments, $R^2$ or $R^3$ comprises at least one cyclic moiety.

In some embodiments, the compound is selected from:

1-{1-[5-Chloro-3-(1-isopropylazetidin-3-yl)-2-methoxy-4-methylphenyl]ethyl}-3-methyl-1H-pyrazolo[3,4-d]pyrimidin-4-amine;

1-{1-[3-(1-Acetylazetidin-3-yl)-5-chloro-2-methoxy-4-methylphenyl]ethyl}-3-methyl-1H-pyrazolo[3,4-d]pyrimidin-4-amine;

1-{1-[5-Chloro-2-methoxy-4-methyl-3-(1-propionylazetidin-3-yl)phenyl]ethyl}-3-methyl-1H-pyrazolo[3,4-d]pyrimidin-4-amine;

1-(1-{5-Chloro-3-[1-(cyclopropylmethyl)azetidin-3-yl]-2-methoxy-4-methylphenyl}ethyl)-3-methyl-1H-pyrazolo[3,4-d]pyrimidin-4-amine;

1-{1-[5-chloro-2-methoxy-4-methyl-3-(1-methylazetidin-3-yl)phenyl]ethyl}-3-methyl-1H-pyrazolo[3,4-d]pyrimidin-4-amine;

1-{1-[5-Chloro-3-(1-ethylazetidin-3-yl)-2-methoxy-4-methylphenyl]ethyl}-3-methyl-1H-pyrazolo[3,4-d]pyrimidin-4-amine;

1-{1-[5-Chloro-3-(1-isobutylazetidin-3-yl)-2-methoxy-4-methylphenyl]ethyl}-3-methyl-1H-pyrazolo[3,4-d]pyrimidin-4-amine;

1-{1-[3-(1-sec-butylazetidin-3-yl)-5-chloro-2-methoxy-4-methylphenyl]ethyl}-3-methyl-1H-pyrazolo[3,4-d]pyrimidin-4-amine;

1-(1-{5-Chloro-2-methoxy-3-[1-(2-methoxyethyl)azetidin-3-yl]-4-methylphenyl}ethyl)-3-methyl-1H-pyrazolo[3,4-d]pyrimidin-4-amine;

3-{3-[1-(4-Amino-3-methyl-1H-pyrazolo[3,4-d]pyrimidin-1-yl)ethyl]-5-chloro-2-methoxy-6-methylphenyl}-N-methylazetidine-1-carboxamide;

5-{3-[1-(4-Amino-3-methyl-1H-pyrazolo[3,4-d]pyrimidin-1-yl)ethyl]-5-chloro-2-methoxy-6-methylphenyl}-N,N-dimethylpyridine-2-carboxamide;

5-{3-[1-(4-Amino-7H-pyrrolo[2,3-d]pyrimidin-7-yl)ethyl]-5-chloro-2-methoxy-6-methylphenyl}-N,N-dimethylpyridine-2-carboxamide;

1-{1-[5-Chloro-4-fluoro-3-(1-isopropylazetidin-3-yl)-2-methoxyphenyl]ethyl}-3-methyl-1H-pyrazolo[3,4-d]pyrimidin-4-amine;

5-{3-[1-(4-Amino-3-methyl-1H-pyrazolo[3,4-d]pyrimidin-1-yl)ethyl]-5-chloro-2-ethoxy-6-methylphenyl}-N,N-dimethylpyridine-2-carboxamide;

5-{3-[1-(4-Amino-3-iodo-1H-pyrazolo[3,4-d]pyrimidin-1-yl)ethyl]-5-chloro-2-ethoxy-6-methylphenyl}-N,N-dimethylpyridine-2-carboxamide;

4-{3-[1-(4-Amino-3-methyl-1H-pyrazolo[3,4-d]pyrimidin-1-yl)ethyl]-5-chloro-2-methoxy-6-methylphenyl}-N,N-dimethylpyridine-2-carboxamide;

4-(3-(1-(4-amino-3-methyl-1H-pyrazolo[3,4-d]pyrimidin-1-yl)ethyl)-5-chloro-2-methoxy-6-methylphenyl)-N-methylpicolinamide;

4-{3-[1-(4-Amino-3-methyl-1H-pyrazolo[3,4-d]pyrimidin-1-yl)ethyl]-5-chloro-2-methoxy-6-methylphenyl}-N-(2-hydroxyethyl)pyridine-2-carboxamide;

4-{3-[1-(4-amino-3-methyl-1H-pyrazolo[3,4-d]pyrimidin-1-yl)ethyl]-5-chloro-2-methoxy-6-methylphenyl}-N-(2-hydroxyethyl)-N-methylpyridine-2-carboxamide;

2-(4-(3-(1-(4-Amino-3-methyl-1H-pyrazolo[3,4-d]pyrimidin-1-yl)ethyl)-5-chloro-2-methoxy-6-methylphenyl)-1H-pyrazol-1-yl) ethanol;

3'-[1-(4-Amino-3-methyl-1H-pyrazolo[3,4-d]pyrimidin-1-yl)ethyl]-5'-chloro-3-fluoro-2'-methoxy-N,N,6'-trimethylbiphenyl-4-carboxamide;

3'-[1-(4-Amino-3-methyl-1H-pyrazolo[3,4-d]pyrimidin-1-yl)ethyl]-5'-chloro-3-fluoro-2'-methoxy-N,6'-dimethylbiphenyl-4-carboxamide;

5-(3-(1-(4-amino-3-methyl-1H-pyrazolo[3,4-d]pyrimidin-1-yl)ethyl)-5-chloro-2-methoxy-6-methylphenyl)-N-(2-hydroxyethyl)picolinamide;

4-{3-[1-(4-Amino-3-methyl-1H-pyrazolo[3,4-d]pyrimidin-1-yl)ethyl]-5-chloro-2-methoxy-6-methylphenyl}-N-(2-hydroxyethyl)-N-methylpyridine-2-carboxamide;

5-{3-[1-(4-Amino-5-oxopyrido[2,3-d]pyrimidin-8(5H)-yl)ethyl]-5-chloro-2-methoxy-6-methylphenyl}-N,N-dimethylpyridine-2-carboxamide;

4-Amino-8-(1-{5-chloro-2-methoxy-4-methyl-3-[5-(methylsulfonyl)pyridin-3-yl]phenyl}ethyl)pyrido[2,3-d]pyrimidin-5(8H)-one;

5-{3-[1-(4-Amino-5-oxopyrido[2,3-d]pyrimidin-8(5H)-yl)ethyl]-5-chloro-2-methoxy-6-methylphenyl}nicotinonitrile;

4-Amino-8-[1-(5-chloro-2-methoxy-4-methyl-3-pyridin-3-ylphenyl)ethyl]pyrido[2,3-d]pyrimidin-5(8H)-one;

4-Amino-8-[1-(5-chloro-2-methoxy-4-methyl-3-pyrimidin-5-ylphenyl)ethyl]pyrido[2,3-d]pyrimidin-5(8H)-one;

3'-[1-(4-Amino-5-oxopyrido[2,3-d]pyrimidin-8(5H)-yl)ethyl]-5'-chloro-2'-methoxy-N,N,6'-trimethylbiphenyl-3-carboxamide;

4-Amino-8-{1-[5-chloro-3-(5-fluoropyridin-3-yl)-2-methoxy-4-methylphenyl]ethyl}pyrido[2,3-d]pyrimidin-5(8H)-one;

3'-[1-(4-Amino-5-oxopyrido[2,3-d]pyrimidin-8(5H)-yl)ethyl]-5'-chloro-2'-methoxy-N,N,6'-trimethylbiphenyl-3-sulfonamide;

5-{3-[1-(4-Amino-5-oxopyrido[2,3-d]pyrimidin-8(5H)-yl)ethyl]-5-chloro-2-methoxy-6-methylphenyl}-N-methylpyridine-2-carboxamide;

4-Amino-8-{1-[5-chloro-3-(1-isopropylazetidin-3-yl)-2-methoxy-4-methylphenyl]ethyl}pyrido[2,3-d]pyrimidin-5(8H)-one;

4-Amino-8-{1-[5-chloro-2-ethoxy-3-(1-isopropylazetidin-3-yl)-4-methylphenyl]ethyl}pyrido[2,3-d]pyrimidin-5(8H)-one;

5-{3-[1-(4-Amino-5-oxopyrido[2,3-d]pyrimidin-8(5H)-yl)ethyl]-5-chloro-2-ethoxy-6-methylphenyl}-N,N-dimethylpyridine-2-carboxamide;

6-[1-(4-amino-3-methyl-1H-pyrazolo[3,4-d]pyrimidin-1-yl)ethyl]-4-chloro-N-ethyl-3',5'-difluoro-3-methylbiphenyl-2-carboxamide;

4-{3-[1-(4-amino-1H-pyrazolo[3,4-d]pyrimidin-1-yl)ethyl]-5-chloro-2-methoxy-6-methylphenyl}-N,N-dimethylpyridine-2-carboxamide;

4-{3-[1-(4-amino-1H-pyrazolo[3,4-d]pyrimidin-1-yl)ethyl]-5-chloro-2-methoxy-6-methylphenyl}-N-(2-hydroxyethyl)pyridine-2-carboxamide;

4-{3-[1-(4-amino-3-methyl-1H-pyrazolo[3,4-d]pyrimidin-1-yl)ethyl]-5-cyano-2-methoxy-6-methylphenyl)-N-(2-hydroxyethyl)-N-methylpyridine-2-carboxamide;

5-{3-[1-(4-Amino-3-methyl-1H-pyrazolo[4,3-c]pyridin-1-yl)ethyl]-5-chloro-2-methoxy-6-methylphenyl}-N,N-dimethylpyridine-2-carboxamide;

5-{3-[1-(4-Amino-5-methyl-7H-pyrrolo[2,3-d]pyrimidin-7-yl)ethyl]-5-chloro-2-methoxy-6-methylphenyl}-N,N-dimethylpyridine-2-carboxamide;

4-[1-(4-amino-3-methyl-1H-pyrazolo[3,4-d]pyrimidin-1-yl)ethyl]-6-chloro-3-ethoxy-2-[5-(methylsulfonyl)pyridin-3-yl]benzonitrile;

5-(3-(1-(4-amino-3-methyl-1H-pyrazolo[3,4-d]pyrimidin-1-yl)ethyl)-5-chloro-6-cyano-2-ethoxyphenyl)-N,N-dimethylpicolinamide;

5-{3-[1-(4-amino-5-oxopyrido[2,3-d]pyrimidin-8 (5H)-yl)ethyl]-5-chloro-6-cyano-2-ethoxyphenyl}-N,N-dimethylpyridine-2-carboxamide;

4-(1-(4-amino-5-oxopyrido[2,3-d]pyrimidin-8 (5H)-yl)ethyl)-6-chloro-3-ethoxy-2-(5-(methylsulfonyl)pyridin-3-yl)benzonitrile;

5-(3-{1-[4-amino-3-(3-fluorophenyl)-1H-pyrazolo[3,4-d]pyrimidin-1-yl]ethyl}-5-chloro-2-ethoxy-6-methylphenyl)-N,N-dimethylpyridine-2-carboxamide;

5-(3-{1-[4-amino-3-(1H-pyrazol-4-yl)-1H-pyrazolo[3,4-d]pyrimidin-1-yl]ethyl}-5-chloro-2-ethoxy-6-methylphenyl)-N,N-dimethylpyridine-2-carboxamide;

5-(3-{1-[4-amino-3-(1-methyl-1H-pyrazol-4-yl)-1H-pyrazolo[3,4-d]pyrimidin-1-yl]ethyl}-5-chloro-2-ethoxy-6-methylphenyl)-N,N-dimethylpyridine-2-carboxamide;

5-(3-{1-[4-amino-3-(1-methyl-1H-pyrazol-3-yl)-1H-pyrazolo[3,4-d]pyrimidin-1-yl]ethyl}-5-chloro-2-ethoxy-6-methylphenyl)-N,N-dimethylpyridine-2-carboxamide;

5-(3-{1-[4-amino-3-(1H-pyrazol-3-yl)-1H-pyrazolo[3,4-d]pyrimidin-1-yl]ethyl}-5-chloro-2-ethoxy-6-methylphenyl)-N,N-dimethylpyridine-2-carboxamide;

5-[3-(1-{4-amino-3-[1-(2-hydroxyethyl)-1H-pyrazol-4-yl]-1H-pyrazolo[3,4-d]pyrimidin-1-yl}ethyl)-5-chloro-2-ethoxy-6-methylphenyl]-N,N-dimethylpyridine-2-carboxamide;

5-{3-[1-(4-amino-cyclopropyl-1H-pyrazolo[3,4-d]pyrimidin-1-yl)ethyl]-5-chloro-2-ethoxy-6-methylphenyl}-N,N-dimethylpyridine-2-carboxamide;

5-{3-[1-(4-amino-3-cyano-1H-pyrazolo[3,4-d]pyrimidin-1-yl)ethyl]-5-chloro-2-ethoxy-6-methylphenyl}-N,N-dimethylpyridine-2-carboxamide;

5-(3-{1-[4-amino-3-(4-fluorophenyl)-1H-pyrazolo[3,4-d]pyrimidin-1-yl]ethyl}-5-chloro-2-ethoxy-6-methylphenyl)-N,N-dimethylpyridine-2-carboxamide;

5-{4-amino-1-[1-(5-chloro-3-{6-[(dimethylamino)carbonyl]pyridin-3-yl}-2-ethoxy-4-methylphenyl)ethyl]-1H-pyrazolo[3,4-d]pyrimidin-3-yl}-N,N-dimethylpyridine-2-carboxamide;

5-(3-{1-[4-amino-3-(5-cyanopyridin-3-yl)-1H-pyrazolo[3,4-d]pyrimidin-1-yl]ethyl}-5-chloro-2-ethoxy-6-methylphenyl)-N,N-dimethylpyridine-2-carboxamide;

5-(3-{1-[4-amino-3-(2-aminopyrimidin-5-yl)-1H-pyrazolo[3,4-d]pyrimidin-1-yl]ethyl}-5-chloro-2-ethoxy-6-methylphenyl)-N,N-dimethylpyridine-2-carboxamide;

5-{3-[1-(4-amino-3-{6-[(methylamino)carbonyl]pyridin-3-yl}-1H-pyrazolo[3,4-d]pyrimidin-1-yl)ethyl]-5-chloro-2-ethoxy-6-methylphenyl}-N,N-dimethylpyridine-2-carboxamide;

5-{3-[1-(4-amino-3-pyridin-4-yl-1H-pyrazolo[3,4-d]pyrimidin-1-yl)ethyl]-5-chloro-2-ethoxy-6-methylphenyl}-N,N-dimethylpyridine-2-carboxamide;

5-{3-[1-(4-amino-3-pyridin-3-yl-1H-pyrazolo[3,4-d]pyrimidin-1-yl)ethyl]-5-chloro-2-ethoxy-6-methylphenyl}-N,N-dimethylpyridine-2-carboxamide;

5-{3-[1-(4-amino-3-{5-[(dimethylamino)carbonyl]pyridin-3-yl}-1H-pyrazolo[3,4-d]pyrimidin-1-yl)ethyl]-5-chloro-2-ethoxy-6-methylphenyl}-N,N-dimethylpyridine-2-carboxamide;

1-{1-[5-chloro-2-methoxy-4-methyl-3-(1-oxetan-3-yl)azetidin-3-yl)phenyl]ethyl}-3-methyl-1H-pyrazolo[3,4-d]pyrimidin-4-amine;

1-(1-{5-chloro-2-methoxy-4-methyl-3-[1-(tetrahydro-2H-pyran-4-yl)azetidin-3-yl]phenyl}ethyl)-3-methyl-1H-pyrazolo[3,4-d]pyrimidin-4-amine;

5-{3-[1-(4-amino-3-methyl-1H-pyrazolo[3,4-d]pyrimidin-1-yl)ethyl]-5-chloro-2-methoxy-6-methylphenyl}-N,N-dimethylnicotinamide; and 5-{3-[1-(4-amino-3-methyl-1H-pyrazolo[3,4-d]pyrimidin-1-yl)ethyl]-5-chloro-2-methoxy-6-methylphenyl}-N,N-dimethylpyridine-2-carboxamide;

or a pharmaceutically acceptable salt of any of the aforementioned.

In some embodiments, the compound is selected from:

4-(1-(4-amino-3-methyl-1H-pyrazolo[3,4-d]pyrimidin-1-yl)ethyl)-6-chloro-2-(1-(2-hydroxypropyl)azetidin-3-yl)-3-methoxybenzonitrile;

4-((S)-1-(4-amino-3-methyl-1H-pyrazolo[3,4-d]pyrimidin-1-yl)ethyl)-6-chloro-2-(1-((S)-2-hydroxypropyl)azetidin-3-yl)-3-methoxybenzonitrile;

4-((R)-1-(4-amino-3-methyl-1H-pyrazolo[3,4-d]pyrimidin-1-yl)ethyl)-6-chloro-2-(1-((S)-2-hydroxypropyl)azetidin-3-yl)-3-methoxybenzonitrile;

4-((S)-1-(4-amino-3-methyl-1H-pyrazolo[3,4-d]pyrimidin-1-yl)ethyl)-6-chloro-2-(1-((R)-2-hydroxypropyl)azetidin-3-yl)-3-methoxybenzonitrile;

4-((R)-1-(4-amino-3-methyl-1H-pyrazolo[3,4-d]pyrimidin-1-yl)ethyl)-6-chloro-2-(1-((R)-2-hydroxypropyl)azetidin-3-yl)-3-methoxybenzonitrile;

4-(1-(4-amino-3-methyl-1H-pyrazolo[3,4-d]pyrimidin-1-yl)ethyl)-6-chloro-2-(1-(2-hydroxyethyl)azetidin-3-yl)-3-methoxybenzonitrile;

(S)-4-(1-(4-amino-3-methyl-1H-pyrazolo[3,4-d]pyrimidin-1-yl)ethyl)-6-chloro-2-(1-(2-hydroxyethyl)azetidin-3-yl)-3-methoxybenzonitrile; and (R)-4-(1-(4-amino-3-methyl-1H-pyrazolo[3,4-d]pyrimidin-1-yl)ethyl)-6-chloro-2-(1-(2-hydroxyethyl)azetidin-3-yl)-3-methoxybenzonitrile;

or a pharmaceutically acceptable salt of any of the aforementioned.

In some embodiments, the starred carbon in Formula I:

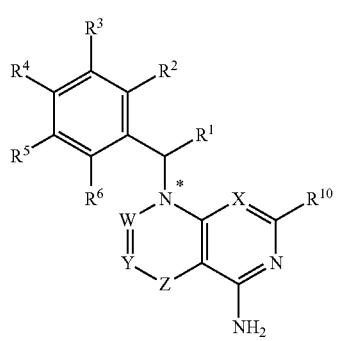

I is a chiral carbon and said compound or said salt is the (S)-enantiomer.

In some embodiments, the compound is a compound of Formula IIa:

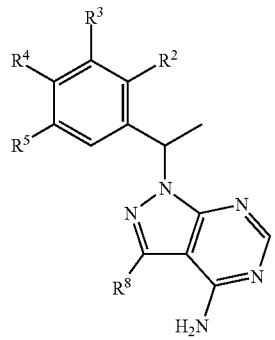

IIa or a pharmaceutically acceptable salt thereof, wherein:
$R^2$ is methoxy, ethoxy, —OCHF$_2$, methyl, —F, or —CHF$_2$;
$R^4$ is methyl, Cl, F, or CN; and
$R^5$ is methyl, Cl, F, or CN.

In some embodiments, the compound is a compound of Formula IIa:

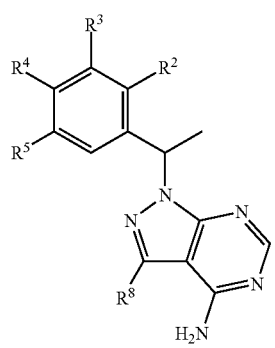

IIa or a pharmaceutically acceptable salt thereof, wherein:
$R^2$ is methoxy, ethoxy, —OCHF$_2$, methyl, —F, or —CHF$_2$;
$R^4$ is methyl, Cl, F, or CN;
$R^5$ is methyl, Cl, F, or CN; and
$R^8$ is H, halo, CN, methyl, or Cy$^2$; wherein said Cy$^2$ is selected from cyclopropyl, phenyl, a pyrazole ring, a pyridine ring, or a pyrimidine ring, each of which is optionally substituted by 1 $R^{11}$ selected from OH, CN, fluoro, methyl, 2-hydroxyethyl, dimethylcarbamyl, amino, methylcarbamyl, and dimethylcarbamyl.

In some embodiments, the compound is a compound of Formula IIb:

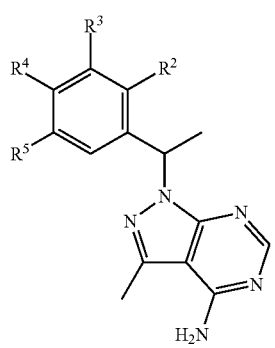

IIb or a pharmaceutically acceptable salt thereof, wherein:
R² is methoxy, ethoxy, —OCHF₂, methyl, —F, or —CHF₂;
R⁴ is methyl, Cl, F, or CN; and
R⁵ is methyl, Cl, F, or CN.

In some embodiments, the compound is a compound of Formula IIIa:

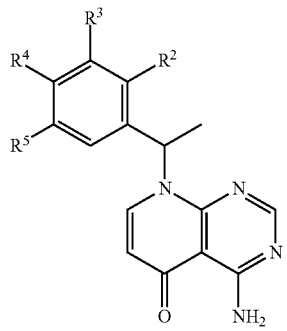

IIIa or a pharmaceutically acceptable salt thereof, wherein:
R² is methoxy, ethoxy, —OCHF₂, methyl, —F, or —CHF₂;
R⁴ is methyl, Cl, F, or CN; and
R⁵ is methyl, Cl, F, or CN.

In some embodiments, the compound is a compound of Formula IVa:

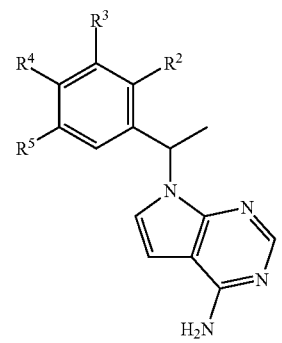

IVa or a pharmaceutically acceptable salt thereof, wherein:
R² is methoxy, ethoxy, —OCHF₂, methyl, —F, or —CHF₂;
R⁴ is methyl, Cl, F, or CN; and
R⁵ is methyl, Cl, F, or CN.

In some embodiments, the compound is a compound of Formula Va:

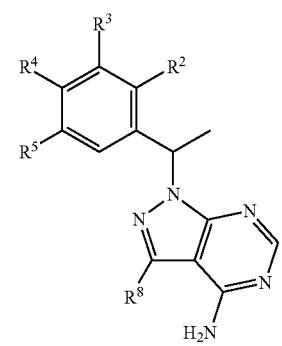

Va or a pharmaceutically acceptable salt thereof, wherein:
R² is methoxy, ethoxy, —OCHF₂, methyl, —F, or —CHF₂;

R⁴ is methyl, Cl, F, or CN; and
R⁵ is methyl, Cl, F, or CN.

In some embodiments, the compound is a compound of Formula VIII:

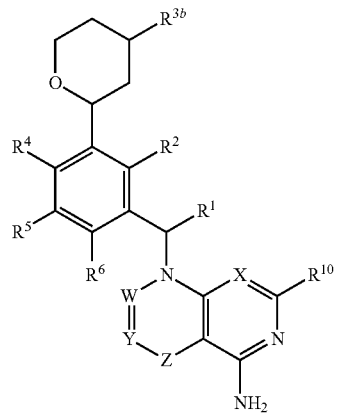

VIII or pharmaceutically acceptable salt thereof.

In some embodiments, the compound is a compound of Formula IX:

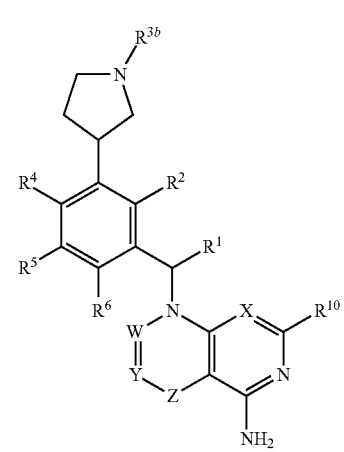

IX or pharmaceutically acceptable salt thereof.

It is further appreciated that certain features of the invention, which are, for clarity, described in the context of separate embodiments, can also be provided in combination in a single embodiment.

The present application further provides a compound of Formula VII:

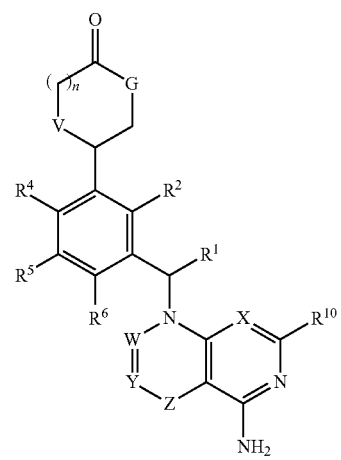

VII or a pharmaceutically acceptable salt thereof, wherein:
G is NH, n is 1, and V is O; or
G is NH, n is 0, and V is O or $CH_2$; or
G is O, n is 0 and V is NH;
X is $CR^9$ or N;
W is $CR^7$ or N;
Y is $CR^8$, $CR^{8a}$, or N;
Z is a bond or C(=O);
provided that —W=Y—Z— is —$CR^7$=$CR^8$—, —N=$CR^8$—, —$CR^7$=$CR^{8a}$—C(=O)—, —N=$CR^{8a}$—C(=O)—, or —$CR^7$=N—C(=O)—;
$R^1$ is $C_{1-3}$ alkyl;
$R^2$ is halo, $C_{1-6}$ alkyl, $C_{1-6}$ alkoxy, $C_{1-6}$ haloalkyl, $C_{1-6}$ haloalkoxy, phenyl, or 5-6 membered heteroaryl; wherein said phenyl and 5-6 membered heteroaryl are each optionally substituted by 1, 2, 3, or 4 substituents independently selected from halo, OH, CN, $C_{1-4}$ alkyl, $C_{1-4}$ alkoxy, and $C_{1-4}$ haloalkoxy;
$R^4$ is H, halo, OH, CN, $C_{1-4}$ alkyl, $C_{1-4}$ haloalkyl, $C_{1-4}$ alkoxy, or $C_{1-4}$ haloalkoxy;
$R^5$ is halo, OH, CN, $C_{1-4}$ alkyl, $C_{1-4}$ haloalkyl, $C_{1-4}$ alkoxy, $C_{1-4}$ haloalkoxy, or cyclopropyl;
$R^6$ is H, halo, OH, CN, $C_{1-4}$ alkyl, $C_{1-4}$ haloalkyl, $C_{1-4}$ alkoxy, or $C_{1-4}$ haloalkoxy;
$R^7$ is H or $C_{1-4}$ alkyl;
$R^8$ is H, halo, —OH, —CN, $C_{1-6}$ alkyl, $C_{2-6}$ alkenyl, $C_{2-6}$ alkynyl, $C_{1-6}$ haloalkyl, $Cy^2$, —($C_{1-3}$ alkylene)-$Cy^2$, $OR^{a2}$, $SR^{a2}$, C(=O)$R^{b2}$, C(=O)$NR^{c2}R^{d2}$, C(=O)$OR^{a2}$, OC(=O)$R^{b2}$, OC(=O)$NR^{c2}R^{d2}$, $NR^{c2}R^{d2}$, $NR^{c2}$C(=O)$R^{b2}$, $NR^{c2}$C(=O)$OR^{b2}$, $NR^{c2}$C(=O)$NR^{c2}R^{d2}$, C(=$NR^e$)$R^{b2}$, C(=$NR^e$)$NR^{c2}R^{d2}$, $NR^{c2}$C(=$NR^e$)$NR^{c2}R^{d2}$, $NR^{c2}$S(=O)$R^{b2}$, $NR^{c2}$S(=O)$_2NR^{c2}R^{d2}$, S(=O)$R^{b2}$, S(=O)$_2R^{b2}$, or S(=O)$_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;
$R^{8a}$ is H, halo, —CN, $C_{1-6}$ alkyl, $C_{2-6}$ alkenyl, $C_{2-6}$ alkynyl, $C_{1-6}$ haloalkyl, $Cy^2$, —($C_{1-3}$ alkylene)-$Cy^2$, C(=O)$R^{b2}$, C(=O)$NR^{c2}R^{d2}$, C(=O)$OR^{a2}$, $NR^{c2}R^{d2}$, $NR^{c2}$C(=O)$R^{b2}$, $NR^{c2}$C(=O)$OR^{b2}$, $NR^{c2}$C(=O)$NR^{c2}R^{d2}$, $NR^{c2}$S(=O)$R^{b2}$, $NR^{c2}$S(=O)$_2NR^{c2}R^{d2}$, S(=O)$R^{b2}$, S(=O)$_2R^{b2}$, or S(=O)$_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;
$R^9$ is H, halo, OH, CN, $C_{1-4}$ alkyl, $C_{1-4}$ haloalkyl, $C_{1-4}$ alkoxy, or $C_{1-4}$ haloalkoxy;
$R^{10}$ is H or $C_{1-4}$ alkyl;
each $R^e$ is independently selected from H, CN, OH, $C_{1-4}$ alkyl, and $C_{1-4}$ alkoxy;
each $Cy^2$ is independently selected from $C_{3-7}$ cycloalkyl, 4-7 membered heterocycloalkyl, phenyl, 5-6 membered heteroaryl, or 9-10-membered bicyclic heteroaryl, each of which is optionally substituted with 1, 2, 3, or 4 independently selected $R^{11}$ groups;
each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups;

or $R^{c2}$ and $R^{d2}$ together with the N atom to which they are attached form a 4-, 5-, 6-, or 7 membered heterocycloalkyl group, which is optionally substituted with —OH or $C_{1-3}$ alkyl; and
each $R^{11}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

In one embodiment, the compound of Formula VII is not the compounds of Examples 310-311 and 323-325. In another embodiment, the compound of Formula VII is selected from the compounds of Examples 310-311 and 323-325.

In some embodiments, $R^1$ is methyl.
In some embodiments, $R^2$ is $C_{1-3}$ alkoxy.
In some embodiments, $R^4$ is halo, CN, or $C_{1-4}$ alkyl.
In some embodiments, $R^4$ is methyl.
In some embodiments, $R^5$ is halo.
In some embodiments, $R^5$ is chloro or fluoro.
In some embodiments, $R^6$ is H.
In some embodiments, $R^8$ is $C_{1-6}$ alkyl.
In some embodiments, $R^8$ is methyl.
In some embodiments, $R^{10}$ is H.
In some embodiments, G is NH, n is 0 and V is O.
In some embodiments, G is NH, n is 0 and V is $CH_2$.
In some embodiments, G is NH, n is 1 and V is O.
In some embodiments, G is O, n is 0 and V is NH.
In some embodiments, the compound is a compound having Formula VIIa:

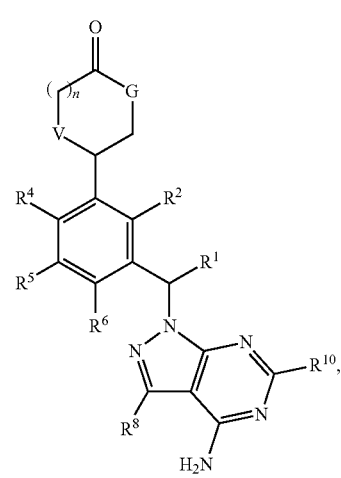

VIIa or a pharmaceutically acceptable salt thereof.
In some embodiments, the compound is a compound having Formula VIIb:

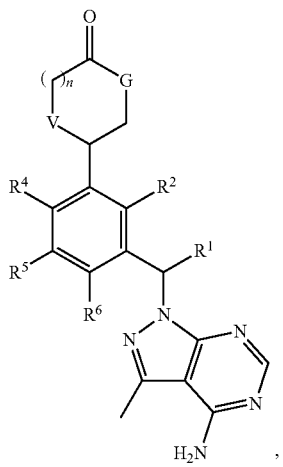

or a pharmaceutically acceptable salt thereof.

In some embodiments:
G is NH;
n is 0;
V is O;
$R^2$ is $C_{1-3}$ alkoxy;
$R^4$ is halo, CN, or $C_{1-4}$ alkyl;
$R^5$ is halo; and
$R^6$ is H.

In some embodiments:
G is NH;
n is 0;
V is $CH_2$;
$R^2$ is $C_{1-3}$ alkoxy;
$R^4$ is halo, CN, or $C_{1-4}$ alkyl;
$R^5$ is halo; and
$R^6$ is H.

In some embodiments:
G is NH;
n is 1;
V is O;
$R^2$ is $C_{1-3}$ alkoxy;
$R^4$ is halo, CN, or $C_{1-4}$ alkyl;
$R^5$ is halo; and
$R^6$ is H.

In some embodiments:
G is O;
n is 0;
V is NH;
$R^2$ is $C_{1-3}$ alkoxy;
$R^4$ is halo;
$R^5$ is halo; and
$R^6$ is H.

In some embodiments, the compound is selected from:
4-{3-[1-(4-amino-3-methyl-1H-pyrazolo[3,4-d]pyrimidin-1-yl)ethyl]-5-chloro-2-ethoxy-6-methylphenyl}pyrrolidin-2-one;
4-[1-(4-amino-3-methyl-1H-pyrazolo[3,4-d]pyrimidin-1-yl)ethyl]-6-chloro-3-ethoxy-2-(2-oxo-1,3-oxazolidin-5-yl)benzonitrile;
6-{3-[1-(4-Amino-3-methyl-1H-pyrazolo[3,4-d]pyrimidin-1-yl)ethyl]-5-chloro-2-methoxy-6-methylphenyl}morpholin-3-one;
5-{3-[1-(4-Amino-3-methyl-1H-pyrazolo[3,4-d]pyrimidin-1-yl)ethyl]-5-chloro-2-methoxy-6-methylphenyl}-1,3-oxazolidin-2-one;
4-{3-[1-(4-amino-3-methyl-1H-pyrazolo[3,4-d]pyrimidin-1-yl)ethyl]-5-chloro-2-ethoxy-6-fluorophenyl}pyrrolidin-2-one;
4-[1-(4-amino-3-methyl-1H-pyrazolo[3,4-d]pyrimidin-1-yl)ethyl]-6-chloro-3-ethoxy-2-(5-oxopyrrolidin-3-yl)benzonitrile;
4-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one; and
5-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one, or a pharmaceutically acceptable salt thereof of any of the aforementioned.

In some embodiments, the compound is selected from:
4-{3-[1-(4-amino-3-methyl-1H-pyrazolo[3,4-d]pyrimidin-1-yl)ethyl]-5-chloro-2-ethoxy-6-fluorophenyl}pyrrolidin-2-one;
(S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one; and
(R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one;

or a pharmaceutically acceptable salt thereof of any of the aforementioned.

In some embodiments, the starred carbon in Formula VII:

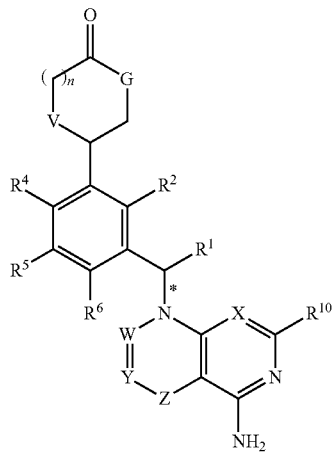

is a chiral carbon and said compound or salt is the (S)-enantiomer.

Conversely, various features of the invention which are, for brevity, described in the context of a single embodiment, can also be provided separately or in any suitable subcombination.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, "$C_{n-m}$ alkenyl" refers to an alkyl group having one or more double carbon-carbon bonds and having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl, and the like.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "alkylene", employed alone or in combination with other terms, refers to a divalent alkyl linking group. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), t-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula NH$_2$.

As used herein, the term "carbamyl" to a group of formula C(O)NH$_2$.

As used herein, the term "carbonyl", employed alone or in combination with other terms, refers to a —C(O)— group.

As used herein, the term "cyano-C$_{1-3}$ alkyl" refers to a group of formula —(C$_{1-3}$ alkylene)-CN.

As used herein, the term "HO—C$_{1-3}$ alkyl" refers to a group of formula —(C$_{1-3}$ alkylene)-OH.

As used herein, the term "C$_{1-3}$alkoxy-C$_{1-3}$ alkyl" refers to a group of formula —(C$_{1-3}$ alkylene)-O(C$_{1-3}$ alkyl).

As used herein, the term "carboxy" refers to a group of formula —C(O)OH.

As used herein, the term "di(C$_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di(C$_{n-m}$-alkyl)carbamyl" refers to a group of formula C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, the halo group is F or Cl.

As used herein, "C$_{n-m}$ haloalkoxy" refers to a group of formula O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "C$_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, or 7 ring-forming carbons (C$_{3-7}$). Ring-forming carbon atoms of a cycloalkyl group can be optionally substituted by oxo or sulfido. Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring.

A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

A "bicyclic C$_{9-10}$ heteroaryl" is bicyclic fused heteroaryl having 9 to 10 ring members.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen or sulfur and having one or more oxidized ring members.

At certain places, the definitions or embodiments refer to specific rings (e.g., an azetidine ring, a pyridine ring, etc.). Unless otherwise indicated, these rings can be attached any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

In some embodiments, the compound has the (R)-configuration. In some embodiments, the compound has the (S)-configuration.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium.

The term, "compound," as used herein is meant to include all stereoisomers, geometric iosomers, tautomers, and isotopes of the structures depicted. Compounds herein identified by name or structure as one particular tautomeric form are intended to include other tautomeric forms unless otherwise specified.

All compounds, and pharmaceutically acceptable salts thereof, can be found together with other substances such as water and solvents (e.g. hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, isopropanol, or butanol) or acetonitrile (ACN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3$^{rd}$ Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

For example, compounds of Formula I can be formed as shown in Scheme I. The compound (i) can be halogenated with N-chlorosuccinamide, N-bromosuccinamide or N-iodosuccinamide to give compound (ii) where $X^1$=Cl, Br, or I. The halo group of (ii) can be coupled to $R^3$-M, where M is a boronic acid, boronic ester or an appropriately substituted metal (e.g., $R^3$-M is $R^3$—B(OH)$_2$, $R^3$—Sn(Bu)$_4$, or Zn—$R^3$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of formula (iii). Alternatively, $R^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine)palladium(0) and a base (e.g., an alkoxide base)) to afford ketone (iii). Reduction of the ketone (iii) with a suitable reagent, such as sodium tetrahydroborate can furnish the alcohol (iv) which can be converted to a derivative bearing a leaving group (v), (e.g., Lg is chloride via reaction with cyanuric chloride or mesylate via reaction with methanesulfonic anhydride). Finally, compound (v) can be reacted with an appropriate heterocycle (vi) (e.g., 3-methyl-1H-pyrazolo[3,4-d]pyrimidin-4-amine or 4-aminopyrido[2,3-d]pyrimidin-5(8H)-one) under basic conditions (e.g., NaH or CsCO$_3$ or K$_2$CO$_3$) to give a compound of Formula I (vii).

Scheme I

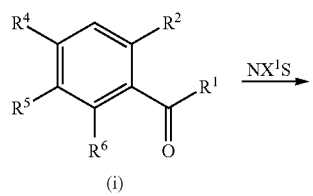

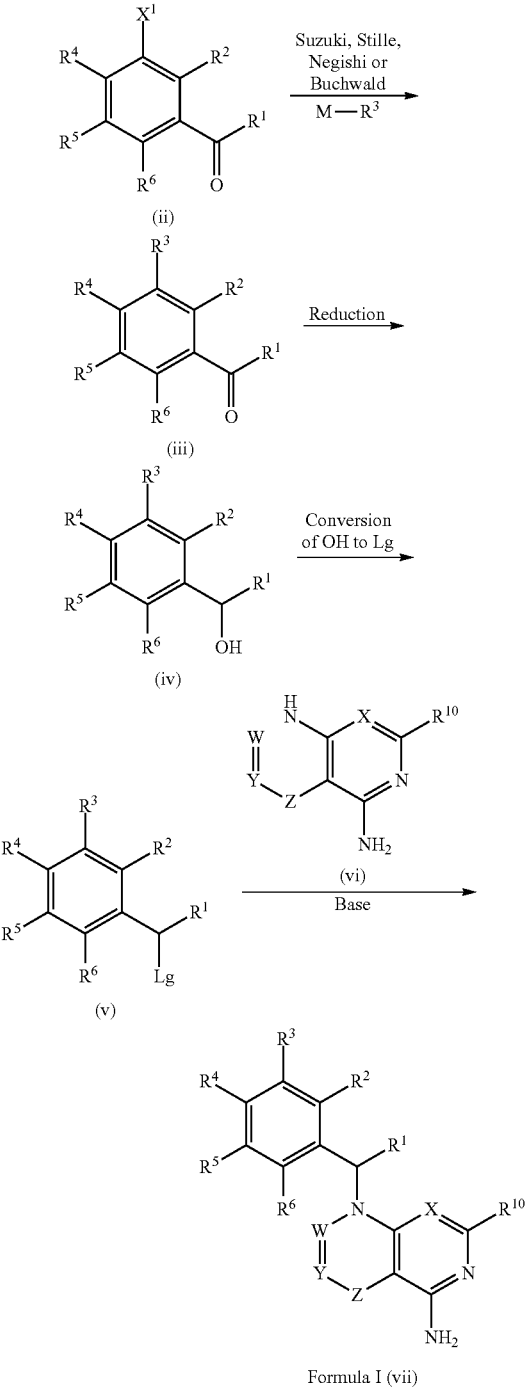

Alternatively, compounds of Formula I can also be formed as shown in Scheme II. The ketone compound (i) can be halogenated with N-chlorosuccinamide, N-bromosuccinamide or N-iodosuccinamide to give compound (ii) where $X^1$=Cl, Br, or I. Ketone (ii) can be reduced with a suitable reagent, such as sodium tetrahydroborate, to give an alcohol (iii) which can be converted to a derivative bearing a leaving group, (e.g., Lg is chloride via reaction with cyanuric chloride or mesylate via reaction with methanesulfonic anhydride) and then reacted with a heterocycle to give a heterocyclic derivative (iv). The enantiomers of compound (iv) can be separated by chiral chromatography to afford a single enantiomer of heterocyclic compound (v). Finally, the halo group of (v) can be coupled to $R^3$-M, where M is a boronic acid, boronic ester or an appropriately substituted metal (e.g., $R^3$-M is $R^3$—$B(OH)_2$, $R^3$—$Sn(Bu)_4$, or Zn—$R^3$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of Formula I (vi).

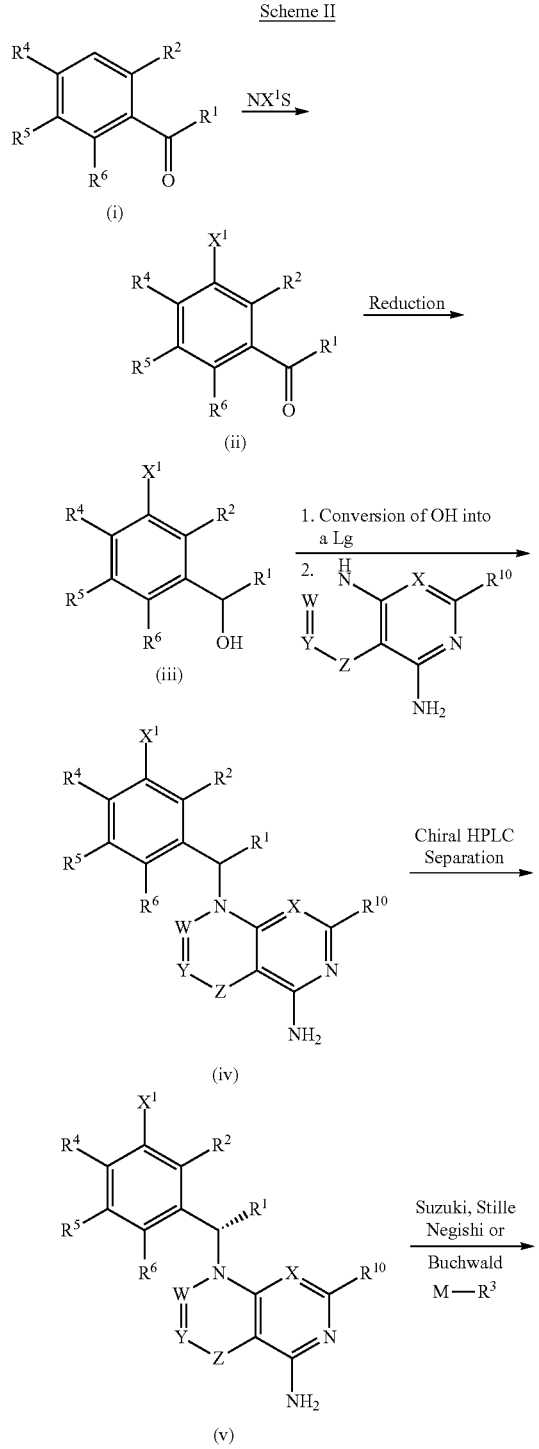

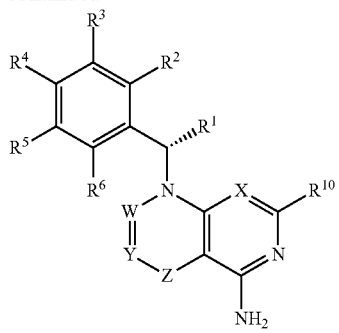

Formula I (vi)

Compounds of Formula I, wherein L is O, N, or S, can be formed as shown in Scheme III. The thiols, phenols or amines (i) can be alkylated using Mitsunobu conditions (e.g., R'OH, DEAD, $Ph_3P$) or standard alkylating conditions (R'-Lg, Lg=leaving group) to afford thioether, ether, or alkylamine derivatives (ii), respectively. The halo group of (ii) can be coupled to $R^3$-M, where M is a boronic acid, boronic ester or an appropriately substituted metal (e.g., $R^3$-M is $R^3$—$B(OH)_2$, $R^3$—$Sn(Bu)_4$, or Zn—$R^3$) under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of formula (iii). Alternatively, $R^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine)-palladium(0) and a base (e.g., an alkoxide base)) to afford compounds of formula (iii). The ketone (iii) can be transformed using similar methods as shown in Scheme I and II to afford compounds of Formula I (iv). Alternatively, the halo-ketone (ii) can be transformed using similar methods as shown in Scheme I and II to afford halo intermediate (v). Suzuki, Stille, Negishi or Buchwald coupling of $R^3$-M with halo intermediate (v) by similar methods described in Schemes I and II can also afford compounds of Formula I (vi).

Scheme III

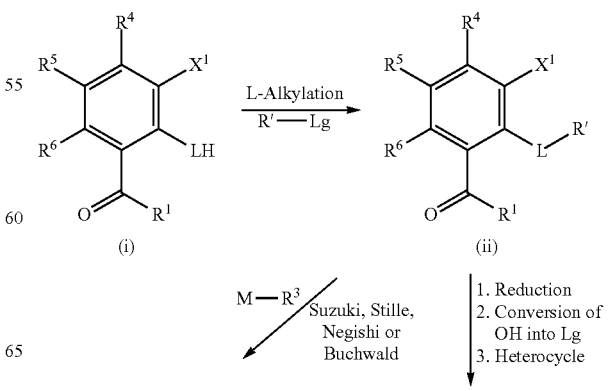

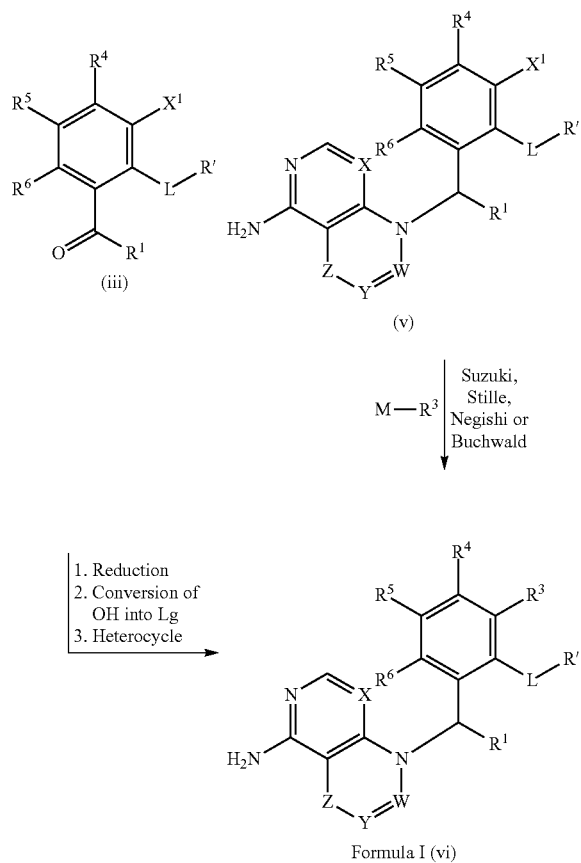

ketone (ii) using $NX^1S$ (e.g., $NX^1S$=N-chlorosuccinamide, N-bromosuccinamide or N-iodosuccinamide) can give compound (iii) where $X^1$=Cl, Br, or I. The phenol can be converted to the triflate (iv) using standard conditions (e.g., $Tf_2O$). The triflate group of (iv) can be coupled to $R^3$-M, where M is a boronic acid, boronic ester or an appropriately substituted metal (e.g., $R^3$-M is $R^3$—$B(OH)_2$, $R^3$—$Sn(Bu)_4$, or Zn—$R^3$) under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence a palladium(0) catalyst, such as tetrakis(triphenylphosphine)palladium(0), to give a derivative of formula (v). Alternatively, $R^2$-M can be a cyclic amine (where M is H and attached to the amine nitrogen) with coupling to compound (iv) being performed by heating in base or under Buchwald conditions (e.g., in the presence of a palladium(0) catalyst, such as tetrakis(triphenylphosphine)palladium(0) and a base (e.g., an alkoxide base)) to afford ketone (v). The halo group of (v) can be coupled to $R^3$-M, where M is a boronic acid, boronic ester or an appropriately substituted metal (e.g., $R^3$-M is $R^3$—B $(OH)_2$, $R^3$—$Sn(Bu)_4$, or Zn—$R^3$), under standard Suzuki conditions or standard Stille conditions (e.g., in the presence of a palladium(0) catalyst, such as tetrakis(triphenylphosphine)palladium(0) and a base (e.g., a bicarbonate or carbonate base)) to give a derivative of formula (vi). Alternatively, $R^3$-M can be a cyclic amine (where M is H and attached to the amine nitrogen) with coupling to compound (iv) being performed by heating in base or under Buchwald conditions (e.g., in the presence of a palladium(0) catalyst, such as tetrakis(triphenylphosphine)palladium(0) and a base (e.g., an alkoxide base)) to afford ketone (vi). The ketone (vi) can be transformed using similar methods as shown in Scheme I and II to afford compounds of Formula I (viii).

Alternatively, the halo-ketone (v) can be transformed using similar methods as shown in Scheme I and II to afford halo intermediate (vii). Suzuki, Stille, Negishi or Buchwald coupling of M-$R^3$ with compound (vii) by similar methods described in Schemes I and II can also afford compounds of Formula I (viii).

Compounds of Formula I can be formed as shown in Scheme IV. Compound (i) can be acylated with a suitable acylating reagent (e.g., $R^1$—COCl) to form an ester which can be rearranged under Lewis acid conditions e.g., $BF_3$/HOAc complex) to afford ketone (ii). Halogenation of Scheme IV

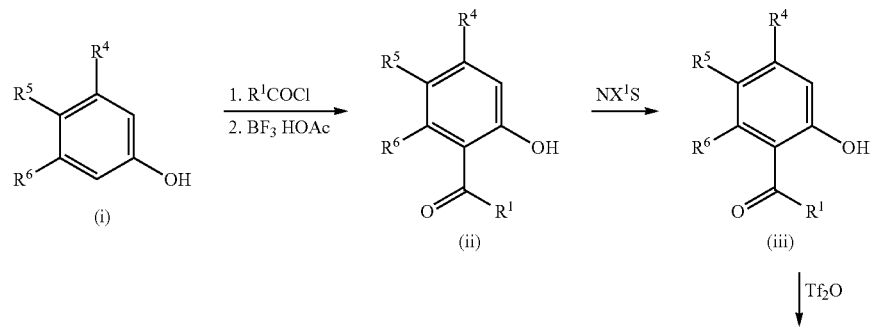

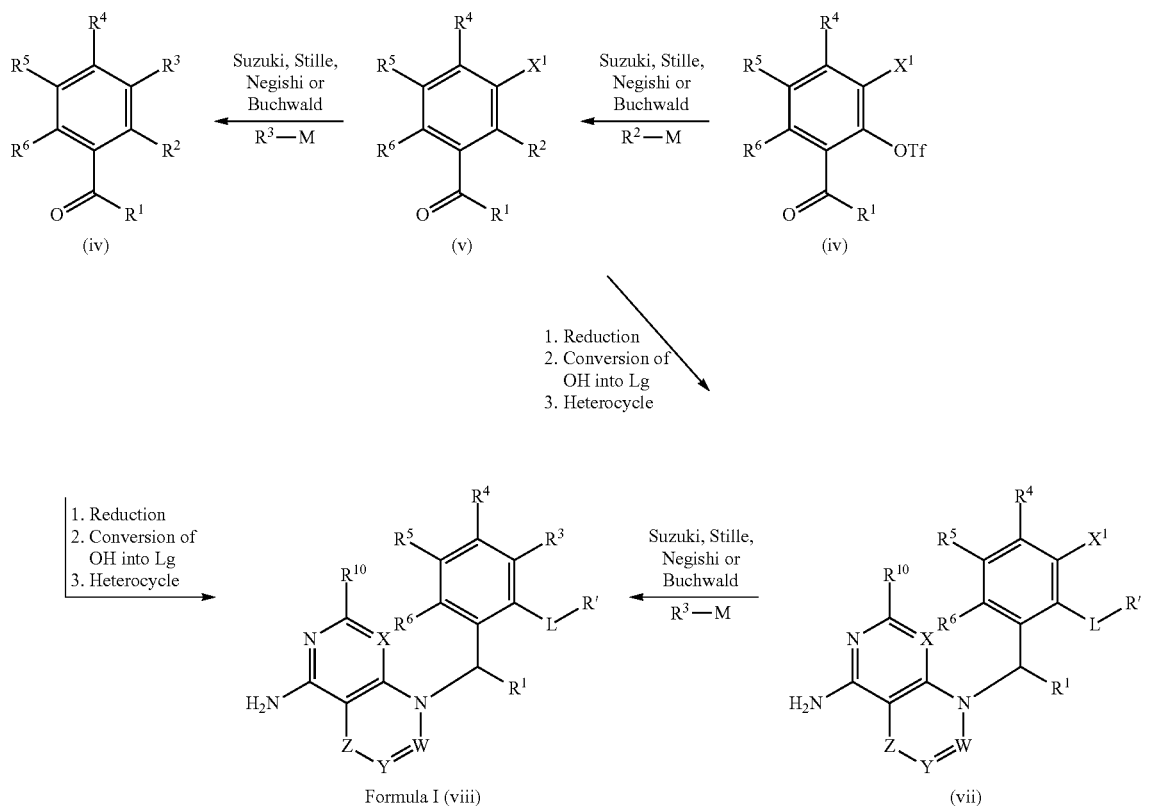

Ketones which can be used in the processes of Scheme I, II and III can be formed as shown in Scheme V below. The carboxylic acid (i) can be activated with a coupling agent (e.g., HBTU, HATU or EDC) and then reacted with N,O-dimethylhydroxylamine to give a N-methoxy-N-methyl-carboxamide derivative (ii). Amide (ii) may then be reacted with a Grignard reagent of formula $R^1$—$MgX^1$ ($X^1$=halo) to give a ketone (iii). The ketone (iii) can be transformed using similar methods as shown in Scheme I, II and III to afford compounds of Formula I.

Scheme V

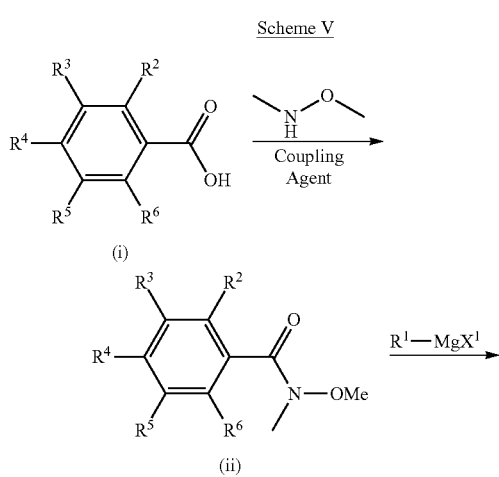

-continued

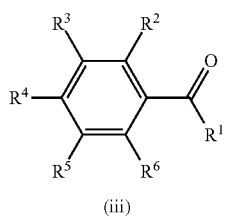

Ketones which can be used in the processes of Scheme I, II and III, can also be formed as shown in Scheme VI below. The carboxylic acid (i) can be activated with a coupling agent (e.g. HBTU or HATU) and then reacted with N,O-dimethylhydroxylamine to give a N-methoxy-N-methyl-carboxamide. The thiols, phenols or amines can be alkylated using Mitsunobu conditions (e.g., ROH, DEAD, $Ph_3P$) or standard alkylating conditions (R'-Lg, Lg=leaving group) to afford thioether, ether or alkylamine derivatives (ii), respectively. The halo group of (ii) ($X^1$ is halo) can be coupled to $R^3$-M, where M is a boronic acid, boronic ester or an appropriately substituted metal (e.g., $R^3$-M is $R^3$—$B(OH)_2$, $R^3$—$Sn(Bu)_4$, or Zn—$R^3$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of formula (iii). Alternatively, $R^3$-M can be a cyclic amine (where M is H and attached to the amine nitrogen) with coupling to compound (ii) being performed by heating in base or under Buchwald conditions (e.g., in the presence of a palladium(0) catalyst, such as tetrakis(triphenylphosphine)palladium(0) and a base (e.g., an alkoxide base)) to afford amides (iii). Reaction of compound (iii) with a Grignard reagent of formula $R^1$—$MgX^2$ ($X^2$=halo) can give ketone (iv). The ketone (iv) can be transformed using similar methods as shown in Scheme I, II and III to afford compounds of Formula I.

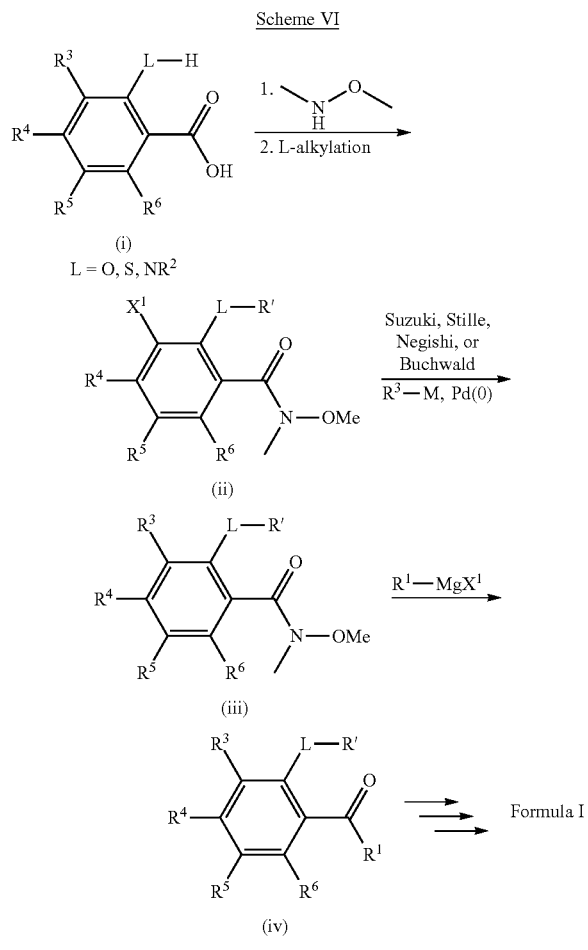

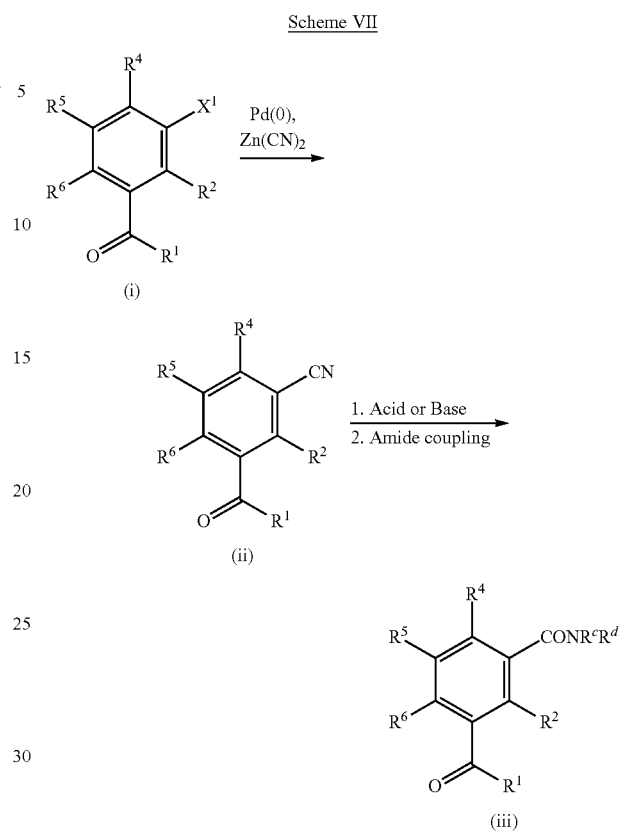

Compounds which can be used in the processes of Schemes I-III can also be formed as shown in Scheme VII. The halo-ketone (i) ($X^1$ is halo) can be converted to the cyano-ketone (ii) using standard cyanation conditions (e.g., Pd(0) and $Zn(CN)_2$). Hydrolysis of the cyano group of (ii) under acid or base conditions can give the carboxylic acid which can be coupled to amines using a coupling agent (e.g., HATU, HBTU, EDC) and appropriate amines ($HNR^cR^d$) to give amide (iii). In some embodiments, $R^c$ and $R^d$, along with the nitrogen atom to which they are attached can optionally cyclize to form a 4-7 membered heterocycloalkyl group (thereby providing compounds wherein $R^3$ is $C(O)R^b$, wherein $R^b$ is 4-7 membered heterocycloalkyl). The ketone of amide (iii) can be transformed using similar methods as shown in Scheme I, II and III to afford compounds of Formula I.

Additional compounds which can be used in the processes of Schemes I-III can be formed as shown in Scheme VIII. The ketone (i) can be converted to the nitro-ketone (ii) using standard nitration conditions (e.g., $HNO_3$). Reduction of the nitro group of (ii) under standard conditions (e.g., Fe, Zn, $H_2$ over Pd/C) can give the amino compound which can be acylated with appropriate acylating agents (e.g., RC=OCl, ROC=OCl, $SO_2Cl$, RRNC=O) to give ketone (iii). The ketone (iii) can be transformed using similar methods as shown in Scheme I, II and III to afford compounds of Formula I. In some embodiments, $R^c$ and $R^d$, along with the nitrogen atom to which they are attached can optionally cyclize to form a 4-7 membered heterocycloalkyl group (thereby providing compounds wherein $R^3$ is $C(O)R^b$, wherein $R^b$ is 4-7 membered heterocycloalkyl).

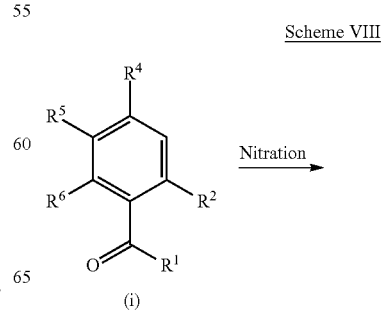

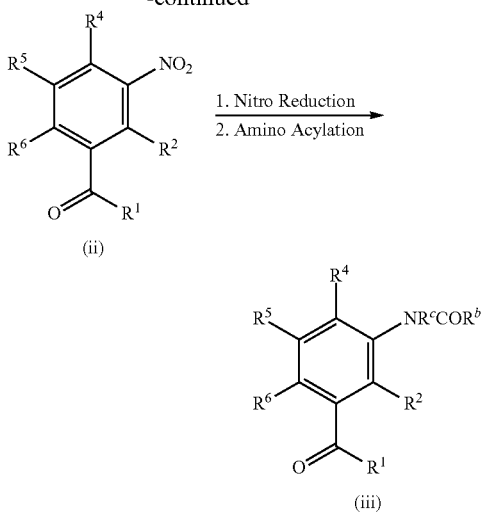

Ketones which can be used in the processes of Scheme I, II and III, can also be formed as shown in Scheme IX below. The halo group (e.g., $X^1$=I) of (i) can be coupled to a zinc reagent $R^3$—Zn (e.g., such as tert-butyl 3-iodoazetidine-1-carboxylate with Zn dust) under standard Knochel/Negishi conditions (e.g., in the presence of a palladium(0) catalyst, such as tri-(2-furyl)phosphine and tris(dibenzylideneacetone)dipalladium(0) and 1,2-dibromoethane and chlorotrimethylsilane) to give a derivative of formula (ii). The azetidine (ii) can be deprotected (e.g., Pg=Boc, using TFA) and then reacted under alkylating, acylating or reductive amination (e.g., RX such as R—Br, RCOCl, R—SO$_2$Cl, RN=C=O or RCHO and a reducing agent) conditions to afford ketone derivatives (iii) which can be converted to compounds of Formula I (v) by similar methods shown in Schemes I, II, and III). Alternatively, the ketone (ii) can be reduced with suitable reagents (NaBH$_4$ or Corey's chiral CBS catalyst to give predominantly one isomer of the alcohol), the resulting alcohol can be converted to a leaving group (e.g., Lg is chloride via reaction with cyanuric chloride or mesylate via reaction with methanesulfonic anhydride) and then the chloride or mesylate reacted with an appropriate heterocycle (e.g., similar to methods shown in Schemes I, II and III) to afford derivatives of formula (iv). The protecting group on the amine can be removed under standard conditions and then reacted under alkylating, acylating or reductive amination conditions (e.g., RX such as R—Br, RCOCl, R—SO$_2$Cl, RN=C=O or RCHO and a reducing agent) to give compounds of Formula I (v).

Scheme IX

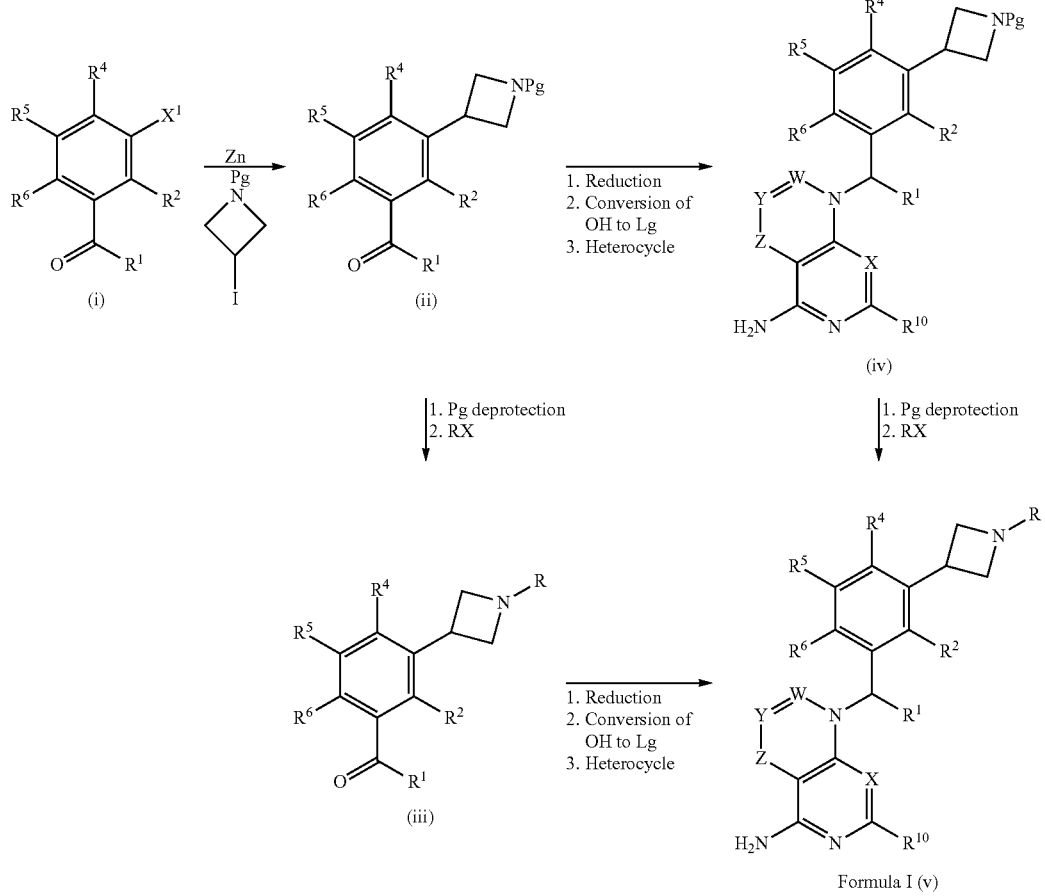

Compounds of Formula I can also be formed as shown in Scheme X. The compound (i) can be reacted with a halo-substituted heterocycle (ii) (e.g., 3-iodo-1H-pyrazolo[3,4-d]pyrimidin-4-amine or 4-amino-6-iodopyrido[2,3-d]pyrimidin-5(8H)-one) under basic conditions (e.g., NaH or CsCO$_3$ or K$_2$CO$_3$) to give compound (iii) where V=Cl, Br, or I. The halo group of (iii) can be coupled to R$^3$-M, where M is a boronic acid, boronic ester or an appropriately substituted metal (e.g., R$^8$-M is R$^8$—B(OH)$_2$, R$^8$—Sn(Bu)$_4$, or Zn—R$^8$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of formula (iii). Alternatively, R$^8$-M can be a cyclic amine (where M is H and attached to the amine nitrogen) with coupling to compound (iii) being performed by heating in base or under Buchwald conditions (e.g., in the presence of a palladium(0) catalyst, such as tetrakis(triphenylphosphine)palladium(0) and a base (e.g., an alkoxide base)) to afford compounds of Formula I (iv).

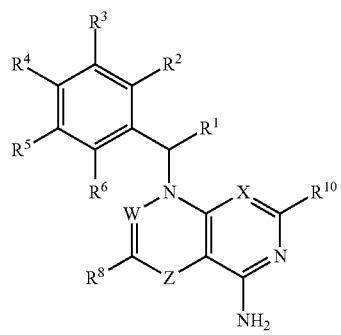

Formula I (iv)

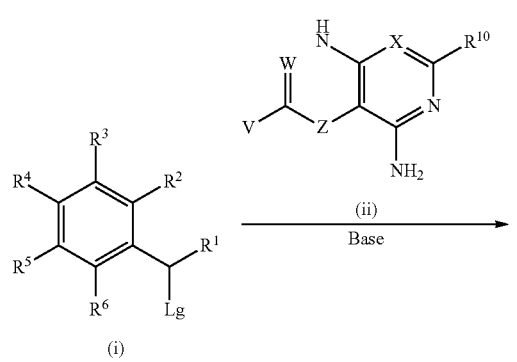

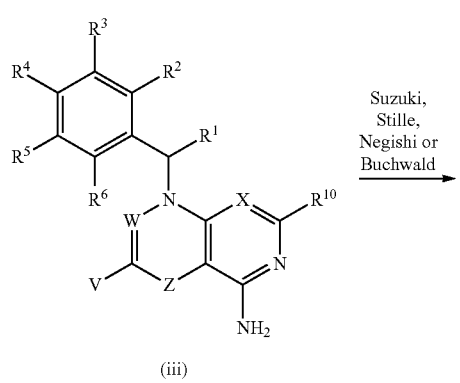

Compounds of Formula I can also be formed as shown in Scheme XI. Cyano derivative (i) can be hydrolyzed to the acid (e.g. in the presence of acid or base) to give the corresponding acid (ii). The carboxylic acid (ii) can be coupled to an amine (e.g., HNR$^{c2}$R$^{d2}$ is dimethylamine) (iii) using appropriate coupling agents (e.g. HATU, HBTU, EDC) in the presence of a base, such as TEA or DIEA to give the amide (iii). The carboxylic acid (ii) can also be reduced to the alcohol (iv) where R$^t$=H with an appropriate reducing agent (e.g. LAH or NaBH$_4$) or converted to the ester and reacted with a Grignard reagent (e.g. R$^t$MgBr) or an alkyllithium (e.g. R$^t$Li) to give the secondary or tertiary alcohols (iv). The alcohol (iv) can be activated by converting to a leaving group, such as a halide by reacting with suitable reagents, such as cyanuric chloride, and then reacted with an appropriate amine (e.g. HNR$^{c2}$R$^{d2}$) to give compounds of Formula I (v). Alternatively, the alcohol (iv) can be reacted under Mitsunobu conditions (e.g. in the presence of DEAD, triphenylphosphine and a compound A (e.g. a phenol or heteroaryl bearing an NH, e.g. imidazole) to give compounds of Formula I (vi). Other modifications would be readily apparent to one of skill in the art, starting from the compounds depicted in Scheme XI (e.g., esterification of alcohols, etc.).

Scheme XI

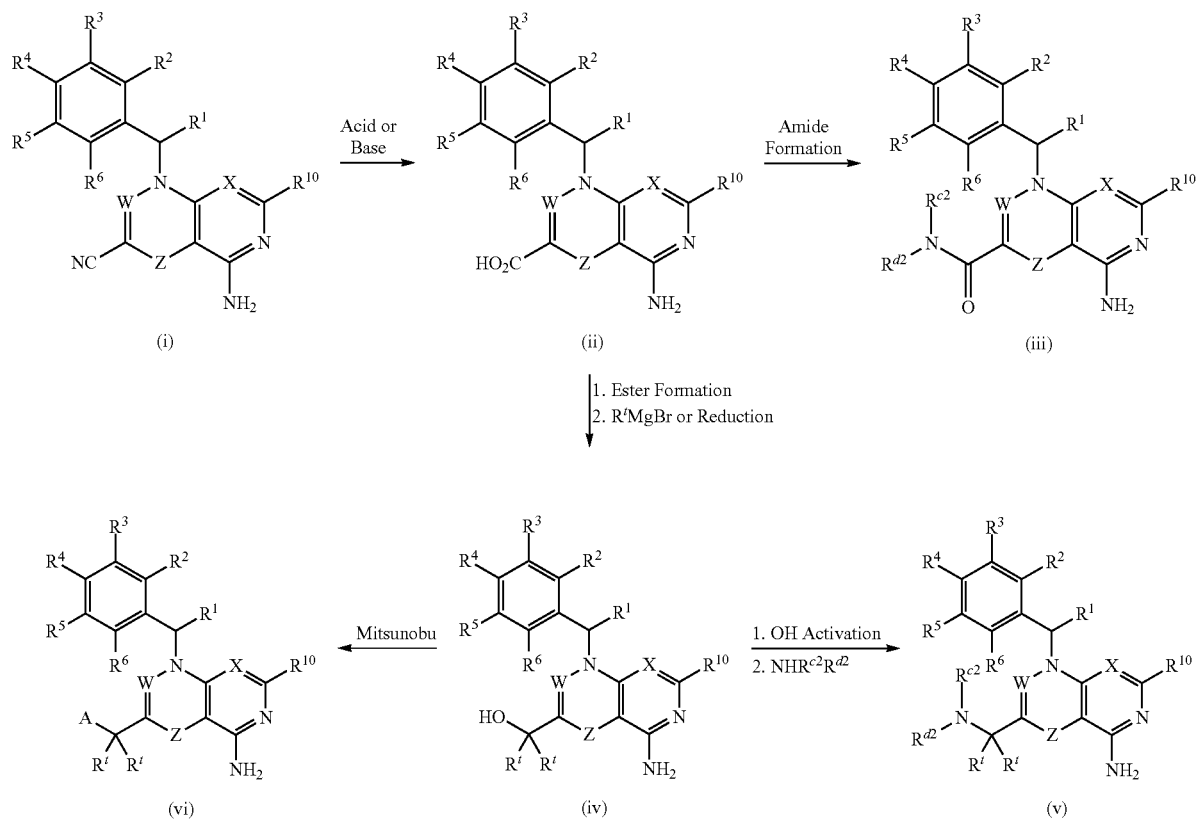

Compound of Formula I can be synthesized from an acid chloride compound (i) as illustrated in Scheme XII. Condensation of an acid chloride (i) with malononitrile in the presence of a base, such as sodium hydride, can give a dicyanoenol intermediate, which can be O-methylated with an appropriate reagent, such as dimethyl sulfate in the presence of an appropriate base, such as sodium bicarbonate, to yield an enol ether (ii). Reaction of enol ether (ii) with hydrazine dihydrochloride in the presence of a suitable base, such as triethylamine, can give a pyrazole compound (iii). Pyrazole compound (iii) can then be reacted with formamide to give pyrazolopyrimidine (iv). Finally, compound (iv) can be reacted with appropriate compound bearing a leaving group (v) under basic conditions to give a compound of Formula I (vi).

Scheme XII

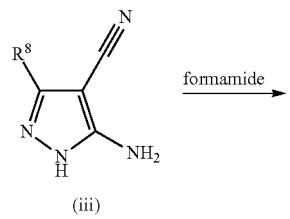

-continued

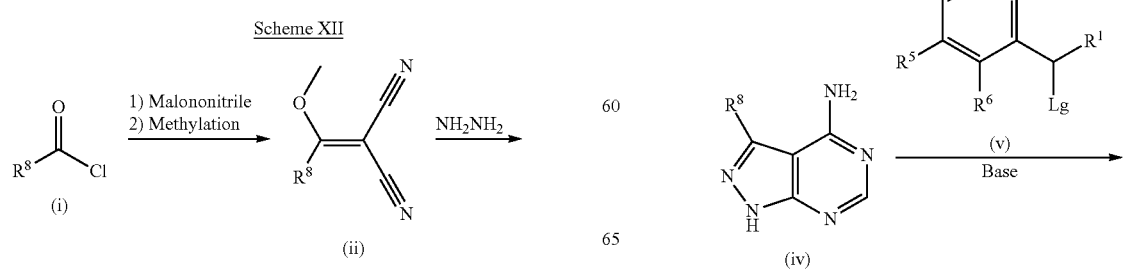

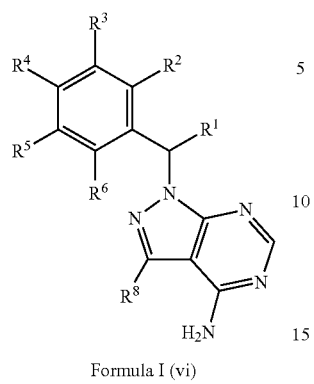

Formula I (vi)

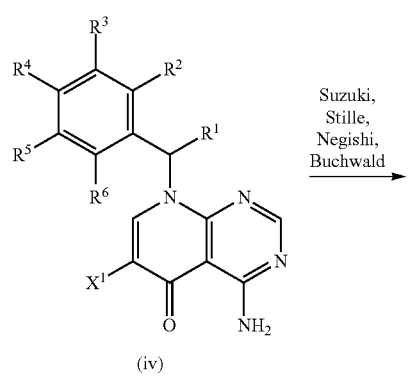

(iv)

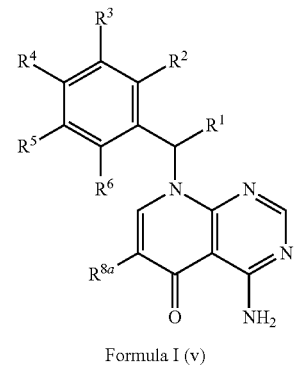

Formula I (v)

Compounds of Formula I can be synthesized from commercially available 4-aminopyrido[2,3-d]pyrimidine-5(8H)-one (i). Halogenation of compound (i) with suitable reagents, such as N-halo succinamide ($NX^1S$, where $X^1$=Cl, Br or I) can give the corresponding halo compound (ii). Reaction of the halo derivative (ii) with a compound (iii) bearing a leaving group in the presence of a suitable base (e.g. diisopropylethylamine) can give compound (iv). The halo compound (iv) can be coupled to $R^{8a}$-M, where M is a boronic acid, boronic ester or an appropriately substituted metal (e.g., $R^{8a}$-M is $R^{8a}$—$B(OH)_2$, $R^{8a}$—$Sn(Bu)_4$, or Zn—$R^{8a}$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0), to give a derivative of formula (iii). Alternatively, $R^{8a}$-M can be a cyclic amine (where M is H and attached to the amine nitrogen) with coupling to compound (iii) being performed by heating in base or under Buchwald conditions (e.g., in the presence of a palladium(0) catalyst, such as tetrakis(triphenylphosphine)palladium(0) and a base (e.g., an alkoxide base)) to afford compounds of Formula I (v).

Compounds of Formula I can also be formed as shown in Scheme XIV. The halo group, $X^1$, of (i) can be coupled to an alkene (e.g., acrylate or acrylamide) under standard Heck conditions (e.g., in the presence of a palladium(II) catalyst, such as palladium acetate) to give an alkene of formula (ii). Reaction of alkene (ii) with nitromethane in the presence of DBU can afford the nitro derivative (iii) which can be reduced under standard conditions (e.g., $NiCl_2$/$NaBH_4$) to give a free amine which cyclizes to form lactam (iv). The lactam can be alkylated under standard conditions (e.g., $R^{3a}$—$X^2$, where $X^2$=halo, in the presence of a base, such as TEA or NaH) to give an N-alkyl-lactam (v). Compounds of formula (v), and pyrrolidines derived from the reduction of the lactam (v) with suitable reducing agents, such as $LiAlH_4$, can be converted to compounds of Formula I using conditions described in Schemes I, II and III.

Scheme XIII

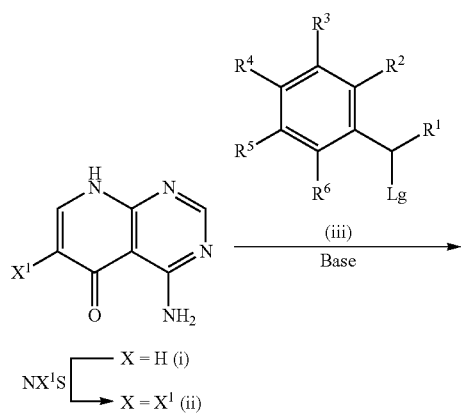

Scheme XIV

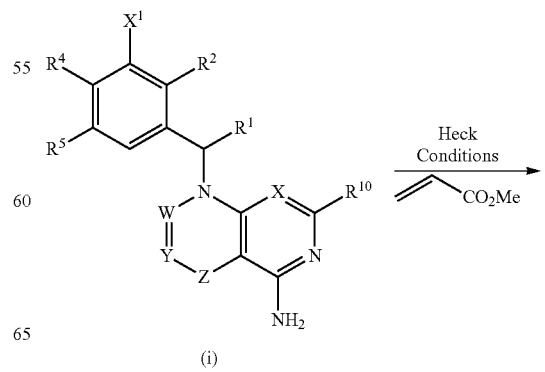

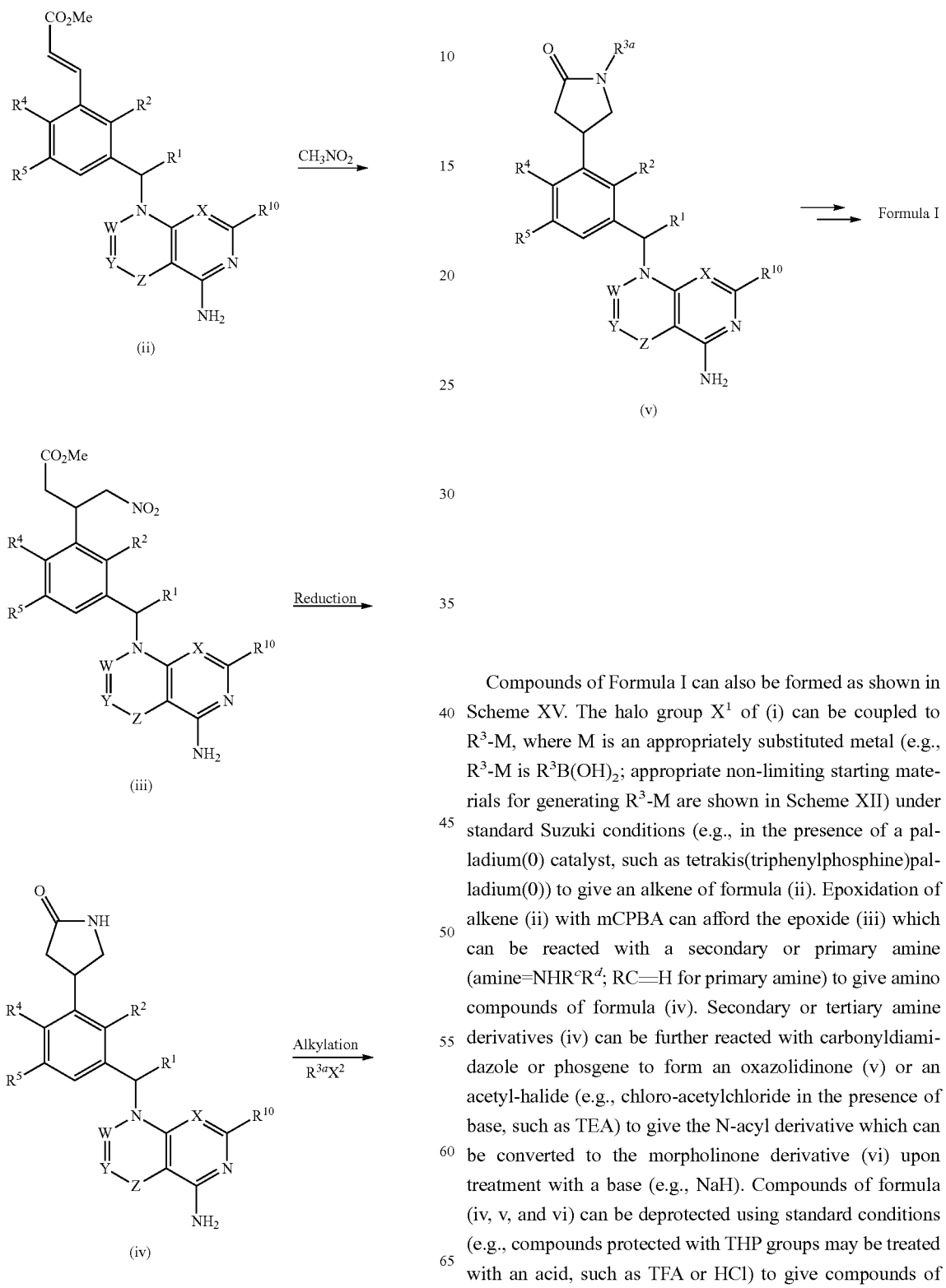

Compounds of Formula I can also be formed as shown in Scheme XV. The halo group $X^1$ of (i) can be coupled to $R^3$-M, where M is an appropriately substituted metal (e.g., $R^3$-M is $R^3B(OH)_2$; appropriate non-limiting starting materials for generating $R^3$-M are shown in Scheme XII) under standard Suzuki conditions (e.g., in the presence of a palladium(0) catalyst, such as tetrakis(triphenylphosphine)palladium(0)) to give an alkene of formula (ii). Epoxidation of alkene (ii) with mCPBA can afford the epoxide (iii) which can be reacted with a secondary or primary amine (amine=NHR$^c$R$^d$; RC=H for primary amine) to give amino compounds of formula (iv). Secondary or tertiary amine derivatives (iv) can be further reacted with carbonyldiamidazole or phosgene to form an oxazolidinone (v) or an acetyl-halide (e.g., chloro-acetylchloride in the presence of base, such as TEA) to give the N-acyl derivative which can be converted to the morpholinone derivative (vi) upon treatment with a base (e.g., NaH). Compounds of formula (iv, v, and vi) can be deprotected using standard conditions (e.g., compounds protected with THP groups may be treated with an acid, such as TFA or HCl) to give compounds of Formula I.

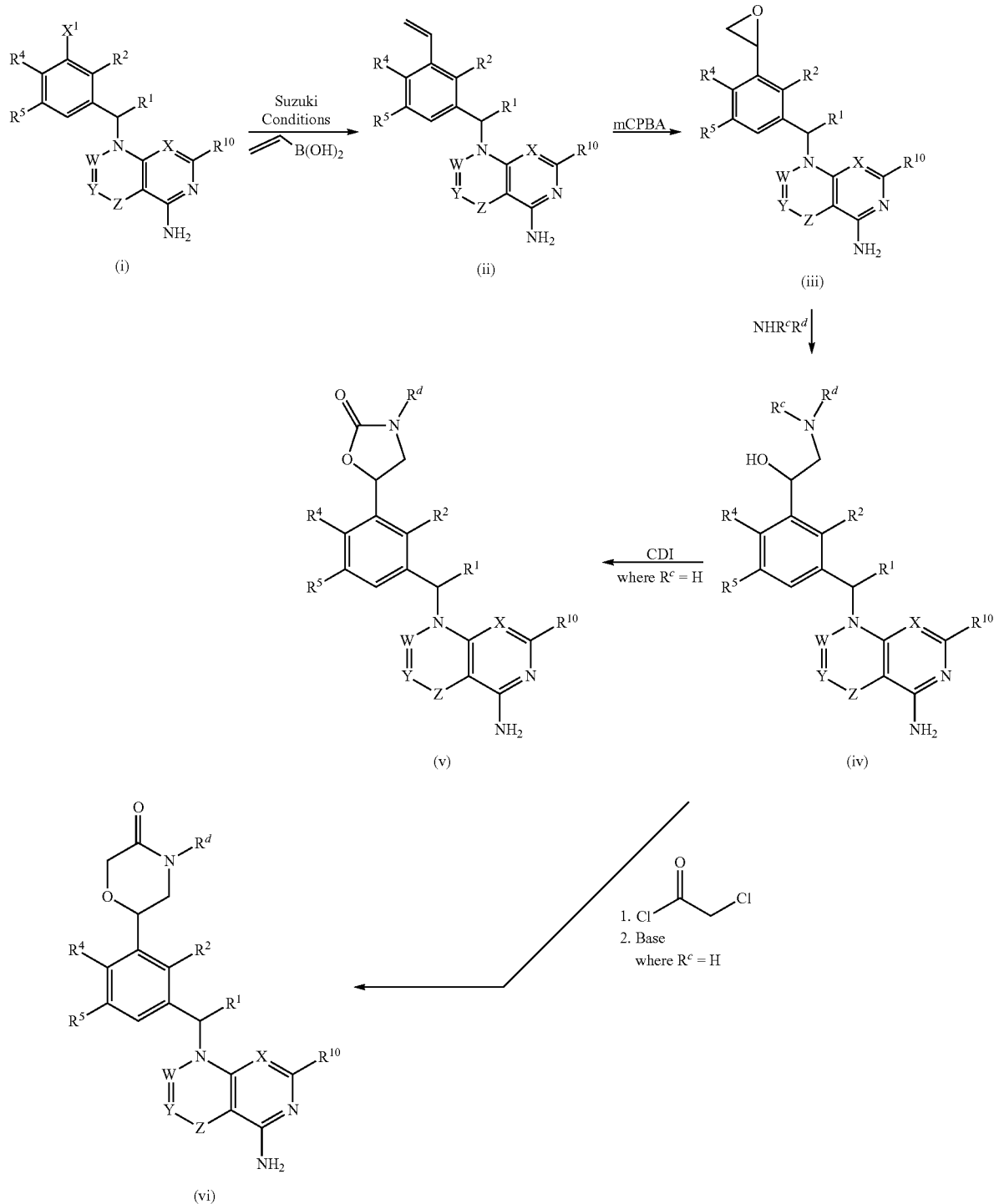

Compounds of Formula I can also be formed as shown in Scheme XVI. Sharpless amino-hydroxylation of an alkene of formula (i) under suitable conditions (A or B, as described in *JACS*, 2001, 123(9), 1862-1871 and *J. Org. Chem*, 2011, 76, 358-372) can give either amino-hydroxy isomer (ii) or (iii). Compounds (ii) and (iii) can be reacted with carbonyldiamidazole or phosgene to form an oxazolidinone (iv), or an acetyl-halide (e.g., chloro-acetylchloride in the presence of base, such as TEA) to give an N-acyl derivative which can be converted to the morpholinone derivative (v) upon treatment with a base (e.g., NaH). The alternate amino-hydroxy isomer (iii) can be converted to oxazolidinone and morpholinone derivatives as shown in Scheme XV.

Scheme XVI

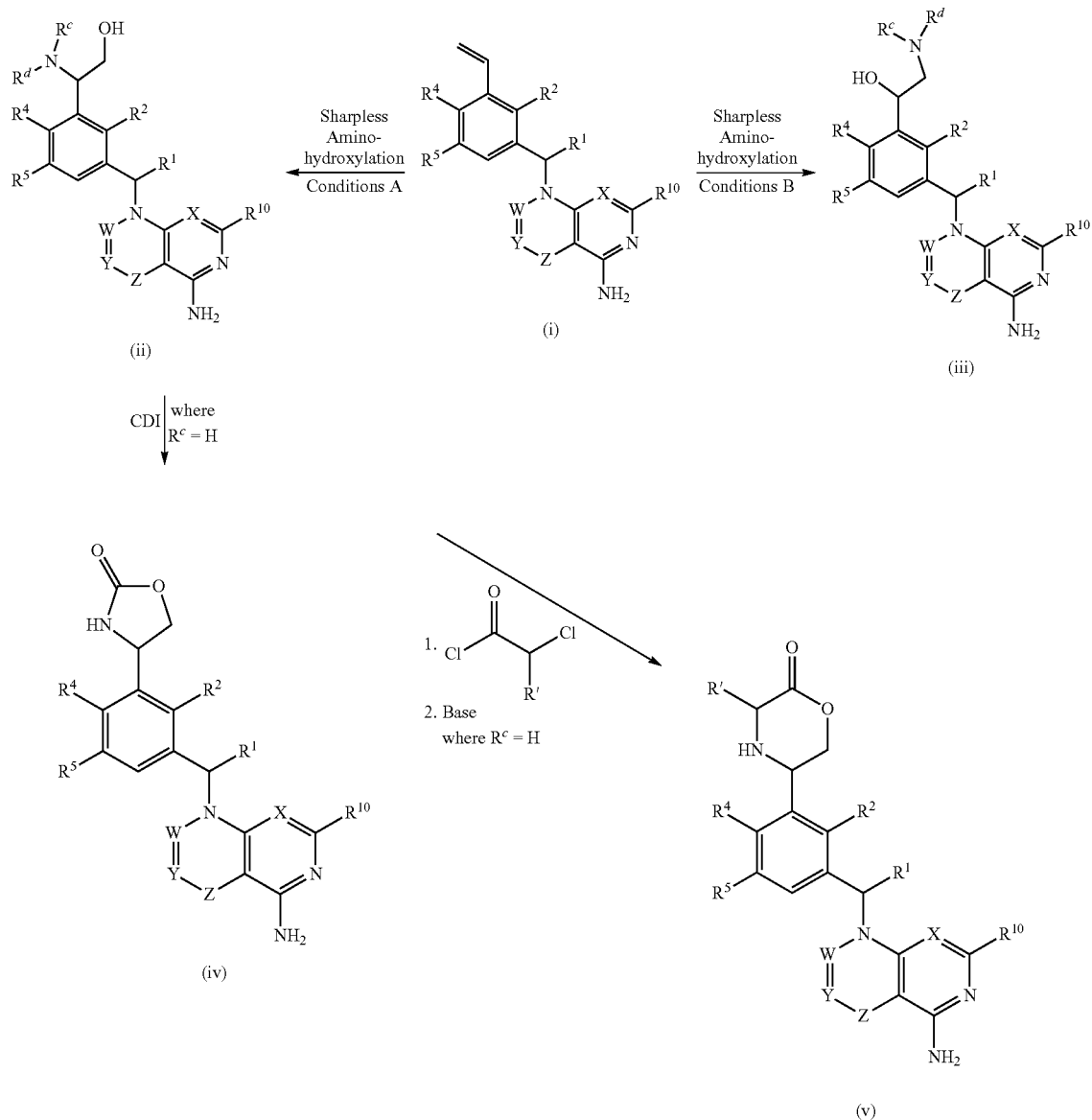

Compounds of Formula I can be synthesized as shown in Scheme XVII. The halo group (e.g., $X^1$=Cl, Br, I) of (i) can be converted to the boronate ester (ii) under standard conditions (e.g., pinnacle boronate ester in the presence of a palladium(0) catalyst, such as tetrakis(triphenylphosphine)palladium(0)). Boronate (ii) can be reacted with an arylhalide or heteroarylhalide (e.g., $R^3$—$X^2$) under Suzuki conditions (e.g., in the presence of a palladium(0) catalyst, such as tetrakis(triphenylphosphine)palladium(0) and a base, such as $Na_2CO_3$) to give formula (iii). Formula (iii) can be converted to Formula I using the reaction conditions described in Schemes I, II or III.

Scheme XVII

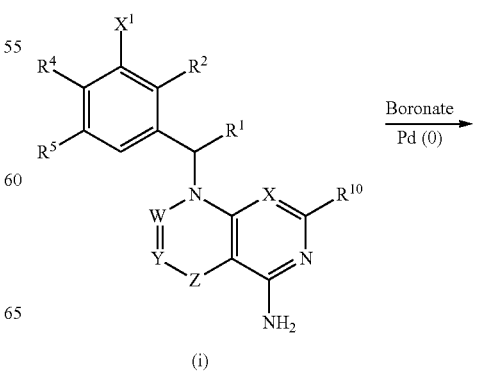

-continued

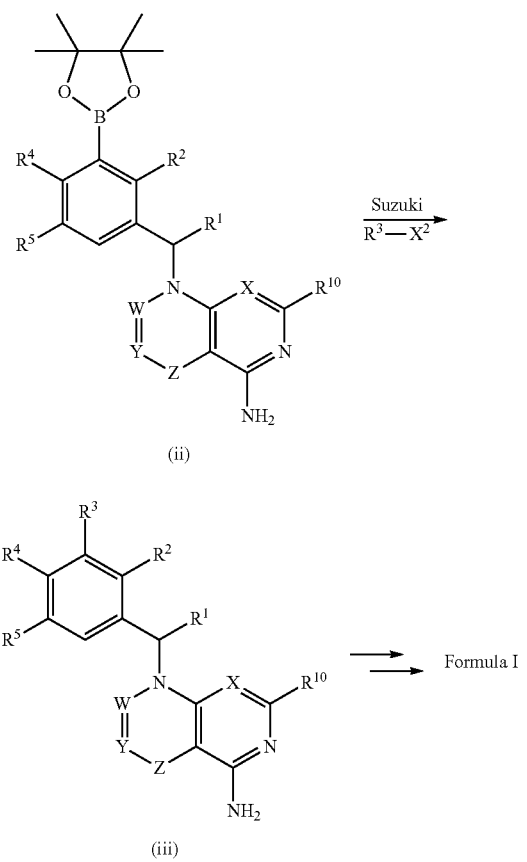

Compounds of Formula I, where $R^4$=F or CN, can be formed as shown in Scheme XVIII. Compound (i) can be acylated with a suitable acylating reagent (e.g., $R^1$—COCl) to form an ester which can be rearranged under Lewis acid conditions (e.g., $BF_3$/HOAc complex) to afford ketone (ii). Ketone (ii) can be halogenated with N-chlorosuccinamide, N-bromosuccinamide or N-iodosuccinamide to give phenol (iii), where $X^1$=Cl, Br, or I. Compound (iii) can be alkylated (e.g. $R^2$—X and a base, such as NaH or $Na_2CO_3$; or under Mitsunobu conditions) to afford the ether (iv). The fluoro group of (iv) can be displaced (e.g., with NaCN or KCN) to give cyano derivative (v). The halo group of (v) can be coupled to $R^3$-M, where M is a boronic acid, boronic ester or an appropriately substituted metal (e.g., $R^3$-M is $R^3$—B$(OH)_2$, $R^3$—Sn$(Bu)_4$, or Zn—$R^3$), under standard Suzuki conditions or standard Stille conditions (e.g., in the presence of a palladium(0) catalyst, such as tetrakis(triphenylphosphine)palladium(0) and a base (e.g., a bicarbonate or carbonate base) or standard Negishi conditions (e.g., in the presence of a palladium(0) catalyst, such as tetrakis(triphenylphosphine)palladium(0)), to give a derivative of formula (vi). Alternatively, $R^3$-M can be a cyclic amine (where M is H and attached to the amine nitrogen) and coupled to compound (v) by heating in base or under Buchwald conditions (e.g., in the presence of a palladium(0) catalyst, such as tetrakis(triphenylphosphine)palladium(0) and a base (e.g., an alkoxide base)) to afford ketone (vi). Reduction of the ketone (vi) with a suitable reagent, such as sodium tetrahydroborate or the Corey CBS reagent can furnish the alcohol which can be converted to a derivative bearing a leaving group, (e.g., Lg is chloride via reaction with cyanuric chloride or mesylate via reaction with methanesulfonic anhydride) and then reacted with an appropriate heterocycle (e.g., 3-methyl-1H-pyrazolo[3,4-d]pyrimidin-4-amine or 4-aminopyrido[2,3-d]pyrimidin-5(8H)-one) under basic conditions (e.g., NaH or $CsCO_3$ or $K_2CO_3$) to give a compound of Formula I (viii). Alternatively, the last two steps can be inverted so that the ketone (v) can be reduced to give an alcohol which is converted to a leaving group and displaced with the heterocycle first and then the Suzuki, Stille, Negishi or Buchwald coupling is performed to give compounds of Formula I (viii). The fluoro derivatives (iv) can also be converted to compounds of Formula I by eliminating the cyanation step in scheme XVIII.

Scheme XVIII

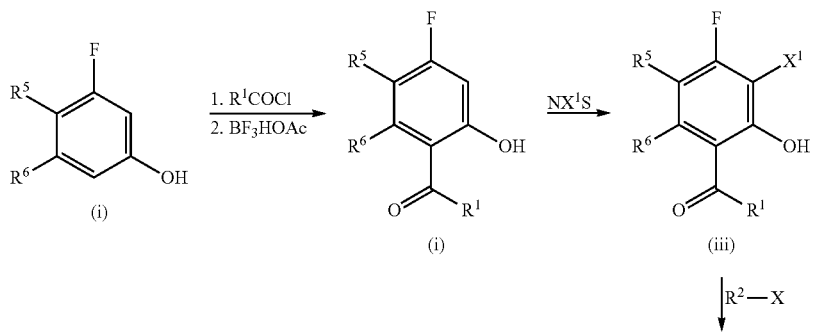

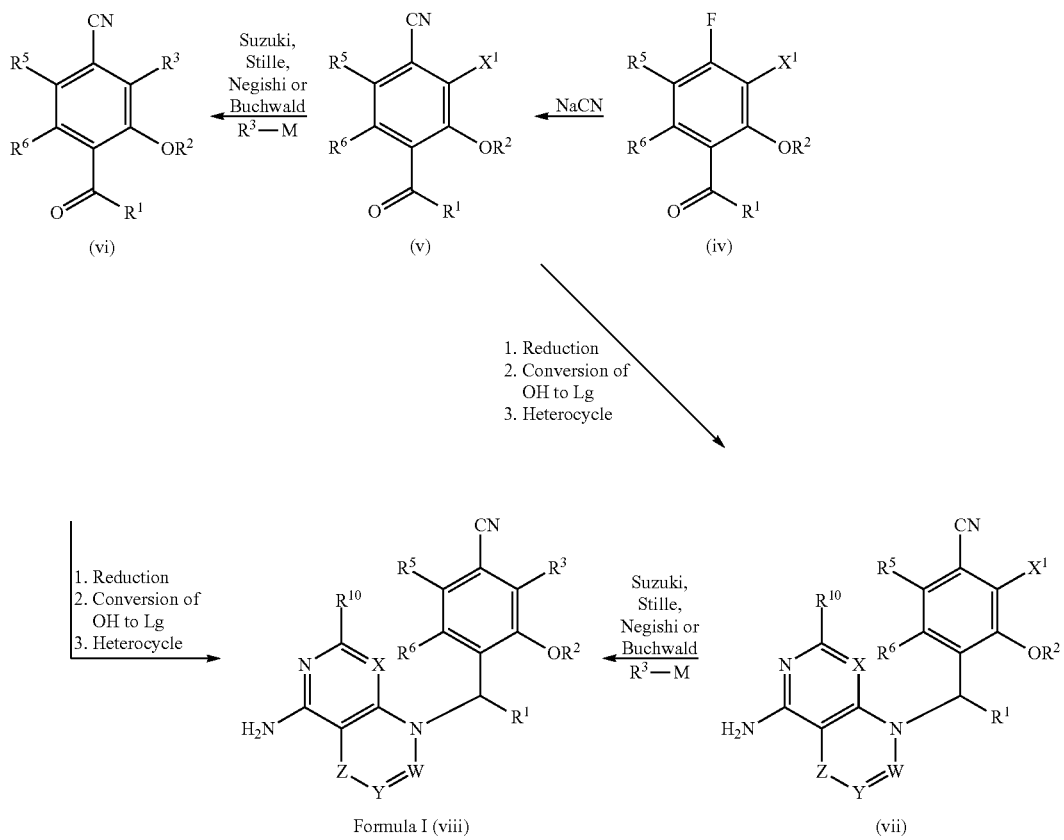

Compounds of Formula I can also be formed as shown in Scheme XIX. Compound (i) can be acylated with a suitable acylating reagent (e.g., $R^1$—COCl) to form an ester which can be rearranged under Lewis acid conditions (e.g., $AlCl_3$ or $BF_3$/HOAc complex) to afford ketone (ii). Halogenation of ketone (ii) using $NX^1S$ (e.g., $NX^1S$=N-chlorosuccinamide, N-bromosuccinamide or N-iodosuccinamide) can give compound (iii), where $X^1$=Cl, Br, or I. The phenol can be converted to an ether (iv) using standard conditions (e.g., inorganic base, such as $K_2CO_3$, and an alkyl halide, such as Et-I). The halo group of (iv) can be coupled to $R^3$-M, where M is a boronic acid, boronic ester or an appropriately substituted metal (e.g., $R^3$-M is $R^3$—$B(OH)_2$, $R^3$—$Sn(Bu)_4$, or Zn—$R^3$ and $R^3$ is a substituted or unsubstituted olefin, such as vinyl) under standard Suzuki conditions or standard Stille conditions (e.g., in the presence of a palladium(0) catalyst, such as tetrakis(triphenylphosphine)palladium(0) and a base (e.g., a bicarbonate or carbonate base) to give a derivative of formula (v). The alkene can then be dihydroxylated using Sharpless conditions to afford the diol (vi) Enhancement of one enantiomer of the secondary alcohol can be achieved using standard Sharpless asymmetric dihydroxylation methods. The secondary alcohol can be converted to the N-Boc protected amine via a 6 step process (e.g. silyl protection (e.g., TBS-Cl and DIEA) of the primary alcohol, mesylation of the secondary alcohol, displacement of the mesylate with $NaN_3$, reduction of the azide with $Ph_3P$, Boc protection of the resulting primary amine and then deprotection of the silyl protecting group on the primary alcohol with TBAF) to afford amino-alcohol (vii). The amino-alcohol (vii) can be converted into the oxazolidinone by treatment with phosgene and subsequent reduction of the ketone with a suitable reagent, such as sodium tetrahydroborate or sodium borohydride can furnish the alcohol (viii) which can be converted to a derivative bearing a leaving group (ix) (e.g., Lg is chloride via reaction with cyanuric chloride or mesylate via reaction with methanesulfonic anhydride). Finally, compound (ix) can be reacted with an appropriate heterocycle (x) (e.g., 3-methyl-1H-pyrazolo[3,4-d]pyrimidin-4-amine or 4-aminopyrido[2,3-d]pyrimidin-5(8H)-one) under basic conditions (e.g., NaH or $Cs_2CO_3$ or $K_2CO_3$) to give a compound of Formula I (xi).

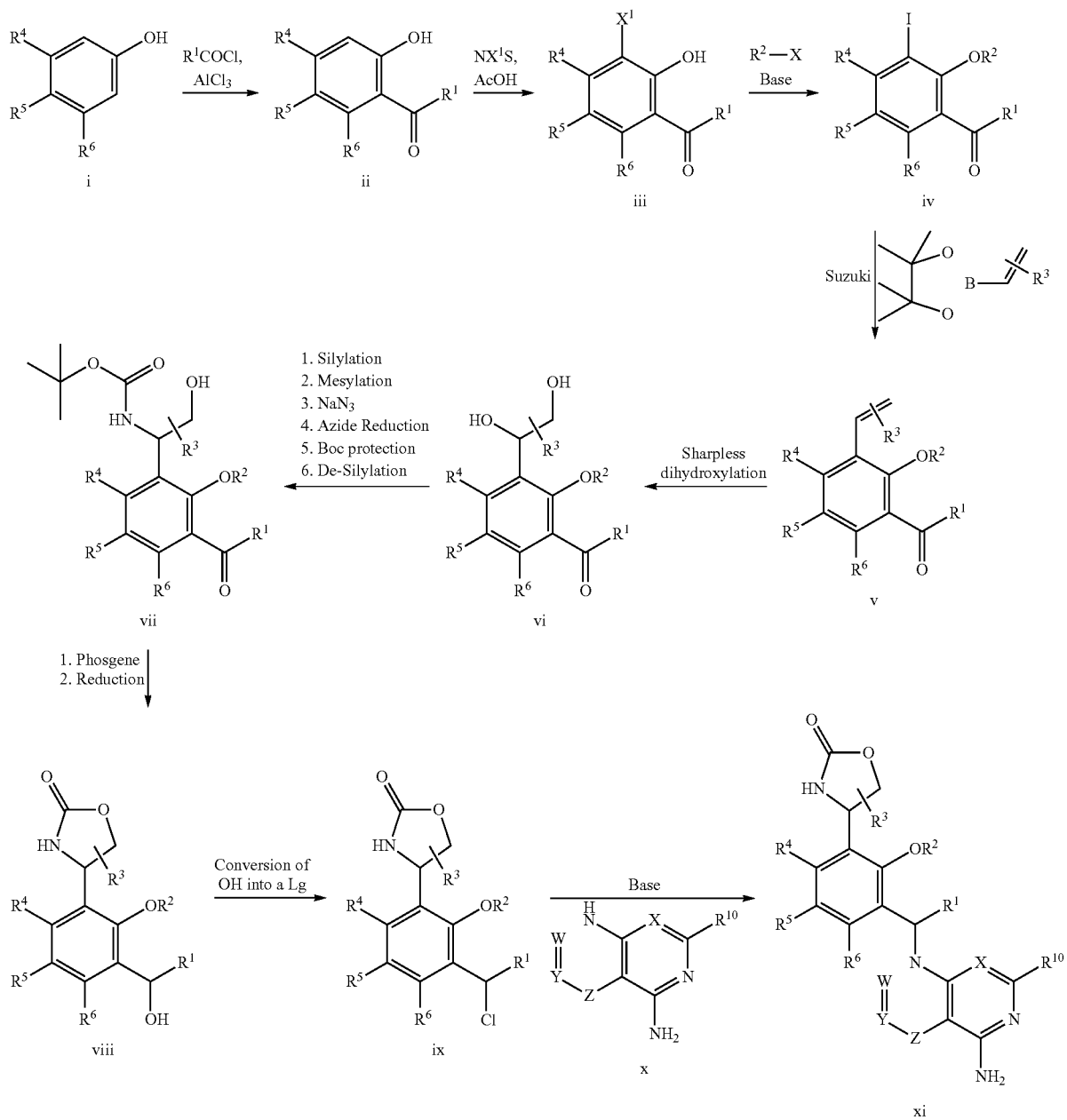

Scheme XIX

Methods

The compounds of the invention can modulate activity of one or more of various kinases including, for example, phosphoinositide 3-kinases (PI3Ks). The term "modulate" is meant to refer to an ability to increase or decrease the activity of one or more members of the PI3K family. Accordingly, the compounds of the invention can be used in methods of modulating a PI3K by contacting the PI3K with any one or more of the compounds or compositions described herein. In some embodiments, compounds of the present invention can act as inhibitors of one or more PI3Ks. In further embodiments, the compounds of the invention can be used to modulate activity of a PI3K in an individual in need of modulation of the receptor by administering a modulating amount of a compound of the invention, or a pharmaceutically acceptable salt thereof. In some embodiments, modulating is inhibiting.

Given that cancer cell growth and survival is impacted by multiple signaling pathways, the present invention is useful for treating disease states characterized by drug resistant kinase mutants. In addition, different kinase inhibitors, exhibiting different preferences in the kinases which they modulate the activities of, may be used in combination. This approach could prove highly efficient in treating disease states by targeting multiple signaling pathways, reduce the likelihood of drug-resistance arising in a cell, and reduce the toxicity of treatments for disease.

Kinases to which the present compounds bind and/or modulate (e g, inhibit) include any member of the PI3K family. In some embodiments, the PI3K is PI3Kα, PI3Kβ, PI3Kγ, or PI3Kδ. In some embodiments, the PI3K is PI3Kγ or PI3Kδ. In some embodiments, the PI3K is PI3Kγ. In some embodiments, the PI3K is PI3Kδ. In some embodiments, the PI3K includes a mutation. A mutation can be a replacement of one amino acid for another, or a deletion of one or more amino acids. In such embodiments, the mutation can be present in the kinase domain of the PI3K.

In some embodiments, more than one compound of the invention is used to inhibit the activity of one kinase (e.g., PI3Kγ or PI3Kδ).

In some embodiments, more than one compound of the invention is used to inhibit more than one kinase, such as at least two kinases (e.g., PI3Kγ and PI3Kδ).

In some embodiments, one or more of the compounds is used in combination with another kinase inhibitor to inhibit the activity of one kinase (e.g., PI3Kγ or PI3Kδ).

In some embodiments, one or more of the compounds is used in combination with another kinase inhibitor to inhibit the activities of more than one kinase (e.g., PI3Kγ or PI3Kδ), such as at least two kinases.

The compounds of the invention can be selective. By "selective" is meant that the compound binds to or inhibits a kinase with greater affinity or potency, respectively, compared to at least one other kinase. In some embodiments, the compounds of the invention are selective inhibitors of PI3Kγ or PI3Kδ over PI3Kα and/or PI3Kβ. In some embodiments, the compounds of the invention are selective inhibitors of PI3Kδ (e.g., over PI3Kα, PI3Kβ and PI3Kγ). In some embodiments, the compounds of the invention are selective inhibitors of PI3Kγ (e.g., over PI3Kα, PI3Kβ and PI3Kδ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold. Selectivity can be measured by methods routine in the art. In some embodiments, selectivity can be tested at the $K_m$ ATP concentration of each enzyme. In some embodiments, the selectivity of compounds of the invention can be determined by cellular assays associated with particular PI3K kinase activity.

Another aspect of the present invention pertains to methods of treating a kinase (such as PI3K)-associated disease or disorder in an individual (e.g., patient) by administering to the individual in need of such treatment a therapeutically effective amount or dose of one or more compounds of the present invention or a pharmaceutical composition thereof. A PI3K-associated disease can include any disease, disorder or condition that is directly or indirectly linked to expression or activity of the PI3K, including overexpression and/or abnormal activity levels. In some embodiments, the disease can be linked to Akt (protein kinase B), mammalian target of rapamycin (mTOR), or phosphoinositide-dependent kinase 1 (PDK1). In some embodiments, the mTOR-related disease can be inflammation, atherosclerosis, psoriasis, restenosis, benign prostatic hypertrophy, bone disorders, pancreatitis, angiogenesis, diabetic retinopathy, atherosclerosis, arthritis, immunological disorders, kidney disease, or cancer. A PI3K-associated disease can also include any disease, disorder or condition that can be prevented, ameliorated, or cured by modulating PI3K activity. In some embodiments, the disease is characterized by the abnormal activity of PI3K. In some embodiments, the disease is characterized by mutant PI3K. In such embodiments, the mutation can be present in the kinase domain of the PI3K.

Examples of PI3K-associated diseases include immune-based diseases involving the system including, for example, rheumatoid arthritis, allergy, asthma, glomerulonephritis, lupus, or inflammation related to any of the above.

Further examples of PI3K-associated diseases include cancers such as breast, prostate, colon, endometrial, brain, bladder, skin, uterus, ovary, lung, pancreatic, renal, gastric, or hematological cancer.

In some embodiments, the hematological cancer is acute myeloblastic leukemia (AML) or chronic myeloid leukemia (CML), or B cell lymphoma.

Further examples of PI3K-associated diseases include lung diseases such as acute lung injury (ALI) and adult respiratory distress syndrome (ARDS).

Further examples of PI3K-associated diseases include osteoarthritis, restenosis, atherosclerosis, bone disorders, arthritis, diabetic retinopathy, psoriasis, benign prostatic hypertrophy, inflammation, angiogenesis, pancreatitis, kidney disease, inflammatory bowel disease, myasthenia gravis, multiple sclerosis, or Sjögren's syndrome, and the like.

As used herein, the term "contacting" refers to the bringing together of indicated moieties in an in vitro system or an in vivo system. For example, "contacting" a PI3K with a compound of the invention includes the administration of a compound of the present invention to an individual or patient, such as a human, having a PI3K, as well as, for example, introducing a compound of the invention into a sample containing a cellular or purified preparation containing the PI3K.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the dosage of the compound, or a pharmaceutically acceptable salt thereof, administered to a patient or individual is about 1 mg to about 2 g, about 1 mg to about 1000 mg, about 1 mg to about 500 mg, about 1 mg to about 100 mg, about 1 mg to 50 mg, or about 50 mg to about 500 mg.

As used herein, the term "treating" or "treatment" refers to one or more of (1) preventing the disease; for example, preventing a disease, condition or disorder in an individual who may be predisposed to the disease, condition or disorder but does not yet experience or display the pathology or symptomatology of the disease; (2) inhibiting the disease; for example, inhibiting a disease, condition or disorder in an individual who is experiencing or displaying the pathology or symptomatology of the disease, condition or disorder (i.e., arresting further development of the pathology and/or symptomatology); and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

Combination Therapies

One or more additional pharmaceutical agents such as, for example, chemotherapeutics, anti-inflammatory agents, steroids, immunosuppressants, as well as Bcr-Abl, Flt-3, EGFR, HER2, JAK (e.g., JAK1 or JAK2), c-MET, VEGFR, PDGFR, cKit, IGF-1R, RAF, FAK, Akt mTOR, PIM, and AKT (e.g., AKT1, AKT2, or AKT3) kinase inhibitors such as, for example, those described in WO 2006/056399, or other agents such as, therapeutic antibodies can be used in combination with the compounds of the present invention for treatment of PI3K-associated diseases, disorders or conditions. The one or more additional pharmaceutical agents can be administered to a patient simultaneously or sequentially.

Example antibodies for use in combination therapy include but are not limited to Trastuzumab (e.g. anti-HER2), Ranibizumab (e.g. anti-VEGF-A), Bevacizumab (trade name Avastin, e.g. anti-VEGF, Panitumumab (e.g. anti-EGFR), Cetuximab (e.g. anti-EGFR), Rituxan (anti-CD20) and antibodies directed to c-MET.

One or more of the following agents may be used in combination with the compounds of the present invention and are presented as a non limiting list: a cytostatic agent, cisplatin, doxorubicin, taxotere, taxol, etoposide, irinotecan, camptostar, topotecan, paclitaxel, docetaxel, epothilones, tamoxifen, 5-fluorouracil, methoxtrexate, temozolomide, cyclophosphamide, SCH 66336, R115777, L778,123, BMS 214662, Iressa, Tarceva, antibodies to EGFR, Gleevec™, intron, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, ELOXATIN™, Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Fulvestrant, Ifosfomide, Rituximab, C225, Campath, Clofarabine, cladribine, aphidicolon, rituxan, sunitinib, dasatinib, tezacitabine, Sml1, fludarabine, pentostatin, triapine, didox, trimidox, amidox, 3-AP, MDL-101,731, and bendamustine (Treanda).

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include compounds, and their pharmaceutically acceptable salts, as disclosed in WO 03/037347, WO 03/099771, and WO 04/046120.

Example suitable RAF inhibitors include compounds, and their pharmaceutically acceptable salts, as disclosed in WO 00/09495 and WO 05/028444.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable mTOR inhibitors include compounds, and their pharmaceutically acceptable salts, as disclosed in WO 2011/025889.

In some embodiments, the compounds of the invention can be used in combination with one or more other kinase inhibitors including imatinib, particularly for treating patients resistant to imatinib or other kinase inhibitors.

In some embodiments, the compounds of the invention can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a PI3K inhibitor of the present invention with an additional agent. Furthermore, resistance of multiple myeloma cells to agents such as dexamethasone may be reversible upon treatment with the PI3K inhibitor of the present invention. The agents can be combined with the present compound in a single or continuous dosage form, or the agents can be administered simultaneously or sequentially as separate dosage forms.

In some embodiments, a corticosteroid such as dexamethasone is administered to a patient in combination with the compounds of the invention where the dexamethasone is administered intermittently as opposed to continuously.

In some further embodiments, combinations of the compounds of the invention with other therapeutic agents can be administered to a patient prior to, during, and/or after a bone marrow transplant or stem cell transplant.

Pharmaceutical Formulations and Dosage Forms

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions of the invention contain from about 5 to about 50 mg of the active ingredient. One having ordinary skill in the art will appreciate that this embodies compositions containing about 5 to about 10, about 10 to about 15, about 15 to about 20, about 20 to about 25, about 25 to about 30, about 30 to about 35, about 35 to about 40, about 40 to about 45, or about 45 to about 50 mg of the active ingredient.

In some embodiments, the compositions of the invention contain from about 50 to about 500 mg of the active ingredient. One having ordinary skill in the art will appreciate that this embodies compositions containing about 50 to about 100, about 100 to about 150, about 150 to about 200, about 200 to about 250, about 250 to about 300, about 350 to about 400, or about 450 to about 500 mg of the active ingredient.

In some embodiments, the compositions of the invention contain from about 500 to about 1000 mg of the active ingredient. One having ordinary skill in the art will appreciate that this embodies compositions containing about 500 to about 550, about 550 to about 600, about 600 to about 650, about 650 to about 700, about 700 to about 750, about 750 to about 800, about 800 to about 850, about 850 to about 900, about 900 to about 950, or about 950 to about 1000 mg of the active ingredient.

Similar dosages may be used of the compounds described herein in the methods and uses of the invention.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 mg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed herein.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating PI3K in tissue samples, including human, and for identifying PI3K ligands by inhibition binding of a labeled compound. Accordingly, the present invention includes PI3K assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro PI3K labeling and competition assays, compounds that incorporate $^3H$, $^{14}C$, $^{82}Br$, $^{125}I$, $^{131}I$, $^{35}S$ or will generally be most useful. For radio imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$. In some embodiments, one or more H atoms for any compound described herein is each replaced by a deuterium atom.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a PI3K by monitoring its concentration variation when contacting with the PI3K, through tracking of the labeling. For example, a test compound (labeled) can be evaluated for its ability to reduce binding of another compound which is known to bind to a PI3K (i.e., standard compound). Accordingly, the ability of a test compound to compete with the standard compound for binding to the PI3K directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present invention also includes pharmaceutical kits useful, for example, in the treatment or prevention of PI3K-associated diseases or disorders, such as cancer, which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner Those of skill in the art will readily recognize a variety of non-critical parameters which can be changed or modified to yield essentially the same results. The compounds of the Examples have been found to be PI3K inhibitors according to at least one assay described herein.

EXAMPLES

The example compounds below containing one or more chiral centers were obtained in racemate form or as isomeric mixtures, unless otherwise specified. Salt stoichiometry which is indicated any of the products below is meant only to indicate a probable stoichiometry, and should not be construed to exclude the possible formation of salts in other stoichiometries. The abbreviations "h" and "min" refer to hour(s) and minute(s), respectively.

Example 1

1-{1-[5-Chloro-3-(1-isopropylazetidin-3-yl)-2-methoxy-4-methylphenyl]ethyl}-3-methyl-1H-pyrazolo[3,4-d]pyrimidin-4-amine bis(trifluoroacetate)

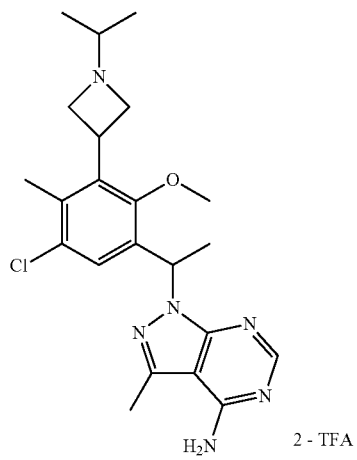 [SMILES: COc1c(C(C)n2nc(C)c3c(N)ncnc32)cc(Cl)c(C)c1C1CN(C(C)C)C1]

Step 1. 1-(5-Chloro-2-hydroxy-3-iodo-4-methylphenyl)ethanone

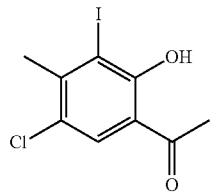

To a stirred solution of 1-(5-chloro-2-hydroxy-4-methylphenyl)ethanone (from Oakwood, 50.0 g, 271 mmol) in acetic acid (300 mL) was added N-iodosuccinimide (73.1 g, 325 mmol) and the resulting mixture was stirred on a heating mantle between 60~80° C. over 3.5 hours then cooled to room temperature and stirred overnight. Water (500 mL) was added to the mixture in portions, which caused a dark solid to form. After stirring for 10 minutes, the solids were filtered, washing with additional water. The light to dark brown solids were dried under vacuum for 4 hours then air dried over the weekend to give 81.3 g (97%) of the desired product. LCMS calculated for $C_9H_9ClIO_2$ (M+H)$^+$: m/z=310.9. Found: 311.0. $^1$H NMR (300 MHz, CDCl$_3$): δ 13.21 (s, 1H), 7.71 (s, 1H), 2.65 (s, 3H), 2.63 (s, 3H) ppm.

Step 2. 1-(5-Chloro-3-iodo-2-methoxy-4-methylphenyl)ethanone

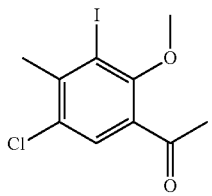

Potassium carbonate (72.4 g, 524 mmol) was added to a mixture of 1-(5-chloro-2-hydroxy-3-iodo-4-methylphenyl)ethanone (81.3 g, 262 mmol) and methyl iodide (19.6 mL, 314 mmol) in N,N-dimethylformamide (250 mL). The mixture was stirred at room temperature for 4 hours. Water (500 mL) was added and stirred for 15 minutes. The dark solids were filtered and dried in vacuo to give 42.3 g of the desired product. The filtrate was extracted with EtOAc (4×). The combined filtrates were washed with water (2×) and brine, dried (MgSO$_4$), filtered and concentrated. The solids were dried in vacuo to give an additional 37.2 g of the desired product. The product was used without further purification. LCMS calculated for $C_{10}H_{11}ClIO_2$ (M+H)$^+$: m/z=324.9. Found: 325.0. $^1$H NMR (300 MHz, CDCl$_3$): δ 7.62 (s, 1H), 3.78 (s, 3H), 2.65 (s, 3H), 2.62 (s, 3H) ppm.

Step 3. tert-Butyl 3-(3-acetyl-5-chloro-2-methoxy-6-methylphenyl)azetidine-1-carboxylate

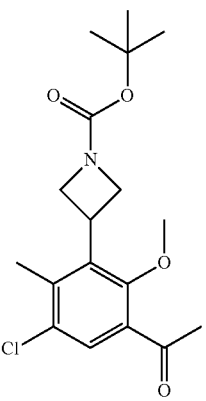 [SMILES: COc1c(C(C)=O)cc(Cl)c(C)c1C1CN(C(=O)OC(C)(C)C)C1]

Zinc (1.71 g, 26.2 mmol) was suspended in N,N-dimethylformamide (45.0 mL) and 1,2-dibromoethane (210 μL, 2.5 mmol) was added. The mixture was heated at 60° C. for 10 minutes and then cooled to room temperature. Chlorotrimethylsilane (330 μL, 2.6 mmol) was added and stirred at 60° C. for 10 minutes and cooled to room temperature. A solution of tert-butyl 3-iodoazetidine-1-carboxylate (from Oakwood, 6.25 g, 22.1 mmol) in N,N-dimethylformamide (5.0 mL) was then added and the mixture stirred at room temperature for 1 hour. 1-(5-chloro-3-iodo-2-methoxy-4-methylphenyl)ethanone (5.00 g, 15.4 mmol), tri-(2-furyl)phosphine (358 mg, 1.54 mmol), and tris(dibenzylideneacetone)dipalladium(0) (0.70 g, 0.77 mmol) were added in order and the reaction mixture was warmed to 70° C. and stirred overnight. The mixture was cooled to room temperature and partitioned between ethyl acetate (EtOAc) and sat. NH$_4$Cl solution. The layers were separated and the aqueous extracted further with EtOAc (2×). The combined organics were washed with water and brine, dried over MgSO$_4$, and concentrated. The residue was purified on silica gel, eluting with 0-30% EtOAc in hexanes to give 3.0 g (55%) of the desired product as an orange solid. LCMS calculated for C$_{18}$H$_{24}$ClNO$_4$Na (M+Na)$^+$: m/z=376.1. Found: 376.0. $^1$H NMR (400 MHz, CDCl$_3$): δ 7.52 (s, 1H), 4.32, (m, 2H), 4.16 (m, 3H), 3.66 (s, 3H), 2.59 (s, 3H), 2.31 (s, 3H), 1.45 (s, 9H) ppm.

Step 4. tert-Butyl 3-[3-chloro-5-(1-hydroxyethyl)-6-methoxy-2-methylphenyl]azetidine-1-carboxylate

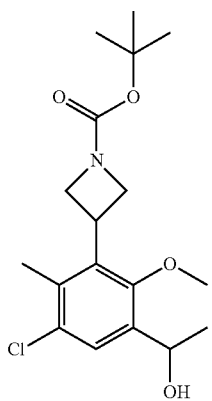 [SMILES: COc1c(C(C)O)cc(Cl)c(C)c1C1CN(C(=O)OC(C)(C)C)C1]

To a solution of tert-butyl 3-(3-acetyl-5-chloro-2-methoxy-6-methylphenyl)azetidine-1-carboxylate (1.3 g, 3.7 mmol) in methanol (20 mL) stirring at 0° C. was added sodium tetrahydroborate (0.167 g, 4.41 mmol). The mixture was stirred at 0~5° C. for 1 hour. The reaction was quenched with water and extracted with EtOAc (3×). The combined extracts were dried over MgSO$_4$, filtered and concentrated to give 1.3 g (100%) of the desired product. LCMS calculated for C$_{18}$H$_{26}$ClNO$_4$Na (M+Na)$^+$: m/z=378.2. Found: 378.1. $^1$H NMR (400 MHz, CDCl$_3$): δ 7.37 (s, 1H), 5.10 (q, 1H), 4.30 (m, 2H), 4.14 (m, 3H), 3.63 (s, 3H), 2.25 (s, 3H), 1.48 (d, 3H), 1.44 (s, 9H) ppm.

Step 5. tert-Butyl 3-[3-chloro-5-(1-chloroethyl)-6-methoxy-2-methylphenyl]azetidine-1-carboxylate

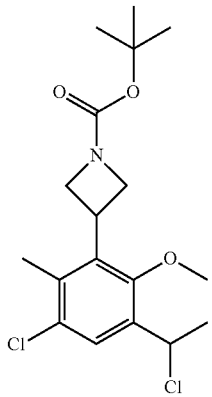 [SMILES: COc1c(C(C)Cl)cc(Cl)c(C)c1C1CN(C(=O)OC(C)(C)C)C1]

Cyanuric chloride (from Aldrich, 1.22 g, 6.62 mmol) was weighed into a flask and N,N-dimethylformamide (0.512 mL, 6.62 mmol) was added. After stirring for a few minutes a solution of tert-butyl 3-[3-chloro-5-(1-hydroxyethyl)-6-methoxy-2-methylphenyl]azetidine-1-carboxylate (1.5 g, 4.2 mmol) in methylene chloride (30 mL) was added. The resulting mixture was stirred at room temperature overnight. Water was added, and then diluted with dichloromethane. The layers were separated and the organics were washed with sat. NaHCO$_3$ solution, water, brine, dried over MgSO$_4$, and concentrated. The resulting residue was purified on silica gel, eluting with 0-35% EtOAc in hexanes to give the desired product (1.36 g, 86%). LCMS calculated for C$_{13}$H$_{17}$ClNO (M-Cl-Boc+H)$^+$: m/z=238.1. Found: 238.1. $^1$H NMR (400 MHz, CDCl$_3$): δ 7.46 (s, 1H), 5.44, (q, 1H), 4.32 (m, 2H), 4.18-4.10 (m, 3H), 3.67 (s, 3H), 2.27 (s, 3H), 1.79 (d, 3H), 1.44 (s, 9H) ppm.

Step 6. tert-Butyl 3-{3-[1-(4-amino-3-methyl-1H-pyrazolo[3,4-d]pyrimidin-1-yl)ethyl]-5-chloro-2-methoxy-6-methylphenyl}azetidine-1-carboxylate

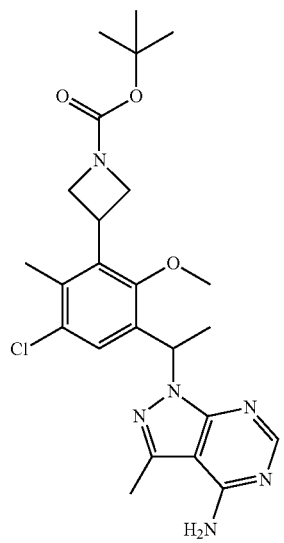 [SMILES: COc1c(C(C)n2nc(C)c3c(N)ncnc32)cc(Cl)c(C)c1C1CN(C(=O)OC(C)(C)C)C1]

At room temperature, sodium hydride (0.32 g, 8.0 mmol) was added to a suspension of 3-methyl-1H-pyrazolo[3,4-d]pyrimidin-4-amine (from ChemBridge, 0.59 g, 4.0 mmol) in N,N-dimethylformamide (20 mL). The resulting mixture was stirred at room temperature for 25 minutes during which time the suspension became a nearly clear solution. To the resultant mixture was added a solution of tert-butyl 3-[3-chloro-5-(1-chloroethyl)-6-methoxy-2-methylphenyl]azetidine-1-carboxylate (1.35 g, 3.61 mmol, from Example 1, step 5) in N,N-dimethylformamide (10 mL). The mixture was stirred at 50° C. overnight. After cooling, the mixture was diluted with water and extracted with EtOAc (2×). The combined extracts were washed with water and brine, dried over $MgSO_4$ and concentrated. The resulting residue was purified on silica gel, eluted with 0-10% MeOH in dichloromethane to give 1.03 g (59%) of the desired product as a yellow gum. The racemic products were applied on a Phenomenex Lux-Cellulose 2 column (21.1×250 mm, 5 micron particle size), eluting with 10% ethanol in hexanes at a flow rate of 18 mL/min, 4 mg/injection, to provide two enantiomers. The retention time of the first peak was 8.34 min and the retention time for the second peak was 10.92 min. Peak 1 (463 mg), LCMS calculated for $C_{24}H_{32}ClN_6O_3$ $(M+H)^+$: m/z=487.2. Found: 487.1. $^1$H NMR (400 MHz, $CDCl_3$): δ 8.21 (s, 1H), 7.37 (s, 1H), 6.30, (q, 1H), 5.40 (s, 2H), 4.23 (m, 2H), 4.17-4.00 (m, 3H), 3.57 (s, 3H), 2.58 (s, 3H), 2.16 (s, 3H), 1.76 (d, 3H), 1.37 (s, 9H) ppm.

Step 7. 1-[1-(3-Azetidin-3-yl-5-chloro-2-methoxy-4-methylphenyl)ethyl]-3-methyl-1H-pyrazolo[3,4-d]pyrimidin-4-amine dihydrochloride

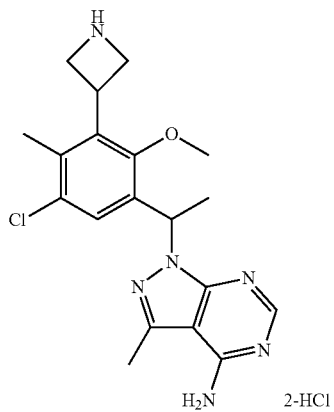 [SMILES: COc1c(C(C)n2nc(C)c3c(N)ncnc32)cc(Cl)c(C)c1C1CNC1]

To a solution of tert-butyl 3-{3-[1-(4-amino-3-methyl-1H-pyrazolo[3,4-d]pyrimidin-1-yl)ethyl]-5-chloro-2-methoxy-6-methylphenyl}azetidine-1-carboxylate (318 mg, 0.653 mmol) (peak 1 from above) in methylene chloride (3.2 mL) was added 4.0 M hydrogen chloride in 1,4-dioxane (1.6 mL, 6.5 mmol). The resulting mixture was stirred at room temperature for 75 minutes. The solvents were evaporated and the residue dried in vacuo to give 0.30 g of the desired product as the bis-HCl salt. LCMS calculated for $C_{19}H_{24}ClN_6O$ $(M+H)^+$: m/z=387.2. Found: 387.1.

Step 8. 1-{1-[5-Chloro-3-(1-isopropylazetidin-3-yl)-2-methoxy-4-methylphenyl]ethyl}-3-methyl-1H-pyrazolo[3,4-d]pyrimidin-4-amine bis(trifluoroacetate)

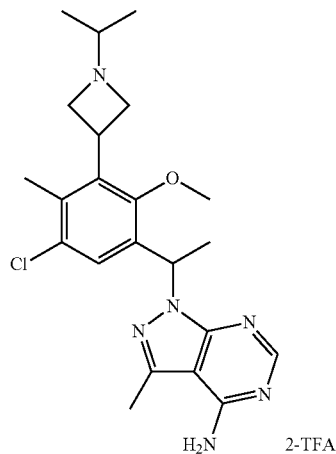 [SMILES: COc1c(C(C)n2nc(C)c3c(N)ncnc32)cc(Cl)c(C)c1C1CN(C(C)C)C1]

To a mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (58 mg, 0.13 mmol), acetone (18.5 µL, 0.252 mmol) and triethylamine (54.5 µL, 0.391 mmol) in methylene chloride (1.0 mL) was added resin of sodium triacetoxyborohydride (108 mg, 0.249 mmol). The resulting mixture was stirred for 3 hours at room temperature. The mixture was filtered and concentrated. The crude product was purified using RP-HPLC (XBridge C18 column, eluting with a gradient of acetonitrile/water containing 0.05% TFA, at flow rate of 30 mL/min) to give 50 mg (60%) of the desired product as the TFA salt. LCMS calculated for $C_{22}H_{30}ClN_6O$ $(M+H)^+$: m/z=429.2. Found: 429.1. The product was isolated as a single enantiomer. $^1$H NMR (500 MHz, DMSO-$d_6$): δ 8.47 (s, 1H), 7.46 (s, 1H), 6.29 (q, J=6.9 Hz, 1H), 4.52 (m, 2H), 4.21 (m, 1H), 4.15 (t, J=9.8 Hz, 1H), 4.06 (t, J=9.7 Hz, 1H), 3.53 (s, 3H), 3.39~3.27 (m, 1H), 2.61 (s, 3H), 2.11 (s, 3H), 1.75 (d, J=6.8 Hz, 3H), 1.11 (dd, J=6.0, 3.8 Hz, 6H) ppm.

Example 2

1-{1-[3-(1-Acetylazetidin-3-yl)-5-chloro-2-methoxy-4-methylphenyl]ethyl}-3-methyl-1H-pyrazolo[3,4-d]pyrimidin-4-amine trifluoroacetate

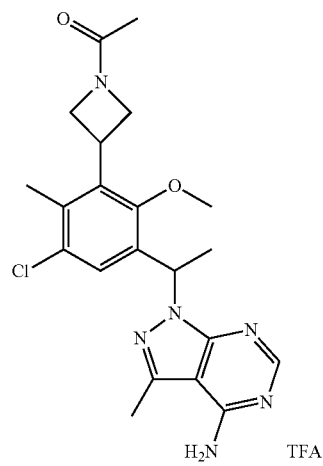 [SMILES: COc1c(C(C)n2nc(C)c3c(N)ncnc32)cc(Cl)c(C)c1C1CN(C(C)=O)C1 ; "TFA"]

Step 1. 1-[1-(3-azetidin-3-yl-5-chloro-2-methoxy-4-methylphenyl)ethyl]-3-methyl-1H-pyrazolo[3,4-d]pyrimidin-4-amine dihydrochloride

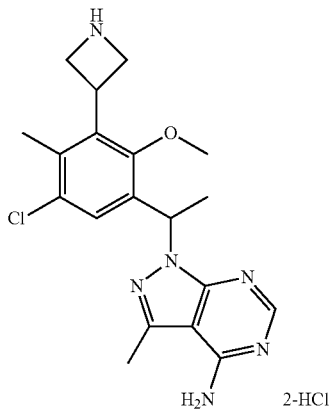 [SMILES: COc1c(C(C)n2nc(C)c3c(N)ncnc32)cc(Cl)c(C)c1C1CNC1]

To a solution of the racemic tert-butyl 3-{3-[1-(4-amino-3-methyl-1H-pyrazolo[3,4-d]pyrimidin-1-yl)ethyl]-5-chloro-2-methoxy-6-methylphenyl}azetidine-1-carboxylate (146 mg, 0.300 mmol) (racemic intermediate from Example 1 Step 6) in methylene chloride (1.5 mL) was added 4.0 M hydrogen chloride in 1,4-dioxane (0.75 mL, 3.0 mmol). After stirred at rt for 2 h, the solvents were evaporated and the resulting residue dried in vacuo to give 138 mg of the desired product as the HCl salt. LCMS calculated for $C_{19}H_{24}ClN_6O$ (M+H)$^+$: m/z=387.2. Found: 387.1.

Step 2. 1-{1-[3-(1-Acetylazetidin-3-yl)-5-chloro-2-methoxy-4-methylphenyl]ethyl}-3-methyl-1H-pyrazolo[3,4-d]pyrimidin-4-amine trifluoroacetate

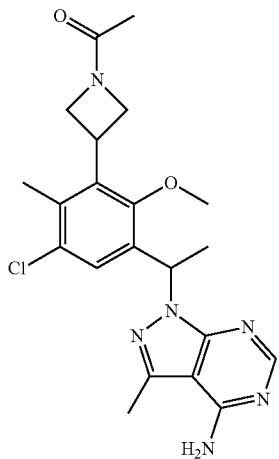 [SMILES: COc1c(C(C)n2nc(C)c3c(N)ncnc32)cc(Cl)c(C)c1C1CN(C(C)=O)C1]

To a mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (20.0 mg, 0.0435 mmol, from Example 2, step 1) and triethylamine (30.3 μL, 0.217 mmol) in methylene chloride (0.20 mL) was added acetyl chloride (6.18 μL, 0.0870 mmol). The resulting mixture was stirred overnight at room temperature. The solvents were evaporated and the crude purified using RP-HPLC (XBridge C18 column, eluting with a gradient of acetonitrile/water containing 0.05% TFA, at flow rate of 30 mL/min) to give the desired product as the TFA salt. The product was isolated as a racemic mixture. LCMS calculated for $C_{21}H_{26}ClN_6O_2$ (M+H)$^+$: m/z=429.2. Found: 429.1. $^1$H NMR (400 MHz, DMSO-d$_6$): δ 8.35 (s, 1H), 7.34 (s, 1H), 6.26 (q, 1H), 4.50 (m, 1H), 4.28~4.20 (m, 2H), 4.01 (m, 1H), 3.88 (m, 1H), 3.52 (s, 3H), 2.58 (s, 3H), 2.18 (s, 3H), 1.75~1.71 (m, 6H) ppm.

Example 3

1-{1-[5-Chloro-2-methoxy-4-methyl-3-(1-propionylazetidin-3-yl)phenyl]ethyl}-3-methyl-1H-pyrazolo[3,4-d]pyrimidin-4-amine trifluoroacetate

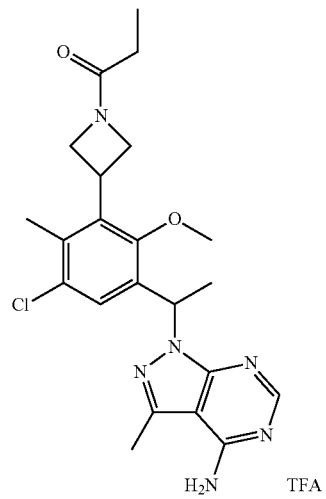 [SMILES: CCC(=O)N1CC(c2c(C)c(Cl)cc(C(C)n3nc(C)c4c(N)ncnc43)c2OC)C1 ; "TFA"]

This compound was prepared using procedures analogous to those for Example 2, with propanoyl chloride instead of acetyl chloride. The product was isolated as a racemic mixture. LCMS calculated for $C_{22}H_{28}ClN_6O_2$ (M+H)$^+$: m/z=443.2. Found: 443.2. $^1$H NMR (400 MHz, DMSO-d$_6$) δ 8.30 (s, 1H), 7.33 (s, 1H), 6.25 (q, 1H), 4.49 (m, 1H), 4.27~4.18 (m, 2H), 4.02 (m, 1H), 3.90 (m, 1H), 3.54 (s, 3H), 2.57 (s, 3H), 2.18 (s, 3H), 2.05 (q, 2H), 1.72 (d, 3H), 0.93 (t, 3H) ppm.

Example 4

1-(1-{5-Chloro-3-[1-(cyclopropylmethyl)azetidin-3-yl]-2-methoxy-4-methylphenyl}ethyl)-3-methyl-1H-pyrazolo[3,4-d]pyrimidin-4-amine bis(trifluoroacetate)

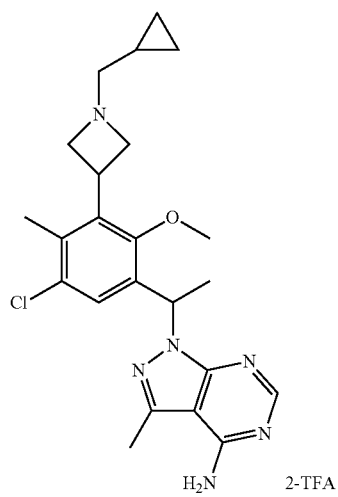 [SMILES: COc1c(C(C)n2nc(C)c3c(N)ncnc32)cc(Cl)c(C)c1C1CN(CC2CC2)C1]

This compound was prepared using procedures analogous to those for Example 1, with racemic 1-[1-(3-azetidin-3-yl- 5-chloro-2-methoxy-4-methylphenyl)ethyl]-3-methyl-1H-pyrazolo[3,4-d]pyrimidin-4-amine dihydrochloride from Example 2, Step 1 and cyclopropanecarboxaldehyde (from Aldrich) instead of acetone. The product was isolated as a racemic mixture. LCMS calculated for $C_{23}H_{30}ClN_6O$ (M+H)$^+$: m/z=441.2. Found: 441.1. $^1$H NMR (400 MHz, DMSO-$d_6$): δ 8.06 (s, 1H), 7.13 (s, 1H), 5.96 (q, 1H), 4.22 (m, 2H), 4.07 (m, 1H), 3.90 (m, 1H), 3.80 (m, 1H), 3.24 (s, 3H), 2.68 (t, 2H), 2.21 (s, 3H), 1.80 (s, 3H), 1.45 (d, 3H), 0.64 (m, 1H), 0.24 (m, 2H), 0.01 (m, 2H) ppm.

Example 5

1-{1-[5-chloro-2-methoxy-4-methyl-3-(1-methylazetidin-3-yl)phenyl]ethyl}-3-methyl-1H-pyrazolo[3,4-d]pyrimidin-4-amine

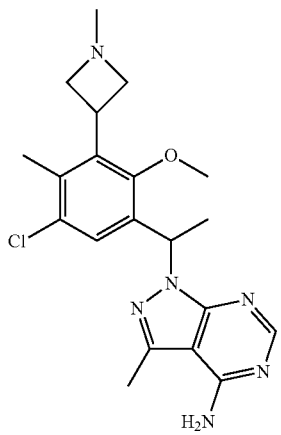 [SMILES: COc1c(C(C)n2nc(C)c3c(N)ncnc32)cc(Cl)c(C)c1C1CN(C)C1]

This compound was prepared using procedures analogous to those for Example 1, with racemic 1-[1-(3-azetidin-3-yl-5-chloro-2-methoxy-4-methylphenyl)ethyl]-3-methyl-1H-pyrazolo[3,4-d]pyrimidin-4-amine dihydrochloride from Example 2, Step 1 and formaldehyde instead of acetone. The crude purified using RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{20}H_{26}ClN_6O$ (M+H)$^+$: m/z=401.2. Found: 401.2.

Example 6

1-{1-[5-Chloro-3-(1-ethylazetidin-3-yl)-2-methoxy-4-methylphenyl]ethyl}-3-methyl-1H-pyrazolo[3,4-d]pyrimidin-4-amine

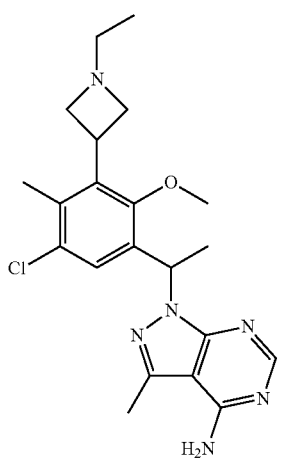 [SMILES: CCN1CC(c2c(C)c(Cl)cc(C(C)n3nc(C)c4c(N)ncnc43)c2OC)C1]

This compound was prepared using procedures analogous to those for Example 1, with racemic 1-[1-(3-azetidin-3-yl-5-chloro-2-methoxy-4-methylphenyl)ethyl]-3-methyl-1H-pyrazolo[3,4-d]pyrimidin-4-amine dihydrochloride from Example 2, Step 1 and acetaldehyde instead of acetone. The crude purified using RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{21}H_{28}ClN_6O$ (M+H)$^+$: m/z=415.2. Found: 415.1.

Example 7

1-{1-[5-Chloro-3-(1-isobutylazetidin-3-yl)-2-methoxy-4-methylphenyl]ethyl}-3-methyl-1H-pyrazolo[3,4-d]pyrimidin-4-amine

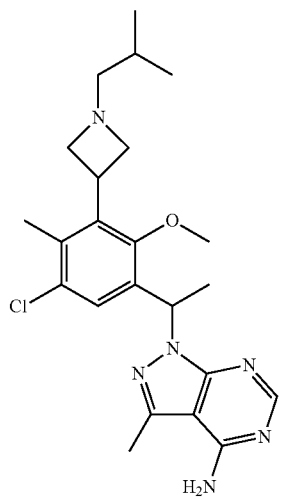 [SMILES: COc1c(C(C)n2nc(C)c3c(N)ncnc32)cc(Cl)c(C)c1C1CN(CC(C)C)C1]

This compound was prepared using procedures analogous to those for Example 1, with racemic 1-[1-(3-azetidin-3-yl-5-chloro-2-methoxy-4-methylphenyl)ethyl]-3-methyl-1H-pyrazolo[3,4-d]pyrimidin-4-amine dihydrochloride from Example 2, Step 1 and isobutyraldehyde instead of acetone. The crude purified using RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{23}H_{32}ClN_6O$ (M+H)$^+$: m/z=443.2. Found: 443.1. $^1$H NMR (400 MHz, CDCl$_3$): δ 8.29 (s, 1H), 7.38 (s, 1H), 6.37 (q, 1H), 5.37 (s, 2H), 4.01 (m, 2H), 3.87 (m, 1H), 3.57 (s, 3H), 3.05 (t, 1H), 2.86 (t, 1H), 2.64 (s, 3H), 2.18 (d, 2H), 2.11 (s, 3H), 1.82 (d, 3H), 1.62 (m, 1H), 0.89 (d, 6H) ppm.

Example 8

1-{1-[3-(1-sec-butylazetidin-3-yl)-5-chloro-2-methoxy-4-methylphenyl]ethyl}-3-methyl-1H-pyrazolo[3,4-d]pyrimidin-4-amine

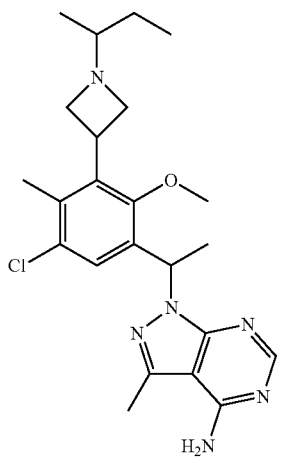 [SMILES: CCC(C)N1CC(c2c(C)c(Cl)cc(C(C)n3nc(C)c4c(N)ncnc43)c2OC)C1]

This compound was prepared using procedures analogous to those for Example 1, with racemic 1-[1-(3-azetidin-3-yl-5-chloro-2-methoxy-4-methylphenyl)ethyl]-3-methyl-1H-pyrazolo[3,4-d]pyrimidin-4-amine dihydrochloride from Example 2, Step 1 and 2-butanone instead of acetone. The crude was purified using RP-HPLC (XBridge C18 column, eluting with a gradient of acetonitrile/water containing 0.1% ammonium hydroxide, at flow rate of 30 mL/min) to give the desired product. The product was isolated as a mixture of diastereomers. LCMS calculated for $C_{23}H_{32}ClN_6O$ $(M+H)^+$: m/z=443.2. Found: 443.1.

Example 9

1-(1-{5-Chloro-2-methoxy-3-[1-(2-methoxyethyl)azetidin-3-yl]-4-methylphenyl}ethyl)-3-methyl-1H-pyrazolo[3,4-d]pyrimidin-4-amine

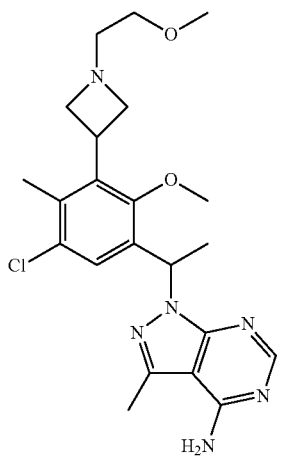 [SMILES: COCCN1CC(c2c(C)c(Cl)cc(C(C)n3nc(C)c4c(N)ncnc43)c2OC)C1]

This compound was prepared using procedures analogous to those for Example 1, with racemic 1-[1-(3-azetidin-3-yl-5-chloro-2-methoxy-4-methylphenyl)ethyl]-3-methyl-1H-pyrazolo[3,4-d]pyrimidin-4-amine dihydrochloride from Example 2, Step 1 and methoxyacetaldehyde instead of acetone. The crude was purified using RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{22}H_{30}ClN_6O_2$ $(M+H)^+$: m/z=445.2. Found: 445.2.

Example 10

3-{3-[1-(4-Amino-3-methyl-1H-pyrazolo[3,4-d]pyrimidin-1-yl)ethyl]-5-chloro-2-methoxy-6-methylphenyl}-N-methylazetidine-1-carboxamide

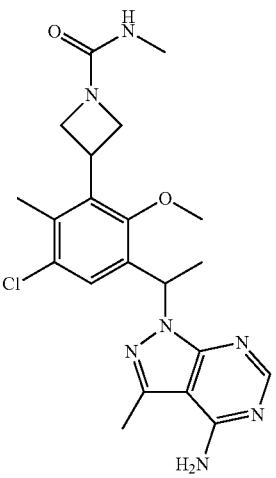 [SMILES: CNC(=O)N1CC(c2c(C)c(Cl)cc(C(C)n3nc(C)c4c(N)ncnc43)c2OC)C1]

This compound was prepared using procedures analogous to those for Example 2, with methyl isocyanate instead of acetyl chloride. The crude purified using RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{21}H_{27}ClN_7O_2$ $(M+H)^+$: m/z=444.2. Found: 444.2.

Example 11

5-{3-[1-(4-Amino-3-methyl-1H-pyrazolo[3,4-d]pyrimidin-1-yl)ethyl]-5-chloro-2-methoxy-6-methylphenyl}-N,N-dimethylpyridine-2-carboxamide bis(trifluoroacetate)

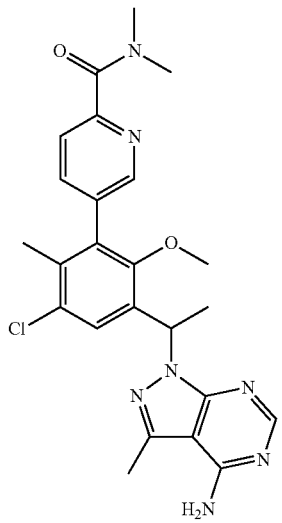

Step 1. 1-(3-Bromo-5-chloro-2-methoxy-4-methyl-phenyl)ethanone

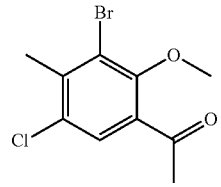

To a stirred solution of 1-(5-chloro-2-methoxy-4-methylphenyl)ethanone (5.00 g, 25.2 mmol, from Oakwood) in acetic acid (100 mL) was added N-bromosuccinimide (4.93 g, 27.7 mmol) and the resulting mixture heated at 100° C. for 18 hours. After cooling to ambient temperature, the reaction mixture was concentrated in vacuo, then neutralized with sat. sodium bicarbonate, filtered off insoluble succinimide. The filtrate was extracted with EtOAc. The combined organic layers were washed with brine, dried over sodium sulfate, and then concentrated to dryness under reduced pressure. The residue was purified on silica gel, eluting with 0 to 50% EtOAc in hexanes, to give the desired products (2.66 g, 38%). LCMS calculated for $C_{10}H_{11}BrClO_2(M+H)^+$: m/z=277.0. found: 277.0. $^1$H NMR (DMSO-$d_6$, 300 MHz): δ 7.70 (1H, s), 3.77 (3H, s), 2.57 (3H, s), 2.50 (3H, s) ppm.

Step 2. 5-(3-Acetyl-5-chloro-2-methoxy-6-methylphenyl)-N,N-dimethylpyridine-2-carboxamide

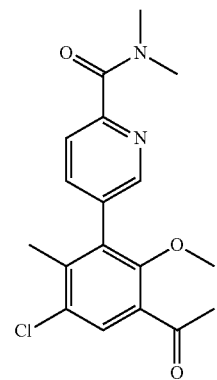

To a mixture of 1-(3-bromo-5-chloro-2-methoxy-4-methylphenyl)ethanone (0.38 g, 1.4 mmol) and N,N-dimethyl-5-(4,4,5,5-tetramethyl-1,3,2-dioxaborolan-2-yl)pyridine-2-carboxamide (from PepTech, 0.46 g, 1.6 mmol) in 1,4-dioxane (6 mL), potassium carbonate (0.38 g, 2.7 mmol) in water (2 mL) was added. The reaction mixture was bubbled with $N_2$. Tetrakis(triphenylphosphine)palladium(0) (0.095 g, 0.082 mmol) was added and the reaction was stirred overnight at 100° C. The reaction was diluted with water, extracted with EtOAc. The combined organic layers were dried over $MgSO_4$, concentrated and purified on silica gel (eluting with 0-100% EtOAc in hexanes) to give the desired product. LCMS calculated for $C_{18}H_{20}ClN_2O_3$ $(M+H)^+$: m/z=347.1. Found: 347.1.

Step 3. 5-[3-chloro-5-(1-hydroxyethyl)-6-methoxy-2-methylphenyl]-N,N-dimethylpyridine-2-carboxamide

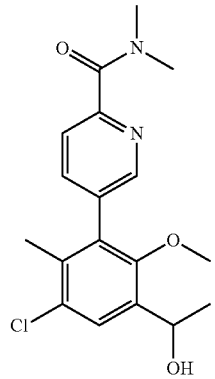

To a solution of 5-(3-acetyl-5-chloro-2-methoxy-6-methylphenyl)-N,N-dimethylpyridine-2-carboxamide (106 mg, 0.306 mmol) in methanol (2 mL) cooled at 0° C. was added sodium tetrahydroborate (14 mg, 0.37 mmol). The mixture was stirred at room temperature for 1 hour, then quenched with water, extracted with EtOAc. The organic layers were dried over $MgSO_4$ and concentrated to give crude alcohol. LCMS calculated for $C_{18}H_{22}ClN_2O_3$ $(M+H)^+$: m/z=349.1. Found: 349.1.

Step 4. 5-[3-chloro-5-(1-chloroethyl)-6-methoxy-2-methylphenyl]-N,N-dimethylpyridine-2-carboxamide

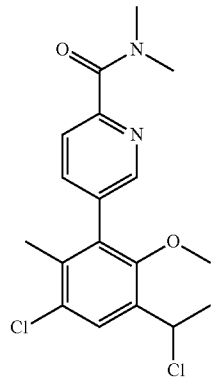

Cyanuric chloride (85 mg, 0.46 mmol) was added to N,N-dimethylformamide (0.036 mL, 0.46 mmol) at room temperature. After the formation of a white solid (10 minutes), methylene chloride (2 mL) was added, followed by 5-[3-chloro-5-(1-hydroxyethyl)-6-methoxy-2-methylphenyl]-N,N-dimethylpyridine-2-carboxamide (115 mg, 0.330 mmol, from Example 11, step 3). After the addition, the mixture was stirred at room temperature overnight. Water was added, and then diluted with dichloromethane. The organic phase was washed with sat. $NaHCO_3$ solution, water and brine, then dried over $MgSO_4$, concentrated. The residue was purified on silica gel (eluting with 0 to 80% EtOAc in hexanes) to give the desired product (76 mg, 63%). LCMS calculated for $C_{18}H_{21}Cl_2N_2O_2$ $(M+H)^+$: m/z=367.1. Found: 367.0.

93

Step 5. 5-{3-[1-(4-Amino-3-methyl-1H-pyrazolo[3,4-c]pyrimidin-1-yl)ethyl]-5-chloro-2-methoxy-6-methylphenyl}-N,N-dimethylpyridine-2-carboxamide bis(trifluoroacetate)

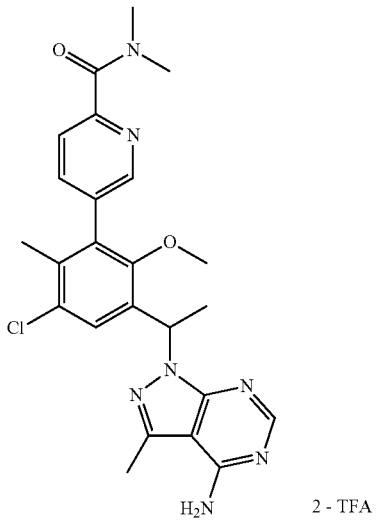 [SMILES: COc1c(C(C)n2nc(C)c3c(N)ncnc32)cc(Cl)c(C)c1-c1ccc(C(=O)N(C)C)nc1]

To a solution of 3-methyl-1H-pyrazolo[3,4-d]pyrimidin-4-amine (6.1 mg, 0.041 mmol) in N,N-dimethylformamide (0.4 mL) was added sodium hydride (60%, 2.0 mg, 0.082 mmol) at 0° C. and the mixture was stirred at room temperature for 10 minutes. To the resultant mixture was added a solution of 5-[3-chloro-5-(1-chloroethyl)-6-methoxy-2-methylphenyl]-N,N-dimethylpyridine-2-carboxamide (15.0 mg, 0.0408 mmol) in N,N-dimethylformamide (0.2 mL). The mixture was stirred at room temperature overnight. The crude mixture was purified on RP-HPLC (XBridge C18 column, eluting with a gradient of acetonitrile/water containing 0.05% TFA, at flow rate of 30 mL/min) to give the desired product as bis-TFA salt. The product was isolated as a racemic mixture. LCMS calculated for $C_{24}H_{27}ClN_7O_2$ (M+H)$^+$: m/z=480.2. Found: 480.1.

Example 12

5-{3-[1-(4-Amino-7H-pyrrolo[2,3-d]pyrimidin-7-yl)ethyl]-5-chloro-2-methoxy-6-methylphenyl}-N,N-dimethylpyridine-2-carboxamide trifluoroacetate

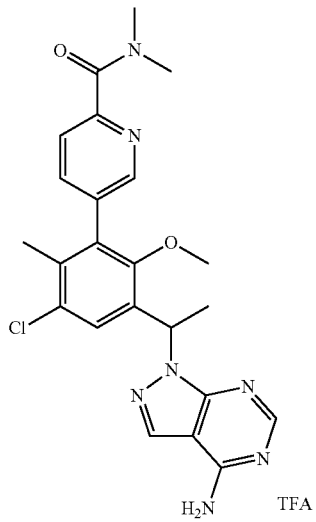 [SMILES: COc1c(C(C)n2ncc3c(N)ncnc32)cc(Cl)c(C)c1-c1ccc(C(=O)N(C)C)nc1]

94

To a mixture of 7H-pyrrolo[2,3-d]pyrimidin-4-amine sulfate (from Oakwood, 20 mg, 0.086 mmol), cesium carbonate (42 mg, 0.13 mmol) and potassium iodide (1.4 mg, 0.0086 mmol) in N,N-dimethylformamide (0.91 mL) was added 5-[3-chloro-5-(1-chloroethyl)-6-methoxy-2-methylphenyl]-N,N-dimethylpyridine-2-carboxamide (32 mg, 0.086 mmol) and the resulting mixture was stirred at 140° C. for 1 hour. The mixture was diluted with methanol and purified on RP-HPLC (XBridge C18 column, eluting with a gradient of acetonitrile/water containing 0.05% TFA, at flow rate of 30 mL/min) to give the desired product. The product was isolated as a racemic mixture. LCMS calculated for $C_{24}H_{26}ClN_6O_2$ (M+H)$^+$: m/z=465.2. Found: 465.1.

Example 13

1-{1-[5-Chloro-4-fluoro-3-(1-isopropylazetidin-3-yl)-2-methoxyphenyl]ethyl}-3-methyl-1H-pyrazolo[3,4-d]pyrimidin-4-amine bis(trifluoroacetate)

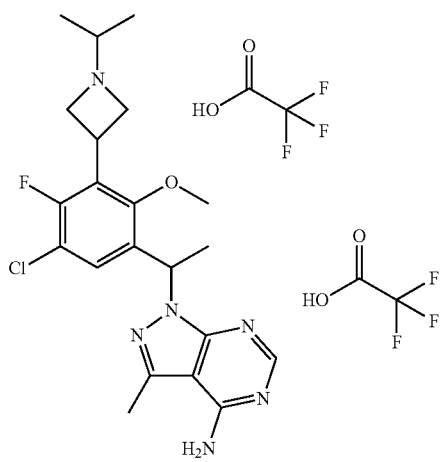 [SMILES: COc1c(C(C)n2nc(C)c3c(N)ncnc32)cc(Cl)c(F)c1C1CN(C(C)C)C1 ; O=C(O)C(F)(F)F ; O=C(O)C(F)(F)F]

Step 1.
1-(5-Chloro-4-fluoro-2-hydroxyphenyl)ethanone

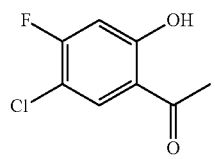

To 4-chloro-3-fluorophenol (from Aldrich, 20 g, 100 mmol) was added acetyl chloride (14.1 mL, 199 mmol) under $N_2$ with stirring. The resulting mixture turned into a clear solution at room temperature quickly and it was heated at 60° C. for 2 hours. To the resultant mixture was added aluminum trichloride (25.0 g, 187 mmol) in portions and the reaction mixture was heated at 180° C. for 30 minutes. The solids slowly dissolved at high temperature. The reaction mixture was then cooled to room temperature while the flask was swirled carefully in order for the solid to form a thin layer inside the flask and then slowly quenched with 1.0 N HCl (300 mL) while cooling in an ice-bath and stirred overnight. The yellow precipitate was washed with water and dried under vacuum to give the desired product as a yellow solid (23.8 g), which was directly used in the next step without further purification.

Step 2. 1-(5-Chloro-4-fluoro-2-hydroxy-3-iodophenyl)ethanone

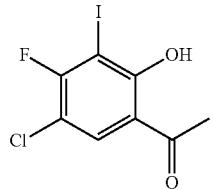

A solution of 1-(5-chloro-4-fluoro-2-hydroxyphenyl)ethanone (23.8 g, 126 mmol) in acetic acid (100 mL) was treated with N-iodosuccinimide (34.1 g, 151 mmol) and stirred at 70° C. for 2 hr. The reaction mixture was concentrated, diluted with EtOAc and quenched with sat. NaHCO$_3$ solution until the bubbling stopped. The organic layers were separated, washed with water, dried over MgSO$_4$ and stripped to give the desired product which was used in the next step without further purification.

Step 3. 1-(5-Chloro-4-fluoro-3-iodo-2-methoxyphenyl)ethanone

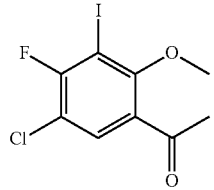

1-(5-Chloro-4-fluoro-2-hydroxy-3-iodophenyl)ethanone (13 g, 41 mmol) was dissolved in N,N-dimethylformamide (41.3 mL). Methyl iodide (3.9 mL, 62 mmol) was added followed by potassium carbonate (11 g, 83 mmol). The reaction was heated at 60° C. for 1 hour. The mixture was cooled to room temperature, diluted with ether. The organic layers were separated and combined, washed with water, dried over MgSO$_4$, concentrated and purified on silica gel (eluting with 0 to 10% EtOAc in hexanes) to give the desired product (10 g, 70%). LCMS calculated for C$_9$H$_8$ClFIO$_2$ (M+H)$^+$: m/z=328.9. Found: 328.9.

Step 4. tert-Butyl 3-(3-acetyl-5-chloro-6-fluoro-2-methoxyphenyl)azetidine-1-carboxylate

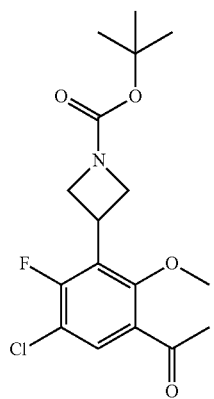 [SMILES: COc1c(C(C)=O)cc(Cl)c(F)c1C1CN(C(=O)OC(C)(C)C)C1]

Zinc (0.682 g, 10.4 mmol) was suspended with 1,2-dibromoethane (0.0598 mL, 0.694 mmol) in N,N-dimethylformamide (12 mL). The mixture was heated at 70° C. for 10 minutes and then cooled to room temperature. Chlorotrimethylsilane (0.088 mL, 0.69 mmol) was added dropwise and stirring was continued for 1 hour. A solution of tert-butyl 3-iodoazetidine-1-carboxylate (2.5 g, 8.7 mmol) in N,N-dimethylformamide (10 mL) was then added and the mixture was heated at 40° C. for 1 hour before a mixture of 1-(5-chloro-4-fluoro-3-iodo-2-methoxyphenyl)ethanone (3.0 g, 9.1 mmol), tris(dibenzylideneacetone)dipalladium(0) (0.16 g, 0.17 mmol) and tri-(2-furyl)phosphine (0.081 g, 0.35 mmol) in N,N-dimethylformamide (20 mL) was added. The reaction mixture was warmed to 70° C. and stirred overnight. The mixture was then cooled to room temperature and partitioned between ether and sat. NH$_4$Cl solution. The organic layers were washed with water, dried over MgSO$_4$, concentrated and purified on silica gel (eluting with 0 to 25% EtOAc in hexanes) to give the desired product (0.8 g). LCMS calculated for C$_{17}$H$_{21}$ClFNO$_4$Na (M+Na)$^+$: m/z=380.1. Found: 380.1.

Step 5. tert-Butyl 3-[3-chloro-2-fluoro-5-(1-hydroxyethyl)-6-methoxyphenyl]azetidine-1-carboxylate

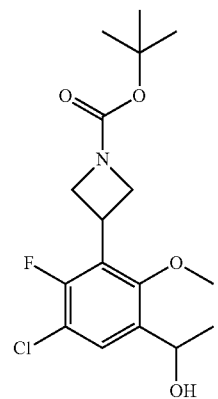

To a solution of tert-butyl 3-(3-acetyl-5-chloro-6-fluoro-2-methoxyphenyl)azetidine-1-carboxylate (0.17 g, 0.48 mmol) in methanol (3 mL) cooled at 0° C. was added sodium tetrahydroborate (0.022 g, 0.57 mmol). The mixture was stirred at room temperature for 1 hour, then quenched with water, extracted with EtOAc. The organic layers were combined, dried over MgSO$_4$ and concentrated to give the crude alcohol (0.19 g). LCMS calculated for C$_{17}$H$_{23}$ClFNO$_4$Na (M+Na)$^+$: m/z=382.1. Found: 382.0.

Step 6. tert-Butyl 3-[3-chloro-5-(1-chloroethyl)-2-fluoro-6-methoxyphenyl]azetidine-1-carboxylate

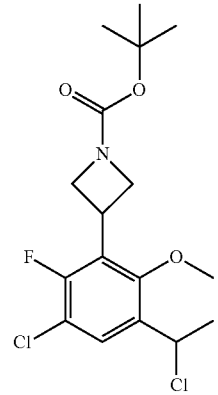

Cyanuric chloride (140 mg, 0.78 mmol) was added to N,N-dimethylformamide (0.059 mL, 0.77 mmol) at room temperature. After the formation of a white solid (ca. 10 minutes), methylene chloride (4 mL) was added, followed by tert-butyl 3-[3-chloro-2-fluoro-5-(1-hydroxyethyl)-6-methoxyphenyl]azetidine-1-carboxylate (197 mg, 0.547 mmol). After addition, the mixture was stirred at room temperature overnight. Water was added, and then diluted with dichloromethane. The organic phases were washed with sat. NaHCO₃ solution, water and brine, dried over MgSO₄, and concentrated. The resulting residue was purified on silica gel (eluting with 0 to 30% EtOAc in hexanes) to give the desired product (110 mg, 53%).

Step 7. tert-Butyl 3-{3-[1-(4-amino-3-methyl-1H-pyrazolo[3,4-d]pyrimidin-1-yl)ethyl]-5-chloro-6-fluoro-2-methoxyphenyl}azetidine-1-carboxylate

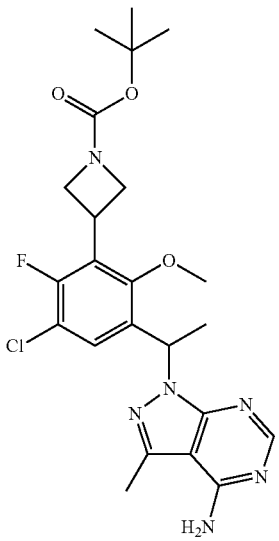 [SMILES: COc1c(C(C)n2nc(C)c3c(N)ncnc32)cc(Cl)c(F)c1C1CN(C(=O)OC(C)(C)C)C1]

To a solution of 3-methyl-1H-pyrazolo[3,4-d]pyrimidin-4-amine (7.9 mg, 0.053 mmol) in N,N-dimethylformamide (0.6 mL) was added sodium hydride (60%, 2.5 mg, 0.11 mmol) at 0° C. and the mixture was stirred at room temperature for 10 minutes. To the mixture was added a solution of tert-butyl 3-[3-chloro-5-(1-chloroethyl)-2-fluoro-6-methoxyphenyl]azetidine-1-carboxylate (20 mg, 0.053 mmol) in N,N-dimethylformamide (0.3 mL). The reaction mixture was stirred at 35° C. overnight, then quenched with water, extracted with ether. The combined organic layers were dried over MgSO₄ and concentrated to afford the desired product which was used in next step directly. LCMS calculated for $C_{23}H_{29}ClFN_6O_3$ (M+H)⁺: m/z=491.2. Found: 491.1.

Step 8. 1-{1-[5-Chloro-4-fluoro-3-(1-isopropylazetidin-3-yl)-2-methoxyphenyl]ethyl}-3-methyl-1H-pyrazolo[3,4-d]pyrimidin-4-amine bis(trifluoroacetate)

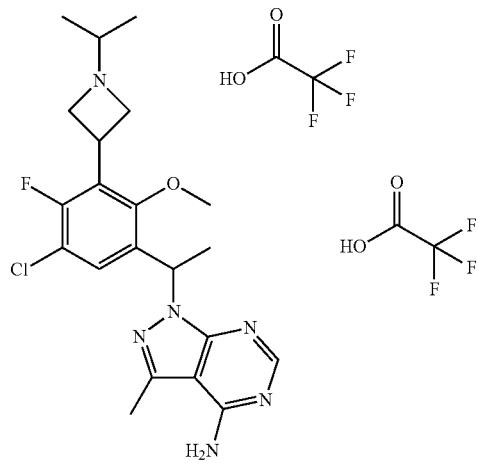 [SMILES: COc1c(C(C)n2nc(C)c3c(N)ncnc32)cc(Cl)c(F)c1C1CN(C(C)C)C1 ; O=C(O)C(F)(F)F ; O=C(O)C(F)(F)F]

A mixture of tert-butyl 3-{3-[1-(4-amino-3-methyl-1H-pyrazolo[3,4-d]pyrimidin-1-yl)ethyl]-5-chloro-6-fluoro-2-methoxyphenyl}azetidine-1-carboxylate (14 mg, 0.028 mmol) in methylene chloride (0.2 mL) was treated with 4.0 M hydrogen chloride in dioxane (0.2 mL, 0.8 mmol) at room temperature for 1 hour and then the solvent removed to give 1-[1-(3-azetidin-3-yl-5-chloro-4-fluoro-2-methoxyphenyl)ethyl]-3-methyl-1H-pyrazolo[3,4-d]pyrimidin-4-amine HCl salt. To a mixture of the crude HCl salt in acetonitrile (0.1 mL)/methanol (0.1 mL)/tetrahydrofuran (0.1 mL) was added N,N-diisopropylethylamine (0.1 mL, 0.6 mmol), followed by acetone (0.050 mL, 0.68 mmol). The mixture was stirred for 30 minutes before the addition of sodium triacetoxyborohydride (0.030 g, 0.14 mmol). The reaction was stirred at room temperature overnight, then quenched and purified on RP-HPLC (XBridge C18 column, eluting with a gradient of acetonitrile/water containing 0.05% TFA, at flow rate of 30 mL/min) to give the desired product as TFA salt. The product was isolated as a racemic mixture. LCMS calculated for $C_{21}H_{27}ClFN_6O$ (M+H)⁺: m/z=433.2. Found: 433.1.

Example 14

5-{3-[1-(4-Amino-3-methyl-1H-pyrazolo[3,4-d]pyrimidin-1-yl)ethyl]-5-chloro-2-ethoxy-6-methylphenyl}-N,N-dimethylpyridine-2-carboxamide bis(trifluoroacetate)

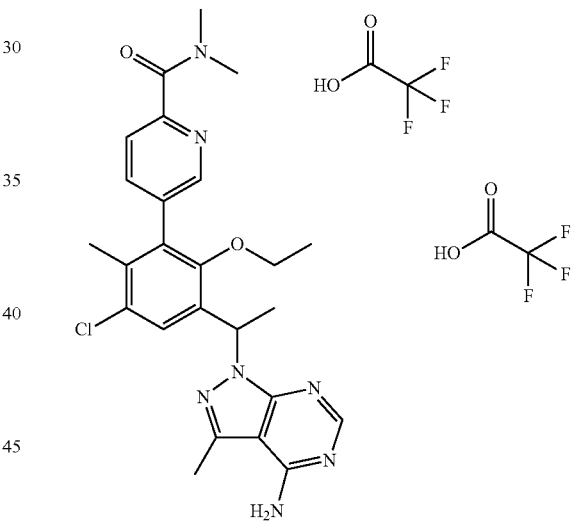

Step 1. 1-(5-Chloro-2-ethoxy-3-iodo-4-methylphenyl)ethanone

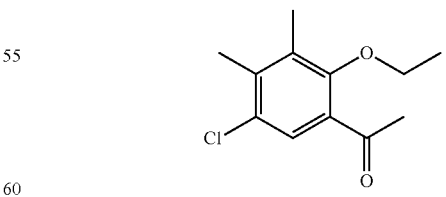

1-(5-Chloro-2-hydroxy-3-iodo-4-methylphenyl)ethanone (18.9 g, 60.9 mmol) (from Example 1, Step 1) was dissolved in N,N-dimethylformamide (60.8 mL). Iodoethane (7.3 mL, 91 mmol) was added followed by potassium carbonate (17 g, 120 mmol). The reaction was heated at 60° C. for 1 hour. The mixture was cooled to room temperature, diluted with ether. The organic layers were combined, washed with water, dried over MgSO₄, concentrated and purified on silica gel (eluting with 0-10% EtOAc in hexanes) to give the desired product (18.9 g, 91.7%). LCMS calculated for $C_{11}H_{13}ClIO_2$ (M+H)⁺: m/z=339.0. Found: 339.0.

Step 2. 5-(3-Acetyl-5-chloro-2-ethoxy-6-methylphenyl)-N,N-dimethylpyridine-2-carboxamide

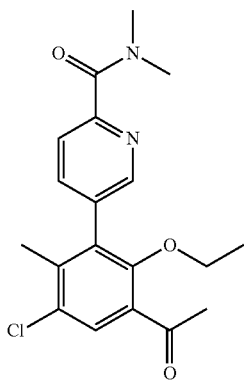 [SMILES: CCOc1c(C(C)=O)cc(Cl)c(C)c1-c1ccc(C(=O)N(C)C)nc1]

To a mixture of 1-(5-chloro-2-ethoxy-3-iodo-4-methylphenyl)ethanone (0.69 g, 2.0 mmol) and N,N-dimethyl-5-(4,4,5,5-tetramethyl-1,3,2-dioxaborolan-2-yl)pyridine-2-carboxamide (0.68 g, 2.4 mmol) in 1,4-dioxane (10 mL), potassium carbonate (0.56 g, 4.1 mmol) in water (3 mL, 200 mmol) was added. The reaction was bubbled with N₂. Tetrakis(triphenylphosphine)palladium(0) (0.24 g, 0.20 mmol) was added and N₂ was bubbled. Reaction was stirred overnight at 95° C. The reaction was diluted with water, extracted with EtOAc. The combined organic layers were dried over MgSO₄, concentrated and purified on silica gel (eluting with 0 to 90% EtOAc in hexanes) to give the desired product (0.6 g, 82%). LCMS calculated for $C_{19}H_{22}ClN_2O_3$ (M+H)⁺: m/z=361.1. Found: 361.0.

Step 3. 5-[3-Chloro-6-ethoxy-5-(1-hydroxyethyl)-2-methylphenyl]-N,N-dimethylpyridine-2-carboxamide

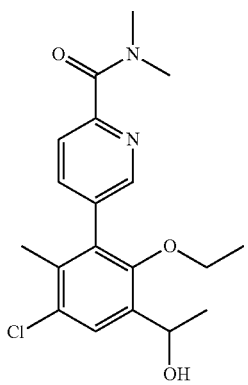 [SMILES: CCOc1c(C(C)O)cc(Cl)c(C)c1-c1ccc(C(=O)N(C)C)nc1]

To a solution of 5-(3-acetyl-5-chloro-2-ethoxy-6-methylphenyl)-N,N-dimethylpyridine-2-carboxamide (0.60 g, 1.7 mmol) in methanol (10 mL) cooled at 0° C. was added sodium tetrahydroborate (0.075 g, 2.0 mmol). The mixture was stirred at room temperature for 1 hour, then quenched with water, extracted with EtOAc. The extracts were dried over MgSO₄ and concentrated to give crude alcohol (0.6 g). LCMS calculated for $C_{19}H_{24}ClN_2O_3$ (M+H)⁺: m/z=363.1. Found: 363.0.

Step 4. 5-[3-Chloro-5-(1-chloroethyl)-6-ethoxy-2-methylphenyl]-N,N-dimethylpyridine-2-carboxamide

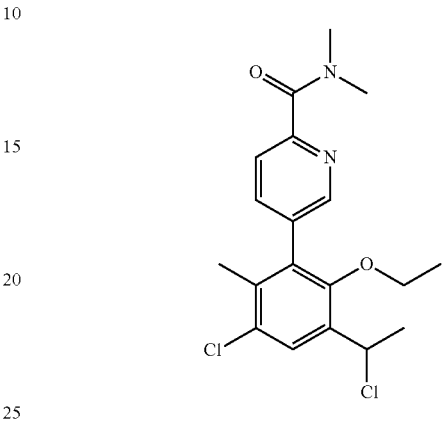

Cyanuric chloride (0.43 g, 2.3 mmol) was added to N,N-dimethylformamide (0.18 mL, 2.3 mmol) at room temperature. After the formation of a white solid (10 minutes), methylene chloride (10 mL) was added, followed by 5-[3-chloro-6-ethoxy-5-(1-hydroxyethyl)-2-methylphenyl]-N,N-dimethylpyridine-2-carboxamide (0.6 g, 2 mmol). After addition, the mixture was stirred at room temperature overnight, then diluted with dichloromethane and washed with sat. NaHCO₃ solution. The organic layers were dried over MgSO₄, concentrated. The residue was purified on silica gel (eluting with 0 to 50% EtOAc in hexanes) to give the desired product (0.58, 90%). LCMS calculated for $C_{19}H_{23}Cl_2NO_2$ (M+H)⁺: m/z=381.1. Found: 381.0.

Step 5. 5-{3-[1-(4-Amino-3-methyl-1H-pyrazolo[3,4-c]pyrimidin-1-yl)ethyl]-5-chloro-2-ethoxy-6-methylphenyl}-N,N-dimethylpyridine-2-carboxamide bis(trifluoroacetate)

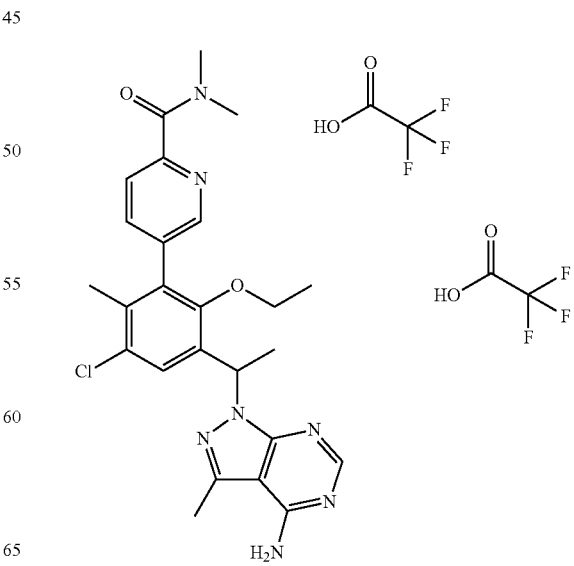

To a solution of 3-methyl-1H-pyrazolo[3,4-d]pyrimidin-4-amine (47 mg, 0.31 mmol) in N,N-dimethylformamide (3 mL) was added sodium hydride (60%, 12.6 mg, 0.524 mmol) at 0° C. and the resultant mixture was stirred at room temperature for 10 minutes. To the mixture was added a solution of 5-[3-chloro-5-(1-chloroethyl)-6-ethoxy-2-methylphenyl]-N,N-dimethylpyridine-2-carboxamide (100 mg, 0.3 mmol, from Example 14, step 4) in N,N-dimethylformamide (1 mL). The reaction was stirred at 35° C. overnight. The reaction was quenched and applied on RP-HPLC (XBridge C18 column, eluting with a gradient of acetonitrile/water containing 0.05% TFA, at flow rate of 30 mL/min) to give the desired product as bis-TFA salt. The product was isolated as a racemic mixture. LCMS calculated for $C_{25}H_{29}ClN_7O_2$ (M+H)$^+$: m/z=494.2. Found: 494.1.

Example 15

5-{3-[1-(4-Amino-3-iodo-1H-pyrazolo[3,4-d]pyrimidin-1-yl)ethyl]-5-chloro-2-ethoxy-6-methylphenyl}-N,N-dimethylpyridine-2-carboxamide

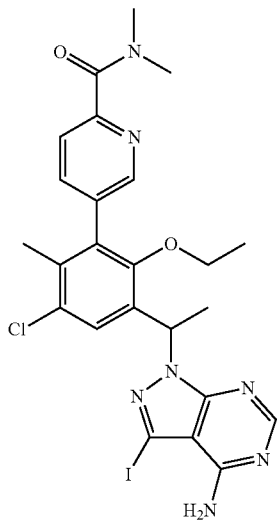 [SMILES: CCOc1c(C(C)n2nc(I)c3c(N)ncnc32)cc(Cl)c(C)c1-c1ccc(C(=O)N(C)C)nc1]

To a mixture of 3-iodo-1H-pyrazolo[3,4-d]pyrimidin-4-amine (from CNH Technologies, 120 mg, 0.46 mmol), cesium carbonate (200 mg, 0.62 mmol) and potassium iodide (7.0 mg, 0.042 mmol) in N,N-dimethylformamide (1 mL) was added 5-[3-chloro-5-(1-chloroethyl)-6-ethoxy-2-methylphenyl]-N,N-dimethylpyridine-2-carboxamide (160 mg, 0.42 mmol, from Example 14, step 4) and the mixture was stirred at 140° C. for 1 hour. The reaction mixture was diluted with water, extracted with ether. The combined organic layers were dried over MgSO$_4$, concentrated and purified on silica gel (eluting with 0 to 10% MeOH in dichloromethane) to give the desired product (0.12 g, 47%). The product was isolated as a racemic mixture. LCMS calculated for $C_{24}H_{26}ClIN_7O_2$ (M+H)$^+$: m/z=606.1. Found: 606.0.

Example 16

4-{3-[1-(4-Amino-3-methyl-1H-pyrazolo[3,4-d]pyrimidin-1-yl)ethyl]-5-chloro-2-methoxy-6-methylphenyl}-N,N-dimethylpyridine-2-carboxamide

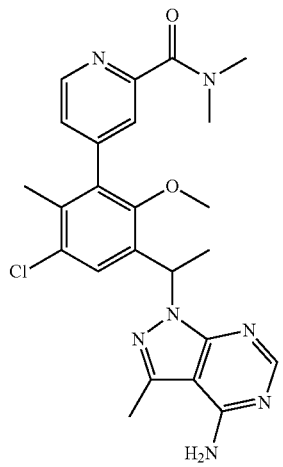

Step 1. 1-(3-Bromo-5-chloro-2-methoxy-4-methylphenyl)ethanol

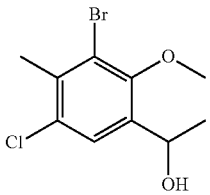

Sodium tetrahydroborate (0.31 g, 8.1 mmol) was added to a mixture of 1-(3-bromo-5-chloro-2-methoxy-4-methylphenyl)ethanone (from Example 11, Step 1) (1.5 g, 5.4 mmol) in methanol (25 mL) at 0° C. and the resultant reaction mixture was stirred at room temperature for 1 hour. The solvent was removed and the resulting residue was diluted with ethyl acetate, washed with sat. NaHCO$_3$, water, brine, then dried over Na$_2$SO$_4$, filtered and concentrated. The crude product was purified by silica gel chromatography, eluting with 0 to 40% EtOAc in hexanes (0.30 g, 90%).

Step 2. 4-[3-Chloro-5-(1-hydroxyethyl)-6-methoxy-2-methylphenyl]pyridine-2-carbonitrile

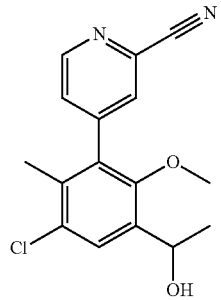 [SMILES: COc1c(C(C)O)cc(Cl)c(C)c1-c1ccnc(C#N)c1]

A mixture of 1-(3-bromo-5-chloro-2-methoxy-4-methylphenyl)ethanol (0.30 g, 1.1 mmol), 4-(4,4,5,5-tetramethyl- 1,3,2-dioxaborolan-2-yl)pyridine-2-carbonitrile (from Combi-Blocks, 0.27 g, 1.2 mmol), sodium carbonate (230 mg, 2.1 mmol) and [1,1'-bis(diphenylphosphino)ferrocene]dichloropalladium(II), complex with dichloromethane (1:1) (100 mg, 0.13 mmol) in acetonitrile (8 mL)/water (2 mL) was degassed and then refilled with $N_2$. The reaction was stirred at 95° C. for 2 hours, then cooled and diluted with ethyl acetate, washed with sat. NaHCO$_3$, water, brine, dried over Na$_2$SO$_4$, filtered and concentrated. The crude product was purified by silica gel chromatography, eluting with 0 to 40% EtOAc in hexanes (0.249 g, 75%). LCMS calculated for $C_{16}H_{16}ClN_2O_2$ (M+H)$^+$: m/z=303.1. Found: 303.0.

Step 3. 4-[3-Chloro-5-(1-chloroethyl)-6-methoxy-2-methylphenyl]pyridine-2-carbonitrile

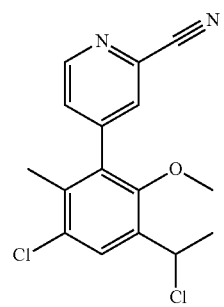 [SMILES: COc1c(C(C)Cl)cc(Cl)c(C)c1-c1ccnc(C#N)c1]

A mixture of cyanuric chloride (170 mg, 0.94 mmol) and N,N-dimethylformamide (73 μL, 0.94 mmol) was stirred at room temperature for 10 minutes and then a solution of 4-[3-chloro-5-(1-hydroxyethyl)-6-methoxy-2-methylphenyl]pyridine-2-carbonitrile (190 mg, 0.628 mmol) in methylene chloride (4 mL) was added and the reaction was stirred at room temperature overnight. The mixture was diluted with methylene chloride, washed with sat. NaHCO$_3$, water, brine, dried over Na$_2$SO$_4$, filtered and concentrated. The crude product was used directly in the next step without purification (121 mg, 60%). LCMS calculated for $C_{16}H_{15}Cl_2N_2O$ (M+H)$^+$: m/z=321.0. Found: 321.0.

Step 4. 4-{3-[1-(4-Amino-3-methyl-1H-pyrazolo[3,4-d]pyrimidin-1-yl)ethyl]-5-chloro-2-methoxy-6-methylphenyl}pyridine-2-carbonitrile

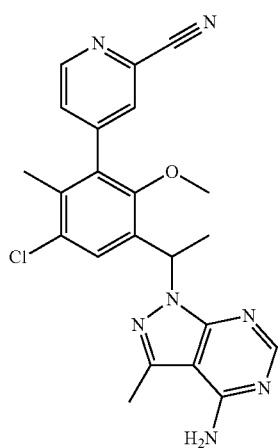 [SMILES: COc1c(C(C)n2nc(C)c3c(N)ncnc32)cc(Cl)c(C)c1-c1ccnc(C#N)c1]

Sodium hydride (20 mg, 0.50 mmol) was added to a mixture of 4-[3-chloro-5-(1-chloroethyl)-6-methoxy-2-methylphenyl]pyridine-2-carbonitrile (90 mg, 0.28 mmol), 3-methyl-1H-pyrazolo[3,4-d]pyrimidin-4-amine (63 mg, 0.42 mmol) in N,N-dimethylformamide (4 mL) and the reaction was stirred et 30° C. overnight. The mixture was cooled, treated with water and then filtered to provide the desired product. LCMS calculated for $C_{22}H_{21}ClN_7O$ (M+H)$^+$: m/z=434.1. Found: 434.2.

Step 5. 4-{3-[1-(4-Amino-3-methyl-1H-pyrazolo[3,4-d]pyrimidin-1-yl)ethyl]-5-chloro-2-methoxy-6-methylphenyl}pyridine-2-carboxylic acid

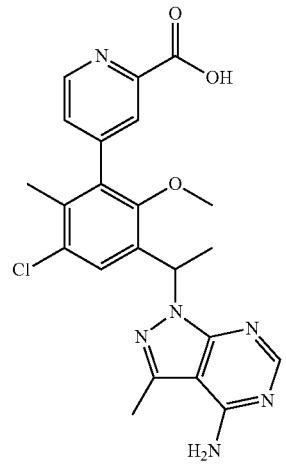 [SMILES: COc1c(C(C)n2nc(C)c3c(N)ncnc32)cc(Cl)c(C)c1-c1ccnc(C(=O)O)c1]

Sodium hydroxide (1.0 M) in water (0.70 mL, 0.70 mmol) was added to a mixture of 4-{3-[1-(4-amino-3-methyl-1H-pyrazolo[3,4-d]pyrimidin-1-yl)ethyl]-5-chloro-2-methoxy-6-methylphenyl}pyridine-2-carbonitrile (0.060 g, 0.14 mmol) in ethanol (1.0 mL) and the resultant mixture was heated at 95° C. for 6 hours. At this time, conc. HCl was added to adjust pH to ~3. The solvent was removed and the residue was used in the next step without further purification. LCMS calculated for $C_{22}H_{22}ClN_6O_3$ (M+H)$^+$: m/z=453.1. Found: 453.2.

Step 6. 4-{3-[1-(4-Amino-3-methyl-1H-pyrazolo[3,4-d]pyrimidin-1-yl)ethyl]-5-chloro-2-methoxy-6-methylphenyl}-N,N-dimethylpyridine-2-carboxamide

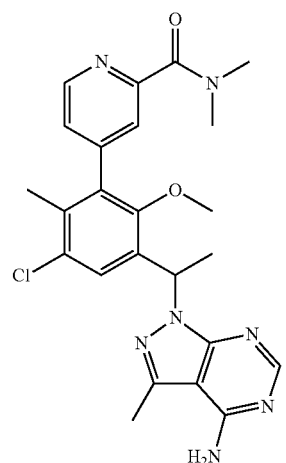

2.0 M Dimethylamine in THF (0.14 mL, 0.28 mmol) was added to a solution of 4-{3-[1-(4-amino-3-methyl-1H-pyrazolo[3,4-d]pyrimidin-1-yl)ethyl]-5-chloro-2-methoxy-6-methylphenyl}pyridine-2-carboxylic acid (9.6 mg, 0.021 mmol) and benzotriazol-1-yloxytris(dimethylamino)phosphonium hexafluorophosphate (10 mg, 0.03 mmol) in N,N- dimethylformamide (0.7 mL) at room temperature followed by addition of triethylamine (8.8 μL, 0.064 mmol). The reaction was stirred for 1 hour. The crude mixture was purified using RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{24}H_{27}ClN_7O_2$ (M+H)$^+$: m/z=480.2. Found: 480.2.

Example 17

4-(3-(1-(4-amino-3-methyl-1H-pyrazolo[3,4-d]pyrimidin-1-yl)ethyl)-5-chloro-2-methoxy-6-methylphenyl)-N-methylpicolinamide

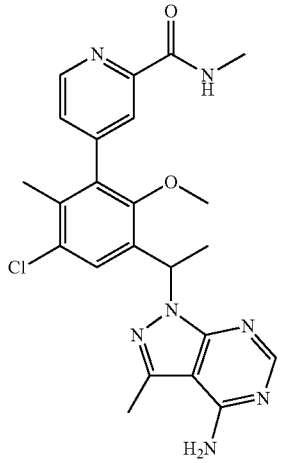 [SMILES: CNC(=O)c1cc(-c2c(C)c(Cl)cc(C(C)n3nc(C)c4c(N)ncnc43)c2OC)ccn1]

This compound was prepared using procedures analogous to those for Example 16, Step 6, with 2.0 M solution of methylamine in THF replacing 2.0 M dimethylamine in THF. The product was isolated as a racemic mixture. LCMS calculated for $C_{23}H_{25}ClN_7O_2$ (M+H)$^+$: m/z=466.2. Found: 466.2.

Example 18

4-{3-[1-(4-Amino-3-methyl-1H-pyrazolo[3,4-d]pyrimidin-1-yl)ethyl]-5-chloro-2-methoxy-6-methylphenyl}-N-(2-hydroxyethyl)pyridine-2-carboxamide

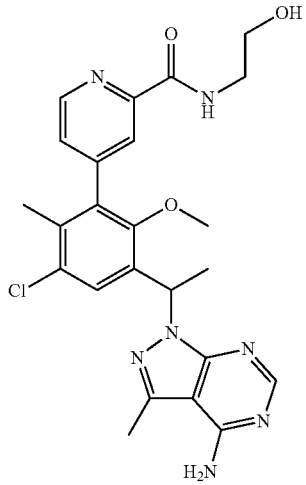 [SMILES: COc1c(C(C)n2nc(C)c3c(N)ncnc32)cc(Cl)c(C)c1-c1ccnc(C(=O)NCCO)c1]

This compound was prepared using procedures analogous to those for Example 16, Step 6, with ethanolamine replacing 2.0 M dimethylamine in THF. The product was isolated as a racemic mixture. LCMS calculated for $C_{24}H_{27}ClN_7O_3$ (M+H)$^+$: m/z=496.2. Found: 496.2.

Example 19

4-{3-[1-(4-amino-3-methyl-1H-pyrazolo[3,4-d]pyrimidin-1-yl)ethyl]-5-chloro-2-methoxy-6-methylphenyl}-N-(2-hydroxyethyl)-N-methylpyridine-2-carboxamide

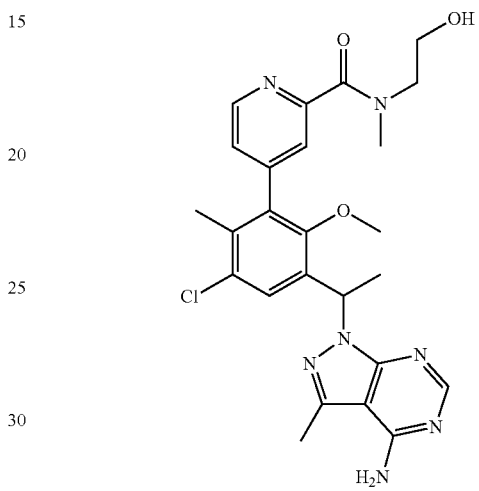

This compound was prepared using procedures analogous to those for Example 16, Step 6, with 2-(methylamino)ethanol replacing 2.0 M dimethylamine in THF. The product was isolated as a racemic mixture. LCMS calculated for $C_{25}H_{29}ClN_7O_3$ (M+H)$^+$: m/z=510.2. Found: 510.2.

Example 20

2-(4-(3-(1-(4-Amino-3-methyl-1H-pyrazolo[3,4-d]pyrimidin-1-yl)ethyl)-5-chloro-2-methoxy-6-methylphenyl)-1H-pyrazol-1-yl)ethanol

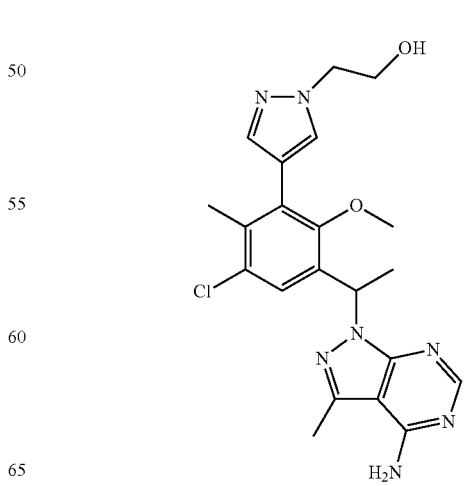

Step 1. 3-Bromo-1-chloro-5-(1-chloroethyl)-4-methoxy-2-methylbenzene

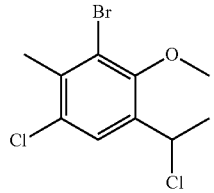

A mixture of cyanuric chloride (1.7 g, 9.2 mmol) and N,N-dimethylformamide (710 µL, 9.2 mmol) was stirred at room temperature for 10 minutes and then a solution of 1-(3-bromo-5-chloro-2-methoxy-4-methylphenyl)ethanol (from Example 16, Step 1) (1.72 g, 6.15 mmol) in methylene chloride (34 mL) was added and the reaction was stirred at room temperature overnight. The mixture was diluted with methylene chloride, washed with sat. NaHCO$_3$, water, brine, dried over Na$_2$SO$_4$, filtered and concentrated. The crude product was purified by silica gel chromatography, eluting with 0 to 10% EtOAc in hexanes (1.01 g, 60%).

Step 2. 1-[1-(3-Bromo-5-chloro-2-methoxy-4-methylphenyl)ethyl]-3-methyl-1H-pyrazolo[3,4-d]pyrimidin-4-amine

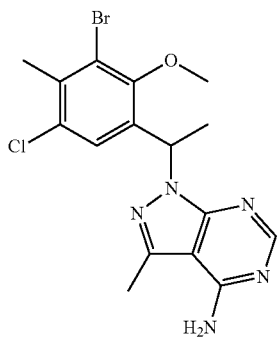 [SMILES: COc1c(C(C)n2nc(C)c3c(N)ncnc32)cc(Cl)c(C)c1Br]

Sodium hydride (36 mg, 0.91 mmol) was added to a mixture of 3-bromo-1-chloro-5-(1-chloroethyl)-4-methoxy-2-methylbenzene (150 mg, 0.503 mmol), 3-methyl-1H-pyrazolo[3,4-d]pyrimidin-4-amine (110 mg, 0.76 mmol) in N,N-dimethylformamide (8 mL) and the reaction was stirred at 30° C. overnight. The mixture was diluted with methylene chloride, washed with sat. NaHCO$_3$, water, brine, dried over Na$_2$SO$_4$, filtered and concentrated. The crude product was purified by silica gel chromatography, eluting with 0 to 70% EtOAc in CH$_2$Cl$_2$ (103 mg, 50%). LCMS calculated for C$_{16}$H$_{18}$BrClN$_5$O (M+H)$^+$: m/z=410.0. Found: 410. The racemic products were applied on a Phenomenex Lux-Cellulose 1 column (21.1×250 mm, 5 micron particle size), eluting with 5% ethanol in hexanes at a flow rate of 18 mL/min, ~13 mg/injection, to provide two enantiomers.

Step 3. 1-(2-{[tert-Butyl(dimethyl)silyl]oxy}ethyl)-4-(4,4,5,5-tetramethyl-1,3,2-dioxaborolan-2-yl)-1H-pyrazole

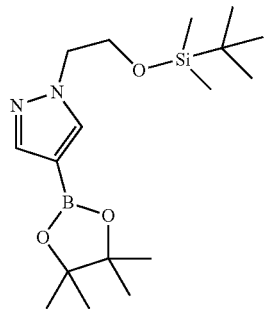 [SMILES: CC1(C)OB(c2cnn(CCO[Si](C)(C)C(C)(C)C)c2)OC1(C)C]

Potassium tert-butoxide (1.0 M) in THF (0.60 mL, 0.60 mmol) was added to a solution of 4-(4,4,5,5-tetramethyl-1,3,2-dioxaborolan-2-yl)-1H-pyrazole (0.1 g, 0.5 mmol) in N,N-dimethylformamide (1.5 mL) at 0° C. The reaction mixture was stirred at room temperature for 5 minutes, then cooled to 0° C. and treated with (2-bromoethoxy)(tert-butyl)dimethylsilane (0.2 mL, 0.8 mmol). The reaction was stirred at room temperature overnight, then diluted with ethyl acetate, washed with sat. NaHCO$_3$, water, brine, dried over Na$_2$SO$_4$, filtered and concentrated to provide the crude product which was purified by silica gel chromatography eluting with 0 to 30% EtOAc in hexanes. Calculated for C$_{17}$H$_{34}$BN$_2$O$_3$Si (M+H)$^+$: m/z=353.2. Found: 353.1.

Step 4. 2-(4-(3-(1-(4-Amino-3-methyl-1H-pyrazolo[3,4-d]pyrimidin-1-yl)ethyl)-5-chloro-2-methoxy-6-methylphenyl)-1H-pyrazol-1-yl)ethanol

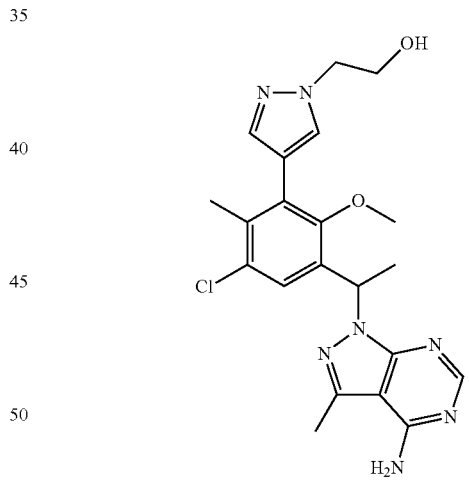

A mixture of 1-[1-(3-bromo-5-chloro-2-methoxy-4-methylphenyl)ethyl]-3-methyl-1H-pyrazolo[3,4-d]pyrimidin-4-amine (0.026 g, 0.062 mmol) (chiral pure, first peak from Step 2), 1-(2-{[tert-butyl(dimethyl)silyl]oxy}ethyl)-4-(4,4,5,5-tetramethyl-1,3,2-dioxaborolan-2-yl)-1H-pyrazole (0.024 g, 0.069 mmol), sodium carbonate (13 mg, 0.12 mmol) and [1,1'-bis(diphenylphosphino)ferrocene]dichloropalladium(II), complex with dichloromethane (1:1) (6.1 mg, 0.0075 mmol) in acetonitrile (0.5 mL)/water (0.1 mL) was degassed and then refilled with N$_2$. The reaction mixture was stirred at 95° C. for 2 hours, then treated with conc. HCl (0.1 mL) and then stirred at room temperature for 1 hour. The crude mixture was purified using RP-HPLC (XBridge C18 column, eluting with a gradient of acetonitrile/water containing 0.1% ammonium hydroxide, at flow rate of 30 mL/min) to give the desired product. The product was isolated as a single enantiomer. LCMS calculated for $C_{21}H_{25}ClN_7O_2$ (M+H)$^+$: m/z=442.2. Found: 442.2.

Example 21

3'-[1-(4-Amino-3-methyl-1H-pyrazolo[3,4-d]pyrimidin-1-yl)ethyl]-5'-chloro-3-fluoro-2'-methoxy-N,N,6'-trimethylbiphenyl-4-carboxamide trifluoroacetate

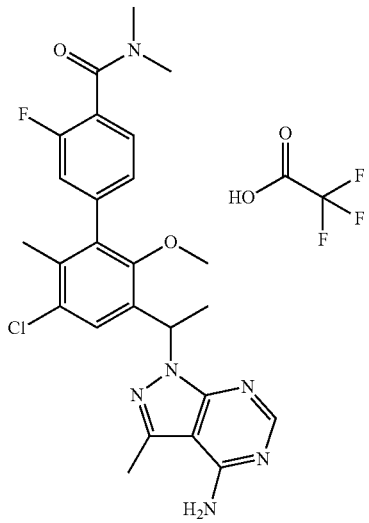 [SMILES: COc1c(C(C)n2nc(C)c3c(N)ncnc32)cc(Cl)c(C)c1-c1ccc(C(=O)N(C)C)c(F)c1 ; O=C(O)C(F)(F)F]

Step 1. Methyl 3'-(1-(4-amino-3-methyl-1H-pyrazolo[3,4-d]pyrimidin-1-yl)ethyl)-5'-chloro-3-fluoro-2'-methoxy-6'-methylbiphenyl-4-carboxylate

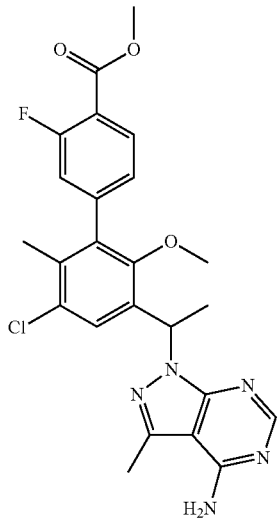 [SMILES: COC(=O)c1ccc(-c2c(C)c(Cl)cc(C(C)n3nc(C)c4c(N)ncnc43)c2OC)cc1F]

A mixture of 1-[1-(3-bromo-5-chloro-2-methoxy-4-methylphenyl)ethyl]-3-methyl-1H-pyrazolo[3,4-d]pyrimidin-4-amine (60 mg, 0.15 mmol, chiral pure, first peak from Example 20, Step 2), [3-fluoro-4-(methoxycarbonyl)phenyl]boronic acid (from Combi-Blocks, 0.041 g, 0.20 mmol), sodium carbonate (36 mg, 0.34 mmol) and [1,1'-bis(diphenylphosphino)ferrocene]dichloropalladium(II), complex with dichloromethane (1:1) (6 mg, 0.007 mmol) in acetonitrile (1.2 mL)/water (0.3 mL) was vacuumed and then refilled with $N_2$. The reaction was stirred at 95° C. for 2 hours. Then solvent was removed and the crude mixture was purified by silica gel chromatography, eluting with 0 to 70% EtOAc in $CH_2Cl_2$, to give the desired product (54 mg, 75%). LCMS calculated for $C_{24}H_{24}ClFN_5O_3$ (M+H)$^+$: m/z=484.2. Found: 484.1.

Step 2. 3'-[1-(4-Amino-3-methyl-1H-pyrazolo[3,4-d]pyrimidin-1-yl)ethyl]-5'-chloro-3-fluoro-2'-methoxy-6'-methylbiphenyl-4-carboxylic acid

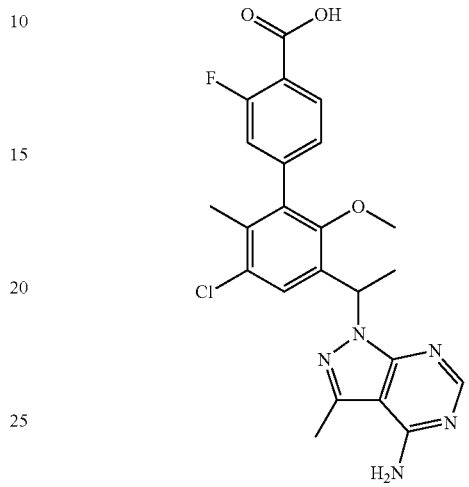

Lithium hydroxide, monohydrate (13 mg, 0.31 mmol) was added to a solution of methyl 3'-[1-(4-amino-3-methyl-1H-pyrazolo[3,4-d]pyrimidin-1-yl)ethyl]-5'-chloro-3-fluoro-2'-methoxy-6'-methylbiphenyl-4-carboxylate made above (0.030 g, 0.062 mmol) in methanol (0.2 mL)/tetrahydrofuran (0.2 mL)/water (0.09 mL). The reaction was stirred at room temperature for 1.5 h, then treated with conc. HCl (60 uL) to adjust pH to 2. The solvent was removed to provide the crude product which was used in next step without further purification. LCMS calculated for $C_{23}H_{22}ClFN_5O_3$ (M+H)$^+$: m/z=470.1. Found: 470.2.

Step 3. 3'-[1-(4-Amino-3-methyl-1H-pyrazolo[3,4-c]pyrimidin-1-yl)ethyl]-5'-chloro-3-fluoro-2'-methoxy-N,N,6'-trimethylbiphenyl-4-carboxamide trifluoroacetate

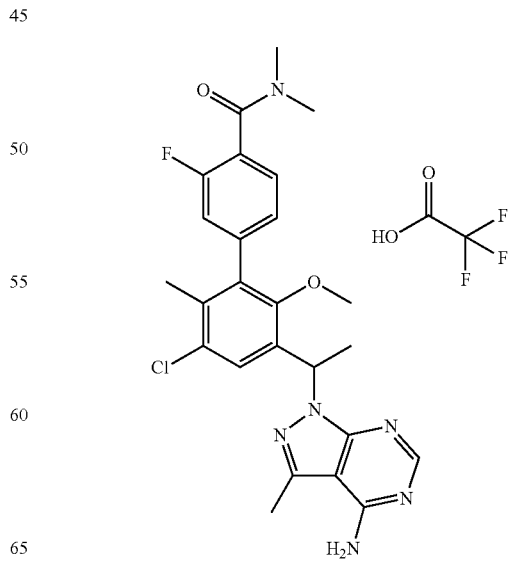

2.0 M Dimethylamine in THF (0.1 mL, 0.2 mmol) was added to a solution of 3'-[1-(4-amino-3-methyl-1H-pyrazolo[3,4-d]pyrimidin-1-yl)ethyl]-5'-chloro-3-fluoro-2'-methoxy-6'-methylbiphenyl-4-carboxylic acid (12 mg, 0.026 mmol) made above and benzotriazol-1-yloxytris(dimethylamino)phosphonium hexafluorophosphate (20 mg, 0.04 mmol) in N,N-dimethylformamide (0.7 mL) at room temperature followed by addition of triethylamine (11 μL, 0.077 mmol). The reaction was stirred for 1 hour, quenched with water. The crude mixture was applied on RP-HPLC (XBridge C18 column, eluting with a gradient of acetonitrile/water containing 0.05% TFA, at flow rate of 30 mL/min) to give the desired product as TFA salt. The product was isolated as a single enantiomer. LCMS calculated for $C_{25}H_{27}ClFN_6O_2$ (M+H)$^+$: m/z=497.2. Found: 497.2.

Example 22

3'-[1-(4-Amino-3-methyl-1H-pyrazolo[3,4-d]pyrimidin-1-yl)ethyl]-5'-chloro-3-fluoro-2'-methoxy-N,6'-dimethylbiphenyl-4-carboxamide trifluoroacetate

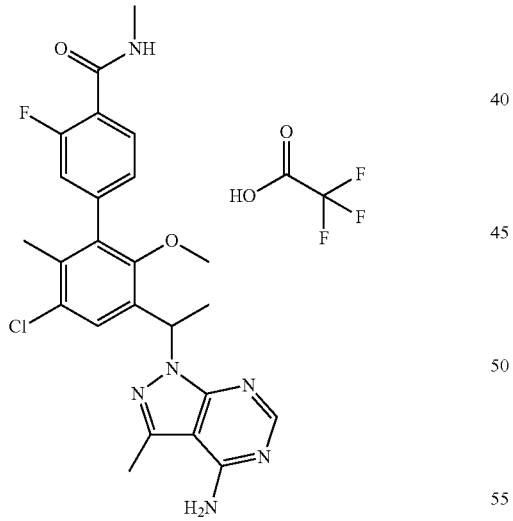

This compound was prepared using procedures analogous to those for Example 21, Step 3, with 2.0 M methylamine in THF replacing 2.0 M dimethylamine in THF. The product was isolated as a single enantiomer. LCMS calculated for $C_{24}H_{25}ClFN_6O_2$ (M+H)$^+$: m/z=483.2. Found: 483.2.

Example 23

5-(3-(1-(4-amino-3-methyl-1H-pyrazolo[3,4-d]pyrimidin-1-yl)ethyl)-5-chloro-2-methoxy-6-methylphenyl)-N-(2-hydroxyethyl)picolinamide trifluoroacetate

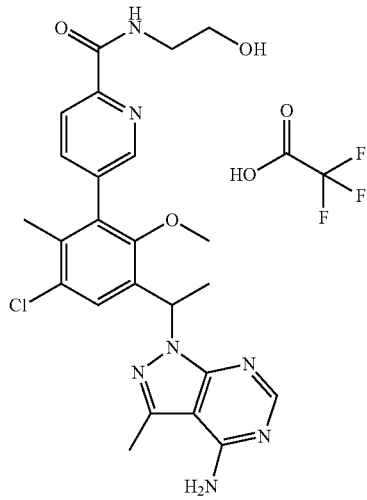 [SMILES: COc1c(C(C)n2nc(C)c3c(N)ncnc32)cc(Cl)c(C)c1-c1ccc(C(=O)NCCO)nc1 ; O=C(O)C(F)(F)F]

Step 1. 5-[3-Chloro-5-(1-hydroxyethyl)-6-methoxy-2-methylphenyl]pyridine-2-carbonitrile

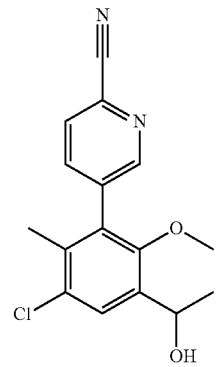

A mixture of 1-(3-bromo-5-chloro-2-methoxy-4-methylphenyl)ethanol (0.15 g, 0.54 mmol), 5-(4,4,5,5-tetramethyl-1,3,2-dioxaborolan-2-yl)pyridine-2-carbonitrile (from Frontier, 0.14 g, 0.59 mmol), sodium carbonate (110 mg, 1.1 mmol) and [1,1'-bis(diphenylphosphino)ferrocene]dichloropalladium(II), complex with dichloromethane (1:1) (52 mg, 0.064 mmol) in acetonitrile (4 mL)/water (1 mL) was degassed and then refilled with $N_2$. The reaction was stirred at 95° C. for 2 h, cooled, diluted with ethyl acetate, washed with sat. NaHCO$_3$, water, brine, and then dried over Na$_2$SO$_4$, filtered and concentrated. The crude product was purified by silica gel chromatography, eluting with 0 to 40% EtOAc in hexanes, to give the desired product (114 mg, 70%). LCMS calculated for $C_{16}H_{16}ClN_2O_2$ (M+H)$^+$: m/z=303.1. Found: 303.0.

Step 2. 5-[3-Chloro-5-(1-chloroethyl)-6-methoxy-2-methylphenyl]pyridine-2-carbonitrile

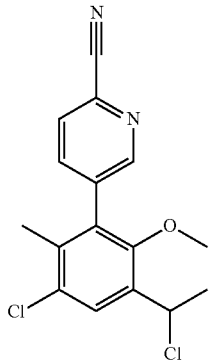

A mixture of cyanuric chloride (170 mg, 0.94 mmol) and N,N-dimethylformamide (73 µL, 0.94 mmol) was stirred at room temperature for 10 minutes and then a solution of 5-[3-chloro-5-(1-hydroxyethyl)-6-methoxy-2-methylphenyl]pyridine-2-carbonitrile (190 mg, 0.628 mmol) in methylene chloride (4 mL) was added and the reaction was stirred at room temperature overnight. The mixture was diluted with methylene chloride, washed with sat. NaHCO$_3$, water, brine, dried over Na$_2$SO$_4$, then filtered and concentrated. The resultant crude product was used directly in the next step without further purification (110 mg, 55%). LCMS calculated for C$_{16}$H$_{15}$Cl$_2$N$_2$O (M+H)$^+$: m/z=321.0. Found: 321.0.

Step 3. 5-{3-[1-(4-Amino-3-methyl-1H-pyrazolo[3,4-d]pyrimidin-1-yl)ethyl]-5-chloro-2-methoxy-6-methylphenyl}pyridine-2-carbonitrile

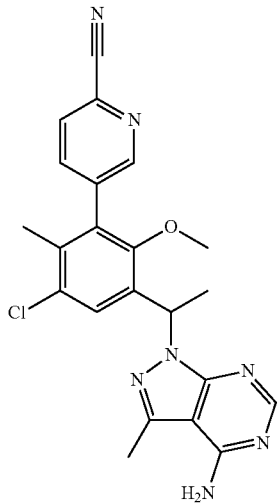 [SMILES: COc1c(C(C)n2nc(C)c3c(N)ncnc32)cc(Cl)c(C)c1-c1ccc(C#N)nc1]

Sodium hydride (20 mg, 0.50 mmol) was added to a mixture of 5-[3-chloro-5-(1-chloroethyl)-6-methoxy-2-methylphenyl]pyridine-2-carbonitrile (90 mg, 0.28 mmol), 3-methyl-1H-pyrazolo[3,4-d]pyrimidin-4-amine (63 mg, 0.42 mmol) in N,N-dimethylformamide (4 mL) and the reaction was stirred at 30° C. overnight. The mixture was treated with water and then filtered to provide the desired product. LCMS calculated for C$_{22}$H$_{21}$ClN$_7$O (M+H)$^+$: m/z=434.1. Found: 434.2.

Step 4. 5-{3-[1-(4-Amino-3-methyl-1H-pyrazolo[3,4-d]pyrimidin-1-yl)ethyl]-5-chloro-2-methoxy-6-methylphenyl}pyridine-2-carboxylic acid

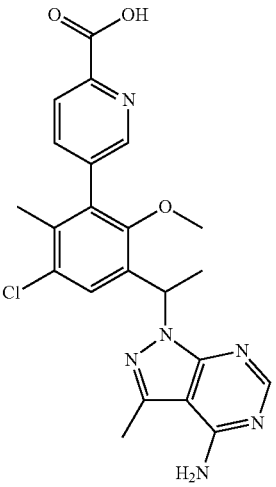 [SMILES: COc1c(C(C)n2nc(C)c3c(N)ncnc32)cc(Cl)c(C)c1-c1ccc(C(=O)O)nc1]

Sodium hydroxide (1.0 M) in water (0.70 mL, 0.70 mmol) was added to a mixture of 5-{3-[1-(4-amino-3-methyl-1H-pyrazolo[3,4-d]pyrimidin-1-yl)ethyl]-5-chloro-2-methoxy-6-methylphenyl}pyridine-2-carbonitrile (0.060 g, 0.14 mmol) in ethanol (1.0 mL). The reaction was heated at 95° C. for 6 hours, followed by the addition of conc. HCl to adjust pH to ~3. The solvent was removed and the resultant residue was used in the next step without further purification. LCMS calculated for C$_{22}$H$_{22}$ClN$_6$O$_3$ (M+H)$^+$: m/z=453.1. Found: 453.2.

Step 5. 5-(3-(1-(4-amino-3-methyl-1H-pyrazolo[3,4-c]pyrimidin-1-yl)ethyl)-5-chloro-2-methoxy-6-methylphenyl)-N-(2-hydroxyethyl)picolinamide trifluoroacetate

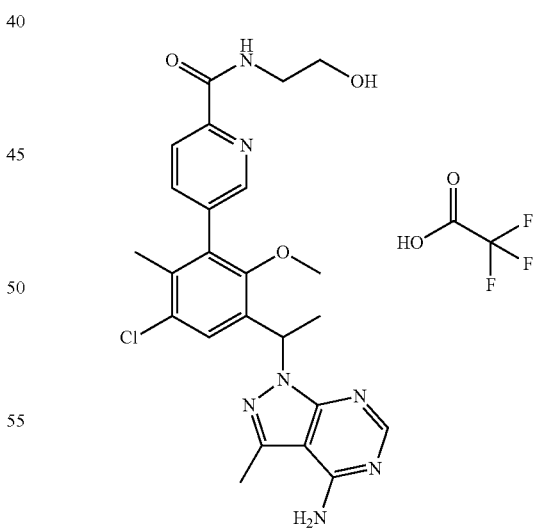

Ethanolamine (15 µL, 0.25 mmol) was added to a solution of 5-{3-[1-(4-amino-3-methyl-1H-pyrazolo[3,4-d]pyrimidin-1-yl)ethyl]-5-chloro-2-methoxy-6-methylphenyl}pyridine-2-carboxylic acid (9.6 mg, 0.021 mmol) and benzotriazol-1-yloxytris(dimethylamino)phosphonium hexafluorophosphate (10 mg, 0.03 mmol) in N,N-dimethylformamide (0.7 mL) at room temperature followed by addition of triethylamine (8.8 µL, 0.064 mmol). The reaction was stirred for 1 hour, and then quenched with water. The crude mixture was applied on RP-HPLC (XBridge C18 column, eluting with a gradient of acetonitrile/water containing 0.05% TFA, at flow rate of 30 mL/min) to give the desired product as TFA salt. The product was isolated as a racemic mixture. LCMS calculated for $C_{24}H_{27}ClN_7O_3$ (M+H)$^+$: m/z=496.2. Found: 496.2.

Example 24

4-{3-[1-(4-Amino-3-methyl-1H-pyrazolo[3,4-d]pyrimidin-1-yl)ethyl]-5-chloro-2-methoxy-6-methylphenyl}-N-(2-hydroxyethyl)-N-methylpyridine-2-carboxamide trifluoroacetate

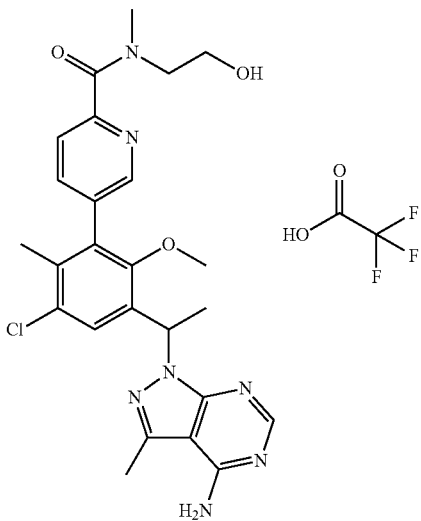 [SMILES: COc1c(C(C)n2nc(C)c3c(N)ncnc32)cc(Cl)c(C)c1-c1ccc(C(=O)N(C)CCO)nc1 ; O=C(O)C(F)(F)F]

This compound was prepared using procedures analogous to those for Example 23, with 2-(methylamino)ethanol replacing ethanolamine. The product was isolated as a racemic mixture. LCMS calculated for $C_{25}H_{29}ClN_7O_3$ (M+H)$^+$: m/z=510.2. Found: 510.2.

Example 25

5-{3-[1-(4-Amino-5-oxopyrido[2,3-d]pyrimidin-8(5H)-yl)ethyl]-5-chloro-2-methoxy-6-methylphenyl}-N,N-dimethylpyridine-2-carboxamide

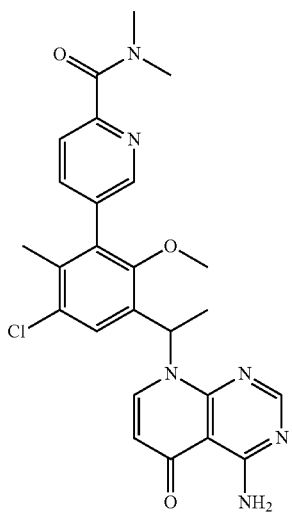 [SMILES: COc1c(C(C)n2ccc(=O)c3c(N)ncnc32)cc(Cl)c(C)c1-c1ccc(C(=O)N(C)C)nc1]

Step 1. 5-[3-Chloro-5-(1-chloroethyl)-6-methoxy-2-methylphenyl]-N,N-dimethylpyridine-2-carboxamide

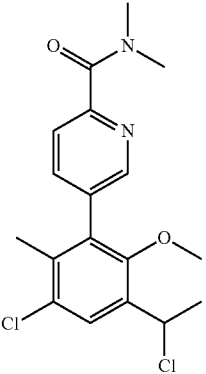

A mixture of cyanuric chloride (from Aldrich, 690 mg, 3.7 mmol) and N,N-dimethylformamide (290 µL, 3.7 mmol) was stirred at room temperature for 10 minutes and then a solution of 5-[3-chloro-5-(1-hydroxyethyl)-6-methoxy-2-methylphenyl]-N,N-dimethylpyridine-2-carboxamide (869 mg, 2.49 mmol) in methylene chloride (14 mL) was added and the reaction was stirred at room temperature overnight. The mixture was diluted with methylene chloride, washed with sat. NaHCO$_3$, water, brine, dried over Na$_2$SO$_4$, filtered and concentrated. The product was purified by silica gel chromatography, eluting with 0 to 100% EtOAc in hexanes.

Step 2. 5-{3-[1-(4-Amino-5-oxopyrido[2,3-d]pyrimidin-8(5H)-yl)ethyl]-5-chloro-2-methoxy-6-methylphenyl}-N,N-dimethylpyridine-2-carboxamide

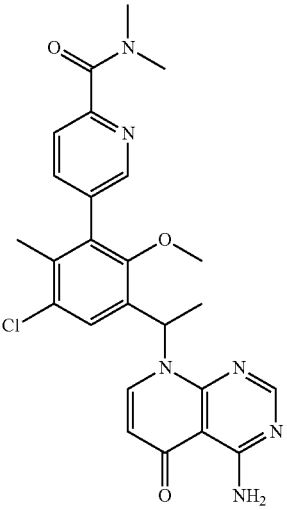 [SMILES: COc1c(C(C)n2ccc(=O)c3c(N)ncnc32)cc(Cl)c(C)c1-c1ccc(C(=O)N(C)C)nc1]

To a mixture of 4-aminopyrido[2,3-d]pyrimidin-5(8H)-one (from VWR, 4.8 mg, 0.030 mmol), cesium carbonate (14 mg, 0.044 mmol) and potassium iodide (0.50 mg, 0.0030 mmol) in N,N-dimethylformamide (0.1 mL) was added 5-[3-chloro-5-(1-chloroethyl)-6-methoxy-2-methylphenyl]-N,N-dimethylpyridine-2-carboxamide (11 mg, 0.030 mmol). The mixture was stirred at 140° C. for 1 hour. The reaction mixture was applied on RP-HPLC (XBridge C18 column, eluting with a gradient of acetonitrile/water containing 0.1% ammonium hydroxide, at flow rate of 30 mL/min) to give the desired product. LCMS calculated for $C_{25}H_{26}ClN_6O_3$ $(M+H)^+$: m/z=493.2. Found: 493.1. The racemic products were applied on a Phenomenex Lux-Cellulose 1 column (21.1×250 mm, 5 micron particle size), eluting with 30% ethanol in hexanes at a flow rate of 18 mL/min, 4.2 mg/injection, to provide two isolated enantiomers. This first isolated peak had a retention time of 15.39 min and the second peak had a retention time of 22.98. For the second peak: $^1$H NMR (CDCl$_3$, 400 MHz) δ 9.86 (d, J=5.6 Hz, 1H), 8.36 (m, 1H), 8.30 (s, 1H), 7.65~7.58 (m, 2H), 7.37 (m, 2H), 6.84 (q, J=7.2 Hz, 1H), 6.22 (d, J=8.0 Hz), 5.95 (d, J=5.2 Hz, 1H), 3.08 (s, 3H), 3.05 (s, 3H), 2.93 (m, 3H), 2.09 (s, 3H), 1.68 (d, J=7.2 Hz, 3H) ppm.

Example 26

4-Amino-8-(1-{5-chloro-2-methoxy-4-methyl-3-[5-(methylsulfonyl)pyridin-3-yl]phenyl}ethyl)pyrido[2,3-d]pyrimidin-5(8H)-one bis(trifluoroacetate)

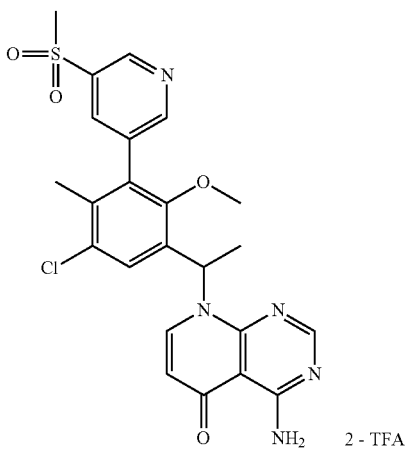 [SMILES: COc1c(C(C)n2ccc(=O)c3c(N)ncnc32)cc(Cl)c(C)c1-c1cncc(S(C)(=O)=O)c1]

Step 1. 3-Bromo-1-chloro-5-(1-chloroethyl)-4-methoxy-2-methylbenzene

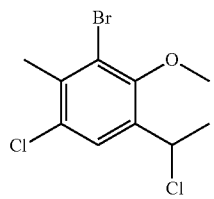

A mixture of cyanuric chloride (1.7 g, 9.2 mmol) and N,N-dimethylformamide (710 μL, 9.2 mmol) was stirred at room temperature for 10 minutes and then a solution of 1-(3-bromo-5-chloro-2-methoxy-4-methylphenyl)ethanol (1.72 g, 6.15 mmol) in methylene chloride (34 mL) was added and the reaction was stirred at room temperature overnight. The mixture was diluted with methylene chloride, washed with sat. NaHCO$_3$, water, brine, dried over Na$_2$SO$_4$, filtered and concentrated. The crude product was purified by silica gel chromatography, eluting with 0 to 10% EtOAc in hexanes.

Step 2. 4-Amino-8-[1-(3-bromo-5-chloro-2-methoxy-4-methylphenyl)ethyl]pyrido[2,3-d]pyrimidin-5(8H)-one

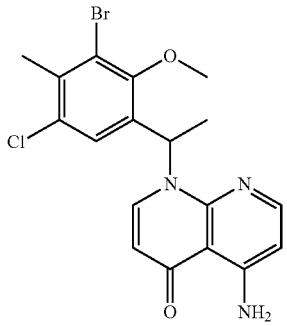 [SMILES: COc1c(C(C)n2ccc(=O)c3c(N)ccnc32)cc(Cl)c(C)c1Br]

To a mixture of 4-aminopyrido[2,3-d]pyrimidin-5(8H)-one (0.80 g, 4.9 mmol), cesium carbonate (2.4 g, 7.3 mmol) and potassium iodide (82 mg, 0.49 mmol) in N,N-dimethylformamide (20 mL) was added 3-bromo-1-chloro-5-(1-chloroethyl)-4-methoxy-2-methylbenzene (1.47 g, 4.93 mmol) and the mixture was stirred at 140° C. for 1 hour. The mixture was diluted with water and ethyl acetate. The precipitate was collected and dried to give the desired compound. LCMS calculated for $C_{17}H_{17}BrClN_4O_2$ $(M+H)^+$: m/z=423.0. Found: 423.0.

Step 3. 4-Amino-8-(1-{5-chloro-2-methoxy-4-methyl-3-[5-(methylsulfonyl)pyridin-3-yl]phenyl}ethyl)pyrido[2,3-d]pyrimidin-5(8H)-one bis(trifluoroacetate)

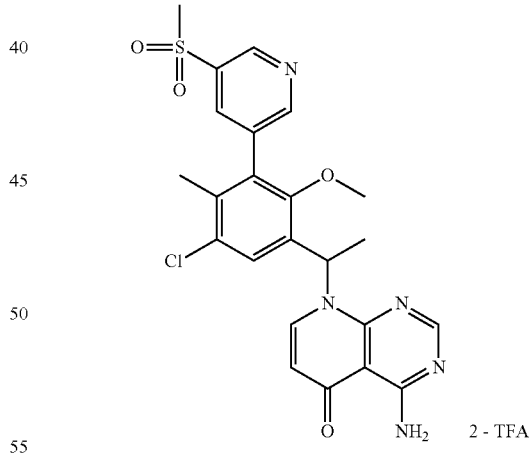

A mixture of 4-amino-8-[1-(3-bromo-5-chloro-2-methoxy-4-methylphenyl)ethyl]pyrido[2,3-d]pyrimidin-5(8H)-one (25 mg, 0.059 mmol), 3-(methylsulfonyl)-5-(4,4,5,5-tetramethyl-1,3,2-dioxaborolan-2-yl)pyridine (from PepTech, 18 mg, 0.065 mmol), sodium carbonate (13 mg, 0.12 mmol) and [1,1'-bis(diphenylphosphino)ferrocene]dichloropalladium(II), complex with dichloromethane (1:1) (5.8 mg, 0.0071 mmol) in acetonitrile (0.5 mL)/water (0.1 mL) was degassed with N$_2$ and the then stirred at 90° C. for 2 hour. The crude mixture was cooled and purified by RP-HPLC (XBridge C18 column, eluting with a gradient of acetonitrile/water containing 0.05% trifluoroacetic acid, at flow rate of 30 mL/min) to give the desired product. The product was isolated as a racemic mixture. LCMS calculated for $C_{23}H_{23}ClN_5O_4S$ (M+H)$^+$: m/z=500.1. Found: 500.0.

Example 27

5-{3-[1-(4-Amino-5-oxopyrido[2,3-d]pyrimidin-8 (5H)-yl)ethyl]-5-chloro-2-methoxy-6-methylphenyl}nicotinonitrile bis(trifluoroacetate)

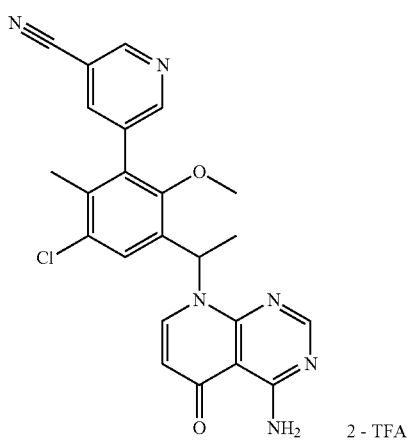 [SMILES: COc1c(C(C)n2ccc(=O)c3c(N)ncnc32)cc(Cl)c(C)c1-c1cncc(C#N)c1]

This compound was prepared using procedures analogous to those for Example 26, with 3-cyanopyridine-5-boronic acid pinacol ester (from Frontier) replacing 3-(methylsulfonyl)-5-(4,4,5,5-tetramethyl-1,3,2-dioxaborolan-2-yl)pyridine. The product was isolated as a racemic mixture. LCMS calculated for $C_{23}H_{20}ClN_6O_2$ (M+H)$^+$: m/z=447.1. Found: 447.1.

Example 28

4-Amino-8-[1-(5-chloro-2-methoxy-4-methyl-3-pyridin-3-ylphenyl)ethyl]pyrido[2,3-d]pyrimidin-5 (8H)-one bis(trifluoroacetate)

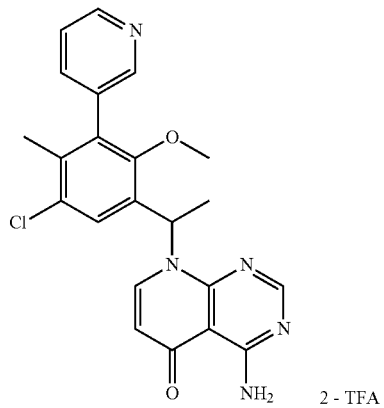 [SMILES: COc1c(C(C)n2ccc(=O)c3c(N)ncnc32)cc(Cl)c(C)c1-c1cccnc1]

This compound was prepared using procedures analogous to those for Example 26, with pyridine-3-boronic acid (from Aldrich) replacing 3-(methylsulfonyl)-5-(4,4,5,5-tetramethyl-1,3,2-dioxaborolan-2-yl)pyridine. The product was isolated as a racemic mixture. LCMS calculated for $C_{22}H_{21}ClN_5O_2$ (M+H)$^+$: m/z=422.1. Found: 422.0.

Example 29

4-Amino-8-[1-(5-chloro-2-methoxy-4-methyl-3-pyrimidin-5-ylphenyl)ethyl]pyrido[2,3-d]pyrimidin-5(8H)-one bis(trifluoroacetate)

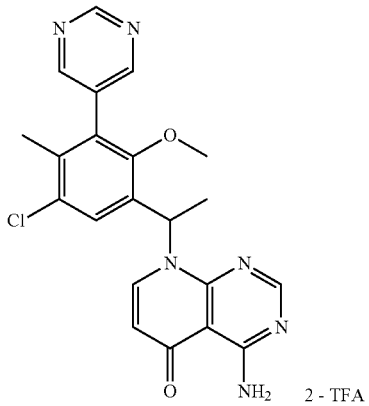 [SMILES: COc1c(C(C)n2ccc(=O)c3c(N)ncnc32)cc(Cl)c(C)c1-c1cncnc1]

This compound was prepared using procedures analogous to those for Example 26, with pyrimidine-5-boronic acid (from Frontier) replacing 3-(methylsulfonyl)-5-(4,4,5,5-tetramethyl-1,3,2-dioxaborolan-2-yl)pyridine. The product was isolated as a racemic mixture. LCMS calculated for $C_{21}H_{20}ClN_6O_2$ (M+H)$^+$: m/z=423.1. Found: 423.0.

Example 30

3'-[1-(4-Amino-5-oxopyrido[2,3-d]pyrimidin-8(5H)-yl)ethyl]-5'-chloro-2'-methoxy-N,N,6'-trimethylbiphenyl-3-carboxamide bis(trifluoroacetate)

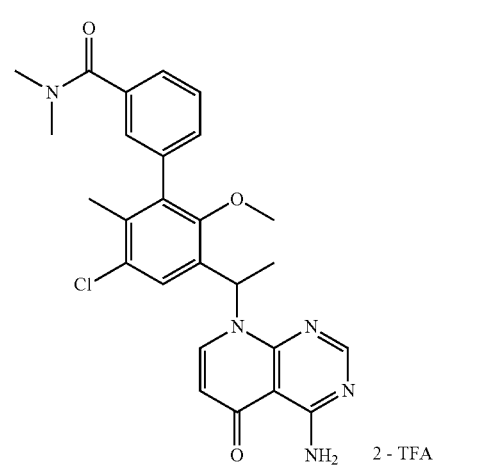 [SMILES: COc1c(C(C)n2ccc(=O)c3c(N)ncnc32)cc(Cl)c(C)c1-c1cccc(C(=O)N(C)C)c1]

This compound was prepared using procedures analogous to those for Example 26, with 3-(N,N-dimethylaminocarbonyl)benzene boronic acid (from Frontier) replacing 3-(methylsulfonyl)-5-(4,4,5,5-tetramethyl-1,3,2-dioxaborolan-2-yl)

pyridine. The product was isolated as a racemic mixture. LCMS calculated for $C_{26}H_{27}ClN_5O_3$ (M+H)⁺: m/z=492.2. Found: 492.1.

Example 31

4-Amino-8-{1-[5-chloro-3-(5-fluoropyridin-3-yl)-2-methoxy-4-methylphenyl]ethyl}pyrido[2,3-d]pyrimidin-5(8H)-one bis(trifluoroacetate)

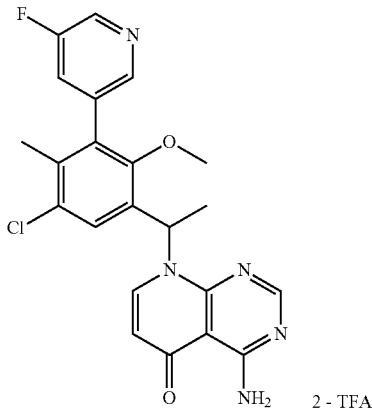 [SMILES: COc1c(C(C)n2ccc(=O)c3c(N)ncnc32)cc(Cl)c(C)c1-c1cncc(F)c1]

This compound was prepared using procedures analogous to those for Example 26, with 5-fluoropyridine-3-boronic acid (from Combi-Blocks) replacing 3-(methylsulfonyl)-5-(4,4,5,5-tetramethyl-1,3,2-dioxaborolan-2-yl)pyridine. The product was isolated as a racemic mixture. LCMS calculated for $C_{22}H_{20}ClFN_5O_2$ (M+H)⁺: m/z=440.1. Found: 440.0.

Example 32

3'-[1-(4-Amino-5-oxopyrido[2,3-d]pyrimidin-8(5H)-yl)ethyl]-5'-chloro-2'-methoxy-N,N,6'-trimethylbiphenyl-3-sulfonamide bis(trifluoroacetate)

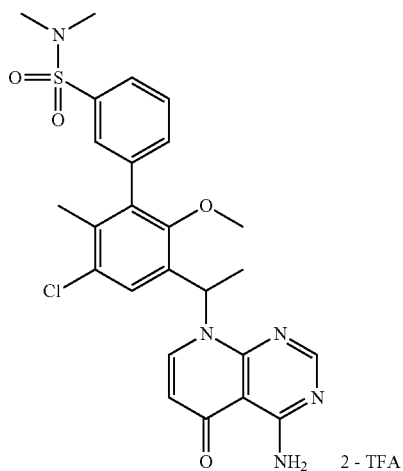 [SMILES: COc1c(C(C)n2ccc(=O)c3c(N)ncnc32)cc(Cl)c(C)c1-c1cccc(S(=O)(=O)N(C)C)c1]

This compound was prepared using procedures analogous to those for Example 26, with N,N-dimethyl 3-boronobenzenesulfonamide (from Combi-Blocks) replacing 3-(methylsulfonyl)-5-(4,4,5,5-tetramethyl-1,3,2-dioxaborolan-2-yl)

pyridine. The product was isolated as a racemic mixture. LCMS calculated for $C_{25}H_{27}ClN_5O_4S$ (M+H)⁺: m/z=528.1. Found: 528.1.

Example 33

5-{3-[1-(4-amino-5-oxopyrido[2,3-d]pyrimidin-8(5H)-yl)ethyl]-5-chloro-2-methoxy-6-methylphenyl}-N-methylpyridine-2-carboxamide bis(trifluoroacetate)

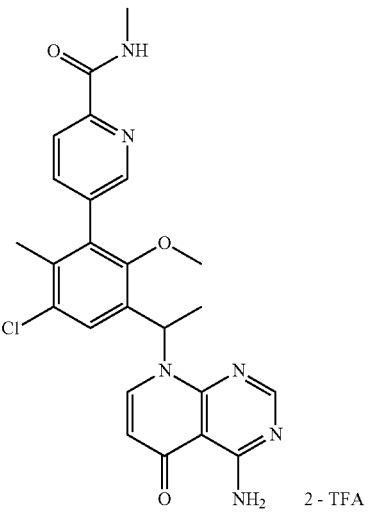 [SMILES: CNC(=O)c1ccc(-c2c(C)c(Cl)cc(C(C)n3ccc(=O)c4c(N)ncnc43)c2OC)cn1]

This compound was prepared using procedures analogous to those for Example 26, with 2-(N-methylamidocarboxy)-5-pyridine boronic acid pincol ester (from Frontier) replacing 3-(methylsulfonyl)-5-(4,4,5,5-tetramethyl-1,3,2-dioxaborolan-2-yl)pyridine. The product was isolated as a racemic mixture. LCMS calculated for $C_{24}H_{24}ClN_6O_3$ (M+H)⁺: m/z=479.2. Found: 479.1.

Example 34

4-Amino-8-{1-[5-chloro-3-(1-isopropylazetidin-3-yl)-2-methoxy-4-methylphenyl]ethyl}pyrido[2,3-d]pyrimidin-5 (8H)-one

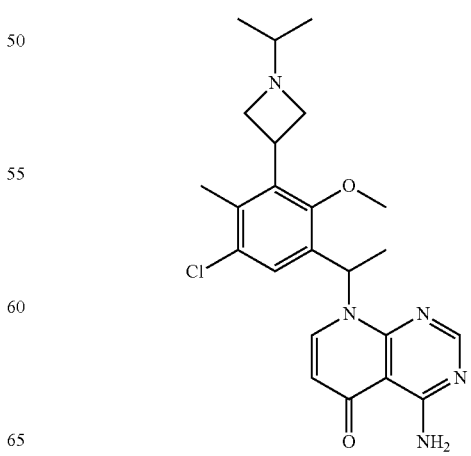

Step 1. tert-Butyl 3-{3-[1-(4-amino-5-oxopyrido[2,3-c]pyrimidin-8(5H)-yl)ethyl]-5-chloro-2-methoxy-6-methylphenyl}azetidine-1-carboxylate

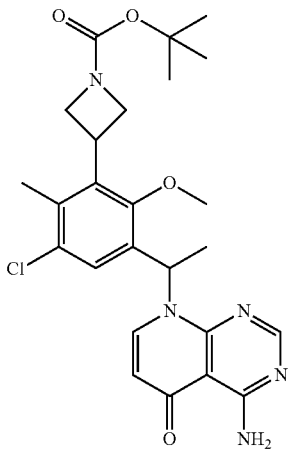 [SMILES: COc1c(C(C)n2ccc(=O)c3c(N)ncnc32)cc(Cl)c(C)c1C1CN(C(=O)OC(C)(C)C)C1]

To a mixture of 4-aminopyrido[2,3-d]pyrimidin-5(8H)-one (from VWR) (8.6 mg, 0.053 mmol), cesium carbonate (26 mg, 0.080 mmol) and potassium iodide (0.89 mg, 0.0053 mmol) in N,N-dimethylformamide (0.2 mL) was added tert-butyl 3-[3-chloro-5-(1-chloroethyl)-6-methoxy-2-methylphenyl]azetidine-1-carboxylate (20 mg, 0.05 mmol, from Example 1, step 5, racemic intermediate). The mixture was stirred at 140° C. for 1 hour, then cooled and was diluted with water, extracted with ether. The organic layers were dried over MgSO$_4$ and concentrated to afford the crude product which was used in the next step directly. LCMS calculated for $C_{25}H_{31}ClN_5O_4$ (M+H)$^+$: m/z=500.2. Found: 500.1.

Step 2. 4-Amino-8-{1-[5-chloro-3-(1-isopropylazetidin-3-yl)-2-methoxy-4-methylphenyl]ethyl}pyrido[2,3-d]pyrimidin-5(8H)-one

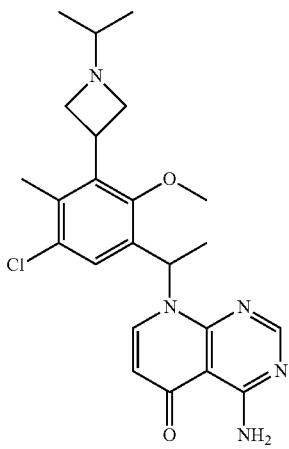 [SMILES: COc1c(C(C)n2ccc(=O)c3c(N)ncnc32)cc(Cl)c(C)c1C1CN(C(C)C)C1]

A solution of tert-butyl 3-{3-[1-(4-amino-5-oxopyrido[2,3-d]pyrimidin-8(5H)-yl)ethyl]-5-chloro-2-methoxy-6-methylphenyl}azetidine-1-carboxylate (27 mg, 0.053 mmol) in methylene chloride (0.25 mL) was treated with 4.0 M hydrogen chloride in dioxane (0.13 mL, 0.50 mmol) at room temperature for 1 hour, then stripped to dryness to give 4-amino-8-[1-(3-azetidin-3-yl-5-chloro-2-methoxy-4-methylphenyl)ethyl]pyrido[2,3-d]pyrimidin-5(8H)-one as HCl salt.

To a mixture of the crude HCl salt in acetonitrile (0.2 mL)/methanol (0.2 mL)/tetrahydrofuran (0.2 mL) was added N,N-diisopropylethylamine (0.046 mL, 0.27 mmol). The mixture was stirred at room temperature until the solid dissolved, then treated with acetone (0.032 mL, 0.43 mmol). The resulting mixture was stirred for 30 minutes before the addition of sodium triacetoxyborohydride (0.034 g, 0.16 mmol). The reaction mixture was stirred at room temperature for 4 hours, then quenched and applied on RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{23}H_{29}ClN_5O_2$ (M+H)$^+$: m/z=442.2. Found: 442.1.

Example 35

4-Amino-8-{1-[5-chloro-2-ethoxy-3-(1-isopropylazetidin-3-yl)-4-methylphenyl]ethyl}pyrido[2,3-d]pyrimidin-5 (8H)-one bis(trifluoroacetate)

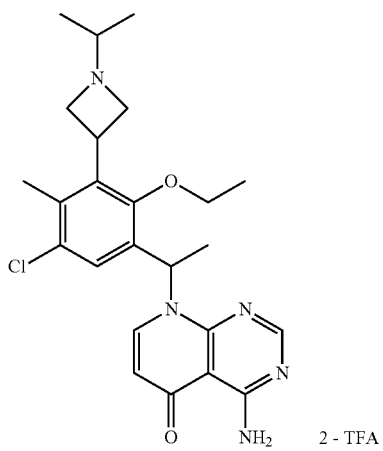 [SMILES: CCOc1c(C(C)n2ccc(=O)c3c(N)ncnc32)cc(Cl)c(C)c1C1CN(C(C)C)C1]

Step 1. Benzyl 3-(3-acetyl-5-chloro-2-ethoxy-6-methylphenyl)azetidine-1-carboxylate

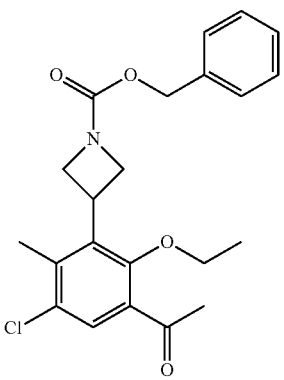 [SMILES: CCOc1c(C(C)=O)cc(Cl)c(C)c1C1CN(C(=O)OCc2ccccc2)C1]

Zinc (0.967 g, 14.8 mmol) was suspended with 1,2-dibromoethane (0.085 mL, 0.98 mmol) in N,N-dimethylformamide (17 mL). The mixture was heated at 70° C. for 10 minutes and then cooled to room temperature. Chlorotrimethylsilane (0.125 mL, 0.984 mmol) was added dropwise and stirring was continued for 1 hour. A solution of benzyl 3-iodoazetidine-1-carboxylate (from PharmaBlock) (3.9 g, 12 mmol) in N,N-dimethylformamide (10 mL) was then added and the mixture was heated at 40° C. for 1 hour before a mixture of 1-(5-chloro-2-ethoxy-3-iodo-4-methylphenyl)ethanone (4.4 g, 13 mmol), tris(dibenzylideneacetone)dipalladium(0) (0.22 g, 0.24 mmol) and tri-(2-furyl)phosphine (0.12 g, 0.50 mmol) in N,N-dimethylformamide (30 mL) was added. The reaction mixture was warmed to 70° C. and stirred overnight. The mixture was then cooled to room temperature and partitioned between ether and sat. NH$_4$Cl solutions. The organic layers were washed with water, dried over MgSO$_4$, concentrated and purified on silica gel (eluting with 0 to 20% EtOAc in hexanes) to give the desired product (3.87 g, 78%). LCMS calculated for C$_{22}$H$_{25}$ClNO$_4$ (M+H)$^+$: m/z=402.1. Found: 402.1.

Step 2. Benzyl 3-[3-chloro-6-ethoxy-5-(1-hydroxyethyl)-2-methylphenyl]azetidine-1-carboxylate

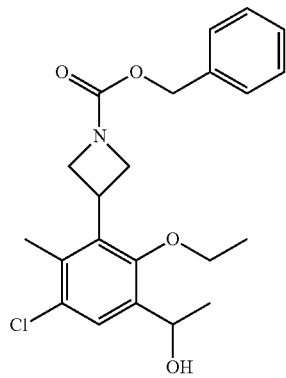 [SMILES: CCOc1c(C(C)O)cc(Cl)c(C)c1C1CN(C(=O)OCc2ccccc2)C1]

To a solution of benzyl 3-(3-acetyl-5-chloro-2-ethoxy-6-methylphenyl)azetidine-1-carboxylate (0.35 g, 0.87 mmol) in methanol (5 mL) cooled at 0° C. was added sodium tetrahydroborate (0.040 g, 1.0 mmol). The mixture was stirred at room temperature for 1 hour, then diluted with water, extracted with EtOAc. The organic layers were dried over MgSO$_4$ and concentrated to give the crude alcohol (0.31 g, 88%). LCMS calculated for C$_{22}$H$_{27}$ClNO$_4$ (M+H)$^+$: m/z=404.2. Found: 404.0.

Step 3. Benzyl 3-[3-chloro-5-(1-chloroethyl)-6-ethoxy-2-methylphenyl]azetidine-1-carboxylate

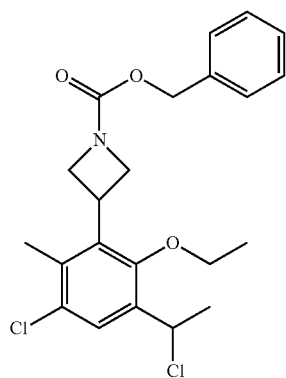 [SMILES: CCOc1c(C(C)Cl)cc(Cl)c(C)c1C1CN(C(=O)OCc2ccccc2)C1]

Cyanuric chloride (200 mg, 1.1 mmol) was added to N,N-dimethylformamide (0.083 mL, 1.1 mmol) at room temperature. After the formation of a white solid (ca. 10 minutes), methylene chloride (5 mL) was added, followed by benzyl 3-[3-chloro-6-ethoxy-5-(1-hydroxyethyl)-2-methylphenyl]azetidine-1-carboxylate (310 mg, 0.77 mmol). After addition, the resultant mixture was stirred at room temperature overnight. Water was added, and then diluted with dichloromethane. The organic phases were washed with sat. NaHCO$_3$ solution, water and brine, dried over MgSO$_4$, concentrated and purified on silica gel (eluting with 0 to 40% EtOAc/hexanes) to give the desired product (140 mg, 43%). LCMS calculated for C$_{22}$H$_{26}$Cl$_2$NO$_3$ (M+H)$^+$: m/z=422.1. Found: 422.0.

Step 4. Benzyl 3-{3-[1-(4-amino-5-oxopyrido[2,3-d]pyrimidin-8(5H)-yl)ethyl]-5-chloro-2-ethoxy-6-methylphenyl}azetidine-1-carboxylate

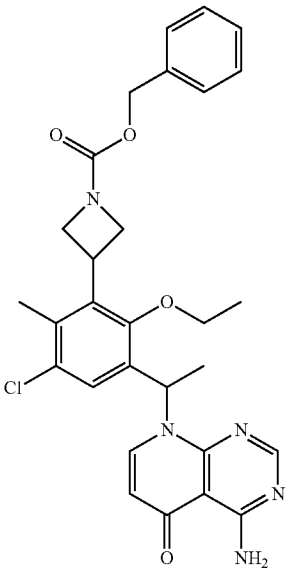 [SMILES: CCOc1c(C(C)n2ccc(=O)c3c(N)ncnc32)cc(Cl)c(C)c1C1CN(C(=O)OCc2ccccc2)C1]

To a mixture of 4-aminopyrido[2,3-d]pyrimidin-5(8H)-one (11.5 mg, 0.0708 mmol), cesium carbonate (34 mg, 0.10 mmol) and potassium iodide (1.2 mg, 0.0071 mmol) in N,N-dimethylformamide (0.2 mL) was added benzyl 3-[3-chloro-5-(1-chloroethyl)-6-ethoxy-2-methylphenyl]azetidine-1-carboxylate (30 mg, 0.07 mmol). The mixture was stirred at 140° C. for 1 hour, cooled and then diluted with water, extracted with ether. The combined organic layers were dried over MgSO$_4$ and concentrated to afford the crude product which was used in the next step directly. LCMS calculated for C$_{29}$H$_{31}$ClN$_5$O$_4$ (M+H)$^+$: m/z=548.2. Found: 548.2.

127

Step 5. 4-Amino-8-{1-[5-chloro-2-ethoxy-3-(1-iso-propylazetidin-3-yl)-4-methylphenyl]ethyl}pyrido[2,3-d]pyrimidin-5(8H)-one bis(trifluoroacetate)

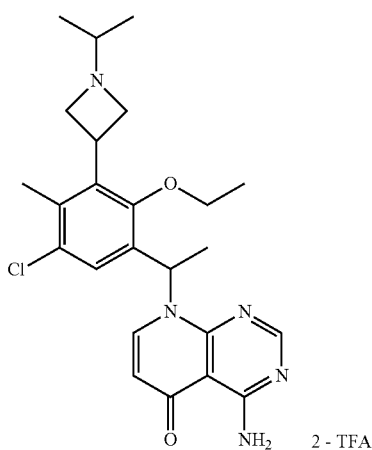 [SMILES: CCOc1c(C(C)n2ccc(=O)c3c(N)ncnc32)cc(Cl)c(C)c1C1CN(C(C)C)C1]

To a mixture of benzyl 3-{3-[1-(4-amino-5-oxopyrido[2,3-d]pyrimidin-8(5H)-yl)ethyl]-5-chloro-2-ethoxy-6-methylphenyl}azetidine-1-carboxylate (23 mg, 0.042 mmol) and 5% palladium on carbon (10 mg) in methanol (1.6 mL) was added 0.25 M hydrogen chloride in water (0.42 mL, 0.10 mmol). The suspension was hydrogenated under balloon pressure of H$_2$ at room temperature for 2 hours. After filtered off the catalyst, the filtrate was neutralized with sat. NaHCO$_3$ solution, extracted with dichloromethane. The combined organic layers were dried over MgSO$_4$ and concentrated to give 4-amino-8-[1-(3-azetidin-3-yl-5-chloro-2-ethoxy-4-methylphenyl)ethyl]pyrido[2,3-d]pyrimidin-5(8H)-one (7 mg, 40%). To a mixture of the crude amine in acetonitrile (0.1 mL)/methanol (0.1 mL)/tetrahydrofuran (0.1 mL) was added N,N-diisopropylethylamine (0.02 mL, 0.1 mmol), followed by acetone (0.03 mL, 0.4 mmol). The mixture was stirred for 30 minutes before the addition of sodium triacetoxyborohydride (0.044 g, 0.21 mmol). The reaction was stirred at room temperature for 4 hours, then quenched with water and purified on RP-HPLC (XBridge C18 column, eluting with a gradient of acetonitrile/water containing 0.05% TFA, at flow rate of 30 mL/min) to give the desired product as TFA salt. The product was isolated as a racemic mixture. LCMS calculated for C$_{24}$H$_{31}$ClN$_5$O$_2$ (M+H)$^+$: m/z=456.2. Found: 456.1.

128

Example 36

5-{3-[1-(4-Amino-5-oxopyrido[2,3-d]pyrimidin-8(5H)-yl)ethyl]-5-chloro-2-ethoxy-6-methylphenyl}-N,N-dimethylpyridine-2-carboxamide bis(trifluoroacetate)

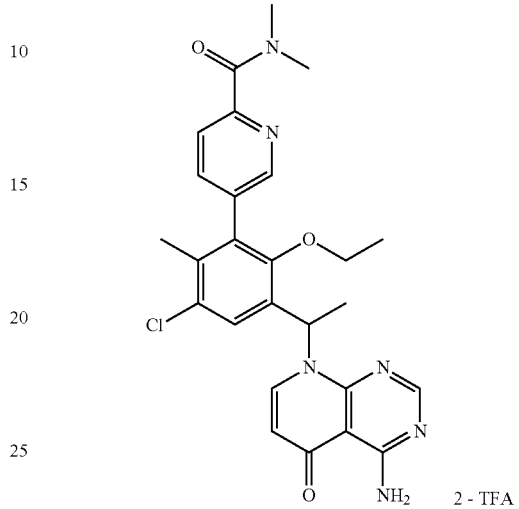

To a mixture of 4-aminopyrido[2,3-d]pyrimidin-5(8H)-one (47 mg, 0.29 mmol), cesium carbonate (130 mg, 0.39 mmol) and potassium iodide (4.4 mg, 0.026 mmol) in N,N-dimethylformamide (0.8 mL) was added 5-[3-chloro-5-(1-chloroethyl)-6-ethoxy-2-methylphenyl]-N,N-dimethylpyridine-2-carboxamide (100 mg, 0.3 mmol, from Example 14, step 4, racemic intermediate) and the mixture was stirred at 140° C. for 1 hour. The resultant mixture was diluted with MeOH, filtered and the filtrate was purified on RP-HPLC (XBridge C18 column, eluting with a gradient of acetonitrile/water containing 0.05% TFA, at flow rate of 30 mL/min) to give the desired product as TFA salt. The product was isolated as a racemic mixture. LCMS calculated for C$_{26}$H$_{28}$ClN$_6$O$_3$ (M+H)$^+$: m/z=507.2. Found: 507.1.

Example 37

6-[1-(4-amino-3-methyl-1H-pyrazolo[3,4-d]pyrimidin-1-yl)ethyl]-4-chloro-N-ethyl-3',5'-difluoro-3-methylbiphenyl-2-carboxamide

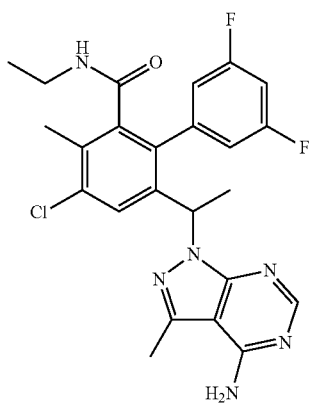 [SMILES: CCNC(=O)c1c(C)c(Cl)cc(C(C)n2nc(C)c3c(N)ncnc32)c1-c1cc(F)cc(F)c1]

Step 1. 3-Acetyl-5-chloro-2-hydroxy-6-methylbenzonitrile

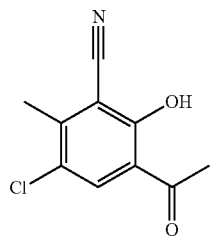

A mixture of 1-(3-bromo-5-chloro-2-hydroxy-4-methylphenyl)ethanone (4.85 g, 18.4 mmol) and copper cyanide (2.47 g, 27.6 mmol) in N-methylpyrrolidinone (15 mL) was heated at 200° C. for 1 h. After cooled to rt, the mixture was diluted with EtOAc and 1 N HCl. The layers were separated and the aqueous layer was extracted with EtOAc. The combined organic layers were washed with water, then brine and dried over magnesium sulfate, then concentrated to dry under reduced pressure. The residue was used directly in next step (3.7 g, 96%). LCMS calculated for $C_{10}H_9ClNO_2$ (M+H)$^+$: m/z=210.0. Found: 210.1.

Step 2. 6-Acetyl-4-chloro-2-cyano-3-methylphenyl trifluoromethanesulfonate

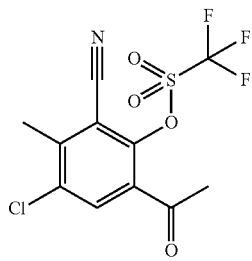 [SMILES: CC(=O)c1cc(Cl)c(C)c(C#N)c1OS(=O)(=O)C(F)(F)F]

To a mixture of 3-acetyl-5-chloro-2-hydroxy-6-methylbenzonitrile (3.70 g, 17.6 mmol) in methylene chloride (70 mL) was added triethylamine (7.4 mL, 53 mmol) followed by trifluoromethanesulfonic anhydride (4.4 mL, 26 mmol) at −78° C. The reaction was allowed to warm up to rt gradually and stirred at rt for 30 min After quenched with water, the mixture was extracted with dichloromethane. The combined organic layers were washed with brine, dried over sodium sulfate, and concentrated to dry. The residue was purified on silica gel, eluting with 0 to 40% EtOAc in hexanes, to give the desired product (2.54 g, 42%). LCMS calculated for $C_{11}H_8ClF_3NO_4S$ (M+H)$^+$: m/z=342.0. Found: 342.1.

Step 3. 6-Acetyl-4-chloro-3',5'-difluoro-3-methylbiphenyl-2-carbonitrile

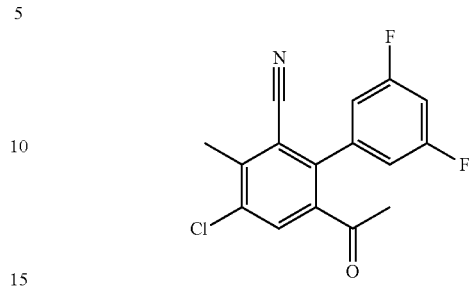

A biphasic solution of 6-acetyl-4-chloro-2-cyano-3-methylphenyl trifluoromethanesulfonate (3.07 g, 8.98 mmol) and (3,5-difluorophenyl)boronic acid (1.70 g, 10.8 mmol) in toluene (30 mL)/0.8 M sodium hydrogenecarbonate in water (30 mL, 30 mmol) (this was saturated NaHCO$_3$ in water) was degassed with N$_2$. Tetrakis(triphenylphosphine)palladium(0) (0.414 g, 0.359 mmol) was added. The mixture was degassed with N$_2$ for 5 min and heated at 80° C. for 2 h. After cool to rt, the mixture was diluted with EtOAc. The layers were separated and the aq. layer was extracted with more EtOAc. The combined extracts were washed with brine, dried over Na$_2$SO$_4$, filtered, and concentrated to crude, dark solid. The material was dissolved in CHCl$_3$ and purified on silica gel column, eluting with 0 to 20% of EtOAc in hexanes, to give the desired product (2.71 g, 99%). LCMS calculated for $C_{16}H_{11}ClF_2NO$ (M+H)$^+$: m/z=306.0. Found: 306.1.

Step 4. 4-Chloro-3',5'-difluoro-6-(1-hydroxyethyl)-3-methylbiphenyl-2-carbaldehyde

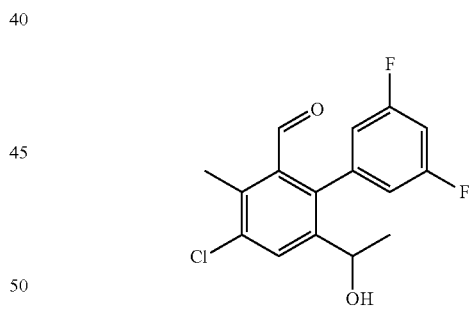

To a mixture of 6-acetyl-4-chloro-3',5'-difluoro-3-methylbiphenyl-2-carbonitrile (2.43 g, 7.95 mmol) in methylene chloride (50 mL) was added 1.0 M diisobutylaluminum hydride in hexane (19.9 mL, 19.9 mmol) at −78° C. The reaction was warmed to rt over 2 h with stirring. 5.0 M Hydrogen chloride in water (70 mL) was added slowly, and stirring was continued for 1 h. The resultant mixture was extracted with EtOAc. The combined organic layers were washed with brine, dried over sodium sulfate and then concentrated to dry. The residue was purified on silica gel, eluting with 0 to 50% EtOAc in hexanes, to give the desired product (2.4 g, 97%). LCMS calculated for $C_{16}H_{12}ClF_2O$ (M−OH)$^+$: m/z=293.1. Found: 293.1.

Step 5. 4-Chloro-3',5'-difluoro-6-(1-hydroxyethyl)-3-methylbiphenyl-2-carboxylic acid

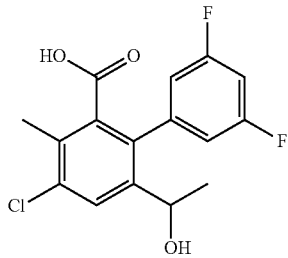 [SMILES: Cc1c(Cl)cc(C(C)O)c(-c2cc(F)cc(F)c2)c1C(=O)O]

To a solution of 4-chloro-3',5'-difluoro-6-(1-hydroxyethyl)-3-methylbiphenyl-2-carbaldehyde (1.00 g, 3.22 mmol) in methanol (40 mL) was added 1.0 M sodium hydroxide in water (16 mL, 16 mmol), followed by 1.0 M sodium hydroxide in water. After stirred at rt overnight, the mixture was slowly acidified to pH 5 with 1 N HCl, then extracted with EtOAc. The combined organic layers were washed with brine, dried over magnesium sulfate, and concentrated to dry under reduced pressure. The crude residue was used directly in next step (1.05 g, 100%).

Step 6. 4-Chloro-N-ethyl-3',5'-difluoro-6-(1-hydroxyethyl)-3-methylbiphenyl-2-carboxamide

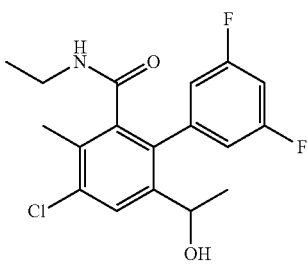 [SMILES: CCNC(=O)c1c(C)c(Cl)cc(C(C)O)c1-c1cc(F)cc(F)c1]

A mixture of 4-chloro-3',5'-difluoro-6-(1-hydroxyethyl)-3-methylbiphenyl-2-carboxylic acid (250 mg, 0.76 mmol), ethylamine hydrochloride (94 mg, 1.1 mmol) and benzotriazol-1-yloxytris(dimethylamino)phosphonium hexafluorophosphate (0.51 g, 1.1 mmol) in N,N-dimethylformamide (4 mL) was stirred at rt for 10 min. To the resulting mixture was added N,N-diisopropylethylamine (0.40 mL, 2.3 mmol). After stirred at rt overnight, the reaction was quenched with water, extracted with EtOAc. The combined organic layers were washed with water, brine, dried over magnesium sulfate, and then concentrated to dry. The residue was purified on silica gel, eluting with 0 to 80% EtOAc in hexanes, to give the desired product (185 mg, 68%). LCMS calculated for $C_{18}H_{91}ClF_2NO_2$ (M+H)$^+$: m/z=354.1. Found: 354.0.

Step 7. 1-{4-Chloro-6-[(ethylamino)carbonyl]-3',5'-difluoro-5-methylbiphenyl-2-yl}ethyl methanesulfonate

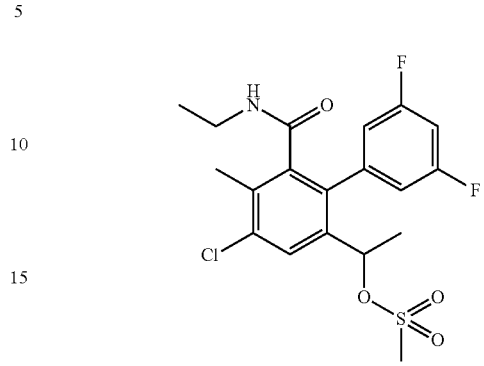

To a mixture of 4-chloro-N-ethyl-3',5'-difluoro-6-(1-hydroxyethyl)-3-methylbiphenyl-2-carboxamide (185 mg, 0.523 mmol) in methylene chloride (3 mL) was added N,N-diisopropylethylamine (0.18 mL, 1.0 mmol), followed by methanesulfonyl chloride (0.061 mL, 0.78 mmol). The reaction was stirred at rt for 10 min, quenched by pouring onto iced water, and extracted with dichloromethane. The combined organic layers were washed with aq. sodium bicarbonate, dried over magnesium sulfate, and evaporated to dry. The residue was used directly in next step (0.226 g, 100%). LCMS calculated for $C_{19}H_{21}ClF_2NO_4S$ (M+H)$^+$: m/z=432.1. Found: 432.1.

Step 8. 6-[1-(4-amino-3-methyl-1H-pyrazolo[3,4-c]pyrimidin-1-yl)ethyl]-4-chloro-N-ethyl-3',5'-difluoro-3-methylbiphenyl-2-carboxamide

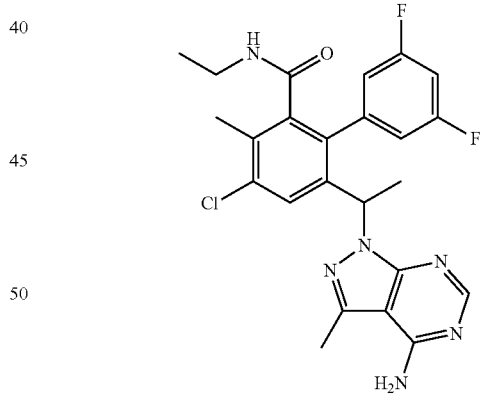

To a mixture of 3-methyl-1H-pyrazolo[3,4-d]pyrimidin-4-amine (from ChemBridge) (26 mg, 0.17 mmol) in N,N-dimethylformamide (0.5 mL) was added sodium hydride (14 mg, 0.35 mmol). After stirring at room temperature for 30 minutes, to the resulting mixture was added to a mixture of 1-{4-chloro-6-[(ethylamino)carbonyl]-3',5'-difluoro-5-methylbiphenyl-2-yl}ethyl methanesulfonate (50 mg, 0.1 mmol) in N,N-dimethylformamide (0.5 mL). The reaction was stirred at room temperature overnight and then quenched with water. The resultant mixture was purified on RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{24}H_{24}ClF_2N_6O$ (M+H)$^+$: m/z=485.2. Found: 485.1.

Example 38

4-{3-[1-(4-amino-1H-pyrazolo[3,4-d]pyrimidin-1-yl)ethyl]-5-chloro-2-methoxy-6-methylphenyl}-N,N-dimethylpyridine-2-carboxamide

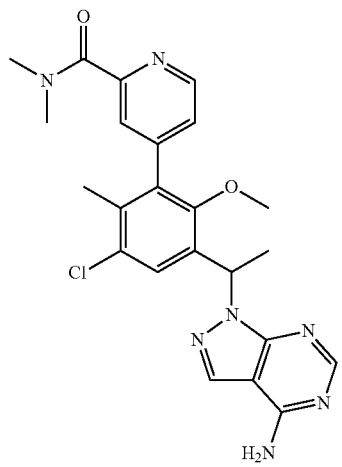 [SMILES: COc1c(C(C)n2ncc3c(N)ncnc32)cc(Cl)c(C)c1-c1ccnc(C(=O)N(C)C)c1]

Step 1. 4-{3-[1-(4-amino-1H-pyrazolo[3,4-d]pyrimidin-1-yl)ethyl]-5-chloro-2-methoxy-6-methylphenyl}pyridine-2-carbonitrile

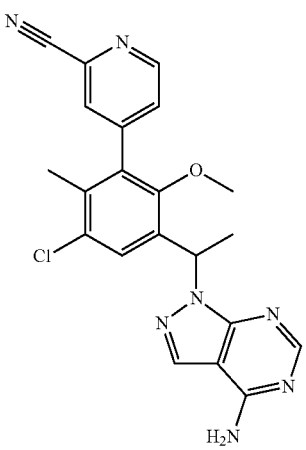 [SMILES: COc1c(C(C)n2ncc3c(N)ncnc32)cc(Cl)c(C)c1-c1ccnc(C#N)c1]

Sodium hydride (20. mg, 0.50 mmol) was added to a mixture of 4-[3-chloro-5-(1-chloroethyl)-6-methoxy-2-methylphenyl]pyridine-2-carbonitrile (from Example 16, Step 3) (90 mg, 0.28 mmol), 4-aminopyrazolo[3,4-d]pyrimidine (from Acros Organics) (57 mg, 0.42 mmol) in N,N-dimethylformamide (4 mL) and the reaction was stirred at 30° C. overnight. The mixture was treated with water and then filtered to provide the desired product. LCMS calculated for $C_{21}H_{19}ClN_7O$ (M+H)$^+$: m/z=420.1. Found: 420.1.

Step 2. 4-{3-[1-(4-amino-1H-pyrazolo[3,4-d]pyrimidin-1-yl)ethyl]-5-chloro-2-methoxy-6-methylphenyl}pyridine-2-carboxylic acid

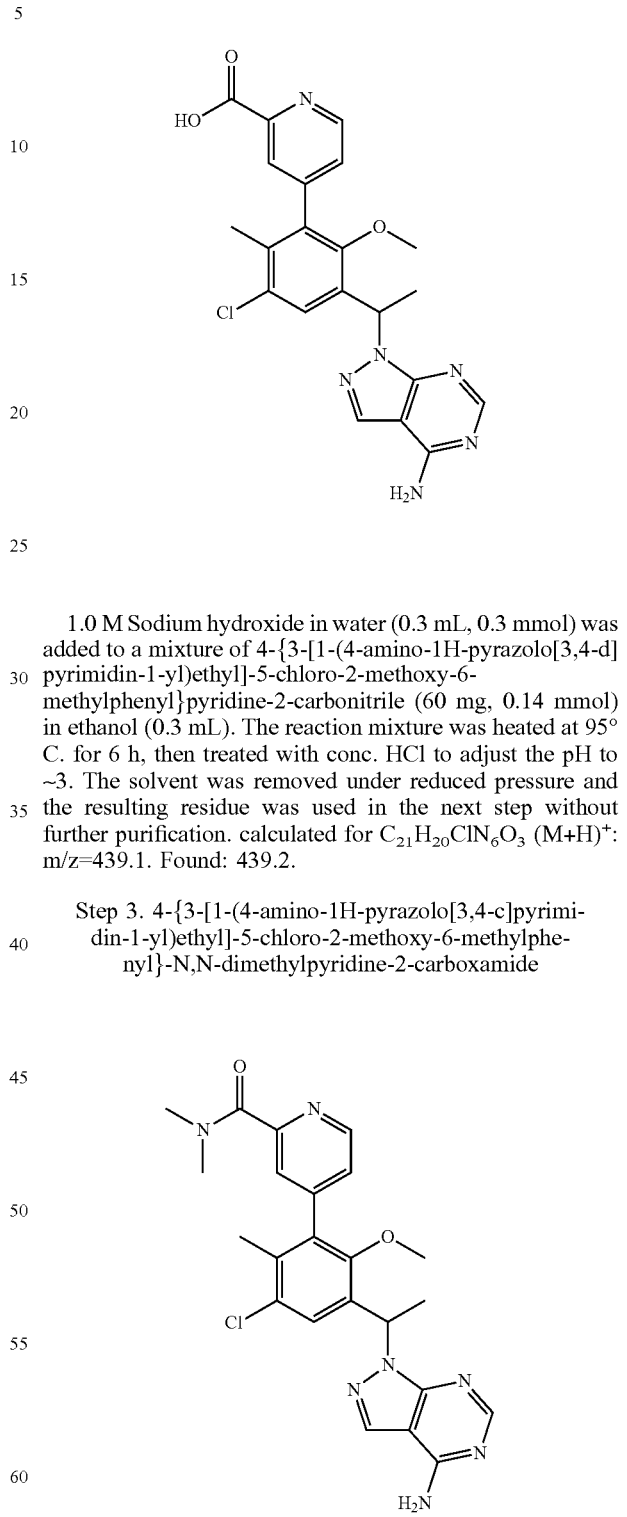

1.0 M Sodium hydroxide in water (0.3 mL, 0.3 mmol) was added to a mixture of 4-{3-[1-(4-amino-1H-pyrazolo[3,4-d]pyrimidin-1-yl)ethyl]-5-chloro-2-methoxy-6-methylphenyl}pyridine-2-carbonitrile (60 mg, 0.14 mmol) in ethanol (0.3 mL). The reaction mixture was heated at 95° C. for 6 h, then treated with conc. HCl to adjust the pH to ~3. The solvent was removed under reduced pressure and the resulting residue was used in the next step without further purification. calculated for $C_{21}H_{20}ClN_6O_3$ (M+H)$^+$: m/z=439.1. Found: 439.2.

Step 3. 4-{3-[1-(4-amino-1H-pyrazolo[3,4-c]pyrimidin-1-yl)ethyl]-5-chloro-2-methoxy-6-methylphenyl}-N,N-dimethylpyridine-2-carboxamide

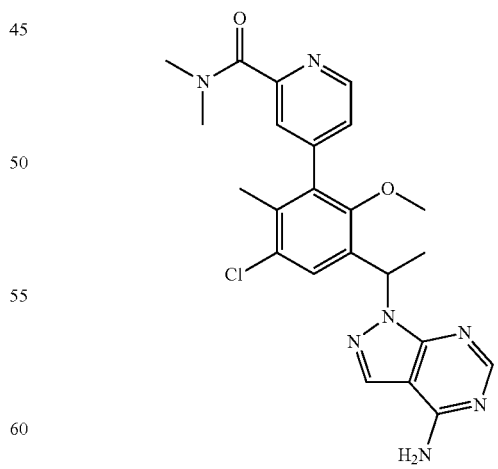

Dimethylamine (2.0 M) in THF (0.14 mL, 0.28 mmol) was added to a solution of 4-{3-[1-(4-amino-1H-pyrazolo

[3,4-d]pyrimidin-1-yl)ethyl]-5-chloro-2-methoxy-6-methylphenyl}pyridine-2-carboxylic acid (18.6 mg, 0.042 mmol) and benzotriazol-1-yloxytris(dimethylamino)phosphonium hexafluorophosphate (10 mg, 0.03 mmol) in N,N-dimethylformamide (0.7 mL) at room temperature followed by the addition of triethylamine (8.8 μL, 0.064 mmol). The reaction was stirred for 1 hour, then quenched with water. The mixture was purified on RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{23}H_{25}ClN_7O_2$ (M+H)$^+$: m/z=466.2. Found: 466.2.

Example 39

4-{3-[1-(4-amino-1H-pyrazolo[3,4-d]pyrimidin-1-yl)ethyl]-5-chloro-2-methoxy-6-methylphenyl}-N-(2-hydroxyethyl)pyridine-2-carboxamide

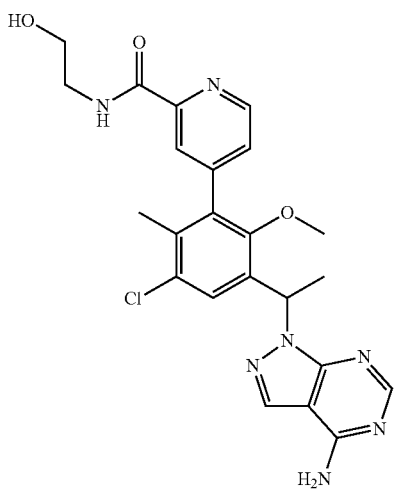 [SMILES: COc1c(C(C)n2ncc3c(N)ncnc32)cc(Cl)c(C)c1-c1ccnc(C(=O)NCCO)c1]

Ethanolamine (2.0 M) in THF (0.14 mL, 0.28 mmol) was added to a solution of 4-{3-[1-(4-amino-1H-pyrazolo[3,4-d]pyrimidin-1-yl)ethyl]-5-chloro-2-methoxy-6-methylphenyl}pyridine-2-carboxylic acid (from Example 38, Step 2) (18.6 mg, 0.042 mmol), benzotriazol-1-yloxytris(dimethylamino)phosphonium hexafluorophosphate (10 mg, 0.03 mmol) in N,N-dimethylformamide (0.7 mL) at room temperature followed by adding triethylamine (8.8 μL, 0.064 mmol). The reaction was stirred for 1 hour, then quenched with water. The mixture was purified on RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{23}H_{25}ClN_7O_3$ (M+H)$^+$: m/z=482.2. Found: 482.2.

Example 40

4-{3-[1-(4-amino-3-methyl-1H-pyrazolo[3,4-d]pyrimidin-1-yl)ethyl]-5-cyano-2-methoxy-6-methylphenyl}-N-(2-hydroxyethyl)-N-methylpyridine-2-carboxamide

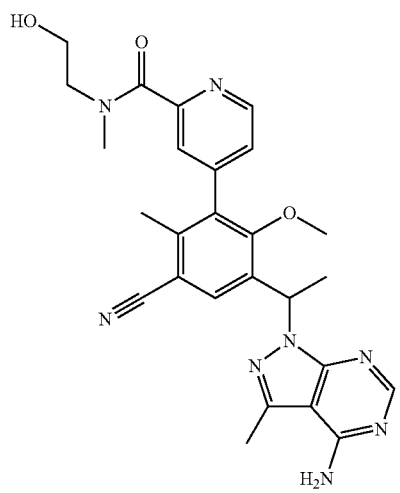 [SMILES: COc1c(C(C)n2nc(C)c3c(N)ncnc32)cc(C#N)c(C)c1-c1ccnc(C(=O)N(C)CCO)c1]

Catalyst preformation: Anhydrous dimethylacetamide (DMA) was purged with a gentle stream of $N_2$ for 30 minutes prior to use. A 50 mM solution of $H_2SO_4$ was prepared with 10 mL dimethylacetamide and 26.8 μL of conc. $H_2SO_4$ and then purged with $N_2$ for 10 minutes. To an 8 mL vial equipped with a magnetic stir bar and septum cap were added Pd(OAc)$_2$ (22.5 mg, 100 μmol) and 2-dicyclohexylphosphino-2',4',6'-triisopropylbiphenyl (95.3 mg, 200 μmol). The vial was evacuated and filled with $N_2$ three times, purged with a gentle stream of $N_2$ for 10 minutes. $H_2SO_4$ (2.0 mL, 50 mM in DMA) was added, and the catalyst mixture was stirred in an oil bath at 80° C. for 30 minutes to give a homogeneous coffee-brown solution.

The above catalyst (0.05 mL) was added to a mixture of 4-{3-[1-(4-amino-3-methyl-1H-pyrazolo[3,4-d]pyrimidin-1-yl)ethyl]-5-chloro-2-methoxy-6-methylphenyl}-N-(2-hydroxyethyl)-N-methylpyridine-2-carboxamide (from Example 19) (4.0 mg, 0.0078 mmol), zinc (0.22 mg, 0.0034 mmol) and zinc cyanide (0.92 mg, 0.0078 mmol) in N,N-dimethylacetamide (0.1 mL). The mixture was degassed and then the reaction was heated at 120° C. for 1.5 hours. The crude mixture was applied on RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{26}H_{29}N_8O_3$ (M+H)$^+$: m/z=501.2. Found: 501.2.

Example 41

5-{3-[1-(4-Amino-3-methyl-1H-pyrazolo[4,3-c]pyridin-1-yl)ethyl]-5-chloro-2-methoxy-6-methylphenyl}-N,N-dimethylpyridine-2-carboxamide bis(trifluoroacetate)

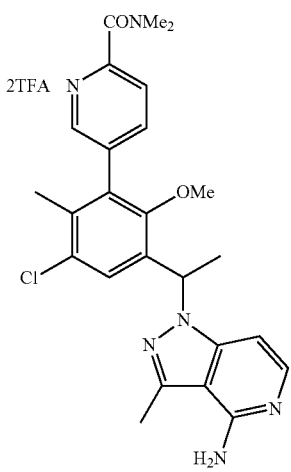

Step 1: N-(2,4-Dimethoxybenzyl)-3-methyl-1H-pyrazolo[4,3-c]pyridin-4-amine

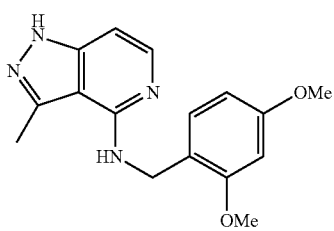 [SMILES: COc1ccc(CNc2nccc3[nH]nc(C)c23)c(OC)c1]

A solution of 4-chloro-3-methyl-1H-pyrazolo[4,3-c]pyridine (330 mg, 1.9 mmol) and 1-(2,4-dimethoxyphenyl)methanamine (0.58 mL, 3.9 mmol) in 1-butanol was heated in the microwave at 150° C. for 40 minutes. Purification via preparative LCMS (XBridge C18 column, eluting with a gradient of acetonitrile/water containing 0.1% ammonium hydroxide, at flow rate of 60 mL/min) gave the desired product (240 mg, 42%). LCMS for $C_{16}H_{19}N_4O_2$ (M+H)$^+$: m/z=299.1. Found: 299.2.

Step 2: 5-[3-Chloro-5-(1-{4-[(2,4-dimethoxybenzyl)amino]-3-methyl-1H-pyrazolo[4,3-c]pyridin-1-yl}ethyl)-6-methoxy-2-methylphenyl]-N,N-dimethylpyridine-2-carboxamide

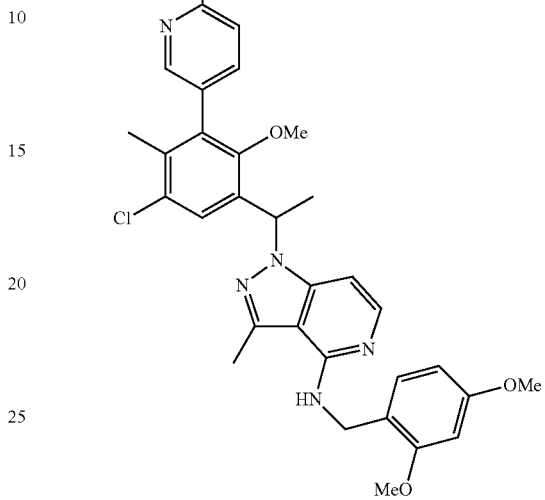

A solution of N-(2,4-dimethoxybenzyl)-3-methyl-1H-pyrazolo[4,3-c]pyridin-4-amine (110 mg, 0.37 mmol) in N,N-dimethylformamide (2 mL) was treated with sodium hydride (30 mg, 0.75 mmol) and stirred at 20° C. for 30 minutes. The reaction mixture was treated with a solution of 5-[3-chloro-5-(1-chloroethyl)-6-methoxy-2-methylphenyl]-N,N-dimethylpyridine-2-carboxamide (130 mg, 0.34 mmol) in N,N-dimethylformamide (1 mL) and heated at 50° C. overnight. The reaction mixture was diluted with water and extracted with ethyl acetate (2×). The combined organic extracts were washed with water and brine, dried with magnesium sulfate, filtered, and concentrated to a crude residue. Purification via preparative LCMS (XBridge C18 column, eluting with a gradient of acetonitrile/water containing 0.1% ammonium hydroxide, at flow rate of 60 mL/min) gave the desired product (110 mg, 49%). LCMS for $C_{34}H_{38}ClN_6O_4$ (M+H)$^+$: m/z=629.3. Found: 629.1.

Step 3: 5-{3-[1-(4-Amino-3-methyl-1H-pyrazolo[4,3-c]pyridin-1-yl)ethyl]-5-chloro-2-methoxy-6-methylphenyl}-N,N-dimethylpyridine-2-carboxamide bis(trifluoroacetate)

A solution of 5-[3-chloro-5-(1-{4-[(2,4-dimethoxybenzyl)amino]-3-methyl-1H-pyrazolo[4,3-c]pyridin-1-yl}ethyl)-6-methoxy-2-methylphenyl]-N,N-dimethylpyridine-2-carboxamide (85 mg, 0.14 mmol) in methylene chloride (2 mL) was treated with trifluoroacetic acid (2 mL) and stirred at 20° C. for 3 hours and at 40° C. for 20 minutes. Purification via preparative LCMS (XBridge C18 column, eluting with a gradient of acetonitrile/water containing 0.1% trifluoroacetic acid, at flow rate of 60 mL/min) gave the desired product (44 mg, 46%). The product was isolated as a racemic mixture. LCMS for $C_{25}H_{28}ClN_6O_2$ (M+H)$^+$: m/z=479.2. Found: 479.0. $^1$H NMR (300 MHz, DMSO-d$_6$): δ 12.8 (br s, 0.5; H), 8.50 (br s, 0.5; H), 8.37 (br s, 2H), 7.91-7.86 (m, 0.5; H), 7.80-7.75 (m, 0.5; H), 7.68-7.58 (m, 3H), 7.17 (d, J=7.3 Hz, 1H), 6.19 (q, J=6.9 Hz, 1H), 3.04 (s, 3H), 3.01 (s, 3H), 2.94 (s, 3H), 2.61 (s, 3H), 2.05 (s, 3H), 1.83 (d, J=6.9 Hz, 3H).

Example 42

5-{3-[1-(4-Amino-5-methyl-7H-pyrrolo[2,3-d]pyrimidin-7-yl)ethyl]-5-chloro-2-methoxy-6-methylphenyl}-N,N-dimethylpyridine-2-carboxamide

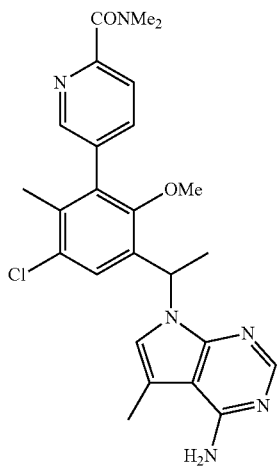

The desired compound was prepared according to the procedure of Example 41, step 2, using 5-methyl-7H-pyrrolo[2,3-d]pyrimidin-4-amine [ACES Pharma, 57974] as the starting material in 18% yield. The product was isolated as a racemic mixture. LCMS for $C_{25}H_{28}ClN_6O_2$ $(M+H)^+$: m/z=479.2. Found: 479.3. $^1$H NMR (300 MHz, DMSO-d$_6$): δ 8.46 (br s, 1H), 8.31 (br s, 1H), 8.28 (s, 1H), 7.87-7.83 (m, 1H), 7.65-7.61 (m, 1H), 7.51 (s, 1H), 7.48 (s, 1H), 6.24 (q, J=7.0 Hz, 1H), 3.08 (s, 3H), 3.01 (s, 3H), 2.95 (s, 3H), 2.40 (s, 3H), 2.05 (s, 3H), 1.78 (d, J=7.2 Hz, 3H).

Example 43

4-[1-(4-amino-3-methyl-1H-pyrazolo[3,4-d]pyrimidin-1-yl)ethyl]-6-chloro-3-ethoxy-2-[5-(methylsulfonyl)pyridin-3-yl]benzonitrile

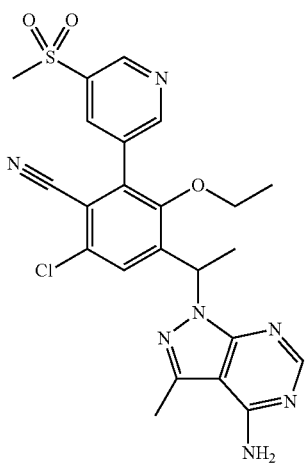 [SMILES: CCOc1c(C(C)n2nc(C)c3c(N)ncnc32)cc(Cl)c(C#N)c1-c1cncc(S(C)(=O)=O)c1]

Step 1. 1-(3-bromo-5-chloro-4-fluoro-2-hydroxyphenyl)ethanone

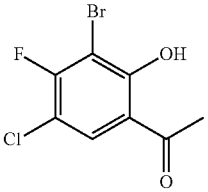

1-(5-Chloro-4-fluoro-2-hydroxyphenyl)ethanone (e.g., from Example 13, step 1) (20.0 g, 101 mmol, 1.00 eq) and a 50% aqueous sulfuric acid (120 mL) were added to the flask. The resulting mixture was heated to 60° C. in a water bath with stirring. N-Bromosuccinimide (21.52 g, 120.9 mmol, 1.20 eq) was added in three portions [7.0 g+7.0 g+7.52 g] in 8 minute intervals. After the reaction mixture was heated at 60° C. for 3 hours, the reaction was complete. The reaction mixture was diluted with water (160 ml) and dichloromethane (DCM) (300 ml), and the mixture was stirred for 0.5 hour. The organic layer was separated and the aqueous layer was extracted with dichloromethane (100 ml). The combined organic layers were washed with 1 N HCl (100 ml×2), water (100 ml), brine (60 ml), and concentrated under reduced pressure to afford the crude product (29.1 g) as a yellowish solid. The crude product was dissolved in HOAc (100 ml) and then diluted with water (200 ml) under stirring. The resulting mixture was stirred for 20 min at room temperature and the product was collected by filtration and dried to give 1-(3-bromo-5-chloro-4-fluoro-2-hydroxyphenyl)ethanone (21.8 g, 80.9%) as a yellowish solid. $^1$H-NMR (300 MHz, CDCl$_3$) δ 13.18 (s, 1H, —OH), 7.78 (d, J=7.78 Hz, 1H), 2.63 (s, 3H).

Step 2.
4-Acetyl-2-bromo-6-chloro-3-ethoxybenzonitrile

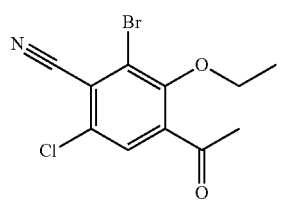 [SMILES: CCOc1c(C(C)=O)cc(Cl)c(C#N)c1Br]

1-(3-Bromo-5-chloro-4-fluoro-2-hydroxyphenyl)ethanone (2.0 g, 7.5 mmol) was combined with potassium cyanide (0.58 g, 9.0 mmol) in N,N-dimethylformamide (16 mL, 210 mmol) and heated to 85° C. in an oil bath. After heating for 18 hours, the reaction was allowed to cool to room temperature and iodoethane (0.90 mL, 11 mmol) and potassium carbonate (2.1 g, 15 mmol) were added. The reaction was heated to 65° C. and monitored by LC/MS. After heating for 3 hours the reaction was complete and allowed to cool to room temperature, then taken up in ethyl acetate and washed with water, brine, and dried over magnesium sulfate. The resultant solution was concentrated to give the crude product as a dark oil. The product was purified by flash column chromatography on silica gel eluting hexane: ethyl acetate gradient to give 4-acetyl-2- bromo-6-chloro-3-ethoxybenzonitrile (1.15 gm, 50%) as a solid residue, LCMS calculated for $C_{11}H_{19}BrClNO_2(M+H)^+$: m/z=301.9, 303.9. found: (no ionization).

Step 3. 2-Bromo-6-chloro-3-ethoxy-4-(1-hydroxyethyl)benzonitrile

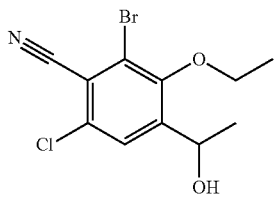 [SMILES: CCOc1c(C(C)O)cc(Cl)c(C#N)c1Br]

Sodium tetrahydroborate (38 mg, 0.99 mmol) was added to a mixture of 4-acetyl-2-bromo-6-chloro-3-ethoxybenzonitrile (200 mg, 0.7 mmol) in methanol (5 mL, 100 mmol) at 0° C. The reaction was stirred at room temperature for 1 hour, concentrated and partitioned between water and EtOAc. The combined organic layers were washed with brine, dried over MgSO$_4$, filtered and concentrated to give crude 2-bromo-6-chloro-3-ethoxy-4-(1-hydroxyethyl)benzonitrile as a clear oil (0.15 gm, 100%), LCMS calculated for $C_{11}H_{11}BrClNO_2(M+H)^+$: m/z=303.9, 305.9. found: 304.0, 305.9.

Step 4. 2-Bromo-6-chloro-4-(1-chloroethyl)-3-ethoxybenzonitrile

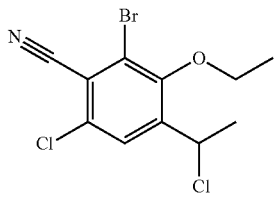 [SMILES: CCOc1c(C(C)Cl)cc(Cl)c(C#N)c1Br]

Cyanuric chloride (0.11 g, 0.59 mmol) was dissolved in N,N-dimethylformamide (3 mL, 40 mmol). After stirring for a few minutes, a solution of 2-bromo-6-chloro-3-ethoxy-4-(1-hydroxyethyl)benzonitrile (150 mg, 0.49 mmol) in methylene chloride (3 mL, 50 mmol) was added. The resulting mixture was stirred at room temperature overnight. The reaction was partitioned between water and dichloromethane. The organic layer was washed with sat. NaHCO$_3$ solution, water, brine, dried over MgSO$_4$, and concentrated. The crude product was purified by flash column chromatography, eluting a gradient of 0-30% EtOAc/Hexane to give 2-bromo-6-chloro-4-(1-chloroethyl)-3-ethoxybenzonitrile (0.12 gm, 75%) as a semisolid, LCMS calculated for $C_{11}H_{10}BrCl_2NO (M+H)^+$: m/z=323.9, 320.9. found: (poor ionization).

Step 5. 4-[1-(4-amino-3-methyl-1H-pyrazolo[3,4-d]pyrimidin-1-yl)ethyl]-2-bromo-6-chloro-3-ethoxybenzonitrile

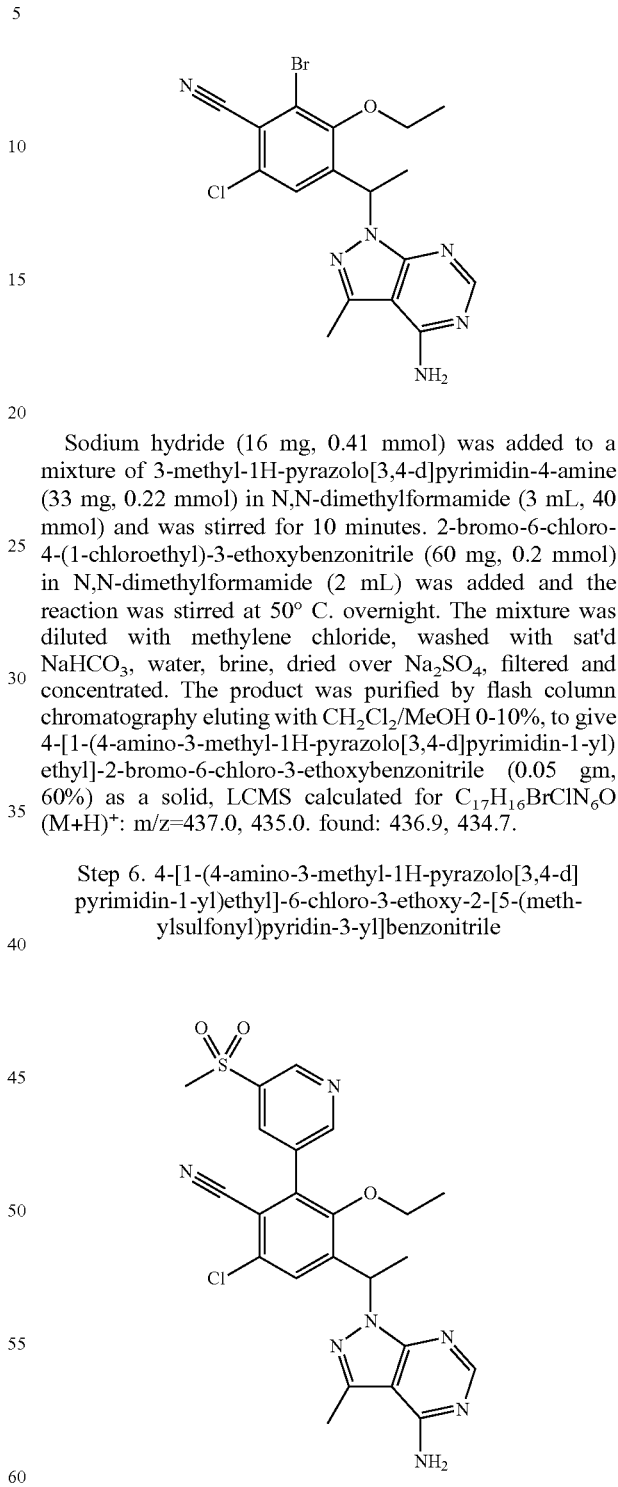

Sodium hydride (16 mg, 0.41 mmol) was added to a mixture of 3-methyl-1H-pyrazolo[3,4-d]pyrimidin-4-amine (33 mg, 0.22 mmol) in N,N-dimethylformamide (3 mL, 40 mmol) and was stirred for 10 minutes. 2-bromo-6-chloro-4-(1-chloroethyl)-3-ethoxybenzonitrile (60 mg, 0.2 mmol) in N,N-dimethylformamide (2 mL) was added and the reaction was stirred at 50° C. overnight. The mixture was diluted with methylene chloride, washed with sat'd NaHCO$_3$, water, brine, dried over Na$_2$SO$_4$, filtered and concentrated. The product was purified by flash column chromatography eluting with CH$_2$Cl$_2$/MeOH 0-10%, to give 4-[1-(4-amino-3-methyl-1H-pyrazolo[3,4-d]pyrimidin-1-yl)ethyl]-2-bromo-6-chloro-3-ethoxybenzonitrile (0.05 gm, 60%) as a solid, LCMS calculated for $C_{17}H_{16}BrClN_6O$ $(M+H)^+$: m/z=437.0, 435.0. found: 436.9, 434.7.

Step 6. 4-[1-(4-amino-3-methyl-1H-pyrazolo[3,4-d]pyrimidin-1-yl)ethyl]-6-chloro-3-ethoxy-2-[5-(methylsulfonyl)pyridin-3-yl]benzonitrile To a mixture of 4-[1-(4-amino-3-methyl-1H-pyrazolo[3,4-d]pyrimidin-1-yl)ethyl]-2-bromo-6-chloro-3-ethoxybenzonitrile (20 mg, 0.04 mmol) and 3-(methylsulfonyl)-5-(4,4,5,5-tetramethyl-1,3,2-dioxaborolan-2-yl)pyridine (19 mg, 0.069 mmol) in acetonitrile (2 mL, 40 mmol) was added sodium carbonate (10 mg, 0.09 mmol) in water (0.5 mL, 30 mmol). The reaction was degassed with bubbling nitrogen. [1,1'-bis(diphenylphosphino)ferrocene]dichloropalladium (II) complex with dichloromethane (1:1) (2 mg, 0.002 mmol) was added and degassed more with N$_2$. Reaction was heated at 100° C. for 2 hours. The crude product was purified on preparative LC-MS (acetonitrile, water, TFA) to give the desired product (0.004 g, 20%) as white amorphous solid. The product was isolated as a racemic mixture. LCMS calculated for C$_{23}$H$_{22}$ClN$_7$O$_3$S (M+H)$^+$: m/z=512.1. found: 512.2. $^1$H NMR (500 MHz, DMSO) δ 9.20 (d, J=2.1 Hz, 1H), 9.12 (d, J=1.9 Hz, 1H), 8.61 (t, J=2.0 Hz, 1H), 8.12 (s, 1H), 7.80 (s, 1H), 6.36 (q, J=7.0 Hz, 1H), 3.54 (dt, J=14.0, 7.0 Hz, 1H), 3.37 (s, 3H), 3.36-3.30 (m, 1H), 2.58 (s, 3H), 1.81 (d, J=7.0 Hz, 3H), 0.92 (t, J=6.9 Hz, 3H).

Example 44

5-(3-(1-(4-amino-3-methyl-1H-pyrazolo[3,4-d]pyrimidin-1-yl)ethyl)-5-chloro-6-cyano-2-ethoxyphenyl)-N,N-dimethylpicolinamide

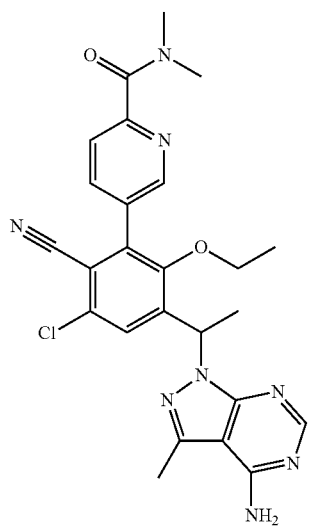 [SMILES: CCOc1c(C(C)n2nc(C)c3c(N)ncnc32)cc(Cl)c(C#N)c1-c1ccc(C(=O)N(C)C)nc1]

The title compound was prepared in analogous manor as Example 43, step 6 but using N,N-dimethyl-5-(4,4,5,5-tetramethyl-1,3,2-dioxaborolan-2-yl)picolinamide (Peptech, Cat#BE1622) to give the crude product which was purified on preparative LC-MS (acetonitrile, water, TFA) to give the desired product (0.005 g, 22%) as white amorphous solid. The product was isolated as a racemic mixture. LCMS calculated for C$_{25}$H$_{25}$ClN$_8$O$_2$ (M+H)$^+$: m/z=505.1. found: 505.1. $^1$H NMR (500 MHz, DMSO) δ 8.72 (dd, J=2.1, 0.7 Hz, 1H), 8.14-8.12 (m, 1H), 8.11 (s, 1H), 7.75 (s, 1H), 7.71 (dd, J=8.0, 0.7 Hz, 1H), 6.35 (q, J=7.0 Hz, 1H), 3.61-3.48 (m, 1H), 3.42-3.31 (m, 1H), 3.03 (s, 3H), 2.95 (s, 3H), 2.57 (s, 3H), 1.80 (d, J=7.1 Hz, 3H), 0.92 (t, J=7.0 Hz, 3H).

Example 45

5-{3-[1-(4-amino-5-oxopyrido[2,3-d]pyrimidin-8(5H)-yl)ethyl]-5-chloro-6-cyano-2-ethoxyphenyl}-N,N-dimethylpyridine-2-carboxamide

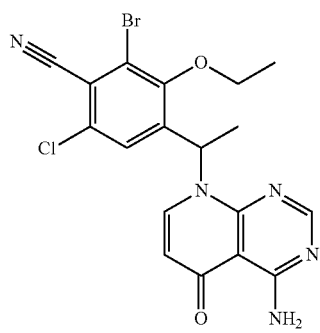 [SMILES: CCOc1c(C(C)n2ccc(=O)c3c(N)ncnc32)cc(Cl)c(C#N)c1Br]

Step 1. 4-[1-(4-amino-5-oxopyrido[2,3-d]pyrimidin-8(5H)-yl)ethyl]-2-bromo-6-chloro-3-ethoxybenzonitrile Sodium hydride (16 mg, 0.41 mmol) was added to a mixture of 4-aminopyrido[2,3-d]pyrimidin-5(8H)-one (36 mg, 0.22 mmol) in N,N-dimethylformamide (3 mL, 40 mmol) and was stirred for 10 minutes. 2-Bromo-6-chloro-4-(1-chloroethyl)-3-ethoxybenzonitrile (Example 43, step 4) (60 mg, 0.2 mmol in N,N-dimethylformamide (2 mL) was added and the reaction was stirred at 50° C. overnight. The mixture was diluted with methylene chloride, washed with sat'd NaHCO$_3$, water, brine, dried over Na$_2$SO$_4$, filtered and concentrated. The product was purified by FCC eluting with CH$_2$Cl$_2$/MeOH (0-10%), to give 4-[1-(4-amino-5-oxopyrido[2,3-d]pyrimidin-8(5H)-yl)ethyl]-2-bromo-6-chloro-3-ethoxybenzonitrile (0.04 g, 50%) as a solid, LCMS calculated for C$_{18}$H$_{15}$BrClN$_5$O$_2$ (M+H)$^+$: m/z=450.0, 448.0. found: 450.0, 448.0.

145

Step 2. 5-{3-[1-(4-amino-5-oxopyrido[2,3-d]pyrimidin-8(5H)-yl)ethyl]-5-chloro-6-cyano-2-ethoxyphenyl}-N,N-dimethylpyridine-2-carboxamide

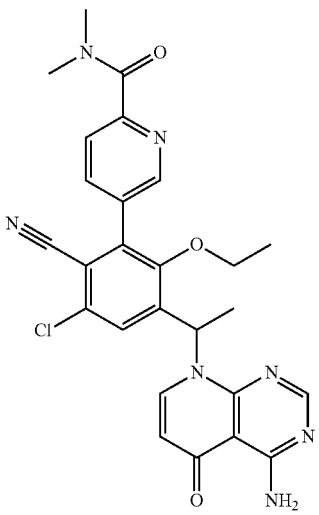 [SMILES: CCOc1c(C(C)n2ccc(=O)c3c(N)ncnc32)cc(Cl)c(C#N)c1-c1ccc(C(=O)N(C)C)nc1]

To a mixture of 4-[1-(4-amino-5-oxopyrido[2,3-d]pyrimidin-8(5H)-yl)ethyl]-2-bromo-6-chloro-3-ethoxybenzonitrile (20 mg, 0.04 mmol) and {6-[(dimethylamino)carbonyl]pyridin-3-yl}boronic acid (13 mg, 0.069 mmol) in acetonitrile (2 mL, 40 mmol) was added sodium carbonate (10 mg, 0.09 mmol) in water (0.5 mL, 30 mmol). The reaction was degassed with bubbling nitrogen. [1,1'-bis(diphenylphosphino)ferrocene]dichloropalladium(II) complex with dichloromethane (1:1) (2 mg, 0.002 mmol) was added and degassed more with $N_2$. Reaction was heated at 100° C. for 1 h. The crude product was purified on preparative LC-MS (acetonitrile, water, TFA) to give the desired product (0.005 g, 20%) as white amorphous solid. The product was isolated as a racemic mixture. LCMS calculated for $C_{26}H_{24}ClN_7O_3$ (M+H)$^+$: m/z=518.1. found: 518.1.

Example 46

4-(1-(4-amino-5-oxopyrido[2,3-d]pyrimidin-8(5H)-yl)ethyl)-6-chloro-3-ethoxy-2-(5-(methylsulfonyl)pyridin-3-yl)benzonitrile

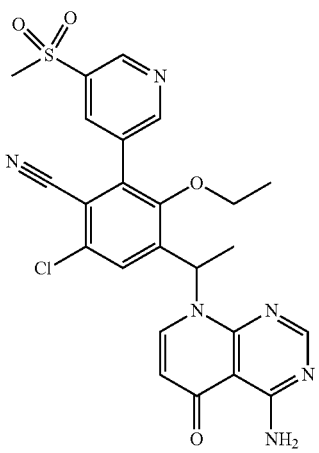 [SMILES: CCOc1c(C(C)n2ccc(=O)c3c(N)ncnc32)cc(Cl)c(C#N)c1-c1cncc(S(C)(=O)=O)c1]

146

The title compound was prepared in an analogous manor as Example 45, Step 2, but using 3-(methylsulfonyl)-5-(4,4,5,5-tetramethyl-1,3,2-dioxaborolan-2-yl)pyridine (from Anisyn Inc., Cat# CT601515-3) to give the crude product which was purified on preparative LC-MS (acetonitrile, water, TFA) to give the desired product (0.005 g, 22%) as white amorphous solid. The product was isolated as a racemic mixture. LCMS calculated for $C_{24}H_{21}ClN_6O_2S$ (M+H)$^+$: m/z=525.1. found: 525.2.

Example 47

5-(3-{1-[4-amino-3-(3-fluorophenyl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

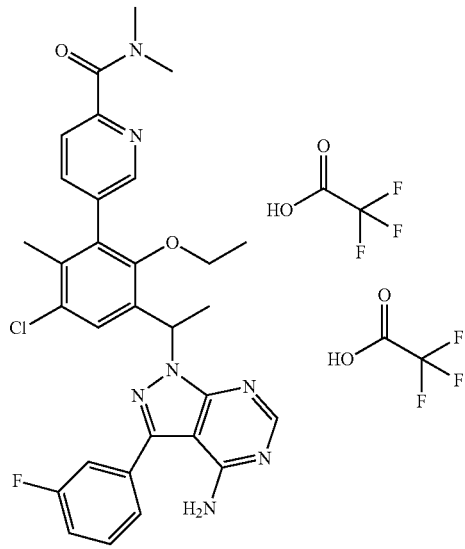

To a solution of 5-{3-[1-(4-amino-3-iodo-1H-pyrazolo[3,4-d]pyrimidin-1-yl)ethyl]-5-chloro-2-ethoxy-6-methylphenyl}-N,N-dimethylpyridine-2-carboxamide (from Example 15) (15 mg, 0.025 mmol), (3-fluorophenyl)boronic acid (from Aldrich) (6.9 mg, 0.050 mmol), sodium carbonate (16 mg, 0.15 mmol) in N,N-dimethylformamide (0.1 mL)/water (74 µL) under $N_2$ was added tetrakis(triphenylphosphine) palladium (0) (2.9 mg, 0.0025 mmol). The mixture was heated at 100° C. overnight. After cooling to room temperature, the mixture was filtered and the filtrate purified on RP-HPLC (XBridge C18 column, eluting with a gradient of acetonitrile/water containing 0.05% trifluoroacetic acid, at flow rate of 30 mL/min) to give the desired product as bis-TFA salt. The product was isolated as a racemic mixture. LCMS calculated for $C_{30}H_{30}ClFN_7O_2$ (M+H)$^+$: m/z=574.2. Found: 574.2.

Example 48

5(3-{1-[4-amino-3-(1H-pyrazol-4-yl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

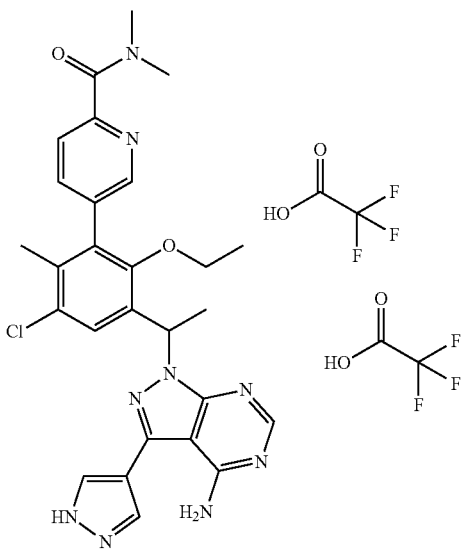

This compound was prepared according to the procedure described in Example 47, using 4-(4,4,5,5-tetramethyl-1,3,2-dioxaborolan-2-yl)-1H-pyrazole (from Aldrich) instead of (3-fluorophenyl)boronic acid. The product was isolated as a racemic mixture. LCMS calculated for $C_{27}H_{29}ClN_9O_2$ (M+H)$^+$: m/z=546.2. Found: 546.2.

Example 49

5-(3-{1-[4-amino-3-(1-methyl-1H-pyrazol-4-yl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

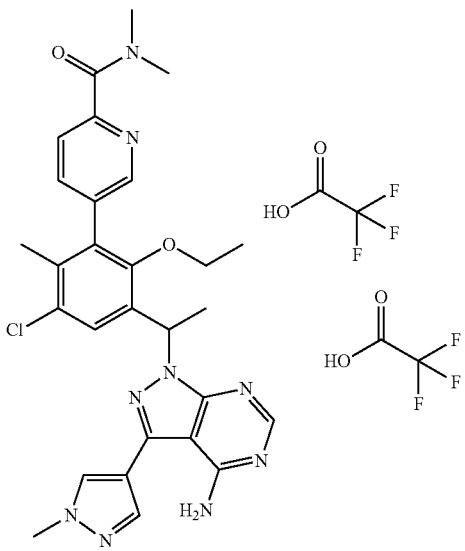

This compound was prepared according to the procedure described in Example 47, using 1-methyl-4-(4,4,5,5-tetramethyl-1,3,2-dioxaborolan-2-yl)-1H-pyrazole (from Aldrich) instead of (3-fluorophenyl)boronic acid. The product was isolated as a racemic mixture. LCMS calculated for $C_{28}H_{31}ClN_9O_2$ (M+H)$^+$: m/z=560.2. Found: 560.2.

Example 50

5-(3-{1-[4-amino-3-(1-methyl-1H-pyrazol-3-yl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

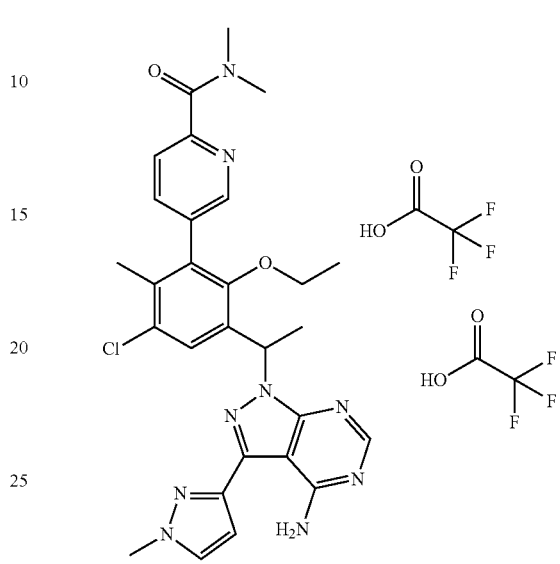

This compound was prepared according to the procedure described in Example 47, using 1-methyl-3-(4,4,5,5-tetramethyl-1,3,2-dioxaborolan-2-yl)-1H-pyrazole (from Frontier) instead of (3-fluorophenyl)boronic acid. The product was isolated as a racemic mixture. LCMS calculated for $C_{28}H_{31}ClN_9O_2$ (M+H)$^+$: m/z=560.2. Found: 560.2.

Example 51

5-(3-{1-[4-amino-3-(1H-pyrazol-3-yl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

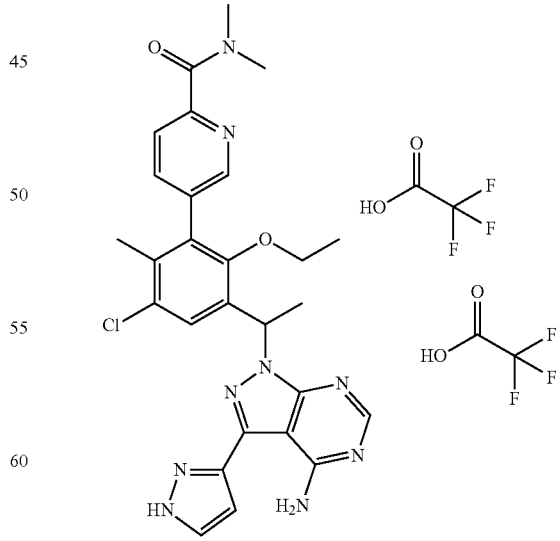

This compound was prepared according to the procedure described in Example 47, using 1-(tetrahydro-2H-pyran-2-yl)-3-(4,4,5,5-tetramethyl-1,3,2-dioxaborolan-2-yl)-1H-pyrazole (from Aldrich) instead of (3-fluorophenyl)boronic acid. The crude mixture was treated with conc. HCl (0.1 mL) at room temperature for 1 hour before purification. The product was isolated as a racemic mixture. LCMS calculated for $C_{27}H_{29}ClN_9O_2$ (M+H)$^+$: m/z=546.2. Found: 546.2.

Example 52

5-[3-(1-{4-amino-3-[1-(2-hydroxyethyl)-1H-pyrazol-4-yl]-1H-pyrazolo[3,4-d]pyrimidin-1-yl}ethyl)-5-chloro-2-ethoxy-6-methylphenyl]-N,N-dimethylpyridine-2-carboxamide bis(trifluoroacetate)

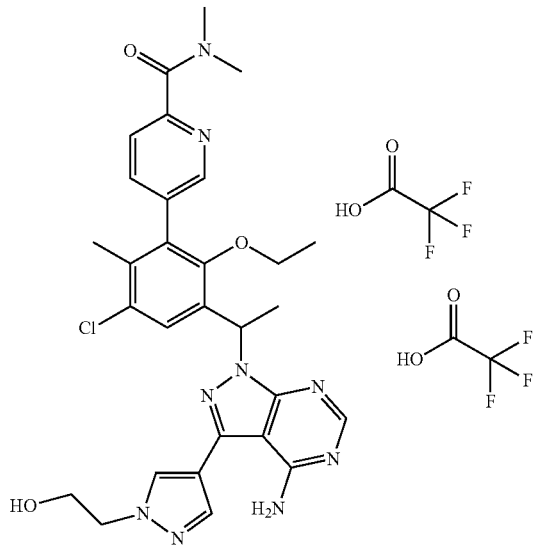

This compound was prepared according to the procedure described in Example 47, using 1-(2-{[tert-butyl(dimethyl)silyl]oxy}ethyl)-4-(4,4,5,5-tetramethyl-1,3,2-dioxaborolan-2-yl)-1H-pyrazole (from Example 20, Step 3) instead of (3-fluorophenyl)boronic acid. The crude mixture was treated with conc. HCl (0.1 mL) at rt for 1 hour before purification. The product was isolated as a racemic mixture. LCMS calculated for $C_{29}H_{33}ClN_9O_3$ (M+H)$^+$: m/z=590.2. Found: 590.2.

Example 53

5-{3-[1-(4-amino-3-cyclopropyl-1H-pyrazolo[3,4-d]pyrimidin-1-yl)ethyl]-5-chloro-2-ethoxy-6-methylphenyl}-N,N-dimethylpyridine-2-carboxamide bis(trifluoroacetate)

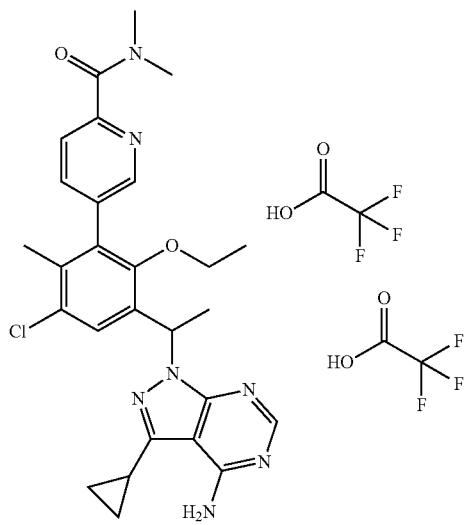

A mixture of 5-{3-[1-(4-amino-3-iodo-1H-pyrazolo[3,4-d]pyrimidin-1-yl)ethyl]-5-chloro-2-ethoxy-6-methylphenyl}-N,N-dimethylpyridine-2-carboxamide (11 mg, 0.018 mmol, racemic intermediate from Example 15), potassium cyclopropyltrifluoroborate (3.2 mg, 0.022 mmol), potassium phosphate (12 mg, 0.054 mmol) and tetrakis(triphenylphosphine)palladium (0) (0.42 mg, 0.00036 mmol) in toluene (0.05 mL)/water (0.02 mL) (v/v, 3/1) was heated at reflux overnight. The mixture was diluted with MeOH, and then filtered. The filtrate was purified on RP-HPLC (XBridge C18 column, eluting with a gradient of acetonitrile/water containing 0.05% trifluoroacetic acid, at flow rate of 30 mL/min) to give the desired product as bis-TFA salt. The product was isolated as a racemic mixture. LCMS calculated for $C_{27}H_{31}ClN_7O_2$ (M+H)$^+$: m/z=520.2. Found: 520.2.

Example 54

5-{3-[1-(4-amino-3-cyano-1H-pyrazolo[3,4-d]pyrimidin-1-yl)ethyl]-5-chloro-2-ethoxy-6-methylphenyl}-N,N-dimethylpyridine-2-carboxamide

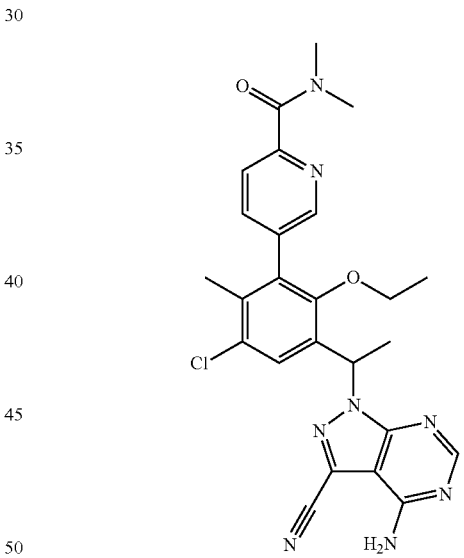

A mixture of 5-{3-[1-(4-amino-3-iodo-1H-pyrazolo[3,4-d]pyrimidin-1-yl)ethyl]-5-chloro-2-ethoxy-6-methylphenyl}-N,N-dimethylpyridine-2-carboxamide (13 mg, 0.021 mmol, racemic intermediate from Example 15) and copper cyanide (12 mg, 0.13 mmol) in N,N-dimethylformamide (0.2 mL) was heated at 120° C. overnight. The mixture was filtered and purified on RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{25}H_{26}ClN_8O_2$ (M+H)$^+$: m/z=505.2. Found: 505.2.

Example 55

5-(3-{1-[4-amino-3-(4-fluorophenyl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

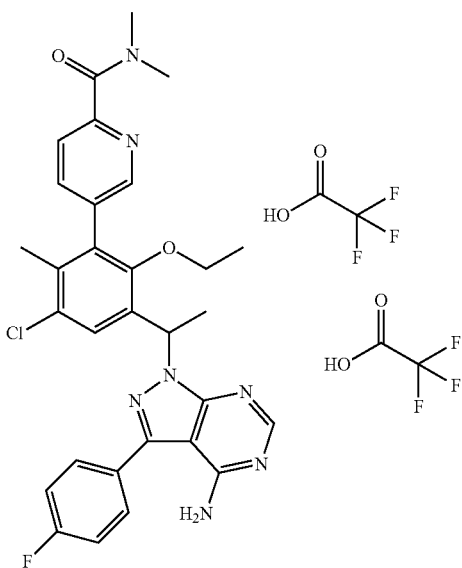

This compound was prepared according to the procedure described in Example 47, using 4-fluorophenylboronic acid (from Aldrich) instead of (3-fluorophenyl)boronic acid. The product was isolated as a racemic mixture. LCMS calculated for $C_{30}H_{30}ClFN_7O_2$ (M+H)$^+$: m/z=574.2. Found: 574.2.

Example 56

5-{4-amino-1-[1-(5-chloro-3-{6-[(dimethylamino)carbonyl]pyridin-3-yl}-2-ethoxy-4-methylphenyl)ethyl]-1H-pyrazolo[3,4-d]pyrimidin-3-yl}-N,N-dimethylpyridine-2-carboxamide tris(trifluoroacetate)

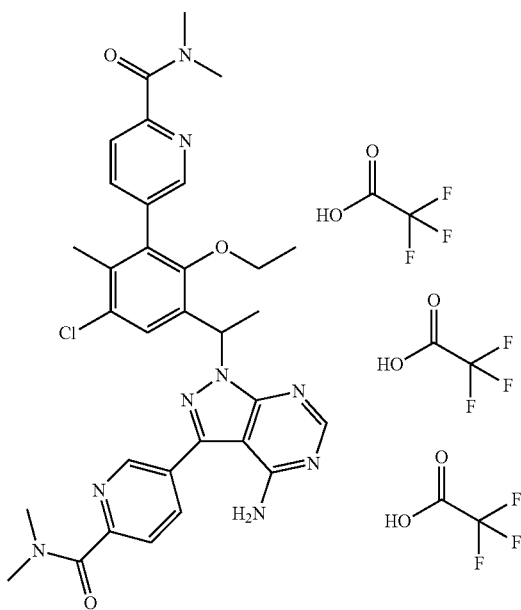

This compound was prepared according to the procedure described in Example 47, using N,N-dimethyl-5-(4,4,5,5-tetramethyl-1,3,2-dioxaborolan-2-yl)pyridine-2-carboxamide (from PepTech) instead of (3-fluorophenyl)boronic acid. The product was isolated as a racemic mixture. LCMS calculated for $C_{32}H_{35}ClN_9O_3$ (M+H)$^+$: m/z=628.3. Found: 628.3.

Example 57

5-(3-{1-[4-amino-3-(5-cyanopyridin-3-yl)-1H-pyrazolo[3,4-d]pyrimidin-1-yl]ethyl}-5-chloro-2-ethoxy-6-methylphenyl)-N,N-dimethylpyridine-2-carboxamide tris(trifluoroacetate)

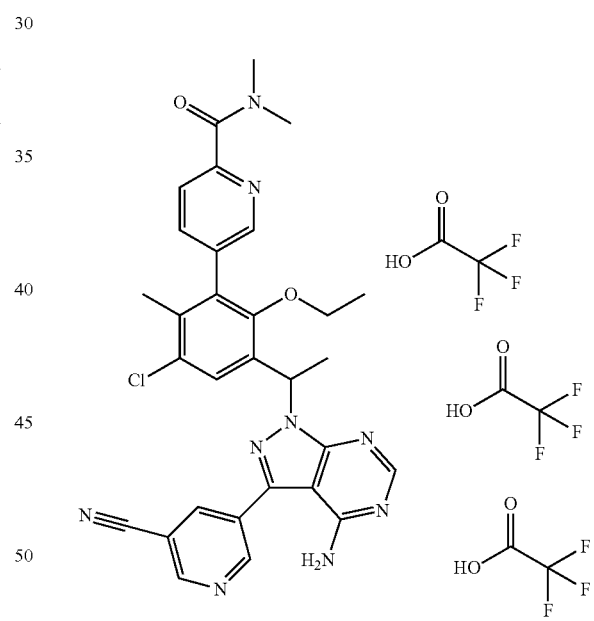

This compound was prepared according to the procedure described in Example 47, using 5-(4,4,5,5-tetramethyl-1,3,2-dioxaborolan-2-yl)nicotinonitrile (from Frontier) instead of (3-fluorophenyl)boronic acid. The product was isolated as a racemic mixture. LCMS calculated for $C_{30}H_{29}ClN_9O_2$ (M+H)$^+$: m/z=582.2. Found: 582.2.

Example 58

5-(3-{1-[4-amino-3-(2-aminopyrimidin-5-yl)-1H-pyrazolo[3,4-d]pyrimidin-1-yl]ethyl}-5-chloro-2-ethoxy-6-methylphenyl)-N,N-dimethylpyridine-2-carboxamide tris(trifluoroacetate)

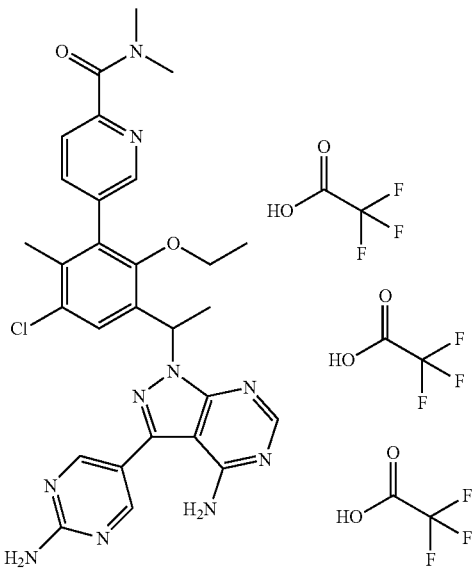

This compound was prepared according to the procedure described in Example 47, using 5-(4,4,5,5-tetramethyl-1,3,2-dioxaborolan-2-yl)pyrimidin-2-amine instead of (3-fluorophenyl)boronic acid. The product was isolated as a racemic mixture. LCMS calculated for $C_{28}H_{30}ClN_{10}O_2$ (M+H)$^+$: m/z=573.2. Found: 573.2.

Example 59

5-{3-[1-(4-amino-3-{6-[(methylamino)carbonyl]pyridin-3-yl}-1H-pyrazolo[3,4-d]pyrimidin-1-yl)ethyl]-5-chloro-2-ethoxy-6-methylphenyl}-N,N-dimethylpyridine-2-carboxamide tris(trifluoroacetate)

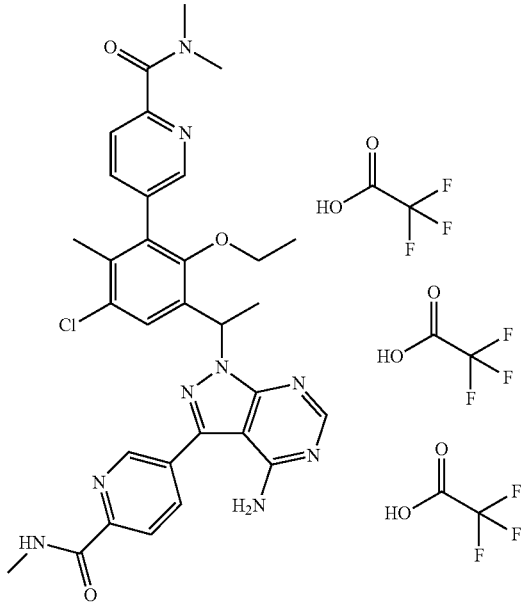

This compound was prepared according to the procedure described in Example 47, using N-methyl-5-(4,4,5,5-tetramethyl-1,3,2-dioxaborolan-2-yl)pyridine-2-carboxamide (from Frontier) instead of (3-fluorophenyl)boronic acid. The product was isolated as a racemic mixture. LCMS calculated for $C_{31}H_{33}ClN_9O_3$ (M+H)$^+$: m/z=614.2. Found: 614.2.

Example 60

5-{3-[1-(4-amino-3-pyridin-4-yl-1H-pyrazolo[3,4-d]pyrimidin-1-yl)ethyl]-5-chloro-2-ethoxy-6-methylphenyl}-N,N-dimethylpyridine-2-carboxamide tris(trifluoroacetate)

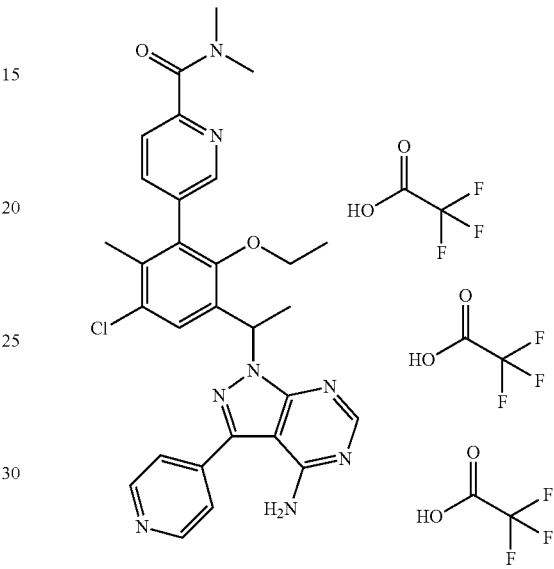

This compound was prepared according to the procedure described in Example 47, using 4-pyridinylboronic acid (from Aldrich) instead of (3-fluorophenyl)boronic acid. The product was isolated as a racemic mixture. LCMS calculated for $C_{29}H_{30}ClN_8O_2$ (M+H)$^+$: m/z=557.2. Found: 557.2.

Example 61

5-{3-[1-(4-amino-3-pyridin-3-yl-1H-pyrazolo[3,4-d]pyrimidin-1-yl)ethyl]-5-chloro-2-ethoxy-6-methylphenyl}-N,N-dimethylpyridine-2-carboxamide tris(trifluoroacetate)

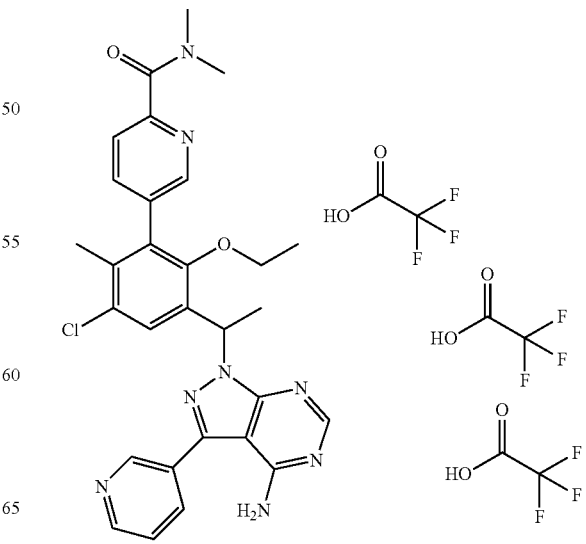

This compound was prepared according to the procedure described in Example 47, using 3-pyridinylboronic acid (from Aldrich) instead of (3-fluorophenyl)boronic acid. The product was isolated as a racemic mixture. LCMS calculated for $C_{29}H_{30}ClN_8O_2$ (M+H)$^+$: m/z=557.2. Found: 557.2.

Example 62

5-{3-[1-(4-amino-3-{5-[(dimethylamino)carbonyl] pyridin-3-yl}-1H-pyrazolo[3,4-d]pyrimidin-1-yl) ethyl]-5-chloro-2-ethoxy-6-methylphenyl}-N,N-dimethylpyridine-2-carboxamide tris (trifluoroacetate)

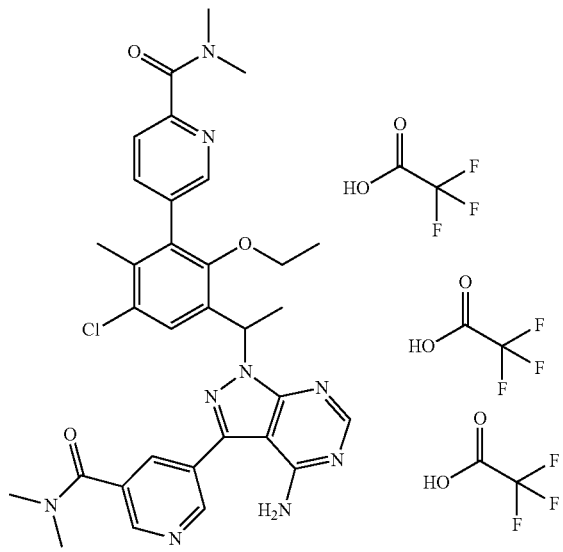

This compound was prepared according to the procedure described in Example 47, using N,N-dimethyl-5-(4,4,5,5-tetramethyl-1,3,2-dioxaborolan-2-yl)nicotinamide (from PepTech) instead of (3-fluorophenyl)boronic acid. The product was isolated as a racemic mixture. LCMS calculated for $C_{32}H_{35}ClN_9O_3$ (M+H)$^+$: m/z=628.3. Found: 628.3.

Example 63

1-{1-[5-chloro-2-methoxy-4-methyl-3-(1-oxetan-3-ylazetidin-3-yl)phenyl]ethyl}-3-methyl-1H-pyrazolo [3,4-d]pyrimidin-4-amine

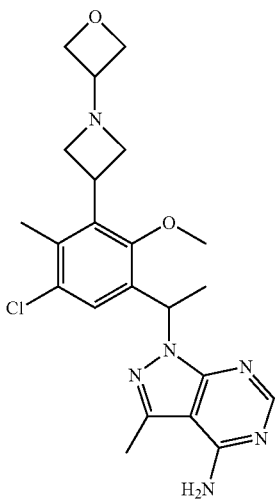 [SMILES: COc1c(C(C)n2nc(C)c3c(N)ncnc32)cc(Cl)c(C)c1C1CN(C2COC2)C1]

To a mixture of 1-[1-(3-azetidin-3-yl-5-chloro-2-methoxy-4-methylphenyl)ethyl]-3-methyl-1H-pyrazolo[3, 4-d]pyrimidin-4-amine dihydrochloride (21 mg, 0.046 mmol, racemic intermediate from Example 2, Step 1), oxetan-3-one (from Synthonix, 3.6 mg, 0.050 mmol), and triethylamine (20 μL, 0.14 mmol) in methylene chloride (0.32 mL) was added resin of sodium triacetoxyborohydride (40 mg, 0.091 mmol). The resulting mixture was stirred overnight at room temperature. The mixture was filtered and concentrated and then purified by RP-HPLC (XBridge C18 column, eluting with a gradient of acetonitrile/water containing 0.1% ammonium hydroxide, at flow rate of 30 mL/min) to give the desired product (2 mg, 9.9%). The product was isolated as a racemic mixture. LCMS calculated for $C_{22}H_{28}ClN_6O_2$ (M+H)$^+$: m/z=443.2. Found: 443.1.

Example 64

1-(1-{5-chloro-2-methoxy-4-methyl-3-[1-(tetrahydro-2H-pyran-4-yl)azetidin-3-yl]phenyl}ethyl)-3-methyl-1H-pyrazolo[3,4-d]pyrimidin-4-amine

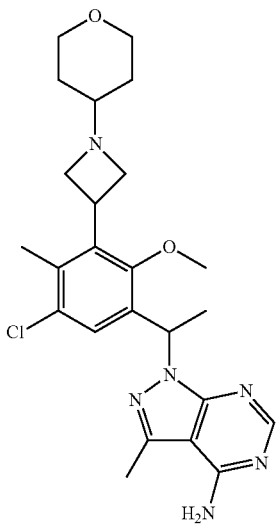 [SMILES: COc1c(C(C)n2nc(C)c3c(N)ncnc32)cc(Cl)c(C)c1C1CN(C2CCOCC2)C1]

To a mixture of 1-[1-(3-azetidin-3-yl-5-chloro-2-methoxy-4-methylphenyl)ethyl]-3-methyl-1H-pyrazolo[3, 4-d]pyrimidin-4-amine dihydrochloride (21 mg, 0.046 mmol, racemic intermediate from Example 2, Step 1)), tetrahydro-4H-pyran-4-one (from Aldrich, 4.6 μL, 0.050 mmol), and triethylamine (20 μL, 0.14 mmol) in methylene chloride (0.32 mL) was added resin of sodium triacetoxyborohydride (40 mg, 0.091 mmol). The resulting mixture was stirred overnight at rt. The mixture was filtered and concentrated and then purified by RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{24}H_{32}ClN_6O_2$ (M+H)$^+$: m/z=471.2. Found: 471.2.

Example 65

5-{3-[1-(4-amino-3-methyl-1H-pyrazolo[3,4-d]pyrimidin-1-yl)ethyl]-5-chloro-2-methoxy-6-methylphenyl}-N,N-dimethylnicotinamide

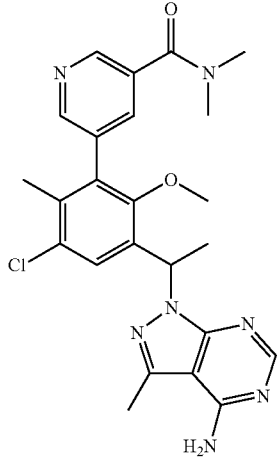 [SMILES: COc1c(C(C)n2nc(C)c3c(N)ncnc32)cc(Cl)c(C)c1-c1cncc(C(=O)N(C)C)c1]

A mixture of 1-[1-(3-bromo-5-chloro-2-methoxy-4-methylphenyl)ethyl]-3-methyl-1H-pyrazolo[3,4-d]pyrimidin-4-amine (25 mg, 0.061 mmol) (chiral pure, first peak from Example 20, Step 2), N,N-dimethyl-5-(4,4,5,5-tetramethyl-1,3,2-dioxaborolan-2-yl)nicotinamide (from PepTech) (25 mg, 0.091 mmol), sodium carbonate (13 mg, 0.12 mmol) and [1,1'-bis(diphenylphosphino)ferrocene]dichloropalladium (II), complex with dichloromethane (1:1) (9.9 mg, 0.012 mmol) in acetonitrile (0.8 mL)/water (0.3 mL) was degassed with N$_2$ and then stirred at 95° C. for 2 h. The mixture was filtered and the filtrate purified by RP-HPLC (XBridge C18 column, eluting with a gradient of acetonitrile/water containing 0.1% ammonium hydroxide, at flow rate of 30 mL/min) to give the desired product. The product was isolated as a single enantiomer. LCMS calculated for C$_{24}$H$_{27}$ClN$_7$O$_2$ (M+H)$^+$: m/z=480.2. Found: 480.2. $^1$H NMR (500 MHz, DMSO-d$_6$) δ 8.64 (1H, s), 8.54 (1H, br s), 8.13 (1H, s), 7.82 (1H, m), 7.53 (1H, s), 7.42 (2H, br s), 6.28 (1H, q, J=6.5 Hz), 3.22 (3H, s), 2.95 (6H, m), 2.58 (3H, s), 2.04 (3H, s), 1.77 (3H, d, J=6.5 Hz) ppm.

Example 66

5-{3-[1-(4-amino-3-methyl-1H-pyrazolo[3,4-d]pyrimidin-1-yl)ethyl]-5-chloro-2-methoxy-6-methylphenyl}-N,N-dimethylpyridine-2-carboxamide bis (trifluoroacetate)

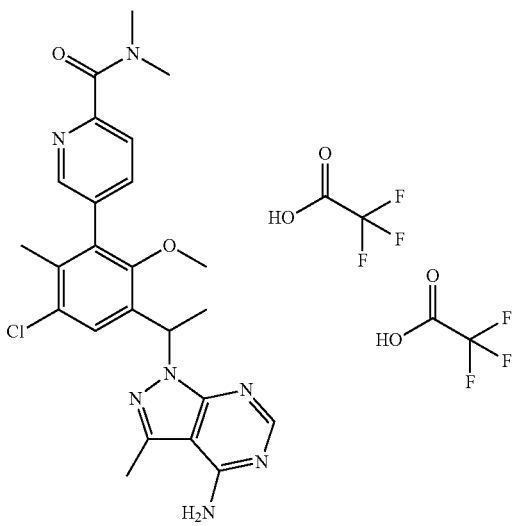

A mixture of 1-[1-(3-bromo-5-chloro-2-methoxy-4-methylphenyl)ethyl]-3-methyl-1H-pyrazolo[3,4-d]pyrimidin-4-amine (25 mg, 0.061 mmol) (chiral pure, first peak from Example 20, Step 2), N,N-dimethyl-5-(4,4,5,5-tetramethyl-1,3,2-dioxaborolan-2-yl)pyridine-2-carboxamide (25 mg, 0.091 mmol), sodium carbonate (13 mg, 0.12 mmol) and [1,1'-bis(diphenylphosphino)ferrocene]-dichloropalladium (II), complex with dichloromethane (1:1) (9.9 mg, 0.012 mmol) in acetonitrile (0.8 mL)/water (0.3 mL) was degassed with N$_2$ and then stirred at 95° C. for 2 hours. After cooling to room temperature, the mixture was filtered and the filtrate purified on RP-HPLC (XBridge C18 column, eluting with a gradient of acetonitrile/water containing 0.05% trifluoroacetic acid, at flow rate of 30 mL/min) to give the desired product as bis-TFA salt. The product was isolated as a single enantiomer. LCMS calculated for C$_{24}$H$_{27}$ClN$_7$O$_2$ (M+H)$^+$: m/z=480.2. Found: 480.2. $^1$H NMR (500 MHz, DMSO-d$_6$) δ: 8.78 (2H, br s), 8.48 (1H, m), 8.36 (1H, s), 7.86 (1H, br s), 7.65 (1H, br s), 7.58 (1H, s), 6.33 (1H, q, J=7.0 Hz), 3.19 (3H, s), 3.03 (3H, s), 2.97 (3H, s), 2.62 (3H, s), 2.06 (3H, s), 1.81 (3H, d, J=7.0 Hz) ppm.

Example 67

1-{1-[5-Chloro-4-fluoro-3-(1-isopropylazetidin-3-yl)-2-methoxyphenyl]ethyl}-3-methyl-1H-pyrazolo[3,4-d]pyrimidin-4-amine

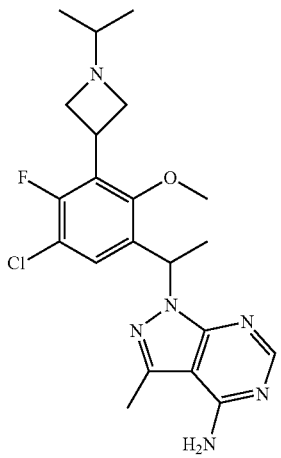 [SMILES: COc1c(C(C)n2nc(C)c3c(N)ncnc32)cc(Cl)c(F)c1C1CN(C(C)C)C1]

Step 1. 1-[1-(3-Azetidin-3-yl-5-chloro-4-fluoro-2-methoxyphenyl)ethyl]-3-methyl-1H-pyrazolo[3,4-d]pyrimidin-4-amine dihydrochloride tert-Butyl 3-{3-[1-(4-amino-3-methyl-1H-pyrazolo[3,4-d]pyrimidin-1-yl)ethyl]-5-chloro-6-fluoro-2-methoxyphenyl}azetidine-1-carboxylate (1.6 g, 3.2 mmol, from Example 13, Step 7) was treated with 4.0 M hydrogen chloride in dioxane (8.15 mL, 32.6 mmol) in methylene chloride (17 mL) at room temperature for 2 h. The mixture was concentrated to dryness to give the desired product. LCMS calculated for C$_{18}$H$_{21}$ClFN$_6$O (M+H)$^+$: m/z=391.1. Found: 391.1.

Step 2. 1-{1-[5-Chloro-4-fluoro-3-(1-isopropylazetidin-3-yl)-2-methoxyphenyl]ethyl}-3-methyl-1H-pyrazolo[3,4-d]pyrimidin-4-amine To a mixture of 1-[1-(3-azetidin-3-yl-5-chloro-4-fluoro-2-methoxyphenyl)ethyl]-3-methyl-1H-pyrazolo[3,4-d]pyrimidin-4-amine dihydrochloride (0.90 g, 1.9 mmol, Example 67, step 1), acetone (1.0 mL, 14 mmol) and triethylamine (2.5 mL, 18 mmol) in methylene chloride (20 mL) was added sodium triacetoxyborohydride resin (2.5 g, 5.8 mmol). The mixture was stirred at room temperature for 2 h, then filtered, washed with water, dried over MgSO$_4$, filtered and concentrated to give crude product (870 mg, 100%). LCMS calculated for $C_{21}H_{27}ClFN_6O$ (M+H)$^+$: m/z=433.2. Found: 433.1.

Step 3. Single enantiomer of 1-{1-[5-chloro-4-fluoro-3-(1-isopropylazetidin-3-yl)-2-methoxyphenyl]ethyl}-3-methyl-1H-pyrazolo[3,4-d]pyrimidin-4-amine Enantiomers of 1-{1-[5-chloro-4-fluoro-3-(1-isopropylazetidin-3-yl)-2-methoxyphenyl]ethyl}-3-methyl-1H-pyrazolo[3,4-d]pyrimidin-4-amine (870 mg, 2.0 mmol) were separated on a Phenomenex Lux Cellulose-2 column, eluting with 10% ethanol in hexanes, at flow rate of 18 mL/min, and column loading of ~8 mg/injection to separate two enantiomers. First peak retention time 10.9 min; second peak retention time 13.6 min. The fractions of the 1st peak (110 mg, 13%) were concentrated and purified using RP-HPLC (XBridge C18 column, eluting with a gradient of acetonitrile/water containing 0.1% ammonium hydroxide, at flow rate of 30 mL/min) to give the desired product. The product was isolated as a single enantiomer. LCMS calculated for $C_{21}H_{27}ClFN_6O$ (M+H)$^+$: m/z=433.2. Found: 433.1.

Example 68

(2S)-1-(3-{3-[1-(4-Amino-3-methyl-1H-pyrazolo[3,4-d]pyrimidin-1-yl)ethyl]-5-chloro-6-fluoro-2-methoxyphenyl}azetidin-1-yl)propan-2-ol

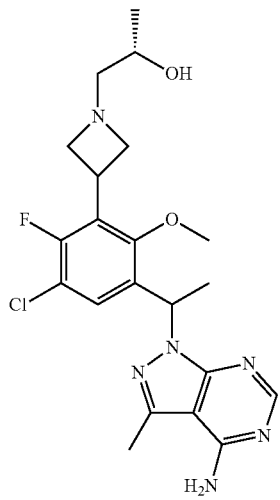 [SMILES: COc1c(C(C)n2nc(C)c3c(N)ncnc32)cc(Cl)c(F)c1C1CN(C[C@H](C)O)C1]

To a mixture of 1-[1-(3-azetidin-3-yl-5-chloro-4-fluoro-2-methoxyphenyl)ethyl]-3-methyl-1H-pyrazolo[3,4-d]pyrimidin-4-amine dihydrochloride (15 mg, 0.032 mmol, from Example 67, Step 1) and triethylamine (18 μL, 0.13 mmol) in ethanol (0.53 mL) was added (S)-(−)-methyloxirane (6.8 μL, 0.097 mmol). The resulting mixture was heated at 90° C. for 3 h, then purified on RP-HPLC (XBridge C18 column, eluting with a gradient of acetonitrile/water containing 0.1% ammonium hydroxide, at flow rate of 30 mL/min) to give the desired product. The enantiomers were separated on a Phenomenex Lux Cellulose C-4 column (5 μM, 21.2×250 mm), eluting with 20% ethanol in hexanes, at flow rate of 18 mL/min, to give two enantiomers. First peak (2.7 mg, 18%) retention time 8.9 min; LCMS calculated for $C_{21}H_{27}ClFN_6O_2$ (M+H)$^+$: m/z=449.2. Found: 449.1. $^1$H NMR (DMSO-d$_6$, 500 MHz) δ 8.11 (1H, s), 7.42 (1H, d, J=8.5 Hz), 7.25 (2H, br s), 6.21 (1H, q, J=7.5 Hz), 4.28 (1H, d, J=4.0 Hz), 3.82 (3H, m), 3.62 (3H, s), 3.55 (1H, m), 3.05 (1H, m), 2.97 (1H, m), 2.55 (3H, s), 2.28 (2H, m), 1.70 (2H, d, J=7.5 Hz), 1.00 (3H, d, J=6.0 Hz) ppm. Second peak retention time 10.0 min.

Example 71

2-(3-{3-[1-(4-Amino-3-methyl-1H-pyrazolo[3,4-d]pyrimidin-1-yl)ethyl]-5-chloro-6-fluoro-2-methoxyphenyl}azetidin-1-yl)ethanol

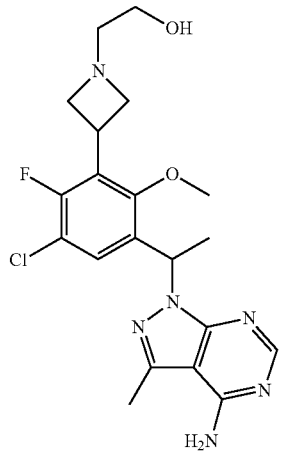 [SMILES: COc1c(C(C)n2nc(C)c3c(N)ncnc32)cc(Cl)c(F)c1C1CN(CCO)C1]

To a mixture of 1-[1-(3-azetidin-3-yl-5-chloro-4-fluoro-2-methoxyphenyl)ethyl]-3-methyl-1H-pyrazolo[3,4-d]pyrimidin-4-amine dihydrochloride (19 mg, 0.041 mmol, racemic intermediate from Example 67, Step 1) and triethylamine (28 μL, 0.20 mmol) in methanol (0.1 mL)/acetonitrile (0.1 mL)/tetrahydrofuran (0.1 mL) was added {[tert-butyl(dimethyl)silyl]oxy}acetaldehyde (39 μL, 0.20 mmol), followed by sodium triacetoxyborohydride (22 mg, 0.10 mmol). The resulting mixture was stirred overnight at room temperature. The mixture was treated with 6.0 M hydrogen chloride in water (0.07 mL, 0.4 mmol) at room temperature for 10 min and then purified on RP-HPLC (XBridge C18 column, eluting with a gradient of acetonitrile/water containing 0.1% ammonium hydroxide, at flow rate of 30 mL/min) to give the desired product (2.5 mg, 13%). The product was isolated as a racemic mixture. LCMS calculated for $C_{20}H_{25}ClFN_6O_2$ (M+H)$^+$: m/z=435.2. Found: 435.1.

Example 72

1-{1-[5-Chloro-4-fluoro-2-methoxy-3-(1-oxetan-3-ylazetidin-3-yl)phenyl]ethyl}-3-methyl-1H-pyrazolo[3,4-d]pyrimidin-4-amine

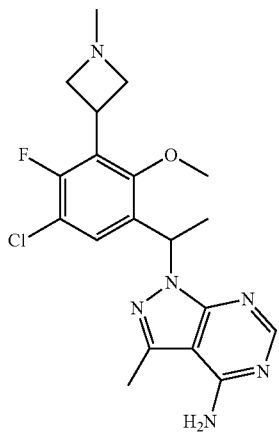 [SMILES: COc1c(C(C)n2nc(C)c3c(N)ncnc32)cc(Cl)c(F)c1C1CN(C)C1]

To a mixture of 1-[1-(3-azetidin-3-yl-5-chloro-4-fluoro-2-methoxyphenyl)ethyl]-3-methyl-1H-pyrazolo[3,4-d]pyrimidin-4-amine dihydrochloride (19 mg, 0.041 mmol racemic intermediate from Example 67, Step 1) and triethylamine (28 μL, 0.20 mmol) in methanol (0.1 mL)/acetonitrile (0.1 mL)/tetrahydrofuran (0.1 mL) was added 37% formaldehyde (15 μL, 0.20 mmol), followed by sodium triacetoxyborohydride (22 mg, 0.10 mmol). The resulting mixture was stirred overnight at room temperature. The mixture was purified on RP-HPLC (XBridge C18 column, eluting with a gradient of acetonitrile/water containing 0.1% ammonium hydroxide, at flow rate of 30 mL/min) to give the desired product (1.2 mg, 6.3%). The product was isolated as a racemic mixture. LCMS calculated for $C_{19}H_{23}ClFN_6O$ (M+H)$^+$: m/z=405.2. Found: 405.1.

Example 73

1-{1-[5-Chloro-4-fluoro-3-(1-isopropylazetidin-3-yl)-2-methoxyphenyl]ethyl}-3-(difluoromethyl)-1H-pyrazolo[3,4-d]pyrimidin-4-amine

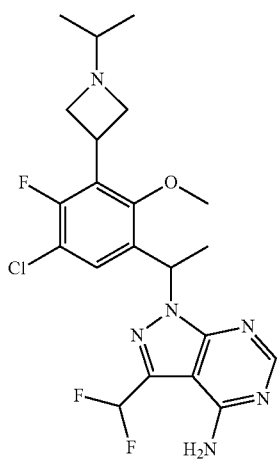 [SMILES: COc1c(C(C)n2nc(C(F)F)c3c(N)ncnc32)cc(Cl)c(F)c1C1CN(C(C)C)C1]

Step 1. tert-Butyl 3-{3-[1-(4-amino-3-iodo-1H-pyrazolo[3,4-d]pyrimidin-1-yl)ethyl]-5-chloro-6-fluoro-2-methoxyphenyl}azetidine-1-carboxylate To a mixture of tert-butyl 3-[3-chloro-5-(1-chloroethyl)-2-fluoro-6-methoxyphenyl]azetidine-1-carboxylate (0.77 g, 2.0 mmol, racemic intermediate from Example 13, Step 6,), 3-iodo-1H-pyrazolo[3,4-d]pyrimidin-4-amine (0.58 g, 2.2 mmol) in N,N-dimethylformamide (6.9 mL) was added potassium iodide (34 mg, 0.20 mmol) and cesium carbonate (0.99 g, 3.0 mmol). The resulting mixture was heated at 140° C. and stirred for 3 h. After cooling, the clear solution was taken into water and ethyl acetate (EtOAc). The solid was diluted with water and EtOAc, and stirred until dissolved. The organic layers were combined, concentrated and purified on silica gel (eluting with 0 to 100% EtOAc in hexanes) to give the desired product (0.55 g, 45%). LCMS calculated for $C_{22}H_{26}ClFIN_6O_3$ (M+H)$^+$: m/z=603.1. Found: 602.9.

Step 2. tert-Butyl 3-{3-[1-(4-amino-3-vinyl-1H-pyrazolo[3,4-d]pyrimidin-1-yl)ethyl]-5-chloro-6-fluoro-2-methoxyphenyl}azetidine-1-carboxylate To a solution of tert-butyl 3-{3-[1-(4-amino-3-iodo-1H-pyrazolo[3,4-d]pyrimidin-1-yl)ethyl]-5-chloro-6-fluoro-2-methoxyphenyl}azetidine-1-carboxylate (0.55 g, 0.91 mmol), 4,4,5,5-tetramethyl-2-vinyl-1,3,2-dioxaborolane (0.281 g, 1.82 mmol), sodium carbonate (0.580 g, 5.47 mmol) in N,N-dimethylformamide (5 mL)/water (2.73 mL) under $N_2$ was added tetrakis(triphenylphosphine)-palladium (0) (0.105 g, 0.0910 mmol). The mixture was heated at 100° C. overnight. After cooling to room temperature, the mixture was diluted with water, and extracted with EtOAc. The combined organic layers were concentrated and purified on silica gel (eluting with 0 to 100% EtOAc in hexanes followed by 0 to 10% MeOH in dichloromethane) to give the desired product (0.34 g, 74%). LCMS calculated for $C_{24}H_{29}ClFN_6O_3$ (M+H)$^+$: m/z=503.2. Found: 503.1.

Step 3. tert-Butyl 3-(3-{1-[4-amino-3-(1,2-dihydroxyethyl)-1H-pyrazolo[3,4-d]pyrimidin-1-yl]ethyl}-5-chloro-6-fluoro-2-methoxyphenyl)azetidine-1-carboxylate To a solution of tert-butyl 3-{3-[1-(4-amino-3-vinyl-1H-pyrazolo[3,4-d]pyrimidin-1-yl)ethyl]-5-chloro-6-fluoro-2-methoxyphenyl}azetidine-1-carboxylate (340 mg, 0.680 mmol) in tert-butyl alcohol (5 mL) was added N-methylmorpholine N-oxide (87 mg, 0.74 mmol) and water (2.1 mL). To this solution was then added 4% osmium tetraoxide (0.21 mL, 0.034 mmol). After stirring for 3 h, another equivalent of N-methylmorpholine N-oxide was added. The reaction was stirred at room temperature overnight. The solution was diluted with water, and extracted with EtOAc. The combined organic layers were dried over $MgSO_4$, filtered and concentrated to give the crude product (0.4 g, 100%) which was used directly in the next step. LCMS calculated for $C_{24}H_{31}ClFN_6O_5$ (M+H)$^+$: m/z=537.2. Found: 537.2.

Step 4. tert-Butyl 3-{3-[1-(4-amino-3-formyl-1H-pyrazolo[3,4-d]pyrimidin-1-yl)ethyl]-5-chloro-6-fluoro-2-methoxyphenyl}azetidine-1-carboxylate To a solution of tert-butyl 3-(3-{1-[4-amino-3-(1,2-dihydroxyethyl)-1H-pyrazolo[3,4-d]pyrimidin-1-yl]ethyl}-5-chloro-6-fluoro-2-methoxyphenyl)azetidine-1-carboxylate (0.40 g, 0.74 mmol) in tetrahydrofuran (5.6 mL)/water (3.4 mL) was added acetic acid (0.011 mL, 0.19 mmol) and sodium periodate (0.478 g, 2.23 mmol) at 0° C. After stirring for 2 h, the reaction mixture was diluted with water, and extracted with EtOAc. The organic layers were combined, washed with brine, dried over MgSO$_4$, filtered and concentrated to give the desired product (0.35 g, 92%) which was used directly in the next step. LCMS calculated for C$_{23}$H$_{27}$ClFN$_6$O$_4$ (M+H)$^+$: m/z=505.2. Found: 505.1.

Step 5. tert-Butyl 3-(3-{1-[4-amino-3-(difluoromethyl)-1H-pyrazolo[3,4-d]pyrimidin-1-yl]ethyl}-5-chloro-6-fluoro-2-methoxyphenyl)azetidine-1-carboxylate To a solution of tert-butyl 3-{3-[1-(4-amino-3-formyl-1H-pyrazolo[3,4-d]pyrimidin-1-yl)ethyl]-5-chloro-6-fluoro-2-methoxyphenyl}azetidine-1-carboxylate (0.35 g, 0.69 mmol) in methylene chloride (4 mL) cooled at 0° C. was added dropwise diethylaminosulfur trifluoride (0.23 mL, 1.7 mmol). The mixture was stirred at room temperature for 2 h, then diluted with dichloromethane, washed with water, dried over MgSO$_4$, filtered then concentrated and purified on silica gel (eluting with 0 to 100% EtOAc in hexanes) to give the desired product (0.21 g, 57%). LCMS calculated for C$_{23}$H$_{27}$ClF$_3$N$_6$O$_3$ (M+H)$^+$: m/z=527.2. Found: 527.2.

Step 6. 1-[1-(3-Azetidin-3-yl-5-chloro-4-fluoro-2-methoxyphenyl)ethyl]-3-(difluoromethyl)-1H-pyrazolo[3,4-d]pyrimidin-4-amine dihydrochloride tert-Butyl 3-(3-{1-[4-amino-3-(difluoromethyl)-1H-pyrazolo[3,4-d]pyrimidin-1-yl]ethyl}-5-chloro-6-fluoro-2-methoxyphenyl)azetidine-1-carboxylate (0.21 g, 0.40 mmol) was treated with 4.0 M hydrogen chloride in dioxane (1 mL, 4 mmol) in methylene chloride (4 mL) at room temperature for 2 h. The mixture was concentrated to give the desired product (0.177 g, 89%). LCMS calculated for C$_{18}$H$_{19}$ClF$_3$N$_6$O (M+H)$^+$: m/z=427.1. Found: 427.1.

Step 7. 1-{1-[5-Chloro-4-fluoro-3-(1-isopropylazetidin-3-yl)-2-methoxyphenyl]ethyl}-3-(difluoromethyl)-1H-pyrazolo[3,4-d]pyrimidin-4-amine To a mixture of 1-[1-(3-azetidin-3-yl-5-chloro-4-fluoro-2-methoxyphenyl)ethyl]-3-(difluoromethyl)-1H-pyrazolo[3,4-d]pyrimidin-4-amine dihydrochloride (45 mg, 0.090 mmol), acetone (37 mg, 0.63 mmol) and triethylamine (63 μL, 0.45 mmol) in methylene chloride (0.9 mL) was added sodium triacetoxyborohydride resin (0.12 g, 0.27 mmol). The mixture was stirred at room temperature for 2 h, then filtered, concentrated and purified on RP-HPLC (XBridge C18 column, eluting with a gradient of acetonitrile/water containing 0.1% ammonium hydroxide, at flow rate of 30 mL/min) to give the desired product (2.5 mg, 6.8%). The product was isolated as a racemic mixture. LCMS calculated for C$_{21}$H$_{25}$ClF$_3$N$_6$O (M+H)$^+$: m/z=469.2. Found: 469.2.

Example 74

2-[3-(3-{1-[4-Amino-3-(difluoromethyl)-1H-pyrazolo[3,4-d]pyrimidin-1-yl]ethyl}-5-chloro-6-fluoro-2-methoxyphenyl)azetidin-1-yl]ethanol

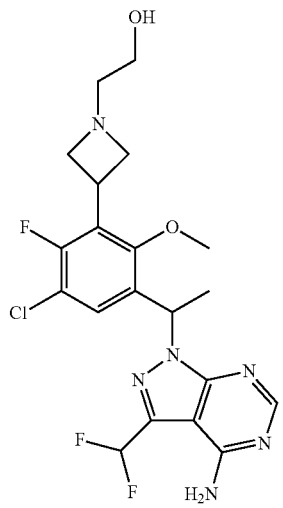 [SMILES: COc1c(C(C)n2nc(C(F)F)c3c(N)ncnc32)cc(Cl)c(F)c1C1CN(CCO)C1]

To a mixture of 1-[1-(3-azetidin-3-yl-5-chloro-4-fluoro-2-methoxyphenyl)ethyl]-3-(difluoromethyl)-1H-pyrazolo[3,4-d]pyrimidin-4-amine dihydrochloride (45 mg, 0.090 mmol), {[ten-butyl(dimethyl)silyl]oxy}acetaldehyde (110 mg, 0.63 mmol) and triethylamine (63 μL, 0.45 mmol) in methylene chloride (0.9 mL) was added sodium triacetoxyborohydride resin (0.12 g, 0.27 mmol). The mixture was stirred at room temperature for 2 h, then filtered. The filtrate was treated with 6.0 M hydrogen chloride in water (0.2 mL, 0.9 mmol), and purified on RP-HPLC (XBridge C18 column, eluting with a gradient of acetonitrile/water containing 0.1% ammonium hydroxide, at flow rate of 30 mL/min) to give the desired product (2.5 mg, 5.6%). LCMS calculated for C$_{20}$H$_{23}$ClF$_3$N$_6$O$_2$ (M+H)$^+$: m/z=471.1. Found: 471.2. The racemic product was separated on a Phenomenex Lux Cellulose-4 column, eluting with 20% ethanol in hexanes, at flow rate of 18 mL/min, and column loading of ~4 mg/injection to separate two enantiomers. First peak retention time 13.1 min; second peak retention time 16.3 min.

Example 76

(2S)-1-[3-(3-{1-[4-amino-3-(difluoromethyl)-1H-pyrazolo[3,4-d]pyrimidin-1-yl]ethyl}-5-chloro-6-fluoro-2-methoxyphenyl)azetidin-1-yl]propan-2-ol

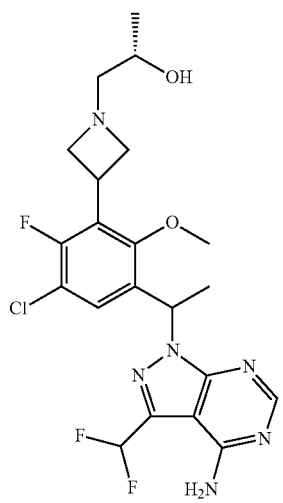 [SMILES: COc1c(C(C)n2nc(C(F)F)c3c(N)ncnc32)cc(Cl)c(F)c1C1CN(C[C@H](C)O)C1]

To a mixture of 1-[1-(3-azetidin-3-yl-5-chloro-4-fluoro-2-methoxyphenyl)ethyl]-3-(difluoromethyl)-1H-pyrazolo[3,4-d]pyrimidin-4-amine dihydrochloride (51 mg, 0.10 mmol, racemic intermediate from Example 73, Step 6) and triethylamine (57 μL, 0.41 mmol) in ethanol (1.7 mL) was added (S)-(−)-methyloxirane (18 μL, 0.26 mmol). The resulting mixture was heated at 90° C. for 3 h, and purified on RP-HPLC (XBridge C18 column, eluting with a gradient of acetonitrile/water containing 0.1% ammonium hydroxide, at flow rate of 30 mL/min) to give the desired product (2.7 mg, 5.3%). The product was isolated as a racemic mixture. LCMS calculated for $C_{21}H_{25}ClF_3N_6O_2$ (M+H)$^+$: m/z=485.2. Found: 485.1.

Example 77

5-(1-(4-Amino-3-(difluoromethyl)-1H-pyrazolo[3,4-d]pyrimidin-1-yl)ethyl)-2-fluoro-3-(1-((S)-2-hydroxypropyl)azetidin-3-yl)-4-methoxybenzonitrile

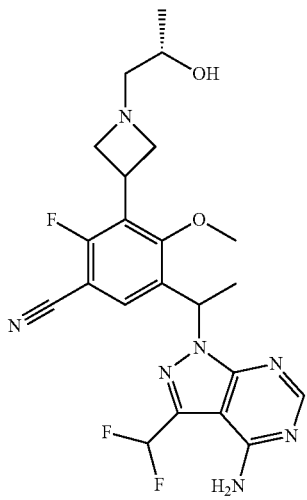 [SMILES: COc1c(C(C)n2nc(C(F)F)c3c(N)ncnc32)cc(C#N)c(F)c1C1CN(C[C@H](C)O)C1]

To a microwave vial containing (2S)-1-[3-(3-{1-[4-amino-3-(difluoromethyl)-1H-pyrazolo[3,4-d]pyrimidin-1-yl]ethyl}-5-chloro-6-fluoro-2-methoxyphenyl)azetidin-1-yl]propan-2-ol (16 mg, 0.032 mmol, from Example 76) was added zinc (1.0 mg, 0.016 mmol), bis(tri-t-butylphosphine) palladium (6.5 mg, 0.013 mmol) and N-methylpyrrolidinone (0.20 mL, 2.0 mmol). The mixture was degassed with N$_2$ for a few minutes before adding zinc cyanide (7.5 mg, 0.064 mmol). The resulting mixture was stirred at 130° C. overnight and then cooled and purified on RP-HPLC (XBridge C18 column, eluting with a gradient of acetonitrile/water containing 0.1% ammonium hydroxide, at flow rate of 30 mL/min) to give the desired product (1.8 mg, 11.2%). The product was isolated as a racemic mixture. LCMS calculated for $C_{22}H_{25}F_3N_7O_2$ (M+H)$^+$: m/z=476.2. Found: 476.2.

Example 79

5-[3-(1-{4-Amino-3-[(3R)-3-hydroxybut-1-yn-1-yl]-1H-pyrazolo[3,4-d]pyrimidin-1-yl}ethyl)-5-chloro-2-ethoxy-6-methylphenyl]-N,N-dimethylpyridine-2-carboxamide bis(trifluoroacetate)

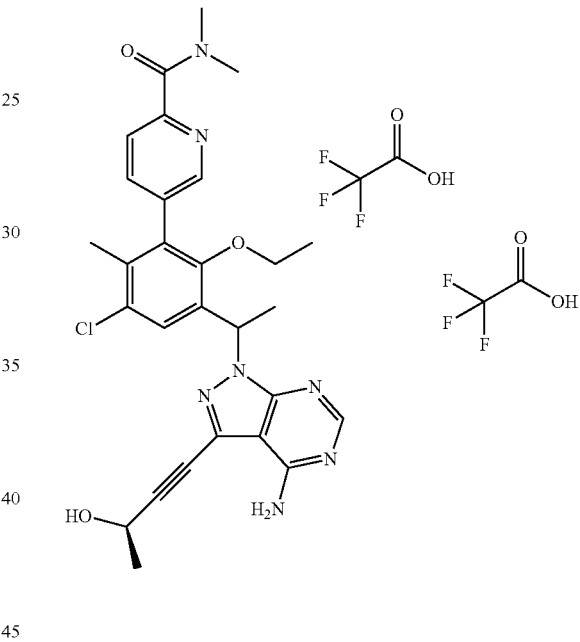

A mixture of 5-{3-[1-(4-amino-3-iodo-1H-pyrazolo[3,4-d]pyrimidin-1-yl)ethyl]-5-chloro-2-ethoxy-6-methylphenyl}-N,N-dimethylpyridine-2-carboxamide (9.8 mg, 0.016 mmol, racemic intermediate from Example 15) and copper (I) iodide (0.6 mg, 0.003 mmol) in N,N-dimethylformamide (0.32 mL) was treated with (2R)-but-3-yn-2-ol (11.3 mg, 0.162 mmol), triethylamine (4.5 μL, 0.032 mmol) and tetrakis-(triphenylphosphine)-palladium(0) (1.9 mg, 0.0016 mmol) under N$_2$. The mixture was stirred under N$_2$ at room temperature for 1 h. The mixture was then purified on RP-HPLC (XBridge C18 column, eluting with a gradient of acetonitrile/water containing 0.05% TFA, at flow rate of 30 mL/min) to give the desired product as a bis-TFA salt (4.3 mg, 44%). The product was isolated as a racemic mixture. LCMS calculated for $C_{28}H_{31}ClN_7O_3$ (M+H)$^+$: m/z=548.2. Found: 548.1.

Example 80

5-[3-(1-{4-Amino-3-[(3S)-3-hydroxybut-1-yn-1-yl]-1H-pyrazolo[3,4-d]pyrimidin-1-yl}ethyl)-5-chloro-2-ethoxy-6-methylphenyl]-N,N-dimethylpyridine-2-carboxamide bis(trifluoroacetate)

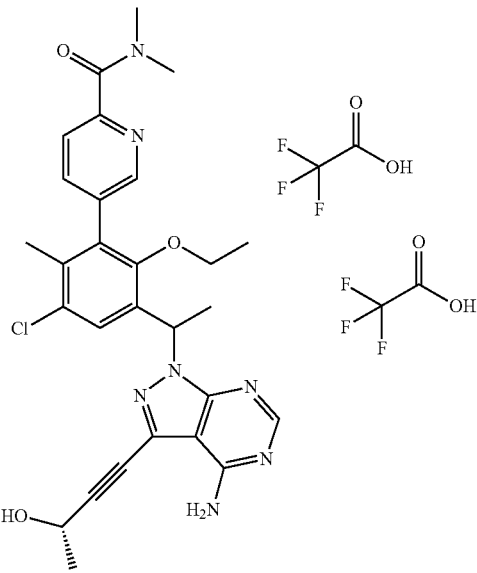 [SMILES: CCOc1c(C(C)n2nc(C#C[C@H](C)O)c3c(N)ncnc32)cc(Cl)c(C)c1-c1ccc(C(=O)N(C)C)nc1 ; O=C(O)C(F)(F)F ; O=C(O)C(F)(F)F]

This compound was prepared using procedures analogous to Example 79, with (2S)-but-3-yn-2-ol replacing (2R)-but-3-yn-2-ol. The product was isolated as a mixture of diastereomers. LCMS calculated for $C_{28}H_{31}ClN_7O_3$ (M+H)$^+$: m/z=548.2. Found: 548.1.

Example 81

5-{3-[1-(4-Amino-3-ethyl-1H-pyrazolo[3,4-d]pyrimidin-1-yl)ethyl]-5-chloro-2-ethoxy-6-methylphenyl}-N,N-dimethylpyridine-2-carboxamide Step 1. 5-{3-[1-(4-Amino-3-vinyl-1H-pyrazolo[3,4-d]pyrimidin-1-yl)ethyl]-5-chloro-2-ethoxy-6-methylphenyl}-N,N-dimethylpyridine-2-carboxamide To a solution of 5-{3-[1-(4-amino-3-iodo-1H-pyrazolo[3,4-d]pyrimidin-1-yl)ethyl]-5-chloro-2-ethoxy-6-methylphenyl}-N,N-dimethylpyridine-2-carboxamide (130 mg, 0.21 mmol, racemic intermediate from Example 15), 4,4,5,5-tetramethyl-2-vinyl-1,3,2-dioxaborolane (66 mg, 0.43 mmol), sodium carbonate (136 mg, 1.29 mmol) in N,N-dimethylformamide (1 mL)/water (0.64 mL) under $N_2$ was added tetrakis(triphenylphosphine)palladium(0) (25 mg, 0.021 mmol). The mixture was heated at 100° C. overnight. After cooling to room temperature, the mixture was diluted with water, and extracted with dichloromethane. The organic layers were concentrated and purified on silica gel (eluting with 0 to 100% EtOAc in hexanes followed by 0 to 10% MeOH in dichloromethane) to give the desired product (94 mg, 86%). LCMS calculated for $C_{26}H_{29}ClN_7O_2$ (M+H)$^+$: m/z=506.2. Found: 506.2.

Step 2. 5-{3-[1-(4-Amino-3-ethyl-1H-pyrazolo[3,4-d]pyrimidin-1-yl)ethyl]-5-chloro-2-ethoxy-6-methylphenyl}-N,N-dimethylpyridine-2-carboxamide 5-{3-[1-(4-Amino-3-vinyl-1H-pyrazolo[3,4-d]pyrimidin-1-yl)ethyl]-5-chloro-2-ethoxy-6-methylphenyl}-N,N-dimethylpyridine-2-carboxamide (14 mg, 0.028 mmol) and 5% platinum on carbon (14 mg) was combined in methanol (1 mL), to which was added 0.25 M hydrogen chloride in water (0.28 mL, 0.069 mmol). The suspension was hydrogenated under balloon pressure of $H_2$ at room temperature for 3 h. The suspension was filtered and the filtrate purified on RP-HPLC (XBridge C18 column, eluting with a gradient of acetonitrile/water containing 0.1% ammonium hydroxide, at flow rate of 30 mL/min) to give the desired product (3.9 mg, 28%). The product was isolated as a racemic mixture. LCMS calculated for $C_{26}H_{31}ClN_7O_2$ (M+H)$^+$: m/z=508.2. Found: 508.3.

Example 82

5(3-{1-[4-Amino-3-(difluoromethyl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

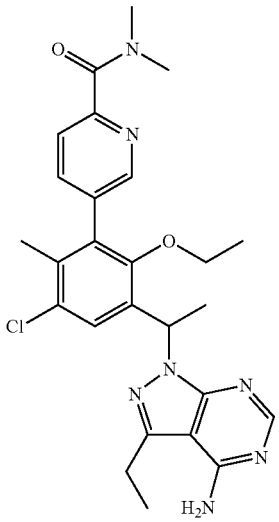 [SMILES: CCOc1c(C(C)n2nc(CC)c3c(N)ncnc32)cc(Cl)c(C)c1-c1ccc(C(=O)N(C)C)nc1]

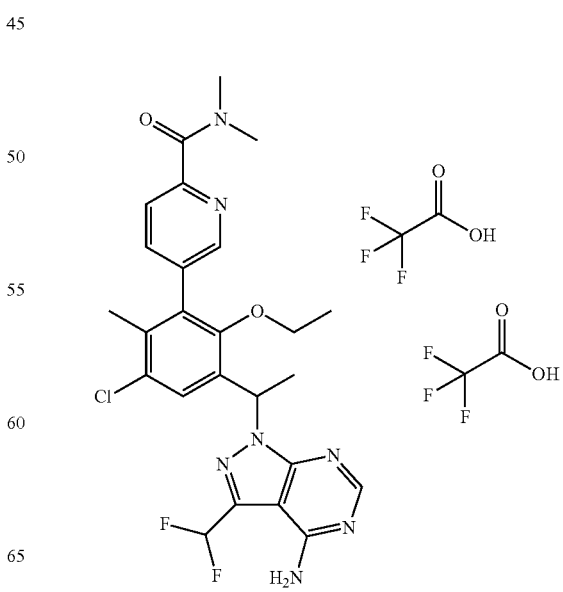

Step 1. 5-(3-{1-[4-Amino-3-(1,2-dihydroxyethyl)-1H-pyrazolo[3,4-d]pyrimidin-1-yl]ethyl}-5-chloro-2-ethoxy-6-methylphenyl)-N,N-dimethylpyridine-2-carboxamide To a solution of 5-{3-[1-(4-amino-3-vinyl-1H-pyrazolo[3,4-d]pyrimidin-1-yl)ethyl]-5-chloro-2-ethoxy-6-methylphenyl}-N,N-dimethylpyridine-2-carboxamide (80 mg, 0.16 mmol, from Example 81, Step 1) in tert-butyl alcohol (1 mL) was added N-methylmorpholine N-oxide (20 mg, 0.17 mmol) and water (0.50 mL). To this solution was then added 4% osmium tetraoxide (5.0 µL, 0.00079 mmol). After stirring for 3 h, another equivalent of N-methylmorpholine N-oxide was added. The reaction was stirred at room temperature overnight. The solution was diluted with water, and extracted with EtOAc. The combined organic layers were dried over $MgSO_4$ and filtered, concentrated to give the desired product (0.64 g, 95%). LCMS calculated for $C_{26}H_{31}ClN_7O_4$ (M+H)$^+$: m/z=540.2. Found: 540.2.

Step 2. 5-{3-[1-(4-Amino-3-formyl-1H-pyrazolo[3,4-d]pyrimidin-1-yl)ethyl]-5-chloro-2-ethoxy-6-methylphenyl}-N,N-dimethylpyridine-2-carboxamide To a solution of 5-(3-{1-[4-amino-3-(1,2-dihydroxyethyl)-1H-pyrazolo[3,4-d]pyrimidin-1-yl]ethyl}-5-chloro-2-ethoxy-6-methylphenyl)-N,N-dimethylpyridine-2-carboxamide (70 mg, 0.13 mmol) in tetrahydrofuran (0.98 mL) and water (0.59 mL) was added acetic acid (1.9 µL, 0.034 mmol) and sodium periodate (83 mg, 0.39 mmol) at 0° C. After stirring for 2 h, the reaction mixture was diluted with water, and extracted with dichloromethane. The combined organic layers were washed with brine, dried over $MgSO_4$, filtered and concentrated to give the desired product (0.059 g, 90%). LCMS calculated for $C_{25}H_{27}ClN_7O_3$ (M+H)$^+$: m/z=508.2. Found: 508.1.

Step 3. 5-(3-{1-[4-Amino-3-(difluoromethyl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

To a solution of 5-{3-[1-(4-amino-3-formyl-1H-pyrazolo[3,4-d]pyrimidin-1-yl)ethyl]-5-chloro-2-ethoxy-6-methylphenyl}-N,N-dimethylpyridine-2-carboxamide (8.8 mg, 0.017 mmol) in methylene chloride (0.1 mL) cooled at 0° C. was added dropwise diethylaminosulfur trifluoride (5.7 µL, 0.043 mmol). The mixture was stirred at room temperature for 3 h, diluted with MeOH and purified on RP-HPLC (XBridge C18 column, eluting with a gradient of acetonitrile/water containing 0.05% TFA, at flow rate of 30 mL/min) to give the desired product as a bis-TFA salt (0.7 mg, 8%). The product was isolated as a racemic mixture. LCMS calculated for $C_{25}H_{27}ClF_2N_7O_2$ (M+H)$^+$: m/z=530.2. Found: 530.0.

Example 83

5-(3-{1-[4-Amino-3-(hydroxymethyl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

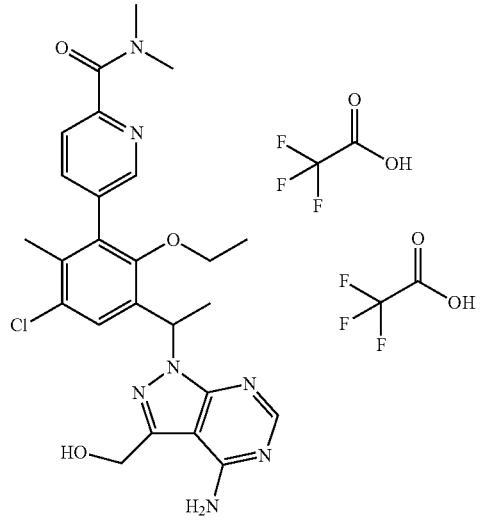 [SMILES: CCOc1c(C(C)n2nc(CO)c3c(N)ncnc32)cc(Cl)c(C)c1-c1ccc(C(=O)N(C)C)nc1 ; O=C(O)C(F)(F)F ; O=C(O)C(F)(F)F]

5-{3-[1-(4-Amino-3-formyl-1H-pyrazolo[3,4-d]pyrimidin-1-yl)ethyl]-5-chloro-2-ethoxy-6-methylphenyl}-N,N-dimethylpyridine-2-carboxamide (5.6 mg, 0.011 mmol, from Example 82, Step 2) was treated with sodium tetrahydroborate (0.5 mg, 0.01 mmol) in methanol (0.09 mL) at room temperature for 1 h. The mixture was purified on RP-HPLC (XBridge C18 column, eluting with a gradient of acetonitrile/water containing 0.05% TFA, at flow rate of 30 mL/min) to give the desired product as bis-TFA salt (2.5 mg, 45%). The product was isolated as a racemic mixture. LCMS calculated for $C_{25}H_{29}ClN_7O_3$ (M+H)$^+$: m/z=510.2. Found: 510.0.

Example 84

5-[3-(1-{4-Amino-3-[(methylamino)methyl]-1H-pyrazolo[3,4-d]pyrimidin-1-yl}ethyl)-5-chloro-2-ethoxy-6-methylphenyl]-N,N-dimethylpyridine-2-carboxamide tris(trifluoroacetate)

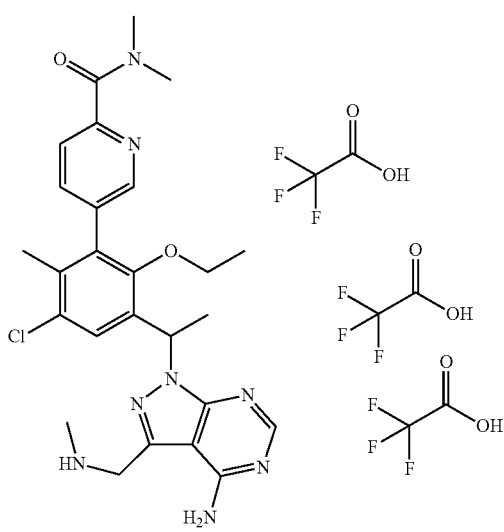

To a solution of 5-{3-[1-(4-amino-3-formyl-1H-pyrazolo[3,4-d]pyrimidin-1-yl)ethyl]-5-chloro-2-ethoxy-6-methylphenyl}-N,N-dimethylpyridine-2-carboxamide (8.8 mg, 0.017 mmol, from Example 82, Step 2) in methanol (1 mL) was added 2.0 M methylamine in THF (43 µL, 0.087 mmol). The mixture was stirred at room temperature overnight before the addition of sodium tetrahydroborate (1.3 mg, 0.035 mmol). The mixture was stirred at room temperature for 2 h, then diluted with MeOH and purified on RP-HPLC (XBridge C18 column, eluting with a gradient of acetonitrile/water containing 0.05% TFA, at flow rate of 30 mL/min) to give the desired product as TFA salt (4.2 mg, 48%). The product was isolated as a racemic mixture. LCMS calculated for $C_{26}H_{32}ClN_8O_2$ (M+H)$^+$: m/z=523.2. Found: 523.0.

Example 85

5-[3-(1-{4-Amino-3-[(dimethylamino)methyl]-1H-pyrazolo[3,4-d]pyrimidin-1-yl}ethyl)-5-chloro-2-ethoxy-6-methylphenyl]-N,N-dimethylpyridine-2-carboxamide tris(trifluoroacetate)

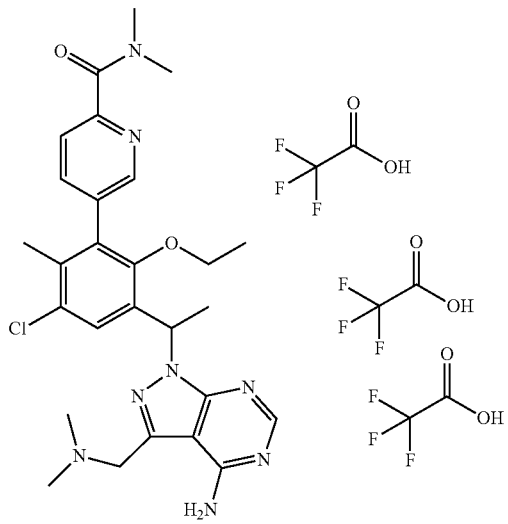

This compound was prepared using procedures analogous to Example 84, with 2.0 dimethylamine in THF replacing 2.0 M methylamine in THF. The product was isolated as a racemic mixture. LCMS calculated for $C_{27}H_{34}ClN_8O_2$ (M+H)$^+$: m/z=537.2. Found: 537.1.

Example 86

5-(3-{1-[4-Amino-3-(fluoromethyl)-1H-pyrazolo[3,4-d]pyrimidin-1-yl]ethyl}-5-chloro-2-ethoxy-6-methylphenyl)-N,N-dimethylpyridine-2-carboxamide bis(trifluoroacetate)

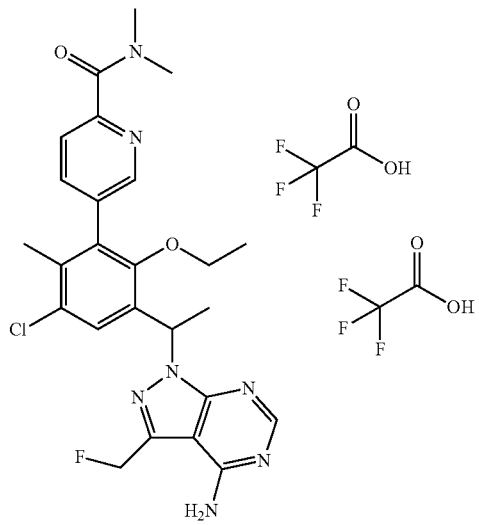 [SMILES: CCOc1c(C(C)n2nc(CF)c3c(N)ncnc32)cc(Cl)c(C)c1-c1ccc(C(=O)N(C)C)nc1 ; O=C(O)C(F)(F)F ; O=C(O)C(F)(F)F]

To a solution of 5-(3-{1-[4-amino-3-(hydroxymethyl)-1H-pyrazolo[3,4-d]pyrimidin-1-yl]ethyl}-5-chloro-2-ethoxy-6-methylphenyl)-N,N-dimethylpyridine-2-carboxamide (22 mg, 0.043 mmol, from Example 83) in methylene chloride (0.1 mL) cooled at 0° C. was added slowly 2-methoxy-N-(2-methoxyethyl)-N-(trifluoro-λ(4)-sulfanyl)ethanamine (12 µL, 0.065 mmol). The mixture was stirred at room temperature for 4 h, diluted with MeOH and purified on RP-HPLC (XBridge C18 column, eluting with a gradient of acetonitrile/water containing 0.05% TFA, at flow rate of 30 mL/min) to give the desired product as TFA salt (3.9 mg, 18%). The product was isolated as a racemic mixture. LCMS calculated for $C_{25}H_{28}ClFN_7O_2$ (M+H)$^+$: m/z=512.2. Found: 512.0.

Example 87

3-{1-[4-Amino-3-(1H-pyrazol-4-yl)-1H-pyrazolo[3,4-d]pyrimidin-1-yl]ethyl}-5-chloro-2-ethoxy-N-ethyl-6-methylbenzamide

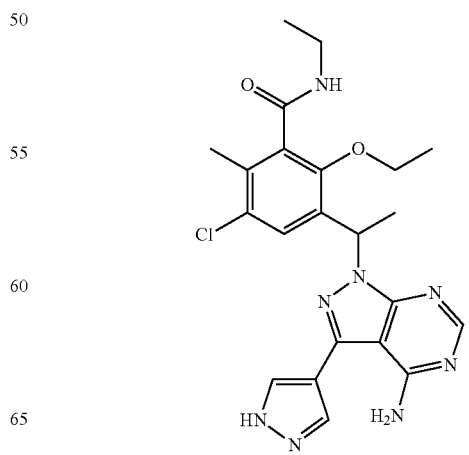

Step 1. 1-(5-Chloro-2-ethoxy-4-methyl-3-vinylphenyl)ethanone

A mixture of 1-(5-chloro-2-ethoxy-3-iodo-4-methylphenyl)ethanone (1.1 g, 3.2 mmol, from Example 14, Step 1), 4,4,5,5-tetramethyl-2-vinyl-1,3,2-dioxaborolane (0.66 mL, 3.9 mmol), [1,1'-bis(diphenylphosphino)ferrocene]dichloropalladium(II), complex with dichloromethane (1:1) (0.26 g, 0.32 mmol) and potassium carbonate (1.3 g, 9.4 mmol) in 1,4-dioxane (10 mL)/water (5 mL) was degassed with $N_2$ and heated at 80° C. overnight. After cooling to room temperature, the reaction mixture was extracted with EtOAc. The combined organic layers were washed with brine, dried over $MgSO_4$, filtered, concentrated and purified on silica gel (eluting with 0 to 10% EtOAc in hexanes) to give the desired product (0.64 g, 82%). LCMS calculated for $C_{13}H_{16}ClO_2$ $(M+H)^+$: m/z=239.1. Found: 239.1.

Step 2. 1-[5-Chloro-3-(1,2-dihydroxyethyl)-2-ethoxy-4-methylphenyl]ethanone

To a solution of 1-(5-chloro-2-ethoxy-4-methyl-3-vinylphenyl)ethanone (0.59 g, 2.5 mmol) in tert-butyl alcohol (20 mL) was added N-methylmorpholine N-oxide (0.318 g, 2.72 mmol) and water (7.8 mL). To this solution was then added 4% osmium tetraoxide (0.078 mL, 0.012 mmol). After 3 h, another equivalent of N-methylmorpholine N-oxide was added. The reaction was stirred for another 3 h. The solution was diluted with water, extracted with EtOAc. The combined organic layers were dried over $MgSO_4$ and concentrated to give the desired product (0.64 g, 95%). LCMS calculated for $C_{13}H_{17}ClO_4Na$ $(M+Na)^+$: m/z=295.1. Found: 295.1.

Step 3. 3-Acetyl-5-chloro-2-ethoxy-6-methylbenzaldehyde

To a solution of 1-[5-chloro-3-(1,2-dihydroxyethyl)-2-ethoxy-4-methylphenyl]ethanone (0.64 g, 2.3 mmol) in tetrahydrofuran (18 mL) and water (11 mL) was added acetic acid (35 µL, 0.61 mmol) and sodium periodate (1.50 g, 7.04 mmol) at 0° C. After stirring for 30 min, the reaction mixture was diluted with water, and extracted with EtOAc. The combined extracts were washed with brine, dried over $MgSO_4$, filtered and concentrated to give the desired product (0.58 g, 100%). LCMS calculated for $Cl_2H_{14}ClO_3$ $(M+H)^+$: m/z=241.1. Found: 241.1.

Step 4. 3-Acetyl-5-chloro-2-ethoxy-6-methylbenzoic acid

A solution of 3-acetyl-5-chloro-2-ethoxy-6-methylbenzaldehyde (0.58 g, 2.4 mmol) and sodium phosphate monobasic monohydrate (116 mg, 0.844 mmol) in acetonitrile (11.8 mL) and water (2.5 mL) was cooled in an ice bath. 30% Hydrogen peroxide (0.98 mL, 9.6 mmol) was added followed by solid sodium chlorite (0.545 g, 4.82 mmol). The mixture was stirred for 1 h. The mixture was diluted with 1 M HCl solution, and extracted with EtOAc. The combined organic layers were dried over $MgSO_4$, filtered and concentrated to give the desired product (0.67 g, 100%). LCMS calculated for $C_{12}H_{13}ClO_4Na$ $(M+Na)^+$: m/z=279.1. Found: 279.0.

Step 5. 3-Acetyl-5-chloro-2-ethoxy-N-ethyl-6-methylbenzamide

To a solution of 3-acetyl-5-chloro-2-ethoxy-6-methylbenzoic acid (0.26 g, 1.0 mmol) in N,N-dimethylformamide (5 mL) was added benzotriazol-1-yloxytris(dimethylamino)phosphonium hexafluorophosphate (0.67 g, 1.5 mmol). After stirring for 10 min, N,N-diisopropylethylamine (0.35 mL, 2.0 mmol) and 2.0 M ethylamine in THF (2.5 mL, 5.1 mmol) was added. The resulting mixture was stirred at room temperature for 2 h. The reaction solution was diluted with water, and extracted with dichloromethane. The combined organic layers were concentrated and purified on silica gel column (eluting with 0% to 50% EtOAc in hexanes) to give the desired product (0.2 g, 70%). LCMS calculated for $C_{14}H_{19}ClNO_3$ $(M+H)^+$: m/z=284.1. Found: 284.1.

Step 6. 3-Chloro-6-ethoxy-N-ethyl-5-(1-hydroxyethyl)-2-methylbenzamide

3-Acetyl-5-chloro-2-ethoxy-N-ethyl-6-methylbenzamide (0.2 g, 0.7 mmol) was treated with sodium tetrahydroborate (0.032 g, 0.84 mmol) in methanol (6 mL) at room temperature for 1 h. The mixture was diluted with water, extracted with dichloromethane. The combined organic layers were dried over $MgSO_4$ and filtered, concentrated to give the desired product. LCMS calculated for $C_{14}H_{21}ClNO_3$ $(M+H)^+$: m/z=286.1. Found: 286.1.

Step 7. 3-Chloro-5-(1-chloroethyl)-6-ethoxy-N-ethyl-2-methylbenzamide

A mixture of cyanuric chloride (0.15 g, 0.84 mmol) and N,N-dimethylformamide (0.065 mL, 0.84 mmol) was stirred at room temperature for 10 min and then a solution of 3-chloro-6-ethoxy-N-ethyl-5-(1-hydroxyethyl)-2-methylbenzamide (0.16 g, 0.56 mmol) in methylene chloride (3.1 mL) was added and the reaction was stirred at room temperature overnight. The mixture was diluted with methylene chloride, washed with water, concentrated and purified on silica gel (eluting with 0 to 40% EtOAc in hexanes) to give the desired product (0.13 g, 76%). LCMS calculated for $C_{14}H_{20}Cl_2NO_2$ $(M+H)^+$: m/z=304.1. Found: 304.1.

Step 8. 3-[1-(4-Amino-3-iodo-1H-pyrazolo[3,4-d]pyrimidin-1-yl)ethyl]-5-chloro-2-ethoxy-N-ethyl-6-methylbenzamide A mixture of 3-chloro-5-(1-chloroethyl)-6-ethoxy-N-ethyl-2-methylbenzamide (130 mg, 0.43 mmol), 3-iodo-1H-pyrazolo[3,4-d]pyrimidin-4-amine (120 mg, 0.47 mmol), cesium carbonate (210 mg, 0.64 mmol) and potassium iodide (7.1 mg, 0.043 mmol) in N,N-dimethylformamide (1 mL) was heated at 140° C. for 1 h. The mixture was diluted with ether, washed with water, and concentrated. The residue was purified on silica gel (eluting with 0 to 100% EtOAc in hexanes) to give the desired product (0.14 g, 62%). LCMS calculated for $C_{19}H_{23}ClIN_6O_2$ $(M+H)^+$: m/z=529.1. Found: 528.9.

Step 9. 3-{1-[4-Amino-3-(1H-pyrazol-4-yl)-1H-pyrazolo[3,4-d]pyrimidin-1-yl]ethyl}-5-chloro-2-ethoxy-N-ethyl-6-methylbenzamide To a solution of 3-[1-(4-amino-3-iodo-1H-pyrazolo[3,4-d]pyrimidin-1-yl)ethyl]-5-chloro-2-ethoxy-N-ethyl-6-methylbenzamide (9.0 mg, 0.017 mmol), 4-(4,4,5,5-tetramethyl-1,3,2-dioxaborolan-2-yl)-1H-pyrazole (6.6 mg, 0.034 mmol), sodium carbonate (11 mg, 0.10 mmol) in N,N-dimethylformamide (0.1 mL)/water (51 µL) under $N_2$ was added tetrakis(triphenylphosphine)palladium(0) (2.0 mg, 0.0017 mmol). The mixture was heated at 100° C. overnight. After cooling to room temperature, the mixture was filtered and purified on RP-HPLC (XBridge C18 column, eluting with a gradient of acetonitrile/water containing 0.1% ammonium hydroxide, at flow rate of 30 mL/min) to give the desired product (0.9 mg, 10%). The product was isolated as a racemic mixture. LCMS calculated for $C_{22}H_{26}ClN_8O_2$ (M+H)$^+$: m/z=469.2. Found: 469.0.

Example 88

3-{1-[4-Amino-3-(3-fluoro-5-hydroxyphenyl)-1H-pyrazolo[3,4-d]pyrimidin-1-yl]ethyl}-5-chloro-2-ethoxy-N-ethyl-6-methylbenzamide

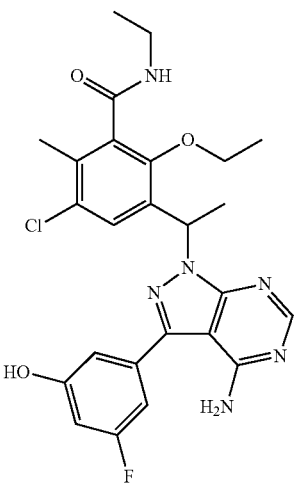 [SMILES: CCNC(=O)c1c(C)c(Cl)cc(C(C)n2nc(-c3cc(O)cc(F)c3)c3c(N)ncnc32)c1OCC]

This compound was prepared using procedures analogous to Example 87, Step 9 (racemic intermediate), with (3-fluoro-5-hydroxyphenyl)boronic acid replacing 4-(4,4,5,5-tetramethyl-1,3,2-dioxaborolan-2-yl)-1H-pyrazole. The product was isolated as a racemic mixture. LCMS calculated for $C_{25}H_{27}ClFN_6O_3$ (M+H)$^+$: m/z=513.2. Found: 513.0.

Example 89

3-(1-(4-Amino-3-(2-aminobenzo[d]oxazol-5-yl)-1H-pyrazolo[3,4-d]pyrimidin-1-yl)ethyl)-5-chloro-2-ethoxy-N-ethyl-6-methylbenzamide

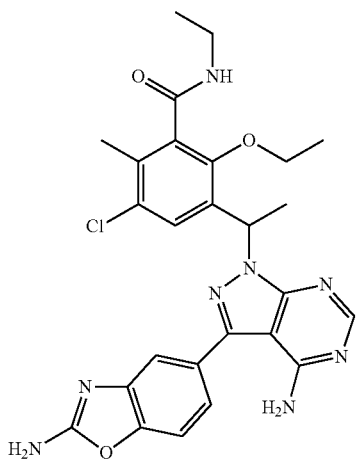 [SMILES: CCNC(=O)c1c(C)c(Cl)cc(C(C)n2nc(-c3ccc4oc(N)nc4c3)c3c(N)ncnc32)c1OCC]

This compound was prepared using procedures analogous to Example 87, Step 9 (racemic intermediate), with 5-(4,4,5,5-tetramethyl-1,3,2-dioxaborolan-2-yl)-1,3-benzoxazol-2-amine replacing 4-(4,4,5,5-tetramethyl-1,3,2-dioxaborolan-2-yl)-1H-pyrazole. The product was isolated as a racemic mixture. LCMS calculated for $C_{26}H_{28}ClN_8O_3$ (M+H)$^+$: m/z=535.2. Found: 535.0.

Example 90

3-{1-[4-Amino-3-(2-amino-1,3-benzothiazol-6-yl)-1H-pyrazolo[3,4-d]pyrimidin-1-yl]ethyl}-5-chloro-2-ethoxy-N-ethyl-6-methylbenzamide

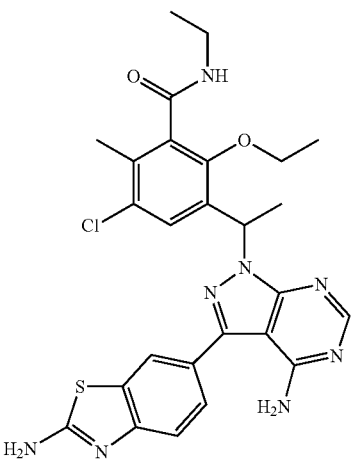 [SMILES: CCNC(=O)c1c(C)c(Cl)cc(C(C)n2nc(-c3ccc4nc(N)sc4c3)c3c(N)ncnc32)c1OCC]

This compound was prepared using procedures analogous to Example 87, Step 9 (racemic intermediate), with 6-(4,4,5,5-tetramethyl-1,3,2-dioxaborolan-2-yl)-1,3-benzothiazol-2-amine replacing 4-(4,4,5,5-tetramethyl-1,3,2-dioxaborolan-2-yl)-1H-pyrazole. The product was isolated as a racemic mixture. LCMS calculated for $C_{26}H_{28}ClN_8O_2S$ (M+H)$^+$: m/z=551.2. Found: 551.0.

Example 91

3-{1-[4-Amino-3-(1H-pyrrolo[2,3-b]pyridin-5-yl)-1H-pyrazolo[3,4-d]pyrimidin-1-yl]ethyl}-5-chloro-2-ethoxy-N-ethyl-6-methylbenzamide

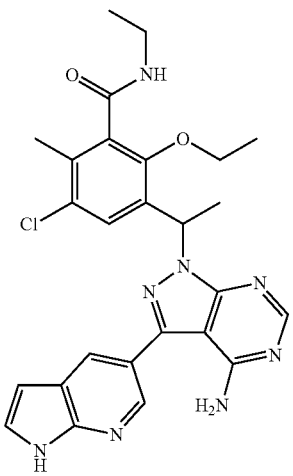 [SMILES: CCNC(=O)c1c(C)c(Cl)cc(C(C)n2nc(-c3cnc4[nH]ccc4c3)c3c(N)ncnc32)c1OCC]

This compound was prepared using procedures analogous to Example 87, Step 9 (racemic intermediate), with 5-(4,4,5,5-tetramethyl-1,3,2-dioxaborolan-2-yl)-1H-pyrrolo[2,3-b]pyridine replacing 4-(4,4,5,5-tetramethyl-1,3,2-dioxaborolan-2-yl)-1H-pyrazole. The product was isolated as a racemic mixture. LCMS calculated for $C_{26}H_{28}ClN_8O_2$ (M+H)+: m/z=519.2. Found: 519.0.

Example 92

3-{1-[4-Amino-3-(1H-indazol-6-yl)-1H-pyrazolo[3,4-d]pyrimidin-1-yl]ethyl}-5-chloro-2-ethoxy-N-ethyl-6-methylbenzamide

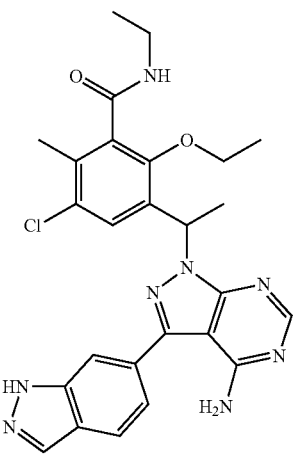 [SMILES: CCNC(=O)c1c(C)c(Cl)cc(C(C)n2nc(-c3ccc4cn[nH]c4c3)c3c(N)ncnc32)c1OCC]

This compound was prepared using procedures analogous to Example 87, Step 9 (racemic intermediate), with 6-(4,4,5,5-tetramethyl-1,3,2-dioxaborolan-2-yl)-1H-indazole replacing 4-(4,4,5,5-tetramethyl-1,3,2-dioxaborolan-2-yl)-1H-pyrazole. The product was isolated as a racemic mixture. LCMS calculated for $C_{26}H_{28}ClN_8O_2$ (M+H)+: m/z=519.2. Found: 519.0.

Example 93

3-{1-[4-Amino-3-(1H-indol-5-yl)-1H-pyrazolo[3,4-d]pyrimidin-1-yl]ethyl}-5-chloro-2-ethoxy-N-ethyl-6-methylbenzamide

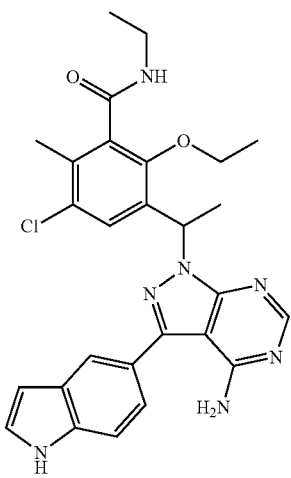 [SMILES: CCNC(=O)c1c(C)c(Cl)cc(C(C)n2nc(-c3ccc4[nH]ccc4c3)c3c(N)ncnc32)c1OCC]

This compound was prepared using procedures analogous to Example 87, Step 9 (racemic intermediate), with 5-(4,4,5,5-tetramethyl-1,3,2-dioxaborolan-2-yl)-1H-indole replacing 4-(4,4,5,5-tetramethyl-1,3,2-dioxaborolan-2-yl)-1H-pyrazole. The product was isolated as a racemic mixture. LCMS calculated for $C_{27}H_{29}ClN_7O_2$ (M+H)+: m/z=518.2. Found: 518.0.

Example 94

1-{1-[5-Chloro-2-ethoxy-3-(1-isopropylazetidin-3-yl)-4-methylphenyl]ethyl}-3-methyl-1H-pyrazolo[3,4-d]pyrimidin-4-amine bis(trifluoroacetate)

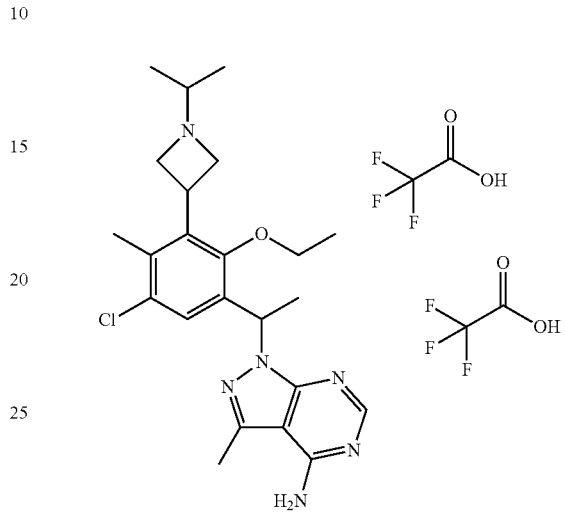

Step 1. Benzyl 3-{3-[1-(4-amino-3-methyl-1H-pyrazolo[3,4-d]pyrimidin-1-yl)ethyl]-5-chloro-2-ethoxy-6-methylphenyl}azetidine-1-carboxylate A mixture of benzyl 3-[3-chloro-5-(1-chloroethyl)-6-ethoxy-2-methylphenyl]azetidine-1-carboxylate (0.375 g, 0.888 mmol, from Example 35, Step 3), 3-methyl-1H-pyrazolo[3,4-d]pyrimidin-4-amine (0.16 g, 1.1 mmol), cesium carbonate (0.43 g, 1.3 mmol) and potassium iodide (15 mg, 0.089 mmol) in N,N-dimethylformamide (2.8 mL) was heated at 140° C. for 1 h. The mixture was diluted with ether, and washed with water. The organic layers were concentrated and purified on silica gel (eluting with 0 to 100% EtOAc in hexanes) to give the desired product (0.24 g, 50%). LCMS calculated for $C_{28}H_{32}ClN_6O_3$ (M+H)+: m/z=535.2. Found: 535.0. The enantionmers were separated on a Phenomenex Lux Cellulose C-2 column (5 µM, 21.2× 250 mm), eluting with 20% ethanol in hexanes, at flow rate of 18 mL/min, and column loading of ~4.5 mg/injection to separate two enantiomers. First peak retention time: 21.2 min; second peak retention time: 24.6 min.

Step 2. 1-[1-(3-Azetidin-3-yl-5-chloro-2-ethoxy-4-methylphenyl)ethyl]-3-methyl-1H-pyrazolo[3,4-d]pyrimidin-4-amine Benzyl 3-{3-[1-(4-amino-3-methyl-1H-pyrazolo[3,4-d]pyrimidin-1-yl)ethyl]-5-chloro-2-ethoxy-6-methylphenyl}azetidine-1-carboxylate (170 mg, 0.32 mmol, racemic intermediate) and 5% palladium (80 mg) were combined in methanol (12 mL), to which was added 0.25 M hydrogen chloride in water (3.2 mL, 0.79 mmol). The suspension was hydrogenated under balloon pressure of $H_2$ at room temperature for 2 h. The suspension was filtered. The filtrate was neutralized with sat. NaHCO$_3$ solution, and extracted with dichloromethane. The combined organic layers were dried over MgSO$_4$ and filtered, concentrated to give the desired product (117 mg, 92%). LCMS calculated for $C_{20}H_{26}ClN_6O$ (M+H)+: m/z=401.2. Found: 401.1.

Step 3. 1-{1-[5-Chloro-2-ethoxy-3-(1-isopropylazetidin-3-yl)-4-methylphenyl]ethyl}-3-methyl-1H-pyrazolo[3,4-d]pyrimidin-4-amine bis(trifluoroacetate)

Acetone (9.3 µL, 0.13 mmol) was added to 1-[1-(3-azetidin-3-yl-5-chloro-2-ethoxy-4-methylphenyl)ethyl]-3-methyl-1H-pyrazolo[3,4-d]pyrimidin-4-amine (10.2 mg, 0.0254 mmol) in methanol (0.1 mL)/tetrahydrofuran (0.1 mL)/acetonitrile (0.1 mL) and the mixture was stirred at room temperature for 10 min, before the addition of sodium triacetoxyborohydride (16 mg, 0.076 mmol). The reaction mixture was stirred at room temperature for 4 h and then purified on RP-HPLC (XBridge C18 column, eluting with a gradient of acetonitrile/water containing 0.05% TFA, at flow rate of 30 mL/min) to give the desired product as TFA salt (2.3 mg, 22%). The product was isolated as a single enantiomer. LCMS calculated for $C_{23}H_{32}ClN_6O$ (M+H)$^+$: m/z=443.2. Found: 443.1.

Example 95

2-(3-{3-[1-(4-Amino-3-methyl-1H-pyrazolo[3,4-d]pyrimidin-1-yl)ethyl]-5-chloro-2-ethoxy-6-methylphenyl}azetidin-1-yl)ethanol bis(trifluoroacetate)

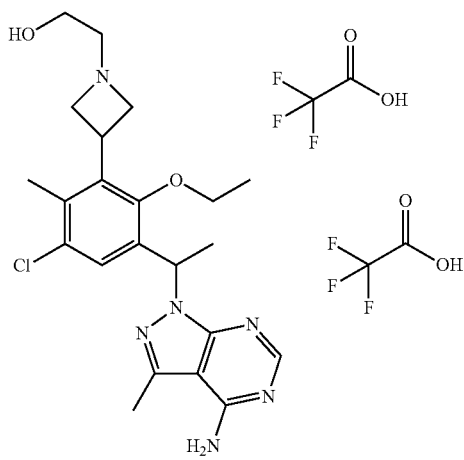 [SMILES: CCOc1c(C(C)n2nc(C)c3c(N)ncnc32)cc(Cl)c(C)c1C1CN(CCO)C1 ; O=C(O)C(F)(F)F ; O=C(O)C(F)(F)F]

To a mixture of 1-[1-(3-azetidin-3-yl-5-chloro-2-ethoxy-4-methylphenyl)ethyl]-3-methyl-1H-pyrazolo[3,4-d]pyrimidin-4-amine (7.9 mg, 0.020 mmol, racemic intermediate from Example 94, Step 2) in tetrahydrofuran (0.09 mL)/acetonitrile (0.09 mL)/methanol (0.09 mL) was added {[tert-butyl(dimethyl)silyl]oxy}acetaldehyde (19 µL, 0.098 mmol) and the mixture was stirred for 10 min before the addition of sodium triacetoxyborohydride (12 mg, 0.059 mmol). The resulting mixture was stirred at room temperature for 4 h, then treated with 6.0 M hydrogen chloride in water (30 µL, 0.2 mmol) for 10 min. The mixture was purified on RP-HPLC (XBridge C18 column, eluting with a gradient of acetonitrile/water containing 0.05% TFA, at flow rate of 30 mL/min) to give the desired product as TFA salt (3.2 mg, 40%). The product was isolated as a racemic mixture. LCMS calculated for $C_{22}H_{30}ClN_6O_2$ (M+H)$^+$: m/z=445.2. Found: 445.1.

Example 96

(2S)-1-(3-{3-[1-(4-Amino-3-methyl-1H-pyrazolo[3,4-d]pyrimidin-1-yl)ethyl]-5-chloro-2-ethoxy-6-methylphenyl}azetidin-1-yl)propan-2-ol bis(trifluoroacetate)

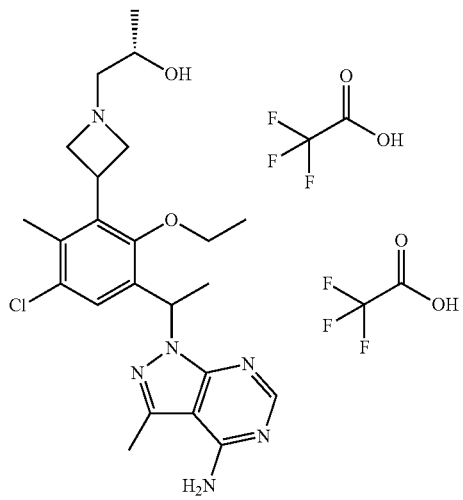 [SMILES: CCOc1c(C(C)n2nc(C)c3c(N)ncnc32)cc(Cl)c(C)c1C1CN(C[C@H](C)O)C1 ; O=C(O)C(F)(F)F ; O=C(O)C(F)(F)F]

Step 1. Benzyl 3-{3-[1-(4-amino-3-methyl-1H-pyrazolo[3,4-d]pyrimidin-1-yl)ethyl]-5-chloro-2-ethoxy-6-methylphenyl}azetidine-1-carboxylate The enantionmers from Example 94, Step 1 were separated on a Phenomenex Lux Cellulose C-2 column (5 µM, 21.2×250 mm), eluting with 20% ethanol in hexanes, at flow rate of 18 mL/min, and column loading of ?4.5 mg/injection to separate two enantiomers. First peak retention time: 21.2 min; second peak retention time: 24.6 min.

Step 2. 1-[1-(3-Azetidin-3-yl-5-chloro-2-ethoxy-4-methylphenyl)ethyl]-3-methyl-1H-pyrazolo[3,4-d]pyrimidin-4-amine Benzyl 3-{3-[1-(4-amino-3-methyl-1H-pyrazolo[3,4-d]pyrimidin-1-yl)ethyl]-5-chloro-2-ethoxy-6-methylphenyl}azetidine-1-carboxylate (chiral intermediate from first peak of previous step) was hydrogenated in the presence of 5% palladium as described in Example 94, Step 2 to give the desired chiral product. LCMS calculated for $C_{20}H_{26}ClN_6O$ (M+H)$^+$: m/z=401.2. Found: 401.1.

Step 3. (2S)-1-(3-{3-[1-(4-Amino-3-methyl-1H-pyrazolo[3,4-d]pyrimidin-1-yl)ethyl]-5-chloro-2-ethoxy-6-methylphenyl}azetidin-1-yl)propan-2-ol bis(trifluoroacetate)

To a mixture of 1-[1-(3-azetidin-3-yl-5-chloro-2-ethoxy-4-methylphenyl)ethyl]-3-methyl-1H-pyrazolo[3,4-d]pyrimidin-4-amine (10 mg, 0.02 mmol, chiral intermediate from step 2) and triethylamine (9 µL, 0.07 mmol) in isopropyl alcohol (0.05 mL) was added (S)-(−)-methyloxirane (4.5 µL, 0.064 mmol). The resulting mixture was stirred at 90° C. overnight, cooled and purified on RP-HPLC (XBridge C18 column, eluting with a gradient of acetonitrile/water containing 0.05% TFA, at flow rate of 30 mL/min) to give the desired product as TFA salt (3.4 mg, 34%). The product was isolated as a single diastereomer. LCMS calculated for $C_{23}H_{32}ClN_6O_2$ (M+H)$^+$: m/z=459.2. Found: 459.1.

Example 99

(2S)-1-(3-{3-[1-(4-Amino-3-methyl-1H-pyrazolo[3,4-d]pyrimidin-1-yl)ethyl]-5-chloro-2-ethoxy-6-methylphenyl}azetidin-1-yl)-1-oxopropan-2-ol trifluoroacetate

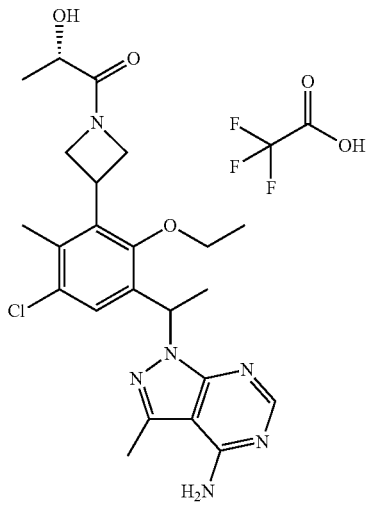

To a mixture of 1-[1-(3-azetidin-3-yl-5-chloro-2-ethoxy-4-methylphenyl)ethyl]-3-methyl-1H-pyrazolo[3,4-d]pyrimidin-4-amine (9.8 mg, 0.024 mmol, racemic intermediate from Example 94, Step 2), N,N, N',N'-tetramethyl-O-(7-azabenzotriazol-1-yl)uronium hexafluorophosphate (14 mg, 0.037 mmol) and triethylamine (10 µL, 0.073 mmol) in N,N-dimethylformamide (0.15 mL) was added 85% (2S)-2-hydroxypropanoic acid in water (3.2 µL, 0.037 mmol). The resulting mixture was stirred for 2 h at room temperature. The mixture was purified on RP-HPLC (XBridge C18 column, eluting with a gradient of acetonitrile/water containing 0.05% TFA, at flow rate of 30 mL/min) to give the desired product as trifluoroacetic acid (TFA) salt (2.9 mg, 29%). The product was isolated as a racemic mixture. LCMS calculated for $C_{23}H_{30}ClN_6O_3$ (M+H)$^+$: m/z=473.2. Found: 473.1.

Example 101

1-[1-(5-Chloro-2-ethoxy-4-methyl-3-{1-[(1-methyl-1H-pyrazol-4-yl)carbonyl]azetidin-3-yl}phenyl)ethyl]-3-methyl-1H-pyrazolo[3,4-d]pyrimidin-4-amine trifluoroacetate

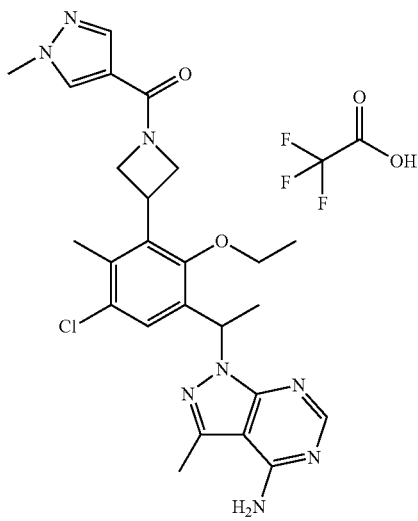

To a mixture of 1-[1-(3-azetidin-3-yl-5-chloro-2-ethoxy-4-methylphenyl)ethyl]-3-methyl-1H-pyrazolo[3,4-d]pyrimidin-4-amine (9.6 mg, 0.024 mmol, racemic intermediate from Example 94, Step 2) and triethylamine (10 µL, 0.072 mmol) in methylene chloride (0.2 mL) was added 1-methyl-1H-pyrazole-4-carbonyl chloride (5.2 mg, 0.036 mmol). The mixture was stirred at room temperature for 4 h, and evaporated to dry under reduced pressure. The resultant residue was diluted with MeOH and purified on RP-HPLC (XBridge C18 column, eluting with a gradient of acetonitrile/water containing 0.05% TFA, at flow rate of 30 mL/min) to give the desired product as TFA salt (1.3 mg, 13%). The product was isolated as a racemic mixture. LCMS calculated for $C_{25}H_{30}ClN_8O_2$ (M+H)$^+$: m/z=509.2. Found: 509.1.

Example 102

(2S)-1-(3-{3-[1-(4-Amino-3-methyl-1H-pyrazolo[3,4-d]pyrimidin-1-yl)ethyl]-5-chloro-2-methoxy-6-methylphenyl}azetidin-1-yl)propan-2-ol

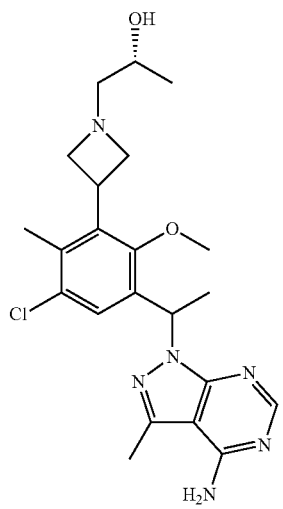 [SMILES: COc1c(C(C)n2nc(C)c3c(N)ncnc32)cc(Cl)c(C)c1C1CN(C[C@@H](C)O)C1]

To a mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (21 mg, 0.046 mmol) (Example 1, step 7, chiral intermediate from peak 1) and triethylamine (20 µL, 0.1 mmol) in isopropyl alcohol (0.10 mL) was added (S)-(−)-methyloxirane (3.2 µL, 0.046 mmol). The resulting mixture was stirred at 90° C. After 90 min, additional (S)-(−)-methyloxirane (6.4 uL) was added and stirred at 90° C. overnight. After cooling, the mixture was diluted with methanol and purified using RP-HPLC (XBridge C18 column, eluting with a gradient of acetonitrile/water containing 0.1% ammonium hydroxide, at flow rate of 30 mL/min) to give 6 mg (30%) of the product. The product was isolated as a single diastereomer. LCMS calculated for $C_{22}H_{30}ClN_6O_2$ (M+H)$^+$: m/z=445.2. Found: 445.2.

Example 104

2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)ethanol

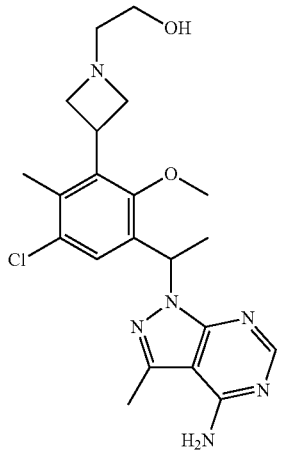 [SMILES: COc1c(C(C)n2nc(C)c3c(N)ncnc32)cc(Cl)c(C)c1C1CN(CCO)C1]

To a mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (20 mg, 0.04 mmol) (Example 1, step 7, chiral intermediate from peak 1), {[tert-butyl(dimethyl)silyl]oxy}acetaldehyde (8.3 mg, 0.048 mmol), and triethylamine (19 µL, 0.14 mmol) in methylene chloride (0.3 mL) was added sodium triacetoxyborohydride resin (38 mg, 0.087 mmol). The resulting mixture was stirred overnight at room temperature. The mixture was filtered and concentrated. The crude product was dissolved in tetrahydrofuran (1 mL) and cooled to 0° C. 1.0 M Tetra-n-butylammonium fluoride in THF (0.44 mL, 0.44 mmol) was added and warmed to room temperature. After 3 h, the solvents were evaporated. The crude was purified using RP-HPLC (XBridge C18 column, eluting with a gradient of acetonitrile/water containing 0.1% ammonium hydroxide, at flow rate of 30 mL/min) to give 8.1 mg (40%) of the desired product. The product was isolated as a single enantiomer. LCMS calculated for $C_{21}H_{28}ClN_6O_2$ (M+H)$^+$: m/z=431.2. Found: 431.3.

Example 105

(3-{3-[1-(4-Amino-3-methyl-1H-pyrazolo[3,4-d]pyrimidin-1-yl)ethyl]-5-chloro-2-methoxy-6-methylphenyl}azetidin-1-yl)acetonitrile

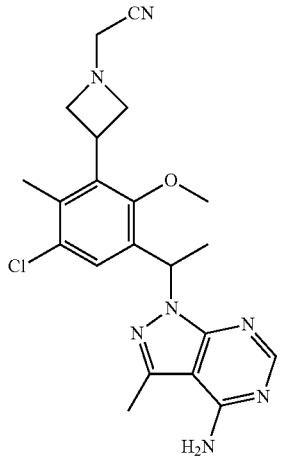 [SMILES: COc1c(C(C)n2nc(C)c3c(N)ncnc32)cc(Cl)c(C)c1C1CN(CC#N)C1]

To a mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (16 mg, 0.035 mmol, chiral intermediate from peak 1 of Example 1, Step 7) and triethylamine (14 µL, 0.10 mmol) in acetonitrile (0.7 mL) was added bromoacetonitrile (2.7 µL, 0.038 mmol). The resulting mixture was stirred at room temperature for 2.5 h. The mixture was diluted with acetonitrile and purified by using RP-HPLC (XBridge C18 column, eluting with a gradient of acetonitrile/water containing 0.05% TFA, at flow rate of 30 mL/min) to give the desired product as the TFA salt. The pure fractions were partially evaporated and then made basic by the addition of 1 N NaOH. The aqueous mixture was extracted with dichloromethane (2×). The extracts were dried (MgSO4), filtered, and concentrated. The solid was dried in vacuo to give 6.9 mg (46%) of the desired product. The product was isolated as a single enantiomer. LCMS calculated for $C_{21}H_{25}ClN_7O$ (M+H)$^+$: m/z=426.2. Found: 426.0.

Example 108

1-(1-{5-Chloro-2-methoxy-4-methyl-3-[1-(2,2,2-trifluoroethyl)azetidin-3-yl]phenyl}ethyl)-3-methyl-1H-pyrazolo[3,4-d]pyrimidin-4-amine

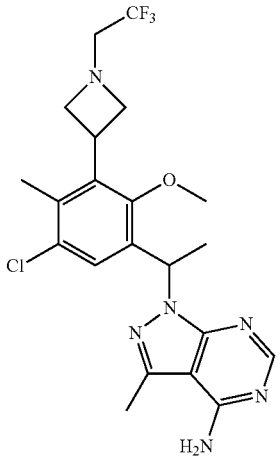 [SMILES: COc1c(C(C)n2nc(C)c3c(N)ncnc32)cc(Cl)c(C)c1C1CN(CC(F)(F)F)C1]

A mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (15 mg, 0.024 mmol, chrial intermediate from first peak of Example 1, step 7), 2,2,2-trifluoroethyl trifluoromethanesulfonate (6.8 mg, 0.029 mmol) and triethylamine (12 µL, 0.085 mmol) in methylene chloride (0.3 mL) was stirred over a weekend at room temperature. The solvents were evaporated and the crude purified using RP-HPLC (XBridge C18 column, eluting with a gradient of acetonitrile/water containing 0.1% ammonium hydroxide, at flow rate of 30 mL/min) to give 4.5 mg (39%) of the desired product. The product was isolated as a single enantiomer. LCMS calculated for $C_{21}H_{25}ClF_3N_6O$ (M+H)$^+$: m/z=469.2. Found: 469.1.

Example 110

(2R)-2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-N-methylpropanamide trifluoroacetate

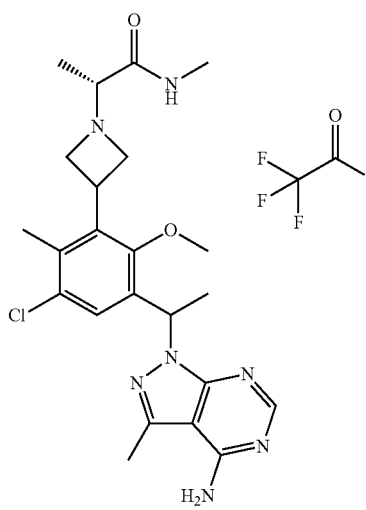

A mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (26 mg, 0.067 mmol, chrial intermediate from peak 1 of Example 1, Step 7), (2R)-2-bromopropanoic acid (7.3 µL, 0.081 mmol) and triethylamine (19 µL, 0.13 mmol) in acetonitrile (0.8 mL) was stirred overnight at room temperature. The reaction was not complete so it was heated to 50° C. After 4 h, the solvents were evaporated. To the crude residue was added methylammonium chloride (4.5 mg, 0.067 mmol), N,N-dimethylformamide (0.2 mL), triethylamine (19 µL, 0.13 mmol), and benzotriazol-1-yloxytris(dimethylamino)phosphonium hexafluorophosphate (45 mg, 0.10 mmol). The resulting mixture was stirred overnight at room temperature. The reaction mixture was added to a vial containing sat. NaHCO$_3$ and extracted with EtOAc (2×). The organics were dried (MgSO$_4$), filtered, and concentrated. The crude was purified using RP-HPLC (XBridge C18 column, eluting with a gradient of acetonitrile/water containing 0.05% TFA, at flow rate of 30 mL/min) to give 1.4 mg (3.6%) of the desired product as the TFA salt. The product was isolated as a single diastereomer. LCMS calculated for C$_{23}$H$_{31}$ClN$_7$O$_2$ (M+H)$^+$: m/z=472.2. Found: 472.2.

Example 113

2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-3,3,3-trifluoropropan-1-ol

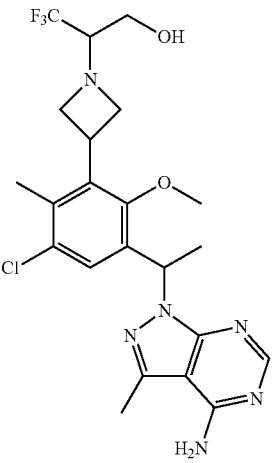 [SMILES: COc1c(C(C)n2nc(C)c3c(N)ncnc32)cc(Cl)c(C)c1C1CN(C(CO)C(F)(F)F)C1]

To a mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (20 mg, 0.04 mmol, chrial intermediate from peak 1 of Example 1, step 7) and triethylamine (19 µL, 0.13 mmol) in acetonitrile (0.6 mL) was added 2-bromo-3,3,3-trifluoropropan-1-ol (from Synquest Labs, 9.2 mg, 0.048 mmol). N,N-dimethylformamide (0.3 mL) was added, which created a clear solution that was stirred at 70° C. overnight. The mixture was diluted water and purified using RP-HPLC (XBridge C18 column, eluting with a gradient of acetonitrile/water containing 0.1% ammonium hydroxide, at flow rate of 30 mL/min) to give 6.6 mg (30%) of the desired product. The product was isolated as a mixture of diastereomers. LCMS calculated for C$_{22}$H$_{27}$ClF$_3$N$_6$O$_2$ (M+H)$^+$: m/z=499.2. Found: 499.1.

Example 115

(2R)-3-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-1,1,1-trifluoropropan-2-ol

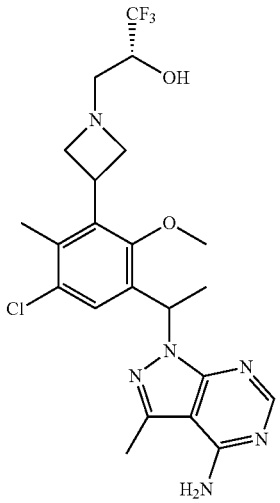 [SMILES: COc1c(C(C)n2nc(C)c3c(N)ncnc32)cc(Cl)c(C)c1C1CN(C[C@@H](O)C(F)(F)F)C1]

A mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (20 mg, 0.044 mmol, chrial intermediate from peak 1 of Example 1, Step 7), (2R)-2-(trifluoromethyl)oxirane (9.4 µL, 0.11 mmol), and triethylamine (18 µL, 0.13 mmol) in ethanol (0.3 mL) was heated in a microwave at 120° C. for 25 min. The mixture was diluted with MeOH and purified by RP-HPLC (XBridge C18 column, eluting with a gradient of acetonitrile/water containing 0.1% ammonium hydroxide, at flow rate of 30 mL/min) to give 6.2 mg (28%) of the desired product. The product was isolated as a single enantiomer. LCMS calculated for $C_{22}H_{27}ClF_3N_6O_2$ (M+H)$^+$: m/z=499.2. Found: 499.1.

Example 117

1-[1-(5-Chloro-2-methoxy-4-methyl-3-{1-[(1-methyl-1H-pyrazol-4-yl)carbonyl]azetidin-3-yl}phenyl)ethyl]-3-methyl-1H-pyrazolo[3,4-d]pyrimidin-4-amine

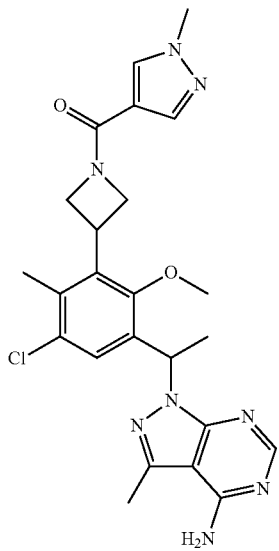 [SMILES: COc1c(C(C)n2nc(C)c3c(N)ncnc32)cc(Cl)c(C)c1C1CN(C(=O)c2cnn(C)c2)C1]

To a mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (15 mg, 0.033 mmol) (chiral material, from Example 1, step 7, peak 1) and triethylamine (14 µL, 0.098 mmol) in methylene chloride (0.2 mL) was added 1-methyl-1H-pyrazole-4-carbonyl chloride (from Maybridge, 6.1 mg, 0.042 mmol). The resulting mixture was stirred overnight at room temperature. The solvents were evaporated and the crude material was purified using RP-HPLC (XBridge C18 column, eluting with a gradient of acetonitrile/water containing 0.1% ammonium hydroxide, at flow rate of 30 mL/min) to give 7.1 mg (44%) of the product. The product was isolated as a single enantiomer. LCMS calculated for $C_{24}H_{28}ClN_8O_2$ (M+H)$^+$: m/z=495.2. Found: 495.2.

Example 118

(2S)-1-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-1-oxopropan-2-ol

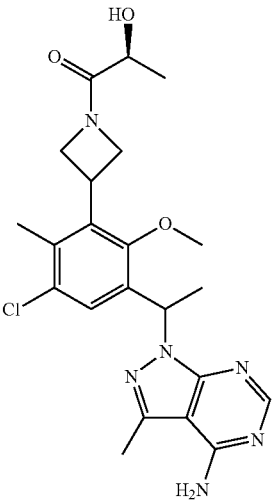 [SMILES: COc1c(C(C)n2nc(C)c3c(N)ncnc32)cc(Cl)c(C)c1C1CN(C(=O)[C@H](C)O)C1]

To a mixture of 1-[1-(3-azetidin-3-yl-5-chloro-2-methoxy-4-methylphenyl)ethyl]-3-methyl-1H-pyrazolo[3,4-d]pyrimidin-4-amine dihydrochloride (15 mg, 0.033 mmol, chrial intermediate from Example 1, Step 7, peak 1), mixture of (2S)-2-hydroxypropanoic acid (4.3 µL, 0.049 mmol) (L-lactic acid, 85% aq.) and triethylamine (14 µL, 0.098 mmol) in N,N-dimethylformamide (0.2 mL) was added N,N,N',N'-tetramethyl-O-(7-azabenzotriazol-1-yl) uronium hexafluorophosphate (19 mg, 0.049 mmol). The resulting mixture was stirred overnight at room temperature. The mixture was diluted with MeOH and purified using RP-HPLC (XBridge C18 column, eluting with a gradient of acetonitrile/water containing 0.1% ammonium hydroxide, at flow rate of 30 mL/min) to give 3.0 mg (20%) of the desired product. The product was isolated as a single enantiomer. LCMS calculated for $C_{22}H_{28}ClN_6O_3$ (M+H)$^+$: m/z=459.2. Found: 459.2.

Example 121

(2R)-1-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-1-oxopropan-2-ol trifluoroacetate

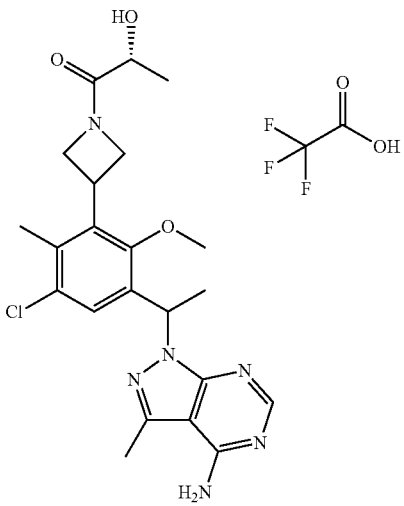 [SMILES: COc1c(C(C)n2nc(C)c3c(N)ncnc32)cc(Cl)c(C)c1C1CN(C(=O)[C@@H](C)O)C1 ; O=C(O)C(F)(F)F]

This compound was prepared using procedures analogous to those for Example 118 (starting from chiral material from Example 1, Step 7, peak 1), with (R)-2-hydroxypropanoic acid instead of (2S)-2-hydroxypropanoic acid (4.3 μL, 0.049 mmol) and benzotriazol-1-yloxytris(dimethylamino)phosphonium hexafluorophosphate instead of N,N,N',N'-tetramethyl-O-(7-azabenzotriazol-1-yl)uronium hexafluorophosphate. The crude was purified using RP-HPLC (XBridge C18 column, eluting with a gradient of acetonitrile/water containing 0.05% TFA, at flow rate of 30 mL/min) to give the desired product as the TFA salt. The product was isolated as a single enantiomer. LCMS calculated for $C_{22}H_{28}ClN_6O_3$ $(M+H)^+$: m/z=459.2. Found: 459.2.

Example 125

[3-(3-{1-[4-Amino-3-(1-methyl-1H-pyrazol-4-yl)-1H-pyrazolo[3,4-d]pyrimidin-1-yl]ethyl}-5-chloro-2-methoxy-6-methylphenyl)azetidin-1-yl]acetonitrile bis(trifluoroacetate)

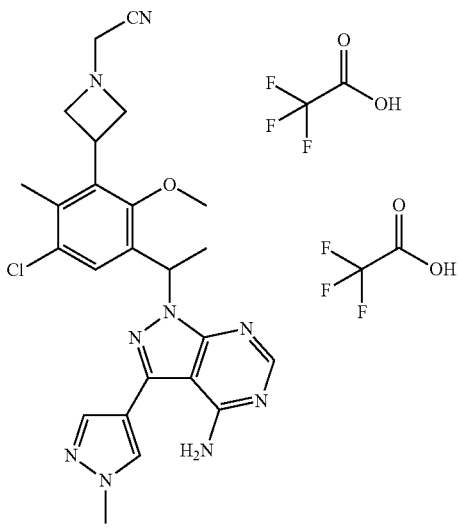 [SMILES: COc1c(C(C)n2nc(-c3cnn(C)c3)c3c(N)ncnc32)cc(Cl)c(C)c1C1CN(CC#N)C1 ; O=C(O)C(F)(F)F ; O=C(O)C(F)(F)F]

Step 1. tert-Butyl 3-{3-[1-(4-amino-3-bromo-1H-pyrazolo[3,4-d]pyrimidin-1-yl)ethyl]-5-chloro-2-methoxy-6-methylphenyl}azetidine-1-carboxylate To a mixture of tert-butyl 3-[3-chloro-5-(1-chloroethyl)-6-methoxy-2-methylphenyl]azetidine-1-carboxylate (1.0 g, 2.7 mmol) (from Example 1, Step 5, racemic intermediate) and 3-bromo-1H-pyrazolo[3,4-d]pyrimidin-4-amine (0.629 g, 2.94 mmol) in N,N-dimethylformamide (8 mL) was added potassium iodide (44 mg, 0.27 mmol) and cesium carbonate (1.30 g, 4.01 mmol). The resulting mixture was heated to 120° C. and stirred for 4 h. After cooling, water was added and stirred briefly before the solids were filtered. The resulting solids were washed with water, purified on silica gel (eluted with 0-10% MeOH in dichloromethane) to give 1.11 g (75%) of the desired product as a yellow gum. LCMS calculated for $C_{23}H_{29}BrClN_6O_3$ $(M+H)^+$: m/z=551.1. Found: 551.1.

Step 2. 1-[1-(3-Azetidin-3-yl-5-chloro-2-methoxy-4-methylphenyl)ethyl]-3-bromo-1H-pyrazolo[3,4-d]pyrimidin-4-amine Trifluoroacetic acid (1.2 mL, 16 mmol) was added to a solution of tert-butyl 3-{3-[1-(4-amino-3-bromo-1H-pyrazolo[3,4-d]pyrimidin-1-yl)ethyl]-5-chloro-2-methoxy-6-methylphenyl}azetidine-1-carboxylate (224 mg, 0.407 mmol) in methylene chloride (2.5 mL) and stirred for 2 h at room temp. The mixture was diluted with dichloromethane and 1 N NaOH was added and stirred rapidly for a few minutes. The layers were separated and the aqueous extracted with dichloromethane. The combined organics were dried (MgSO$_4$), filtered, and concentrated. Drying in vacuo gave 163 mg (91%) of the freebase. LCMS calculated for $C_{18}H_{21}BrClN_6O$ $(M+H)^+$: m/z=451.1. Found: 451.0.

Step 3. (3-{3-[1-(4-Amino-3-bromo-1H-pyrazolo[3,4-d]pyrimidin-1-yl)ethyl]-5-chloro-2-methoxy-6-methylphenyl}azetidin-1-yl)acetonitrile To a mixture of 1-[1-(3-azetidin-3-yl-5-chloro-2-methoxy-4-methylphenyl)ethyl]-3-bromo-1H-pyrazolo[3,4-d]pyrimidin-4-amine (100 mg, 0.2 mmol) and triethylamine (37 μL, 0.27 mmol) in acetonitrile (3 mL) was added bromoacetonitrile (19 μL, 0.27 mmol). The resulting mixture was stirred at room temp. After an hour, the reaction mixture was still cloudy with not all of the material in solution. Several drops of DMF were added which allowed for a clear solution. The mixture was stirred overnight at room temperature and then most of the solvents were evaporated. The resulting residue was purified on silica gel (eluted with 0-10% MeOH in dichloromethane) to give 29 mg (30%) of the desired product. LCMS calculated for $C_{20}H_{22}BrClN_7O$ $(M+H)^+$: m/z=490.1. Found: 490.1.

Step 4. [3-(3-{1-[4-Amino-3-(1-methyl-1H-pyrazol-4-yl)-1H-pyrazolo[3,4-d]pyrimidin-1-yl]ethyl}-5-chloro-2-methoxy-6-methylphenyl)azetidin-1-yl]acetonitrile bis(trifluoroacetate)

Into a microwave vial was added (3-{3-[1-(4-amino-3-bromo-1H-pyrazolo[3,4-d]pyrimidin-1-yl)ethyl]-5-chloro-2-methoxy-6-methylphenyl}azetidin-1-yl)acetonitrile (14 mg, 0.029 mmol), 1-methyl-4-(4,4,5,5-tetramethyl-1,3,2-dioxaborolan-2-yl)-1H-pyrazole (12 mg, 0.058 mmol), tetrakis(triphenylphosphine)palladium(0) (3.4 mg, 0.0029 mmol), N,N-dimethylformamide (0.15 mL), and 2.0 M sodium carbonate in water (73 μL, 0.14 mmol). The vial was capped and heated at 100° C. for 3 h. The mixture was diluted with dichloromethane, filtered, and concentrated. The crude material was purified using RP-HPLC (XBridge C18 column, eluting with a gradient of acetonitrile/water containing 0.05% TFA, at flow rate of 30 mL/min) to give 4.6 mg (22%) of the product as the TFA salt. The product was isolated as a racemic mixture. LCMS calculated for $C_{24}H_{27}ClN_9O$ $(M+H)^+$: m/z=492.2. Found: 492.1.

Example 126

[3-(3-{1-[4-Amino-3-(1H-pyrazol-4-yl)-1H-pyrazolo[3,4-d]pyrimidin-1-yl]ethyl}-5-chloro-2-methoxy-6-methylphenyl)azetidin-1-yl]acetonitrile

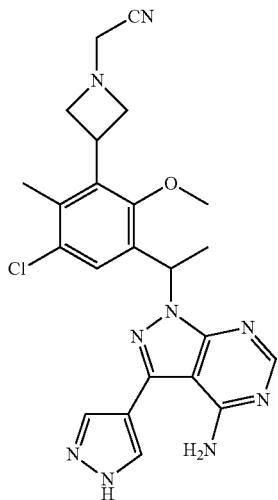 [SMILES: COc1c(C(C)n2nc(-c3cn[nH]c3)c3c(N)ncnc32)cc(Cl)c(C)c1C1CN(CC#N)C1]

Into a microwave vial was weighed 1-(1-ethoxyethyl)-4-(4,4,5,5-tetramethyl-1,3,2-dioxaborolan-2-yl)-1H-pyrazole (16 mg, 0.058 mmol) and tetrakis(triphenylphosphine)palladium(0) (3.4 mg, 0.0029 mmol). A solution of (3-{3-[1-(4-amino-3-bromo-1H-pyrazolo[3,4-d]pyrimidin-1-yl)ethyl]-5-chloro-2-methoxy-6-methylphenyl}azetidin-1-yl)acetonitrile (14 mg, 0.029 mmol, racemic intermediate from Example 125, Step 3) in N,N-dimethylformamide (0.25 mL) was added followed by 2.0 M sodium carbonate in water (73 µL, 0.14 mmol). The resulting mixture was stirred at 120° C. for 5 h. The mixture was filtered and concentrated. To a mixture of the crude coupling product in tetrahydrofuran (0.3 mL) was added 3.0 M hydrochloric acid solution in water (100 µL, 0.3 mmol) and stirred for 2 h at room temperature. The mixture was neutralized with sat. NaHCO$_3$ and extracted with dichloromethane. The organic was dried (MgSO$_4$), filtered, and concentrated. The crude was purified using RP-HPLC (XBridge C18 column, eluting with a gradient of acetonitrile/water containing 0.1% ammonium hydroxide, at flow rate of 30 mL/min) to give 1.0 mg (7.2% for 2 steps) of the desired product. The product was isolated as a racemic mixture. LCMS calculated for $C_{23}H_{25}ClN_9O$ (M+H)$^+$: m/z=478.2. Found: 478.1.

Examples 127 and 128

1-{1-[5-Chloro-3-(1-isopropylazetidin-3-yl)-2-methoxy-4-methylphenyl]ethyl}-3-(difluoromethyl)-1H-pyrazolo[3,4-d]pyrimidin-4-amine and 5-{1-[4-amino-3-(difluoromethyl)-1H-pyrazolo[3,4-d]pyrimidin-1-yl]ethyl}-3-(1-isopropylazetidin-3-yl)-4-methoxy-2-methylbenzonitrile

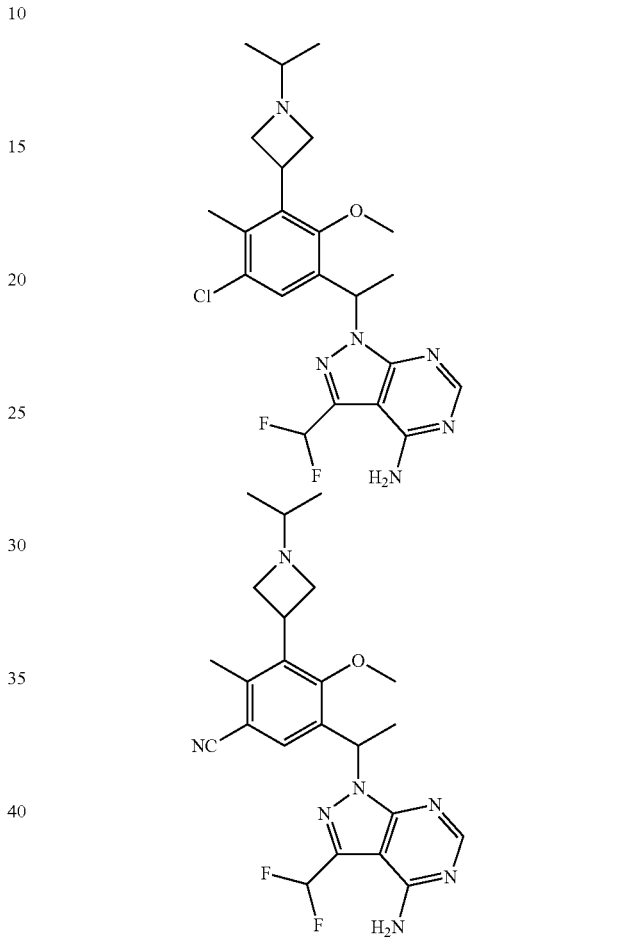

Step 1. tert-Butyl 3-{3-[1-(4-amino-3-vinyl-1H-pyrazolo[3,4-d]pyrimidin-1-yl)ethyl]-5-chloro-2-methoxy-6-methylphenyl}azetidine-1-carboxylate To a solution of tert-butyl 3-{3-[1-(4-amino-3-bromo-1H-pyrazolo[3,4-d]pyrimidin-1-yl)ethyl]-5-chloro-2-methoxy-6-methylphenyl}azetidine-1-carboxylate (1.1 g, 2.0 mmol, racemic intermediate from Example 125, Step 1) in N,N-dimethylformamide (10 mL) was added tetrakis(triphenylphosphine)palladium(0) (230 mg, 0.20 mmol) and 4,4,5,5-tetramethyl-2-vinyl-1,3,2-dioxaborolane (0.68 mL, 4.0 mmol). 2.0 M sodium carbonate in water (5.0 mL, 1.0 mmol) was added under N$_2$ and the mixture heated at 100° C. for 3 h then stirred at room temperature overnight. The reaction mixture was filtered through Celite, and washed with EtOAc. The filtrates were washed with water and brine, dried (MgSO$_4$), filtered, and concentrated. The crude material was purified on silica gel (eluted with 40-100% ethyl acetate in hexanes) to give 0.75 g (75%) of the desired product. LCMS calculated for $C_{25}H_{32}ClN_6O_3$ (M+H)$^+$: m/z=499.2. Found: 499.0 (M+H); $^1$H NMR (300 MHz, CDCl$_3$): δ 8.30 (s, 1H), 7.50-7.40 (m, 1H), 6.99 (dd, J=17.7, 11.3 Hz, 1H), 6.44 (q, J=7.0 Hz, 1H), 5.95 (dd, J=17.7, 1.3 Hz, 1H), 5.83 (br s, 1H), 5.65 (dd, J=11.3, 1.3 Hz, 1H), 4.39-3.96 (m, 4H), 3.63 (d, J=6.7 Hz, 3H), 2.99-2.78 (m, 1H), 2.22 (s, 4H), 1.84 (d, J=7.1 Hz, 3H), 1.43 (s, 9H).

Step 2. tert-Butyl 3-(3-{1-[4-amino-3-(1,2-dihydroxyethyl)-1H-pyrazolo[3,4-d]pyrimidin-1-yl]ethyl}-5-chloro-2-methoxy-6-methylphenyl)azetidine-1-carboxylate To a suspension of tert-butyl 3-{3-[1-(4-amino-3-vinyl-1H-pyrazolo[3,4-d]pyrimidin-1-yl)ethyl]-5-chloro-2-methoxy-6-methylphenyl}azetidine-1-carboxylate (0.87 g, 1.7 mmol) in tert-butyl alcohol (11 mL) was added N-methylmorpholine N-oxide (225 mg, 1.92 mmol), water (5.5 mL), and osmium tetraoxide (26 mg, 0.10 mmol). The resulting mixture was stirred overnight at room temp. Water was added to the reaction followed by EtOAc. The layers were separated and the aqueous extracted with EtOAc. The combined organics were washed with brine, dried ($Na_2SO_4$), filtered, and concentrated to give 0.93 g of the crude product. LCMS calculated for $C_{25}H_{34}ClN_6O_5$ (M+H)$^+$: m/z=533.2. Found: 533.2.

Step 3. tert-Butyl 3-{3-[1-(4-amino-3-formyl-1H-pyrazolo[3,4-d]pyrimidin-1-yl)ethyl]-5-chloro-2-methoxy-6-methylphenyl}azetidine-1-carboxylate To a solution of tert-butyl 3-(3-{1-[4-amino-3-(1,2-dihydroxyethyl)-1H-pyrazolo[3,4-d]pyrimidin-1-yl]ethyl}-5-chloro-2-methoxy-6-methylphenyl)azetidine-1-carboxylate (0.93 g, 1.7 mmol) in tetrahydrofuran (13 mL) and water (8 mL) was added acetic acid (26 µL, 0.45 mmol) and sodium periodate (1.12 g, 5.23 mmol) at 0° C. After stirring for 3 h with only slight warming, the reaction was not yet complete so it was placed in the refrigerator overnight. Water was added to the reaction and extracted with dichloromethane (3×). The combined extracts were washed with brine, dried ($Na_2SO_4$), filtered, and concentrated. The crude was purified on silica gel (eluted with 40-85% ethyl acetate in hexanes) to give 0.47 g (54%) of the desired product. LCMS calculated for $C_{24}H_{30}ClN_6O_4$ (M+H)$^+$: m/z=501.2. Found: 501.3. $^1$H NMR (300 MHz, CDCl$_3$) δ 10.05 (s, 1H), 8.37 (s, 1H), 7.39 (s, 1H), 6.55 (q, J=7.1 Hz, 1H), 5.89 (s, 1H), 4.42-3.95 (m, 6H), 3.67 (s, 3H), 2.25 (s, 3H), 1.90 (d, J=7.1 Hz, 3H), 1.44 (s, 9H) ppm.

Step 4. tert-Butyl 3-(3-{1-[4-amino-3-(difluoromethyl)-1H-pyrazolo[3,4-d]pyrimidin-1-yl]ethyl}-5-chloro-2-methoxy-6-methylphenyl)azetidine-1-carboxylate To a solution of tert-butyl 3-{3-[1-(4-amino-3-formyl-1H-pyrazolo[3,4-d]pyrimidin-1-yl)ethyl]-5-chloro-2-methoxy-6-methylphenyl}azetidine-1-carboxylate (0.96 g, 1.9 mmol) in methylene chloride (10 mL) stirring at 0° C. was added diethylaminosulfur trifluoride (0.63 mL, 4.8 mmol). The mixture was stirred at 0° C. for a few minutes then warmed to room temp and stirred for 2.5 h. Water and dichloromethane were added and the layers separated. The organic layer was washed with brine, dried (MgSO$_4$), filtered and concentrated. The crude was purified on silica gel (eluted with 0-5% MeOH in dichloromethane) to give the desired product. LCMS calculated for $C_{24}H_{30}ClF_2N_6O_3$ (M+H)$^+$: m/z=523.2. Found: 523.2.

Step 5. 1-[1-(3-Azetidin-3-yl-5-chloro-2-methoxy-4-methylphenyl)ethyl]-3-(difluoromethyl)-1H-pyrazolo[3,4-d]pyrimidin-4-amine dihydrochloride To a mixture of tert-butyl 3-(3-{1-[4-amino-3-(difluoromethyl)-1H-pyrazolo[3,4-d]pyrimidin-1-yl]ethyl}-5-chloro-2-methoxy-6-methylphenyl)azetidine-1-carboxylate (30 mg, 0.057 mmol) in dichloromethane (0.2 mL) was added 4.0 M hydrogen chloride in 1,4-dioxane (0.10 mL, 0.40 mmol). The resulting mixture was stirred for 3 h at room temperature and then concentrated. The residue was dried in vacuo to give 27 mg (100%) of the product as a salt. LCMS calculated for $C_{19}H_{22}ClF_2N_6O$ (M+H)$^+$: m/z=423.1. Found: 423.0.

Step 6. 1-{1-[5-Chloro-3-(1-isopropylazetidin-3-yl)-2-methoxy-4-methylphenyl]ethyl}-3-(difluoromethyl)-1H-pyrazolo[3,4-d]pyrimidin-4-amine To a mixture of 1-[1-(3-azetidin-3-yl-5-chloro-2-methoxy-4-methylphenyl)ethyl]-3-(difluoromethyl)-1H-pyrazolo[3,4-d]pyrimidin-4-amine dihydrochloride (27 mg, 0.054 mmol), acetone (4.4 µL, 0.060 mmol), and triethylamine (23.5 µL, 0.169 mmol) in methylene chloride (0.4 mL) was added sodium triacetoxyborohydride resin (47 mg, 0.11 mmol). The resulting mixture was stirred for 2 h at room temperature. The mixture was filtered and concentrated and dried in vacuo to give 22 mg of the crude the product which will be used without purification. LCMS calculated for $C_{22}H_{28}ClF_2N_6O$ (M+H)$^+$: m/z=465.2. Found: 465.1.

Step 7. 5-{1-[4-Amino-3-(difluoromethyl)-1H-pyrazolo[3,4-d]pyrimidin-1-yl]ethyl}-3-(1-isopropylazetidin-3-yl)-4-methoxy-2-methylbenzonitrile 0.5 mL of the preformed catalyst (from Example 40) was added to a mixture of 1-{1-[5-chloro-3-(1-isopropylazetidin-3-yl)-2-methoxy-4-methylphenyl]ethyl}-3-(difluoromethyl)-1H-pyrazolo[3,4-d]pyrimidin-4-amine (22 mg, 0.047 mmol), zinc (1.3 mg, 0.021 mmol) and zinc cyanide (5.6 mg, 0.047 mmol) in N,N-dimethylacetamide (0.7 mL). The mixture was flushed with N$_2$ and heated at 120° C. overnight. The reaction was about 50% complete and was stopped there so that both compounds could be isolated. The reaction mixture was filtered, washing with dichloromethane, and concentrated. The crude was purified using RP-HPLC (XBridge C18 column, eluting with a gradient of acetonitrile/water containing 0.1% ammonium hydroxide, at flow rate of 30 mL/min) to give both title compounds. The products were isolated as a racemic mixture. Example 126: Yield=6.6 mg (30%); LCMS calculated for $C_{22}H_{28}ClF_2N_6O$ (M+H)$^+$: m/z=465.2. Found: 465.2; Example 127: Yield=3.0 mg (14%); LCMS calculated for $C_{23}H_{28}F_2N_7O$ (M+H)$^+$: m/z=456.2. Found: 456.2.

Example 129

5-{1-[4-Amino-3-(difluoromethyl)-1H-pyrazolo[3,4-d]pyrimidin-1-yl]ethyl}-4-methoxy-2-methyl-3-[1-(2,2,2-trifluoroethyl)azetidin-3-yl]benzonitrile

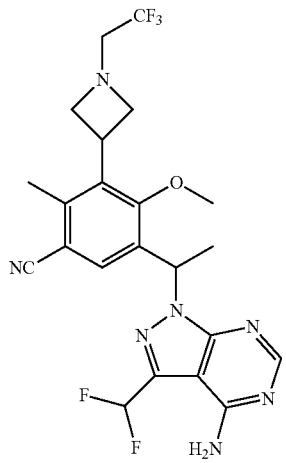 [SMILES: COc1c(C(C)n2nc(C(F)F)c3c(N)ncnc32)cc(C#N)c(C)c1C1CN(CC(F)(F)F)C1]

Step 1. tert-Butyl 3-(3-{1-[4-amino-3-(difluoromethyl)-1H-pyrazolo[3,4-d]pyrimidin-1-yl]ethyl}-5-cyano-2-methoxy-6-methylphenyl)azetidine-1-carboxylate Zinc (11 mg, 0.17 mmol) and bis(tri-t-butylphosphine) palladium (71 mg, 0.14 mmol) were weighed into a microwave vial then a solution of tert-butyl 3-(3-{1-[4-amino-3-(difluoromethyl)-1H-pyrazolo[3,4-d]pyrimidin-1-yl]ethyl}-5-chloro-2-methoxy-6-methylphenyl)azetidine-1-carboxylate (182 mg, 0.348 mmol, racemic intermediate from Examples 127/128, step 4) in N-methylpyrrolidinone (2.0 mL) was added. The mixture was degassed with $N_2$ for a few minutes before adding zinc cyanide (82 mg, 0.70 mmol). The resulting mixture was stirred at 130° C. for 3 h. After cooling, the mixture was filtered through a pad of Celite and concentrated. The crude was purified on silica gel, eluted with 0-5% MeOH in dichloromethane. The product eluted right away, along with NMP. The fractions were combined and concentrated then taken up in EtOAc and washed with brine (3×). The organic was dried, filtered, and concentrated to give 0.17 g (96%) of the desired product. LCMS calculated for $C_{25}H_{30}F_2N_7O_3$ (M+H)$^+$: m/z=514.2. Found: 514.1.

Step 2. 5-{1-[4-Amino-3-(difluoromethyl)-1H-pyrazolo[3,4-d]pyrimidin-1-yl]ethyl}-3-azetidin-3-yl-4-methoxy-2-methylbenzonitrile dihydrochloride To a solution of tert-butyl 3-(3-{1-[4-amino-3-(difluoromethyl)-1H-pyrazolo[3,4-d]pyrimidin-1-yl]ethyl}-5-cyano-2-methoxy-6-methylphenyl)azetidine-1-carboxylate (0.20 g, 0.39 mmol) in methylene chloride (5 mL) was added 4.0 M hydrogen chloride in 1,4-dioxane (0.60 mL, 2.4 mmol). The resulting mixture was stirred at room temp for 3.5 h. The solvents were evaporated and the residue dried in vacuo to give 0.23 g of the product as the HCl salt. LCMS calculated for $C_{20}H_{22}F_2N_7O$ (M+H)$^+$: m/z=414.2. Found: 414.1.

Step 3. 5-{1-[4-Amino-3-(difluoromethyl)-1H-pyrazolo[3,4-d]pyrimidin-1-yl]ethyl}-4-methoxy-2-methyl-3-[1-(2,2,2-trifluoroethyl)azetidin-3-yl]benzonitrile To a mixture of 5-{1-[4-amino-3-(difluoromethyl)-1H-pyrazolo[3,4-d]pyrimidin-1-yl]ethyl}-3-azetidin-3-yl-4-methoxy-2-methylbenzonitrile dihydrochloride (20 mg, 0.04 mmol) and triethylamine (20 µL, 0.14 mmol) in methylene chloride (0.3 mL) was added 2,2,2-trifluoroethyl trifluoromethanesulfonate (11 mg, 0.049 mmol). The resulting mixture was stirred at 40° C. for 3 h. The solvents were evaporated and the crude material purified using RP-HPLC (XBridge C18 column, eluting with a gradient of acetonitrile/water containing 0.1% ammonium hydroxide, at flow rate of 30 mL/min) to give 3.4 mg (20%) of the desired product. The product was isolated as a racemic mixture. LCMS calculated for $C_{22}H_{23}F_5N_7O$ (M+H)$^+$: m/z=496.2. Found: 496.1.

Example 130

5-{1-[4-Amino-3-(difluoromethyl)-1H-pyrazolo[3,4-d]pyrimidin-1-yl]ethyl}-3-[1-(2-hydroxyethyl)azetidin-3-yl]-4-methoxy-2-methylbenzonitrile

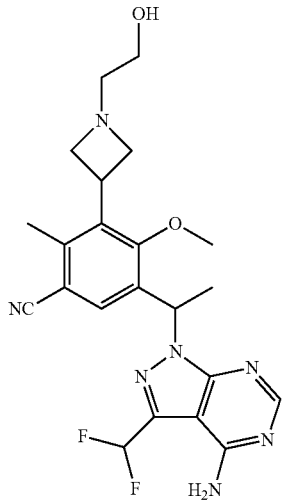 [SMILES: COc1c(C(C)n2nc(C(F)F)c3c(N)ncnc32)cc(C#N)c(C)c1C1CN(CCO)C1]

To a mixture of 5-{1-[4-amino-3-(difluoromethyl)-1H-pyrazolo[3,4-d]pyrimidin-1-yl]ethyl}-3-azetidin-3-yl-4-methoxy-2-methylbenzonitrile dihydrochloride (20 mg, 0.04 mmol, Example 129, Step 2), {[tert-butyl(dimethyl)silyl]oxy}acetaldehyde (9.1 µL, 0.048 mmol), and triethylamine (19 µL, 0.14 mmol) in methylene chloride (0.3 mL) was added sodium triacetoxyborohydride resin (38 mg, 0.087 mmol). The resulting mixture was stirred at room temperature for 3 h. The mixture was filtered and concentrated. The crude product was dissolved in tetrahydrofuran (1.0 mL) and 1.0 M tetra-n-butylammonium fluoride in THF (0.44 mL, 0.44 mmol) was added and stirred at room temperature. After 1.5 h, the solvents were evaporated. The crude residue was purified using RP-HPLC (XBridge C18 column, eluting with a gradient of acetonitrile/water containing 0.1% ammonium hydroxide, at flow rate of 30 mL/min) to give 4.1 mg (20%) of the desired product. The product was isolated as a racemic mixture. LCMS calculated for $C_{22}H_{26}F_2N_7O_2$ (M+H)$^+$: m/z=458.2. Found: 458.2.

Example 131

5-{1-[4-Amino-3-(difluoromethyl)-1H-pyrazolo[3,4-d]pyrimidin-1-yl]ethyl}-3-{1-[(2S)-2-hydroxypropyl]azetidin-3-yl}-4-methoxy-2-methylbenzonitrile

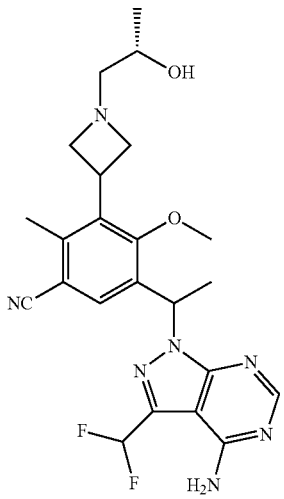 [SMILES: COc1c(C(C)n2nc(C(F)F)c3c(N)ncnc32)cc(C#N)c(C)c1C1CN(C[C@H](C)O)C1]

To a mixture of 5-{1-[4-amino-3-(difluoromethyl)-1H-pyrazolo[3,4-d]pyrimidin-1-yl]ethyl}-3-azetidin-3-yl-4-methoxy-2-methylbenzonitrile dihydrochloride (20 mg, 0.04 mmol, racemic intermediate from Example 129, Step 2) and triethylamine (18 μL, 0.13 mmol) in isopropyl alcohol (0.1 mL) was added (S)-(−)-methyloxirane (9.1 μL, 0.13 mmol). The resulting mixture was stirred at 90° C. for 5 h. The crude mixture was purified using RP-HPLC (XBridge C18 column, eluting with a gradient of acetonitrile/water containing 0.1% ammonium hydroxide, at flow rate of 30 mL/min) to 2.5 mg (10%) of give the desired product. The product was isolated as a mixture of diastereomers. LCMS calculated for $C_{23}H_{28}F_2N_7O_2$ (M+H)$^+$: m/z=472.2. Found: 472.2.

Example 133

5-{1-[4-Amino-3-(difluoromethyl)-1H-pyrazolo[3,4-d]pyrimidin-1-yl]ethyl}-3-[1-(2-hydroxy-2-methylpropyl)azetidin-3-yl]-4-methoxy-2-methylbenzonitrile

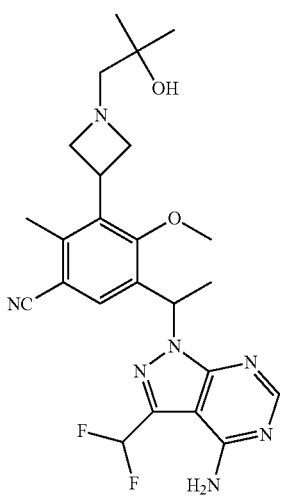 [SMILES: COc1c(C(C)n2nc(C(F)F)c3c(N)ncnc32)cc(C#N)c(C)c1C1CN(CC(C)(C)O)C1]

A mixture of 5-{1-[4-amino-3-(difluoromethyl)-1H-pyrazolo[3,4-d]pyrimidin-1-yl]ethyl}-3-azetidin-3-yl-4-methoxy-2-methylbenzonitrile dihydrochloride (21 mg, 0.043 mmol, racemic intermediate from Example 129, Step 2), oxirane, 2,2-dimethyl-(11 μL, 0.13 mmol), N,N-diisopropylethylamine (19 μL, 0.11 mmol) and ethanol (0.5 mL) was heated in a microwave at 120° C. for 30 min. The crude mixture was diluted with acetonitrile and purified using RP-HPLC (XBridge C18 column, eluting with a gradient of acetonitrile/water containing 0.1% ammonium hydroxide, at flow rate of 30 mL/min) to give 6.1 mg (29%) of the desired product. The product was isolated as a racemic mixture. LCMS calculated for $C_{24}H_{30}F_2N_7O_2$ (M+H)$^+$: m/z=486.2. Found: 486.2.

Example 134

(2S)-2-[3-(3-{1-[4-Amino-3-(difluoromethyl)-1H-pyrazolo[3,4-d]pyrimidin-1-yl]ethyl}-5-cyano-2-methoxy-6-methylphenyl)azetidin-1-yl]-N-methylpropanamide

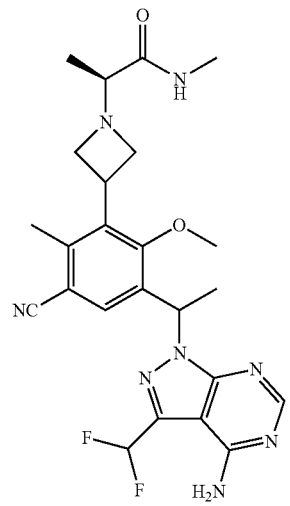 [SMILES: CNC(=O)[C@H](C)N1CC(c2c(C)c(C#N)cc(C(C)n3nc(C(F)F)c4c(N)ncnc43)c2OC)C1]

Step 1. (2S)-2-[3-(3-{1-[4-Amino-3-(difluoromethyl)-1H-pyrazolo[3,4-d]pyrimidin-1-yl]ethyl}-5-cyano-2-methoxy-6-methylphenyl)azetidin-1-yl]propanoic acid To a mixture of 5-{1-[4-amino-3-(difluoromethyl)-1H-pyrazolo[3,4-d]pyrimidin-1-yl]ethyl}-3-azetidin-3-yl-4-methoxy-2-methylbenzonitrile dihydrochloride (30 mg, 0.06 mmol, racemic intermediate from Example 129, step 2) and methyl (2S)-2-chloropropanoate (7.9 μL, 0.074 mmol) in N,N-dimethylformamide (0.35 mL) was added potassium carbonate (26 mg, 0.19 mmol). The resulting mixture was stirred at 60° C. overnight. After cooling, water was added and extracted with EtOAc (3×). The combined extracts were dried (MgSO$_4$), filtered, and concentrated. To the crude residue was added methanol (0.3 mL), water (40 μL, 2 mmol), and lithium hydroxide monohydrate (13 mg, 0.31 mmol). The resulting mixture was stirred at room temperature for 2.5 h. The mixture was concentrated and used as is for the next reaction. LCMS calculated for $C_{23}H_{26}F_2N_7O_3$ (M+H)$^+$: m/z=486.2. Found: 486.2.

Step 2. (2S)-2-[3-(3-{1-[4-Amino-3-(difluoromethyl)-1H-pyrazolo[3,4-d]pyrimidin-1-yl]ethyl}-5-cyano-2-methoxy-6-methylphenyl)azetidin-1-yl]-N-methylpropanamide To a mixture of (2S)-2-[3-(3-{1-[4-amino-3-(difluoromethyl)-1H-pyrazolo[3,4-d]pyrimidin-1-yl]ethyl}-5-cyano-2- methoxy-6-methylphenyl)azetidin-1-yl]propanoic acid (30 mg, 0.06 mmol), methylammonium chloride (6.6 mg, 0.098 mmol) and triethylamine (18 µL, 0.13 mmol) in N,N-dimethylformamide (0.3 mL) was added benzotriazol-1-yloxytris(dimethylamino)phosphonium hexafluorophosphate (43 mg, 0.098 mmol). The resulting mixture was stirred for 3 h at room temperature. The mixture was diluted with acetonitrile, filtered, and purified using RP-HPLC (XBridge C18 column, eluting with a gradient of acetonitrile/water containing 0.1% ammonium hydroxide, at flow rate of 30 mL/min) to give 4.7 mg (10%, 3 steps) of the desired product. The product was isolated as mixture of diastereomers. LCMS calculated for $C_{24}H_{29}F_2N_8O_2$ (M+H)$^+$: m/z=499.2. Found: 499.1.

Example 136

5-{1-[4-Amino-3-(difluoromethyl)-1H-pyrazolo[3,4-d]pyrimidin-1-yl]ethyl}-3-[1-(2,2-difluoroethyl)azetidin-3-yl]-4-methoxy-2-methylbenzonitrile

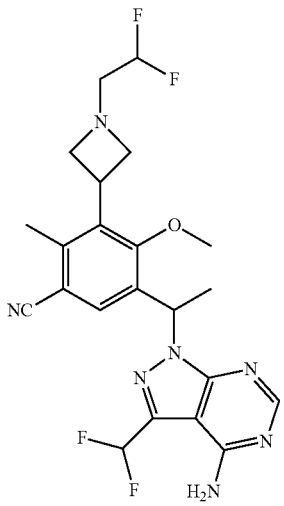 [SMILES: COc1c(C(C)n2nc(C(F)F)c3c(N)ncnc32)cc(C#N)c(C)c1C1CN(CC(F)F)C1]

A mixture of 5-{1-[4-amino-3-(difluoromethyl)-1H-pyrazolo[3,4-d]pyrimidin-1-yl]ethyl}-3-azetidin-3-yl-4-methoxy-2-methylbenzonitrile dihydrochloride (21 mg, 0.043 mmol, racemic intermediate from Example 129, Step 2), 2-bromo-1,1-difluoroethane (3.8 µL, 0.048 mmol), and triethylamine (18 µL, 0.13 mmol) in N,N-dimethylformamide (0.3 mL) was stirred overnight at 70° C. The mixture was diluted with methanol (MeOH) and purified using RP-HPLC (XBridge C18 column, eluting with a gradient of acetonitrile/water containing 0.1% ammonium hydroxide, at flow rate of 30 mL/min) to give 3.3 mg (16%) of the desired product. The product was isolated as a racemic mixture. LCMS calculated for $C_{22}H_{24}F_4N_7O$ (M+H)$^+$: m/z=478.2. Found: 478.1.

Example 137

5-{1-[4-Amino-3-(difluoromethyl)-1H-pyrazolo[3,4-d]pyrimidin-1-yl]ethyl}-3-{1-[(2S)-2-hydroxypropyl]azetidin-3-yl}-4-methoxy-2-methylbenzonitrile

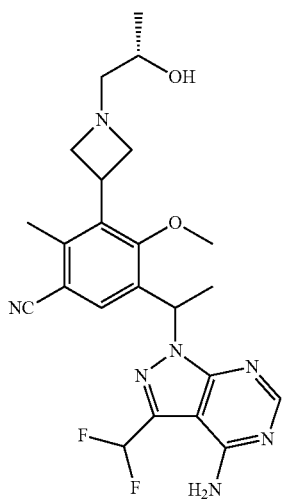 [SMILES: COc1c(C(C)n2nc(C(F)F)c3c(N)ncnc32)cc(C#N)c(C)c1C1CN(C[C@H](C)O)C1]

Step 1. tert-Butyl 3-(3-{1-[4-amino-3-(difluoromethyl)-1H-pyrazolo[3,4-d]pyrimidin-1-yl]ethyl}-5-cyano-2-methoxy-6-methylphenyl)azetidine-1-carboxylate This compound was prepared using procedures analogous to Example 129, step 1, with the exception that the product was purified using a Phenomenex Lux-Cellulose 1 column (21.1×250 mm, 5 micron particle size), eluting with 10% ethanol in hexanes at a flow rate of 18 mL/min, 5 mg/injection, to provide two enantiomers. For Peak 1: retention time: 1.12 min; LCMS calculated for $C_{25}H_{30}F_2N_7O_3$ (M+H)$^+$: m/z=514.2. Found: 514.1. Peak 2 retention time was 2.58 min.

Step 2. 5-{1-[4-Amino-3-(difluoromethyl)-1H-pyrazolo[3,4-d]pyrimidin-1-yl]ethyl}-3-azetidin-3-yl-4-methoxy-2-methylbenzonitrile dihydrochloride This compound was prepared using procedures analogous to Example 128, step 2, with tert-butyl 3-(3-{1-[4-amino-3-(difluoromethyl)-1H-pyrazolo[3,4-d]pyrimidin-1-yl]ethyl}-5-cyano-2-methoxy-6-methylphenyl)azetidine-1-carboxylate (peak 1 from step 1) instead of tert-butyl 3-(3-{1-[4-amino-3-(difluoromethyl)-1H-pyrazolo[3,4-d]pyrimidin-1-yl]ethyl}-5-cyano-2-methoxy-6-methylphenyl)azetidine-1-carboxylate. LCMS calculated for $C_{20}H_{22}F_2N_7O$ (M+H)$^+$: m/z=414.2. Found: 414.1.

Step 3. 5-{1-[4-Amino-3-(difluoromethyl)-1H-pyrazolo[3,4-d]pyrimidin-1-yl]ethyl}-3-{1-[(2S)-2-hydroxypropyl]azetidin-3-yl}-4-methoxy-2-methylbenzonitrile To a mixture of 5-{1-[4-amino-3-(difluoromethyl)-1H-pyrazolo[3,4-d]pyrimidin-1-yl]ethyl}-3-azetidin-3-yl-4- methoxy-2-methylbenzonitrile dihydrochloride (25 mg, 0.051 mmol), (2S)-2-{[tert-butyl(diphenyl)silyl]oxy}propanal (18 mg, 0.057 mmol) and triethylamine (22 µL, 0.15 mmol) in methylene chloride (0.3 mL) was added sodium triacetoxyborohydride resin (45 mg, 0.10 mmol). The mixture was stirred overnight then filtered and concentrated. To the residue was added tetrahydrofuran (1.0 mL) and 1.0 M tetra-n-butylammonium fluoride in THF (0.51 mL, 0.51 mmol). The resulting mixture was stirred overnight at room temp. The solvent was evaporated and the crude material was purified using RP-HPLC (XBridge C18 column, eluting with a gradient of acetonitrile/water containing 0.1% ammonium hydroxide, at flow rate of 30 mL/min) to give 1.6 mg (6.6%) of the desired product. The product was isolated as a single diastereomer. LCMS calculated for $C_{23}H_{28}F_2N_7O_2$ (M+H)$^+$: m/z=472.2. Found: 472.2.

Example 138

3-(1-Acetylazetidin-3-yl)-5-{1-[4-amino-3-(difluoromethyl)-1H-pyrazolo[3,4-d]pyrimidin-1-yl]ethyl}-4-methoxy-2-methylbenzonitrile

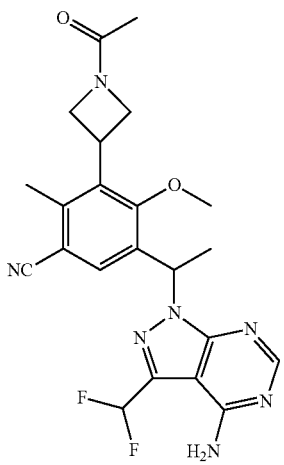 [SMILES: COc1c(C(C)n2nc(C(F)F)c3c(N)ncnc32)cc(C#N)c(C)c1C1CN(C(C)=O)C1]

A mixture of 5-{1-[4-amino-3-(difluoromethyl)-1H-pyrazolo[3,4-d]pyrimidin-1-yl]ethyl}-3-azetidin-3-yl-4-methoxy-2-methylbenzonitrile dihydrochloride (21 mg, 0.043 mmol, racemic intermediate from Example 129, Step 2), acetyl chloride (3.4 µL, 0.048 mmol), and triethylamine (18 µL, 0.13 mmol) in methylene chloride (0.3 mL) was stirred overnight at room temperature. The solvents were evaporated and the crude material was purified using RP-HPLC (XBridge C18 column, eluting with a gradient of acetonitrile/water containing 0.1% ammonium hydroxide, at flow rate of 30 mL/min) to give the desired product. The product was isolated as a racemic mixture. LCMS calculated for $C_{22}H_{24}F_2N_7O_2$ (M+H)$^+$: m/z=456.2. Found: 456.2.

Example 139

Enantiomers of 1-{1-[5-Chloro-2-ethoxy-4-fluoro-3-(1-isopropylazetidin-3-yl)phenyl]ethyl}-3-methyl-1H-pyrazolo[3,4-d]pyrimidin-4-amine

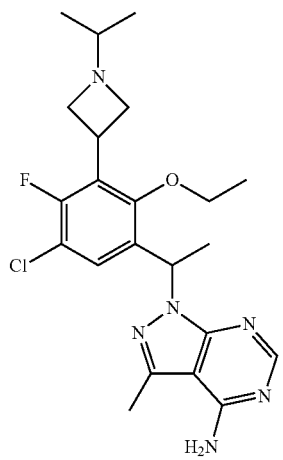 [SMILES: CCOc1c(C(C)n2nc(C)c3c(N)ncnc32)cc(Cl)c(F)c1C1CN(C(C)C)C1]

Step 1. 1-(5-Chloro-2-ethoxy-4-fluoro-3-iodophenyl)ethanone

This compound was prepared according to the procedure of Example 13 Step 3, using 1-(5-chloro-4-fluoro-2-hydroxy-3-iodophenyl)ethanone and iodoethane as the starting materials. LCMS calculated for $C_{10}H_{10}ClFIO_2$ (M+H)$^+$: m/z=342.9. Found: 342.9.

Step 2. tert-Butyl 3-(3-acetyl-5-chloro-2-ethoxy-6-fluorophenyl)azetidine-1-carboxylate A round-bottom flask equipped with a magnetic stir bar and a rubber septum was charged with lithium chloride (3.9 g, 91 mmol). The flask was heated at 140° C. for 10 min under high vacuum and backfilled with nitrogen after cooling to room temperature. Zinc (6.0 g, 91 mmol) was added and the flask was heated at 140° C. for 10 min under high vacuum and backfilled with nitrogen after cooling to room temperature. Tetrahydrofuran (THF) (38 mL) and 1,2-dibromoethane (233 µL, 2.70 mmol) were added via syringe. The mixture was heated at 60° C. for 10 min and then cooled to room temperature. Chlorotrimethylsilane (68 µL, 0.54 mmol) and iodine (69 mg, 0.27 mmol) in THF (1 mL) were added and the resulting mixture was stirred at 60° C. for 10 min then cooled to room temperature. A solution of tert-butyl 3-iodoazetidine-1-carboxylate (12.17 g, 42.99 mmol) in THF (10 mL) was then added and the mixture stirred at 40° C. for 1 h and at room temperature for 1 h. Another flask charged with 1-(5-chloro-2-ethoxy-4-fluoro-3-iodophenyl)ethanone (13.0 g, 38.0 mmol), palladium acetate (170 mg, 0.76 mmol), 2'-(dicyclohexylphosphino)-N,N,N',N'-tetramethylbiphenyl-2,6-diamine (660 mg, 1.5 mmol), and toluene (35 mL) was evacuated under high vacuum and backfilled with nitrogen. The mixture was cooled to 0° C. and the zinc reagent made above was added slowly via syringe. After addition, the reaction was heated to 50° C. overnight. The reaction solution was partitioned between EtOAc and sat. NH$_4$Cl solution. The layers were separated and the aqueous extracted further with EtOAc (2×). The combined organics were washed with water, brine, then dried over MgSO4, and concentrated. The crude mixture was purified on silica gel column to give the desired product as an orange oil (6.3 g, 45%). LCMS calculated for $C_{18}H_{23}ClFNO_4Na$ (M+Na)$^+$: m/z=394.1. Found: 394.1.

Step 3. tert-Butyl 3-[3-chloro-6-ethoxy-2-fluoro-5-(1-hydroxyethyl)phenyl]azetidine-1-carboxylate This compound was prepared according to the procedure of Example 13 Step 5, using tert-butyl 3-(3-acetyl-5-chloro-2-ethoxy-6-fluorophenyl)azetidine-1-carboxylate and sodium tetrahydroborate as the starting materials. LCMS calculated for $C_{18}H_{25}ClFNO_4Na$ (M+Na)$^+$: m/z=396.1. Found: 396.1.

Step 4. tert-Butyl 3-[3-chloro-5-(1-chloroethyl)-6-ethoxy-2-fluorophenyl]azetidine-1-carboxylate This compound was prepared according to the procedure of Example 13 step 6, using tert-butyl 3-[3-chloro-6-ethoxy-2-fluoro-5-(1-hydroxyethyl)phenyl]azetidine-1-carboxylate (racemic) and cyanuric chloride as the starting materials.

Step 5. tert-Butyl 3-{3-[1-(4-amino-3-methyl-1H-pyrazolo[3,4-d]pyrimidin-1-yl)ethyl]-5-chloro-2-ethoxy-6-fluorophenyl}azetidine-1-carboxylate To a mixture of 3-methyl-1H-pyrazolo[3,4-d]pyrimidin-4-amine (1.10 g, 7.37 mmol), cesium carbonate (3.2 g, 10 mmol) and potassium iodide (111 mg, 0.670 mmol) in DMF (20 mL) was added tert-butyl 3-[3-chloro-5-(1-chloroethyl)-6-ethoxy-2-fluorophenyl]azetidine-1-carboxylate (2.63 g, 6.70 mmol) and the mixture was stirred at 90° C. for 3 h. The solvent was removed in vacuo. The residue was diluted with ethyl acetate and water. Aqueous layer was extracted with ethyl acetate twice. The combined organic layers were washed with water, brine, dried over $Na_2SO_4$, filtered and concentrated. The residue was purified on silica gel column (eluting with 100% ethyl acetate) to give the desired product as a foam (2.15 g, 63%). LCMS calculated for $C_{24}H_{31}ClFN_6O_3$ (M+H)$^+$: m/z=505.2. Found: 505.2.

Step 6. 1-[1-(3-Azetidin-3-yl-5-chloro-2-ethoxy-4-fluorophenyl)ethyl]-3-methyl-1H-pyrazolo[3,4-d]pyrimidin-4-amine dihydrochloride To a solution of tert-butyl 3-{3-[1-(4-amino-3-methyl-1H-pyrazolo[3,4-d]pyrimidin-1-yl)ethyl]-5-chloro-2-ethoxy-6-fluorophenyl}azetidine-1-carboxylate (275 mg, 0.544 mmol) in dichloromethane (2.4 mL) was added 4.0 M hydrogen chloride in dioxane (1.1 mL, 4.4 mmol). The reaction solution was stirred at room temperature for 6 h. The solvent was removed under reduced pressure to give the desired product as a white solid (250 mg, 96%). LCMS calculated for $C_{19}H_{23}ClFN_6O$ (M+H)$^+$: m/z=405.2. Found: 405.1.

Step 7. 1-{1-[5-Chloro-2-ethoxy-4-fluoro-3-(1-isopropylazetidin-3-yl)phenyl]ethyl}-3-methyl-1H-pyrazolo[3,4-d]pyrimidin-4-amine To a mixture of 1-[1-(3-azetidin-3-yl-5-chloro-2-ethoxy-4-fluorophenyl)ethyl]-3-methyl-1H-pyrazolo[3,4-d]pyrimidin-4-amine dihydrochloride (49 mg, 0.10 mmol), acetone (8.28 µL, 0.113 mmol), and triethylamine (44.3 µL, 0.318 mmol) in dichloromethane (0.67 mL) was added sodium triacetoxyborohydride resin (89 mg, 0.20 mmol). The resulting mixture was stirred overnight at room temperature. The mixture was filtered and concentrated and then purified by preparative LCMS (XBridge C18 column, eluting with a gradient of acetonitrile/water containing 0.05% TFA, at flow rate of 60 mL/min) to give the racemic product. LCMS: found m/z=447.2 (M+H)$^+$. The racemic mixture was separated by chiral HPLC (column IA, eluting with 5% ethanol/95% hexanes, at flow rate 18 mL/min) to give two peaks (isomer 1: 9.5 mg, 21%; isomer 2: 9.2 mg, 20%).

Isomer 1 (first to elute, retention time: 4.4 min)$^1$H NMR (400 MHz, DMSO-d$_6$): δ 8.10 (s, 1H), 7.45 (d, 1H), 6.21 (m, 1H), 3.70 (m, 5H), 2.91 (m, 2H), 2.53 (s, 3H), 2.17 (m, 1H), 1.66 (d, 3H), 1.31 (t, 3H), 0.81 (m, 6H) ppm; LCMS calculated for $C_{22}H_{29}ClFN_6O$ (M+H)$^+$: m/z=447.2. Found: 447.2. Isomer 2 (second to elute, retention time: 19.5 min): LCMS calculated for $C_{22}H_{29}ClFN_6O$ (M+H)$^+$: m/z=447.2. Found: 447.2.

Example 140

1-(3-{1-[1-(4-Amino-3-methyl-1H-pyrazolo[3,4-d]pyrimidin-1-yl)ethyl]-5-chloro-2-ethoxy-6-fluorophenyl}azetidin-1-yl)-2-methylpropan-2-ol

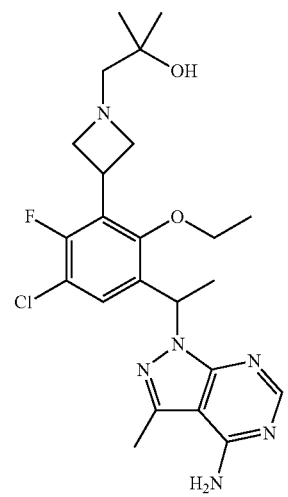 [SMILES: CCOc1c(C(C)n2nc(C)c3c(N)ncnc32)cc(Cl)c(F)c1C1CN(CC(C)(C)O)C1]

To a mixture of 1-[1-(3-azetidin-3-yl-5-chloro-2-ethoxy-4-fluorophenyl)ethyl]-3-methyl-1H-pyrazolo[3,4-d]pyrimidin-4-amine dihydrochloride (20 mg, 0.042 mmol, racemic intermediate from Example 139, Step 6) and triethylamine (18 µL, 0.12 mmol) in ethanol (1 mL) was added oxirane, 2,2-dimethyl-(6.98 µL, 0.0837 mmol). The resulting mixture was heated at 120° C. in microwave reactor for 45 min. The reaction was diluted with methanol and purified on RP-HPLC (XBridge C18 column, eluting with a gradient of acetonitrile/water containing 0.1% ammonium hydroxide, at flow rate of 30 mL/min) to give the desired product as white a solid (3.4 mg, 17%). The product was isolated as a racemic mixture. LCMS calculated for $C_{23}H_{31}ClFN_6O_2$ (M+H)$^+$: m/z=477.2. Found: 477.3.

Example 141

1-(1-{5-Chloro-2-ethoxy-4-fluoro-3-[1-(2,2,2-trifluoroethyl)azetidin-3-yl]phenyl}ethyl)-3-methyl-1H-pyrazolo[3,4-d]pyrimidin-4-amine

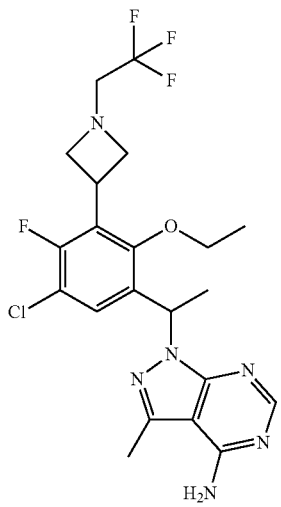 [SMILES: CCOc1c(C(C)n2nc(C)c3c(N)ncnc32)cc(Cl)c(F)c1C1CN(CC(F)(F)F)C1]

To a mixture of 1-[1-(3-azetidin-3-yl-5-chloro-2-ethoxy-4-fluorophenyl)ethyl]-3-methyl-1H-pyrazolo[3,4-d]pyrimidin-4-amine dihydrochloride (19 mg, 0.040 mmol, racemic intermediate from Example 139, Step 6) and triethylamine (20 µL, 0.14 mmol) in dichloromethane (0.5 mL) was added 2,2,2-trifluoroethyl trifluoromethanesulfonate (11 mg, 0.048 mmol). The resulting mixture was stirred overnight at room temperature. The solvents were evaporated under reduced pressure and the crude mixture purified on RP-HPLC (XBridge C18 column, eluting with a gradient of acetonitrile/water containing 0.1% ammonium hydroxide, at flow rate of 30 mL/min) to give the desired product (3.8 mg, 19%). The product was isolated as a racemic mixture. LCMS calculated for $C_{21}H_{24}ClF_4N_6O$ (M+H)$^+$: m/z=487.2. Found: 487.1.

Example 149

(2S)-1-(3-{3-[1-(4-Amino-3-methyl-1H-pyrazolo[3,4-d]pyrimidin-1-yl)ethyl]-5-chloro-2-ethoxy-6-fluorophenyl}azetidin-1-yl)propan-2-ol

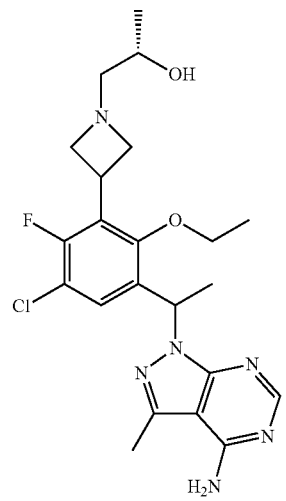 [SMILES: CCOc1c(C(C)n2nc(C)c3c(N)ncnc32)cc(Cl)c(F)c1C1CN(C[C@H](C)O)C1]

Step 1. Enantiomers of tert-Butyl 3-{3-[1-(4-amino-3-methyl-1H-pyrazolo[3,4-d]pyrimidin-1-yl)ethyl]-5-chloro-2-ethoxy-6-fluorophenyl}azetidine-1-carboxylate The racemic mixture was separated by chiral HPLC (column IA, eluting with 5% ethanol/95% hexanes, flow rate 18 mL/min) to give two peaks; Isomer 1 (first to elute): Retention time: 16.8 min; LCMS calculated for $C_{24}H_{31}ClFN_6O_3$ (M+H)$^+$: m/z=505.2. Found: 505.2; Isomer 2 (second to elute): Retention time: 19.5 min; LCMS calculated for $C_{24}H_{31}ClFN_6O_3$ (M+H)$^+$: m/z=505.2. Found: 505.2.

Step 2 1-[1-(3-Azetidin-3-yl-5-chloro-2-ethoxy-4-fluorophenyl)ethyl]-3-methyl-1H-pyrazolo[3,4-d]pyrimidin-4-amine dihydrochloride This compound was prepared using procedures analogous to those for Example 139 step 6 with tert-butyl 3-{3-[(1S)-1-(4-amino-3-methyl-1H-pyrazolo[3,4-d]pyrimidin-1-yl)ethyl]-5-chloro-2-ethoxy-6-fluorophenyl}azetidine-1-carboxylate (first peak from chiral separation) as starting material. LCMS calculated for $C_{19}H_{23}ClFN_6O$ (M+H)$^+$: m/z=405.2. Found: 405.1.

Step 3. (2S)-1-(3-{3-[1-(4-Amino-3-methyl-1H-pyrazolo[3,4-d]pyrimidin-1-yl)ethyl]-5-chloro-2-ethoxy-6-fluorophenyl}azetidin-1-yl)propan-2-ol To a mixture of 1-[1-(3-azetidin-3-yl-5-chloro-2-ethoxy-4-fluorophenyl)ethyl]-3-methyl-1H-pyrazolo[3,4-d]pyrimidin-4-amine dihydrochloride (46 mg, 0.11 mmol) (from isomer 1) and triethylamine (50 µL, 0.4 mmol) in isopropyl alcohol (0.3 mL) was added (S)-(−)-methyloxirane (16 µL, 0.23 mmol). The resulting mixture was stirred at 90° C. for 3 h. After cooling, the mixture was diluted with acetonitrile and purified by RP-HPLC (XBridge C18 column, eluting with a gradient of acetonitrile/water containing 0.1% ammonium hydroxide, at flow rate of 30 mL/min) to give the desired product (12 mg, 23%). The product was isolated as a single diastereomer. ¹H NMR (400 MHz, DMSO-d₆): δ 8.05 (s, 1H), 7.38 (d, 1H), 6.15 (m, 1H), 4.26 (d, 1H), 3.76-3.60 (m, 6H), 2.99 (m, 2H), 2.48 (s, 3H), 2.22 (m, 2H), 1.62 (d, 3H), 1.25 (t, 3H), 0.93 (d, 3H) ppm; LCMS calculated for $C_{22}H_{29}ClFN_6O_2$ (M+H)⁺: m/z=463.2. Found: 463.2.

Example 150

1-{1-[5-Chloro-2-ethoxy-4-fluoro-3-(1-isopropylazetidin-3-yl)phenyl]ethyl}-3-(difluoromethyl)-1H-pyrazolo[3,4-d]pyrimidin-4-amine

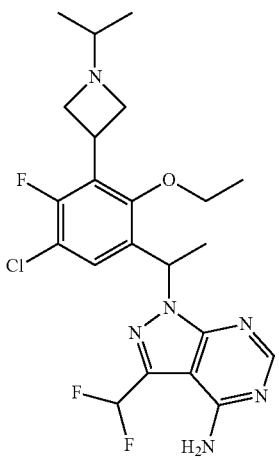 [SMILES: CCOc1c(C(C)n2nc(C(F)F)c3c(N)ncnc32)cc(Cl)c(F)c1C1CN(C(C)C)C1]

Step 1: tert-Butyl 3-{3-[1-(4-amino-3-iodo-1H-pyrazolo[3,4-d]pyrimidin-1-yl)ethyl]-5-chloro-2-ethoxy-6-fluorophenyl}azetidine-1-carboxylate This compound was prepared using procedures analogous to those for Example 139 step 5, with racemic tert-butyl 3-[3-chloro-5-(1-chloroethyl)-6-ethoxy-2-fluorophenyl]azetidine-1-carboxylate from Example 139 Step 4 and 3-iodo-1H-pyrazolo[3,4-d]pyrimidin-4-amine as starting materials. LCMS calculated for $C_{23}H_{28}ClFIN_6O_3$ (M+H)⁺: m/z=617.1. Found: 617.1.

Step 2 tert-Butyl 3-{3-[1-(4-amino-3-vinyl-1H-pyrazolo[3,4-d]pyrimidin-1-yl)ethyl]-5-chloro-2-ethoxy-6-fluorophenyl}azetidine-1-carboxylate A mixture of tert-butyl 3-{3-[1-(4-amino-3-iodo-1H-pyrazolo[3,4-d]pyrimidin-1-yl)ethyl]-5-chloro-2-ethoxy-6-fluorophenyl}azetidine-1-carboxylate (1.32 g, 2.14 mmol), pyridine-trivinylboroxin (1:1) (0.51 g, 2.1 mmol), [1,1'-bis(diphenylphosphino)ferrocene]dichloropalladium(II), complex with dichloromethane (1:1) (90 mg, 0.1 mmol) and potassium carbonate (0.89 g, 6.4 mmol) in 1,4-dioxane (10 mL)/water (7 mL) was heated at 100° C. overnight. After cooled to room temperature, the reaction mixture was diluted with water and ethyl acetate. The aqueous layer was extracted with ethyl acetate. The combined extracts were washed with brine, dried over MgSO₄, concentrated and purified on a silica gel column to give the desired product (0.71 g, 64%). LCMS calculated for $C_{25}H_{31}ClFN_6O_3$ (M+H)⁺: m/z=517.2. Found: 517.2.

Step 3. tert-Butyl 3-(3-{1-[4-amino-3-(1,2-dihydroxyethyl)-1H-pyrazolo[3,4-d]pyrimidin-1-yl]ethyl}-5-chloro-2-ethoxy-6-fluorophenyl)azetidine-1-carboxylate To a suspension of tert-butyl 3-{3-[1-(4-amino-3-vinyl-1H-pyrazolo[3,4-d]pyrimidin-1-yl)ethyl]-5-chloro-2-ethoxy-6-fluorophenyl}azetidine-1-carboxylate (0.707 g, 1.37 mmol) in tert-butyl alcohol (8.6 mL) was added N-methylmorpholine N-oxide (176 mg, 1.50 mmol), water (4.3 mL), and osmium tetraoxide (20 mg, 0.080 mmol). The resulting mixture was stirred overnight at room temperature. Water was added to the reaction followed by EtOAc. The layers were separated and the aqueous extracted with EtOAc. The combined organics were washed with brine, dried over Na₂SO₄, filtered, and concentrated to give the crude product. LCMS calculated for $C_{25}H_{33}ClFN_6O_5$ (M+H)⁺: m/z=551.2. Found: 551.2.

Step 4. tert-Butyl 3-{3-[1-(4-amino-3-formyl-1H-pyrazolo[3,4-d]pyrimidin-1-yl)ethyl]-5-chloro-2-ethoxy-6-fluorophenyl}azetidine-1-carboxylate To a solution of tert-butyl 3-(3-{1-[4-amino-3-(1,2-dihydroxyethyl)-1H-pyrazolo[3,4-d]pyrimidin-1-yl]ethyl}-5-chloro-2-ethoxy-6-fluorophenyl)azetidine-1-carboxylate (0.754 g, 1.37 mmol) in THF (10 mL) and water (6 mL) was added acetic acid (20 µL, 0.36 mmol) and sodium periodate (0.878 g, 4.10 mmol) at 0° C. After stirring overnight, water was added to the reaction and extracted with dichloromethane (3×). The combined extracts were washed with brine, dried over Na₂SO₄, filtered, and concentrated to yield the crude product. LCMS calculated for $C_{24}H_{29}ClFN_6O_4$ (M+H)⁺: m/z=519.2. Found: 519.2.

Step 5. tert-Butyl 3-(3-{1-[4-amino-3-(difluoromethyl)-1H-pyrazolo[3,4-d]pyrimidin-1-yl]ethyl}-5-chloro-2-ethoxy-6-fluorophenyl)azetidine-1-carboxylate To a solution of tert-butyl 3-{3-[1-(4-amino-3-formyl-1H-pyrazolo[3,4-d]pyrimidin-1-yl)ethyl]-5-chloro-2-ethoxy-6-fluorophenyl}azetidine-1-carboxylate (0.61 g, 1.2 mmol) in dichloromethane (7 mL) at 0° C. was added diethylaminosulfur trifluoride (0.39 mL, 2.9 mmol). The mixture was stirred at 0° C. for a few minutes then warmed to room temperature and stirred for 2.5 h. Water and dichloromethane were added and the layers separated. The organics were washed with brine, dried over MgSO₄, filtered and concentrated. The yellow gum was dried in vacuo to give the desired product (0.60 g, 94%). LCMS calculated for $C_{24}H_{29}ClF_3N_6O_3$ (M+H)⁺: m/z=541.2. Found: 541.2.

Step 6. 1-[1-(3-Azetidin-3-yl-5-chloro-2-ethoxy-4-fluorophenyl)ethyl]-3-(difluoromethyl)-1H-pyrazolo[3,4-d]pyrimidin-4-amine dihydrochloride To a solution of tert-butyl 3-(3-{1-[4-amino-3-(difluoromethyl)-1H-pyrazolo[3,4-d]pyrimidin-1-yl]ethyl}-5-chloro-2-ethoxy-6-fluorophenyl)azetidine-1-carboxylate (0.64 g, 1.2 mmol) in dichloromethane (5 mL) was added 4.0 M hydrogen chloride in dioxane (2.4 mL, 9.5 mmol). The reaction solution was stirred at room temperature for 6 h. The solvent was removed to give the desired product as a white solid (0.61 g, 100%). LCMS calculated for $C_{19}H_{21}ClF_3N_6O$ (M+H)⁺: m/z=441.1. Found: 441.1.

Step 7. 1-{1-[5-Chloro-2-ethoxy-4-fluoro-3-(1-isopropylazetidin-3-yl)phenyl]ethyl}-3-(difluoromethyl)-1H-pyrazolo[3,4-d]pyrimidin-4-amine This compound was prepared using procedures analogous to those for Example 1 step 8, with 1-[1-(3-azetidin-3-yl-5-chloro-2-ethoxy-4-fluorophenyl)ethyl]-3-(difluoromethyl)-1H-pyrazolo[3,4-d]pyrimidin-4-amine dihydrochloride and acetone as starting materials. The product was isolated as a racemic mixture. LCMS calculated for $C_{22}H_{27}ClF_3N_6O$ (M+H)⁺: m/z=483.2. Found: 483.2.

Example 152

2-[3-(3-{1-[4-Amino-3-(difluoromethyl)-1H-pyrazolo[3,4-d]pyrimidin-1-yl]ethyl}-5-chloro-2-ethoxy-6-fluorophenyl)azetidin-1-yl]ethanol

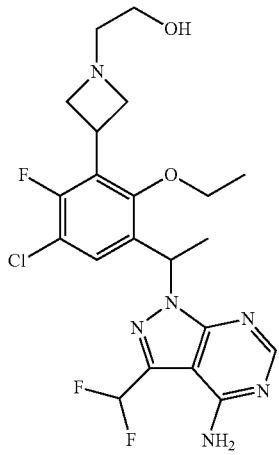 [SMILES: CCOc1c(C(C)n2nc(C(F)F)c3c(N)ncnc32)cc(Cl)c(F)c1C1CN(CCO)C1]

This compound was prepared using procedures analogous to those for Example 1 step 8, with 1-[1-(3-azetidin-3-yl-5-chloro-2-ethoxy-4-fluorophenyl)ethyl]-3-(difluoromethyl)-1H-pyrazolo[3,4-d]pyrimidin-4-amine dihydrochloride (racemic) and {[tert-butyl(dimethyl)silyl]oxy}acetaldehyde as starting materials. After reductive amination, tetrabutylammonium fluoride was added to remove the tert-butyl(dimethyl)silyl group. The product was isolated as a racemic mixture. LCMS calculated for $C_{21}H_{25}ClF_3N_6O_2$ (M+H)$^+$: m/z=485.2. Found: 485.2. $^1$H NMR (300 MHz, DMSO-d$_6$): δ 8.23 (s, 1H), 7.38 (m, 2H), 6.29 (m, 1H), 3.78-3.67 (m, 4H), 3.53 (m, 1H), 3.12 (m, 2H), 2.99-2.87 (m, 2H), 2.34 (m, 2H), 1.68 (d, 3H), 1.22 (m, 3H) ppm.

Example 156

(2R)-2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)propan-1-ol

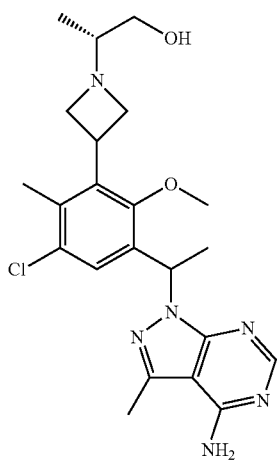 [SMILES: COc1c(C(C)n2nc(C)c3c(N)ncnc32)cc(Cl)c(C)c1C1CN([C@H](C)CO)C1]

Step 1. Methyl (2S)-2-bromopropanoate

DMF (28 μL, 0.36 mmol) was added to a mixture of (2S)-2-bromopropanoic acid (0.552 g, 3.61 mmol) and oxalyl chloride (0.61 mL, 7.2 mmol) in dichloromethane (4.6 mL) at 0° C. The reaction mixture was stirred at room temperature overnight. The solvent was removed in vacuo. The residue was dissolved in dichloromethane and treated with methanol (1.5 mL, 36 mmol) and pyridine (0.44 mL, 5.4 mmol). The reaction solution was stirred at room temperature for 2 h. The reaction solution was quenched with saturated sodium bicarbonate solution and washed with brine, dried over Na$_2$SO$_4$, filtered and concentrated to give the desired product (0.51 g, 85%).

Step 2. Methyl (2R)-2-(3-{3-[1-(4-amino-3-methyl-1H-pyrazolo[3,4-d]pyrimidin-1-yl)ethyl]-5-chloro-2-methoxy-6-methylphenyl}azetidin-1-yl)propanoate To a solution of 1-[1-(3-azetidin-3-yl-5-chloro-2-methoxy-4-methylphenyl)ethyl]-3-methyl-1H-pyrazolo[3,4-d]pyrimidin-4-amine hydrochloride (20.1 mg, 0.0475 mmol, chiral intermediate from Example 1, Step 7) in acetonitrile (1 mL) was added triethylamine (23 μL, 0.17 mmol) and methyl (2S)-2-bromopropanoate (9.5 mg, 0.057 mmol). The reaction solution was stirred at room temperature for 4 h. The solvent was removed to give the desired product (6.2 mg, 28%). LCMS calculated for $C_{23}H_{30}ClN_6O_3$ (M+H)$^+$: m/z=473.2. Found: 473.3.

Step 3. (2R)-2-(3-{3-[(1S)-1-(4-Amino-3-methyl-1H-pyrazolo[3,4-d]pyrimidin-1-yl)ethyl]-5-chloro-2-methoxy-6-methylphenyl}azetidin-1-yl)propan-1-ol A solution of methyl (2R)-2-(3-{3-[(1-(4-amino-3-methyl-1H-pyrazolo[3,4-d]pyrimidin-1-yl)ethyl]-5-chloro-2-methoxy-6-methylphenyl}azetidin-1-yl)propanoate (6.2 mg, 0.013 mmol) in dichloromethane (0.5 mL) was treated with 1.0 M diisobutylaluminum hydride in toluene (0.1 mL, 0.1 mmol) at 0° C. for 3 h. The reaction was quenched with methanol and purified with preparative RP-HPLC (XBridge C18 column, eluting with a gradient of acetonitrile/water containing 0.1% ammonium hydroxide, at flow rate of 30 mL/min) to give the desired product (0.8 mg, 14%). The product was isolated as a single diastereomer. LCMS calculated for $C_{22}H_{30}ClN_6O_2$ (M+H)$^+$: m/z=445.2. Found: 445.1.

Example 158

1-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-2-methylpropan-2-ol

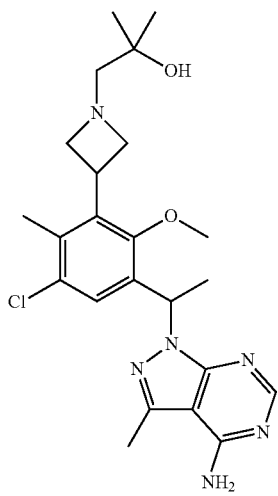 [SMILES: COc1c(C(C)n2nc(C)c3c(N)ncnc32)cc(Cl)c(C)c1C1CN(CC(C)(C)O)C1]

This compound was prepared using procedures analogous to t Example 140 with 1-[1-(3-azetidin-3-yl-5-chloro-2-methoxy-4-methylphenyl)ethyl]-3-methyl-1H-pyrazolo[3,4-d]pyrimidin-4-amine hydrochloride (chiral intermediate from Example 1, Step 7) and oxirane, 2,2-dimethyl- as starting materials. The product was isolated as single enatiomer. LCMS calculated for $C_{23}H_{32}ClN_6O_2$ $(M+H)^+$: m/z=459.2. Found: 459.1 $^1$H NMR (300 MHz, DMSO-d$_6$): δ 8.04 (s, 1H), 7.23 (bs, 2H), 7.16 (s, 1H), 6.14 (m, 1H), 3.96 (s, 1H), 3.85 (m, 3H), 3.45 (s, 3H), 2.94 (m, 1H), 2.80 (m, 1H), 2.49 (s, 3H), 2.14 (s, 2H), 2.00 (s, 3H), 1.63 (d, 3H), 0.98 (s, 6H) ppm.

Example 159

(2R)-2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-N,N-dimethylpropanamide

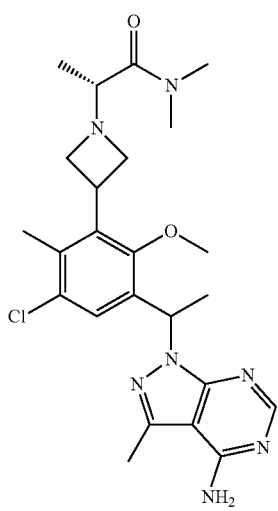 [SMILES: COc1c(C(C)n2nc(C)c3c(N)ncnc32)cc(Cl)c(C)c1C1CN([C@H](C)C(=O)N(C)C)C1]

Step 1. (2R)-2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)propanoic acid To a solution of methyl (2R)-2-(3-{3-[1-(4-amino-3-methyl-1H-pyrazolo[3,4-d]pyrimidin-1-yl)ethyl]-5-chloro-2-methoxy-6-methylphenyl}azetidin-1-yl)propanoate (chiral intermediate from example 156 step 2) (13 mg, 0.027 mmol) in acetonitrile (0.6 mL) and water (0.2 mL) was added lithium hydroxide (2.4 mg, 0.10 mmol). The reaction mixture was stirred at room temperature overnight. The reaction solution was diluted with ethyl acetate and 1 M HCl solution. The organic layer was separated and dried over Na$_2$SO$_4$, filtered and concentrated to give the desired product (10.2 mg, 83%). LCMS calculated for $C_{22}H_{28}ClN_6O_3$ $(M+H)^+$: m/z=459.2. Found: 459.1.

Step 2. (2R)-2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-N,N-dimethylpropanamide To a solution of (2R)-2-(3-{3-[1-(4-amino-3-methyl-1H-pyrazolo[3,4-d]pyrimidin-1-yl)ethyl]-5-chloro-2-methoxy-6-methylphenyl}azetidin-1-yl)propanoic acid (4 mg, 0.009 mmol) and benzotriazol-1-yloxytris(dimethylamino)phosphonium hexafluorophosphate (4 mg, 0.009 mmol) in DMF (0.3 mL) at room temperature was added triethylamine (4 µL, 0.03 mmol) and dimethylamine hydrochloride (0.9 mg, 0.01 mmol). The reaction mixture was stirred for 1 h, then diluted with methanol and purified by preparative RP-HPLC (XBridge C18 column, eluting with a gradient of acetonitrile/water containing 0.1% ammonium hydroxide, at flow rate of 30 mL/min) to give the desired product (2.7 mg, 63%). The product was isolated as a single diastereomer. LCMS calculated for $C_{24}H_{33}ClN_7O_2$ $(M+H)^+$: m/z=486.2. Found: 486.1. $^1$H NMR (300 MHz, DMSO-d$_6$): δ 8.09 (s, 1H), 7.23 (s, 1H), 6.18 (m, 1H), 3.78 (m, 3H), 3.50 (s, 3H), 3.01 (s, 3H), 3.0-2.9 (m, 3H), 2.77 (s, 3H), 2.54 (s, 3H), 2.06 (s, 3H), 1.67 (d, 3H), 0.98 (d, 3H) ppm.

Example 161

[1-(3-{3-[1-(4-Amino-3-methyl-1H-pyrazolo[3,4-d]pyrimidin-1-yl)ethyl]-5-chloro-2-methoxy-6-methylphenyl}azetidin-1-yl)cyclobutyl]acetonitrile

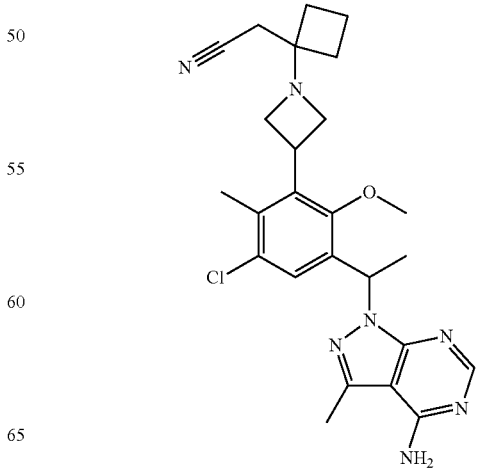

To a solution of 1-[(1-(3-azetidin-3-yl-5-chloro-2-methoxy-4-methylphenyl)ethyl]-3-methyl-1H-pyrazolo[3,4-d]pyrimidin-4-amine dihydrochloride (10 mg, 0.022 mmol, chiral intermediate from Example 1, Step 7) in acetonitrile (0.1 mL) was added cyclobutylideneacetonitrile (4.1 mg, 0.044 mmol), followed by 1,8-diazabicyclo[5.4.0]undec-7-ene (13 μL, 0.087 mmol). The resulting mixture was stirred at room temperature overnight. The reaction mixture was diluted with acetonitrile and purified by preparative RP-HPLC (XBridge C18 column, eluting with a gradient of acetonitrile/water containing 0.1% ammonium hydroxide, at flow rate of 30 mL/min) to give the desired product (4.3 mg, 41%). The product was isolated as a single enantiomer. LCMS calculated for $C_{25}H_{31}ClN_7O$ (M+H)$^+$: m/z=480.2. Found: 480.0.

Example 163

1-{1-[5-Chloro-2-methoxy-4-methyl-3-(1-methylpiperidin-4-yl)phenyl]ethyl}-3-methyl-1H-pyrazolo[3,4-d]pyrimidin-4-amine

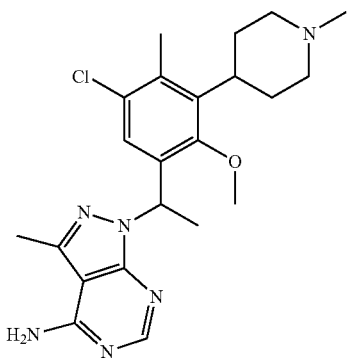

Step 1. tert-Butyl 4-(3-acetyl-5-chloro-2-methoxy-6-methylphenyl)piperidine-1-carboxylate This compound was prepared using procedures analogous to those for Example 139 step 2 with 1-(5-chloro-3-iodo-2-methoxy-4-methylphenyl)ethanone and tert-butyl 4-iodopiperidine-1-carboxylate as starting materials. LCMS calculated for $C_{20}H_{28}ClNO_4Na$ (M+Na)$^+$: m/z=404.1. Found: 404.1.

Step 2. tert-Butyl 4-[3-chloro-5-(1-hydroxyethyl)-6-methoxy-2-methylphenyl]piperidine-1-carboxylate This compound was prepared according to the procedure of Example 13 step 5, using of tert-butyl 4-(3-acetyl-5-chloro-2-methoxy-6-methylphenyl)piperidine-1-carboxylate and sodium tetrahydroborate as the starting materials. LCMS calculated for $C_{20}H_{30}ClNO_4Na$ (M+Na)$^+$: m/z=406.1. Found: 406.1.

Step 3. tert-Butyl 4-[3-chloro-5-(1-chloroethyl)-6-methoxy-2-methylphenyl]piperidine-1-carboxylate This compound was prepared according to the procedure of Example 13 step 6, using tert-butyl 4-[3-chloro-5-(1-hydroxyethyl)-6-methoxy-2-methylphenyl]piperidine-1-carboxylate (racemic) and cyanuric chloride as the starting materials. $^1$H NMR (400 MHz, CDCl$_3$): δ 7.44 (s, 1H), 5.46 (m, 1H), 4.23 (bs, 2H), 3.73 (s, 3H), 3.29 (bs, 1H), 2.78 (bs, 2H), 2.40 (s, 3H), 2.27-2.09 (m, 2H), 1.78 (d, 3H), 1.63 (m, 2H), 1.43 (s, 9H) ppm.

Step 4. tert-Butyl 4-{3-[1-(4-amino-3-methyl-1H-pyrazolo[3,4-d]pyrimidin-1-yl)ethyl]-5-chloro-2-methoxy-6-methylphenyl}piperidine-1-carboxylate This compound was prepared according to the procedure of Example 139 step 5, using of tert-butyl 4-[3-chloro-5-(1-chloroethyl)-6-methoxy-2-methylphenyl]piperidine-1-carboxylate and 3-methyl-1H-pyrazolo[3,4-d]pyrimidin-4-amine as the starting materials. LCMS calculated for $C_{26}H_{36}ClN_6O_3$ (M+H)$^+$: m/z=515.3. Found: 515.2.

Step 5. 1-[1-(5-Chloro-2-methoxy-4-methyl-3-piperidin-4-ylphenyl)ethyl]-3-methyl-1H-pyrazolo[3,4-d]pyrimidin-4-amine dihydrochloride This compound was prepared according to the procedure of Example 139 step 6, using of tert-butyl 4-{3-[1-(4-amino-3-methyl-1H-pyrazolo[3,4-d]pyrimidin-1-yl)ethyl]-5-chloro-2-methoxy-6-methylphenyl}piperidine-1-carboxylate as the starting material. LCMS calculated for $C_{21}H_{28}ClN_6O$ (M+H)$^+$: m/z=415.2. Found: 415.2.

Step 6. 1-{1-[5-Chloro-2-methoxy-4-methyl-3-(1-methylpiperidin-4-yl)phenyl]ethyl}-3-methyl-1H-pyrazolo[3,4-d]pyrimidin-4-amine This compound was prepared according to the procedure of Example 139 step 7, using of 1-[1-(5-chloro-2-methoxy-4-methyl-3-piperidin-4-ylphenyl)ethyl]-3-methyl-1H-pyrazolo[3,4-d]pyrimidin-4-amine dihydrochloride and formaldehyde as the starting materials. The product was isolated as a racemic mixture. LCMS calculated for $C_{22}H_{30}ClN_6O$ (M+H)$^+$: m/z=429.2. Found: 429.1.

Example 164

1-(4-{3-[1-(4-Amino-3-methyl-1H-pyrazolo[3,4-d]pyrimidin-1-yl)ethyl]-5-chloro-2-methoxy-6-methylphenyl}piperidin-1-yl)-2-methylpropan-2-ol

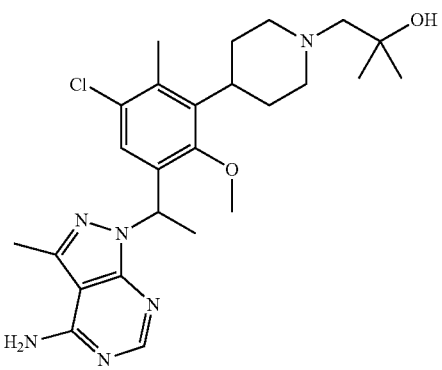 [SMILES: COc1c(C(C)n2nc(C)c3c(N)ncnc32)cc(Cl)c(C)c1C1CCN(CC(C)(C)O)CC1]

This compound was prepared using procedures analogous to those for Example 140 with 1-[1-(5-chloro-2-methoxy-4-methyl-3-piperidin-4-ylphenyl)ethyl]-3-methyl-1H-pyrazolo[3,4-d]pyrimidin-4-amine dihydrochloride (racemic intermediate from Example 163, Step 5) and oxirane, 2,2-dimethyl- as starting materials. The product was isolated as a racemic mixture. LCMS calculated for $C_{25}H_{36}ClN_6O_2$ (M+H)$^+$: m/z=487.3. Found: 487.3. $^1$H NMR (300 MHz, DMSO-d$_6$): δ 8.05 (s, 1H), 7.24 (bs, 2H), 7.22 (s, 1H), 6.16

(m, 1H), 4.01 (bs, 1H), 3.67 (s, 3H), 2.97 (m, 3H), 2.49 (s, 3H), 2.32 (s, 3H), 2.15-2.04 (m, 6H), 1.63 (d, 3H), 1.40 (m, 2H), 1.03 (s, 6H) ppm.

Example 165

5-(3-{1-[4-Amino-3-(cyanomethyl)-1H-pyrazolo[3,4-d]pyrimidin-1-yl]ethyl}-5-chloro-2-ethoxy-6-methylphenyl)-N,N-dimethylpyridine-2-carboxamide

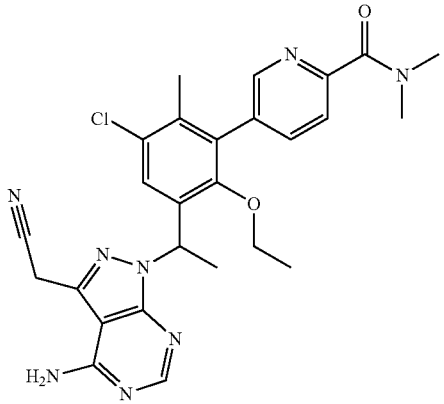 [SMILES: CCOc1c(C(C)n2nc(CC#N)c3c(N)ncnc32)cc(Cl)c(C)c1-c1ccc(C(=O)N(C)C)nc1]

This compound was prepared according to the procedure described in Example 47, using 4-(4,4,5,5-tetramethyl-1,3,2-dioxaborolan-2-yl)isoxazole (from Frontier) instead of (3-fluorophenyl)boronic acid. The product was isolated as a racemic mixture. LCMS calculated for $C_{26}H_{28}ClN_8O_2$ $(M+H)^+$: m/z=519.2. Found: 519.2.

Example 166

3-{3-[1-(4-Amino-3-methyl-1H-pyrazolo[3,4-d]pyrimidin-1-yl)ethyl]-5-chloro-2-methoxy-6-methylphenyl}cyclobutanol trifluoroacetate

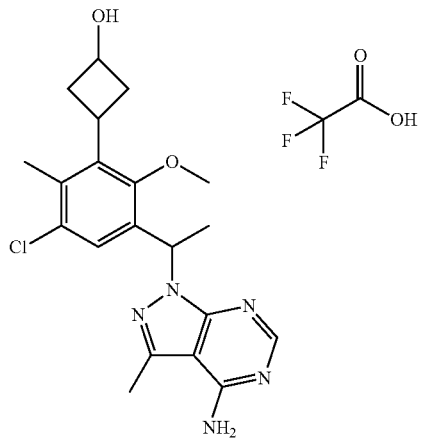 [SMILES: COc1c(C(C)n2nc(C)c3c(N)ncnc32)cc(Cl)c(C)c1C1CC(O)C1 ; O=C(O)C(F)(F)F]

Step 1. 1-(5-Chloro-2-methoxy-4-methyl-3-vinylphenyl)ethanone

A mixture of 1-(5-chloro-3-iodo-2-methoxy-4-methylphenyl)ethanone (1.0 g, 3.2 mmol, from Example 1, Step 2), 4,4,5,5-tetramethyl-2-vinyl-1,3,2-dioxaborolane (0.66 mL, 3.9 mmol), [1,1'-bis(diphenylphosphino)ferrocene]dichloropalladium(II), complex with dichloromethane (1:1) (0.26 g, 0.32 mmol) and potassium carbonate (1.3 g, 9.4 mmol) in 1,4-dioxane (10 mL) and water (5 mL) was degassed with $N_2$ and heated at 80° C. overnight. After cooled to room temperature, the reaction mixture was diluted with water and ethyl acetate. The organic layer was washed with brine, dried over $MgSO_4$, concentrated and purified on a silica gel column (eluting with 0 to 10% EtOAc in hexanes) to give the desired product (0.60 g, 82%). LCMS calculated for $C_{12}H_{14}ClO_2$ $(M+H)^+$: m/z=225.1. Found: 225.1.

Step 2. 3-(3-Acetyl-5-chloro-2-methoxy-6-methylphenyl)cyclobutanone

To a solution of 1-(5-chloro-2-methoxy-4-methyl-3-vinylphenyl)ethanone (530 mg, 2.4 mmol) in ether (10 mL) was added zinc-copper couple (1.8 g, 14 mmol). The reaction mixture was heated at 40° C. and a solution of trichloroacetyl chloride (1.4 mL, 13 mmol) and phosphoryl chloride (1.2 mL, 13 mmol) in 1,2-dimethoxyethane (3 mL) was added slowly over 2 h. After addition, the reaction mixture was stirred under reflux overnight. The reaction was quenched with saturated $NaHCO_3$ solution and diluted with ether. The organic layer was washed with brine, dried over $Na_2SO_4$, filtered and concentrated. The residue and zinc (0.31 g, 4.7 mmol) in acetic acid (10 mL) was stirred at room temperature for 2 h and then reflux overnight. Another portion of zinc was added and reflux for another 4 h. The mixture was diluted with water and extracted with ether. The organic phase was washed successively with a saturated $NaHCO_3$ solution, water and brine, then dried over $MgSO_4$ and concentrated. The crude material was purified with flash chromatography (eluting with 0 to 30% ethyl acetate in hexanes) to give the desired product (0.17 g, 27%). LCMS calculated for $C_{14}H_{16}ClO_3$ $(M+H)^+$: m/z=267.1. Found: 267.0.

Step 3. 3-[3-Chloro-5-(1-hydroxyethyl)-6-methoxy-2-methylphenyl]cyclobutanol

This compound was prepared according to the procedure of Example 13 step 5, using of 3-(3-acetyl-5-chloro-2-methoxy-6-methylphenyl)cyclobutanone and sodium tetrahydroborate as the starting materials. LCMS calculated for $C_{14}H_{19}ClO_3Na$ $(M+Na)^+$: m/z=293.1. Found: 293.1.

Step 4. 3-[3-Chloro-5-(1-chloroethyl)-6-methoxy-2-methylphenyl]cyclobutanol

To a solution of 3-[3-chloro-5-(1-hydroxyethyl)-6-methoxy-2-methylphenyl]cyclobutanol (170 mg, 0.628 mmol) in dimethyl sulfoxide (1 mL) was added cyanuric chloride (64 mg, 0.34 mmol). After stirred overnight, the reaction mixture was diluted with ether and water. The aqueous layer was extracted with ethyl acetate once. The combined organic extracts were washed with brine, dried over $Na_2SO_4$, filtered and concentrated. The crude was purified with silica gel column to give the desired product (39.6 mg, 22%). LCMS calculated for $C_{14}H_{18}ClO_2$ $(M-Cl)^+$: m/z=253.1. Found: 253.2.

Step 5. 3-{3-[1-(4-Amino-3-methyl-1H-pyrazolo[3,4-c]pyrimidin-1-yl)ethyl]-5-chloro-2-methoxy-6-methylphenyl}cyclobutanol trifluoroacetate This compound was prepared according to the procedure of Example 139 step 5, using of 3-[3-chloro-5-(1-chloroethyl)-6-methoxy-2-methylphenyl]cyclobutanol and 3-methyl-1H-pyrazolo[3,4-d]pyrimidin-4-amine as the starting materials. The product was isolated as a racemic mixture. LCMS calculated for $C_{20}H_{25}ClN_5O_2(M+H)^+$: m/z=402.2. Found: 402.2.

Example 167

5-(3-(1-(4-Amino-3-methyl-1H-pyrazolo[3,4-d]pyrimidin-1-yl)ethyl)-5-chloro-2-methoxy-6-methylphenyl)-N,N-dimethylpicolinamide bis(2,2,2-trifluoroacetate)

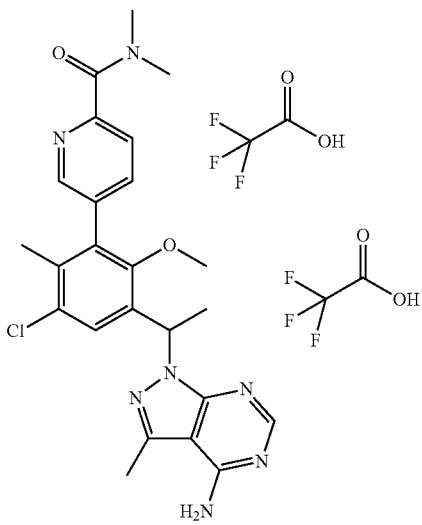 [SMILES: COc1c(C(C)n2nc(C)c3c(N)ncnc32)cc(Cl)c(C)c1-c1ccc(C(=O)N(C)C)nc1 ; O=C(O)C(F)(F)F ; O=C(O)C(F)(F)F]

Step 1. 1-(3-Bromo-5-chloro-2-methoxy-4-methylphenyl)ethanone

To a stirred solution of 1-(5-chloro-2-methoxy-4-methylphenyl)ethanone (5.00 g, 25.2 mmol, from Oakwood) in acetic acid (100 mL) was added N-bromosuccinimide (4.93 g, 27.7 mmol) and the resulting mixture heated at 100° C. for 18 hours. After cooling to ambient temperature, the reaction mixture was concentrated in vacuo, then neutralized with sat. sodium bicarbonate, filtered off insoluble succinimide. The filtrate was extracted with EtOAc. The combined organic layers were washed with brine, dried over sodium sulfate, and then concentrated to dryness under reduced pressure. The residue was purified on silica gel, eluting with 0 to 50% EtOAc in hexanes, to give the desired products (2.66 g, 38%). LCMS calculated for $C_{10}H_{11}BrClO_2$ $(M+H)^+$: m/z=277.0. found: 277.0. $^1H$ NMR (DMSO-$d_6$, 300 MHz): δ 7.70 (1H, s), 3.77 (3H, s), 2.57 (3H, s), 2.50 (3H, s) ppm.

Step 2. 1-(3-Bromo-5-chloro-2-methoxy-4-methylphenyl)ethanol

Sodium tetrahydroborate (0.31 g, 8.1 mmol) was added to a mixture of 1-(3-bromo-5-chloro-2-methoxy-4-methylphenyl)ethanone (1.5 g, 5.4 mmol) in methanol (25 mL) at 0° C. and the resultant reaction mixture was stirred at room temperature for 1 hour. The solvent was removed and the resulting residue was diluted with ethyl acetate, washed with sat. NaHCO$_3$, water, brine, then dried over Na$_2$SO$_4$, filtered and concentrated. The crude product was purified by silica gel chromatography, eluting with 0 to 40% EtOAc in hexanes, to give the desired product (0.30 g, 90%).

Step 3. 3-Bromo-1-chloro-5-(1-chloroethyl)-4-methoxy-2-methylbenzene

A mixture of cyanuric chloride (1.7 g, 9.2 mmol) and N,N-dimethylformamide (710 μL, 9.2 mmol) was stirred at room temperature for 10 minutes and then a solution of 1-(3-bromo-5-chloro-2-methoxy-4-methylphenyl)ethanol (from Example 16, Step 1) (1.72 g, 6.15 mmol) in methylene chloride (34 mL) was added and the reaction was stirred at room temperature overnight. The mixture was diluted with methylene chloride, washed with sat. NaHCO$_3$, water, brine, dried over Na$_2$SO$_4$, filtered and concentrated. The crude product was purified by silica gel chromatography, eluting with 0 to 10% EtOAc in hexanes, to give the desired product (1.01 g, 60%).

Step 4. 1-[1-(3-Bromo-5-chloro-2-methoxy-4-methylphenyl)ethyl]-3-methyl-1H-pyrazolo[3,4-d]pyrimidin-4-amine A mixture of 3-bromo-1-chloro-5-(1-chloroethyl)-4-methoxy-2-methylbenzene (150 mg, 0.503 mmol), 3-methyl-1H-pyrazolo[3,4-d]pyrimidin-4-amine (110 mg, 0.76 mmol, ACES Pharma Product List, item 47024), potassium iodide (9.0 mg, 0.05 mmol) and cesium carbonate (330 mg, 1.0 mmol) in N,N-dimethylformamide (4 mL) and was stirred at 140° C. for 1 h. The mixture was diluted with methylene chloride, washed with sat. NaHCO$_3$, water, brine, dried over Na$_2$SO$_4$, filtered and concentrated. The crude product was purified by silica gel chromatography, eluting with 0 to 70% EtOAc in CH$_2$Cl$_2$, to give the desired product (103 mg, 50%). LCMS calculated for $C_{16}H_{18}BrClN_5O$ $(M+H)^+$: m/z=410.0. Found: 410.2. The racemic products were applied on a Phenomenex Lux-Cellulose 1 column (21.1×250 mm, 5 micron particle size), eluting with 5% ethanol in hexanes at a flow rate of 18 mL/min, ~13 mg/injection, to provide two enantiomers. Peak 1, retention time: 12.35 min; Peak 2, retention time: 14.98 min.

Step 5. 5-(3-(1-(4-Amino-3-methyl-1H-pyrazolo[3,4-d]pyrimidin-1-yl)ethyl)-5-chloro-2-methoxy-6-methylphenyl)-N,N-dimethylpicolinamide bis(2,2,2-trifluoroacetate)

A mixture of 1-[1-(3-bromo-5-chloro-2-methoxy-4-methylphenyl)ethyl]-3-methyl-1H-pyrazolo[3,4-d]pyrimidin-4-amine (25 mg, 0.061 mmol) (first peak from previous step chiral separation), N,N-dimethyl-5-(4,4,5,5-tetramethyl-1,3,2-dioxaborolan-2-yl)pyridine-2-carboxamide (25 mg, 0.091 mmol, from PepTech Corp. Encyclopedia of Amino Acid Analogs and Boronic Acids, item #BE1622-1), sodium carbonate (13 mg, 0.12 mmol) and [1,1'-bis(diphenylphosphino)ferrocene]dichloropalladium (II), complex with dichloromethane (1:1) (9.9 mg, 0.012 mmol) in acetonitrile (0.8 mL)/water (0.3 mL) was degassed with N$_2$ and then stirred at 95° C. for 2 h. After cooling to room temperature, the mixture was filtered and the filtrate purified on RP-HPLC (XBridge C18 column, eluting with a gradient of acetonitrile/water containing 0.05% trifluoroacetic acid, at flow rate of 30 mL/min) to give the desired product as bis-TFA salt (2.9 mg, 6.7%). The product was isolated as a single enantiomer. LCMS calculated for $C_{24}H_{27}ClN_7O_2$ $(M+H)^+$: m/z=480.2. Found: 480.2. $^1H$ NMR (500 MHz, DMSO-$d_6$) δ: 8.78 (2H, br s), 8.48 (1H, m), 8.36 (1H, s), 7.86 (1H, br s), 7.65 (1H, br s), 7.58 (1H, s), 6.33 (1H, q, J=7.0 Hz), 3.19 (3H, s), 3.03 (3H, s), 2.97 (3H, s), 2.62 (3H, s), 2.06 (3H, s), 1.81 (3H, d, J=7.0 Hz) ppm.

Example 174

5-(3-(1-(4-Amino-3-methyl-1H-pyrazolo[3,4-d]pyrimidin-1-yl)ethyl)-5-chloro-2-methoxy-6-methylphenyl)-N-cyclopropyl-N-methylnicotinamide bis(2,2,2-trifluoroacetate)

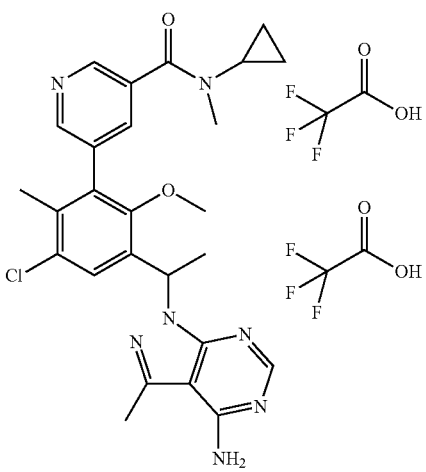

Step 1. 5-{3-[1-(4-Amino-3-methyl-1H-pyrazolo[3,4-d]pyrimidin-1-yl)ethyl]-5-chloro-2-methoxy-6-methylphenyl}nicotinonitrile A mixture of 1-[1-(3-bromo-5-chloro-2-methoxy-4-methylphenyl)ethyl]-3-methyl-1H-pyrazolo[3,4-d]pyrimidin-4-amine (first peak from Example 167, step 4 chiral separation, 106 mg, 0.25 mmol), 5-(4,4,5,5-tetramethyl-1,3,2-dioxaborolan-2-yl)nicotinonitrile (70. mg, 0.31 mmol, from Combi-Blocks Catalog, item #PN-8893), sodium carbonate (43 mg, 0.41 mmol) and [1,1'-bis(diphenylphosphino)ferrocene]-dichloropalladium(II), complex with dichloromethane (1:1) (33 mg, 0.041 mmol) in acetonitrile (2 mL)/water (0.6 mL) was degassed with $N_2$ and then stirred at 95° C. for 2 h. The mixture was diluted with methylene chloride, washed with sat. $NaHCO_3$, water, brine, dried over $Na_2SO_4$, filtered and concentrated. The product (95 mg, 87%) was purified by chromatography eluting with $CH_2Cl_2$/MeOH (max. MeOH 5%). LCMS calculated for $C_{22}H_{21}ClN_7O$ $(M+H)^+$: m/z=434.2. Found: 434.2.

Step 2. 5-(3-(1-(4-Amino-3-methyl-1H-pyrazolo[3,4-d]pyrimidin-1-yl)ethyl)-5-chloro-2-methoxy-6-methylphenyl)nicotinic acid dihydrochloride 4.0 M Sodium hydroxide in water (0.3 mL, 1 mmol) was added to a mixture of 5-{3-[1-(4-amino-3-methyl-1H-pyrazolo[3,4-d]pyrimidin-1-yl)ethyl]-5-chloro-2-methoxy-6-methylphenyl}nicotinonitrile (0.090 g, 0.21 mmol) in ethanol (1.0 mL) and the mixture was then heated at 95° C. for 6 h. At this time, conc. HCl was added to adjust PH to ~3. The solvent was removed and the residue was used in the next step without further purification LCMS calculated for $C_{22}H_{22}ClN_6O_3$ $(M+H)^+$: m/z=453.1. Found: 453.2.

Step 3. 5-{3-[1-(4-Amino-3-methyl-1H-pyrazolo[3,4-d]pyrimidin-1-yl)ethyl]-5-chloro-2-methoxy-6-methylphenyl}-N-cyclopropyl-N-methylnicotinamide N-Methylcyclopropanamine hydrochloride (4.0 mg, 0.04 mmol) was added to a solution of 5-(3-(1-(4-amino-3-methyl-1H-pyrazolo[3,4-d]pyrimidin-1-yl)ethyl)-5-chloro-2-methoxy-6-methylphenyl)nicotinic acid dihydrochloride (9.6 mg, 0.021 mmol) and BOP (10 mg, 0.03 mmol) in DMF (0.7 mL) at room temperature followed by the addition of triethylamine (13 µL, 0.10 mmol). The reaction was stirred for 1 h. The product was purified on RP-HPLC (XBridge C18 column, eluting with a gradient of acetonitrile/water containing 0.05% trifluoroacetic acid, at flow rate of 30 mL/min) to give the desired product as bis-TFA salt (2.6 mg, 17%). The product was isolated as a single enantiomer. LCMS calculated for $C_{26}H_{29}ClN_7O_2$ $(M+H)^+$: m/z=506.2. Found: 506.2.

Example 179

3-(3-(1-(4-Amino-3-methyl-1H-pyrazolo[3,4-d]pyrimidin-1-yl)ethyl)-5-chloro-2-methoxy-6-methylphenyl)-N-methylpropanamide 2,2,2-trifluoroacetate

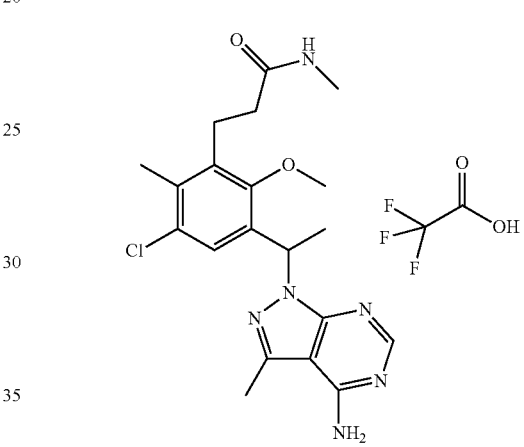

Step 1. tert-Butyl 3-{3-[1-(4-amino-3-methyl-1H-pyrazolo[3,4-d]pyrimidin-1-yl)ethyl]-5-chloro-2-methoxy-6-methylphenyl}propanoate To a microwave vial was added 1-[1-(3-bromo-5-chloro-2-methoxy-4-methylphenyl)ethyl]-3-methyl-1H-pyrazolo[3,4-d]pyrimidin-4-amine (Peak 1 from Example 167, step 4 chiral separation, 35 mg, 0.085 mmol), potassium (3-tert-butoxy-3-oxopropyl)trifluoroborate (30. mg, 0.13 mmol, from Frontier Scientific, item #P10370), potassium phosphate (54 mg, 0.26 mmol) and tetrakis(triphenylphosphine)palladium(0) (9.8 mg, 0.0085 mmol) and toluene (0.7 mL)/water (0.2 mL). The vial was sealed and degassed with $N_2$ three times. The reaction was heated at 110° C. for 20 h. The crude was filtered and the product (20 mg, 50%) was purified by chromatography eluting with $CH_2Cl_2$/MeOH (max. MeOH 6%). LCMS calculated for $C_{23}H_{31}ClN_5O_3$ $(M+H)^+$: m/z=460.2. Found: 460.3.

Step 2. 3-{3-[1-(4-Amino-3-methyl-1H-pyrazolo[3,4-d]pyrimidin-1-yl)ethyl]-5-chloro-2-methoxy-6-methylphenyl}propanoic acid trifluoroacetate TFA (0.3 mL, 4 mmol) was added to a solution of tert-butyl 3-{3-[1-(4-amino-3-methyl-1H-pyrazolo[3,4-b]pyrimidin-1-yl)ethyl]-5-chloro-2-methoxy-6-methylphenyl}propanoate (35 mg, 0.076 mmol) in methylene chloride (0.2 mL) and the mixture was stirred at room temperature for 2 h. The solvent was removed and the product was used in the next step without further purification. LCMS calculated for $C_{19}H_{23}ClN_5O_3$ (M+H)+: m/z=404.1. Found: 404.0.

Step 3. 3-(3-(1-(4-Amino-3-methyl-1H-pyrazolo[3,4-d]pyrimidin-1-yl)ethyl)-5-chloro-2-methoxy-6-methylphenyl)-N-methylpropanamide 2,2,2-trifluoroacetate 2.0 M Methylamine in THF (30 μL, 0.06 mmol) was added to a solution of 3-{3-[1-(4-amino-3-methyl-1H-pyrazolo[3,4-d]pyrimidin-1-yl)ethyl]-5-chloro-2-methoxy-6-methylphenyl}propanoic acid (8.9 mg, 0.022 mmol) and BOP (10 mg, 0.03 mmol) in N,N-dimethylformamide (0.7 mL) at room temperature followed by adding triethylamine (8.8 μL, 0.064 mmol). The reaction was stirred for 1 h. The product was purified on RP-HPLC (XBridge C18 column, eluting with a gradient of acetonitrile/water containing 0.05% trifluoroacetic acid, at flow rate of 30 mL/min) to give the desired product as TFA salt (3.2 mg, 27%). The product was isolated as a single enantiomer. LCMS calculated for $C_{20}H_{26}ClN_6O_2$ (M+H)+: m/z=417.2. Found: 417.0.

Example 181

1-(1-(5-Chloro-2-methoxy-4-methyl-3-(1-(1-methylpiperidin-4-yl)-1H-pyrazol-4-yl)phenyl)ethyl)-3-methyl-1H-pyrazolo[3,4-d]pyrimidin-4-amine

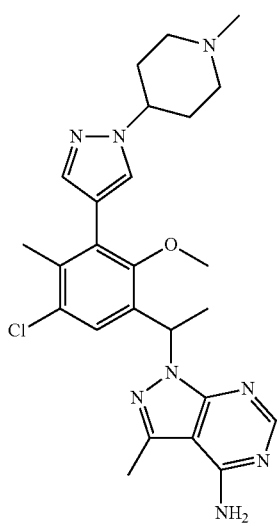 [SMILES: COc1c(C(C)n2nc(C)c3c(N)ncnc32)cc(Cl)c(C)c1-c1cnn(C2CCN(C)CC2)c1]

Step 1. tert-Butyl 4-(4-{3-[1-(4-amino-3-methyl-1H-pyrazolo[3,4-d]pyrimidin-1-yl)ethyl]-5-chloro-2-methoxy-6-methylphenyl}-1H-pyrazol-1-yl)piperidine-1-carboxylate A mixture of 1-[1-(3-bromo-5-chloro-2-methoxy-4-methylphenyl)ethyl]-3-methyl-1H-pyrazolo[3,4-d]pyrimidin-4-amine (Peak 1 from Example 167, step 4 chiral separation, 42 mg, 0.1 mmol), tert-butyl 4-[4-(4,4,5,5-tetramethyl-1,3,2-dioxaborolan-2-yl)-1H-pyrazol-1-yl]piperidine-1-carboxylate (48 mg, 0.13 mmol, from Combi-Blocks Catalog, item #FM-2957), sodium carbonate (18 mg, 0.17 mmol) and [1,1'-bis(diphenylphosphino)ferrocene]dichloropalladium (II), complex with dichloromethane (1:1) (14 mg, 0.017 mmol) in acetonitrile (2 mL)/water (0.4 mL) was degassed with $N_2$ and the stirred at 95° C. for 2 h. The mixture was diluted with methylene chloride, washed with sat. NaHCO$_3$, water, brine, dried over $Na_2SO_4$, filtered and concentrated. The product was purified by chromatography eluting with $CH_2Cl_2$/MeOH (max. MeOH 5%). LCMS calculated for $C_{29}H_{38}ClN_8O_3$ (M+H)+: m/z=581.2. Found: 581.3.

Step 2. 1-(1-(5-Chloro-2-methoxy-4-methyl-3-(1-(piperidin-4-yl)-1H-pyrazol-4-yl)phenyl)ethyl)-3-methyl-1H-pyrazolo[3,4-d]pyrimidin-4-amine TFA (0.3 mL, 4 mmol) was added to a solution of tert-butyl 4-(4-{3-[1-(4-amino-3-methyl-1H-pyrazolo[3,4-d]pyrimidin-1-yl)ethyl]-5-chloro-2-methoxy-6-methylphenyl}-1H-pyrazol-1-yl)piperidine-1-carboxylate (30 mg, 0.052 mmol) in methylene chloride (0.2 mL) at room temperature and the mixture was stirred for 1 h. The crude was purified using RP-HPLC (XBridge C18 column, eluting with a gradient of acetonitrile/water containing 0.1% ammonium hydroxide, at flow rate of 30 mL/min) to give the desired product. LCMS calculated for $C_{24}H_{30}ClN_8O$ (M+H)+: m/z=481.2. Found: 481.1.

Step 3. 1-(1-{5-Chloro-2-methoxy-4-methyl-3-[1-(1-methylpiperidin-4-yl)-1H-pyrazol-4-yl]phenyl}ethyl)-3-methyl-1H-pyrazolo[3,4-d]pyrimidin-4-amine 12.0 M Formaldehyde in water (0.01 mL, 0.2 mmol) was added to a mixture of 1-{-1-[5-chloro-2-methoxy-4-methyl-3-(1-piperidin-4-yl-1H-pyrazol-4-yl)phenyl]ethyl}-3-methyl-1H-pyrazolo[3,4-d]pyrimidin-4-amine (8.0 mg, 0.017 mmol) and N,N-diisopropylethylamine (0.012 mL, 0.066 mmol) in methylene chloride (0.2 mL) at 0° C. The reaction mixture was stirred for 10 min, at this time sodium triacetoxyborohydride (5.3 mg, 0.025 mmol) was added and the reaction was stirred at 0° C. for 1 h. The crude was purified using RP-HPLC (XBridge C18 column, eluting with a gradient of acetonitrile/water containing 0.1% ammonium hydroxide, at flow rate of 30 mL/min) to give the desired product (2.0 mg, 24%). The product was isolated as a single enantiomer. LCMS calculated for $C_{25}H_{32}ClN_8O$ (M+H)+: m/z=495.2. Found: 495.0.

Example 182

1-(1-{3-[1-(1-Acetylpiperidin-4-yl)-1H-pyrazol-4-yl]-5-chloro-2-methoxy-4-methylphenyl}ethyl)-3-methyl-1H-pyrazolo[3,4-d]pyrimidin-4-amine

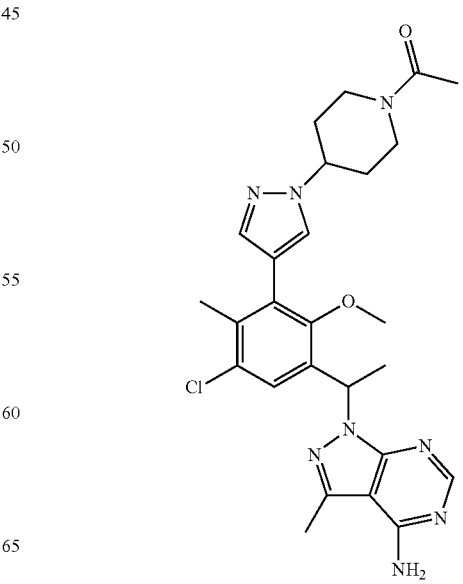

223

Acetyl chloride (2.4 μL, 0.033 mmol) was added to a solution of 1-{1-[5-chloro-2-methoxy-4-methyl-3-(1-piperidin-4-yl-1H-pyrazol-4-yl)phenyl]ethyl}-3-methyl-1H-pyrazolo[3,4-d]pyrimidin-4-amine (8.0 mg, 0.017 mmol, chiral intermediate from Example 181, Step 2) and N,N-diisopropylethylamine (14 μL, 0.083 mmol) in methylene chloride (0.3 mL) at 0° C. and the reaction was stirred at room temperature for 15 min. The crude was purified using RP-HPLC (XBridge C18 column, eluting with a gradient of acetonitrile/water containing 0.1% ammonium hydroxide, at flow rate of 30 mL/min) to give the desired product (1.0 mg, 7.8%). The product was isolated as a single enantiomer. LCMS calculated for $C_{26}H_{32}ClN_8O_2$ $(M+H)^+$: m/z=523.2. Found: 523.2.

Example 183

1-[1-(5-Chloro-3-{1-[2-(dimethylamino)ethyl]-1H-pyrazol-4-yl}-2-methoxy-4-methylphenyl)ethyl]-3-methyl-1H-pyrazolo[3,4-d]pyrimidin-4-amine

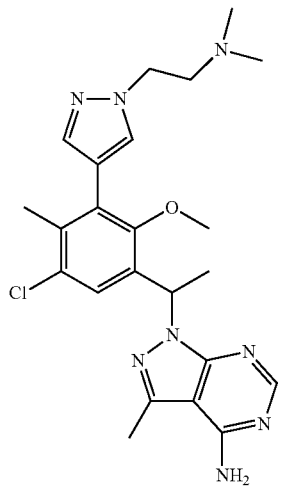 [SMILES: COc1c(C(C)n2nc(C)c3c(N)ncnc32)cc(Cl)c(C)c1-c1cnn(CCN(C)C)c1]

Step 1. 1-(2-Chloroethyl)-4-(4,4,5,5-tetramethyl-1,3,2-dioxaborolan-2-yl)-1H-pyrazole A mixture of 4-(4,4,5,5-tetramethyl-1,3,2-dioxaborolan-2-yl)-1H-pyrazole (0.39 g, 2.0 mmol), 1-bromo-2-chloroethane (0.3 mL, 3 mmol) and cesium carbonate (1.3 g, 4.0 mmol) in acetonitrile (6 mL) was stirred at 75° C. for 5 h. The mixture was diluted with ethyl acetate, washed with sat. $NaHCO_3$, water, brine, dried over $Na_2SO_4$, filtered and concentrated and the product (0.45 g, 88%) was purified by chromatography eluting with hexanes/EtOAc (max. EtOAc 30%). LCMS calculated for $C_{11}H_{19}BClN_2O_2$ $(M+H)^+$: m/z=257.1. Found: 257.0.

Step 2. N,N-Dimethyl-2-[4-(4,4,5,5-tetramethyl-1,3,2-dioxaborolan-2-yl)-1H-pyrazol-1-yl]ethanamine A mixture of 1-(2-chloroethyl)-4-(4,4,5,5-tetramethyl-1,3,2-dioxaborolan-2-yl)-1H-pyrazole (0.10 g, 0.39 mmol), sodium iodide (58 mg, 0.39 mmol) and 2.0 M dimethylamine in THF (1.0 mL, 2.0 mmol) in N,N-dimethylformamide (0.5 mL) was stirred at 80° C. overnight. The solvent was removed to provide the desired product which was used in the next step. LCMS calculated for $C_{13}H_{25}BN_3O_2$ $(M+H)^+$: m/z=266.2. Found: 266.3.

224

Step 3. 1-[1-(5-chloro-3-{1-[2-(dimethylamino)ethyl]-1H-pyrazol-4-yl}-2-methoxy-4-methylphenyl)ethyl]-3-methyl-1H-pyrazolo[3,4-c]pyrimidin-4-amine A mixture of 1-[1-(3-bromo-5-chloro-2-methoxy-4-methylphenyl)ethyl]-3-methyl-1H-pyrazolo[3,4-d]pyrimidin-4-amine (Peak 1 from Example 167, step 4, 10 mg, 0.024 mmol), N,N-dimethyl-2-[4-(4,4,5,5-tetramethyl-1,3,2-dioxaborolan-2-yl)-1H-pyrazol-1-yl]-ethanamine (8.6 mg, 0.036 mmol), sodium carbonate (5.2 mg, 0.049 mmol) and [1,1'-bis(diphenylphosphino)ferrocene]dichloropalladium (II), complex with dichloromethane (1:1) (4.0 mg, 0.0049 mmol) in acetonitrile (0.5 mL)/water (0.1 mL) was vacuumed and the refilled with $N_2$ and the stirred at 95° C. for 2 h. The crude was purified using RP-HPLC (XBridge C18 column, eluting with a gradient of acetonitrile/water containing 0.1% ammonium hydroxide, at flow rate of 30 mL/min) to give the desired product (3.1 mg, 28%). The product was isolated as a single enantiomer. LCMS calculated for $C_{23}H_{30}ClN_8O$ $(M+H)^+$: m/z=469.2. Found: 469.2.

Example 184

2-[(5-{3-[1-(4-Amino-3-methyl-1H-pyrazolo[3,4-d]pyrimidin-1-yl)ethyl]-5-chloro-2-methoxy-6-methylphenyl}pyridin-2-yl)amino]ethanol

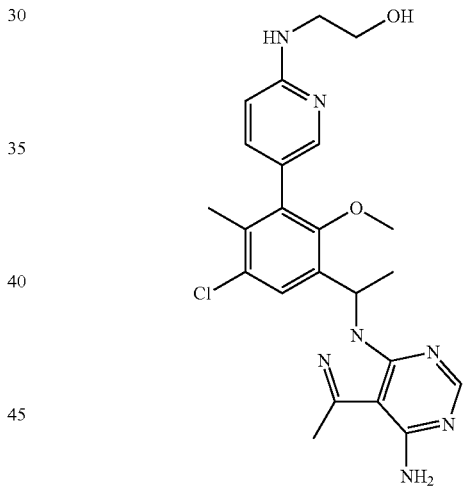

Step 1. 1-{1-[5-Chloro-3-(6-fluoropyridin-3-yl)-2-methoxy-4-methylphenyl]ethyl}-3-methyl-1H-pyrazolo[3,4-d]pyrimidin-4-amine A mixture of 1-[1-(3-bromo-5-chloro-2-methoxy-4-methylphenyl)ethyl]-3-methyl-1H-pyrazolo[3,4-d]pyrimidin-4-amine (Peak 1 from Example 167, step 4, 25.0 mg, 0.06 mmol), 2-fluoro-5-(4,4,5,5-tetramethyl-1,3,2-dioxaborolan-2-yl)pyridine (20. mg, 0.088 mmol), sodium carbonate (12 mg, 0.12 mmol) and [1,1'-bis(diphenylphosphino)ferrocene]dichloropalladium(II), complex with dichloromethane (1:1) (9.5 mg, 0.012 mmol) in acetonitrile (1 mL)/water (0.3 mL) was degassed with $N_2$ and the stirred at 95° C. for 2 h. The mixture was diluted with methylene chloride, washed with sat. $NaHCO_3$, water, brine, dried over $Na_2SO_4$, filtered and concentrated. The product was purified by chromatography eluting with $CH_2Cl_2$/MeOH (max. MeOH 5%). LCMS calculated for $C_{21}H_{21}ClFN_6O$ $(M+H)^+$: m/z=427. Found: 427.2.

Step 2. 2-[(5-{3-[1-(4-Amino-3-methyl-1H-pyrazolo [3,4-d]pyrimidin-1-yl)ethyl]-5-chloro-2-methoxy-6-methylphenyl}pyridin-2-yl)amino]ethanol A mixture of 1-{1-[5-chloro-3-(6-fluoropyridin-3-yl)-2-methoxy-4-methylphenyl]ethyl}-3-methyl-1H-pyrazolo[3,4-d]pyrimidin-4-amine (10 mg, 0.023 mmol) and ethanolamine (0.10 mL) in 1-butanol (1 mL) was stirred at 130° C. for 5 h. The crude was purified using RP-HPLC (XBridge C18 column, eluting with a gradient of acetonitrile/water containing 0.1% ammonium hydroxide, at flow rate of 30 mL/min) to give the desired product (1.6 mg, 15%). The product was isolated as a single enantiomer. LCMS calculated for $C_{23}H_{27}ClN_7O_2$ (M+H)$^+$: m/z=468.2. Found: 468.2.

Example 188

2-(5-(3-(1-(4-Amino-3-methyl-1H-pyrazolo[3,4-d]pyrimidin-1-yl)ethyl)-5-chloro-2-methoxy-6-methylphenyl)pyridin-2-yloxy)ethanol

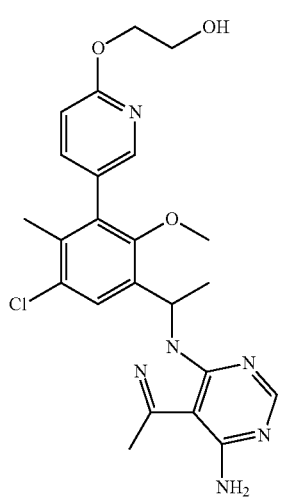 [SMILES: COc1c(C(C)Nc2ncnc(N)c2C(C)=N)cc(Cl)c(C)c1-c1ccc(OCCO)nc1]

Sodium hydride (20 mg, 0.5 mmol) was added to 1,2-ethanediol (0.5 mL, 9 mmol) and the mixture was stirred at room temperature for 10 min. At this time 1-{1-[5-chloro-3-(6-fluoropyridin-3-yl)-2-methoxy-4-methylphenyl] ethyl}-3-methyl-1H-pyrazolo[3,4-d]pyrimidin-4-amine (10 mg, 0.023 mmol) was added and then the reaction was stirred at 110° C. overnight. The crude was purified using RP-HPLC (XBridge C18 column, eluting with a gradient of acetonitrile/water containing 0.1% ammonium hydroxide, at flow rate of 30 mL/min) to give the desired product (1.8 mg, 17%). The product was isolated as a single enantiomer. LCMS calculated for $C_{23}H_{26}ClN_6O_3$ (M+H)$^+$: m/z=469.2. Found: 469.1.

Example 189

5-(3-(1-(4-Amino-3-methyl-1H-pyrazolo[3,4-d]pyrimidin-1-yl)ethyl)-5-chloro-2-(2,2-difluoroethoxy)-6-methylphenyl)-N,N-dimethylpicolinamide bis(2,2,2-trifluoroacetate)

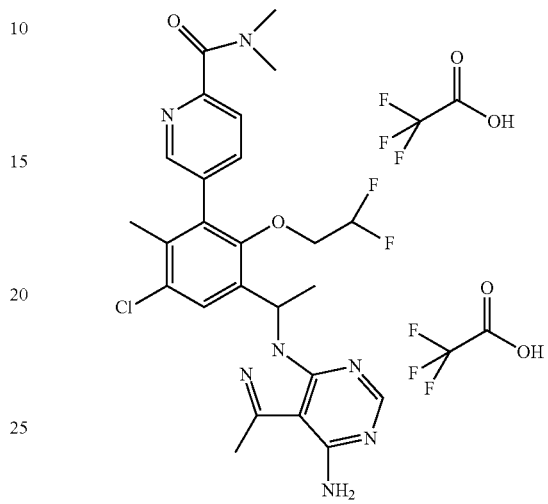

Step 1. 5-(3-(1-(4-Amino-3-methyl-1H-pyrazolo[3,4-d]pyrimidin-1-yl)ethyl)-5-chloro-2-hydroxy-6-methylphenyl)-N,N-dimethylpicolinamide 1.0 M Boron tribromide in $CH_2Cl_2$ (250 µL, 0.25 mmol) was added to a mixture of 5-{3-[1-(4-amino-3-methyl-1H-pyrazolo[3,4-d]pyrimidin-1-yl)ethyl]-5-chloro-2-methoxy-6-methylphenyl}-N,N-dimethylpyridine-2-carboxamide (Example 167, step 5, (first peak) 60 mg, 0.13 mmol) in methylene chloride (1.2 mL) at −78° C. and then the reaction was warmed to room temperature. At this time conc. HCl (0.1 mL) was added and the mixture was stirred for 4 h. The reaction was quenched by the addition of sat. NaHCO$_3$. The mixture was then extracted with methylene chloride. The combined extracts were washed with brine, dried and concentrated to give the desired crude product (40 mg, 68%) which was used in the next step without further purification. LCMS calculated for $C_{23}H_{25}ClN_7O_2$ (M+H)$^+$: m/z=466.2. Found: 466.2.

Step 2. 5-[3-[1-(4-Amino-3-methyl-1H-pyrazolo[3,4-d]pyrimidin-1-yl)ethyl]-5-chloro-2-(2,2-difluoroethoxy)-6-methylphenyl]-N,N-dimethylpyridine-2-carboxamide Diisopropyl azodicarboxylate (13 µL, 0.064 mmol) was added to a mixture of 5-{3-[1-(4-amino-3-methyl-1H-pyrazolo[3,4-d]pyrimidin-1-yl)ethyl]-5-chloro-2-hydroxy-6-methylphenyl}-N,N-dimethylpyridine-2-carboxamide (15.0 mg, 0.0322 mmol), 2,2-difluoroethanol (7.9 mg, 0.096 mmol, from Alfa Aesar, item #B22201) and triphenylphosphine (17 mg, 0.064 mmol) in tetrahydrofuran (0.5 mL) at 0° C. and then the reaction was stirred at room temperature for 24 h. The crude was purified on RP-HPLC (XBridge C18 column, eluting with a gradient of acetonitrile/water containing 0.05% trifluoroacetic acid, at flow rate of 30 mL/min) to give the desired product as bis-TFA salt (1.6 mg, 6.6%). The product was isolated as a single enantiomer. LCMS calculated for $C_{25}H_{27}ClF_2N_7O_2$ (M+H)$^+$: m/z=530.2. Found: 530.2.

Example 190

5-(3-(1-(4-Amino-3-methyl-1H-pyrazolo[3,4-d]pyrimidin-1-yl)ethyl)-5-chloro-2-(cyclopropylmethoxy)-6-methylphenyl)-N,N-dimethylpicolinamide bis(2,2,2-trifluoroacetate)

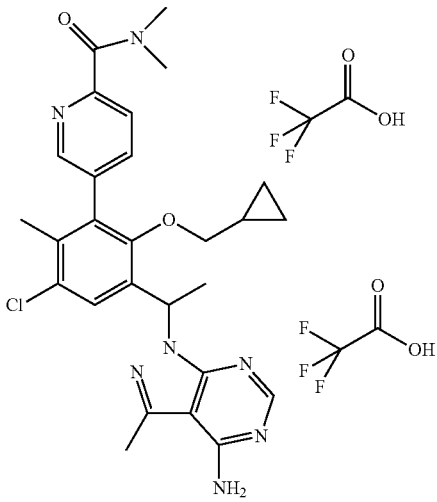

Diisopropyl azodicarboxylate (13 μL, 0.064 mmol) was added to a mixture of 5-{3-[1-(4-amino-3-methyl-1H-pyrazolo[3,4-d]pyrimidin-1-yl)ethyl]-5-chloro-2-hydroxy-6-methylphenyl}-N,N-dimethylpyridine-2-carboxamide (15 mg, 0.032 mmol, chiral intermediate from Example 189, Step 1), cyclopropyl carbinol (7.0 mg, 0.096 mmol) and triphenylphosphine (17 mg, 0.064 mmol) in tetrahydrofuran (0.5 mL) at 0° C. and then the reaction was stirred at room temperature for 24 h. The crude was purified on RP-HPLC (XBridge C18 column, eluting with a gradient of acetonitrile/water containing 0.05% trifluoroacetic acid, at flow rate of 30 mL/min) to give the desired product as bis-TFA salt (2.4 mg, 10%). The product was isolated as a single enantiomer. LCMS calculated for $C_{27}H_{31}ClN_7O_2$ (M+H)$^+$: m/z=520.2. Found: 520.3.

Example 191

5-(3-{1-[4-Amino-3-(difluoromethyl)-1H-pyrazolo[3,4-d]pyrimidin-1-yl]ethyl}-5-chloro-2-methoxy-6-methylphenyl)-N,N-dimethylpyridine-2-carboxamide

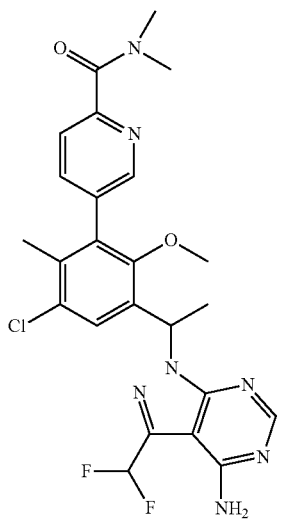 [SMILES: COc1c(C(C)Nc2ncnc(N)c2C(=N)C(F)F)cc(Cl)c(C)c1-c1ccc(C(=O)N(C)C)nc1]

Step 1. 1-[1-(3-Bromo-5-chloro-2-methoxy-4-methylphenyl)ethyl]-3-iodo-1H-pyrazolo[3,4-d]pyrimidin-4-amine A mixture of 3-bromo-1-chloro-5-(1-chloroethyl)-4-methoxy-2-methylbenzene (0.60 g, 2.0 mmol, from Example 167, Step 3), 3-iodo-1H-pyrazolo[3,4-d]pyrimidin-4-amine (590 mg, 2.2 mmol, from AnaSpec), cesium carbonate (0.98 g, 3.0 mmol) and potassium iodide (30 mg, 0.2 mmol) in N,N-dimethylformamide (8 mL) was stirred at 140° C. for 1 h. The mixture was cooled down and then the solvent was completely removed. The residue was stirred with $CH_2Cl_2$ (30 mL) at room temperature for 20 min and then filtered. The filtrate was concentrated and the product (0.65 g, 63%) was purified by chromatography eluting with $CH_2Cl_2$/EtOAc (max. EtOAc 60%). LCMS calculated for $C_{15}H_{15}BrClIN_5O$ (M+H)$^+$: m/z=521.9. Found: 521.9.

Step 2. 1-[1-(3-Bromo-5-chloro-2-methoxy-4-methylphenyl)ethyl]-3-vinyl-1H-pyrazolo[3,4-d]pyrimidin-4-amine Dichloro(bis{di-tert-butyl[4-(dimethylamino)phenyl]phosphoranyl})palladium (12 mg, 0.017 mmol) was added to a mixture of vinyl boronic acid MIDA (110 mg, 0.6 mmol, from Aldrich, item #704415), 1-[1-(3-bromo-5-chloro-2-methoxy-4-methylphenyl)ethyl]-3-iodo-1H-pyrazolo[3,4-d]pyrimidin-4-amine (0.30 g, 0.57 mmol) and sodium carbonate (0.14 g, 1.1 mmol) in 1,4-dioxane (1 mL) and water (0.1 mL) and then the reaction was degassed with $N_2$ 3 times. The reaction was stirred at 95° C. for 4 h. The mixture was diluted with methylene chloride, washed with sat. $NaHCO_3$, water, brine, dried over $Na_2SO_4$, filtered and concentrated. The product was purified by chromatography eluting with $CH_2Cl_2$/EtOAc (max. EtOAc 60%). LCMS calculated for $C_{17}H_{18}BrClN_5O$ (M+H)$^+$: m/z=422.0. Found: 422.2.

Step 3. 1-{4-Amino-1-[1-(3-bromo-5-chloro-2-methoxy-4-methylphenyl)ethyl]-1H-pyrazolo[3,4-d]pyrimidin-3-yl}ethane-1,2-diol To a solution of 1-[1-(3-bromo-5-chloro-2-methoxy-4-methylphenyl)ethyl]-3-vinyl-1H-pyrazolo[3,4-d]pyrimidin-4-amine (100 mg, 0.236 mmol) in t-butyl alcohol (2 mL) was added N-methylmorpholine N-oxide (30.5 mg, 0.260 mmol) and water (0.74 mL). To the solution was then added aqueous osmium tetraoxide (0.075 mL, 4%). After 3 hr, another equivalent of N-methylmorpholine N-oxide was added. The reaction was stirred at room temperature overnight. The solution was diluted with water, extracted with ethyl acetate, dried over $MgSO_4$ and concentrated to give the product which was used directly in the next step. LCMS calculated for $C_{17}H_{20}BrClN_5O_3$ (M+H)$^+$: m/z=456.0. Found: 456.0.

Step 4. 4-Amino-1-[1-(3-bromo-5-chloro-2-methoxy-4-methylphenyl)ethyl]-1H-pyrazolo[3,4-d]pyrimidine-3-carbaldehyde To a solution of 1-{4-amino-1-[1-(3-bromo-5-chloro-2-methoxy-4-methylphenyl)ethyl]-1H-pyrazolo[3,4-d]pyrimidin-3-yl}ethane-1,2-diol (0.10 g, 0.22 mmol) in tetrahydrofuran (1.6 mL)/water (1.0 mL) was added acetic acid (0.0032 mL, 0.057 mmol) and sodium periodate (0.140 g, 0.657 mmol) at 0° C. After stirring for 2 h, the reaction mixture was diluted with water, extracted with ethyl acetate. The combined organic layers were washed with brine, dried over $MgSO_4$ and concentrated to give the desired crude product which was used directly in the next step. LCMS calculated for $C_{16}H_{16}BrClN_5O_2$ (M+H)$^+$: m/z=424.0. Found: 423.9.

Step 5. 5-{3-[1-(4-Amino-3-formyl-1H-pyrazolo[3,4-d]pyrimidin-1-yl)ethyl]-5-chloro-2-methoxy-6-methylphenyl}-N,N-dimethylpyridine-2-carboxamide A mixture of 4-amino-1-[1-(3-bromo-5-chloro-2-methoxy-4-methylphenyl)ethyl]-1H-pyrazolo[3,4-d]pyrimidine-3-carbaldehyde (20 mg, 0.047 mmol), {6-[(dimethylamino)carbonyl]pyridin-3-yl}boronic acid (23 mg, 0.12 mmol), sodium carbonate (10 mg, 0.094 mmol) and [1,1'-bis(diphenylphosphino)ferrocene]dichloropalladium(II), complex with dichloromethane (1:1) (7.7 mg, 0.0094 mmol) in acetonitrile (0.3 mL)/ethanol (0.1 mL)/water (0.1 mL) was degassed with $N_2$ and then stirred at 95° C. for 3 h. The mixture was diluted with methylene chloride, washed with sat. $NaHCO_3$, water, brine, dried over $Na_2SO_4$, filtered and concentrated. The product was purified by chromatography eluting with $CH_2Cl_2$/MeOH (max. MeOH 6%). LCMS calculated for $C_{24}H_{25}ClN_7O_3$ (M+H)$^+$: m/z=494.2. Found: 494.1.

Step 6. 5-(3-{1-[4-Amino-3-(difluoromethyl)-1H-pyrazolo[3,4-d]pyrimidin-1-yl]ethyl}-5-chloro-2-methoxy-6-methylphenyl)-N,N-dimethylpyridine-2-carboxamide To a solution of 5-{3-[1-(4-amino-3-formyl-1H-pyrazolo[3,4-d]pyrimidin-1-yl)ethyl]-5-chloro-2-methoxy-6-methylphenyl}-N,N-dimethylpyridine-2-carboxamide (0.015 g, 0.030 mmol) in methylene chloride (0.5 mL) cooled at 0° C. was added dropwise diethylaminosulfur trifluoride (0.020 mL, 0.15 mmol). The mixture was stirred at room temperature overnight. The crude was purified using RP-HPLC (XBridge C18 column, eluting with a gradient of acetonitrile/water containing 0.1% ammonium hydroxide, at flow rate of 30 mL/min) to give the desired product (1.7 mg, 11%). The product was isolated as a racemic mixture. LCMS calculated for $C_{24}H_{25}ClF_2N_7O_2$ (M+H)$^+$: m/z=516.2. Found: 516.2.

Example 192

1-[1-(5-Chloro-3-cyclopropyl-2-methoxy-4-methylphenyl)ethyl]-3-methyl-1H-pyrazolo[3,4-d]pyrimidin-4-amine

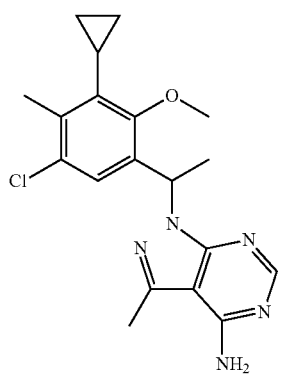 [SMILES: COc1c(C(C)Nc2ncnc(N)c2C(C)=N)cc(Cl)c(C)c1C1CC1]

To a microwave vial was added 1-[1-(3-bromo-5-chloro-2-methoxy-4-methylphenyl)ethyl]-3-methyl-1H-pyrazolo[3,4-d]pyrimidin-4-amine (15 mg, 0.037 mmol, from peak 1 from Example 167, step 4), potassium cyclopropyltrifluoroborate (8 mg, 0.06 mmol, from Frontier Scientific, item #C10298), potassium phosphate (23 mg, 0.11 mmol), and tetrakis(triphenylphosphine)palladium (4.2 mg, 0.0036 mmol) and then toluene (0.3 mL)/water (0.1 mL). The vial was sealed and degassed with $N_2$ three times. The reaction was heat at 110° C. for 20 h. The crude was purified using RP-HPLC (XBridge C18 column, eluting with a gradient of acetonitrile/water containing 0.1% ammonium hydroxide, at flow rate of 30 mL/min) to give the desired product (1.1 mg, 8%). The product was isolated as a single enantiomer. LCMS calculated for $C_{19}H_{23}ClN_5O$ (M+H)$^+$: m/z=372.2. Found: 372.2.

Example 194

{3-[1-(4-Amino-3-methyl-1H-pyrazolo[3,4-d]pyrimidin-1-yl)ethyl]-5-chloro-2-methoxy-6-methylphenyl}acetonitrile

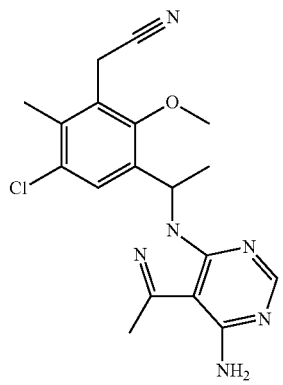 [SMILES: COc1c(C(C)Nc2ncnc(N)c2C(C)=N)cc(Cl)c(C)c1CC#N]

A mixture of 1-[1-(3-bromo-5-chloro-2-methoxy-4-methylphenyl)ethyl]-3-methyl-1H-pyrazolo[3,4-d]pyrimidin-4-amine (30 mg, 0.073 mmol) (Peak 1 from Example 167, step 4), 4-(4,4,5,5-tetramethyl-1,3,2-dioxaborolan-2-yl)isoxazole (0.018 g, 0.095 mmol, from Combi-Blocks Catalog, item # PN-8875), potassium fluoride (13 mg, 0.22 mmol) and [1,1'-bis(diphenylphosphino)ferrocene]-dichloropalladium(II), complex with dichloromethane (1:1) (12 mg, 0.015 mmol) in dimethyl sulfoxide (0.8 mL)/water (0.3 mL) was degassed with $N_2$ and then stirred at 130° C. for 16 h. The crude was purified using RP-HPLC (XBridge C18 column, eluting with a gradient of acetonitrile/water containing 0.1% ammonium hydroxide, at flow rate of 30 mL/min) to give the desired product (2.4 mg, 9%). The product was isolated as a single enantiomer. LCMS calculated for $C_{18}H_{20}ClN_6O$ (M+H)$^+$: m/z=371.1. Found: 371.1.

Example 195

5-(3-(1-(4-Amino-3-methyl-1H-pyrazolo[3,4-d]pyrimidin-1-yl)ethyl)-5-chloro-2-ethoxy-6-methylphenyl)-N,N-dimethylpicolinamide bis(2,2,2-trifluoroacetate)

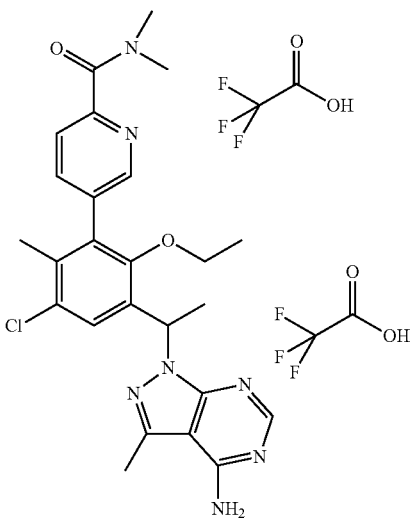

Step 1. 1-(3-Bromo-5-chloro-2-ethoxy-4-methylphenyl)ethanone

Into a round bottom flask was placed 1-(3-bromo-5-chloro-2-hydroxy-4-methylphenyl)ethanone (6.0 g, 23 mmol) in anhydrous DMF (22.8 mL). Potassium carbonate (6.3 g, 46 mmol) was then added followed by iodoethane (2.73 mL, 34.2 mmol). The resulting suspension was stirred at 60° C. for 2 h. The mixture was poured into 100 mL water and extracted with 200 mL of ethyl ether. The organic layers were separated, combined and washed with water and saturated NaCl solution, dried over anhydrous sodium sulfate, filtered, and concentrated to 6.0 g of tan oil. LCMS calculated for $C_{11}H_{13}BrClO_2$ (M+H)$^+$: m/z=293.0. Found: 293.0.

Step 2. 1-(3-Bromo-5-chloro-2-ethoxy-4-methylphenyl)ethanol

Sodium tetrahydroborate (0.31 g, 8.1 mmol) was added to a mixture of 1-(3-bromo-5-chloro-2-ethoxy-4-methylphenyl)ethanone (1.5 g, 5.4 mmol) in methanol (25 mL) at 0° C. and the resultant reaction mixture was stirred at room temperature for 1 hour. The solvent was removed and the resulting residue was diluted with ethyl acetate, washed with sat. NaHCO$_3$, water, brine, then dried over Na$_2$SO$_4$, filtered and concentrated. The crude product was purified by silica gel chromatography, eluting with 0 to 30% EtOAc in hexanes (0.30 g, 90%).

Step 3. 3-Bromo-1-chloro-5-(1-chloroethyl)-4-ethoxy-2-methylbenzene

A mixture of cyanuric chloride (1.7 g, 9.2 mmol) and N,N-dimethylformamide (710 µL, 9.2 mmol) was stirred at room temperature for 10 minutes and then a solution of 1-(3-bromo-5-chloro-2-ethoxy-4-methylphenyl)ethanol (1.72 g, 6.15 mmol) in methylene chloride (34 mL) was added and the reaction was stirred at room temperature overnight. The mixture was diluted with methylene chloride, washed with sat. NaHCO$_3$, water, brine, dried over Na$_2$SO$_4$, filtered and concentrated. The crude product was purified by silica gel chromatography, eluting with 0 to 10% EtOAc in hexanes (1.01 g, 60%).

Step 4. 1-(1-(3-Bromo-5-chloro-2-ethoxy-4-methylphenyl)ethyl)-3-methyl-1H-pyrazolo[3,4-d]pyrimidin-4-amine A mixture of 3-bromo-1-chloro-5-(1-chloroethyl)-4-ethoxy-2-methylbenzene (150 mg, 0.50 mmol), 3-methyl-1H-pyrazolo[3,4-d]pyrimidin-4-amine (110 mg, 0.76 mmol), potassium iodide (9 mg, 0.05 mmol) and cesium carbonate (330 mg, 1.0 mmol) in N,N-dimethylformamide (4 mL) was stirred at 140° C. for 1 h. The mixture was diluted with methylene chloride, washed with sat. NaHCO$_3$, water, brine, dried over Na$_2$SO$_4$, filtered and concentrated. The crude product was purified by silica gel chromatography, eluting with 0 to 70% EtOAc in CH$_2$Cl$_2$ (103 mg, 50%). LCMS calculated for $C_{17}H_{20}BrClN_5O$ (M+H)$^+$: m/z=423.1. Found: 423.0. The racemic products were applied on a Phenomenex Lux-Cellulose 1 column (21.1×250 mm, 5 micron particle size), eluting with 4% ethanol in hexanes at a flow rate of 18 mL/min, ~13 mg/injection, to provide two enantiomers. Peak 1, retention time: 8.64 min; Peak 2, retention time: 10.64 min.

Step 5. 5-(3-(1-(4-Amino-3-methyl-1H-pyrazolo[3,4-c]pyrimidin-1-yl)ethyl)-5-chloro-2-ethoxy-6-methylphenyl)-N,N-dimethylpicolinamide bis(2,2,2-trifluoroacetate)

A mixture of 1-[1-(3-bromo-5-chloro-2-ethoxy-4-methylphenyl)ethyl]-3-methyl-1H-pyrazolo[3,4-d]pyrimidin-4-amine (25 mg, 0.061 mmol) (first peak from previous step chiral separation), N,N-dimethyl-5-(4,4,5,5-tetramethyl-1,3,2-dioxaborolan-2-yl)pyridine-2-carboxamide (25 mg, 0.09 mmol), sodium carbonate (13 mg, 0.12 mmol) and [1,1'-bis(diphenylphosphino)-ferrocene]dichloropalladium (II), complex with dichloromethane (1:1) (9.9 mg, 0.012 mmol) in acetonitrile (0.8 mL)/water (0.3 mL) was degassed with N$_2$ and then stirred at 95° C. for 2 hours. After cooling to room temperature, the mixture was filtered and the filtrate purified on RP-HPLC (XBridge C18 column, eluting with a gradient of acetonitrile/water containing 0.05% trifluoroacetic acid, at flow rate of 30 mL/min) to give the desired product as bis-TFA salt (2.3 mg, 5%). The product was isolated as a single enantiomer. LCMS calculated for $C_{25}H_{29}ClN_7O_2$ (M+H)$^+$: m/z=494.2. Found: 494.2.

Example 200

4-(3-(1-(4-Amino-3-methyl-1H-pyrazolo[3,4-d]pyrimidin-1-yl)ethyl]-5-chloro-2-methoxy-6-methylphenyl)-N,N-dimethylpicolinamide bis(2,2,2-trifluoroacetate)

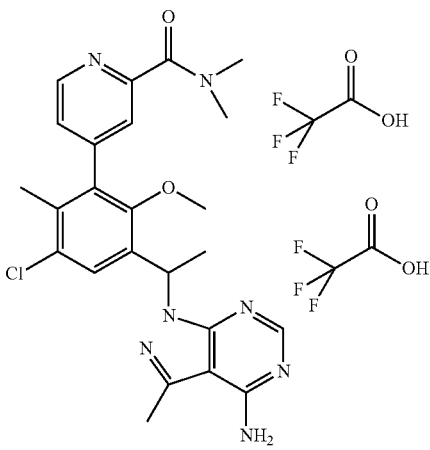

Step 1. 4-{3-[1-(4-Amino-3-methyl-1H-pyrazolo[3,4-d]pyrimidin-1-yl)ethyl]-5-chloro-2-methoxy-6-methylphenyl}pyridine-2-carbonitrile A mixture of 1-[1-(3-bromo-5-chloro-2-methoxy-4-methylphenyl)ethyl]-3-methyl-1H-pyrazolo[3,4-d]pyrimidin-4-amine (peak 1 from Example 167, step 4, 322 mg, 0.76 mmol), 4-(4,4,5,5-tetramethyl-1,3,2-dioxaborolan-2-yl)pyridine-2-carbonitrile (210 mg, 0.91 mmol, from Combi-Blocks Catalog, item # PN-0143), sodium carbonate (130 mg, 1.2 mmol) and [1,1'-bis(diphenylphosphino)ferrocene]-dichloropalladium(II), complex with dichloromethane (1:1) (99 mg, 0.12 mmol) in acetonitrile (5 mL)/water (2 mL) was degassed with $N_2$ and the reaction was stirred at 95° C. for 2 h. The mixture was diluted with methylene chloride, washed with sat. $NaHCO_3$, water, brine, dried over $Na_2SO_4$, filtered and concentrated. The product (0.28 g, 85%) was purified by chromatography eluting with $CH_2Cl_2$/MeOH (max. MeOH 6%). LCMS calculated for $C_{22}H_{21}ClN_7O$ $(M+H)^+$: m/z=434.1. Found: 434.1.

Step 2. 4-(3-(1-(4-Amino-3-methyl-1H-pyrazolo[3,4-d]pyrimidin-1-yl)ethyl]-5-chloro-2-methoxy-6-methylphenyl)picolinic acid dihydrochloride 1.0 M Sodium hydroxide (2.9 mL, 2.9 mmol) was added to a mixture of 4-{3-[1-(4-amino-3-methyl-1H-pyrazolo[3,4-d]pyrimidin-1-yl)ethyl]-5-chloro-2-methoxy-6-methylphenyl}pyridine-2-carbonitrile (0.250 g, 0.576 mmol) in ethanol (4.0 mL) and the resulting mixture was heated at 95° C. for 6 h. At this time, conc. HCl was added to adjust the pH to ~3. The solvent was removed and the residue was used in the next step without further purification. LCMS calculated for $C_{22}H_{22}ClN_6O_3$ $(M+H)^+$: m/z=453.1. Found: 453.2.

Step 3. 4-(3-(1-(4-Amino-3-methyl-1H-pyrazolo[3,4-c]pyrimidin-1-yl)ethyl)-5-chloro-2-methoxy-6-methylphenyl)-N,N-dimethylpicolinamide bis(2,2,2-trifluoroacetate)

2.0 M Dimethylamine in THF (2.0 mL, 4.0 mmol) was added to a solution of 4-{3-[1-(4-amino-3-methyl-1H-pyrazolo[3,4-d]pyrimidin-1-yl)ethyl]-5-chloro-2-methoxy-6-methylphenyl}pyridine-2-carboxylic acid (250 mg, 0.552 mmol) and benzotriazol-1-yloxytris(dimethylamino)phosphonium hexafluorophosphate (370 mg, 0.83 mmol) in N,N-dimethylformamide (4 mL) at 0° C. followed by adding triethylamine (0.23 mL, 1.6 mmol). The reaction was stirred for 1 h. The crude mixture was purified on RP-HPLC (XBridge C18 column, eluting with a gradient of acetonitrile/water containing 0.05% trifluoroacetic acid, at flow rate of 30 mL/min) to give the desired product as bis-TFA salt. The product was isolated as a single enantiomer. LCMS calculated for $C_{24}H_{27}ClN_7O_2$ $(M+H)^+$: m/z=480.2. Found: 480.2. $^1H$ NMR (DMSO-$d_6$, 500 MHz) δ 8.67 (br s, 1H), 8.36 (s, 1H), 7.58 (s, 1H), 7.41 (m, 2H), 6.32 (q, 2H), 3.20 (s, 3H), 3.00 (s, 3H), 2.94 (s, 3H), 2.62 (s, 3H), 2.03 (s, 3H), 1.80 (d, 3H) ppm.

Example 203

2-(4-(3-(1-(4-Amino-3-methyl-1H-pyrazolo[3,4-d]pyrimidin-1-yl)ethyl)-5-chloro-2-ethoxy-6-methylphenyl)-1H-pyrazol-1-yl)acetamide

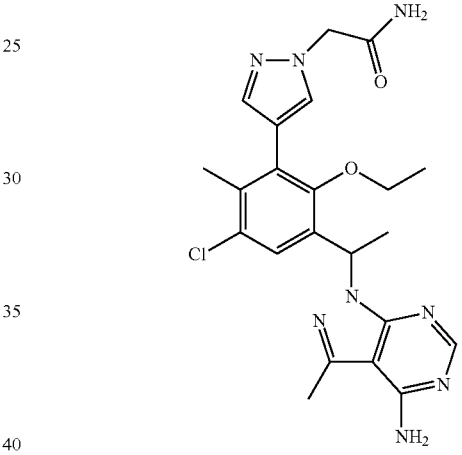

Step 1. tert-Butyl [4-(4,4,5,5-tetramethyl-1,3,2-dioxaborolan-2-yl)-1H-pyrazol-1-yl]acetate 1.0 M Potassium tert-butoxide in THF (2.4 mL, 2.4 mmol) was added to a solution of 4-(4,4,5,5-tetramethyl-1,3,2-dioxaborolan-2-yl)-1H-pyrazole (0.39 g, 2.0 mmol) in N,N-dimethylformamide (6.0 mL) at 0° C. The reaction mixture was stirred at room temperature for 5 min. After cooled to 0° C., to the mixture was added t-butyl bromoacetate (0.5 mL, 3 mmol). The reaction was stirred at room temperature for 2 h, then diluted with ethyl acetate, washed with sat. $NaHCO_3$, water, brine, dried over $Na_2SO_4$, filtered and concentrated. The product (0.5 g, 81%) was purified by chromatography eluting with hexanes/EtOAc (max. EtOAc 30%). LCMS calculated for $C_{15}H_{26}BN_2O_4$ $(M+H)^+$: m/z=309.2. Found: 309.1.

Step 2. tert-Butyl (4-{3-[1-(4-amino-3-methyl-1H-pyrazolo[3,4-d]pyrimidin-1-yl)ethyl]-5-chloro-2-ethoxy-6-methylphenyl}-1H-pyrazol-1-yl)acetate A mixture of 1-[1-(3-bromo-5-chloro-2-ethoxy-4-methylphenyl)ethyl]-3-methyl-1H-pyrazolo[3,4-d]pyrimidin-4-amine (70 mg, 0.16 mmol) (first peak from Example 195, step 4), tert-butyl [4-(4,4,5,5-tetramethyl-1,3,2-dioxaborolan-2-yl)-1H-pyrazol-1-yl]acetate (65 mg, 0.21 mmol), sodium carbonate (30. mg, 0.28 mmol) and [1,1'-bis(diphenylphosphino)ferrocene]dichloropalladium(II), complex with dichloromethane (1:1) (23 mg, 0.028 mmol) in acetonitrile (3 mL)/water (0.7 mL) was degassed with $N_2$ and then stirred at 95° C. for 2 h. The mixture was diluted with methylene chloride, washed with sat. $NaHCO_3$, water, brine, dried over $Na_2SO_4$, filtered and concentrated. The product (65 mg, 78%) was purified by chromatography eluting with $CH_2Cl_2$/MeOH (max. MeOH 5%). LCMS calculated for $C_{26}H_{33}ClN_7O_3$ $(M+H)^+$: m/z=526.2. Found: 526.3.

Step 3. (4-{3-[1-(4-Amino-3-methyl-1H-pyrazolo[3,4-d]pyrimidin-1-yl)ethyl]-5-chloro-2-ethoxy-6-methylphenyl}-1H-pyrazol-1-yl)acetic acid bis trifluoroacetate Trifluoroacetic acid (0.5 mL) was added to a solution of tert-butyl (4-{3-[1-(4-amino-3-methyl-1H-pyrazolo[3,4-d]pyrimidin-1-yl)ethyl]-5-chloro-2-ethoxy-6-methylphenyl}-1H-pyrazol-1-yl)acetate (0.065 g, 0.12 mmol) in methylene chloride (0.5 mL). The reaction was stirred at room temperature for 4 h. The solvent was removed to provide the crude product which was used in the next step. LCMS calculated for $C_{22}H_{25}ClN_7O_3$ $(M+H)^+$: m/z=470.2. Found: 470.1.

Step 4. 2-(4-{3-[1-(4-Amino-3-methyl-1H-pyrazolo[3,4-d]pyrimidin-1-yl)ethyl]-5-chloro-2-ethoxy-6-methylphenyl}-1H-pyrazol-1-yl)acetamide Ammonium carbonate (20 mg, 0.21 mmol) was added to a solution of (4-{3-[1-(4-amino-3-methyl-1H-pyrazolo[3,4-d]pyrimidin-1-yl)ethyl]-5-chloro-2-ethoxy-6-methylphenyl}-1H-pyrazol-1-yl)acetic acid bis trifluoroacetate (10 mg, 0.021 mmol) and benzotriazol-1-yloxytris(dimethylamino)phosphonium hexafluorophosphate (10 mg, 0.03 mmol) in N,N-dimethylformamide (0.7 mL) at room temperature followed by triethylamine (8.8 µL, 0.064 mmol). The reaction was stirred for 1 h. The crude was purified using RP-HPLC (XBridge C18 column, eluting with a gradient of acetonitrile/water containing 0.1% ammonium hydroxide, at flow rate of 30 mL/min) to give the desired product (2.5 mg, 25%). The product was isolated as a single enantiomer. LCMS calculated for $C_{22}H_{26}ClN_8O_2$ $(M+H)^+$: m/z=469.2. Found: 469.2.

Example 208

6-{3-[1-(4-Amino-3-methyl-1H-pyrazolo[3,4-d]pyrimidin-1-yl)ethyl]-5-chloro-2-ethoxy-6-methylphenyl}-N,N-dimethylnicotinamide bis(trifluoroacetate)

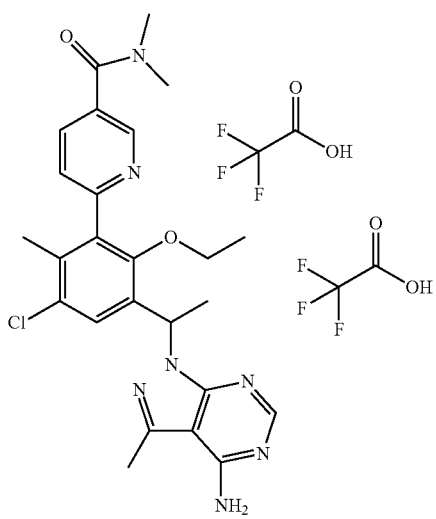

Step 1. 1-{1-[5-Chloro-2-ethoxy-4-methyl-3-(4,4,5,5-tetramethyl-1,3,2-dioxaborolan-2-yl)phenyl]ethyl}-3-methyl-1H-pyrazolo[3,4-d]pyrimidin-4-amine 1-[1-(3-Bromo-5-chloro-2-ethoxy-4-methylphenyl)ethyl]-3-methyl-1H-pyrazolo[3,4-d]pyrimidin-4-amine (0.050 g, 0.12 mmol, Peak 1 from Example 195, step 4) was combined in a microwave vial with potassium acetate (0.035 g, 0.35 mmol) and 4,4,5,5,4',4',5',5'-octamethyl-[2,2']bi[[1,3,2]dioxaborolanyl](0.060 g, 0.24 mmol) in dimethyl sulfoxide (0.44 mL) at room temperature. This was degassed with nitrogen and then [1,1'-bis(diphenylphosphino)ferrocene]-dichloropalladium(II), complex with dichloromethane (1:1) (0.01 g, 0.01 mmol) was added. The reaction was heated in an oil bath to 105° C. overnight. This was allowed to cool, then taken up in ethyl acetate and washed with water, brine, dried over magnesium sulfate and concentrated. The product (15 mg, 20%) was purified by chromatography eluting with $CH_2Cl_2$/MeOH (max. MeOH 10%). LCMS calculated for $C_{23}H_{32}BClN_5O_3$ $(M+H)^+$: m/z=472.2. Found: 472.3.

Step 2. 6-{3-[1-(4-Amino-3-methyl-1H-pyrazolo[3,4-d]pyrimidin-1-yl)ethyl]-5-chloro-2-ethoxy-6-methylphenyl}-N,N-dimethylnicotinamide bis(trifluoroacetate)

A mixture of 1-{1-[5-chloro-2-ethoxy-4-methyl-3-(4,4,5,5-tetramethyl-1,3,2-dioxaborolan-2-yl)phenyl]ethyl}-3-methyl-1H-pyrazolo[3,4-d]pyrimidin-4-amine (15 mg, 0.032 mmol), 6-chloro-N,N-dimethylnicotinamide (12 mg, 0.064 mmol), sodium carbonate (9.0 mg, 0.085 mmol) and [1,1'-bis(diphenylphosphino)ferrocene]-dichloropalladium (II), complex with dichloromethane (1:1) (6.9 mg, 0.0085 mmol) in acetonitrile (0.9 mL)/water (0.2 mL) was degassed with $N_2$ and then stirred at 95° C. overnight. The crude was purified using RP-HPLC (XBridge C18 column, eluting with a gradient of acetonitrile/water containing 0.05% trifluoroacetic acid, at flow rate of 30 mL/min) to give the desired product as TFA salt (2 mg, 9%). The product was isolated as a single enantiomer. LCMS calculated for $C_{25}H_{29}ClN_7O_2$ $(M+H)^+$: m/z=494.2. Found: 494.2.

Example 209

5-[1-(4-Amino-3-methyl-1H-pyrazolo[3,4-d]pyrimidin-1-yl)ethyl]-4-methoxy-2-methyl-3-(1-methyl-1H-pyrazol-4-yl)benzonitrile

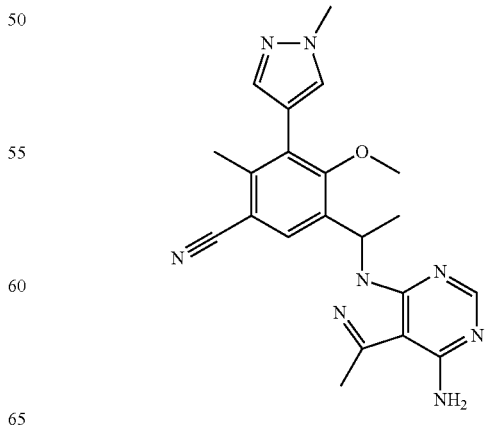

Pre-formed catalyst (0.05 mL, from Example 40) was added to a mixture 1-{1-[5-chloro-2-methoxy-4-methyl-3-

(1-methyl-1H-pyrazol-4-yl)phenyl]ethyl}-3-methyl-1H-pyrazolo[3,4-d]pyrimidin-4-amine (7.7 mg, 0.019 mmol), zinc (0.54 mg, 0.0082 mmol) and zinc cyanide (2.2 mg, 0.019 mmol) in N,N-dimethylacetamide (0.3 mL). The mixture was degassed with nitrogen 3 times. The reaction was heated at 120° C. for 1.5 h. The crude was purified using RP-HPLC (XBridge C18 column, eluting with a gradient of acetonitrile/water containing 0.1% ammonium hydroxide, at flow rate of 30 mL/min) to give the desired product (2.1 mg, 27%). The product was isolated as a single enantiomer. LCMS calculated for $C_{21}H_{23}N_8O$ $(M+H)^+$: m/z=403.2. Found: 403.2.

Example 211

3-[1-(4-Amino-3-methyl-1H-pyrazolo[3,4-d]pyrimidin-1-yl)ethyl]-5-chloro-2-ethoxy-6-methylbenzonitrile

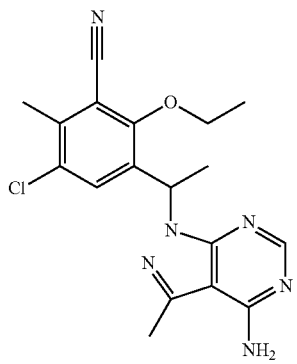 [SMILES: CCOc1c(C(C)Nc2ncnc(N)c2C(C)=N)cc(Cl)c(C)c1C#N]

N,N,N',N'-Tetramethylethylenediamine (10 μL, 0.07 mmol), zinc cyanide (3 mg, 0.03 mmol), tris(dibenzylideneacetone)dipalladium(0) (0.9 mg, 0.001 mmol) and (9,9-dimethyl-9H-xanthene-4,5-diyl)bis(diphenylphosphine) (2 mg, 0.003 mmol) was added successively to a solution of 1-[1-(3-bromo-5-chloro-2-ethoxy-4-methylphenyl)ethyl]-3-methyl-1H-pyrazolo[3,4-d]pyrimidin-4-amine (14 mg, 0.033 mmol, Peak 1 from Example 195, step 4) in N,N-dimethylformamide (0.5 mL) in a microwave tube. The tube was sealed and degassed and refilled with $N_2$ three times, and then heated at 160° C. under microwave irradiation for 400 seconds. The mixture was cooled, filtered and the crude filtrate was purified using RP-HPLC (XBridge C18 column, eluting with a gradient of acetonitrile/water containing 0.1% ammonium hydroxide, at flow rate of 30 mL/min) to give the desired product (2.4 mg, 20%). The product was isolated as a single enantiomer. LCMS calculated for $C_{18}H_{20}ClN_6O$ $(M+H)^+$: m/z=371.1. Found: 371.2.

Experimental procedures for the compounds of Examples 69, 70, 75, 78, 97, 98, 100, 103, 106, 107, 109, 111, 112, 114, 116, 119, 120, 122-124, 132, 135, 142-148, 151, 153-155, 157, 160, 162, 168-173, 175-178, 180, 185-187, 193, 196-199, 201, 202, 204-207, and 210 are summarized in Tables 1 and 2.

TABLE 1

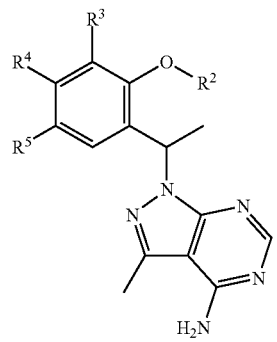

| Ex. No. | Name | $R^2$ | $R^4$ | $R^5$ | $R^3$ | Salt | Proc.[1] |
|---|---|---|---|---|---|---|---|
| 69 | (2R)-1-(3-{3-[1-(4-Amino-3-methyl-1H-pyrazolo[3,4-d]pyrimidin-1-yl)ethyl]-5-eyloro-6-fluoro-2-methoxyphenyl}azetidin-1-yl)propan-2-ol[2] | Me | F | Cl | 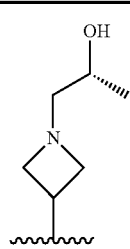 | | 68 |

TABLE 1-continued

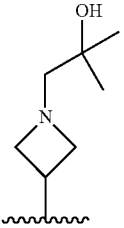 [SMILES: *C1CN(CC(C)(C)O)C1]

| Ex. No. | Name | R² | R⁴ | R⁵ | R³ | Salt | Proc.¹ |
|---|---|---|---|---|---|---|---|
| 70 | 1-(3-{3-[1-(4-Amino-3-methyl-1H-pyrazolo[3,4-d]pyrimidin-1-yl)ethyl]-5-chloro-6-fluoro-2-methoxyphenyl}azetidin-1-yl)-2-methylpropan-2-ol² | Me | F | Cl | 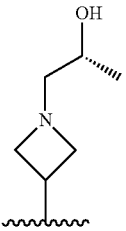 | | 68 |
| 97 | (2R)-1-(3-{3-[1-(4-Amino-3-methyl-1H-pyrazolo[3,4-d]pyrimidin-1-yl)ethyl]-5-chloro-2-ethoxy-6-methylphenyl}azetidin-1-yl)propan-2-ol² | Et | Me | Cl | 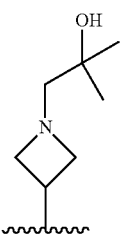 [SMILES: *C1CN(CC(C)(C)O)C1] | 22 TFA | 96 |
| 98 | 1-(3-{3-[1-(4-Amino-3-methyl-1H-pyrazolo[3,4-d]pyrimidin-1-yl)ethyl]-5-chloro-2-ethoxy-6-methylphenyl}azetidin-1-yl)-2-methylpropan-2-ol³ | Et | Me | Cl | | 2 TFA | 96 |
| 100 | (2R)-1-(3-{3-[1-(4-Amino-3-methyl-1H-pyrazolo[3,4-d]pyrimidin-1-yl)ethyl]-5-chloro-2-ethoxy-6-methylphenyl}azetidin-1-yl)-1-oxopropan-2-ol² | Et | Me | Cl | 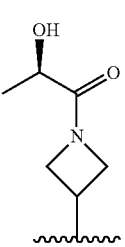 [SMILES: *C1CN(C(=O)[C@@H](C)O)C1] | TFA | 99 |
| 103 | (2R)-1-(3-{3-[1-(4-Amino-3-methyl-1H-pyrazolo[3,4-d]pyrimidin-1-yl)ethyl]-5-chloro-2-methoxy-6-methylphenyl}azetidin-1-yl)propan-2-ol⁵ | Me | Me | Cl | 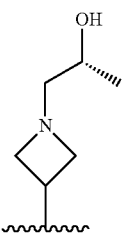 [SMILES: *C1CN(C[C@@H](C)O)C1] | | 102 |

TABLE 1-continued

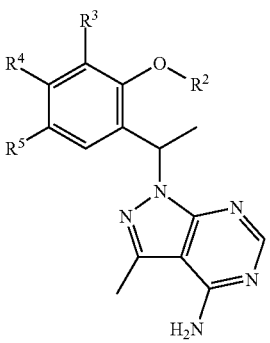

| Ex. No. | Name | R² | R⁴ | R⁵ | R³ | Salt | Proc.¹ |
|---|---|---|---|---|---|---|---|
| 106 | 2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)propanenitrile⁴ | Me | Me | Cl | azetidinyl-CH(CH₃)CN | | 105 |
| 107 | 1-(1-{5-Chloro-2-methoxy-4-methyl-3-[1-(tetrahydrofuran-3-yl)azetidin-3-yl]phenyl}ethyl)-3-methyl-1H-pyrazolo[3,4-d]pyrimidin-4-amine⁴ | Me | Me | Cl | azetidinyl-tetrahydrofuran-3-yl | | 1 |
| 109 | 3-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-1,1,1-trifluoropropan-2-ol⁴ | Me | Me | Cl | azetidinyl-CH₂CH(OH)CF₃ | | 102 |
| 111 | 2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)acetamide³ | Me | Me | Cl | azetidinyl-CH₂C(O)NH₂ | | 105 |
| 112 | 1-(1-{5-Chloro-3-[1-(2,2-difluoroethyl)azetidin-3-yl]-2-methoxy-4-methylphenyl}ethyl)-3-methyl-1H-pyrazolo[3,4-d]pyrimidin-4-amine³ | Me | Me | Cl | azetidinyl-CH₂CHF₂ | | 105 |

TABLE 1-continued

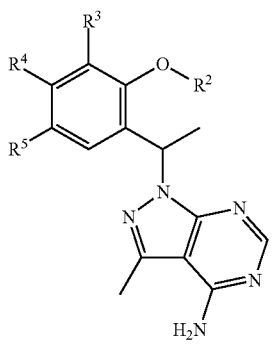

| Ex. No. | Name | R² | R⁴ | R⁵ | R³ | Salt | Proc.¹ |
|---|---|---|---|---|---|---|---|
| 114 | 1-(1-{5-Chloro-3-[1-(2-fluoro-1-methylethyl)azetidin-3-yl]-2-methoxy-4-methylphenyl}ethyl)-3-methyl-1H-pyrazolo[3,4-d]pyrimidin-4-amine⁴ | Me | Me | Cl | 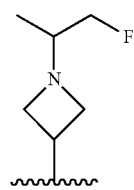 [SMILES: *C1CN(C(C)CF)C1] | | 1 |
| 116 | (2S)-3-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-1,1,1-trifluoropropan-2-ol⁵ | Me | Me | Cl | 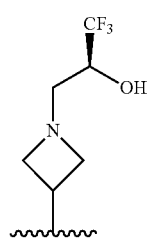 [SMILES: *C1CN(C[C@H](O)C(F)(F)F)C1] | | 115 |
| 119 | 1-(1-{5-Chloro-3-[1-(cyclopropylcarbonyl)azetidin-3-yl]-2-methoxy-4-methylphenyl}ethyl)-3-methyl-1H-pyrazolo[3,4-d]pyrimidin-4-amine³ | Me | Me | Cl | 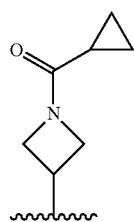 [SMILES: *C1CN(C(=O)C2CC2)C1] | TFA | 117 |
| 120 | 1-[1-(5-Chloro-2-methoxy-4-methyl-3-{1-[(5-methylisoxazol-4-yl)carbonyl]azetidin-3-yl}phenyl)ethyl]-3-methyl-1H-pyrazolo[3,4-d]pyrimidin-4-amine³ | Me | Me | Cl | 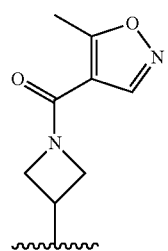 [SMILES: *C1CN(C(=O)c2cnoc2C)C1] | TFA | 117 |
| 122 | 1-[(3-{3-[1-(4-Amino-3-methyl-1H-pyrazolo[3,4-d]pyrimidin-1-yl)ethyl]-5-chloro-2-methoxy-6-methylphenyl}azetidin-1-yl)carbonyl]cyclopropanol³ | Me | Me | Cl | 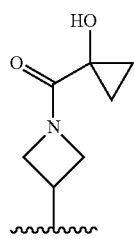 [SMILES: *C1CN(C(=O)C2(O)CC2)C1] | TFA | 121 |

TABLE 1-continued

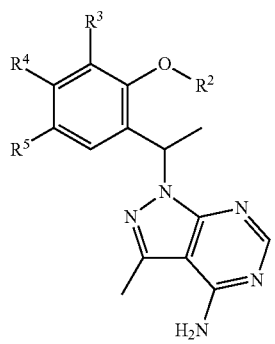

| Ex. No. | Name | R² | R⁴ | R⁵ | R³ | Salt | Proc.¹ |
|---|---|---|---|---|---|---|---|
| 123 | 1-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-2-methyl-1-oxopropan-2-ol³ | Me | Me | Cl | ![structure] | TFA | 121 |
| 124 | 1-(1-{5-Chloro-2-methoxy-4-methyl-3-[1-(1H-pyrazol-4-ylcarbonyl)azetidin-3-yl]phenyl}ethyl)-3-methyl-1H-pyrazolo[3,4-d]pyrimidin-4-amine³ | Me | Me | Cl | ![structure] | TFA | 121 |
| 142 | (2R)-1-(3-{3-[1-(4-Amino-3-methyl-1H-pyrazolo[3,4-d]pyrimidin-1-yl)ethyl]-5-chloro-2-ethoxy-6-fluorophenyl}azetidin-1-yl)propan-2-ol⁴ | Et | F | Cl | ![structure] |  | 140 |
| 143 | (2S)-1-(3-{3-[1-(4-Amino-3-methyl-1H-pyrazolo[3,4-d]pyrimidin-1-yl)ethyl]-5-chloro-2-ethoxy-6-fluorophenyl}azetidin-1-yl)propan-2-ol⁴ | Et | F | Cl | ![structure] |  | 140 |
| 144 | 2-(3-{3-[1-(4-Amino-3-methyl-1H-pyrazolo[3,4-d]pyrimidin-1-yl)ethyl]-5-chloro-2-ethoxy-6-fluorophenyl}azetidin-1-yl)ethanol² | Et | F | Cl | ![structure] |  | 139 |

TABLE 1-continued

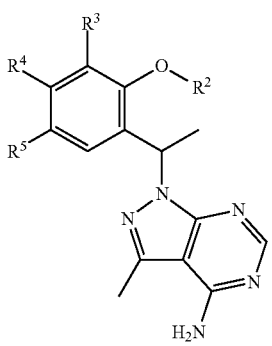

| Ex. No. | Name | R² | R⁴ | R⁵ | R³ | Salt | Proc.¹ |
|---|---|---|---|---|---|---|---|
| 145 | 1-{1-[5-Chloro-2-ethoxy-4-fluoro-3-(1-methylazetidin-3-yl)phenyl]ethyl}-3-methyl-1H-pyrazolo[3,4-d]pyrimidin-4-amine² | Et | F | Cl | 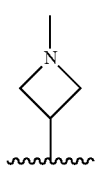 [SMILES: *C1CN(C)C1] | | 139 |
| 146 | 1-{1-[5-Chloro-2-ethoxy-3-(1-ethylazetidin-3-yl)-4-fluorophenyl]ethyl}-3-methyl-1H-pyrazolo[3,4-d]pyrimidin-4-amine² | Et | F | Cl | 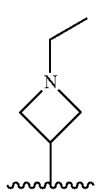 [SMILES: *C1CN(CC)C1] | | 139 |
| 147 | 1-(1-{5-Chloro-3-[1-(2,2-difluoroethyl)azetidin-3-yl]-2-ethoxy-4-fluorophenyl}ethyl)-3-methyl-1H-pyrazolo[3,4-d]pyrimidin-4-amine² | Et | F | Cl | 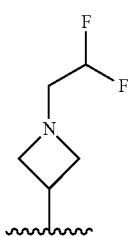 [SMILES: *C1CN(CC(F)F)C1] | | 141 |
| 148 | 2-(3-{3-[1-(4-Amino-3-methyl-1H-pyrazolo[3,4-d]pyrimidin-1-yl)ethyl]-5-chloro-2-ethoxy-6-fluorophenyl}azetidin-1-yl)acetamide² | Et | F | Cl | 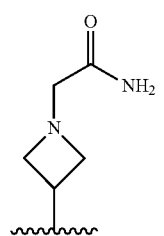 [SMILES: *C1CN(CC(N)=O)C1] | | 141 |
| 157 | (2S)-2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)propan-1-ol⁵ | Me | Me | Cl | 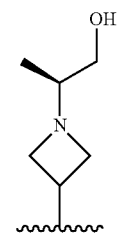 [SMILES: *C1CN([C@@H](C)CO)C1] | | 156 |

TABLE 1-continued

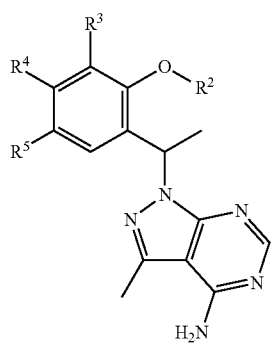

| Ex. No. | Name | R² | R⁴ | R⁵ | R³ | Salt | Proc.¹ |
|---|---|---|---|---|---|---|---|
| 160 | (2S)-2-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-N,N-dimethylpropanamide⁵ | Me | Me | Cl | 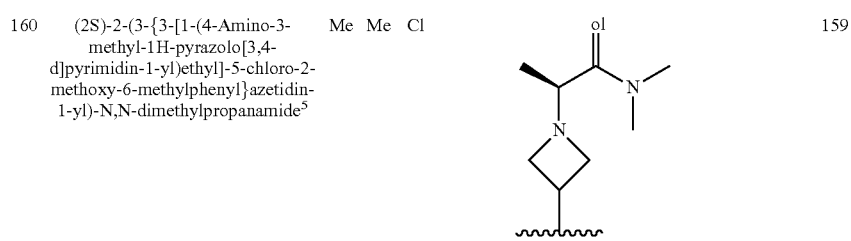 | | 159 |
| 162 | 3-(3-{3-[1-(4-Amino-3-methyl-1H-pyrazolo[3,4-d]pyrimidin-1-yl)ethyl]-5-chloro-2-methoxy-6-methylphenyl}azetidin-1-yl)-2-methylpropanenitrile⁴ | Me | Me | Cl | 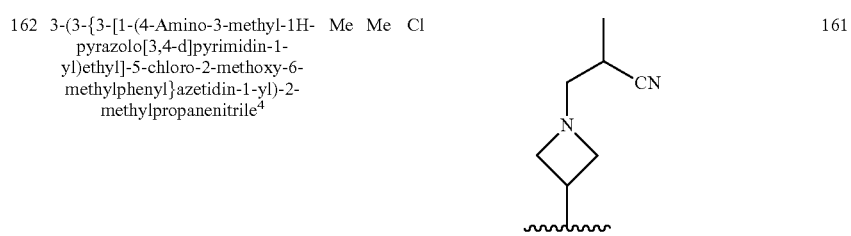 | | 161 |
| 168 | 1-(1-(5-chloro-2-methoxy-4-methyl-3-(pyrimidin-5-yl)phenyl)ethyl)-3-methyl-1H-pyrazolo[3,4-d]pyrimidin-4-amine³ | Me | Me | Cl | 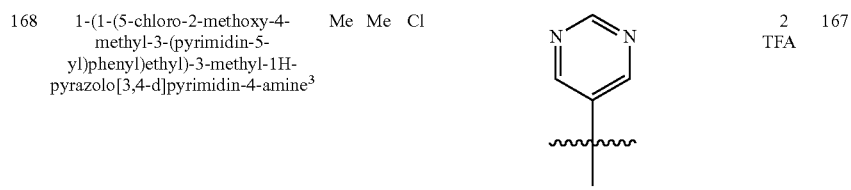 | 2 TFA | 167 |
| 169 | 1-(1-(3-(2-aminopyrimidin-5-yl)-5-chloro-2-methoxy-4-methylphenyl)ethyl)-3-methyl-1H-pyrazolo[3,4-d]pyrimidin-4-amine³ | Me | Me | Cl | 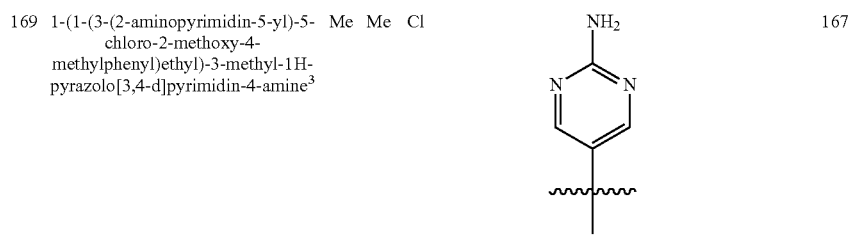 | | 167 |
| 170 | 5-(3-(1-(4-amino-3-methyl-1H-pyrazolo[3,4-d]pyrimidin-1-yl)ethyl)-5-chloro-2-methoxy-6-methylphenyl)nicotinonitrile³ | Me | Me | Cl | 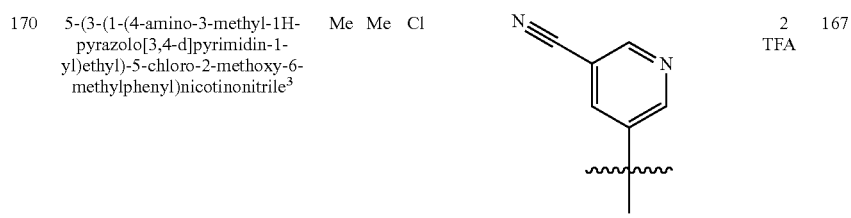 | 2 TFA | 167 |

TABLE 1-continued

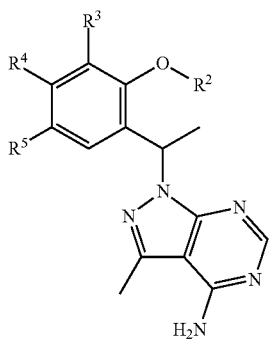

| Ex. No. | Name | R² | R⁴ | R⁵ | R³ | Salt | Proc.¹ |
|---|---|---|---|---|---|---|---|
| 171 | 1-(1-(3-(6-aminopyridin-3-yl)-5-chloro-2-methoxy-4-methylphenyl)ethyl)-3-methyl-1H-pyrazolo[3,4-d]pyrimidin-4-amine³ | Me | Me | Cl | 6-aminopyridin-3-yl | | 167 |
| 172 | 1-(1-(5-chloro-2-methoxy-4-methyl-3-(5-(methylsulfonyl)pyridin-3-yl)phenyl)ethyl)-3-methyl-1H-pyrazolo[3,4-d]pyrimidin-4-amine³ | Me | Me | Cl | 5-(methylsulfonyl)pyridin-3-yl | | 167 |
| 173 | 5-(3-(1-(4-amino-3-methyl-1H-pyrazolo[3,4-d]pyrimidin-1-yl)ethyl)-5-chloro-2-methoxy-6-methylphenyl)-N-methylpicolinamide³ | Me | Me | Cl | N-methylpicolinamide-5-yl | | 167 |
| 175 | 5-{3-[1-(4-amino-3-methyl-1H-pyrazolo[3,4-d]pyrimidin-1-yl)ethyl]-5-chloro-2-methoxy-6-methylphenyl}-N-(2-hydroxyethyl)-N-methylnicotinamide³ | Me | Me | Cl | N-(2-hydroxyethyl)-N-methylnicotinamide-5-yl | 2 TFA | 174 |
| 176 | 1-[(5-{3-[1-(4-amino-3-methyl-1H-pyrazolo[3,4-d]pyrimidin-1-yl)ethyl]-5-chloro-2-methoxy-6-methylphenyl}pyridin-3-yl)carbonyl]piperidin-4-ol³ | Me | Me | Cl | (piperidin-4-ol-1-yl)carbonyl-pyridin-5-yl | 2 TFA | 174 |

TABLE 1-continued

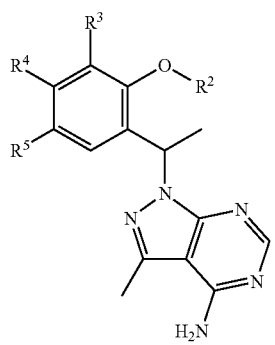

| Ex. No. | Name | R² | R⁴ | R⁵ | R³ | Salt | Proc.¹ |
|---|---|---|---|---|---|---|---|
| 177 | 1-[(5-{3-[1-(4-amino-3-methyl-1H-pyrazolo[3,4-d]pyrimidin-1-yl)ethyl]-5-chloro-2-methoxy-6-methylphenyl}pyridin-3-yl)carbonyl]azetidine-3-carbonitrile³ | Me | Me | Cl | pyridinyl-carbonyl-azetidine-3-carbonitrile | 2 TFA | 174 |
| 178 | 5-(3-(1-(4-amino-3-methyl-1H-pyrazolo[3,4-d]pyrimidin-1-yl)ethyl)-5-chloro-2-methoxy-6-methylphenyl)-N-(2-aminoethyl)-N-methylnicotinamide³ | Me | Me | Cl | N-(2-aminoethyl)-N-methylnicotinamide | 3 TFA | 174 |
| 180 | 3-(3-(1-(4-Amino-3-methyl-1H-pyrazolo[3,4-d]pyrimidin-1-yl)ethyl)-5-chloro-2-methoxy-6-methylphenyl)-N,N-dimethylpropanamide³ | Me | | Cl | N,N-dimethylpropanamide | TFA | 179 |
| 185 | 1-(1-(5-chloro-3-(6-(dimethylamino)pyridin-3-yl)-2-methoxy-4-methylphenyl)ethyl)-3-methyl-1H-pyrazolo[3,4-d]pyrimidin-4-amine³ | Me | Me | Cl | 6-(dimethylamino)pyridin-3-yl | 2 TFA | 184 |
| 186 | 1-(1-(5-chloro-3-(2-(dimethylamino)pyridin-4-yl)-2-methoxy-4-methylphenyl)ethyl)-3-methyl-1H-pyrazolo[3,4-d]pyrimidin-4-amine³ | Me | Me | Cl | 2-(dimethylamino)pyridin-4-yl | | 184 |

TABLE 1-continued

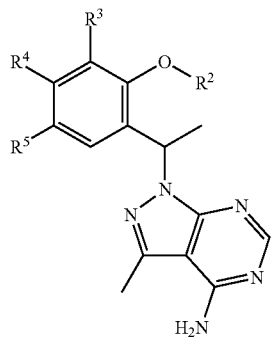

| Ex. No. | Name | R² | R⁴ | R⁵ | R³ | Salt | Proc.¹ |
|---|---|---|---|---|---|---|---|
| 187 | 1-(4-(3-(1-(4-amino-3-methyl-1H-pyrazolo[3,4-d]pyrimidin-1-yl)ethyl)-5-chloro-2-methoxy-6-methylphenyl)pyridin-2-yl)azetidin-3-ol³ | Me | Me | Cl | 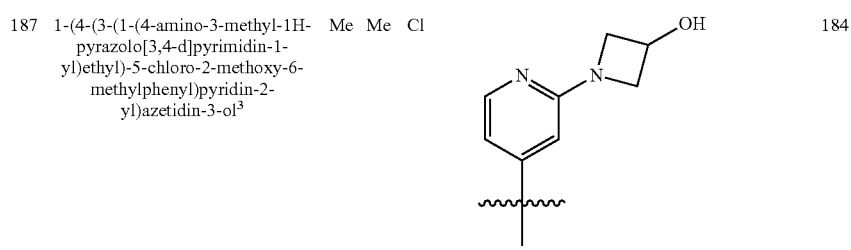 | | 184 |
| 193 | 1-{1-[5-Chloro-3-(cyclopropylmethyl)-2-methoxy-4-methylphenyl]ethyl}-3-methyl-1H-pyrazolo[3,4-d]pyrimidin-4-amine³ | Me | Me | Cl | 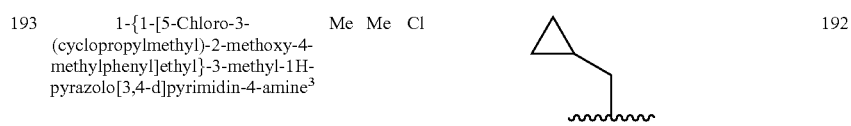 | | 192 |
| 196 | 5-(3-(1-(4-amino-3-methyl-1H-pyrazolo[3,4-d]pyrimidin-1-yl)ethyl)-5-chloro-2-ethoxy-6-methylphenyl)-N,N-dimethylnicotinamide³ | Et | Me | Cl | 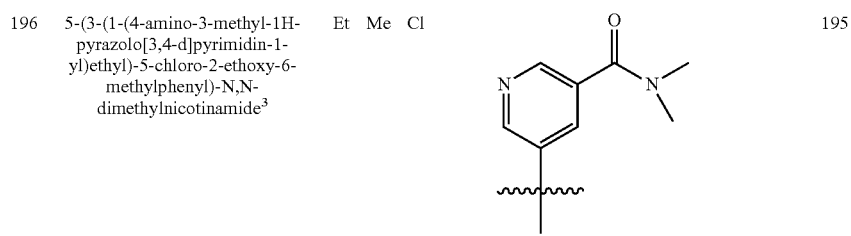 | | 195 |
| 197 | 1-(1-(5-chloro-2-ethoxy-4-methyl-3-(1-methyl-1H-pyrazol-4-yl)phenyl)ethyl)-3-methyl-1H-pyrazolo[3,4-d]pyrimidin-4-amine³ | Et | Me | Cl | 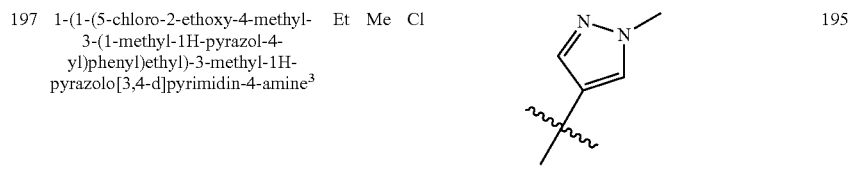 | | 195 |
| 198 | 1-(1-(5-chloro-2-ethoxy-4-methyl-3-(5-(methylsulfonyl)pyridin-3-yl)phenyl)ethyl)-3-methyl-1H-pyrazolo[3,4-d]pyrimidin-4-amine³ | Et | Me | Cl | 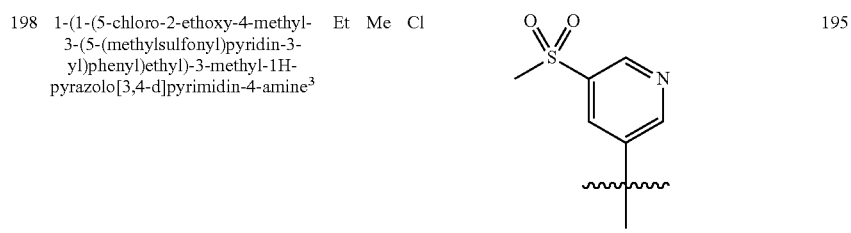 | | 195 |

TABLE 1-continued

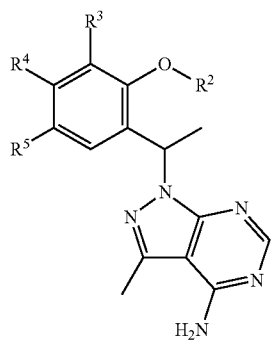

| Ex. No. | Name | R² | R⁴ | R⁵ | R³ | Salt | Proc.¹ |
|---|---|---|---|---|---|---|---|
| 199 | 5-(3-(1-(4-amino-3-methyl-1H-pyrazolo[3,4-d]pyrimidin-1-yl)ethyl)-5-chloro-2-ethoxy-6-methylphenyl)-N-methylpicolinamide³ | Et | Me | Cl | | | 195 |
| 201 | 4-(3-(1-(4-amino-3-methyl-1H-pyrazolo[3,4-d]pyrimidin-1-yl)ethyl)-5-chloro-2-ethoxy-6-methylphenyl)-N,N-dimethylpicolinamide³ | Et | Me | Cl | | | 200 |
| 202 | 4-(3-(1-(4-amino-3-methyl-1H-pyrazolo[3,4-d]pyrimidin-1-yl)ethyl)-5-chloro-2-ethoxy-6-methylphenyl)-N-(2-hydroxyethyl)-N-methylpicolinamide3 | Et | Me | Cl | | | 200 |
| 204 | 2-(4-(3-(1-(4-amino-3-methyl-1H-pyrazolo[3,4-d]pyrimidin-1-yl)ethyl)-5-chloro-2-ethoxy-6-methylphenyl)-1H-pyrazol-1-yl)-N-methylacetamide³ | Et | Me | Cl | | | 203 |
| 205 | 2-(4-(3-(1-(4-amino-3-methyl-1H-pyrazolo[3,4-d]pyrimidin-1-yl)ethyl)-5-chloro-2-ethoxy-6-methylphenyl)-1H-pyrazol-1-yl)-N,N-dimethylacetamide³ | Et | Me | Cl | | | 203 |

TABLE 1-continued

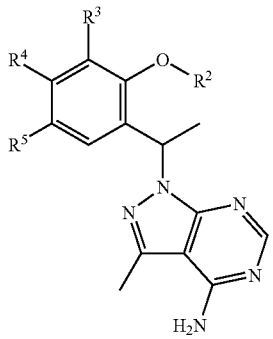

| Ex. No. | Name | R² | R⁴ | R⁵ | R³ | Salt | Proc.¹ |
|---|---|---|---|---|---|---|---|
| 206 | 2-(4-(3-(1-(4-amino-3-methyl-1H-pyrazolo[3,4-d]pyrimidin-1-yl)ethyl)-5-chloro-2-methoxy-6-methylphenyl)-1H-pyrazol-1-yl)-N,N-dimethylacetamide³ | Me | Me | Cl | 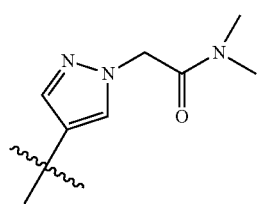 [SMILES: *c1cnn(CC(=O)N(C)C)c1] | | 203 |
| 207 | 2-(4-(3-(1-(4-amino-3-methyl-1H-pyrazolo[3,4-d]pyrimidin-1-yl)ethyl)-5-chloro-2-methoxy-6-methylphenyl)-1H-pyrazol-1-yl)-N,N-dimethylpropanamide⁴ | Me | Me | Cl | 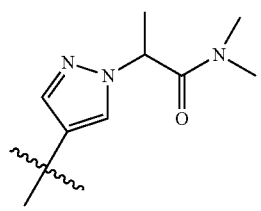 [SMILES: *c1cnn(C(C)C(=O)N(C)C)c1] | | 203 |
| 210 | 5-[1-(4-Amino-3-methyl-1H-pyrazolo[3,4-d]pyrimidin-1-yl)ethyl]-4-ethoxy-2-methyl-3-(1-methyl-1H-pyrazol-4-yl)benzonitrile³ | Et | Me | CN | 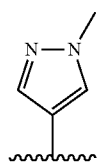 | | 209 |

¹Synthesized according to the experimental procedure of compound listed;
²Compound isolated as a racemic mixture;
³Compound isolated as a single enantiomer;
⁴Compound isolated as a mixture of diastereomers;
⁵Compound isolated as a single diastereomer.

TABLE 2

| Ex. No. | Name | R² | R⁴ | R⁵ | R³ | Salt | Proc.[1] |
|---|---|---|---|---|---|---|---|
| 75 | 1-{1-[5-Chloro-4-fluoro-2-methoxy-3-(1-methylazetidin-3-yl)phenyl]ethyl}-3-(difluoromethyl)-1H-pyrazolo[3,4-d]pyrimidin-4-amine[2] | Me | F | Cl | 1-methylazetidin-3-yl | | 73 |
| 78 | 5-{1-[4-Amino-3-(difluoromethyl)-1H-pyrazolo[3,4-d]pyrimidin-1-yl]ethyl}-2-fluoro-3-[1-(2-hydroxyethyl)azetidin-3-yl]-4-methoxybenzonitrile[2] | Me | F | CN | 1-(2-hydroxyethyl)azetidin-3-yl | | 77 |
| 132 | 5-{1-[4-Amino-3-(difluoromethyl)-1H-pyrazolo[3,4-d]pyrimidin-1-yl]ethyl}-3-{1-[(2R)-2-hydroxypropyl]azetidin-3-yl}-4-methoxy-2-methylbenzonitrile[4] | Me | Me | CN | 1-[(2R)-2-hydroxypropyl]azetidin-3-yl | | 131 |
| 135 | (2R)-2-[3-(3-{1-[4-Amino-3-(difluoromethyl)-1H-pyrazolo[3,4-d]pyrimidin-1-yl]ethyl}-5-cyano-2-methoxy-6-methylphenyl)azetidin-1-yl]-N-methylpropanamide[4] | Me | Me | CN | N-methylpropanamide-azetidin-3-yl | | 134 |
| 151 | 1-{1-[5-Chloro-2-ethoxy-4-fluoro-3-(1-methylazetidin-3-yl)phenyl]ethyl}-3-(difluoromethyl)-1H-pyrazolo[3,4-d]pyrimidin-4-amine[2] | Et | F | Cl | 1-methylazetidin-3-yl | | 150 |
| 153 | 1-[3-(3-{1-[4-Amino-3-(difluoromethyl)-1H-pyrazolo[3,4-d]pyrimidin-1-yl]ethyl}-5-chloro-2-ethoxy-6-fluorophenyl)azetidin-1-yl]-2-methylpropan-2-ol[2] | Et | F | Cl | 1-(2-hydroxy-2-methylpropyl)azetidin-3-yl | | 140 |

TABLE 2-continued

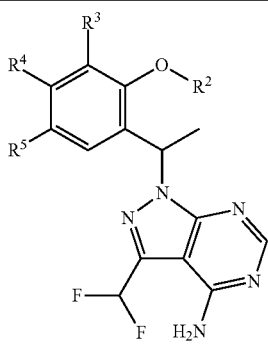

| Ex. No. | Name | R² | R⁴ | R⁵ | R³ | Salt | Proc.¹ |
|---|---|---|---|---|---|---|---|
| 154 | (2S)-1-[3-(3-{1-[4-Amino-3-(difluoromethyl)-1H-pyrazolo[3,4-d]pyrimidin-1-yl]ethyl}-5-chloro-2-ethoxy-6-fluorophenyl)azetidin-1-yl]propan-2-ol⁴ | Et | F | Cl |  |  | 140 |
| 155 | (2R)-1-[3-(3-{1-[4-Amino-3-(difluoromethyl)-1H-pyrazolo[3,4-d]pyrimidin-1-yl]ethyl}-5-chloro-2-ethoxy-6-fluorophenyl)azetidin-1-yl]propan-2-ol⁴ | Et | F | Cl |  |  | 140 |

¹Synthesized according to the experimental procedure of compound listed;
²Compound isolated as a racemic mixture;
⁴Compound isolated as a mixture of diastereomers.

Analytical Data

¹H NMR data (Varian Inova 500 spectrometer, a Mercury 400 spectrometer, or a Varian (or Mercury) 300 spectrometer) and LCMS mass spectral data (MS) for the compounds of Examples 69, 70, 75, 78, 97, 98, 100, 102-138, 142-148, 151, 153-155, 157, 160, 162, 168-173, 175-178, 180, 185-187, 193, 196-199, 201, 202, 204-207, and 210 is provided below in Table 3.

TABLE 3

| Ex. No. | MS [M + H]⁺ | Solvent | MHz | ¹H NMR Spectra |
|---|---|---|---|---|
| 69 | 449.1 | — | — | — |
| 70 | 463.2 | — | — | — |
| 75 | 441.1 | — | — | — |
| 78 | 462.2 | — | — | — |
| 97 | 459.1 | — | — | — |
| 98 | 473.2 | — | — | — |
| 100 | 473.1 | — | — | — |
| 102 | 445.2 | — | — | — |
| 103 | 445.3 | CDCl₃ | 300 | δ 8.29 (s, 1H), 7.41 (s, 1H), 6.37 (q, J = 7.0 Hz, 1H), 5.40 (s, 2H), 4.18-3.66 (m, 4H), 3.58 (s, 3H), 3.27-3.02 (m, 2H), 2.65 (s, 3H), 2.53-2.21 (m, 2H), 2.11 (s, 3H), 1.93-1.60 (m, 4H), 1.12 (d, J = 6.2 Hz, 3H). |
| 104 | 431.3 | — | — | — |
| 105 | 426.0 | CDCl₃ | 400 | δ 8.28 (s, 1H), 7.44 (s, 1H), 6.36 (q, J = 7.1 Hz, 1H), 5.46 (s, 2H), 4.05-3.78 (m, 3H), 3.59 (s, 3H), 3.53-3.38 (m, 3H), 3.25 (dd, J = 8.6, 6.0 Hz, 1H), 2.65 (s, 3H), 2.12 (s, 3H), 1.83 (d, J = 7.1 Hz, 3H). |
| 106 | 440.2 | CDCl₃ | 400 | δ 8.29 (s, 1H), 7.44 (s, 1H), 6.37 (q, J = 6.9 Hz, 1H), 5.40 (s, 2H), 4.08-3.76 (m, 3H), 3.67-3.47 (m, 4H), 3.40 (q, J = 6.6 Hz, 1H), 3.20 (dd, J = 8.0, 4.2 Hz, 1H), 2.65 (s, 3H), 2.13 (d, J = 4.1 Hz, 3H), 1.83 (dd, J = 7.1, 1.1 Hz, 3H), 1.35 (dd, J = 7.1, 2.1 Hz, 3H). |

TABLE 3-continued

| Ex. No. | MS [M + H]+ | Solvent | MHz | 1H NMR Spectra |
|---|---|---|---|---|
| 107 | 457.1 | CDCl3 | 300 | δ 8.29 (s, 1H), 7.41 (s, 1H), 6.37 (q, J = 7.0 Hz, 1H), 5.42 (s, 2H), 4.13-3.70 (m, 6H), 3.70-3.43 (m, 6H), 3.20-2.99 (m, 1H), 2.99-2.77 (m, 2H), 2.65 (s, 3H), 2.12 (d, J = 1.9 Hz, 3H), 1.83 (d, J = 7.1 Hz, 3H). |
| 108 | 469.1 | CDCl3 | 300 | δ 8.28 (d, J = 1.6 Hz, 1H), 7.41 (s, 1H), 6.37 (q, J = 7.1 Hz, 1H), 5.42 (s, 2H), 4.15 (q, J = 8.2, 6.9 Hz, 2H), 4.05-3.88 (m, 1H), 3.58 (s, 3H), 3.40-3.27 (m, 1H), 3.15 (dd, J = 9.3, 6.5 Hz, 1H), 2.95 (q, J = 9.5 Hz, 2H), 2.65 (s, 3H), 2.10 (s, 3H), 1.84 (dd, J = 7.0, 3.4 Hz, 3H). |
| 109 | 440.2 | CDCl3 | 400 | δ 8.28 (s, 1H), 7.42 (s, 1H), 6.37 (q, J = 7.1 Hz, 1H), 5.56 (s, 2H), 4.17-3.99 (m, 2H), 3.98-3.79 (m, 2H), 3.58 (d, J = 5.9 Hz, 3H), 3.39-3.24 (m, 1H), 3.24-3.11 (m, 1H), 2.74 (dd, J = 12.7, 7.9 Hz, 1H), 2.65 (s, 5H), 2.10 (s, 3H), 1.83 (d, J = 7.1 Hz, 3H). |
| 110 | 472.2 | — | — | — |
| 111 | 444.1 | — | — | — |
| 112 | 454.1 | — | — | — |
| 113 | 499.1 | CDCl3 | 300 | δ 8.29 (s, 1H), 7.42 (d, J = 2.1 Hz, 1H), 6.37 (q, J = 7.1 Hz, 1H), 5.48 (s, 2H), 4.07 (m, 3H), 3.98-3.77 (m, 2H), 3.58 (d, J = 3.6 Hz, 3H), 3.45-3.26 (m, 1H), 3.25-3.08 (m, 1H), 2.85-2.53 (m, 5H), 2.11 (s, 3H), 1.83 (d, J = 7.1 Hz, 3H). |
| 114 | 447.2 | CDCl3 | 300 | δ 8.28 (s, 1H), 7.40 (s, 1H), 6.37 (q, J = 7.1 Hz, 1H), 5.49 (s, 2H), 4.35 (dd, J = 5.2, 2.3 Hz, 1H), 4.19 (dd, J = 4.9, 2.8 Hz, 1H), 4.12-3.95 (m, 2H), 3.88 (dt, J = 15.5, 7.9 Hz, 1H), 3.58 (d, J = 6.5 Hz, 2H), 3.28-3.10 (m, 1H), 3.10-2.93 (m, 1H), 2.75-2.54 (m, 3H), 2.20-2.01 (m, 3H), 1.94-1.69 (m, 5H), 0.97 (d, J = 5.7 Hz, 3H). |
| 115 | 499.1 | CDCl3 | 400 | δ 8.28 (s, 1H), 7.42 (s, 1H), 6.37 (q, J = 7.0 Hz, 1H), 5.53 (s, 2H), 4.19-4.00 (m, 2H), 3.90 (dd, J = 9.7, 5.4 Hz, 2H), 3.59 (s, 3H), 3.44-3.34 (m, 1H), 3.13 (dd, J = 9.3, 6.7 Hz, 1H), 2.74 (dd, J = 12.8, 7.7 Hz, 1H), 2.65 (s, 4H), 2.10 (s, 3H), 1.83 (d, J = 7.1 Hz, 3H). |
| 116 | 454.1 | DMSO-d6 | 400 | δ 8.04 (s, 1H), 7.18 (s, 1H), 6.13 (dt, J = 19.6, 6.8 Hz, 1H), 3.97-3.71 (m, 3H), 3.46 (s, 3H), 3.28 (s, 1H), 2.91 (dt, J = 29.4, 7.6 Hz, 1H), 2.43 (m, 6H), 2.36 (dd, J = 12.3, 8.0 Hz, 1H), 2.00 (s, 3H), 1.63 (d, J = 7.1 Hz, 3H). |
| 117 | 495.2 | DMSO-d6 | 400 | δ 8.13 (d, J = 18.4 Hz, 2H), 7.75 (s, 1H), 7.29 (s, 1H), 6.22 (q, J = 7.1 Hz, 1H), 4.41 (s, 1H), 3.86 (s, 2H), 3.61 (d, J = 4.9 Hz, 2H), 3.33 (s, 6H), 2.55 (s, 3H), 2.23 (s, 3H), 1.71 (d, J = 7.0 Hz, 3H). |
| 118 | 459.2 | — | — | — |
| 119 | 455.1 | — | — | — |
| 120 | 496.1 | — | — | — |
| 121 | 459.2 | — | — | — |
| 122 | 471.0 | — | — | — |
| 123 | 473.0 | — | — | — |
| 124 | 481.0 | — | — | — |
| 125 | 492.1 | — | — | — |
| 126 | 478.1 | — | — | — |
| 127 | 465.2 | CDCl3 | 300 | δ 8.40 (s, 1H), 7.36 (s, 1H), 6.48 (q, J = 7.2 Hz, 1H), 5.81 (s, 2H), 4.16-3.95 (m, 2H), 3.94-3.75 (m, 1H), 3.56 (s, 3H), 3.18-3.02 (m, 1H), 3.00-2.83 (m, 1H), 2.31-2.18 (m, 1H), 2.14 (s, 3H), 1.84 (d, J = 7.1 Hz, 4H), 0.97 (dd, J = 6.2, 3.1 Hz, 6H). |
| 128 | 456.2 | — | — | — |
| 129 | 496.1 | — | — | — |
| 130 | 458.2 | CDCl3 | 300 | δ 8.39 (s, 1H), 7.63 (s, 1H), 6.49 (q, J = 7.1 Hz, 1H), 5.85 (s, 2H), 4.16-3.97 (m, 2H), 3.87 (m, 1H), 3.56 (t, J = 5.2 Hz, 2H), 3.14 (dd, J = 9.5, 6.9 Hz, 1H), 2.97 (dd, J = 9.3, 6.4 Hz, 1H), 2.61-2.49 (m, 2H), 2.31 (s, 3H), 1.84 (d, J = 7.1 Hz, 3H), 1.69 (br s, 1H), 1.48-1.34 (m, 2H), 0.97 (t, J = 7.3 Hz, 2H). |
| 131 | 472.2 | — | — | δ 8.39 (s, 1H), 7.63 (d, J = 3.4 Hz, 1H), 6.49 (d, J = 7.1 Hz, 1H), 5.79 (s, 2H), 4.15-3.96 (m, 2H), 3.88 (m, 1H), 3.70 (m, 1H), 3.63 (d, J = 2.0 Hz, 3H), 3.29-2.89 (m, 2H), 2.49-2.34 (m, 1H), 2.31 (s, 4H), 1.85 (d, J = 7.1 Hz, 3H), 1.25 (s, 2H), 1.12 (d, J = 6.2 Hz, 3H). |

TABLE 3-continued

| Ex. No. | MS [M + H]+ | Solvent | MHz | 1H NMR Spectra |
|---|---|---|---|---|
| 132 | 472.2 | — | — | — |
| 133 | 486.2 | CDCl3 | 300 | δ 8.39 (s, 1H), 7.63 (s, 1H), 6.49 (q, J = 6.9 Hz, 1H), 5.84 (s, 2H), 4.10 (q, J = 7.4 Hz, 2H), 3.92 (m, 2H), 3.62 (s, 3H), 3.37-3.21 (m, 1H), 3.20-3.04 (m, 1H), 2.37 (s, 2H), 2.31 (s, 3H), 1.85 (d, J = 7.1 Hz, 3H), 1.70 (br s, 1H), 1.15 (s, 6H). |
| 134 | 499.1 | — | — | — |
| 135 | 499.1 | CDCl3 | 400 | δ 8.38 (d, J = 1.0 Hz, 1H), 7.63 (d, J = 6.8 Hz, 1H), 6.79 (d, J = 3.1 Hz, 1H), 6.54-6.38 (m, 1H), 5.83 (s, 2H), 4.04-3.86 (m, 2H), 3.86-3.70 (m, 1H), 3.64 (d, J = 11.0 Hz, 3H), 3.27-2.87 (m, 2H), 2.84 (dd, J = 4.9, 3.8 Hz, 3H), 2.81-2.70 (m, 1H), 2.31 (d, J = 8.1 Hz, 3H), 1.84 (dd, J = 7.1, 3.8 Hz, 4H), 1.17 (dd, J = 6.8, 5.8 Hz, 3H). |
| 136 | 478.1 | — | — | — |
| 137 | 472.2 | — | — | — |
| 138 | 456.2 | CDCl3 | 400 | δ 8.39 (s, 1H), 7.70 (s, 1H), 6.49 (d, J = 6.2 Hz, 1H), 5.83 (s, 2H), 4.63-4.38 (m, 2H), 4.37-4.03 (m, 2H), 3.74 (d, J = 21.2 Hz, 3H), 2.43 (d, J = 4.6 Hz, 3H), 1.91 (d, J = 3.6 Hz, 4H), 1.85 (d, J = 7.0 Hz, 4H). |
| 142 | 463.1 | — | — | — |
| 143 | 463.2 | — | — | — |
| 144 | 449.1 | — | — | — |
| 145 | 419.1 | DMSO-d6 | 300 | δ 8.10 (s, 1 H), 7.44 (d 1 H), 7.28 (bs, 2 H), 6.20 (m, 1 H), 3.77 (m, 5 H), 2.95 (m, 2 H), 2.53 (s, 3 H), 2.17 (s, 3 H), 1.67(d, 3 H), 1.30 (t, 3 H) ppm. |
| 146 | 433.1 | DMSO-d6 | 300 | δ 8.10 (s, 1 H), 7.44 (d 1 H), 7.31 (bs, 2 H), 6.21 (m, 1 H), 3.80-3.63 (m, 5 H), 2.85 (m, 2 H), 2.49 (s, 3 H), 2.33 (m, 2 H), 1.67(d, 3 H), 1.31 (t, 3 H), 0.85 (t, 3 H) ppm. |
| 147 | 469.1 | — | — | — |
| 148 | 462.2 | — | — | — |
| 151 | 455.1 | — | — | — |
| 153 | 513.2 | — | — | — |
| 154 | 499.1 | DMSO-d6 | 300 | δ 8.24 (s, 1H), 7.37 (m 2H), 6.28 (m, 1H), 4.27 (br s, 1H), 3.72 (m, 4H), 3.50 (m, 2H), 2.99-2.87 (m, 2H), 2.22 (m, 2H), 1.68 (d, 3H), 1.20 (t, 3H), 0.93 (d, 3H) ppm. |
| 155 | 499.2 | — | — | — |
| 157 | 445.1 | — | — | — |
| 160 | 486.2 | DMSO-d6 | 300 | δ 8.09 (s, 1H), 7.23 (s, 1H), 6.18 (m, 1H), 3.78 (m, 3H), 3.50 (s, 3H), 3.01 (s, 3H), 3.0-2.9 (m, 3H), 2.77 (s, 3H), 2.54 (s, 3H), 2.06 (s, 3H), 1.67 (d, 3H), 0.98 (d, 3H) ppm. |
| 162 | 454.1 | — | — | — |
| 168 | 410.2 | — | — | — |
| 169 | 425.1 | — | — | — |
| 170 | 434.2 | — | — | — |
| 171 | 424.2 | — | — | — |
| 172 | 487.3 | — | — | — |
| 173 | 466.2 | — | — | — |
| 175 | 510.2 | — | — | — |
| 176 | 536.3 | — | — | — |
| 177 | 517.2 | — | — | — |
| 178 | 509.2 | — | — | — |
| 180 | 431.0 | — | — | — |
| 185 | 452.1 | — | — | — |
| 186 | 452.2 | — | — | — |
| 187 | 480.2 | — | — | — |
| 193 | 386.2 | — | — | — |
| 196 | 494.2 | — | — | — |
| 197 | 426.2 | — | — | — |
| 198 | 501.2 | — | — | — |
| 199 | 480.1 | — | — | — |
| 201 | 494.2 | — | — | — |
| 202 | 524.2 | — | — | — |
| 204 | 483.2 | — | — | — |
| 205 | 497.2 | — | — | — |
| 206 | 483.1 | — | — | — |
| 207 | 497.2 | — | — | — |
| 210 | 417.3 | — | — | — |

Example 212

4-[1-(4-Amino-3-methyl-1H-pyrazolo[3,4-d]pyrimidin-1-yl)ethyl]-2-azetidin-3-yl-6-chloro-3-ethoxybenzonitrile

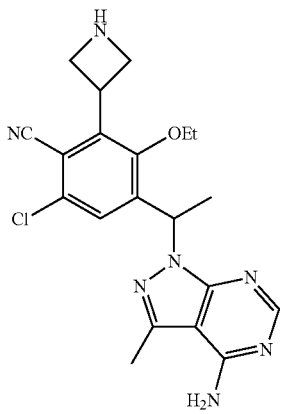

Step 1. 1-(5-Chloro-2-ethoxy-4-fluoro-3-iodophenyl)ethanone

The desired compound was prepared according to the procedure of Example 13, step 3 to form a racemic intermediate, using iodoethane instead of iodomethane as the starting material in 90% yield. $^1$H NMR (300 MHz, CDCl$_3$) δ 7.68 (d, J=8.3 Hz, 1H), 3.94 (q, J=7.0 Hz, 2H), 2.61 (s, 3H), 1.48 (t, J=7.0 Hz, 3H). LCMS for C$_{10}$H$_{10}$ClFIO$_2$ (M+H)$^+$: m/z=342.9, 344.9. Found: 342.9, 344.8.

Step 2. 4-Acetyl-6-chloro-3-ethoxy-2-iodobenzonitrile

A solution of 1-(5-chloro-2-ethoxy-4-fluoro-3-iodophenyl)ethanone (7.3 g, 21 mmol) in N,N-dimethylformamide (80 mL) was treated with potassium cyanide (2.1 g, 32 mmol) and stirred at 40° C. for 5 h. The reaction mixture was diluted with ethyl acetate and poured into saturated sodium bicarbonate solution/water (1:1). The organic layer was separated, washed with saturated sodium bicarbonate solution, dried with magnesium sulfate, filtered, and concentrated to give a crude brown oil. The crude material was purified by flash column chromatography using ethyl acetate in hexanes (0%-30%) to give the desired product (6.1 g, 81%) as a yellow solid. $^1$H NMR (400 MHz, CDCl$_3$) δ 7.57 (s, 1H), 3.93 (q, J=7.0 Hz, 2H), 2.61 (s, 3H), 1.47 (t, J=7.0 Hz, 3H). LCMS for C$_{11}$H$_{10}$ClINO$_2$ (M+H)$^+$: m/z=349.9. Found: 349.9.

Step 3. tert-Butyl 3-(3-acetyl-5-chloro-6-cyano-2-ethoxyphenyl)azetidine-1-carboxylate Zinc (4.60 g, 70.3 mmol) and oven dried Celite (870 mg) was added to a flask and the flask was heated with a heat gun while under high-vac for 5 min and then back-filled with nitrogen. N,N-Dimethylacetamide (57 mL) was added, followed by 1,2-dibromoethane (430 μL, 5.0 mmol) and the mixture was heated at 70° C. for 10 min and then cooled to room temperature. The reaction mixture was treated with chlorotrimethylsilane (630 μL, 5.0 mmol) dropwise and stirred at room temperature for 1 h. The reaction mixture was treated with a solution of tert-butyl 3-iodoazetidine-1-carboxylate (18 g, 62 mmol) in N,N-dimethylacetamide (28 mL) dropwise (internal temperature was kept below 40° C. with a water bath) and heated at 40° C. for 2 h. The zinc-iodo reagent (transferred via canula) was filtered through a plastic filter (that was appropriately sealed to avoid atmospheric exposure) directly into a clean, dry flask that was flushed with nitrogen. The reaction mixture was treated with tris (dibenzylideneacetone)dipalladium(0) (720 mg, 0.79 mmol) and tri-(2-furyl)phosphine (370 mg, 1.6 mmol) and degassed with nitrogen for a few minutes. The reaction mixture was treated with a solution of 4-acetyl-6-chloro-3-ethoxy-2-iodobenzonitrile (14 g, 41 mmol) in N,N-dimethylacetamide (130 mL) (degassed with nitrogen) quickly and heated at 70° C. for 2 h. The reaction mixture was poured into saturated ammonium chloride solution and extracted with ethyl acetate (3×300 mL). The combined organic extracts were washed with water (4×500 mL) and brine (1×500 mL), dried with magnesium sulfate, filtered, and concentrated to a crude dark oil. The crude material was purified by flash column chromatography using ethyl acetate in hexanes (5%-45%) to give the desired product (14 g, 88%). $^1$H NMR (300 MHz, CDCl$_3$) δ 7.46 (s, 1H), 4.42-4.20 (m, 5H), 3.80 (q, J=7.0 Hz, 2H), 2.59 (s, 3H), 1.44 (s, 9H), 1.37 (t, J=7.0 Hz, 3H). LCMS for C$_{15}$H$_{16}$ClN$_2$O$_4$ ([M-(t-Bu)+H]+H)$^+$: m/z=323.1. Found: 323.0.

Step 4. tert-Butyl 3-[3-chloro-2-cyano-6-ethoxy-5-(1-hydroxyethyl)phenyl]azetidine-1-carboxylate A solution of (3aS)-1-methyl-3,3-diphenyltetrahydro-3H-pyrrolo[1,2-c][1,3,2]oxazaborole (9.7 g, 35 mmol) in tetrahydrofuran (100 mL) was treated with 1.0 M borane-THF complex in tetrahydrofuran (42 mL, 42 mmol) and stirred at 20° C. for 15 min. The reaction mixture was cooled to −30° C. and treated with a solution of tert-butyl 3-(3-acetyl-5-chloro-6-cyano-2-ethoxyphenyl)azetidine-1-carboxylate (13 g, 35 mmol) in tetrahydrofuran (110 mL) slowly. The flask containing the starting material ketone was rinsed with additional tetrahydrofuran (20 mL) and added to the reaction mixture. The reaction mixture was warmed to 0° C. over a period of 30 min and stirred at 0° C. for 15 min. The reaction mixture was quenched with water at 0° C., poured into saturated sodium bicarbonate solution, and extracted with ethyl acetate. The aqueous layer was separated and extracted with ethyl acetate. The combined organic layers were washed with water and brine, dried with magnesium sulfate, filtered, and concentrated to a crude dark oil. The crude material was purified by flash column chromatography using ethyl acetate in hexanes (0%-70%) to give the desired product (10.4 g, 78%) as a yellow foam as a 98:2 mixture of enantiomers (Retention times=7.73 min and 9.41 min; ChiralPak AD-H column, 4.6×150 mm, 5 micron particle size, eluting with 5% ethanol in hexanes at 1 ml/min)$^1$H NMR (300 MHz, CDCl$_3$) δ 7.56 (s, 1H), 5.15-5.07 (m, 1H), 4.41-4.17 (m, 5H), 3.74 (q, J=7.0 Hz, 2H), 2.12 (d, J=3.7 Hz, 1H), 1.49-1.37 (m, 15H). LCMS for $C_{15}H_{18}ClN_2O_4$ ([M-(t-Bu)+H]+H)$^+$: m/z=325.1. Found: 325.1.

Step 5. tert-Butyl 3-{3-[1-(4-amino-3-methyl-1H-pyrazolo[3,4-d]pyrimidin-1-yl)ethyl]-5-chloro-6-cyano-2-ethoxyphenyl}azetidine-1-carboxylate A solution of tert-butyl 3-[3-chloro-2-cyano-6-ethoxy-5-(1-hydroxyethyl)phenyl]azetidine-1-carboxylate (98:2 mixture of enantiomers from step 4) (10 g, 27 mmol) in methylene chloride (260 mL) at 0° C. was treated with triethylamine (11 mL, 82 mmol) followed by methanesulphonic anhydride (7.1 g, 41 mmol) and stirred at 0° C. for 15 min. The reaction mixture was diluted with dichloromethane and washed with water and brine, dried with magnesium sulfate, filtered, and concentrated to give the crude mesylate that was used without further purification. A solution of the crude mesylate intermediate in N,N-dimethylformamide (140 mL) was treated with cesium carbonate (13 g, 41 mmol) and 3-methyl-1H-pyrazolo[3,4-d]pyrimidin-4-amine (4.7 g, 31 mmol) and heated at 60° C. for 1 h. The reaction mixture was diluted with water and extracted with ethyl acetate (3×250 mL). The combined organic layers were washed with water and brine, dried with magnesium sulfate, filtered, and concentrated to a crude oil. The crude material was purified by flash column chromatography (100% dichloromethane to 70% acetonitrile containing 3% methanol/30% dichloromethane) to give the desired product (8.7 g, 62% for 2 steps) as a yellow foam as a 95:5 mixture of enantiomers (RT=4.29 min and 6.00 min; Phenomenex Lux Cellulose C-1 column, 4.6×150 mm, 5 micron particle size, eluting with 15% ethanol in hexanes at 1 ml/min) This material was separated by chiral HPLC (Phenomenex Lux Cellulose C-1 column, 21.2×250 mm, 5 micron particle size, eluting with 15% ethanol in hexanes at 10 ml/min) to give 7.0 g of the desired peak 1 material (retention time of 8.20 min). $^1$H NMR (300 MHz, CDCl$_3$) δ 8.24 (s, 1H), 7.51 (s, 1H), 6.32 (q, J=7.1 Hz, 1H), 5.48 (br s, 2H), 4.40-4.18 (m, 5H), 4.05-3.93 (m, 1H), 3.81-3.65 (m, 1H), 2.64 (s, 3H), 1.81 (d, J=7.1 Hz, 3H), 1.48 (t, J=7.0 Hz, 3H), 1.43 (s, 9H). LCMS for $C_{25}H_{31}ClN_7O_3$ (M+H)$^+$: m/z=512.2. Found: 512.3.

Step 6. 4-[1-(4-Amino-3-methyl-1H-pyrazolo[3,4-d]pyrimidin-1-yl)ethyl]-2-azetidin-3-yl-6-chloro-3-ethoxybenzonitrile A solution of tert-butyl 3-{3-[1-(4-amino-3-methyl-1H-pyrazolo[3,4-d]pyrimidin-1-yl)ethyl]-5-chloro-6-cyano-2-ethoxyphenyl}azetidine-1-carboxylate (peak 1 enantiomer from step 5) (2.2 g, 4.2 mmol) in methylene chloride (11 mL) was treated with trifluoroacetic acid (11 mL) dropwise and stirred at room temperature for 30 min. The reaction mixture was concentrated to an oil that was reconcentrated from ethanol (2×) to give a residue. This material was dissolved in a minimum amount of methanol, added dropwise to ice cooled saturated sodium bicarbonate solution (100 ml), and extracted several times with 2:1 dichloromethane/isopropanol to give the desired product (1.8 g, quantitative) that was used without further purification. A small amount of the desired product was purified by preparative LCMS (XBridge C18 column, eluting with a gradient of acetonitrile/water containing 0.1% ammonium hydroxide, at flow rate of 60 mL/min) to give the desired product. The product was isolated as a single enantiomer. $^1$H NMR (400 MHz, DMSO-d$_6$) δ 8.11 (s, 1H), 7.47 (s, 1H), 6.23 (q, J=7.0 Hz, 1H), 4.37-4.26 (m, 1H), 3.91-3.61 (m, 6H), 2.54 (s, 3H), 1.71 (d, J=7.1 Hz, 3H), 1.32 (t, J=7.0 Hz, 3H). LCMS for $C_{20}H_{23}ClN_7O$ (M+H)$^+$: m/z=412.2. Found: 412.1.

Example 213

4-[1-(4-Amino-3-methyl-1H-pyrazolo[3,4-d]pyrimidin-1-yl)ethyl]-6-chloro-3-ethoxy-2-(1-methylazetidin-3-yl)benzonitrile

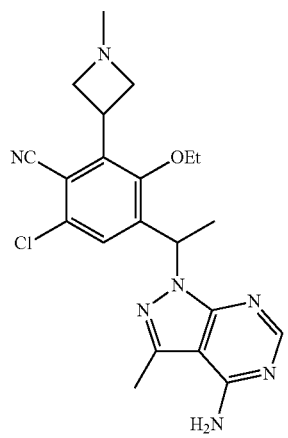 [SMILES: CCOc1c(C(C)n2nc(C)c3c(N)ncnc32)cc(Cl)c(C#N)c1C1CN(C)C1]

A solution of 4-[1-(4-amino-3-methyl-1H-pyrazolo[3,4-d]pyrimidin-1-yl)ethyl]-2-azetidin-3-yl-6-chloro-3-ethoxybenzonitrile (chiral intermediate in Example 212, Step 6) (0.30 g, 0.73 mmol) in methanol (7.3 mL) was treated with formaldehyde (37% in water) (0.54 mL, 7.3 mmol) and this was stirred at room temperature for 5 min. The reaction mixture was treated with sodium cyanoborohydride (0.092 g, 1.5 mmol) and stirred at room temperature for 2 h. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product (0.16 g, 50%). The product was isolated as a single enantiomer. $^1$H NMR (400 MHz, DMSO-d$_6$) δ 8.11 (s, 1H), 7.48 (s, 1H), 6.27-6.18 (m, 1H), 4.10-3.98 (m, 1H), 3.96-3.86 (m, 2H), 3.83-3.74 (m, 1H), 3.72-3.64 (m, 1H), 3.10-2.98 (m, 2H), 2.54 (s, 3H), 2.20 (s, 3H), 1.71 (d, J=6.9 Hz, 3H), 1.32 (t, J=6.7 Hz, 3H). LCMS for $C_{21}H_{25}ClN_7O$ (M+H)$^+$: m/z=426.2. Found: 426.2.

Example 219

4-[1-(4-Amino-3-methyl-1H-pyrazolo[3,4-d]pyrimidin-1-yl)ethyl]-6-chloro-3-ethoxy-2-[1-(2-hydroxyethyl)azetidin-3-yl]benzonitrile

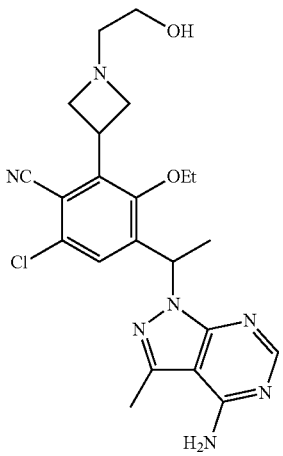 [SMILES: CCOc1c(C(C)n2nc(C)c3c(N)ncnc32)cc(Cl)c(C#N)c1C1CN(CCO)C1]

A solution of 4-[1-(4-amino-3-methyl-1H-pyrazolo[3,4-d]pyrimidin-1-yl)ethyl]-2-azetidin-3-yl-6-chloro-3-ethoxybenzonitrile (300 mg, 0.74 mmol, chiral intermediate from Example 212) in tetrahydrofuran (14 mL) was treated with triethylamine (260 μL, 1.8 mmol) followed by 2-bromoethanol (63 μL, 0.89 mmol) dropwise and stirred at 60° C. for 6 h. The reaction mixture was treated with additional 2-bromoethanol (26 μL, 0.37 mmol) and stirred at 60° C. for another 6 h. The reaction mixture was poured into saturated sodium bicarbonate solution and extracted with ethyl acetate. The organic layer was concentrated and purified by preparative LCMS (XBridge C18 column, eluting with a gradient of acetonitrile/water containing 0.1% ammonium hydroxide, at flow rate of 60 mL/min) to give the desired product (0.15 g, 44%). The product was isolated as a single enantiomer. $^1$H NMR (400 MHz, DMSO-$d_6$) δ 8.19 (s, 1H), 7.56 (s, 1H), 6.36-6.25 (m, 1H), 4.48 (br s, 1H), 4.19-4.07 (m, 1H), 4.04-3.94 (m, 2H), 3.91-3.82 (m, 1H), 3.81-3.72 (m, 2H), 3.20-3.08 (m, 2H), 2.62 (s, 2H), 2.57 (s, 3H), 1.79 (d, J=6.8 Hz, 3H), 1.40 (t, J=6.6 Hz, 3H). LCMS for $C_{22}H_{27}ClN_7O_2$ $(M+H)^+$: m/z=456.2. Found: 456.1.

Example 220

4-[1-(4-Amino-3-methyl-1H-pyrazolo[3,4-d]pyrimidin-1-yl)ethyl]-6-chloro-3-ethoxy-2-{1-[(2S)-2-hydroxypropyl]azetidin-3-yl}benzonitrile

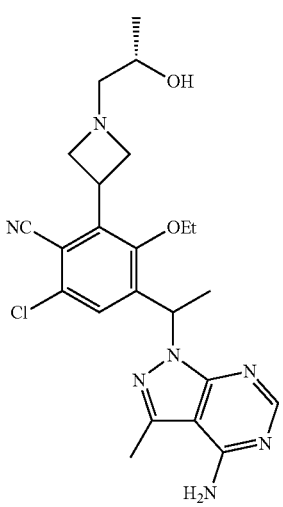 [SMILES: CCOc1c(C(C)n2nc(C)c3c(N)ncnc32)cc(Cl)c(C#N)c1C1CN(C[C@H](C)O)C1]

A solution of 4-[1-(4-amino-3-methyl-1H-pyrazolo[3,4-d]pyrimidin-1-yl)ethyl]-2-azetidin-3-yl-6-chloro-3-ethoxybenzonitrile (50 mg, 0.12 mmol, chiral intermediate from example 212) in ethanol (1.7 mL) was treated with (S)-(−)-methyloxirane (21 μL, 0.30 mmol) and heated in the microwave at 125° C. for 15 min. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product (27 mg, 47%). The product was isolated as a single diastereomer. $^1$H NMR (300 MHz, DMSO-$d_6$) δ 8.11 (s, 1H), 7.48 (s, 1H), 6.23 (q, J=6.9 Hz, 1H), 4.35 (d, J=4.5 Hz, 1H), 4.13-3.99 (m, 1H), 3.97-3.88 (m, 2H), 3.85-3.63 (m, 2H), 3.61-3.51 (m, 1H), 3.15-2.99 (m, 2H), 2.55 (s, 3H), 2.28 (d, J=5.9 Hz, 2H), 1.71 (d, J=7.0 Hz, 3H), 1.32 (t, J=6.9 Hz, 3H), 1.00 (d, J=6.2 Hz, 3H). LCMS for $C_{23}H_{29}ClN_7O_2$ $(M+H)^+$: m/z=470.2. Found: 470.2.

Example 236 tert-Butyl 2-(3-{3-[1-(4-amino-3-methyl-1H-pyrazolo[3,4-d]pyrimidin-1-yl)ethyl]-5-chloro-6-cyano-2-ethoxyphenyl}azetidin-1-yl)-2-methylpropanoate

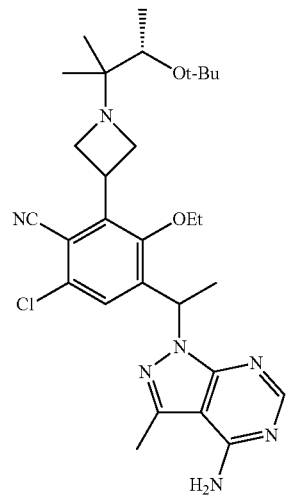 [SMILES: CCOc1c(C(C)n2nc(C)c3c(N)ncnc32)cc(Cl)c(C#N)c1C1CN(C(C)(C)[C@H](C)OC(C)(C)C)C1]

A solution of 4-[1-(4-amino-3-methyl-1H-pyrazolo[3,4-d]pyrimidin-1-yl)ethyl]-2-azetidin-3-yl-6-chloro-3-ethoxybenzonitrile (0.38 g, 0.92 mmol, chiral intermediate from Example 212) in N,N-dimethylformamide (4.6 mL) was treated with potassium carbonate (0.51 g, 3.7 mmol) followed by tert-butyl 2-bromo-2-methylpropanoate (0.86 mL, 4.6 mmol) and heated at 60° C. for 3 h. The reaction mixture was poured into water and extracted with ethyl acetate. The organic layer was separated, dried with magnesium sulfate, filtered, and concentrated to a crude oil. The crude material was purified by flash column chromatography using methanol in dichloromethane (0%-10%) to give the desired product (0.43 g, 83%). The product was isolated as a single enantiomer. $^1$H NMR (300 MHz, DMSO-$d_6$) δ 8.10 (s, 1H), 7.44 (s, 1H), 6.22 (q, J=6.8 Hz, 1H), 4.12-3.97 (m, 1H), 3.88-3.70 (m, 4H), 3.62-3.48 (m, 2H), 2.54 (s, 3H), 1.70 (d, J=7.0 Hz, 3H), 1.33 (t, J=6.9 Hz, 3H), 1.17 (s, 9H), 1.05 (s, 6H). LCMS for $C_{28}H_{37}ClN_7O_3$ $(M+H)^+$: m/z=554.3. Found: 554.3.

Example 237

4-[1-(4-Amino-3-methyl-1H-pyrazolo[3,4-d]pyrimidin-1-yl)ethyl]-6-chloro-3-ethoxy-2-[1-(2-hydroxy-1,1-dimethylethyl)azetidin-3-yl]benzonitrile

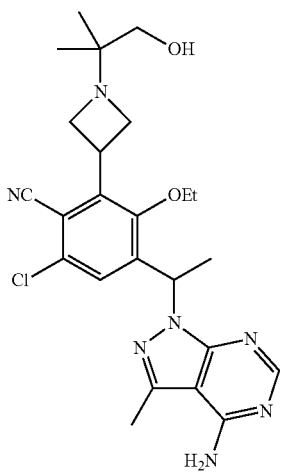 [SMILES: CCOc1c(C(C)n2nc(C)c3c(N)ncnc32)cc(Cl)c(C#N)c1C1CN(C(C)(C)CO)C1]

Step 1. 2-(3-{3-[1-(4-Amino-3-methyl-1H-pyrazolo[3,4-d]pyrimidin-1-yl)ethyl]-5-chloro-6-cyano-2-ethoxyphenyl}azetidin-1-yl)-2-methylpropanoic acid bis(trifluoroacetate)

tert-Butyl 2-(3-{3-[1-(4-amino-3-methyl-1H-pyrazolo[3,4-d]pyrimidin-1-yl)ethyl]-5-chloro-6-cyano-2-ethoxyphenyl}azetidin-1-yl)-2-methylpropanoate (0.36 g, 0.65 mmol, chiral intermediate from Example 236) was dissolved in a premixed solution of trifluoroacetic acid (3.2 mL)/water (0.065 mL) and stirred at room temperature for 3 h and at 50° C. for 30 min. The reaction mixture was concentrated and reconcentrated from acetonitrile (2×) to give the desired product as a gum. This gum was treated with a small amount of methyl-tert-butylether that was swirled until a solid formed. The methyl-tert-butylether was decanted and the residue was concentrated to give the desired product (0.51 g, 109%) that was used without further purification. LCMS for $C_{24}H_{29}ClN_7O_3$ (M+H)$^+$: m/z=498.2. Found: 498.3.

Step 2. 4-[1-(4-Amino-3-methyl-1H-pyrazolo[3,4-d]pyrimidin-1-yl)ethyl]-6-chloro-3-ethoxy-2-[1-(2-hydroxy-1,1-dimethylethyl)azetidin-3-yl]benzonitrile A solution of 2-(3-{3-[1-(4-amino-3-methyl-1H-pyrazolo[3,4-d]pyrimidin-1-yl)ethyl]-5-chloro-6-cyano-2-ethoxyphenyl}azetidin-1-yl)-2-methylpropanoic acid bis(trifluoroacetate) (0.10 g, 0.16 mmol) in tetrahydrofuran (0.9 mL) was cooled to −25° C., treated with 4-methylmorpholine (0.072 mL, 0.65 mmol) and isobutyl chloroformate (0.085 mL, 0.65 mmol), and stirred at −15° C. for 15 min. The reaction mixture was filtered though a disposable filter cartridge into a separate round bottom flask. This solution was then cooled to −20° C. and a solution of sodium tetrahydroborate (0.031 g, 0.82 mmol) in a minimum amount of water was added dropwise. The reaction mixture was stirred at −15° C. for 30 min, poured into water, and extracted with ethyl acetate. The organic layer was separated, concentrated, diluted with methanol, and purified by preparative LCMS (XBridge C18 column, eluting with a gradient of acetonitrile/water containing 0.1% ammonium hydroxide, at flow rate of 30 mL/min) to give the desired product (3.5 mg, 4%). The product was isolated as a single enantiomer. $^1$H NMR (300 MHz, DMSO-d$_6$) δ 8.11 (s, 1H), 7.50 (s, 1H), 7.35 (br s, 2H), 6.23 (q, J=6.7 Hz, 1H), 4.44-4.35 (m, 1H), 4.04-3.88 (m, 1H), 3.86-3.73 (m, 1H), 3.72-3.57 (m, 3H), 3.12 (d, J=4.7 Hz, 2H), 2.54 (s, 3H), 1.71 (d, J=6.9 Hz, 3H), 1.31 (t, J=6.9 Hz, 3H), 0.80 (s, 6H). LCMS for $C_{24}H_{31}ClN_7O_2$ (M+H)$^+$: m/z=484.2. Found: 484.2.

Example 239

2-(3-{3-[1-(4-Amino-3-methyl-1H-pyrazolo[3,4-d]pyrimidin-1-yl)ethyl]-5-chloro-6-cyano-2-ethoxyphenyl}azetidin-1-yl)-2-methylpropanamide

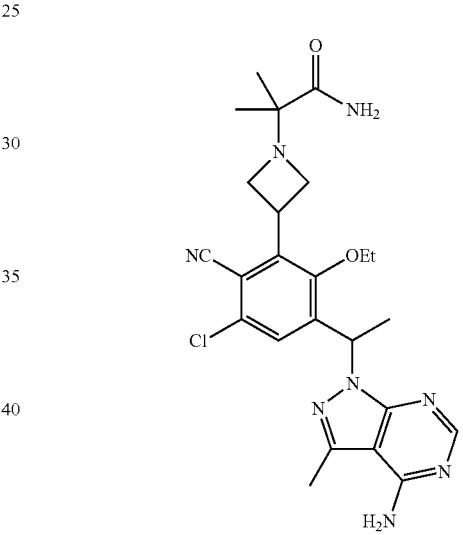

A solution of 2-(3-{3-[1-(4-amino-3-methyl-1H-pyrazolo[3,4-d]pyrimidin-1-yl)ethyl]-5-chloro-6-cyano-2-ethoxyphenyl}azetidin-1-yl)-2-methylpropanoic acid bis(trifluoroacetate) (0.05 g, 0.069 mmol, chiral intermediate from Example 237, Step 1) and 2.0 M ammonia in ethanol (0.17 mL, 0.34 mmol) in N,N-dimethylformamide (1 mL) was treated with triethylamine (0.048 mL, 0.35 mmol) and benzotriazol-1-yloxytris(dimethylamino)phosphonium hexafluorophosphate (0.046 g, 0.10 mmol) and stirred at room temperature for 1 h. The reaction mixture was quenched with a few drops of water, diluted with methanol, and purified by preparative LCMS (XBridge C18 column, eluting with a gradient of acetonitrile/water containing 0.1% ammonium hydroxide, at flow rate of 60 mL/min) to give the desired product (25 mg, 73%). The product was isolated as a single enantiomer. $^1$H NMR (400 MHz, DMSO-d$_6$) δ 8.11 (s, 1H), 7.51 (s, 1H), 7.23 (s, 1H), 6.98 (s, 1H), 6.23 (q, J=7.0 Hz, 1H), 4.09-3.96 (m, 1H), 3.84-3.61 (m, 4H), 3.39-3.34 (m, 1H), 3.32-3.28 (m, 1H), 2.54 (s, 3H), 1.71 (d, J=7.0 Hz, 3H), 1.31 (t, J=6.9 Hz, 3H), 1.02 (s, 6H). LCMS for $C_{24}H_{30}ClN_8O_2$ (M+H)$^+$: m/z=497.2. Found: 497.3.

Example 247

4-[1-(4-Amino-3-methyl-1H-pyrazolo[3,4-d]pyrimidin-1-yl)ethyl]-6-chloro-3-ethoxy-2-[1-(2-hydroxy-2-methylpropanoyl)azetidin-3-yl]benzonitrile

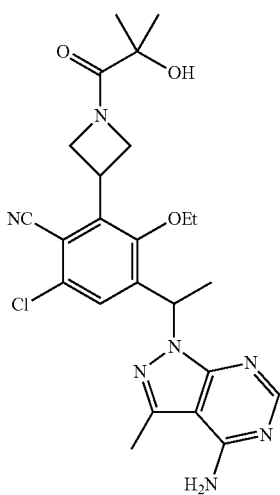 [SMILES: CCOc1c(C(C)n2nc(C)c3c(N)ncnc32)cc(Cl)c(C#N)c1C1CN(C(=O)C(C)(C)O)C1]

A solution of 4-[1-(4-amino-3-methyl-1H-pyrazolo[3,4-d]pyrimidin-1-yl)ethyl]-2-azetidin-3-yl-6-chloro-3-ethoxybenzonitrile (0.04 g, 0.097 mmol, chiral intermediate from Example 212) and propanoic acid, 2-hydroxy-2-methyl- (0.012 g, 0.12 mmol) in N,N-dimethylformamide (0.54 mL) was treated with triethylamine (0.034 mL, 0.24 mmol) followed by O-(benzotriazol-1-yl)-N,N,N',N'-tetramethyluronium hexafluorophosphate (0.048 g, 0.13 mmol) and stirred at room temperature for 30 min. The reaction mixture was diluted with methanol and acetonitrile and purified by preparative LCMS (XBridge C18 column, eluting with a gradient of methanol/water containing 0.1% ammonium hydroxide, at flow rate of 60 mL/min) to give the desired product (7 mg, 14%). The product was isolated as a single enantiomer. $^1$H NMR (300 MHz, DMSO-$d_6$) δ 8.11 (s, 1H), 7.54 (d, J=4.5 Hz, 1H), 6.25 (q, J=7.2 Hz, 1H), 5.08 (s, 1H), 4.88-4.77 (m, 1H), 4.73-4.60 (m, 1H), 4.50-4.35 (m, 1H), 4.29-4.09 (m, 2H), 3.85-3.73 (m, 2H), 2.55 (s, 3H), 1.73 (d, J=7.0 Hz, 3H), 1.37 (t, J=6.3 Hz, 3H), 1.26 (s, 3H), 1.22 (s, 3H). LCMS for $C_{24}H_{29}ClN_7O_3$ (M+H)$^+$: m/z=498.2. Found: 498.2.

Example 261

4-[1-(4-Amino-3-methyl-1H-pyrazolo[3,4-d]pyrimidin-1-yl)ethyl]-2-azetidin-3-yl-6-chloro-3-methoxybenzonitrile

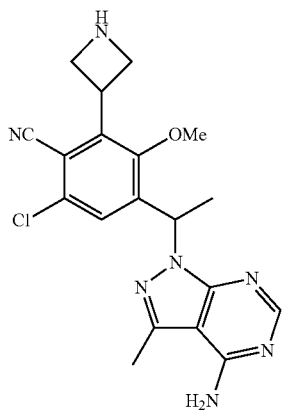 [SMILES: COc1c(C(C)n2nc(C)c3c(N)ncnc32)cc(Cl)c(C#N)c1C1CNC1]

Step 1.
4-Acetyl-6-chloro-2-iodo-3-methoxybenzonitrile

A solution of 1-(5-chloro-4-fluoro-3-iodo-2-methoxyphenyl)ethanone (intermediate from Example 13, Step 3) (18 g, 54 mmol) in N,N-dimethylformamide (200 mL) was treated with potassium cyanide (5.2 g, 81 mmol) and stirred at 40° C. for 6 h. The reaction mixture was diluted with ethyl acetate and poured into saturated sodium bicarbonate solution/water (1:1). The organic layer was separated, washed with saturated sodium bicarbonate solution, dried with magnesium sulfate, filtered, and concentrated to give a crude brown oil. The crude material was purified by flash column chromatography using ethyl acetate in hexanes (0%-30%) to give the desired product (11 g, 61%) as a yellow solid. $^1$H NMR (300 MHz, CDCl$_3$) δ 7.60 (s, 1H), 3.81 (s, 3H), 2.62 (s, 3H). LCMS for $C_{10}H_8ClINO_2$ (M+H)$^+$: m/z=335.9. Found: 335.9.

Step 2. tert-Butyl 3-(3-acetyl-5-chloro-6-cyano-2-methoxyphenyl)azetidine-1-carboxylate Zinc (5.0 g, 77 mmol) and oven dried Celite (520 mg) was added to a flask and the flask was heated with a heat gun while under high-vac for 5 min and then back-filled with nitrogen. N,N-dimethylacetamide (53 mL) was added, followed by 1,2-dibromoethane (400 μL, 4.6 mmol) and the mixture was heated at 70° C. for 15 min and then cooled to room temperature. The reaction mixture was treated with chlorotrimethylsilane (580 μL, 4.6 mmol) dropwise and stirred at room temperature for 1 h. The reaction mixture was treated with a solution of tert-butyl 3-iodoazetidine-1-carboxylate (16 g, 58 mmol) in N,N-dimethylacetamide (26 mL) dropwise (internal temperature was kept below 40° C. with a water bath) and heated at 40° C. for 2 h. The zinc-iodo reagent (transferred via canula) was filtered through a plastic filter (that was appropriately sealed to avoid atmospheric exposure) directly into a clean, dry flask that was flushed with nitrogen. The reaction mixture was treated with tris (dibenzylideneacetone)dipalladium(0) (670 mg, 0.73 mmol) and tri-(2-furyl)phosphine (340 mg, 1.5 mmol) and degassed with nitrogen for a few minutes. The reaction mixture was treated with a solution of 4-acetyl-6-chloro-2-iodo-3-methoxybenzonitrile (13 g, 39 mmol) in N,N-dimethylacetamide (120 mL) (degassed with nitrogen) quickly and heated at 70° C. for 2 h. The reaction mixture was poured into saturated ammonium chloride solution and extracted with ethyl acetate (3×300 mL). The combined organic extracts were washed with water (4×500 mL) and brine (1×500 mL), dried with magnesium sulfate, filtered, and concentrated to a crude dark oil. The crude material was purified by flash column chromatography using ethyl acetate in hexanes (5%-40%) to give the desired product (12 g, 85%). $^1$H NMR (400 MHz, DMSO-$d_6$) δ 7.79 (s, 1H), 4.39-4.29 (m, 1H), 4.28-4.11 (m, 4H), 3.68 (s, 3H), 2.58 (s, 3H), 1.38 (s, 9H).

Step 3. tert-Butyl 3-[3-chloro-2-cyano-5-(1-hydroxyethyl)-6-methoxyphenyl]azetidine-1-carboxylate A solution of (3aS)-1-methyl-3,3-diphenyltetrahydro-3H-pyrrolo[1,2-c][1,3,2]oxazaborole (4.3 g, 16 mmol) in tetrahydrofuran (46 mL) was treated with 1.0 M borane-THF complex in tetrahyrofuran (19 mL, 19 mmol) and stirred at 20° C. for 15 min. The reaction mixture was cooled to −30° C. and treated with a solution of tert-butyl 3-(3-acetyl-5-chloro-6-cyano-2-methoxyphenyl)azetidine-1-carboxylate (5.7 g, 16 mmol) in tetrahydrofuran (49 mL) slowly. The flask containing the starting material ketone was rinsed with additional tetrahydrofuran (9 mL) and added to the reaction mixture. The temperature of the reaction was −20° C. after the addition was complete. The reaction mixture was warmed to −5° C. over a period of 30 min. The reaction mixture was quenched with water at 0° C., poured into saturated sodium bicarbonate solution, and extracted with ethyl acetate. The aqueous layer was separated and extracted with ethyl acetate. The combined organic layers were washed with water and brine, dried with magnesium sulfate, filtered, and concentrated to a crude dark oil. The crude material was purified by flash column chromatography using ethyl acetate in hexanes (0%-100%) to give the desired product (5.5 g, 97%) as a beige foam as a 97:3 mixture of enantiomers (Retention times=12.19 min and 13.18 min; Phenomenex Lux Cellulose C-2 column, 4.6×150 mm, 5 micron particle size, eluting with 8% ethanol in hexanes at 1 ml/min)$^1$H NMR (400 MHz, DMSO-$d_6$) δ 7.62 (s, 1H), 5.48 (d, J=4.6 Hz, 1H), 5.00-4.90 (m, 1H), 4.43-4.31 (m, 1H), 4.30-4.10 (m, 4H), 3.66 (s, 3H), 1.38 (s, 9H), 1.29 (d, J=6.4 Hz, 3H). LCMS for $C_{14}H_{16}ClN_2O_4$ ([M-(t-Bu)+H]+H)$^+$: m/z=311.1. Found: 311.1.

Step 4. tert-Butyl 3-{3-[1-(4-amino-3-methyl-1H-pyrazolo[3,4-d]pyrimidin-1-yl)ethyl]-5-chloro-6-cyano-2-methoxyphenyl}azetidine-1-carboxylate A solution of tert-butyl 3-[3-chloro-2-cyano-5-(1-hydroxyethyl)-6-methoxyphenyl]azetidine-1-carboxylate (8.6 g, 23 mmol) (97:3 mixture of enantiomers from step 3) in methylene chloride (220 mL) at 0° C. was treated with triethylamine (8.2 mL, 59 mmol) followed by methanesulphonic anhydride (6.1 g, 35 mmol) and stirred at 0° C. for 15 min. The reaction mixture was diluted with dichloromethane and washed with water and brine, dried with magnesium sulfate, filtered, and concentrated to give the crude mesylate that was used without further purification. A solution of the crude mesylate intermediate in N,N-dimethylformamide (82 mL) was cooled to 0° C., treated with sodium hydride (1.2 g, 30 mmol) (60% in mineral oil), and stirred at 0° C. for 30 min. The reaction mixture was treated with a solution of tert-butyl 3-(3-chloro-2-cyano-6-methoxy-5-{1-[(methylsulfonyl)oxy]ethyl}phenyl)azetidine-1-carboxylate (11 g, 24 mmol) in N,N-dimethylformamide (170 mL) dropwise over a period of 10 min and stirred at 0° C. for 30 min and heated at 50° C. for 1 h. The reaction mixture was diluted with water and saturated sodium bicarbonate solution and extracted with ethyl acetate (3×200 mL). The combined organic extracts were washed with water (4×150 mL) and brine, dried with magnesium sulfate, filtered, and concentrated to a crude oil. The crude material was purified by flash column chromatography (2% methanol/98% dichloromethane to 7% methanol/93% dichloromethane [the dichloromethane contained 0.5% triethylamine]) to give the desired product (9.1 g, 77% for 2 steps) as a 9:1 mixture of enantiomers. This material was separated by chiral HPLC (retention times=5.81 min and 8.94 min; Chiracel AD-H column, 20×250 mm, 5 micron particle size, eluting with 10% ethanol in hexanes at 18 ml/min, 10 mg/inj) to give 6.9 g of the desired peak 1 material. $^1$H NMR (400 MHz, DMSO-$d_6$) δ 8.11 (s, 1H), 7.52 (s, 1H), 6.25 (q, J=7.0 Hz, 1H), 4.45-4.33 (m, 1H), 4.27-4.13 (m, 4H), 3.70 (s, 3H), 2.55 (s, 3H), 1.73 (d, J=7.1 Hz, 3H), 1.37 (s, 9H). LCMS for $C_{20}H_{21}ClN_7O_3$ ([M-(t-Bu)+H]+H)$^+$: m/z=442.1. Found: 442.1.

Step 5. 4-[1-(4-Amino-3-methyl-1H-pyrazolo[3,4-d]pyrimidin-1-yl)ethyl]-2-azetidin-3-yl-6-chloro-3-methoxybenzonitrile A solution of tert-butyl 3-{3-[1-(4-amino-3-methyl-1H-pyrazolo[3,4-d]pyrimidin-1-yl)ethyl]-5-chloro-6-cyano-2-methoxyphenyl}azetidine-1-carboxylate (1.7 g, 3.3 mmol) in methylene chloride (30 mL) was treated with trifluoroacetic acid (20 mL) and stirred at room temperature for 20 min. The reaction mixture was concentrated to give a residue that was diluted with methanol (50 mL) and saturated sodium bicarbonate solution (50 mL). This aqueous solution was diluted with brine (50 mL) and extracted with a 5:1 mixture of dichloromethane/isopropanol (5×100 mL). The combined organic extracts were dried over sodium sulfate and concentrated to give the desired product (1.4 g, 97%). The product was isolated as a single enantiomer. $^1$H NMR (300 MHz, DMSO-$d_6$) δ 8.11 (s, 1H), 7.46 (s, 1H), 7.34 (br s, 2H), 6.24 (q, J=6.9 Hz, 1H), 4.40-4.26 (m, 1H), 3.90-3.68 (m, 4H), 3.63 (s, 3H), 2.55 (s, 3H), 1.72 (d, J=7.1 Hz, 3H). LCMS for $C_{19}H_{21}ClN_7O$ (M+H)$^+$: m/z=398.1. Found: 398.1.

Example 262

4-[1-(4-Amino-3-methyl-1H-pyrazolo[3,4-d]pyrimidin-1-yl)ethyl]-6-chloro-3-methoxy-2-(1-methylazetidin-3-yl)benzonitrile

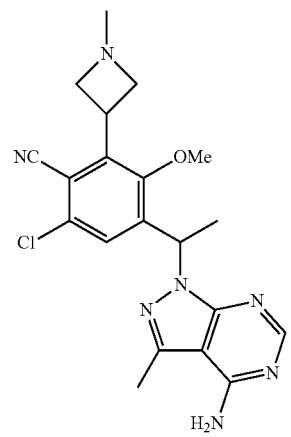 [SMILES: COc1c(C(C)n2nc(C)c3c(N)ncnc32)cc(Cl)c(C#N)c1C1CN(C)C1]

A solution of 4-[1-(4-amino-3-methyl-1H-pyrazolo[3,4-d]pyrimidin-1-yl)ethyl]-2-azetidin-3-yl-6-chloro-3-methoxybenzonitrile (chiral intermediate from Example 261) (50 mg, 0.13 mmol) in methanol (3 mL) was treated with sodium cyanoborohydride (20 mg, 0.31 mmol) followed by formaldehyde (37% in water) (37 μL, 0.50 mmol) and stirred at room temperature for 20 min. The reaction mixture was quenched with acetic acid (170 μL, 2.9 mmol), diluted with methanol, and purified by preparative LCMS (XBridge C18 column, eluting with a gradient of acetonitrile/water containing 0.1% ammonium hydroxide, at flow rate of 60 mL/min) to give the desired product (30 mg, 58%). The product was isolated as a single enantiomer. $^1$H NMR (300 MHz, DMSO-$d_6$) δ 8.11 (s, 1H), 7.46 (s, 1H), 7.37 (br s, 2H), 6.23 (q, J=7.0 Hz, 1H), 4.10-3.96 (m, 1H), 3.95-3.85 (m, 2H), 3.63 (s, 3H), 3.05-2.94 (m, 2H), 2.55 (s, 3H), 2.18 (s, 3H), 1.72 (d, J=7.1 Hz, 3H). LCMS for $C_{20}H_{23}ClN_7O$ (M+H)$^+$: m/z=412.2. Found: 412.1.

Example 268

4-[1-(4-Amino-3-methyl-1H-pyrazolo[3,4-d]pyrimidin-1-yl)ethyl]-6-chloro-2-[1-(2-hydroxyethyl)azetidin-3-yl]-3-methoxybenzonitrile

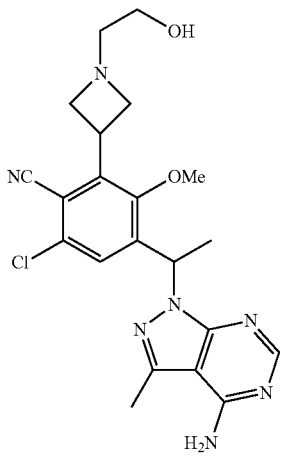 [SMILES: COc1c(C(C)n2nc(C)c3c(N)ncnc32)cc(Cl)c(C#N)c1C1CN(CCO)C1]

A solution of 4-[1-(4-amino-3-methyl-1H-pyrazolo[3,4-d]pyrimidin-1-yl)ethyl]-2-azetidin-3-yl-6-chloro-3-methoxybenzonitrile (chiral intermediate from Example 261) (400 mg, 1.0 mmol) in tetrahydrofuran (14 mL) was treated with triethylamine (350 μL, 2.5 mmol) and 2-bromoethanol (85 μL, 1.2 mmol) and stirred at 60° C. overnight. The reaction mixture was concentrated, diluted with methanol, and purified by preparative LCMS (XBridge C18 column, eluting with a gradient of acetonitrile/water containing 0.1% ammonium hydroxide, at flow rate of 60 mL/min) to give the desired product (0.14 g, 31%). The product was isolated as a single enantiomer. $^1$H NMR (400 MHz, DMSO-$d_6$) δ 8.11 (s, 1H), 7.46 (s, 1H), 6.24 (q, J=6.9 Hz, 1H), 4.41 (t, J=5.4 Hz, 1H), 4.12-4.03 (m, 1H), 3.97-3.88 (m, 2H), 3.64 (s, 3H), 3.38-3.34 (m, 2H), 3.09-3.01 (m, 2H), 2.55 (s, 3H), 2.41 (t, J=5.9 Hz, 2H), 1.72 (d, J=7.0 Hz, 3H). LCMS for $C_{21}H_{25}ClN_7O_2$ (M+H)$^+$: m/z=442.2. Found: 442.2.

The compounds of Example 268 and 269 were synthesized from the same chiral intermediate in Example 261. According to the crystal structure determination in Example 269, the stereochemistry at the carbon at the 1-position of the ethan-1,1-diyl group is S. Because the compound of Example 268 was synthesized from the same chiral intermediate as Example 269, one of ordinary skill in the art would expect that the carbon at the 1-position of the ethan-1,1-diyl group of Example 268 is also in the S-configuration. Accordingly, it is believed that the compound of Example 268 is (S)-4-(1-(4-amino-3-methyl-1H-pyrazolo[3,4-d]pyrimidin-1-yl)ethyl)-6-chloro-2-(1-(2-hydroxyethyl) azetidin-3-yl)-3-methoxybenzonitrile.

Example 269

4-[1-(4-Amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile

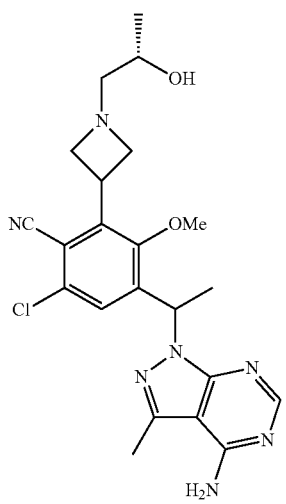 [SMILES: COc1c(C(C)n2nc(C)c3c(N)ncnc32)cc(Cl)c(C#N)c1C1CN(C[C@H](C)O)C1]

A solution of 4-[1-(4-amino-3-methyl-1H-pyrazolo[3,4-d]pyrimidin-1-yl)ethyl]-2-azetidin-3-yl-6-chloro-3-methoxybenzonitrile (chiral intermediate from Example 261) (2.5 g, 6.3 mmol) in ethanol (130 mL) was treated with (S)-(−)-methyloxirane (1.1 mL, 16 mmol) and heated in the microwave at 120° C. for 25 min. The reaction mixture was concentrated to give a residue that was purified by flash column chromatography using methanol in dichloromethane (0%-10%; methanol contained 0.5% triethylamine) and by preparative LCMS (XBridge C18 column, eluting with a gradient of acetonitrile/water containing 0.1% ammonium hydroxide, at flow rate of 60 mL/min) to give the desired product (0.76 g, 26%). The product was isolated as a single diastereomer. $^1$H NMR (300 MHz, DMSO-$d_6$) δ 8.11 (s, 1H), 7.46 (s, 1H), 7.34 (br s, 2H), 6.23 (q, J=7.0 Hz, 1H), 4.35 (br s, 1H), 4.14-3.99 (m, 1H), 3.98-3.87 (m, 2H), 3.64 (s, 3H), 3.60-3.52 (m, 1H), 3.13-2.99 (m, 2H), 2.55 (s, 3H), 2.28 (d, J=5.9 Hz, 2H), 1.75-1.69 (m, 3H), 1.00 (d, J=6.2 Hz, 3H). LCMS for $C_{22}H_{27}ClN_7O_2$ (M+H)$^+$: m/z=456.2. Found: 456.2.

Crystal Structure Determination for the Compound of Example 269

C22,H26,N7,O2,CL1+H$_2$O

CRYSTAL DATA: C22 H28 Cl F0 N7 O3, from ACN/water, colorless, needle, ~0.500×0.070×0.050 mm, monoclinic, C2, a=25.941(7) Å, b=4.9767(13) Å, c=17.787(5) Å, beta=101.967(4)°, Vol=2246.3(10) Å$^3$, Z=4, T=−100.° C., Formula weight=473.96, Density=1.401 g/cm$^3$, μ(Mo)=0.21 mm$^{-1}$ DATA COLLECTION: Bruker SMART APEX-II CCD system, MoKalpha radiation, standard focus tube, anode power=50 kV×42 mA, crystal to plate distance=5.0 cm, 512×512 pixels/frame, beam center=(256.13, 253.14), total frames=704, oscillation/frame=0.50°, exposure/ frame=120.1 sec/frame, SAINT integration, hkl min/max= (−27, 34, −6, 6, −23, 11), data input to shelx=7578, unique data=5186, two-theta range=3.20 to 56.74°, completeness to two-theta 56.74=99.70%, R(int-xl)=0.0331, SADABS correction applied.

SOLUTION AND REFINEMENT: Structure solved using XS(Shelxtl), refined using shelxtl software package, refinement by full-matrix least squares on $F^2$, scattering factors from Int. Tab. Vol C Tables 4.2.6.8 and 6.1.1.4, number of data=5186, number of restraints=2, number of parameters=313, data/parameter ratio=16.57, goodness-of-fit on $F^2$=1.02, R indices[I>4sigma(I)] R1=0.0524, wR2=0.1033, R indices (all data) R1=0.0826, wR2=0.1162, max difference peak and hole=0.294 and −0.221 e/Å$^3$, refined flack parameter=0.05(8), All of the hydrogen atoms except the NH2 and water hydrogens have been idealized using a riding model.

RESULTS: The asymmetric unit contains one molecule and one water molecule as shown in FIG. 1 with thermal ellipsoids drawn to the 50% probability level. The predicted structure is confirmed. The absolute configuration is determined based upon the known S configuration at C21. The configuration at C7 is determined to be S. The flack parameter also confirms the correct configuration. Based on the crystal structure, the compound of Example 269 is believed to be 4-((S)-1-(4-amino-3-methyl-1H-pyrazolo[3,4-d]pyrimidin-1-yl)ethyl)-6-chloro-2-(14S)-2-hydroxypropyl)azetidin-3-yl)-3-methoxybenzonitrile. The crystal structure is shown in FIG. 1.

TABLE A1

Atomic coordinates (×10$^4$) and equivalent isotropic displacement parameters (Å$^2$ × 10$^3$. U(eq) is defined as one third of the trace of the orthogonalized Uij tensor.

|  | x | y | z | U(eq) |
|---|---|---|---|---|
| Cl(1) | 8035(1) | 8495(2) | 305(1) | 36(1) |
| N(1) | 8519(1) | 3404(5) | 3463(1) | 26(1) |
| O(1) | 9561(1) | 4043(4) | 2906(1) | 23(1) |
| C(12) | 9008(1) | 8170(6) | 1221(2) | 21(1) |
| C(10) | 9211(1) | 5217(6) | 2312(2) | 20(1) |
| O(2) | 11255(1) | 1950(5) | 2364(1) | 29(1) |
| N(4) | 9120(1) | 528(5) | 4287(2) | 30(1) |
| N(7) | 10708(1) | 7154(5) | 1712(1) | 24(1) |
| N(2) | 8158(1) | 5432(5) | 3540(1) | 24(1) |
| C(9) | 8688(1) | 4321(6) | 2173(2) | 20(1) |
| N(3) | 9131(1) | 1229(5) | 5640(2) | 30(1) |
| C(1) | 8205(1) | 5793(6) | 4289(2) | 24(1) |
| C(13) | 8494(1) | 7215(6) | 1069(2) | 22(1) |
| C(21) | 11447(1) | 3787(7) | 1864(2) | 27(1) |
| C(7) | 8514(1) | 2255(6) | 2701(2) | 21(1) |
| C(14) | 8337(1) | 5294(6) | 1539(2) | 23(1) |
| C(16) | 9152(1) | 10282(7) | 751(2) | 28(1) |
| C(11) | 9384(1) | 7106(6) | 1834(2) | 20(1) |
| C(20) | 10994(1) | 5251(7) | 1322(2) | 27(1) |
| C(6) | 7877(1) | 7848(6) | 4574(2) | 28(1) |
| C(4) | 9278(1) | 68(7) | 5045(2) | 32(1) |
| C(17) | 9952(1) | 8008(6) | 1945(2) | 23(1) |
| N(5) | 8627(1) | 4376(6) | 6088(2) | 30(1) |
| C(18) | 10398(1) | 6006(7) | 2253(2) | 27(1) |
| C(19) | 10208(1) | 8201(7) | 1229(2) | 27(1) |
| N(6) | 9263(1) | 12004(6) | 392(2) | 39(1) |
| C(2) | 8582(1) | 4004(5) | 4710(2) | 20(1) |
| C(15) | 9743(1) | 5706(7) | 3568(2) | 30(1) |
| C(8) | 7972(1) | 1060(6) | 2388(2) | 26(1) |
| C(3) | 8776(1) | 3257(7) | 5486(2) | 26(1) |
| C(5) | 8770(1) | 2522(6) | 4155(2) | 25(1) |
| C(22) | 11791(1) | 2363(8) | 1403(2) | 42(1) |
| O(3) | 8003(1) | 8621(5) | 6617(1) | 40(1) |

TABLE A2

| Bond lengths [Å] and angles [deg] | |
|---|---|
| Cl(1)—C(13) | 1.731(3) |
| N(1)—C(5) | 1.340(4) |
| N(1)—N(2) | 1.403(3) |
| N(1)—C(7) | 1.468(4) |
| O(1)—C(10) | 1.372(3) |
| O(1)—C(15) | 1.437(4) |
| C(12)—C(13) | 1.390(4) |
| C(12)—C(11) | 1.406(4) |
| C(12)—C(16) | 1.438(4) |
| C(10)—C(9) | 1.400(4) |
| C(10)—C(11) | 1.403(4) |
| O(2)—C(21) | 1.434(4) |
| N(4)—C(5) | 1.333(4) |
| N(4)—C(4) | 1.345(4) |
| N(7)—C(20) | 1.463(4) |
| N(7)—C(18) | 1.491(4) |
| N(7)—C(19) | 1.494(4) |
| N(2)—C(1) | 1.325(4) |
| C(9)—C(14) | 1.382(4) |
| C(9)—C(7) | 1.524(4) |
| N(3)—C(4) | 1.329(4) |
| N(3)—C(3) | 1.355(4) |
| C(1)—C(2) | 1.417(4) |
| C(1)—C(6) | 1.485(4) |
| C(13)—C(14) | 1.385(4) |
| C(21)—C(22) | 1.509(4) |
| C(21)—C(20) | 1.540(4) |
| C(7)—C(8) | 1.522(4) |
| C(16)—N(6) | 1.143(4) |
| C(11)—C(17) | 1.513(4) |
| C(17)—C(18) | 1.538(4) |
| C(17)—C(19) | 1.558(4) |
| N(5)—C(3) | 1.334(4) |
| C(2)—C(5) | 1.398(4) |
| C(2)—C(3) | 1.417(4) |
| C(5)—N(1)—N(2) | 110.6(2) |
| C(5)—N(1)—C(7) | 129.0(3) |
| N(2)—N(1)—C(7) | 119.5(2) |
| C(10)—O(1)—C(15) | 116.0(2) |
| C(13)—C(12)—C(11) | 120.4(3) |
| C(13)—C(12)—C(16) | 119.3(2) |
| C(11)—C(12)—C(16) | 120.3(2) |
| O(1)—C(10)—C(9) | 117.6(2) |
| O(1)—C(10)—C(11) | 120.5(2) |
| C(9)—C(10)—C(11) | 121.7(3) |
| C(5)—N(4)—C(4) | 111.0(3) |
| C(20)—N(7)—C(18) | 116.9(2) |
| C(20)—N(7)—C(19) | 114.6(2) |
| C(18)—N(7)—C(19) | 89.10(19) |
| C(1)—N(2)—N(1) | 105.8(2) |
| C(14)—C(9)—C(10) | 118.9(3) |
| C(14)—C(9)—C(7) | 120.7(2) |
| C(10)—C(9)—C(7) | 120.4(2) |
| C(4)—N(3)—C(3) | 117.2(3) |
| N(2)—C(1)—C(2) | 110.8(3) |
| N(2)—C(1)—C(6) | 119.8(3) |
| C(2)—C(1)—C(6) | 129.4(3) |
| C(14)—C(13)—C(12) | 120.5(3) |
| C(14)—C(13)—Cl(1) | 119.3(2) |
| C(12)—C(13)—Cl(1) | 120.2(2) |
| O(2)—C(21)—C(22) | 111.0(3) |
| O(2)—C(21)—C(20) | 111.8(2) |
| C(22)—C(21)—C(20) | 110.1(3) |
| N(1)—C(7)—C(8) | 108.7(2) |
| N(1)—C(7)—C(9) | 111.1(2) |
| C(8)—C(7)—C(9) | 114.1(2) |
| C(9)—C(14)—C(13) | 120.6(3) |
| N(6)—C(16)—C(12) | 178.3(3) |
| C(10)—C(11)—C(12) | 117.7(2) |
| C(10)—C(11)—C(17) | 123.0(3) |
| C(12)—C(11)—C(17) | 119.3(2) |
| N(7)—C(20)—C(21) | 113.9(2) |
| N(3)—C(4)—N(4) | 130.3(3) |
| C(11)—C(17)—C(18) | 119.6(3) |
| C(11)—C(17)—C(19) | 118.7(2) |
| C(18)—C(17)—C(19) | 85.1(2) |
| N(7)—C(18)—C(17) | 89.4(2) |
| N(7)—C(19)—C(17) | 88.5(2) |

TABLE A2-continued

Bond lengths [A] and angles [deg]

| | |
|---|---|
| C(5)—C(2)—C(3) | 116.4(2) |
| C(5)—C(2)—C(1) | 105.1(2) |
| C(3)—C(2)—C(1) | 138.3(3) |
| N(5)—C(3)—N(3) | 116.5(3) |
| N(5)—C(3)—C(2) | 124.7(3) |
| N(3)—C(3)—C(2) | 118.8(3) |
| N(4)—C(5)—N(1) | 126.1(3) |
| N(4)—C(5)—C(2) | 126.3(3) |
| N(1)—C(5)—C(2) | 107.6(2) |

TABLE A3

Anisotropic displacement parameters ($Å^2 \times 10^3$).
The anisotropic displacement factor exponent takes
the form: $-2\pi^2 [h^2 a^{*2} U11 + \ldots + 2 h k a^* b^* U12]$

| | U11 | U22 | U33 | U23 | U13 | U12 |
|---|---|---|---|---|---|---|
| C1 (1) | 28 (1) | 47 (1) | 29 (1) | 14 (1) | 0 (1) | 2 (1) |
| N (1) | 29 (1) | 25 (1) | 24 (1) | 4 (1) | 8 (1) | 2 (1) |
| C (12) | 24 (1) | 17 (1) | 22 (1) | 2 (1) | 3 (1) | 1 (1) |
| C (10) | 22 (1) | 18 (1) | 19 (1) | 0 (1) | 6 (1) | 8 (1) |
| O (2) | 32 (1) | 29 (1) | 27 (1) | −3 (1) | 8 (1) | −4 (1) |
| N (4) | 30 (1) | 23 (1) | 36 (2) | 6 (1) | 9 (1) | 4 (1) |
| N (7) | 22 (1) | 26 (1) | 27 (1) | −3 (1) | 7 (1) | −1 (1) |
| N (2) | 26 (1) | 20 (1) | 29 (1) | 2 (1) | 11 (1) | 1 (1) |
| C (9) | 23 (1) | 18 (1) | 21 (1) | −1 (1) | 10 (1) | 6 (1) |
| N (3) | 31 (1) | 31 (1) | 28 (1) | 4 (1) | 2 (1) | 3 (1) |
| C (1) | 26 (2) | 21 (2) | 28 (2) | 1 (1) | 9 (1) | −3 (1) |
| C (13) | 25 (1) | 25 (2) | 17 (1) | 6 (1) | 6 (1) | 8 (1) |
| C (21) | 23 (1) | 29 (2) | 32 (2) | −2 (2) | 11 (1) | −2 (1) |
| C (7) | 25 (1) | 18 (1) | 22 (2) | 0 (1) | 8 (1) | 4 (1) |
| C (14) | 23 (1) | 23 (2) | 25 (2) | 1 (1) | 8 (1) | 1 (1) |
| C (16) | 26 (2) | 31 (2) | 25 (2) | 4 (1) | 5 (1) | 2 (1) |
| C (11) | 22 (1) | 19 (1) | 21 (1) | −4 (1) | 7 (1) | −2 (1) |
| C (20) | 26 (2) | 30 (2) | 27 (2) | −5 (1) | 9 (1) | −7 (1) |
| C (6) | 30 (2) | 18 (2) | 39 (2) | −2 (1) | 10 (1) | −1 (1) |
| C (4) | 26 (2) | 30 (2) | 37 (2) | 5 (2) | 3 (2) | 6 (1) |
| C (17) | 22 (1) | 22 (2) | 25 (2) | −3 (1) | 3 (1) | −4 (1) |
| N (5) | 36 (2) | 32 (2) | 23 (2) | 0 (1) | 7 (1) | −1 (1) |
| C (18) | 26 (2) | 33 (2) | 26 (2) | 1 (1) | 10 (1) | 3 (1) |
| C (19) | 27 (1) | 28 (2) | 25 (2) | 6 (1) | 5 (1) | −3 (1) |
| N (6) | 42 (2) | 36 (2) | 39 (2) | 14 (1) | 8 (1) | −2 (1) |
| C (2) | 18 (1) | 15 (1) | 25 (2) | 3 (1) | 3 (1) | −5 (1) |
| C (15) | 30 (2) | 35 (2) | 22 (2) | −8 (1) | 2 (1) | 1 (1) |
| C (8) | 31 (2) | 20 (1) | 29 (2) | 3 (1) | 11 (1) | −1 (1) |
| C (3) | 27 (1) | 26 (2) | 26 (2) | 3 (1) | 5 (1) | −4 (1) |
| C (5) | 27 (2) | 21 (1) | 26 (2) | 4 (1) | 5 (1) | −3 (1) |
| C (22) | 37 (2) | 43 (2) | 48 (2) | −7 (2) | 17 (2) | 4 (2) |
| O (3) | 31 (1) | 37 (1) | 52 (2) | −4 (1) | 5 (1) | 3 (1) |

TABLE A4

Hydrogen coordinates($\times 10^4$) and isotropic displacement parameters($Å^2 \times 10^3$)

| | x | y | z | U(eq) |
|---|---|---|---|---|
| H(21A) | 11662 | 5142 | 2184 | 33 |
| H(7A) | 8769 | 778 | 2769 | 25 |
| H(14A) | 7993 | 4654 | 1427 | 28 |
| H(20A) | 11136 | 6209 | 936 | 32 |
| H(20B) | 10747 | 3924 | 1059 | 32 |
| H(6A) | 7658 | 8739 | 4146 | 43 |
| H(6B) | 8102 | 9141 | 4882 | 43 |
| H(6C) | 7660 | 6994 | 4880 | 43 |
| H(4A) | 9529 | −1277 | 5173 | 38 |
| H(17A) | 10005 | 9684 | 2240 | 28 |
| H(18A) | 10560 | 6271 | 2791 | 33 |
| H(18B) | 10299 | 4141 | 2151 | 33 |
| H(19A) | 10051 | 7013 | 811 | 32 |
| H(19B) | 10235 | 10021 | 1045 | 32 |
| H(15A) | 9984 | 4705 | 3948 | 45 |

TABLE A4-continued

Hydrogen coordinates($\times 10^4$) and isotropic displacement parameters($Å^2 \times 10^3$)

| | x | y | z | U(eq) |
|---|---|---|---|---|
| H(15B) | 9448 | 6265 | 3778 | 45 |
| H(15C) | 9918 | 7259 | 3420 | 45 |
| H(8A) | 7888 | −221 | 2748 | 39 |
| H(8B) | 7971 | 182 | 1907 | 39 |
| H(8C) | 7713 | 2467 | 2310 | 39 |
| H(22C) | 12072 | 1453 | 1746 | 62 |
| H(22D) | 11937 | 3652 | 1104 | 62 |
| H(22A) | 11584 | 1079 | 1067 | 62 |
| H(5) | 8394(11) | 5640(60) | 6006(16) | 11(7) |
| H(5') | 8756(12) | 3720(80) | 6590(20) | 43(10) |
| H(2") | 11091(16) | 700(100) | 2100(30) | 66(15) |
| H(3) | 8231(15) | 9740(80) | 6910(20) | 80(17) |
| H(3') | 7658(11) | 9010(80) | 6510(20) | 52(12) |

TABLE A5

Torsion angles [deg]

| | |
|---|---|
| C(15)—O(1)—C(10)—C(9) | −109.6(3) |
| C(15)—O(1)—C(10)—C(11) | 74.8(3) |
| C(5)—N(1)—N(2)—C(1) | 1.3(3) |
| C(7)—N(1)—N(2)—C(1) | 171.4(2) |
| O(1)—C(10)—C(9)—C(14) | −174.4(2) |
| C(11)—C(10)—C(9)—C(14) | 1.1(4) |
| O(1)—C(10)—C(9)—C(7) | 4.1(4) |
| C(11)—C(10)—C(9)—C(7) | 179.6(2) |
| N(1)—N(2)—C(1)—C(2) | −1.2(3) |
| N(1)—N(2)—C(1)—C(6) | 179.4(2) |
| C(11)—C(12)—C(13)—C(14) | 3.0(4) |
| C(16)—C(12)—C(13)—C(14) | −176.2(3) |
| C(11)—C(12)—C(13)—Cl(1) | −179.0(2) |
| C(16)—C(12)—C(13)—C1(1) | 1.7(4) |
| C(5)—N(1)—C(7)—C(8) | 109.1(3) |
| N(2)—N(1)—C(7)—C(8) | −58.9(3) |
| C(5)—N(1)—C(7)—C(9) | −124.6(3) |
| N(2)—N(1)—C(7)—C(9) | 67.4(3) |
| C(14)—C(9)—C(7)—N(1) | −112.9(3) |
| C(10)—C(9)—C(7)—N(1) | 68.6(3) |
| C(14)—C(9)—C(7)—C(8) | 10.4(4) |
| C(10)—C(9)—C(7)—C(8) | −168.1(3) |
| C(10)—C(9)—C(14)—C(13) | −2.9(4) |
| C(7)—C(9)—C(14)—C(13) | 178.6(3) |
| C(12)—C(13)—C(14)—C(9) | 0.8(4) |
| Cl(1)—C(13)—C(14)—C(9) | −177.1(2) |
| C(13)—C(12)—C(16)—N(6) | 98(12) |
| C(11)—C(12)—C(16)—N(6) | −82(12) |
| O(1)—C(10)—C(11)—C(12) | 178.0(3) |
| C(9)—C(10)—C(11)—C(12) | 2.6(4) |
| O(1)—C(10)—C(11)—C(17) | −1.4(4) |
| C(9)—C(10)—C(11)—C(17) | −176.8(3) |
| C(13)—C(12)—C(11)—C(10) | −4.6(4) |
| C(16)—C(12)—C(11)—C(10) | 174.6(3) |
| C(13)—C(12)—C(11)—C(17) | 174.7(3) |
| C(16)—C(12)—C(11)—C(17) | −6.0(4) |
| C(18)—N(7)—C(20)—C(21) | −66.6(3) |
| C(19)—N(7)—C(20)—C(21) | −168.9(2) |
| O(2)—C(21)—C(20)—N(7) | 68.8(3) |
| C(22)—C(21)—C(20)—N(7) | −167.3(3) |
| C(3)—N(3)—C(4)—N(4) | −1.9(5) |
| C(5)—N(4)—C(4)—N(3) | 1.5(4) |
| C(10)—C(11)—C(17)—C(18) | 33.6(4) |
| C(12)—C(11)—C(17)—C(18) | −145.8(3) |
| C(10)—C(11)—C(17)—C(19) | 135.1(3) |
| C(12)—C(11)—C(17)—C(19) | −44.3(4) |
| C(20)—N(7)—C(18)—C(17) | −138.9(2) |
| C(19)—N(7)—C(18)—C(17) | −21.5(2) |
| C(11)—C(17)—C(18)—N(7) | 141.1(2) |
| C(19)—C(17)—C(18)—N(7) | 20.7(2) |
| C(20)—N(7)—C(19)—C(17) | 140.7(2) |
| C(18)—N(7)—C(19)—C(17) | 21.3(2) |
| C(11)—C(17)—C(19)—N(7) | −141.9(3) |
| C(18)—C(17)—C(19)—N(7) | −20.7(2) |

TABLE A5-continued

| Torsion angles [deg] | |
|---|---|
| N(2)—C(1)—C(2)—C(5) | 0.6(3) |
| C(6)—C(1)—C(2)—C(5) | 179.9(3) |
| N(2)—C(1)—C(2)—C(3) | −173.9(3) |
| C(6)—C(1)—C(2)—C(3) | 5.4(6) |
| C(4)—N(3)—C(3)—N(5) | 179.0(3) |
| C(4)—N(3)—C(3)—C(2) | 0.4(4) |
| C(5)—C(2)—C(3)—N(5) | −177.4(3) |
| C(1)—C(2)—C(3)—N(5) | −3.3(5) |
| C(5)—C(2)—C(3)—N(3) | 1.2(4) |
| C(1)—C(2)—C(3)—N(3) | 175.3(3) |
| C(4)—N(4)—C(5)—N(1) | −177.0(3) |
| C(4)—N(4)—C(5)—C(2) | 0.4(4) |
| N(2)—N(1)—C(5)—N(4) | 176.9(3) |
| C(7)—N(1)—C(5)—N(4) | 8.0(5) |
| N(2)—N(1)—C(5)—C(2) | −1.0(3) |
| C(7)—N(1)—C(5)—C(2) | −169.9(3) |
| C(3)—C(2)—C(5)—N(4) | −1.7(4) |
| C(1)—C(2)—C(5)—N(4) | −177.6(3) |
| C(3)—C(2)—C(5)—N(1) | 176.2(2) |
| C(1)—C(2)—C(5)—N(1) | 0.2(3) |

Examples 272 and 273

Diastereoisomers of 4-[1-(4-amino-3-methyl-1H-pyrazolo[3,4-d]pyrimidin-1-yl)ethyl]-6-chloro-2-[1-(2-hydroxy-1-methylethyl)azetidin-3-yl]-3-methoxybenzonitrile

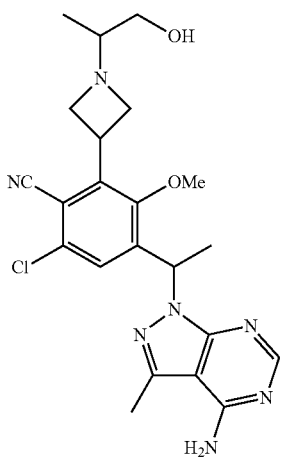 [SMILES: COc1c(C(C)n2nc(C)c3c(N)ncnc32)cc(Cl)c(C#N)c1C1CN(C(C)CO)C1]

A solution of 4-[1-(4-amino-3-methyl-1H-pyrazolo[3,4-d]pyrimidin-1-yl)ethyl]-2-azetidin-3-yl-6-chloro-3-methoxybenzonitrile (40 mg, 0.10 mmol) in methanol (2 mL) was treated with sodium cyanoborohydride (16 mg, 0.25 mmol) followed by acetol (28 μL, 0.40 mmol) and stirred at room temperature for 1 h. The reaction mixture was quenched with acetic acid (100 μL, 1.8 mmol), diluted with methanol, and purified by preparative LCMS (XBridge C18 column, eluting with a gradient of acetonitrile/water containing 0.1% ammonium hydroxide, at flow rate of 60 mL/min) to give the desired products as a mixture of diastereoisomers. This mixture of diastereoisomers was separated by chiral HPLC (RT=3.70 min and 6.58 min; Phenomenex Lux Cellulose C-4 column, 21.2×250 mm, 5 micron particle size, eluting with 20% ethanol in hexanes at 18 ml/min, 5 mg/inj) to give the desired peak 1 isomer (compound 272) (19 mg, 41%) and peak 2 isomer (compound 273) (23 mg, 50%) Peak 1: $^1$H NMR (300 MHz, DMSO-$d_6$) δ 8.11 (s, 1H), 7.47 (s, 1H), 7.34 (br s, 2H), 6.24 (q, J=6.9 Hz, 1H), 4.43 (t, J=5.2 Hz, 1H), 4.07-3.82 (m, 3H), 3.64 (s, 3H), 3.31-3.24 (m, 1H), 3.17-3.06 (m, 2H), 3.06-2.97 (m, 1H), 2.55 (s, 3H), 2.21-2.11 (m, 1H), 1.72 (d, J=7.1 Hz, 3H), 0.81 (d, J=6.3 Hz, 3H). LCMS for $C_{22}H_{27}ClN_7O_2$ (M+H)$^+$: m/z=456.2. Found: 456.2. Peak 2: $^1$H NMR (300 MHz, DMSO-$d_6$) δ 8.11 (s, 1H), 7.47 (s, 1H), 7.35 (br s, 2H), 6.24 (q, J=7.0 Hz, 1H), 4.43 (t, J=5.5 Hz, 1H), 4.06-3.91 (m, 2H), 3.89-3.79 (m, 1H), 3.64 (s, 3H), 3.30-3.24 (m, 1H), 3.15-3.00 (m, 3H), 2.55 (s, 3H), 2.21-2.10 (m, 1H), 1.72 (d, J=7.1 Hz, 3H), 0.82 (d, J=6.2 Hz, 3H). LCMS for $C_{22}H_{27}ClN_7O_2$ (M+H)$^+$: m/z=456.2. Found: 456.2.

Example 281

2-(1-Acetylazetidin-3-yl)-4-[1-(4-amino-3-methyl-1H-pyrazolo[3,4-d]pyrimidin-1-yl)ethyl]-6-chloro-3-methoxybenzonitrile

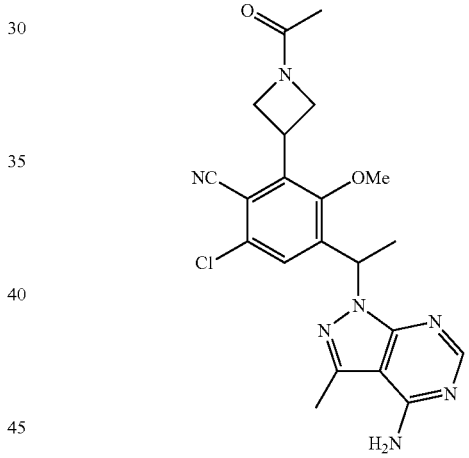

A solution of 4-[1-(4-amino-3-methyl-1H-pyrazolo[3,4-d]pyrimidin-1-yl)ethyl]-2-azetidin-3-yl-6-chloro-3-methoxybenzonitrile (chiral intermediate from Example 261) (60 mg, 0.15 mmol) in tetrahydrofuran (2 mL) at 0° C. was treated with triethylamine (53 μL, 0.38 mmol) followed by acetyl chloride (13 μL, 0.18 mmol) and stirred at 20° C. overnight. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product (39 mg, 59%). The product was isolated as a single enantiomer. $^1$H NMR (300 MHz, DMSO-$d_6$) δ 8.11 (s, 1H), 7.52 (d, J=2.5 Hz, 1H), 7.36 (br s, 2H), 6.26 (q, J=7.0 Hz, 1H), 4.57-4.36 (m, 3H), 4.30-4.21 (m, 1H), 4.18-4.08 (m, 1H), 3.71 (d, J=3.1 Hz, 3H), 2.55 (s, 3H), 1.78-1.71 (m, 6H). LCMS for $C_{21}H_{23}ClN_7O_2$ (M+H)$^+$: m/z=440.2. Found: 440.1.

Example 285

4-[1-(4-Amino-3-methyl-1H-pyrazolo[3,4-d]pyrimidin-1-yl)ethyl]-6-chloro-3-methoxy-2-[1-(methylsulfonyl)azetidin-3-yl]benzonitrile

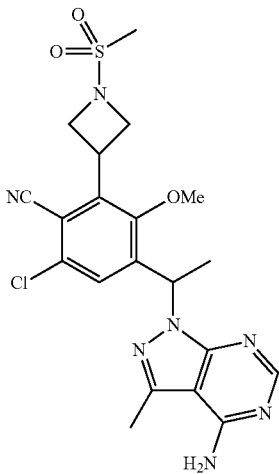 [SMILES: COc1c(C(C)n2nc(C)c3c(N)ncnc32)cc(Cl)c(C#N)c1C1CN(S(C)(=O)=O)C1]

A solution of 4-[1-(4-amino-3-methyl-1H-pyrazolo[3,4-d]pyrimidin-1-yl)ethyl]-2-azetidin-3-yl-6-chloro-3-methoxybenzonitrile (chiral intermediate from Example 261) (40 mg, 0.10 mmol) in dichloromethane (1 mL) was treated with triethylamine (35 µL, 0.25 mmol), cooled to 0° C., treated with methanesulfonyl chloride (9.3 µL, 0.12 mmol) and stirred at 0° C. for 1 h. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product (20 mg, 42%). The product was isolated as a single enantiomer. $^1$H NMR (300 MHz, DMSO-$d_6$) δ 8.12 (s, 1H), 7.55 (s, 1H), 7.35 (br s, 2H), 6.25 (q, J=7.0 Hz, 1H), 4.54-4.40 (m, 1H), 4.27-4.12 (m, 4H), 3.68 (s, 3H), 3.01 (s, 3H), 2.55 (s, 3H), 1.74 (d, J=7.1 Hz, 3H). LCMS for $C_{20}H_{23}ClN_7O_3S$ (M+H)$^+$: m/z=476.1. Found: 476.1.

Example 289

Methyl 3-{3-[1-(4-amino-3-methyl-1H-pyrazolo[3,4-d]pyrimidin-1-yl)ethyl]-5-chloro-6-cyano-2-methoxyphenyl}azetidine-1-carboxylate

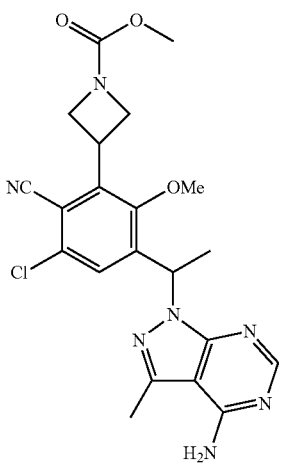 [SMILES: COC(=O)N1CC(c2c(C#N)c(Cl)cc(C(C)n3nc(C)c4c(N)ncnc43)c2OC)C1]

A solution of 4-[1-(4-amino-3-methyl-1H-pyrazolo[3,4-d]pyrimidin-1-yl)ethyl]-2-azetidin-3-yl-6-chloro-3-methoxybenzonitrile (chiral intermediate from Example 261) (20 mg, 0.05 mmol) in dichloromethane (1 mL) was treated with triethylamine (20 µL, 0.14 mmol) followed by methyl chloroformate (4.7 µL, 0.06 mmol) and stirred at room temperature for 1 h. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product (12 mg, 52%). The product was isolated as a single enantiomer. $^1$H NMR (300 MHz, DMSO-$d_6$) δ 8.11 (s, 1H), 7.51 (s, 1H), 7.34 (br s, 2H), 6.25 (q, J=7.0 Hz, 1H), 4.53-4.38 (m, 1H), 4.36-4.17 (m, 4H), 3.71 (s, 3H), 3.55 (s, 3H), 2.55 (s, 3H), 1.73 (d, J=7.1 Hz, 3H). LCMS for $C_{21}H_{23}ClN_7O_3$ (M+H)$^+$: m/z=456.2. Found: 456.1.

Example 292

3-{3-[1-(4-Amino-3-methyl-1H-pyrazolo[3,4-d]pyrimidin-1-yl)ethyl]-5-chloro-6-cyano-2-methoxyphenyl}-N-(tert-butyl)azetidine-1-carboxamide

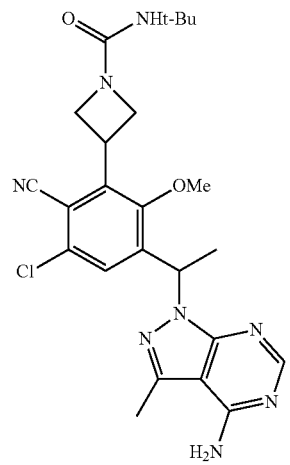

A solution of 4-[1-(4-amino-3-methyl-1H-pyrazolo[3,4-d]pyrimidin-1-yl)ethyl]-2-azetidin-3-yl-6-chloro-3-methoxybenzonitrile (chiral intermediate from Example 261) (20 mg, 0.05 mmol) in N,N-dimethylformamide (1 mL) was treated with triethylamine (20 µL, 0.14 mmol) followed by 2-isocyanato-2-methyl-propane (7.2 µL, 0.063 mmol) and stirred at room temperature overnight. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product (16 mg, 64%). The product was isolated as a single enantiomer. LCMS for $C_{24}H_{30}ClN_8O_2$ (M+H)$^+$: m/z=497.2. Found: 497.2.

Example 293

3-{3-[1-(4-Amino-3-methyl-1H-pyrazolo[3,4-d]pyrimidin-1-yl)ethyl]-5-chloro-6-cyano-2-methoxyphenyl}azetidine-1-carboxamide

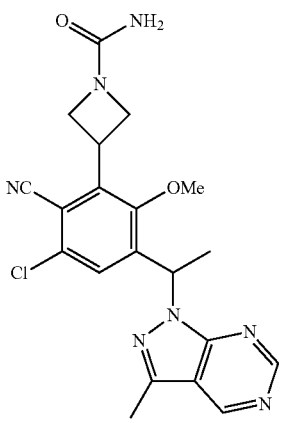 [SMILES: COc1c(C(C)n2nc(C)c3cncnc32)cc(Cl)c(C#N)c1C1CN(C(N)=O)C1]

A solution of 3-{3-[1-(4-amino-3-methyl-1H-pyrazolo[3,4-d]pyrimidin-1-yl)ethyl]-5-chloro-6-cyano-2-methoxyphenyl}-N-(tert-butyl)azetidine-1-carboxamide (chiral intermediate from Example 292) (16 mg, 0.032 mmol) in trifluoroacetic acid (2 mL) was heated in the microwave at 120° C. for 10 min. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product (7 mg, 50%). The product was isolated as a single enantiomer. $^1$H NMR (300 MHz, DMSO-$d_6$) δ 8.12 (s, 1H), 7.62 (s, 1H), 7.35 (br s, 2H), 6.28 (q, J=6.9 Hz, 1H), 5.70 (br s, 1H), 4.62-4.49 (m, 1H), 4.34-4.20 (m, 1H), 3.83 (s, 3H), 3.78-3.49 (m, 2H), 2.55 (s, 3H), 1.73 (d, J=7.0 Hz, 3H). LCMS for $C_{20}H_{22}ClN_8O_2$ (M+H)$^+$: m/z=441.2. Found: 441.1.

Example 296

3-{3-[1-(4-Amino-3-methyl-1H-pyrazolo[3,4-d]pyrimidin-1-yl)ethyl]-5-chloro-6-cyano-2-methoxyphenyl}-N,N-dimethylazetidine-1-carboxamide

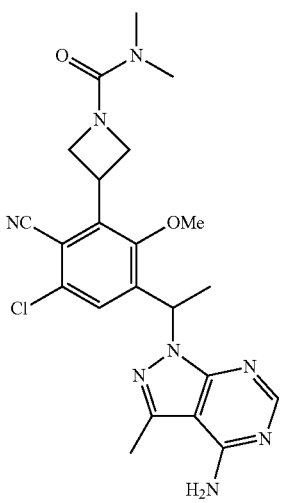 [SMILES: COc1c(C(C)n2nc(C)c3c(N)ncnc32)cc(Cl)c(C#N)c1C1CN(C(=O)N(C)C)C1]

A solution of 4-[1-(4-amino-3-methyl-1H-pyrazolo[3,4-d]pyrimidin-1-yl)ethyl]-2-azetidin-3-yl-6-chloro-3-methoxybenzonitrile (chiral intermediate from Example 261) (40 mg, 0.10 mmol) in N,N-dimethylformamide (2 mL) was treated with triethylamine (40 μL, 0.29 mmol) followed by p-nitrophenyl chloroformate (23 μL, 0.13 mmol) and stirred at room temperature for 1 h. The reaction mixture was diluted with methanol and purified by preparative LCMS (XBridge C18 column, eluting with a gradient of acetonitrile/water containing 0.1% ammonium hydroxide, at flow rate of 60 mL/min) to give the desired product that was used immediately. A solution of the p-nitrophenyl carbamate intermediate in tetrahydrofuran (1 mL) was treated with triethylamine (15 μL, 0.11 mmol) followed by a solution of 1.0 M dimethylamine in tetrahydrofuran (150 μL, 0.15 mmol) and heated in a sealed tube at 60° C. for 2 h. The reaction mixture was concentrated, diluted with methanol and purified by preparative LCMS (XBridge C18 column, eluting with a gradient of acetonitrile/water containing 0.1% ammonium hydroxide, at flow rate of 60 mL/min) to give the desired product (13 mg, 28%). The product was isolated as a single enantiomer. $^1$H NMR (300 MHz, DMSO-$d_6$) δ 8.11 (s, 1H), 7.49 (s, 1H), 7.36 (br s, 2H), 6.25 (q, J=7.0 Hz, 1H), 4.44-4.23 (m, 3H), 4.22-4.10 (m, 2H), 3.69 (s, 3H), 2.76 (s, 6H), 2.55 (s, 3H), 1.73 (d, J=7.1 Hz, 3H). LCMS for $C_{22}H_{26}ClN_8O_2$ (M+H)$^+$: m/z=469.2. Found: 469.1.

Example 298

1-{1-[4,5-Dichloro-3-(1-ethylazetidin-3-yl)-2-methoxyphenyl]ethyl}-3-methyl-1H-pyrazolo[3,4-d]pyrimidin-4-amine

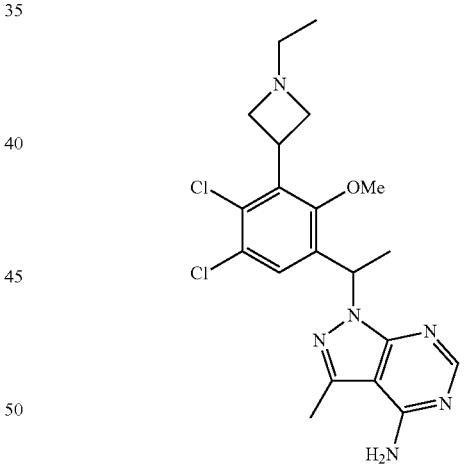

Step 1. 1-(4,5-Dichloro-2-hydroxyphenyl)ethanone

A solution of 3,4-dichlorophenol [AK Scientific] (30 g, 18 mmol) in acetyl chloride (19 mL, 270 mmol) was stirred at 60° C. for 2 h. The reaction mixture was cooled to 20° C., treated with aluminum trichloride (37 g, 280 mmol) portionwise, and heated at 180° C. for 30 min. The reaction mixture was cooled to 20° C. and the solution hardened into a solid block that was not easy to break apart. This material was cooled to 0° C. and quenched slowly with 1 M HCl in portions. The solid block of material slowly broke apart with enough HCl and this heterogenous mixture was stirred at 20° C. overnight to ensure uniformity. The solid was filtered, washed with copious amounts of water, and dried under vacuum to give the desired product (38 g, quantitative) as a tan solid.

Step 2.
1-(4,5-Dichloro-2-hydroxy-3-iodophenyl)ethanone

A solution of 1-(4,5-dichloro-2-hydroxyphenyl)ethanone (12 g, 59 mmol) in acetic acid (70 mL) was treated with N-iodosuccinimide (16 g, 71 mmol) and stirred at 90° C. for 18 h. The reaction mixture was treated with additional N-iodosuccinimide (8 g, 36 mmol) and stirred at 90° C. for 4 h. The reaction mixture was concentrated, diluted with ethyl acetate, and quenched with saturated sodium bicarbonate until the bubbling stopped. The organic layer was separated and the aqueous was re-extracted with ethyl acetate. The combined organic layers were dried and concentrated to give a brown solid. This material was recrystallized from methanol to give desired product (9.0 g, 46%) as a tan solid. $^1$H NMR (300 MHz, CDCl$_3$) δ 13.36 (s, 1H), 7.85 (s, 1H), 2.65 (s, 3H). LCMS for $C_8H_6Cl_2IO_2$ (M+H)$^+$: m/z=330.9, 332.9. Found: 330.8, 332.9.

Step 3.
1-(4,5-Dichloro-3-iodo-2-methoxyphenyl)ethanone

A solution of 1-(4,5-dichloro-2-hydroxy-3-iodophenyl) ethanone (16 g, 47 mmol) and potassium carbonate (17 g, 120 mmol) in N,N-dimethylformamide (40 mL) was treated with methyl iodide (6.4 mL, 100 mmol) and stirred at 60° C. for 1 h. The reaction mixture was diluted with water and extracted with ethyl acetate (2×). The combined organic layers were dried with magnesium sulfate, filtered, and concentrated to give a crude solid. The crude material was purified by flash column chromatography using ethyl acetate in hexanes (5%-30%) to give the desired product (14 g, 84%) as an orange solid. $^1$H NMR (300 MHz, CDCl$_3$) δ 7.69 (s, 1H), 3.79 (s, 3H), 2.60 (s, 3H). LCMS for $C_9H_8Cl_2IO_2$ (M+H)$^+$: m/z=344.9, 346.9. Found: 344.8, 346.9.

Step 4. tert-Butyl 3-(3-acetyl-5,6-dichloro-2-methoxyphenyl)azetidine-1-carboxylate Zinc (4.5 g, 69 mmol) was suspended with 1,2-dibromoethane (420 μL, 4.9 mmol) in N,N-dimethylformamide (54 mL). The mixture was heated at 70° C. for 10 min and then cooled to room temperature. Chlorotrimethylsilane (620 μL, 4.9 mmol) was added dropwise and stirring was continued for 1 h. A solution of tert-butyl 3-iodoazetidine-1-carboxylate (17 g, 61 mmol) in N,N-dimethylformamide (30 mL) was then added and the mixture was heated at 40° C. for 1 h before a mixture of 1-(4,5-dichloro-3-iodo-2-methoxyphenyl)ethanone (14 g, 41 mmol), tris(dibenzylideneacetone)dipalladium(0) (710 mg, 0.77 mmol) and tri-(2-furyl)phosphine (360 mg, 1.6 mmol) in N,N-dimethylformamide (120 mL) was added quickly. The reaction mixture was stirred overnight at room temperature. The reaction mixture was then partitioned between ethyl acetate and saturated ammonium chloride solution. The organic layer was washed with water, dried with magnesium sulfate, filtered, and concentrated to a crude residue that was purified by flash column chromatography using ethyl acetate in hexanes (0%-25%) to give the desired product (12 g, 77%). LCMS for $C_{17}H_{21}Cl_2NO_4Na$ (M+Na)$^+$: m/z=396.1. Found: 396.0.

Step 5. tert-Butyl 3-[2,3-dichloro-5-(1-hydroxyethyl)-6-methoxyphenyl]azetidine-1-carboxylate A solution of tert-butyl 3-(3-acetyl-5,6-dichloro-2-methoxyphenyl)azetidine-1-carboxylate (9.6 g, 26 mmol) in methanol (240 mL) at 0° C. was treated with sodium tetrahydroborate (1.9 g, 51 mmol) portionwise over 5 min and stirred at 0° C. for 30 min. The reaction mixture was quenched with acetic acid (7.3 mL, 130 mmol) at 0° C. and treated with saturated sodium bicarbonate solution (~50 mL). The reaction mixture was concentrated to remove most of the methanol (to 60 mL), poured into saturated sodium bicarbonate solution (150 ml), and extracted with ethyl acetate (2×200 mL). The combined organic extracts were washed with water and brine, dried over sodium sulfate, filtered, and concentrated to give the desired product (9.6 g, quantitative) that was used without further purification. LCMS for $C_{13}H_{16}Cl_2NO_4$ ([M-(t-Bu)+1-1]+H)$^+$: m/z=320.0. Found: 320.0.

Step 6. tert-Butyl 3-[2,3-dichloro-5-(1-chloroethyl)-6-methoxyphenyl]azetidine-1-carboxylate N,N-Dimethylformamide (0.92 mL, 12 mmol) was added to solid cyanuric chloride (2.2 g, 12 mmol) at room temperature (DMF is absorbed by the solid). The mixture was allowed to stand for 10 min, treated with methylene chloride (60 mL), and stirred for a few minutes to break up the solid. The reaction mixture was treated with a solution of tert-butyl 3-[2,3-dichloro-5-(1-hydroxyethyl)-6-methoxyphenyl]azetidine-1-carboxylate (3.0 g, 8.0 mmol) in methylene chloride (30 mL) and stirred at 35-40° C. for 2 h. The reaction mixture was treated with additional N,N-dimethylformamide (1 mL) and stirred at 35-40° C. for 4 h. The reaction required another treatment of N,N-dimethylformamide (1 mL) with stirring at 35-40° C. overnight to proceed to completion. The reaction mixture was diluted with water and dichloromethane. The organic phase was separated and washed with saturated sodium bicarbonate solution, water and brine, dried over magnesium sulfate, filtered, and concentrated to a crude residue. The crude material was purified by flash column chromatography using ethyl acetate in hexanes (5%-40%) to give the desired product (2.8 g, 90%). LCMS for $C_{13}H_{15}Cl_3NO_3$ ([M-(t-Bu)+H]+H)$^+$: m/z=338.0, 340.0. Found: 337.9, 339.9.

Step 7. tert-Butyl 3-{3-[1-(4-amino-3-methyl-1H-pyrazolo[4,3-c]pyridin-1-yl)ethyl]-5,6-dichloro-2-methoxyphenyl}azetidine-1-carboxylate A solution of tert-butyl 3-[2,3-dichloro-5-(1-chloroethyl)-6-methoxyphenyl]azetidine-1-carboxylate (1.0 g, 2.5 mmol) and 3-methyl-1H-pyrazolo[3,4-d]pyrimidin-4-amine (0.43 g, 2.9 mmol) in N,N-dimethylformamide (23 mL) was treated with cesium carbonate (1.2 g, 3.8 mmol) and potassium iodide (42 mg, 0.25 mmol) and heated at 100° C. for 10 h. The reaction mixture was diluted with ethyl acetate (75 mL) and water (75 mL). The aqueous layer was separated and reextracted with ethyl acetate (2×50 mL). The combined organic layers were washed with water, saturated sodium bicarbonate solution, and brine, dried over magnesium sulfate, filtered, and concentrated to a crude residue. The crude material was purified by flash column chromatography using methanol in dichloromethane (0%-10%) to give the desired product (0.97 g, 75%). LCMS for $C_{23}H_{29}Cl_2N_6O_3$ (M+H)$^+$: m/z=507.2, 509.2. Found: 507.0, 509.0.

Step 8. 1-[1-(3-Azetidin-3-yl-4,5-dichloro-2-methoxyphenyl)ethyl]-3-methyl-1H-pyrazolo[3,4-d]pyrimidin-4-amine A solution of tert-butyl 3-{3-[1-(4-amino-3-methyl-1H-pyrazolo[4,3-c]pyridin-1-yl)ethyl]-5,6-dichloro-2-methoxyphenyl}azetidine-1-carboxylate (0.97 g, 1.9 mmol) in methylene chloride (20 mL) was treated with trifluoroacetic acid (10 mL) and stirred at 20° C. for 30 min. The reaction mixture was concentrated and the residue was diluted with methanol (~20 mL) and treated with saturated sodium bicarbonate solution (to pH=8). The reaction mixture was concentrated to remove the methanol. The oil that was suspended in the aqueous layer was extracted into a 5:1 mixture of dichloromethane/isopropanol, dried over magnesium sulfate, filtered, and concentrated to give the desired product (0.77 g, 99%) that was used in the next step without further purification. LCMS for $C_{18}H_{21}Cl_2N_6O$ (M+H)$^+$: m/z=407.1, 409.1. Found: 407.0, 409.0.

Step 9. 1-{1-[4,5-Dichloro-3-(1-ethylazetidin-3-yl)-2-methoxyphenyl]ethyl}-3-methyl-1H-pyrazolo[3,4-d]pyrimidin-4-amine A solution of 1-[1-(3-azetidin-3-yl-4,5-dichloro-2-methoxyphenyl)ethyl]-3-methyl-1H-pyrazolo[3,4-d]pyrimidin-4-amine (40 mg, 0.098 mmol) in methanol (2.6 mL) was treated with sodium cyanoborohydride (15 mg, 0.25 mmol) followed by acetaldehyde (22 µL, 0.39 mmol) and stirred at 20° C. for 20 min. The reaction mixture was quenched with acetic acid (130 µL, 2.3 mmol), diluted with methanol, and purified by preparative LCMS (XBridge C18 column, eluting with a gradient of acetonitrile/water containing 0.1% ammonium hydroxide, at flow rate of 60 mL/min) to give the desired product as a mixture of enantiomers. This racemic mixture was separated by chiral HPLC (RT=18.6 min and 22.0 min; Phenomenex Lux Cellulose C-4 column, 21.2× 250 mm, 5 micron particle size, eluting with 5% ethanol in hexanes at 18 ml/min, 2.5 mg/inj) to give the desired peak 1 isomer (11 mg, 26%). $^1$H NMR (300 MHz, DMSO-d$_6$) δ 8.11 (s, 1H), 7.45 (s, 1H), 7.33 (br s, 2H), 6.21 (q, J=6.9 Hz, 1H), 3.98-3.77 (m, 3H), 3.57 (s, 3H), 2.92-2.83 (m, 1H), 2.79-2.72 (m, 1H), 2.55 (s, 3H), 2.35-2.22 (m, 2H), 1.70 (d, J=7.1 Hz, 3H), 0.86 (t, J=7.1 Hz, 3H). LCMS for $C_{20}H_{25}Cl_2N_6O$ (M+H)$^+$: m/z=435.1. Found: 435.0.

Example 307

4-[1-(4-Amino-5-methyl-7H-pyrrolo[2,3-d]pyrimidin-7-yl)ethyl]-6-chloro-3-ethoxy-2-(1-isopropylazetidin-3-yl)benzonitrile

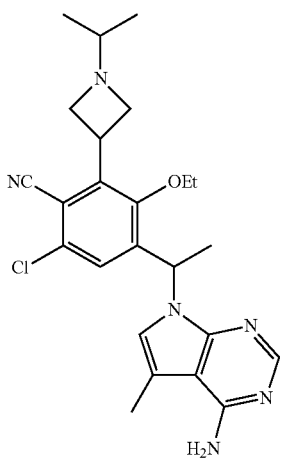 [SMILES: CCOc1c(C(C)n2cc(C)c3c(N)ncnc32)cc(Cl)c(C#N)c1C1CN(C(C)C)C1]

Step 1. tert-Butyl 3-{3-[1-(4-amino-5-methyl-7H-pyrrolo[2,3-d]pyrimidin-7-yl)ethyl]-5-chloro-6-cyano-2-ethoxyphenyl}azetidine-1-carboxylate The desired compound was prepared according to the procedure of Example 212, step 5 (chiral intermediate), using 5-methyl-7H-pyrrolo[2,3-d]pyrimidin-4-amine [ACES Pharma] instead of 3-methyl-1H-pyrazolo[3,4-d]pyrimidin-4-amine as the starting material in 18% yield. $^1$H NMR (500 MHz, CDCl$_3$) δ 8.13 (s, 1H), 6.93 (br s, 1H), 6.79 (s, 1H), 6.17 (q, J=7.1 Hz, 1H), 5.24 (s, 2H), 4.40-4.27 (m, 4H), 4.27-4.18 (m, 1H), 4.03-3.92 (m, 1H), 3.80-3.70 (m, 1H), 2.43 (s, 3H), 1.74 (d, J=7.1 Hz, 3H), 1.43 (s, 9H), 1.40 (t, J=7.0 Hz, 3H). LCMS for $C_{26}H_{32}ClN_6O_3$ (M+H)$^+$: m/z=511.2. Found: 511.2.

Step 2. 4-[1-(4-Amino-5-methyl-7H-pyrrolo[2,3-d]pyrimidin-7-yl)ethyl]-2-azetidin-3-yl-6-chloro-3-ethoxybenzonitrile The desired compound was prepared according to the procedure of Example 212, step 6, using tert-butyl 3-{3-[1-(4-amino-5-methyl-7H-pyrrolo[2,3-d]pyrimidin-7-yl)ethyl]-5-chloro-6-cyano-2-ethoxyphenyl}azetidine-1-carboxylate instead of tert-butyl 3-{3-[1-(4-amino-3-methyl-1H-pyrazolo[3,4-d]pyrimidin-1-yl)ethyl]-5-chloro-6-cyano-2-ethoxyphenyl}azetidine-1-carboxylate as the starting material in 99% yield. LCMS for $C_{21}H_{24}ClN_6O$ (M+H)$^+$: m/z=411.2. Found: 411.1.

Step 3. 4-[1-(4-Amino-5-methyl-7H-pyrrolo[2,3-d]pyrimidin-7-yl)ethyl]-6-chloro-3-ethoxy-2-(1-isopropylazetidin-3-yl)benzonitrile The desired compound was prepared according to the procedure of Example 213 using 4-[1-(4-amino-5-methyl-7H-pyrrolo[2,3-d]pyrimidin-7-yl)ethyl]-2-azetidin-3-yl-6-chloro-3-ethoxybenzonitrile instead of 4-[1-(4-amino-3-methyl-1H-pyrazolo[3,4-d]pyrimidin-1-yl)ethyl]-2-azetidin-3-yl-6-chloro-3-ethoxybenzonitrile and acetone instead of formaldehyde as the starting materials in 65% yield. The product was isolated as a single enantiomer. $^1$H NMR (300 MHz, dmso) δ 7.95 (s, 1H), 7.19 (s, 1H), 7.16-7.13 (m, 1H), 6.58 (s, 2H), 6.11 (q, J=7.1 Hz, 1H), 4.04-3.67 (m, 5H), 3.04-2.92 (m, 2H), 2.36 (s, 3H), 2.27-2.12 (m, 1H), 1.69 (d, J=7.1 Hz, 3H), 1.30 (t, J=6.9 Hz, 3H), 0.85 (dd, J=6.1, 1.8 Hz, 6H). LCMS for $C_{24}H_{30}ClN_6O$ (M+H)$^+$: m/z=453.2. Found: 453.3.

Compounds Synthesized

Experimental procedures for compound Examples 214-218, 221-235, 238, 240-246, 248-260, 263-267, 270, 271, 274-280, 282-284, 286-288, 290, 291, 294, 295, 297, 299-306, 308, and 309 are summarized in Tables 4 and 5.

TABLE 4

| Ex. No. | Name | R² | R⁴ | R⁵ | R⁶ | Salt | Proc.¹ |
|---|---|---|---|---|---|---|---|
| 214 | 4-[1-(4-Amino-3-methyl-1H-pyrazolo[3,4-d]pyrimidin-1-yl)ethyl]-6-chloro-3-ethoxy-2-(1-ethylazetidin-3-yl)benzonitrile³ | Et | CN | Cl | ethyl | — | 213 |
| 215 | 4-[1-(4-Amino-3-methyl-1H-pyrazolo[3,4-d]pyrimidin-1-yl)ethyl]-6-chloro-3-ethoxy-2-(1-isopropylazetidin-3-yl)benzonitrile³ | Et | CN | Cl | isopropyl | — | 213 |
| 216 | 4-[1-(4-Amino-3-methyl-1H-pyrazolo[3,4-d]pyrimidin-1-yl)ethyl]-6-chloro-3-ethoxy-2-(1-isobutylazetidin-3-yl)benzonitrile³ | Et | CN | Cl | isobutyl | — | 213 |
| 217 | 4-[1-(4-Amino-3-methyl-1H-pyrazolo[3,4-d]pyrimidin-1-yl)ethyl]-6-chloro-2-[1-(cyclopropylmethyl)azetidin-3-yl]-3-ethoxybenzonitrile³ | Et | CN | Cl | cyclopropylmethyl | — | 213 |
| 218 | 4-[1-(4-Amino-3-methyl-1H-pyrazolo[3,4-d]pyrimidin-1-yl)ethyl]-6-chloro-2-(1-cyclobutylazetidin-3-yl)-3-ethoxybenzonitrile³ | Et | CN | Cl | cyclobutyl | — | 213 |
| 221 | 4-[1-(4-Amino-3-methyl-1H-pyrazolo[3,4-d]pyrimidin-1-yl)ethyl]-6-chloro-3-ethoxy-2-{1-[(2R)-2-hydroxypropyl]azetidin-3-yl}benzonitrile⁵ | Et | CN | Cl | (R)-2-hydroxypropyl | — | 220 |
| 222 | 4-[1-(4-Amino-3-methyl-1H-pyrazolo[3,4-d]pyrimidin-1-yl)ethyl]-6-chloro-3-ethoxy-2-[1-(2-hydroxy-2-methylpropyl)azetidin-3-yl]benzonitrile³ | Et | CN | Cl | 2-hydroxy-2-methylpropyl | — | 220 |
| 223 | 4-[1-(4-Amino-3-methyl-1H-pyrazolo[3,4-d]pyrimidin-1-yl)ethyl]-6-chloro-3-ethoxy-2-[1-(2-hydroxy-1-methylethyl)azetidin-3-yl]benzonitrile (from peak 1)⁵ | Et | CN | Cl | 2-hydroxy-1-methylethyl | — | 272/273 |
| 224 | 4-[1-(4-Amino-3-methyl-1H-pyrazolo[3,4-d]pyrimidin-1-yl)ethyl]-6-chloro-3-ethoxy-2-[1-(2-hydroxy-1-methylethyl)azetidin-3-yl]benzonitrile (from peak 2)⁵ | Et | CN | Cl | 2-hydroxy-1-methylethyl | — | 272/273 |

TABLE 4-continued

| Ex. No. | Name | R² | R⁴ | R⁵ | R⁶ | Salt | Proc.¹ |
|---|---|---|---|---|---|---|---|
| 225 | 4-[1-(4-Amino-3-methyl-1H-pyrazolo[3,4-d]pyrimidin-1-yl)ethyl]-6-chloro-3-ethoxy-2-[1-(2-methoxyethyl)azetidin-3-yl]benzonitrile³ | Et | CN | Cl |  | — | 213 |
| 226 | 4-[1-(4-Amino-3-methyl-1H-pyrazolo[3,4-d]pyrimidin-1-yl)ethyl]-6-chloro-3-ethoxy-2-{1-[2-methoxy-1-(methoxymethyl)ethyl]azetidin-3-yl}benzonitrile³ | Et | CN | Cl |  | — | 213 |
| 227 | 4-[1-(4-Amino-3-methyl-1H-pyrazolo[3,4-d]pyrimidin-1-yl)ethyl]-6-chloro-3-ethoxy-2-[1-(tetrahydrofuran-3-yl)azetidin-3-yl]benzonitrile (from peak 1)⁵ | Et | CN | Cl |  | — | 272/273 |
| 228 | 4-[1-(4-Amino-3-methyl-1H-pyrazolo[3,4-d]pyrimidin-1-yl)ethyl]-6-chloro-3-ethoxy-2-[1-(tetrahydrofuran-3-yl)azetidin-3-yl]benzonitrile (from peak 2)⁵ | Et | CN | Cl |  | — | 272/273 |
| 229 | 4-[1-(4-Amino-3-methyl-1H-pyrazolo[3,4-d]pyrimidin-1-yl)ethyl]-6-chloro-3-ethoxy-2-[1-(tetrahydro-2H-pyran-4-yl)azetidin-3-yl]benzonitrile³ | Et | CN | Cl | 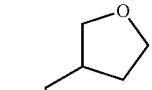 | — | 213 |
| 230 | 4-[1-(4-Amino-3-methyl-1H-pyrazolo[3,4-d]pyrimidin-1-yl)ethyl]-6-chloro-3-ethoxy-2-[1-(tetrahydrofuran-3-ylmethyl)azetidin-3-yl]benzonitrile (from peak 1)⁵ | Et | CN | Cl | 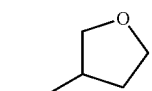 | — | 272/273 |
| 231 | 4-[1-(4-Amino-3-methyl-1H-pyrazolo[3,4-d]pyrimidin-1-yl)ethyl]-6-chloro-3-ethoxy-2-[1-(tetrahydrofuran-3-ylmethyl)azetidin-3-yl]benzonitrile (from peak 2)⁵ | Et | CN | Cl | 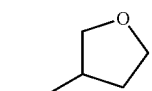 | — | 272/273 |

TABLE 4-continued

| Ex. No. | Name | R² | R⁴ | R⁵ | R⁶ | Salt | Proc.¹ |
|---|---|---|---|---|---|---|---|
| 232 | 4-[1-(4-Amino-3-methyl-1H-pyrazolo[3,4-d]pyrimidin-1-yl)ethyl]-6-chloro-3-ethoxy-2-[1-(tetrahydro-2H-pyran-4-ylmethyl)azetidin-3-yl]benzonitrile³ | Et | CN | Cl | tetrahydropyran-4-ylmethyl | — | 213 |
| 233 | 4-[1-(4-Amino-3-methyl-1H-pyrazolo[3,4-d]pyrimidin-1-yl)ethyl]-6-chloro-3-ethoxy-2-[1-(2,2,2-trifluoroethyl)azetidin-3-yl]benzonitrile³ | Et | CN | Cl | CH₂CF₃ | — | 219 |
| 234 | 4-[1-(4-Amino-3-methyl-1H-pyrazolo[3,4-d]pyrimidin-1-yl)ethyl]-6-chloro-3-ethoxy-2-[1-(3,3,3-trifluoropropyl)azetidin-3-yl]benzonitrile³ | Et | CN | Cl | CH₂CH₂CF₃ | — | 213 |
| 235 | 4-[1-(4-Amino-3-methyl-1H-pyrazolo[3,4-d]pyrimidin-1-yl)ethyl]-6-chloro-2-[1-(cyanomethyl)azetidin-3-yl]-3-ethoxybenzonitrile³ | Et | CN | Cl | CH₂CN | — | 219 |
| 238 | Ethyl 2-(3-{3-[1-(4-amino-3-methyl-1H-pyrazolo[3,4-d]pyrimidin-1-yl)ethyl]-5-chloro-6-cyano-2-ethoxyphenyl}azetidin-1-yl)-2-methylpropanoate³ | Et | CN | Cl | C(CH₃)₂C(O)OEt | — | 236 |
| 240 | 2-(3-{3-[1-(4-Amino-3-methyl-1H-pyrazolo[3,4-d]pyrimidin-1-yl)ethyl]-5-chloro-6-cyano-2-ethoxyphenyl}azetidin-1-yl)-N,2-dimethylpropanamide³ | Et | CN | Cl | C(CH₃)₂C(O)NHCH₃ | — | 239 |
| 241 | 2-(3-{3-[1-(4-Amino-3-methyl-1H-pyrazolo[3,4-d]pyrimidin-1-yl)ethyl]-5-chloro-6-cyano-2-ethoxyphenyl}azetidin-1-yl)-N,N,2-trimethylpropanamide³ | Et | CN | Cl | C(CH₃)₂C(O)N(CH₃)₂ | — | 239 |
| 242 | 2-(1-Acetylazetidin-3-yl)-4-[1-(4-amino-3-methamino-3-methyl-1H-pyrazolo[3,4-d]pyrimidin-1-yl)ethyl]-6-chloro-3-ethoxybenzonitrile³ | Et | CN | Cl | C(O)CH₃ | — | 281 |
| 243 | 4-[1-(4-Amino-3-methyl-1H-pyrazolo[3,4-d]pyrimidin-1-yl)ethyl]-6-chloro-3-ethoxy-2-(1-propionylazetidin-3-yl)benzonitrile³ | Et | CN | Cl | C(O)CH₂CH₃ | TFA | 281 |

TABLE 4-continued

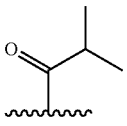 [SMILES: *C(=O)C(C)C]

| Ex. No. | Name | R² | R⁴ | R⁵ | R⁶ | Salt | Proc.¹ |
|---|---|---|---|---|---|---|---|
| 244 | 4-[1-(4-Amino-3-methyl-1H-pyrazolo[3,4-d]pyrimidin-1-yl)ethyl]-6-chloro-3-ethoxy-2-(1-isobutyrylazetidin-3-yl)benzonitrile³ | Et | CN | Cl | 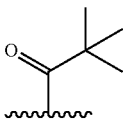 [SMILES: *C(=O)C(C)(C)C] | — | 281 |
| 245 | 4-[1-(4-Amino-3-methyl-1H-pyrazolo[3,4-d]pyrimidin-1-yl)ethyl]-6-chloro-2-[1-(2,2-dimethylpropanoyl)azetidin-3-yl]-3-ethoxybenzonitrile³ | Et | CN | Cl | 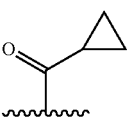 [SMILES: *C(=O)C1CC1] | — | 281 |
| 246 | 4-[1-(4-Amino-3-methyl-1H-pyrazolo[3,4-d]pyrimidin-1-yl)ethyl]-6-chloro-2-[1-(cyclopropylcarbonyl)azetidin-3-yl]-3-ethoxybenzonitrile³ | Et | CN | Cl | 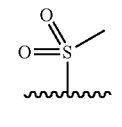 | — | 281 |
| 248 | 4-[1-(4-Amino-3-methyl-1H-pyrazolo[3,4-d]pyrimidin-1-yl)ethyl]-6-chloro-3-ethoxy-2-[1-(methylsulfonyl)azetidin-3-yl]benzonitrile³ | Et | CN | Cl | 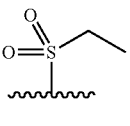 [SMILES: *S(=O)(=O)CC] | — | 285 |
| 249 | 4-[1-(4-Amino-3-methyl-1H-pyrazolo[3,4-d]pyrimidin-1-yl)ethyl]-6-chloro-3-ethoxy-2-[1-(ethylsulfonyl)azetidin-3-yl]benzonitrile³ | Et | CN | Cl | 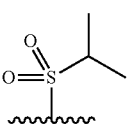 [SMILES: *S(=O)(=O)C(C)C] | — | 285 |
| 250 | 4-[1-(4-Amino-3-methyl-1H-pyrazolo[3,4-d]pyrimidin-1-yl)ethyl]-6-chloro-3-ethoxy-2-[1-(isopropylsulfonyl)azetidin-3-yl]benzonitrile³ | Et | CN | Cl | 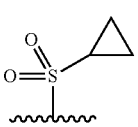 | — | 285 |
| 251 | 4-[1-(4-Amino-3-methyl-1H-pyrazolo[3,4-d]pyrimidin-1-yl)ethyl]-6-chloro-2-[1-(cyclopropylsulfonyl)azetidin-3-yl]-3-ethoxybenzonitrile³ | Et | CN | Cl | 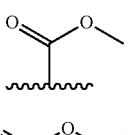 | TFA | 285 |
| 252 | Methyl 3-{3-[1-(4-amino-3-methyl-1H-pyrazolo[3,4-d]pyrimidin-1-yl)ethyl]-5-chloro-6-cyano-2-ethoxyphenyl}azetidine-1-carboxylate³ | Et | CN | Cl | 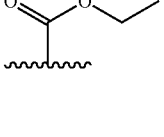 | — | 289 |
| 253 | Ethyl 3-{3-[1-(4-amino-3-methyl-1H-pyrazolo[3,4-d]pyrimidin-1-yl)ethyl]-5-chloro-6-cyano-2-ethoxyphenyl}azetidine-1-carboxylate³ | Et | CN | Cl | | — | 289 |

TABLE 4-continued

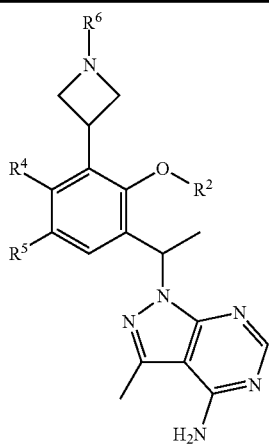

| Ex. No. | Name | R² | R⁴ | R⁵ | R⁶ | Salt | Proc.¹ |
|---|---|---|---|---|---|---|---|
| 254 | Isopropyl 3-{3-[1-(4-amino-3-methyl-1H-pyrazolo[3,4-d]pyrimidin-1-yl)ethyl]-5-chloro-6-cyano-2-ethoxyphenyl}azetidine-1-carboxylate³ | Et | CN | Cl | (isopropyl carbamate group) | — | 289 |
| 255 | 3-{3-[1-(4-Amino-3-methyl-1H-pyrazolo[3,4-d]pyrimidin-1-yl)ethyl]-5-chloro-6-cyano-2-ethoxyphenyl}-N-(tert-butyl)azetidine-1-carboxamide³ | Et | CN | Cl | (tert-butyl carboxamide group) | — | 292 |
| 256 | 3-{3-[1-(4-Amino-3-methyl-1H-pyrazolo[3,4-d]pyrimidin-1-yl)ethyl]-5-chloro-6-cyano-2-ethoxyphenyl}azetidine-1-carboxamide³ | Et | CN | Cl | (carboxamide NH₂ group) | TFA | 293 |
| 257 | 3-{3-[1-(4-Amino-3-methyl-1H-pyrazolo[3,4-d]pyrimidin-1-yl)ethyl]-5-chloro-6-cyano-2-ethoxyphenyl}-N-methylazetidine-1-carboxamide³ | Et | CN | Cl | (N-methyl carboxamide group) | — | 292 |
| 258 | 3-{3-[1-(4-Amino-3-methyl-1H-pyrazolo[3,4-d]pyrimidin-1-yl)ethyl]-5-chloro-6-cyano-2-ethoxyphenyl}-N-ethylazetidine-1-carboxamide³ | Et | CN | Cl | (N-ethyl carboxamide group) | — | 292 |
| 259 | 3-{3-[1-(4-Amino-3-methyl-1H-pyrazolo[3,4-d]pyrimidin-1-yl)ethyl]-5-chloro-6-cyano-2-ethoxyphenyl}-N,N-dimethylazetidine-1-carboxamide³ | Et | CN | Cl | (N,N-dimethyl carboxamide group) | — | 296 |
| 260 | 4-[1-(4-Amino-3-methyl-1H-pyrazolo[3,4-d]pyrimidin-1-yl)ethyl]-6-chloro-3-ethoxy-2-[1-(2-hydroxyethyl)azetidin-3-yl]benzonitrile-d4³ | Et | CN | Cl | (2-hydroxyethyl-d4 group) | — | 219 |
| 263 | 4-[1-(4-Amino-3-methyl-1H-pyrazolo[3,4-d]pyrimidin-1-yl)ethyl]-6-chloro-2-(1-ethylazetidin-3-yl)-3-methoxybenzonitrile³ | Me | CN | Cl | (ethyl group) | — | 262 |
| 264 | 4-[1-(4-Amino-3-methyl-1H-pyrazolo[3,4-d]pyrimidin-1-yl)ethyl]-6-chloro-2-(1-isopropylazetidin-3-yl)-3-methoxybenzonitrile³ | Me | CN | Cl | (isopropyl group) | — | 262 |

TABLE 4-continued

| Ex. No. | Name | R² | R⁴ | R⁵ | R⁶ | Salt | Proc.¹ |
|---|---|---|---|---|---|---|---|
| 265 | 4-[1-(4-Amino-3-methyl-1H-pyrazolo[3,4-d]pyrimidin-1-yl)ethyl]-6-chloro-2-(1-isobutylazetidin-3-yl)-3-methoxybenzonitrile³ | Me | CN | Cl | isobutyl | — | 262 |
| 266 | 4-[1-(4-Amino-3-methyl-1H-pyrazolo[3,4-d]pyrimidin-1-yl)ethyl]-6-chloro-2-[1-(cyclopropylmethyl)azetidin-3-yl]-3-methoxybenzonitrile³ | Me | CN | Cl | cyclopropylmethyl | — | 262 |
| 267 | 4-[1-(4-Amino-3-methyl-1H-pyrazolo[3,4-d]pyrimidin-1-yl)ethyl]-6-chloro-2-(1-cyclobutylazetidin-3-yl)-3-methoxybenzonitrile³ | Me | CN | Cl | cyclobutyl | — | 262 |
| 270 | 4-[1-(4-Amino-3-methyl-1H-pyrazolo[3,4-d]pyrimidin-1-yl)ethyl]-6-chloro-2-{1-[(2R)-2-hydroxypropyl]azetidin-3-yl}-3-methoxybenzonitrile⁵ | Me | CN | Cl | (2R)-2-hydroxypropyl | — | 269 |
| 271 | 4-[1-(4-Amino-3-methyl-1H-pyrazolo[3,4-d]pyrimidin-1-yl)ethyl]-6-chloro-2-[1-(2-hydroxy-2-methylpropyl)azetidin-3-yl]-3-methoxybenzonitrile³ | Me | CN | Cl | 2-hydroxy-2-methylpropyl | — | 269 |
| 274 | 4-[1-(4-Amino-3-methyl-1H-pyrazolo[3,4-d]pyrimidin-1-yl)ethyl]-6-chloro-3-methoxy-2-(1-oxetan-3-ylazetidin-3-yl)benzonitrile³ | Me | CN | Cl | oxetan-3-yl | — | 262 |
| 275 | 4-[1-(4-Amino-3-methyl-1H-pyrazolo[3,4-d]pyrimidin-1-yl)ethyl]-6-chloro-3-methoxy-2-[1-(tetrahydrofuran-3-yl)azetidin-3-yl]benzonitrile (from peak 1)⁵ | Me | CN | Cl | tetrahydrofuran-3-yl | — | 272/273 |
| 276 | 4-[1-(4-Amino-3-methyl-1H-pyrazolo[3,4-d]pyrimidin-1-yl)ethyl]-6-chloro-3-methoxy-2-[1-(tetrahydrofuran-3-yl)azetidin-3-yl]benzonitrile (from peak 2)⁵ | Me | CN | Cl | tetrahydrofuran-3-yl | — | 272/273 |

TABLE 4-continued

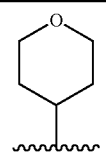

| Ex. No. | Name | R² | R⁴ | R⁵ | R⁶ | Salt | Proc.¹ |
|---|---|---|---|---|---|---|---|
| 277 | 4-[1-(4-Amino-3-methyl-1H-pyrazolo[3,4-d]pyrimidin-1-yl)ethyl]-6-chloro-3-methoxy-2-[1-(tetrahydro-2H-pyran-4-yl)azetidin-3-yl]benzonitrile³ | Me | CN | Cl | 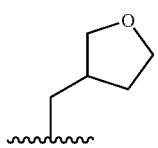 [SMILES: *CC1CCOC1] | — | 262 |
| 278 | 4-[1-(4-Amino-methyl-1H-pyrazolo[3,4-d]pyrimidin-1-yl)ethyl]-6-chloro-3-methoxy-2-[1-(tetrahydrofuran-3-ylmethyl)azetidin-3-yl]benzonitrile (from peak 1)⁵ | Me | CN | Cl | 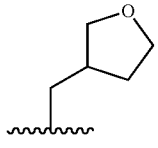 [SMILES: *CC1CCOC1] | — | 272/273 |
| 279 | 4-[1-(4-Amino-3-methyl-1H-pyrazolo[3,4-d]pyrimidin-1-yl)ethyl]-6-chloro-3-methoxy-2-[1-(tetrahydrofuran-3-ylmethyl)azetidin-3-yl]benzonitrile (from peak 2)⁵ | Me | CN | Cl | 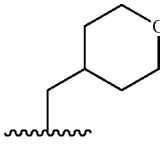 | — | 272/273 |
| 280 | 4-[1-(4-Amino-3-methyl-1H-pyrazolo[3,4-d]pyrimidin-1-yl)ethyl]-6-chloro-3-methoxy-2-[1-(tetrahydro-2H-pyran-4-ylmethyl)azetidin-3-yl]benzonitrile³ | Me | CN | Cl | 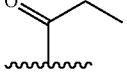 | — | 262 |
| 282 | 4-[1-(4-Amino-3-methyl-1H-pyrazolo[3,4-d]pyrimidin-1-yl)ethyl]-6-chloro-3-methoxy-2-(1-propionylazetidin-3-yl)benzonitrile³ | Me | CN | Cl | 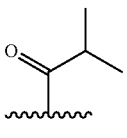 [SMILES: *C(=O)C(C)C] | — | 281 |
| 283 | 4-[1-(4-Amino-3-methyl-1H-pyrazolo[3,4-d]pyrimidin-1-yl)ethyl]-6-chloro-2-(1-isobutyrylazetidin-3-yl)-3-methoxybenzonitrile³ | Me | CN | Cl | 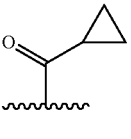 [SMILES: *C(=O)C1CC1] | — | 281 |
| 284 | 4-[1-(4-Amino-3-methyl-1H-pyrazolo[3,4-d]pyrimidin-1-yl)ethyl]-6-chloro-2-[1-(cyclopropylcarbonyl)azetidin-3-yl]-3-methoxybenzonitrile³ | Me | CN | Cl | 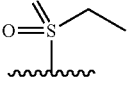 | — | 281 |
| 286 | 4-[1-(4-Amino-3-methyl-1H-pyrazolo[3,4-d]pyrimidin-1-yl)ethyl]-6-chloro-2-[1-(ethylsulfonyl)azetidin-3-yl]-3-methoxybenzonitrile³ | Me | CN | Cl |  | — | 285 |

TABLE 4-continued

| Ex. No. | Name | R² | R⁴ | R⁵ | R⁶ | Salt | Proc.¹ |
|---|---|---|---|---|---|---|---|
| 287 | 4-[1-(4-Amino-3-methyl-1H-pyrazolo[3,4-d]pyrimidin-1-yl)ethyl]-6-chloro-2-[1-(isopropylsulfonyl)azetidin-3-yl]-3-methoxybenzonitrile³ | Me | CN | Cl | isopropylsulfonyl | — | 285 |
| 288 | 4-[1-(4-Amino-3-methyl-1H-pyrazolo[3,4-d]pyrimidin-1-yl)ethyl]-6-chloro-2-[1-(cyclopropylsulfonyl)azetidin-3-yl]-3-methoxybenzonitrile³ | Me | CN | Cl | cyclopropylsulfonyl | — | 285 |
| 290 | Ethyl 3-{3-[1-(4-amino-3-methyl-1H-pyrazolo[3,4-d]pyrimidin-1-yl)ethyl]-5-chloro-6-cyano-2-methoxyphenyl}azetidine-1-carboxylate³ | Me | CN | Cl | ethyl carboxylate | — | 289 |
| 291 | Isopropyl 3-{3-[1-(4-amino-3-methyl-1H-pyrazolo[3,4-d]pyrimidin-1-yl)ethyl]-5-chloro-6-cyano-2-methoxyphenyl}azetidine-1-carboxylate³ | Me | CN | Cl | isopropyl carboxylate | — | 289 |
| 294 | 3-{3-[1-(4-Amino-3-methyl-1H-pyrazolo[3,4-d]pyrimidin-1-yl)ethyl]-5-chloro-6-cyano-2-methoxyphenyl}-N-methylazetidine-1-carboxamide³ | Me | CN | Cl | N-methyl carboxamide | — | 292 |
| 295 | 3-{3-[1-(4-Amino-3-methyl-1H-pyrazolo[3,4-d]pyrimidin-1-yl)ethyl]-5-chloro-6-cyano-2-methoxyphenyl}-N-ethylazetidine-1-carboxamide³ | Me | CN | Cl | N-ethyl carboxamide | — | 292 |
| 297 | 4-[1-(4-Amino-3-methyl-1H-pyrazolo[3,4-d]pyrimidin-1-yl)ethyl]-6-chloro-2-[1-(2-hydroxyethyl)azetidin-3-yl]-3-methoxybenzonitrile-d4³ | Me | CN | Cl | 2-hydroxyethyl-d4 | — | 268 |
| 299 | 1-{1-[4,5-Dichloro-3-(1-isopropylazetidin-3-yl)-2-methoxyphenyl]ethyl}-3-methyl-1H-pyrazolo[3,4-d]pyrimidin-4-amine (peak 1)³ | Me | Cl | Cl | isopropyl | — | 298 |
| 300 | 2-(3-{3-[1-(4-Amino-3-methyl-1H-pyrazolo[3,4-d]pyrimidin-1-yl)ethyl]-5,6-dichloro-2-methoxyphenyl}azetidin-1-yl)ethano (peak 1)³ | Me | Cl | Cl | 2-hydroxyethyl | — | 298 and 219 |

TABLE 4-continued

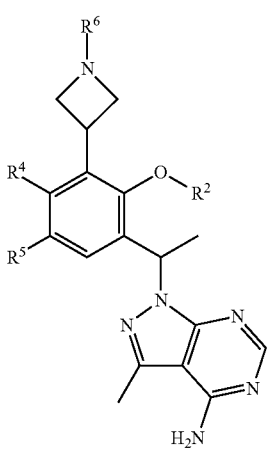

| Ex. No. | Name | R² | R⁴ | R⁵ | R⁶ | Salt | Proc.¹ |
|---|---|---|---|---|---|---|---|
| 301 | (2S)-1-(3-{3-[1-(4-Amino-3-methyl-1H-pyrazolo[3,4-d]pyrimidin-1-yl)ethyl]-5,6-dichloro-2-methoxyphenyl}azetidin-1-yl)propan-2-ol (peak 1)⁵ | Me | Cl | Cl | ⌇⌇⌇CH(OH)CH₃ (S) | — | 298 and 220 |
| 302 | (2R)-1-(3-{3-[1-(4-Amino-3-methyl-1H-pyrazolo[3,4-d]pyrimidin-1-yl)ethyl]-5,6-dichloro-2-methoxyphenyl}azetidin-1-yl)propan-2-ol (peak 1)⁵ | Me | Cl | Cl | ▬CH(OH)CH₃ (R) | — | 298 and 220 |
| 303 | 1-(3-{3-[1-(4-Amino-3-methyl-1H-pyrazolo[3,4-d]pyrimidin-1-yl)ethyl]-5,6-dichloro-2-methoxyphenyl}azetidin-1-yl)-2-methylpropan-2-ol(peak 2)³ | Me | Cl | Cl | -CH₂-C(CH₃)₂-OH | — | 298 and 220 |
| 304 | 1-{1-[4,5-Dichloro-2-methoxy-3-(1-oxetan-3-ylazetidin-3-yl)phenyl]ethyl}-3-methyl-1H-pyrazolo[3,4-d]pyrimidin-4-amine (peak 1)³ | Me | Cl | Cl | oxetan-3-yl | — | 298 and 213 |
| 305 | (3-{3-[1-(4-Amino-3-methyl-1H-pyrazolo[3,4-d]pyrimidin-1-yl)ethyl]-5,6-dichloro-2-methoxyphenyl}azetidin-1-yl)acetonitrile (peak 2)³ | Me | Cl | Cl | -CH₂CN | — | 298 and 219 |
| 306 | 1-{1-[3-(1-Acetylazetidin-3-yl)-4,5-dichloro-2-methoxyphenyl]ethyl}-3-methyl-1H-pyrazolo[3,4-d]pyrimidin-4-amine(peak 2)³ | Me | Cl | Cl | -C(=O)CH₃ | — | 298 and 281 |

¹Synthesized according to the experimental procedure of compound listed;
³Compound isolated as a single enantiomer;
⁵Compound isolated as a single diastereomer.

TABLE 5

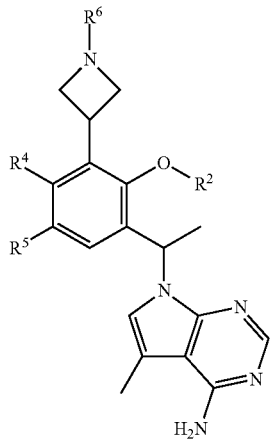

| Ex. No. | Name | R² | R⁴ | R⁵ | R⁶ | Salt | Proc.¹ |
|---|---|---|---|---|---|---|---|
| 308 | 4-[1-(4-Amino-5-methyl-7H-pyrrolo[2,3-d]pyrimidin-7-yl)ethyl]-6-chloro-3-ethoxy-2-[1-(2-hydroxyethyl)azetidin-3-yl]benzonitrile³ | Et | CN | Cl | ⟨CH₂CH₂OH⟩ | — | 307 and 219 |
| 309 | 4-[1-(4-Amino-5-methyl-7H-pyrrolo[2,3-d]pyrimidin-7-yl)ethyl]-6-chloro-3-ethoxy-2-{1-[(2S)-2-hydroxypropyl]azetidin-3-yl}benzonitrile⁵ | Et | CN | Cl | ⟨CH₂CH(OH)CH₃⟩ | — | 220 and 219 |

¹Synthesized according to the experimental procedure of compound listed;
³Compound isolated as a single enantiomer;
⁵Compound isolated as a single diastereomer.

Analytical Data

¹H NMR data (Varian Inova 500 spectrometer, a Mercury 400 spectrometer, or a Varian (or Mercury) 300 spectrometer) and LCMS mass spectral data (MS) for the compounds of Examples 214-218, 221-235, 238, 240-246, 248-260, 263-267, 270, 271, 274-280, 282-284, 286-288, 290, 291, 294, 295, 297, 299, 300-306, 308, and 309 is provided below in Table 6.

TABLE 6

| Ex. No. | MS [M + H]⁺ | Solvent | MHz | ¹H NMR Spectra |
|---|---|---|---|---|
| 214 | 440.2 | DMSO-$d_6$ | 400 | δ 8.11 (s, 1H), 7.48 (s, 1H), 6.23 (q, J = 7.0 Hz, 1H), 4.09-3.98 (m, 1H), 3.93-3.84 (m, 2H), 3.84-3.75 (m, 1H), 3.74-3.65 (m, 1H), 3.01-2.89 (m, 2H), 2.54 (s, 3H), 2.33 (q, J = 7.2 Hz, 2H), 1.71 (d, J = 7.0 Hz, 3H), 1.33 (t, J = 6.9 Hz, 3H), 0.86 (t, J = 7.2 Hz, 3H). |
| 215 | 454.3 | DMSO-$d_6$ | 400 | δ 8.11 (s, 1H), 7.49 (s, 1H), 6.23 (q, J = 7.0 Hz, 1H), 4.02-3.91 (m, 1H), 3.90-3.76 (m, 3H), 3.75-3.65 (m, 1H), 3.05-2.92 (m, 2H), 2.54 (s, 3H), 2.25-2.14 (m, 1H), 1.71 (d, J = 7.0 Hz, 3H), 1.33 (t, J = 6.9 Hz, 3H), 0.90-0.78 (m, 6H). |
| 216 | 468.3 | DMSO-$d_6$ | 300 | δ 8.11 (s, 1H), 7.49 (s, 1H), 7.35 (br s, 2H), 6.22 (q, J = 7.0 Hz, 1H), 4.09 (br s, 1H), 3.92 (brs, 2H), 3.83-3.76 (m, 1H), 3.75-3.65 (m, 1H), 3.01 (br s, 2H), 2.54 (s, 3H), 2.16 (br s, 2H), 1.71 (d, J = 7.0 Hz, 3H), 1.54 (br s, 1H), 1.32 (t, J = 6.9 Hz, 3H), 0.83 (d, J = 6.6 Hz, 6H). |
| 217 | 466.3 | DMSO-$d_6$ | 400 | δ 8.11 (s, 1H), 7.48 (s, 1H), 6.23 (q, J = 7.0 Hz, 1H), 4.12-4.01 (m, 1H), 3.96-3.87 (m, 2H), 3.84-3.75 (m, 1H), 3.74-3.64 (m, 1H), 3.08-2.96 (m, 2H), 2.54 (s, 3H), 2.20 (d, J = 6.7 Hz, 2H), 1.71 (d, J = 7.1 Hz, 3H), 1.32 (t, J = 6.9 Hz, 3H), 0.77-0.66 (m, 1H), 0.40-0.33 (m, 2H), 0.07-0.00 (m, 2H). |
| 218 | 466.2 | DMSO-$d_6$ | 300 | δ 8.11 (s, 1H), 7.49 (s, 1H), 7.34 (br s, 2H), 6.22 (q, J = 6.9 Hz, 1H), 4.10-3.95 (m, 1H), 3.85-3.61 (m, 4H), 3.13-2.92 (m, 3H), 2.54 (s, 3H), 1.92-1.81 (m, 2H), 1.79-1.50 (m, 7H), 1.32 (t, J = 6.9 Hz, 3H). |

TABLE 6-continued

| Ex. No. | MS [M + H]+ | Solvent | MHz | $^1$H NMR Spectra |
|---|---|---|---|---|
| 221 | 470.2 | DMSO-d$_6$ | 400 | δ 8.11 (s, 1H), 7.48 (s, 1H), 6.23 (q, J = 7.1 Hz, 1H), 4.35 (d, J = 4.5 Hz, 1H), 4.12-3.98 (m, 1H), 3.98-3.88 (m, 2H), 3.84-3.74 (m, 1H), 3.73-3.64 (m, 1H), 3.61-3.51 (m, 1H), 3.07 (q, J = 8.4 Hz, 2H), 2.54 (s, 3H), 2.28 (d, J = 5.9 Hz, 2H), 1.71 (d, J = 7.1 Hz, 3H), 1.32 (t, J = 6.9 Hz, 3H), 1.00 (d, J = 6.2 Hz, 3H). |
| 222 | 484.3 | DMSO-d$_6$ | 300 | δ 8.11 (s, 1H), 7.48 (s, 1H), 7.35 (br s, 2H), 6.23 (q, J = 6.9 Hz, 1H), 4.16-3.88 (m, 4H), 3.86-3.61 (m, 2H), 3.19-3.04 (m, 2H), 2.54 (s, 3H), 2.26 (s, 2H), 1.71 (d, J = 7.0 Hz, 3H), 1.32 (t, J = 6.9 Hz, 3H), 1.04 (s, 6H). |
| 223 | 470.2 | DMSO-d$_6$ | 400 | δ 8.11 (s, 1H), 7.48 (s, 1H), 6.23 (q, J = 7.0 Hz, 1H), 4.44 (br s, 1H), 4.05-3.95 (m, 1H), 3.94-3.89 (m, 1H), 3.88-3.82 (m, 1H), 3.82-3.75 (m, 1H), 3.74-3.65 (m, 1H), 3.17-3.07 (m, 2H), 3.07-2.99 (m, 1H), 2.55 (s, 3H), 2.20-2.13 (m, 1H), 1.71 (d, J = 7.0 Hz, 3H), 1.37-1.29 (m, 3H), 0.86-0.78 (m, 3H). |
| 224 | 470.2 | DMSO-d$_6$ | 400 | δ 8.11 (s, 1H), 7.49 (s, 1H), 6.23 (q, J = 6.6 Hz, 1H), 4.43 (br s, 1H), 4.05-3.90 (m, 2H), 3.87-3.75 (m, 2H), 3.73-3.64 (m, 1H), 3.16-3.02 (m, 3H), 2.54 (s, 3H), 2.23-2.11 (m, 1H), 1.71 (d, J = 6.9 Hz, 3H), 1.37-1.29 (m, 3H), 0.86-0.79 (m, 3H). |
| 225 | 470.2 | DMSO-d$_6$ | 400 | δ 8.11 (s, 1H), 7.48 (s, 1H), 6.23 (q, J = 7.0 Hz, 1H), 4.12-4.01 (m, 2H), 3.95-3.84 (m, 2H), 3.83-3.74 (m, 1H), 3.74-3.64 (m, 1H), 3.31-3.26 (m, 3H), 3.20 (s, 3H), 3.13-3.02 (m, 2H), 2.54 (s, 3H), 1.71 (d, J = 7.0 Hz, 3H), 1.32 (t, J = 7.0 Hz, 3H). |
| 226 | 514.2 | DMSO-d$_6$ | 400 | δ 8.11 (s, 1H), 7.50 (s, 1H), 7.33 (br s, 2H), 6.23 (q, J = 7.0 Hz, 1H), 4.08-3.98 (m, 1H), 3.91-3.82 (m, 2H), 3.82-3.74 (m, 1H), 3.74-3.64 (m, 1H), 3.28-3.15 (m, 12H), 2.54 (s, 3H), 1.71 (d, J = 7.0 Hz, 3H), 1.32 (t, J = 6.9 Hz, 3H). |
| 227 | 482.2 | DMSO-d$_6$ | 300 | δ 8.11 (s, 1H), 7.48 (s, 1H), 7.33 (br s, 2H), 6.23 (q, J = 7.0 Hz, 1H), 4.11-3.97 (m, 1H), 3.94-3.77 (m, 3H), 3.76-3.58 (m, 3H), 3.56-3.43 (m, 2H), 3.10-2.97 (m, 2H), 2.96-2.87 (m, 1H), 2.55 (s, 3H), 1.71 (d, J = 7.0 Hz, 3H), 1.67-1.56 (m, 2H), 1.34 (t, J = 6.9 Hz, 3H). |
| 228 | 482.3 | DMSO-d$_6$ | 300 | δ 8.11 (s, 1H), 7.50 (s, 1H), 7.36 (br s, 2H), 6.23 (q, J = 6.9 Hz, 1H), 4.11-3.97 (m, 1H), 3.93-3.57 (m, 6H), 3.56-3.40 (m, 2H), 3.12-3.04 (m, 1H), 3.03-2.96 (m, 1H), 2.95-2.87 (m, 1H), 2.54 (s, 3H), 1.79-1.56 (m, 5H), 1.34 (t, J = 6.9 Hz, 3H). |
| 229 | 496.3 | DMSO-d$_6$ | 300 | δ 8.11 (s, 1H), 7.49 (s, 1H), 7.34 (br s, 2H), 6.23 (q, J = 6.9 Hz, 1H), 4.14-3.95 (m, 1H), 3.94-3.63 (m, 6H), 3.29-3.17 (m, 2H), 3.12-2.96 (m, 2H), 2.55 (s, 3H), 2.23-2.09 (m, 1H), 1.71 (d, J = 7.0 Hz, 3H), 1.65-1.52 (m, 2H), 1.33 (t, J = 6.9 Hz, 3H), 1.19-1.08 (m, 2H). |
| 230 | 496.2 | DMSO-d$_6$ | 300 | δ 8.11 (s, 1H), 7.48 (s, 1H), 7.36 (br s, 2H), 6.22 (q, J = 6.8 Hz, 1H), 4.16-3.99 (m, 1H), 3.98-3.51 (m, 7H), 3.30-3.24 (m, 1H), 3.10-2.98 (m, 2H), 2.54 (s, 3H), 2.33 (d, J = 7.4 Hz, 2H), 2.21-2.09 (m, 1H), 1.97-1.83 (m, 1H), 1.71 (d, J = 7.0 Hz, 3H), 1.52-1.37 (m, 1H), 1.33 (t, J = 6.9 Hz, 3H). |
| 231 | 496.3 | DMSO-d$_6$ | 300 | δ 8.11 (s, 1H), 7.48 (s, 1H), 7.35 (br s, 2H), 6.22 (q, J = 6.7 Hz, 1H), 4.14-4.00 (m, 1H), 3.96-3.86 (m, 2H), 3.84-3.52 (m, 5H), 3.29-3.22 (m, 1H), 3.12-2.96 (m, 2H), 2.54 (s, 3H), 2.33 (d, J = 7.3 Hz, 2H), 2.22-2.09 (m, 1H), 1.99-1.83 (m, 1H), 1.71 (d, J = 7.0 Hz, 3H), 1.53-1.38 (m, 1H), 1.33 (t, J = 6.8 Hz, 3H). |
| 232 | 510.3 | DMSO-d$_6$ | 300 | δ 8.11 (s, 1H), 7.48 (s, 1H), 7.35 (br s, 2H), 6.22 (q, J = 7.0 Hz, 1H), 4.15-4.00 (m, 1H), 3.96-3.84 (m, 2H), 3.83-3.73 (m, 3H), 3.72-3.62 (m, 1H), 3.30-3.18 (m, 2H), 3.08-2.94 (m, 2H), 2.54 (s, 3H), 2.22 (d, J = 6.3 Hz, 2H), 1.71 (d, J = 7.0 Hz, 3H), 1.55 (d, J = 11.7 Hz, 3H), 1.32 (t, J = 6.9 Hz, 3H), 1.17-1.01 (m, 2H). |
| 233 | 494.1 | DMSO-d$_6$ | 400 | δ 8.11 (s, 1H), 7.50 (s, 1H), 7.29 (br s, 2H), 6.23 (q, J = 7.0 Hz, 1H), 4.26-4.15 (m, 1H), 4.03-3.94 (m, 2H), 3.86-3.65 (m, 2H), 3.42 (q, J = 9.1 Hz, 2H), 3.20 (q, J = 10.2 Hz, 2H), 2.55 (s, 3H), 1.71 (d, J = 7.1 Hz, 3H), 1.33 (t, J = 6.9 Hz, 3H). |
| 234 | 508.2 | DMSO-d$_6$ | 400 | δ 8.11 (s, 1H), 7.49 (s, 1H), 7.35 (br s, 2H), 6.23 (q, J = 6.9 Hz, 1H), 4.13-4.02 (m, 1H), 3.98-3.87 (m, 2H), 3.84-3.75 (m, 1H), 3.74-3.65 (m, 1H), 3.13-3.03 (m, 2H), 2.61-2.51 (m, 5H), 2.38-2.23 (m, 2H), 1.71 (d, J = 7.0 Hz, 3H), 1.33 (t, J = 6.9 Hz, 3H). |
| 235 | 451.1 | DMSO-d$_6$ | 400 | δ 8.11 (s, 1H), 7.52 (s, 1H), 7.31 (br s, 2H), 6.23 (q, J = 7.0 Hz, 1H), 4.22-4.11 (m, 1H), 3.91 (q, J = 6.8 Hz, 2H), 3.84-3.74 (m, 1H), 3.72-3.61 (m, 3H), 3.32-3.21 (m, 2H), 2.54 (s, 3H), 1.72 (d, J = 7.0 Hz, 3H), 1.31 (t, J = 6.9 Hz, 3H). |

TABLE 6-continued

| Ex. No. | MS [M + H]+ | Solvent | MHz | $^1$H NMR Spectra |
|---|---|---|---|---|
| 238 | 526.2 | DMSO-$d_6$ | 400 | δ 8.11 (s, 1H), 7.47 (s, 1H), 6.22 (q, J = 7.0 Hz, 1H), 4.09-3.95 (m, 3H), 3.85-3.75 (m, 3H), 3.74-3.64 (m, 1H), 3.53-3.41 (m, 2H), 2.54 (s, 3H), 1.71 (d, J = 7.1 Hz, 3H), 1.31 (t, J = 7.0 Hz, 3H), 1.10 (s, 6H), 0.95 (t, J = 7.1 Hz, 3H). |
| 240 | 511.3 | DMSO-$d_6$ | 400 | δ 8.11 (s, 1H), 7.77 (q, J = 4.4 Hz, 1H), 7.51 (s, 1H), 6.23 (q, J = 7.0 Hz, 1H), 4.08-3.98 (m, 1H), 3.85-3.75 (m, 1H), 3.74-3.62 (m, 3H), 3.38-3.34 (m, 1H), 3.31-3.27 (m, 1H), 2.57 (d, J = 4.7 Hz, 3H), 2.54 (s, 3H), 1.71 (d, J = 7.1 Hz, 3H), 1.32 (t, J = 7.0 Hz, 3H), 1.02 (s, 6H). |
| 241 | 511.3 | DMSO-$d_6$ | 400 | δ 8.11 (s, 1H), 7.53 (s, 1H), 7.01 (s, 2H), 6.26 (q, J = 7.0 Hz, 1H), 4.12-4.00 (m, 1H), 3.88-3.79 (m, 2H), 3.69-3.62 (m, 2H), 3.48-3.35 (m, 2H), 3.15 (br s, 6H), 2.57 (s, 3H), 1.76 (d, J = 7.1 Hz, 3H), 1.36 (t, J = 7.0 Hz, 3H), 1.15 (d, J = 1.7 Hz, 6H). |
| 242 | 454.2 | DMSO-$d_6$ | 400 | δ 8.11 (s, 1H), 7.54 (d, J = 2.1 Hz, 1H), 7.33 (br s, 2H), 6.25 (q, J = 7.0 Hz, 1H), 4.57-4.35 (m, 3H), 4.28-4.19 (m, 1H), 4.18-4.08 (m, 1H), 3.85-3.74 (m, 2H), 2.55 (s, 3H), 1.76 (d, J = 2.3 Hz, 3H), 1.72 (d, J = 7.0 Hz, 3H), 1.37 (t, J = 6.9 Hz, 3H). |
| 243 | 468.2 | DMSO-$d_6$ | 300 | δ 8.28 (s, 1H), 7.59 (s, 1H), 6.28 (q, J = 6.9 Hz, 1H), 4.58-4.35 (m, 3H), 4.31-4.06 (m, 2H), 3.88-3.70 (m, 2H), 2.57 (s, 3H), 2.12-1.99 (m, 2H), 1.75 (d, J = 7.0 Hz, 3H), 1.38 (t, J = 6.9 Hz, 3H), 0.95 (t, J = 7.5 Hz, 3H). |
| 244 | 482.3 | DMSO-$d_6$ | 300 | δ 8.11 (s, 1H), 7.54 (s, 1H), 7.34 (br s, 2H), 6.25 (q, J = 6.9 Hz, 1H), 4.62-4.36 (m, 3H), 4.30-4.06 (m, 2H), 3.87-3.74 (m, 2H), 2.55 (s, 3H), 2.46-2.39 (m, 1H), 1.72 (d, J = 7.0 Hz, 3H), 1.38 (t, J = 6.9 Hz, 3H), 1.01-0.92 (m, 6H). |
| 245 | 496.1 | DMSO-$d_6$ | 300 | δ 8.11 (s, 1H), 7.54 (s, 1H), 6.25 (q, J = 6.9 Hz, 1H), 4.70 (br s, 2H), 4.50-4.36 (m, 1H), 4.22 (br s, 2H), 3.86-3.74 (m, 2H), 2.54 (s, 3H), 1.72 (d, J = 7.1 Hz, 3H), 1.38 (t, J = 6.9 Hz, 3H), 1.11 (s, 9H). |
| 246 | 480.2 | DMSO-$d_6$ | 300 | δ 8.12 (s, 1H), 7.55 (d, J = 3.1 Hz, 1H), 7.36 (br s, 2H), 6.25 (q, J = 7.0 Hz, 1H), 4.72-4.62 (m, 1H), 4.61-4.42 (m, 2H), 4.31-4.10 (m, 2H), 3.87-3.74 (m, 2H), 2.55 (s, 3H), 1.73 (d, J = 7.0 Hz, 3H), 1.61-1.48 (m, 1H), 1.38 (t, J = 6.9 Hz, 3H), 0.76-0.63 (m, 4H). |
| 248 | 490.1 | DMSO-$d_6$ | 300 | δ 8.12 (s, 1H), 7.57 (s, 1H), 7.35 (br s, 2H), 6.24 (q, J = 6.9 Hz, 1H), 4.54-4.39 (m, 1H), 4.25-4.11 (m, 4H), 3.88-3.65 (m, 2H), 3.01 (s, 3H), 2.55 (s, 3H), 1.73 (d, J = 7.1 Hz, 3H), 1.34 (t, J = 6.9 Hz, 3H). |
| 249 | 504.2 | DMSO-$d_6$ | 300 | δ 8.11 (s, 1H), 7.55 (s, 1H), 7.35 (br s, 2H), 6.23 (q, J = 6.7 Hz, 1H), 4.56-4.38 (m, 1H), 4.29-4.10 (m, 4H), 3.88-3.65 (m, 2H), 3.15 (q, J = 7.4 Hz, 2H), 2.55 (s, 3H), 1.73 (d, J = 7.0 Hz, 3H), 1.34 (t, J = 6.9 Hz, 3H), 1.20 (t, J = 7.3 Hz, 3H). |
| 250 | 518.2 | DMSO-$d_6$ | 300 | δ 8.11 (s, 1H), 7.55 (s, 1H), 7.35 (br s, 2H), 6.23 (q, J = 6.9 Hz, 1H), 4.55-4.40 (m, 1H), 4.26-4.10 (m, 4H), 3.88-3.65 (m, 2H), 3.31-3.26 (m, 1H), 2.54 (s, 3H), 1.73 (d, J = 7.0 Hz, 3H), 1.34 (t, J = 6.9 Hz, 3H), 1.23 (d, J = 6.8 Hz, 6H). |
| 251 | 516.2 | DMSO-$d_6$ | 300 | δ 8.27 (s, 1H), 7.61 (s, 1H), 6.27 (q, J = 6.9 Hz, 1H), 4.58-4.42 (m, 1H), 4.31-4.13 (m, 4H), 3.90-3.64 (m, 2H), 2.84-2.69 (m, 1H), 2.57 (s, 3H), 1.75 (d, J = 7.0 Hz, 3H), 1.34 (t, J = 6.9 Hz, 3H), 1.01-0.96 (m, 2H), 0.93-0.88 (m, 2H). |
| 252 | 470.1 | DMSO-$d_6$ | 300 | δ 8.11 (s, 1H), 7.53 (s, 1H), 7.34 (br s, 2H), 6.24 (q, J = 7.0 Hz, 1H), 4.52-4.37 (m, 1H), 4.35-4.19 (m, 4H), 3.79 (q, J = 6.8 Hz, 2H), 3.55 (s, 3H), 2.54 (s, 3H), 1.72 (d, J = 7.0 Hz, 3H), 1.37 (t, J = 6.9 Hz, 3H). |
| 253 | 484.2 | DMSO-$d_6$ | 300 | δ 8.11 (s, 1H), 7.53 (s, 1H), 7.34 (br s, 2H), 6.24 (q, J = 7.0 Hz, 1H), 4.52-4.37 (m, 1H), 4.35-4.17 (m, 4H), 4.00 (q, J = 7.1 Hz, 2H), 3.79 (q, J = 6.9 Hz, 2H), 2.54 (s, 3H), 1.72 (d, J = 7.0 Hz, 3H), 1.37 (t, J = 6.9 Hz, 3H), 1.15 (t, J = 7.1 Hz, 3H). |
| 254 | 498.3 | DMSO-$d_6$ | 300 | δ 8.27 (s, 1H), 7.58 (s, 1H), 6.27 (q, J = 6.8 Hz, 1H), 4.80-4.66 (m, 1H), 4.49-4.35 (m, 1H), 4.33-4.14 (m, 4H), 3.87-3.69 (m, 2H), 2.57 (s, 3H), 1.74 (d, J = 7.0 Hz, 3H), 1.37 (t, J = 6.9 Hz, 3H), 1.15 (d, J = 6.2 Hz, 6H). |
| 255 | 511.3 | DMSO-$d_6$ | 300 | δ 8.11 (s, 1H), 7.52 (s, 1H), 7.31 (br s, 2H), 6.24 (q, J = 7.0 Hz, 1H), 5.84 (s, 1H), 4.35-4.24 (m, 1H), 4.24-4.15 (m, 2H), 4.07-3.94 (m, 2H), 3.83-3.68 (m, 2H), 2.55 (s, 3H), 1.72 (d, J = 7.0 Hz, 3H), 1.36 (t, J = 6.9 Hz, 3H), 1.21 (s, 9H). |
| 256 | 455.2 | DMSO-$d_6$ | 400 | δ 8.15 (s, 1H), 7.53 (s, 1H), 6.25 (q, J = 7.0 Hz, 1H), 5.96 (br s, 2H), 4.40-4.30 (m, 1H), 4.24-4.16 (m, 2H), 4.15-4.01 (m, 2H), 3.85-3.68 (m, 2H), 2.55 (s, 3H), 1.73 (d, J = 7.0 Hz, 3H), 1.36 (t, J = 6.9 Hz, 3H). |
| 257 | 469.2 | DMSO-$d_6$ | 300 | δ 8.11 (s, 1H), 7.51 (s, 1H), 7.35 (br s, 2H), 6.37 (q, J = 4.2 Hz, 1H), 6.24 (q, J = 7.0 Hz, 1H), 4.43-4.29 (m, 1H), 4.24-4.15 (m, 2H), 4.13-3.99 (m, 2H), 3.85-3.68 (m, 2H), 2.54 (s, 3H), 2.51 (d, J = 4.7 Hz, 3H), 1.72 (d, J = 7.0 Hz, 3H), 1.36 (t, J = 6.9 Hz, 3H). |

TABLE 6-continued

| Ex. No. | MS [M + H]+ | Solvent | MHz | 1H NMR Spectra |
|---|---|---|---|---|
| 258 | 483.2 | DMSO-d6 | 300 | δ 8.11 (s, 1H), 7.51 (s, 1H), 7.35 (br s, 2H), 6.44 (t, J = 5.6 Hz, 1H), 6.24 (q, J = 6.9 Hz, 1H), 4.43-4.28 (m, 1H), 4.26-4.14 (m, 2H), 4.12-3.98 (m, 2H), 3.86-3.67 (m, 2H), 3.04-2.92 (m, 2H), 2.54 (s, 3H), 1.72 (d, J = 7.0 Hz, 3H), 1.36 (t, J = 6.9 Hz, 3H), 0.97 (t, J = 7.1 Hz, 3H). |
| 259 | 483.2 | DMSO-d6 | 400 | δ 8.11 (s, 1H), 7.52 (s, 1H), 6.24 (q, J = 6.9 Hz, 1H), 4.42-4.32 (m, 1H), 4.31-4.24 (m, 2H), 4.22-4.12 (m, 2H), 3.85-3.71 (m, 2H), 2.76 (s, 6H), 2.55 (s, 3H), 1.72 (d, J = 7.1 Hz, 3H), 1.36 (t, J = 7.0 Hz, 3H). |
| 260 | 460.2 | DMSO-d6 | 400 | δ 8.11 (s, 1H), 7.48 (s, 1H), 6.23 (q, J = 7.0 Hz, 1H), 4.35 (s, 1H), 4.11-4.01 (m, 1H), 3.95-3.87 (m, 2H), 3.84-3.74 (m, 1H), 3.74-3.64 (m, 1H), 3.12-3.01 (m, 2H), 2.55 (s, 3H), 1.71 (d, J = 7.1 Hz, 3H), 1.33 (t, J = 6.9 Hz, 3H). |
| 263 | 426.2 | DMSO-d6 | 300 | δ 8.11 (s, 1H), 7.46 (s, 1H), 7.38 (br s, 2H), 6.24 (q, J = 7.0 Hz, 1H), 4.11-3.97 (m, 1H), 3.95-3.84 (m, 2H), 3.64 (s, 3H), 3.00-2.88 (m, 2H), 2.55 (s, 3H), 2.39-2.27 (m, 2H), 1.72 (d, J = 7.1 Hz, 3H), 0.86 (t, J = 7.1 Hz, 3H). |
| 264 | 440.2 | DMSO-d6 | 400 | δ 8.11 (s, 1H), 7.47 (s, 1H), 6.28-6.19 (m, 1H), 4.02-3.92 (m, 1H), 3.91-3.82 (m, 2H), 3.64 (s, 3H), 3.03-2.89 (m, 2H), 2.55 (s, 3H), 2.24-2.14 (m, 1H), 1.72 (d, J = 6.9 Hz, 3H), 0.84 (d, J = 5.9 Hz, 6H). |
| 265 | 454.2 | DMSO-d6 | 300 | δ 8.11 (s, 1H), 7.46 (s, 1H), 7.34 (br s, 2H), 6.23 (q, J = 7.0 Hz, 1H), 4.14-4.01 (m, 1H), 3.96-3.84 (m, 2H), 3.64 (s, 3H), 3.04-2.92 (m, 2H), 2.55 (s, 3H), 2.13 (d, J = 6.9 Hz, 2H), 1.72 (d, J = 7.1 Hz, 3H), 1.60-1.45 (m, 1H), 0.83 (d, J = 6.6 Hz, 6H). |
| 266 | 452.2 | DMSO-d6 | 300 | δ 8.11 (s, 1H), 7.46 (s, 1H), 7.37 (br s, 2H), 6.24 (q, J = 7.0 Hz, 1H), 4.15-4.00 (m, 1H), 3.98-3.87 (m, 2H), 3.64 (s, 3H), 3.06-2.95 (m, 2H), 2.55 (s, 3H), 2.28-2.12 (m, 2H), 1.72 (d, J = 7.1 Hz, 3H), 0.78-0.64 (m, 1H), 0.42-0.32 (m, 2H), 0.08--0.01 (m, 2H). |
| 267 | 452.2 | DMSO-d6 | 300 | δ 8.11 (s, 1H), 7.47 (s, 1H), 7.38 (br s, 2H), 6.23 (q, J = 6.9 Hz, 1H), 4.10-3.95 (m, 1H), 3.83-3.70 (m, 2H), 3.63 (s, 3H), 3.10-2.92 (m, 3H), 2.54 (s, 3H), 1.92-1.79 (m, 2H), 1.78-1.50 (m, 7H). |
| 270 | 456.2 | DMSO-d6 | 300 | δ 8.11 (s, 1H), 7.46 (s, 1H), 7.34 (br s, 2H), 6.24 (q, J = 7.0 Hz, 1H), 4.36 (d, J = 4.5 Hz, 1H), 4.13-4.00 (m, 1H), 3.99-3.87 (m, 2H), 3.63 (s, 3H), 3.61-3.52 (m, 1H), 3.11-3.01 (m, 2H), 2.55 (s, 3H), 2.28 (d, J = 5.4 Hz, 2H), 1.72 (d, J = 7.1 Hz, 3H), 1.00 (d, J = 6.2 Hz, 3H). |
| 271 | 470.3 | DMSO-d6 | 300 | δ 8.11 (s, 1H), 7.46 (s, 1H), 7.33 (br s, 2H), 6.23 (q, J = 7.0 Hz, 1H), 4.16-3.91 (m, 4H), 3.63 (s, 3H), 3.17-3.05 (m, 2H), 2.55 (s, 3H), 2.26 (s, 2H), 1.72 (d, J = 7.1 Hz, 3H), 1.04 (s, 6H). |
| 274 | 454.1 | DMSO-d6 | 300 | δ 8.11 (s, 1H), 7.48 (s, 1H), 7.35 (br s, 2H), 6.24 (q, J = 7.0 Hz, 1H), 4.55-4.48 (m, 2H), 4.37-4.29 (m, 2H), 4.21-4.07 (m, 1H), 3.93-3.83 (m, 2H), 3.69-3.58 (m, 4H), 3.24-3.12 (m, 2H), 2.55 (s, 3H), 1.72 (d, J = 7.1 Hz, 3H). |
| 275 | 468.2 | DMSO-d6 | 300 | δ 8.11 (s, 1H), 7.47 (s, 1H), 7.35 (br s, 2H), 6.24 (q, J = 7.1 Hz, 1H), 4.11-3.97 (m, 1H), 3.95-3.82 (m, 2H), 3.75-3.58 (m, 6H), 3.56-3.41 (m, 2H), 3.08-2.97 (m, 2H), 2.94-2.87 (m, 1H), 2.55 (s, 3H), 1.72 (d, J = 7.1 Hz, 3H), 1.68-1.56 (m, 1H). |
| 276 | 468.2 | DMSO-d6 | 300 | δ 8.11 (s, 1H), 7.48 (s, 1H), 7.35 (br s, 2H), 6.24 (q, J = 6.9 Hz, 1H), 4.11-3.98 (m, 1H), 3.94-3.83 (m, 2H), 3.74-3.58 (m, 6H), 3.52 (dd, J = 8.9, 5.1 Hz, 1H), 3.44 (dd, J = 8.9, 2.5 Hz, 1H), 3.11-2.95 (m, 2H), 2.95-2.86 (m, 1H), 2.55 (s, 3H), 1.72 (d, J = 7.0 Hz, 3H), 1.67-1.56 (m, 1H). |
| 277 | 482.2 | DMSO-d6 | 300 | δ 8.11 (s, 1H), 7.47 (s, 1H), 7.37 (br s, 2H), 6.24 (q, J = 6.9 Hz, 1H), 4.12-3.98 (m, 1H), 3.94-3.83 (m, 2H), 3.83-3.73 (m, 2H), 3.65 (s, 3H), 3.29-3.18 (m, 2H), 3.09-2.96 (m, 2H), 2.55 (s, 3H), 2.21-2.10 (m, 1H), 1.72 (d, J = 7.0 Hz, 3H), 1.64-1.53 (m, 2H), 1.24-1.08 (m, 2H). |
| 278 | 482.2 | DMSO-d6 | 300 | δ 8.11 (s, 1H), 7.47 (s, 1H), 7.37 (br s, 2H), 6.23 (q, J = 7.0 Hz, 1H), 4.14-3.99 (m, 1H), 3.98-3.85 (m, 2H), 3.75-3.52 (m, 6H), 3.29 (dd, J = 8.3, 6.4 Hz, 1H), 3.09-2.95 (m, 2H), 2.55 (s, 3H), 2.36-2.29 (m, 2H), 2.23-2.07 (m, 1H), 1.96-1.83 (m, 1H), 1.72 (d, J = 7.1 Hz, 3H), 1.52-1.37 (m, 1H). |
| 279 | 482.2 | DMSO-d6 | 300 | δ 8.11 (s, 1H), 7.47 (s, 1H), 7.38 (br s, 2H), 6.23 (q, J = 6.9 Hz, 1H), 4.14-3.99 (m, 1H), 3.96-3.85 (m, 2H), 3.75-3.51 (m, 6H), 3.32-3.26 (m, 1H), 3.09-2.98 (m, 2H), 2.55 (s, 3H), 2.35-2.30 (m, 2H), 2.23-2.08 (m, 1H), 1.97-1.83 (m, 1H), 1.72 (d, J = 7.1 Hz, 3H), 1.54-1.35 (m, 1H). |
| 280 | 496.2 | DMSO-d6 | 300 | δ 8.11 (s, 1H), 7.46 (s, 1H), 7.36 (br s, 2H), 6.23 (q, J = 7.0 Hz, 1H), 4.14-4.00 (m, 1H), 3.96-3.86 (m, 2H), 3.83-3.74 (m, 2H), 3.64 (s, 3H), 3.29-3.19 (m, 2H), 3.05-2.94 (m, 2H), 2.55 (s, 3H), 2.20 (d, J = 6.3 Hz, 2H), 1.72 (d, J = 7.0 Hz, 3H), 1.59-1.45 (m, 3H), 1.17-1.01 (m, 2H). |

TABLE 6-continued

| Ex. No. | MS [M + H]+ | Solvent | MHz | 1H NMR Spectra |
|---|---|---|---|---|
| 282 | 454.1 | DMSO-$d_6$ | 300 | δ 8.11 (s, 1H), 7.52 (s, 1H), 7.35 (br s, 2H), 6.26 (q, J = 6.9 Hz, 1H), 4.58-4.37 (m, 3H), 4.31-4.21 (m, 1H), 4.19-4.09 (m, 1H), 3.71 (d, J = 3.3 Hz, 3H), 2.55 (s, 3H), 2.11-2.00 (m, 2H), 1.73 (d, J = 7.1 Hz, 3H), 0.95 (t, J = 7.5 Hz, 3H). |
| 283 | 468.2 | DMSO-$d_6$ | 300 | δ 8.11 (s, 1H), 7.52 (s, 1H), 7.35 (br s, 2H), 6.26 (q, J = 7.0 Hz, 1H), 4.64-4.37 (m, 3H), 4.31-4.19 (m, 1H), 4.19-4.08 (m, 1H), 3.72 (d, J = 3.9 Hz, 3H), 2.55 (s, 3H), 2.46-2.39 (m, 1H), 1.73 (d, J = 7.0 Hz, 3H), 1.02-0.92 (m, 6H). |
| 284 | 466.2 | DMSO-$d_6$ | 300 | δ 8.12 (s, 1H), 7.53 (d, J = 2.0 Hz, 1H), 7.35 (br s, 2H), 6.26 (q, J = 7.0 Hz, 1H), 4.73-4.62 (m, 1H), 4.61-4.42 (m, 1H), 4.31-4.22 (m, 1H), 4.22-4.11 (m, 1H), 3.73 (d, J = 2.3 Hz, 3H), 2.56 (s, 3H), 1.74 (d, J = 7.0 Hz, 3H), 1.55 (d, J = 5.6 Hz, 1H), 0.74-0.64 (m, 4H). |
| 286 | 490.1 | DMSO-$d_6$ | 300 | δ 8.11 (s, 1H), 7.54 (s, 1H), 7.35 (br s, 2H), 6.24 (q, J = 7.0 Hz, 1H), 4.54-4.40 (m, 1H), 4.25-4.13 (m, 4H), 3.67 (s, 3H), 3.19-3.10 (m, 2H), 2.55 (s, 3H), 1.73 (d, J = 7.1 Hz, 3H), 1.24-1.17 (m, 3H). |
| 287 | 504.2 | DMSO-$d_6$ | 300 | δ 8.11 (s, 1H), 7.53 (s, 1H), 7.39 (br s, 2H), 6.24 (q, J = 7.0 Hz, 1H), 4.55-4.40 (m, 1H), 4.23-4.15 (m, 4H), 3.68 (s, 3H), 3.30-3.22 (m, 1H), 2.55 (s, 3H), 1.74 (d, J = 7.1 Hz, 3H), 1.24 (d, J = 6.8 Hz, 6H). |
| 288 | 502.1 | DMSO-$d_6$ | 300 | δ 8.12 (s, 1H), 7.55 (s, 1H), 7.42 (br s, 2H), 6.25 (q, J = 7.0 Hz, 1H), 4.56-4.42 (m, 1H), 4.29-4.17 (m, 4H), 3.68 (s, 3H), 2.83-2.72 (m, 1H), 2.55 (s, 3H), 1.74 (d, J = 7.0 Hz, 3H), 1.03-0.95 (m, 2H), 0.93-0.88 (m, 2H). |
| 290 | 470.2 | DMSO-$d_6$ | 300 | δ 8.11 (s, 1H), 7.51 (s, 1H), 7.35 (br s, 2H), 6.25 (q, J = 6.9 Hz, 1H), 4.52-4.37 (m, 1H), 4.36-4.16 (m, 4H), 4.00 (q, J = 7.1 Hz, 2H), 3.70 (s, 3H), 2.55 (s, 3H), 1.73 (d, J = 7.1 Hz, 3H), 1.15 (t, J = 7.1 Hz, 3H). |
| 291 | 484.2 | DMSO-$d_6$ | 300 | δ 8.11 (s, 1H), 7.52 (s, 1H), 7.35 (br s, 2H), 6.25 (q, J = 7.0 Hz, 1H), 4.81-4.66 (m, 1H), 4.52-4.36 (m, 1H), 4.25 (d, J = 8.4 Hz, 4H), 3.70 (s, 3H), 2.55 (s, 3H), 1.73 (d, J = 7.1 Hz, 3H), 1.16 (d, J = 6.3 Hz, 6H). |
| 294 | 455.1 | DMSO-$d_6$ | 300 | δ 8.11 (s, 1H), 7.49 (s, 1H), 7.36 (br s, 2H), 6.36 (q, J = 4.4 Hz, 1H), 6.25 (q, J = 7.0 Hz, 1H), 4.44-4.30 (m, 1H), 4.25-4.14 (m, 2H), 4.13-3.99 (m, 2H), 3.69 (s, 3H), 2.55 (s, 3H), 2.51 (d, J = 4.6 Hz, 3H), 1.73 (d, J = 7.0 Hz, 3H). |
| 295 | 469.1 | DMSO-$d_6$ | 300 | δ 8.11 (s, 1H), 7.49 (s, 1H), 7.33 (br s, 2H), 6.44 (t, J = 5.5 Hz, 1H), 6.25 (q, J = 7.0 Hz, 1H), 4.44-4.30 (m, 1H), 4.26-4.15 (m, 2H), 4.12-3.99 (m, 2H), 3.69 (s, 3H), 3.03-2.92 (m, 2H), 2.55 (s, 3H), 1.73 (d, J = 7.1 Hz, 3H), 0.97 (t, J = 7.1 Hz, 3H). |
| 297 | 469.1 | DMSO-$d_6$ | 300 | δ 8.11 (s, 1H), 7.46 (s, 1H), 7.37 (br s, 2H), 6.24 (q, J = 7.0 Hz, 1H), 4.35 (s, 1H), 4.14-3.99 (m, 1H), 3.99-3.86 (m, 2H), 3.64 (s, 3H), 3.11-3.00 (m, 2H), 2.55 (s, 3H), 1.72 (d, J = 7.1 Hz, 3H). |
| 299 | 449.0 | DMSO-$d_6$ | 300 | δ 8.11 (s, 1H), 7.46 (s, 1H), 6.21 (q, J = 7.0 Hz, 1H), 3.99-3.84 (m, 2H), 3.84-3.69 (m, 1H), 3.57 (s, 3H), 2.97-2.87 (m, 1H), 2.85-2.75 (m, 1H), 2.55 (s, 3H), 2.14-2.07 (m, 1H), 1.70 (d, J = 7.1 Hz, 3H), 0.85 (d, J = 5.9 Hz, 6H). |
| 300 | 451.2 | DMSO-$d_6$ | 300 | δ 8.11 (s, 1H), 7.48 (s, 1H), 7.32 (br s, 2H), 6.21 (q, J = 7.0 Hz, 1H), 4.56 (br s, 1H), 4.12-3.89 (m, 3H), 3.58 (s, 3H), 3.46-3.36 (m, 2H), 3.28-3.04 (m, 2H), 2.55 (s, 3H), 1.71 (d, J = 7.1 Hz, 3H). |
| 301 | 465.0 | | | — |
| 302 | 465.0 | | | — |
| 303 | 479.1 | DMSO-$d_6$ | 300 | δ 8.11 (s, 1H), 7.48 (s, 1H), 7.32 (br s, 2H), 6.21 (q, J = 7.0 Hz, 1H), 4.45-3.83 (m, 4H), 3.58 (s, 3H), 2.55 (s, 3H), 2.45-2.28 (m, 2H), 1.71 (d, J = 7.0 Hz, 3H), 1.06 (s, 6H). |
| 304 | 463.0 | DMSO-$d_6$ | 300 | δ 8.11 (s, 1H), 7.46 (s, 1H), 7.33 (br s, 2H), 6.21 (q, J = 7.0 Hz, 1H), 4.54-4.46 (m, 2H), 4.35-4.27 (m, 2H), 4.01-3.80 (m, 3H), 3.62-3.53 (m, 4H), 3.14-3.06 (m, 1H), 3.03-2.93 (m, 1H), 2.54 (s, 3H), 1.70 (d, J = 7.1 Hz, 3H). |
| 305 | 446.1 | DMSO-$d_6$ | 300 | δ 8.11 (s, 1H), 7.49 (s, 1H), 7.32 (br s, 2H), 6.22 (q, J = 6.9 Hz, 1H), 4.04-3.84 (m, 3H), 3.62 (s, 2H), 3.57 (s, 3H), 3.28-3.21 (m, 1H), 3.17-3.08 (m, 1H), 2.55 (s, 3H), 1.71 (d, J = 7.0 Hz, 3H). |
| 306 | 449.1 | DMSO-$d_6$ | 300 | δ 8.11 (s, 1H), 7.51 (s, 1H), 7.32 (br s, 2H), 6.22 (q, J = 7.0 Hz, 1H), 4.55-4.41 (m, 2H), 4.40-4.29 (m, 1H), 4.26-4.14 (m, 1H), 4.11-4.02 (m, 1H), 3.65 (d, J = 3.3 Hz, 3H), 2.55 (s, 3H), 1.78-1.75 (m, 3H), 1.72 (d, J = 6.2 Hz, 3H). |
| 308 | 455.3 | DMSO-$d_6$ | 300 | δ 7.95 (s, 1H), 7.19 (s, 1H), 7.17-7.13 (m, 1H), 6.58 (s, 2H), 6.11 (q, J = 7.1 Hz, 1H), 4.41 (t, J = 5.4 Hz, 1H), 4.13-3.99 (m, 1H), 3.97-3.86 (m, 2H), 3.84-3.67 (m, 2H), 3.13-3.00 (m, 2H), 2.41 (t, J = 6.0 Hz, 2H), 2.36 (s, 3H), 1.69 (d, J = 7.1 Hz, 3H), 1.30 (t, J = 6.9 Hz, 3H). |

TABLE 6-continued

| Ex. No. | MS [M + H]+ | Solvent | MHz | 1H NMR Spectra |
|---|---|---|---|---|
| 309 | 469.2 | DMSO-$d_6$ | 300 | δ 7.95 (s, 1H), 7.18 (s, 1H), 7.16-7.13 (m, 1H), 6.58 (s, 2H), 6.11 (q, J = 7.0 Hz, 1H), 4.36 (d, J = 4.5 Hz, 1H), 4.15-4.00 (m, 1H), 3.99-3.87 (m, 2H), 3.84-3.67 (m, 2H), 3.63-3.50 (m, 1H), 3.18-2.99 (m, 2H), 2.36 (s, 3H), 2.28 (d, J = 5.9 Hz, 2H), 1.69 (d, J = 7.1 Hz, 3H), 1.29 (t, J = 6.9 Hz, 3H), 1.00 (d, J = 6.2 Hz, 3H). |

Example 313

5-{3-[1-(4-amino-3-methyl-1H-pyrazolo[3,4-d]pyrimidin-1-yl)ethyl]-5-chloro-6-cyano-2-methoxyphenyl}-N,N-dimethylpyridine-2-carboxamide

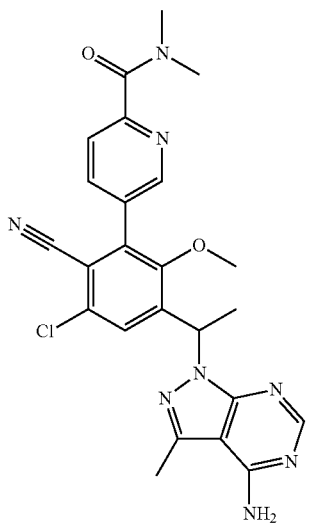

Step 1:
5-Bromo-N,N-dimethylpyridine-2-carboxamide

5-Bromopyridine-2-carboxylic acid (20 g, 100 mmol, Frontier Scientific catalog#B1704) was stirred in methylene chloride (30 mL) and cooled to 0° C. 2.0 M oxalyl chloride in methylene chloride (100 mL) was added slowly, followed by N,N-dimethylformamide (0.8 mL). The mixture was stirred for 30 minutes at 0° C. and then room temperature overnight. The mixture was evaporated, redissolved in methylene chloride (130 mL) and was added slowly to a mixture of dimethylamine hydrochloride (9.8 g, 120 mmol) and triethylamine (56.1 mL, 400 mmol) in methylene chloride (130 mL) cooled to 0° C. The reaction mixture was stirred at room temperature for 2 hrs. This mixture was diluted with methylene chloride (200 mL) and washed with saturated sodium bicarbonate, brine, dried over sodium sulfate, filtered and evaporated. The product was purified by FCC on silica gel using ethyl acetate in hexanes (0-60%) gradient to give 5-bromo-N,N-dimethylpyridine-2-carboxamide, (22.0 g, 100%). LCMS calculated for $C_8H_{10}BrN_2O$ (M+H)+: m/z=229.0, 231.0. found: 228.9, 230.9.

Step 2: {6-[(Dimethylamino)carbonyl]pyridin-3-yl}boronic acid

A mixture of 5-bromo-N,N-dimethylpyridine-2-carboxamide (23 g, 98 mmol), 4,4,5,5,4',4',5',5'-octamethyl-[2,2']bi[[1,3,2]dioxaborolanyl] (27 g, 110 mmol), [1,1'-bis(diphenylphosphino)ferrocene]dichloropalladium(II), complex with dichloromethane (Aldrich, Catalog No. 379670) (1:1) (4.8 g, 5.9 mmol), 1,1'-bis(diphenylphosphino)ferrocene (Aldrich, Catalog No. 177261) (3.3 g, 5.9 mmol), and potassium acetate (30 g, 300 mmol) in 1,4-dioxane (600 mL) was degassed with nitrogen and was heated at 120° C. for 16 hrs. The mixture was cooled to room temperature and diluted with ethyl acetate (600 mL) and water (600 mL). The aqueous layer was concentrated in vacuo to give a solid residue. The solids were taken up in acetonitrile and filtered to remove the residual insoluble salts. The acetonitrile was removed in vacuo to give {6-[(dimethylamino)carbonyl]pyridin-3-yl}boronic acid (12 g, 60%). LCMS calculated for $C_8H_{12}BN_2O_3$ (M+H)+: m/z=195.1. found: 195.1.

Step 3.
4-Acetyl-2-bromo-6-chloro-3-methoxybenzonitrile 1-(3-Bromo-5-chloro-4-fluoro-2-hydroxyphenyl)ethanone (2.0 g, 7.5 mmol, Example 43, Step 1) was combined with potassium cyanide (0.58 g, 9.0 mmol) in N,N-dimethylformamide (16 mL) and heated to 85° C. in an oil bath. After heating for 18 hrs, the reaction was allowed to cool to room temperature and iodomethane (0.90 mL, 11 mmol) and potassium carbonate (2.1 g, 15 mmol) were added. The reaction was heated to 65° C. and monitored by LC/MS. After heating for 3 hrs the reaction was complete and allowed to cool to room temperature, then taken up in ethyl acetate and washed with water, brine, and dried over magnesium sulfate. The resultant solution was concentrated to give the crude product as a dark oil. The product was purified by FCC on silica gel eluting hexane: ethyl acetate gradient to give 4-acetyl-2-bromo-6-chloro-3-methoxybenzonitrile (1.65 g, 75%) as a solid residue. LCMS calculated for $C_{10}H_{18}BrClNO_2$(M+H)+: m/z=287.9, 289.9. found: 288.1, 290.0.

Step 4: 5-(3-Acetyl-5-chloro-6-cyano-2-methoxyphenyl)-N,N-dimethylpyridine-2-carboxamide Sodium carbonate (3.0 g, 20 mmol) in water (20 mL) was added to a mixture 4-acetyl-2-bromo-6-chloro-3-methoxybenzonitrile (2.5 g, 8.7 mmol) and {6-[(dimethylamino)carbonyl]pyridin-3-yl}boronic acid (1.9 g, 10. mmol, Example 301 Step 2) in acetonitrile (100 mL). The reaction was degassed with $N_2$ and [1,1'-bis(diphenylphosphino)ferrocene]dichloropalladium(II), complex with dichloromethane (1:1) (400 mg, 0.4 mmol) was added and the reaction mixture was degassed again with $N_2$. The reaction was heated at 100° C. for 4 hrs and was complete by LC/MS. The reaction was allowed to cool to room temperature and was partitioned between water and EtOAc. The combined organic layer was washed with brine, dried over $MgSO_4$, filtered, concentrated to give the crude product. The product was purified by FCC on silica gel eluting a hexane: ethyl acetate gradient to give 5-(3-acetyl-5-chloro-6-cyano-2-methoxyphenyl)-N,N-dimethylpyridine-2-carboxamide as yellow oil (2.2 g, 71%). LCMS calculated for $C_{18}H_{17}ClN_3O_3(M+H)^+$: m/z=358.1. found: 358.1.

Step 5: 5-[3-Chloro-2-cyano-5-(1-hydroxyethyl)-6-methoxyphenyl]-N,N-dimethylpyridine-2-carboxamide Sodium tetrahydroborate (320 mg, 8.4 mmol) was added to a mixture of 5-(3-acetyl-5-chloro-6-cyano-2-methoxyphenyl)-N,N-dimethylpyridine-2-carboxamide (2 g, 6 mmol) in methanol (100 mL) cooled at 0° C. The reaction was stirred at 0° C. for 1 h, quenched with water and partitioned between water and EtOAc. The combined organic layer was washed with brine, dried over MgSO$_4$, filtered and concentrated to give crude 5-[3-chloro-2-cyano-5-(1-hydroxyethyl)-6-methoxyphenyl]-N,N-dimethylpyridine-2-carboxamide as clear oil (2.0 g, 100%). LCMS calculated for $C_{18}H_{19}ClN_3O_3$ (M+H)$^+$: m/z=360.1. found: 360.1.

Step 6: 5-[3-Chloro-5-(1-chloroethyl)-2-cyano-6-methoxyphenyl]-N,N-dimethylpyridine-2-carboxamide Thionyl chloride (800 µL, 10 mmol) was added dropwise to a solution of 5-[3-chloro-2-cyano-5-(1-hydroxyethyl)-6-methoxyphenyl]-N,N-dimethylpyridine-2-carboxamide (2 g, 6 mmol), methylene chloride (100 mL) and N,N-dimethylformamide (100 µL) at room temperature. The reaction was stirred for 5 hrs and was complete by LC/MS. The reaction mixture was partitioned between EtOAc and water. The combined organic layer was washed with saturated NaHCO$_3$, brine, dried over Na$_2$SO$_4$, filtered and concentrated to give crude 5-[3-chloro-5-(1-chloroethyl)-2-cyano-6-methoxyphenyl]-N,N-dimethylpyridine-2-carboxamide as an oil (1.8 g, 80%). LCMS calculated for $C_{18}H_{18}Cl_2N_3O_2$ (M+H)$^+$: m/z=378.1. found: 378.1.

Step 7: 5-{3-[1-(4-Amino-3-methyl-1H-pyrazolo[3,4-d]pyrimidin-1-yl)ethyl]-5-chloro-6-cyano-2-methoxyphenyl}-N,N-dimethylpyridine-2-carboxamide Cesium carbonate (3000 mg, 10 mmol) was added to a mixture of 3-methyl-1H-pyrazolo[3,4-d]pyrimidin-4-amine (1100 mg, 7.1 mmol) and 5-[3-chloro-5-(1-chloroethyl)-2-cyano-6-methoxyphenyl]-N,N-dimethylpyridine-2-carboxamide (1.8 g, 4.8 mmol) in N,N-dimethylformamide (50 mL). The reaction was stirred at 80° C. for 3 hrs and was allowed to cool to room temperature. The reaction was diluted with EtOAc, washed with water, brine, dried over Na$_2$SO$_4$, filtered and concentrated to give the crude product. This was purified by FCC on silica gel eluting (hexanes/10% EtOH in EtOAc, 0-100%) gradient to give the title compound as light yellow oil (2.0 g, 80%). LCMS calculated for $C_{24}H_{24}ClN_8O_2$ (M+H)$^+$: m/z=491.2. $^1$H NMR (400 MHz, CD$_3$OD) δ 8.74 (d, J=1.4 Hz, 1H), 8.15 (d, J=2.2 Hz, 1H), 8.13 (s, 1H), 7.77 (d, J=8.1 Hz, 1H), 7.74 (s, 1H), 6.43 (q, J=7.0 Hz, 1H), 3.32 (s, 3H), 3.16 (s, 3H), 3.07 (s, 3H), 2.64 (s, 3H), 1.89 (d, J=7.1 Hz, 3H).

The enantiomers were separated by Chiral column HPLC using: Phenomenex Lux-Cellulose 1 column, 21.1×250 mm, 5 micron particle size 15% ethanol in hexanes 18 mL/min~5 mg/injection to give the following: First peak retention time: 2.09 min, 5-{3-[1-(4-amino-3-methyl-1H-pyrazolo[3,4-d]pyrimidin-1-yl)ethyl]-5-chloro-6-cyano-2-methoxyphenyl}-N,N-dimethylpyridine-2-carboxamide; Second peak retention time: 3.92 min, 5-{3-[1-(4-amino-3-methyl-1H-pyrazolo[3,4-d]pyrimidin-1-yl)ethyl]-5-chloro-6-cyano-2-methoxyphenyl}-N,N-dimethylpyridine-2-carboxamide.

Example 314

5-{3-[1-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide

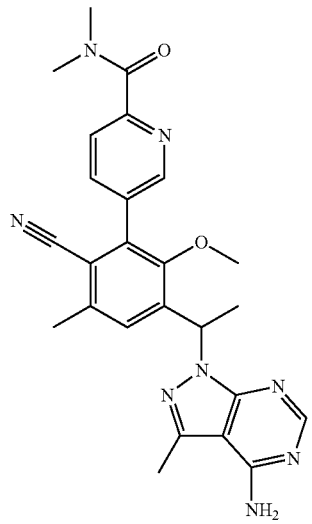 [SMILES: COc1c(C(C)n2nc(C)c3c(N)ncnc32)cc(C)c(C#N)c1-c1ccc(C(=O)N(C)C)nc1]

Step 1: 4-Acetyl-5-hydroxy-2-methylbenzonitrile

The 1-(4-bromo-2-hydroxy-5-methylphenyl)ethanone (8.5 g, 37 mmol, Alfa Aesar catalog#H29125) was combined with zinc cyanide (8.7 g, 74 mmol) in N,N-dimethylformamide (75 mL) degassed with nitrogen and the tris(dibenzylideneacetone)dipalladium(0) (Aldrich Catalog No. 328774) (1.0 g, 1.1 mmol) and (9,9-dimethyl-9H-xanthene-4,5-diyl)bis(diphenylphosphine) (Aldrich Catalog No. 526460) (1.5 g, 2.6 mmol) were added. The reaction was degassed again with nitrogen and heated to 120° C. and monitored by LC/MS. After heating for 18 hrs the reaction was complete, the reaction was allowed to cool to room temperature, taken up in ethyl acetate and washed with water (2×), brine, dried over magnesium sulfate and concentrated to give the crude product as a dark amber oil. The product was purified by FCC on silica gel eluting hexane: ethyl acetate gradient to give 4-acetyl-5-hydroxy-2-methylbenzonitrile as a solid (6.3 g, 98%). LCMS calculated for $C_{10}H_{10}NO_2$(M+H)$^+$: m/z=176.1. found: 176.2.

Step 2: 4-Acetyl-3-hydroxy-2-iodo-6-methylbenzonitrile

The 4-acetyl-5-hydroxy-2-methylbenzonitrile (6.7 g, 38 mmol) was dissolved in acetic acid (80 mL) and the N-iodosuccinimide (10. g, 46 mmol) was added. The reaction was heated to 80° C. in an oil bath and monitored by LC/MS. After heating for 4 hrs the reaction was complete. This was allowed to cool and was concentrated in vacuo to give a dark oil. The oil was taken up in ethyl acetate and washed with water, sodium bicarbonate (3×, until remained slightly basic), brine, dried over magnesium sulfate and concentrated to give the crude product as a dark oil. The product was purified by FCC on silica gel eluting hexane: ethyl acetate gradient to give 4-acetyl-3-hydroxy-2-iodo-6-methylbenzonitrile as pale yellow solid (7.2 g, 62%). LCMS calculated for $C_{10}H_9INO_2(M+H)^+$: m/z=301.9. found: 301.9.

Step 3: 4-Acetyl-2-iodo-3-ethoxy-6-methylbenzonitrile

The 4-acetyl-3-hydroxy-2-iodo-6-methylbenzonitrile (5.0 g, 17 mmol) was dissolved in N,N-dimethylformamide (50.0 mL) and the potassium carbonate (4.6 g, 33 mmol) and ethyl iodide (2.1 mL, 33 mmol) were added. The reaction was heated to 60° C. and monitored by LC/MS. After heating for 2 hrs the reaction was complete. This was allowed to cool, diluted with ethyl acetate (300 mL) and filtered to remove the remaining solids. The organic layer was washed with water (3×), brine, dried over magnesium sulfate and concentrated to give the crude product as a dark solid. The product was purified by FCC on silica gel eluting hexane:ethyl acetate gradient to give 4-acetyl-3-ethoxy-2-iodo-6-methylbenzonitrile as a pale yellow crystalline solid (5.0 g, 96%). LCMS calculated for $Cl_{21}H_{13}INO_2$ $(M+H)^+$: m/z=329.9. found: 330.0.

Step 4: 5-(3-Acetyl-6-cyano-2-ethoxy-5-methylphenyl)-N,N-dimethylpyridine-2-carboxamide Sodium carbonate (3 g, 30 mmol) in water (20 mL) was added to a mixture of 4-acetyl-3-ethoxy-2-iodo-6-methylbenzonitrile (3 g, 9 mmol) and {6-[(dimethylamino)carbonyl]pyridin-3-yl}boronic acid (1700 mg, 8.8 mmol, Example 313, Step 2) in acetonitrile (100 mL). The mixture was degassed with nitrogen and [1,1'-bis(diphenylphosphino)ferrocene]dichloropalladium(II), complex with dichloromethane (1:1) (400 mg, 0.4 mmol) was added. The reaction was degassed again with nitrogen and was heated to 100° C. for 4 hrs. The reaction was allowed to cool to room temperature, diluted with water and extracted with EtOAc. The combined organic layer was washed with brine, dried over $MgSO_4$, filtered and concentrated to give the crude product. The product was purified by FCC on silica gel eluting (hexane/EtOAc, 0-100%) gradient to give 5-(3-acetyl-6-cyano-2-ethoxy-5-methylphenyl)-N,N-dimethylpyridine-2-carboxamide product as yellow solid (2.3 g, 75%). LCMS calculated for $C_{20}H_{22}N_3O_3(M+H)^+$: m/z=352.1. found: 352.2.

Step 5: 5-[2-Cyano-6-ethoxy-5-(1-hydroxyethyl)-3-methylphenyl]-N,N-dimethylpyridine-2-carboxamide Sodium tetrahydroborate (370 mg, 9.8 mmol) was added to a mixture of 5-(3-acetyl-6-cyano-2-ethoxy-5-methylphenyl)-N,N-dimethylpyridine-2-carboxamide (2.3 g, 6.5 mmol) in methanol (100 mL) at 0° C. The reaction was stirred at 0° C. for 1 h. The reaction was partitioned between water and EtOAc. The combined organic layer was washed with brine, dried over $MgSO_4$, filtered and concentrated to give the crude product 5-[2-cyano-6-ethoxy-5-(1-hydroxyethyl)-3-methylphenyl]-N,N-dimethylpyridine-2-carboxamide as a clear oil (2.3 g, 99%). LCMS calculated for $C_{20}H_{24}N_3O_3(M+H)^+$: m/z=354.1. found: 354.2.

Step 6: 5-[3-(1-Chloroethyl)-6-cyano-2-ethoxy-5-methylphenyl]-N,N-dimethylpyridine-2-carboxamide Thionyl chloride (900 μL, 10 mmol) was added dropwise to a solution of 5-[2-cyano-6-ethoxy-5-(1-hydroxyethyl)-3-methylphenyl]-N,N-dimethylpyridine-2-carboxamide (2.3 g, 6.5 mmol) in methylene chloride (100 mL) and N,N-dimethylformamide (100 μL) at room temperature. The reaction was stirred for 3 hrs, was diluted with methylene chloride (100 mL) and washed with water saturated $NaHCO_3$. The combined organic layer was washed with brine, dried over $MgSO_4$, filtered and concentrated to give crude 5-[3-(1-chloroethyl)-6-cyano-2-ethoxy-5-methylphenyl]-N,N-dimethylpyridine-2-carboxamide (2.2 g, 91%). LCMS calculated for $C_{20}H_{23}ClN_3O_2(M+H)^+$: m/z=372.1. found: 372.2.

Step 7: 5-{3-[1-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide Cesium carbonate (4000 mg, 10 mmol) was added to a mixture of 3-methyl-1H-pyrazolo[3,4-d]pyrimidin-4-amine (1300 mg, 8.5 mmol) and 5-[3-(1-chloroethyl)-6-cyano-2-ethoxy-5-methylphenyl]-N,N-dimethylpyridine-2-carboxamide (2.1 g, 5.6 mmol) in N,N-dimethylformamide (100 mL). The reaction was stirred at 80° C. for 3 hrs and monitored by LC/MS. The reaction mixture was diluted with EtOAc, washed with water, brine, dried over $Na_2SO_4$, filtered and concentrated to give the crude product. The product was purified by FCC on silica gel eluting (hexane/ 10% EtOH in EtOAc, gradient 0-100%) gradient to give the title compound (2.1 g, 77%). LCMS calculated for $C_{26}H_{29}N_8O_2(M+H)^+$: m/z=485.2. found: 485.2. $^1H$ NMR (500 MHz, DMSO-$d_6$) δ 8.70-8.63 (m, 1H), 8.10 (s, 1H), 8.06 (dd, J=8.0, 2.2 Hz, 1H), 7.69 (d, J=8.1 Hz, 1H), 7.51 (s, 1H), 6.34 (q, J=7.0 Hz, 1H), 3.59-3.47 (m, 1H), 3.33 (m, 1H), 3.03 (s, 3H), 2.96 (s, 3H), 2.57 (s, 3H), 2.45 (s, 3H), 1.79 (d, J=7.1 Hz, 3H), 0.90 (t, J=7.0 Hz, 3H). The enantiomers were separated by Chiral column HPLC using: AD column 20×25 cm, eluting hexane; 30% ethanol @ 13 mL/min~5 mg/injection to give: First peak retention time: 1.63 minutes, 5-{3-[1-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide; Second peak retention time: 4.13 minutes, 5-{3-[1-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide.

Example 315

4-[-1-(4-amino-3-methyl-1H-pyrazolo[3,4-d]pyrimidin-1-yl)ethyl]-2-{1-[(2S)-2-hydroxypropyl]azetidin-3-yl}-3-methoxy-6-methylbenzonitrile

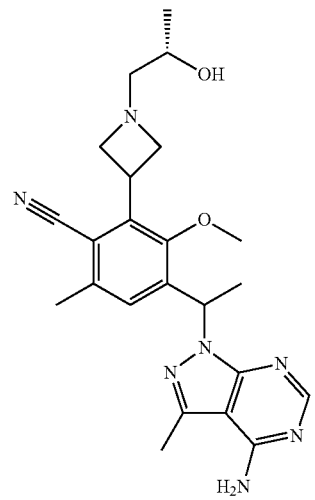 [SMILES: COc1c(C(C)n2nc(C)c3c(N)ncnc32)cc(C)c(C#N)c1C1CN(C[C@H](C)O)C1]

Step 1: 4-Acetyl-5-hydroxy-2-methylbenzonitrile

The 1-(4-bromo-2-hydroxy-5-methylphenyl)ethanone (8.5 g, 37 mmol, Alfa Aesar catalog#H29125) was combined with zinc cyanide (8.7 g, 74 mmol) in N,N-dimethylformamide (75 mL) degassed with nitrogen and the tris(dibenzylideneacetone)dipalladium(0) (1.0 g, 1.1 mmol) and (9,9-dimethyl-9H-xanthene-4,5-diyl)bis(diphenylphosphine) (1.5 g, 2.6 mmol) were added. The reaction was degassed again with nitrogen and heated to 120° C. and monitored by LC/MS. After heating for 18 h, the reaction was complete, the reaction was allowed to cool to room temperature, taken up in ethyl acetate and washed with water (2×), brine, dried over magnesium sulfate and concentrated to give the crude product as a dark amber oil. The product was purified by FCC on silica gel eluting hexane: ethyl acetate gradient to give 4-acetyl-5-hydroxy-2-methylbenzonitrile as a solid (6.3 g, 98%). LCMS calculated for $C_{10}H_{10}NO_2$ $(M+H)^+$: m/z=176.1. found: 176.2.

Step 2: 4-Acetyl-3-hydroxy-2-iodo-6-methylbenzonitrile

The 4-acetyl-5-hydroxy-2-methylbenzonitrile (6.7 g, 38 mmol) was dissolved in acetic acid (80 mL) and the N-Iodosuccinimide (10. g, 46 mmol) was added. The reaction was heated to 80° C. in an oil bath and monitored by LC/MS. After heating for 4 hrs the reaction was complete. This was allowed to cool and was concentrated in vacuo to give a dark oil. The oil was taken up in ethyl acetate and washed with water, sodium bicarbonate (3×, until remained slightly basic), brine, dried over magnesium sulfate and concentrated to give the crude product as a dark oil. The product was purified by FCC on silica gel eluting hexane: ethyl acetate gradient to give 4-acetyl-3-hydroxy-2-iodo-6-methylbenzonitrile as pale yellow solid (7.2 g, 62%). LCMS calculated for $C_{10}H_9INO_2(M+H)^+$: m/z=301.9. found: 301.9.

Step 3: 4-Acetyl-2-iodo-3-methoxy-6-methylbenzonitrile

The 4-acetyl-3-hydroxy-2-iodo-6-methylbenzonitrile (5.0 g, 17 mmol) was dissolved in N,N-dimethylformamide (50 mL) and the potassium carbonate (4.6 g, 33 mmol) and methyl iodide (2.1 mL, 33 mmol) were added. The reaction was heated to 60° C. and monitored by LC/MS. After heating for 2 hrs the reaction was complete. This was allowed to cool, diluted with ethyl acetate (300 mL) and filtered to remove the remaining solids. The organic layer was washed with water (3×), brine, dried over magnesium sulfate and concentrated to give the crude product as a dark solid. The product was purified by FCC on silica gel eluting hexane: ethyl acetate gradient to give 4-acetyl-3-methoxy-2-iodo-6-methylbenzonitrile as a pale yellow crystalline solid (5.0 g, 96%). LCMS calculated for $C_{11}H_{11}INO_2$ $(M+H)^+$: m/z=315.9. found: 316.0.

Step 4: tert-butyl 3-(3-acetyl-6-cyano-2-methoxy-5-methylphenyl)azetidine-1-carboxylate Zinc (1.70 g, 26.0 mmol) and celite (oven dried, 500 mg) were ground together in a flask until the solids appeared homogenous, the flask was heated with a heat gun while under high-vac for 5 minutes and then back-filled with nitrogen. The solids were suspended in N,N-dimethylacetamide (4.2 mL) and 1,2-dibromoethane (0.13 mL, 1.5 mmol) was added. The reaction mixture was heated at 70° C. for 30 min and then cooled to room temperature. Chlorotrimethylsilane (0.16 mL, 1.3 mmol) was added dropwise and stirring was continued for 2 hrs at room temperature. A solution of tert-butyl 3-iodoazetidine-1-carboxylate (2.70 g, 9.52 mmol) in N,N-dimethylacetamide (4.35 mL) was then added slowly and the resulting mixture was heated at 50° C. for 2 hrs. The zinc-iodo reagent was allowed to cool to room temperature and was taken up in a syringe and filtered through a PTFE filter (adapted with a needle) directly into a suspension of tris(dibenzylideneacetone)dipalladium(0) (0.111 g, 0.121 mmol) and tri-(2-furyl)phosphine (0.056 g, 0.24 mmol) and 4-acetyl-2-iodo-3-methoxy-6-methylbenzonitrile (2.0 g, 6.3 mmol) in N,N-dimethylacetamide (19.6 mL) pre-degassed by bubbling $N_2$. The reaction mixture was degassed with nitrogen again and heated to 70° C. After heating for 30 minutes the reaction was complete by LC/MS. This was allowed to cool, taken up in ethyl acetate and washed with water, brine, dried over magnesium sulfate and concentrated to give the crude product as an oil. The product was purified by FCC on silica gel eluting hexane: ethyl acetate gradient to give tert-butyl 3-(3-acetyl-6-cyano-2-methoxy-5-methylphenyl)azetidine-1-carboxylate as a clear oil. (1.8 g, 82%). LCMS calculated for $C_{15}H_{11}N_2O_4$ $(M+H)^+$: m/z=289.1. found: 289.1.

Step 5: tert-butyl 3-[2-cyano-5-(1-hydroxyethyl)-6-methoxy-3-methylphenyl]azetidine-1-carboxylate The tert-butyl 3-(3-acetyl-6-cyano-2-methoxy-5-methylphenyl)azetidine-1-carboxylate (2.2 g, 6.4 mmol) was dissolved in methanol (20 mL) and cooled in ice bath. The sodium tetrahydroborate (0.26 g, 7.0 mmol) was added portionwise and the reaction was monitored by LC/MS. After stirring for 1 h the reaction was complete. This was diluted with ethyl acetate and water. The combined organic layer was washed with water, saturated sodium bicarbonate, brine, dried over magnesium sulfate and concentrated to give crude tert-butyl 3-[2-cyano-5-(1-hydroxyethyl)-6-methoxy-3-methylphenyl]azetidine-1-carboxylate as a yellow foam (2.1 g, 99%). LCMS calculated for $C_{15}H_{19}N_2O_4$ $(M+H)^+$: m/z=291.1. found: 291.1.

Step 6: tert-butyl 3-[3-(1-chloroethyl)-6-cyano-2-methoxy-5-methylphenyl]azetidine-1-carboxylate The tert-butyl 3-[2-cyano-5-(1-hydroxyethyl)-6-methoxy-3-methylphenyl]azetidine-1-carboxylate (2.1 g, 6.4 mmol) was taken up in methylene chloride (50.0 mL) and N,N-dimethylformamide (0.59 mL), cooled in an ice bath and the thionyl chloride (0.56 mL, 7.7 mmol) was added slowly. After stirring for 2 hrs the reaction was complete by LC/MS and was partitioned between ethyl acetate and water. The combined organic layer was washed with water saturated sodium bicarbonate, brine, dried over magnesium sulfate and concentrated to give crude tert-butyl 3-[3-(1-chloroethyl)-6-cyano-2-methoxy-5-methylphenyl] azetidine-1-carboxylate as an oil (2.2 g, 100%). LCMS calculated for $C_{15}H_{18}ClN_2O_3(M+H)^+$: m/z=309.1. found: 309.1.

Step 7: tert-butyl 3-{3-[1-(4-amino-3-methyl-1H-pyrazolo[3,4-d]pyrimidin-1-yl)ethyl]-6-cyano-2-methoxy-5-methylphenyl}azetidine-1-carboxylate The tert-butyl 3-[3-(1-chloroethyl)-6-cyano-2-methoxy-5-methylphenyl]azetidine-1-carboxylate (2.3 g, 6.3 mmol) was dissolved in N,N-dimethylformamide (68 mL) with cesium carbonate (4.1 g, 13 mmol) and 3-methyl-1H-pyrazolo[3,4-d]pyrimidin-4-amine (1.4 g, 9.4 mmol) and was heated in an oil bath to 80° C. The reaction was stirred for 18 hrs and allowed to cool to room temperature. The reaction mixture was taken up in ethyl acetate, filtered, washed with water, brine, dried over magnesium sulfate and concentrated to give the crude product. The product was purified by FCC on silica gel eluting a (hexane: 10% ethanol ethyl acetate) gradient to give tert-butyl 3-{3-[-1-(4-amino-3-methyl-1H-pyrazolo[3,4-d]pyrimidin-1-yl)ethyl]-6-cyano-2-methoxy-5-methylphenyl}azetidine-1-carboxylate as a semisolid (1.5 g, 50%). LCMS calculated for $C_{25}H_{32}N_7O_3(M+H)^+$: m/z=478.2. found: 478.2. The enantiomers were separated by Chiral column HPLC using: Phenomenex LUX Cellulose Column, 21.1×250 mm, 5 micron, 15% ethanol in hexane, 18 mL/min~5 mg/injection to give: First peak retention time: 2.1 minutes, tert-butyl 3-{3-[-1-(4-amino-3-methyl-1H-pyrazolo[3,4-d]pyrimidin-1-yl)ethyl]-6-cyano-2-methoxy-5-methylphenyl}azetidine-1-carboxylate; Second peak retention time: 3.9 minutes, tert-butyl 3-{3-[-1-(4-amino-3-methyl-1H-pyrazolo[3,4-d]pyrimidin-1-yl)ethyl]-6-cyano-2-methoxy-5-methylphenyl}azetidine-1-carboxylate.

Step 8: 4-[1-(4-amino-3-methyl-1H-pyrazolo[3,4-d]pyrimidin-1-yl)ethyl]-2-azetidin-3-yl-3-methoxy-6-methylbenzonitrile bis(trifluoroacetate)

The tert-butyl 3-{3-[1-(4-amino-3-methyl-1H-pyrazolo[3,4-d]pyrimidin-1-yl)ethyl]-6-cyano-2-methoxy-5-methylphenyl}azetidine-1-carboxylate (0.35 g, 0.73 mmol) (Step 7, peak 1) was dissolved in methylene chloride (3.0 mL) and trifluoroacetic acid (1.0 mL) at room temperature. After stirring for 1 h the reaction was complete by LC/MS. The reaction was concentrated in vacuo to give 4-[1-(4-amino-3-methyl-1H-pyrazolo[3,4-d]pyrimidin-1-yl)ethyl]-2-azetidin-3-yl-3-methoxy-6-methylbenzonitrile (bis(trifluoroacetate) as a viscous amber oil (0.50 g, 100%). LCMS calculated for $C_{20}H_{24}N_7O$ (M+H)$^+$: m/z=378.2. found: 378.2.

Step 9: 4-[1-(4-amino-3-methyl-1H-pyrazolo[3,4-d]pyrimidin-1-yl)ethyl]-2-{1-[(2S)-2-hydroxypropyl]azetidin-3-yl}-3-methoxy-6-methylbenzonitrile The 4-[1-(4-amino-3-methyl-1H-pyrazolo[3,4-d]pyrimidin-1-yl)ethyl]-2-azetidin-3-yl-3-methoxy-6-methylbenzonitrile bis(trifluoroacetate) (0.074 g, 0.10 mmol) was dissolved in ethanol (3.0 mL) and DIPEA (0.071 mL, 0.41 mmol) and the (S)-(–)-methyloxirane (0.0071 g, 0.12 mmol) was added. The reaction was heated in a sealed tube to 90° C. and monitored by LC/MS. After heating for 6 hrs the reaction was purified without workup by prep HPLC on a C-18 column eluting water: acetonitrile gradient buffered pH 10 to give the title compound as a white amorphous solid (0.018 g, 40%). The product was isolated as a single enantiomer. LCMS calculated for $C_{23}H_{30}N_7O_2(M+H)^+$: m/z=436.2. found: 436.3. $^1$H NMR (300 MHz, DMSO-$d_6$) δ 8.09 (s, 1H), 7.21 (s, 1H), 6.22 (q, J=7.1 Hz, 1H), 4.34 (d, J=4.5 Hz, 1H), 4.09-3.83 (m, 3H), 3.60 (s, 3H), 3.58-3.51 (m, 1H), 3.12-2.95 (m, 2H), 2.55 (s, 3H), 2.33 (s, 3H), 2.27 (d, J=5.9 Hz, 2H), 1.71 (d, J=7.1 Hz, 3H), 1.00 (d, J=6.2 Hz, 3H).

Example 316

4-[1-(4-amino-3-methyl-1H-pyrazolo[3,4-d]pyrimidin-1-yl)ethyl]-6-chloro-3-ethoxy-2-[6-(1-hydroxy-1-methylethyl)pyridin-3-yl]benzonitrile

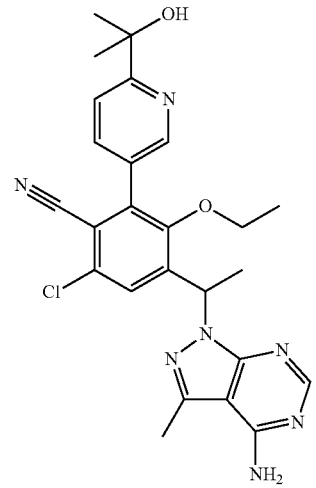 [SMILES: CCOc1c(C(C)n2nc(C)c3c(N)ncnc32)cc(Cl)c(C#N)c1-c1ccc(C(C)(C)O)nc1]

Step 1.
5-bromo-N-methoxy-N-methylpyridine-2-carboxamide

N,O-dimethylhydroxylamine hydrochloride (500 mg, 5 mmol) was added to a mixture of N,N,N',N'-tetramethyl-O-(7-azabenzotriazol-1-yl)uronium hexafluorophosphate (1400 mg, 3.7 mmol), N,N-diisopropylethylamine (1000 μL, 7 mmol) and 5-bromopyridine-2-carboxylic acid (500 mg, 2 mmol, Frontier Scientific catalog# B1704) in N,N-dimethylformamide (10 mL). The reaction mixture was stirred overnight at room temperature and was complete by LC/MS. The reaction was partitioned between water and EtOAc. The combined organic layer was washed with brine, dried over MgSO$_4$, filtered and concentrated to give the crude product. The product was purified on by FCC on silica gel eluting a hexane: EtOAc (0-30%) gradient to give 5-bromo-N-methoxy-N-methylpyridine-2-carboxamide clear oil (0.50 g, 60%). LCMS calculated for $C_8H_{10}BrN_2O_2(M+H)^+$: m/z=244.9, 246.9. found: 244.9, 246.9.

Step 2. 1-(5-bromopyridin-2-yl)ethanone

Methylmagnesium chloride 3.0 M in THF (0.5 mL) was added dropwise to a mixture of 5-bromo-N-methoxy-N-methylpyridine-2-carboxamide (200 mg, 0.8 mmol) in tetrahydrofuran (10 mL) at 0° C. After stirring for 1 hr at room temperature, the reaction was quenched with 1 N NH$_4$Cl and was extracted with EtOAc. The combined organic layer was washed with brine and dried over MgSO$_4$, concentrated to give the crude product 1-(5-bromopyridin-2-yl)ethanone (0.15 g, 90%). LCMS calculated for $C_7H_7BrNO$ (M+H)$^+$: m/z=199.9, 201.9. found: 199.9, 201.9.

Step 3. 2-(5-bromopyridin-2-yl)propan-2-ol

Methylmagnesium chloride 3.0 M in THF (0.3 mL) was added dropwise to a mixture of 1-(5-bromopyridin-2-yl)ethanone (100 mg, 0.5 mmol) in tetrahydrofuran (10 mL) at 0° C. After stirring for 1 h at room temperature, the reaction was quenched with 1 N NH$_4$Cl and was extracted with EtOAc. The combined organic layer was washed with brine and dried over MgSO$_4$, concentrated to give crude 2-(5-bromopyridin-2-yl)propan-2-ol (0.1 g, 100%). LCMS calculated for $C_8H_{11}BrNO$ (M+H)$^+$: m/z=215.9, 217.9. found: 215.8, 217.8.

Step 4. [6-(1-hydroxy-1-methylethyl)pyridin-3-yl]boronic acid

A mixture of 2-(5-bromopyridin-2-yl)propan-2-ol (70 mg, 0.3 mmol), 4,4,5,5,4',4',5',5'-octamethyl-[2,2']bi[[1,3,2]dioxaborolanyl] (90. mg, 0.36 mmol), [1,1'-bis(diphenylphosphino)ferrocene]dichloropalladium(II), complex with dichloromethane (1:1) (10 mg, 0.01 mmol), and potassium acetate (100 mg, 1 mmol) in 1,4-dioxane (5 mL) was heated at 120° C. overnight. The reaction was complete by LC/MS, was concentrated in vacuo to give crude [6-(1-hydroxy-1-methylethyl)pyridin-3-yl]boronic acid. LCMS calculated for $C_8H_{13}BNO_3$ (M+H)$^+$: m/z=182.1. found: 182.1.

Step 5. 4-[1-(4-amino-3-methyl-1H-pyrazolo[3,4-d]pyrimidin-1-yl)ethyl]-6-chloro-3-ethoxy-2-[6-(1-hydroxy-1-methylethyl)pyridin-3-yl]benzonitrile bis(2,2,2-trifluoroacetate)

Sodium carbonate (10 mg, 0.09 mmol) in water (0.5 mL) was added to a mixture of 4-[1-(4-amino-3-methyl-1H-pyrazolo[3,4-d]pyrimidin-1-yl)ethyl]-2-bromo-6-chloro-3-ethoxybenzonitrile (20 mg, 0.04 mmol, racemic intermediate from Example 43, Step 5) and [6-(1-hydroxy-1-methylethyl)pyridin-3-yl]boronic acid (12 mg, 0.069 mmol, Example 306, Step 4) in acetonitrile (1 mL). The reaction mixture was degassed with $N_2$ and [1,1'-bis(diphenylphosphino)ferrocene]dichloropalladium(II), complex with dichloromethane (1:1) (2 mg, 0.002 mmol) was added. The reaction was degassed with $N_2$ again and heated to 100° C. for 1 h. The reaction was allowed to cool to room temperature and was purified without workup by prep HPLC on a C-18 column eluting a water; acetonitrile gradient buffered with TFA to give the title compound as white amorphous solid. The product was isolated as a racemic mixture. LCMS calculated for $C_{25}H_{27}ClN_7O_2$ (M+H)$^+$: m/z=492.1. found: 492.1. $^1$H NMR (500 MHz, DMSO-$d_6$) δ 8.60 (d, J=2.0 Hz, 1H), 8.22 (s, 1H), 7.96 (dd, J=8.2, 2.3 Hz, 1H), 7.80 (d, J=8.3 Hz, 1H), 7.73 (s, 1H), 6.36 (q, J=7.0 Hz, 1H), 3.52-3.40 (m, 1H), 3.40-3.30 (m, 1H), 2.59 (s, 3H), 1.80 (d, J=7.0 Hz, 3H), 1.48 (d, J=2.3 Hz, 6H), 0.88 (t, J=7.0 Hz, 3H).

Example 317

4-[1-(4-amino-3-methyl-1H-pyrazolo[3,4-d]pyrimidin-1-yl)ethyl]-3-methoxy-6-methyl-2-[5-(methylsulfonyl)pyridin-3-yl]benzonitrile

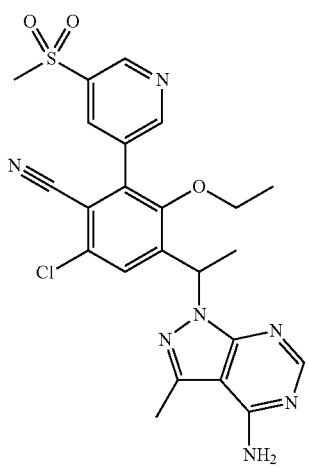 [SMILES: CCOc1c(C(C)n2nc(C)c3c(N)ncnc32)cc(Cl)c(C#N)c1-c1cncc(S(C)(=O)=O)c1]

Using procedures analogous to Example 314, but using methyl iodide instead of ethyl iodide in Step 3,4-acetyl-2-iodo-3-methoxy-6-methylbenzonitrile was prepared and using 3-(methylsulfonyl)-5-(4,4,5,5-tetramethyl-1,3,2-dioxaborolan-2-yl)pyridine instead of {6-[(dimethylamino)carbonyl]pyridin-3-yl}boronic acid (racemic intermediate from Step 4), the title compound 4-[1-(4-amino-3-methyl-1H-pyrazolo[3,4-d]pyrimidin-1-yl)ethyl]-3-methoxy-6-methyl-2-[5-(methylsulfonyl)pyridin-3-yl]benzonitrile was prepared. The product was isolated as a racemic mixture. LCMS calculated for $C_{23}H_{24}N_7O_3S$ (M+H)$^+$: m/z=478.1. found: 478.2. $^1$H NMR (300 MHz, CD$_3$OD) δ 9.24 (d, J=2.2 Hz, 1H), 9.03 (d, J=2.0 Hz, 1H), 8.59 (t, J=2.1 Hz, 1H), 8.31 (s, 1H), 7.68 (s, 1H), 6.56 (q, J=7.1 Hz, 1H), 3.38 (s, 3H), 3.31 (s, 3H), 2.72 (s, 3H), 2.59 (s, 3H), 1.98 (d, J=7.1 Hz, 3H).

Example 318

4-[1-(4-amino-3-methyl-1H-pyrazolo[3,4-d]pyrimidin-1-yl)ethyl]-6-chloro-3-ethoxy-2-pyrrolidin-1-ylbenzonitrile

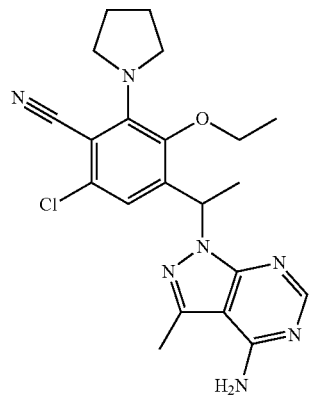 [SMILES: CCOc1c(C(C)n2nc(C)c3c(N)ncnc32)cc(Cl)c(C#N)c1N1CCCC1]

Step 1. 4-acetyl-6-chloro-3-ethoxy-2-iodobenzonitrile

The 4-acetyl-6-chloro-3-ethoxy-2-iodobenzonitrile was prepared by analogous methods described in Example 43, Step 1 and Step 2, but using N-iodosuccinimide LCMS calculated for $C_{11}H_{10}ClINO_2$(M+H)$^+$: m/z=349.9. found: 350.0.

Step 2. 4-acetyl-6-chloro-3-ethoxy-2-pyrrolidin-1-ylbenzonitrile

The 4-acetyl-6-chloro-3-ethoxy-2-iodobenzonitrile (0.20 g, 0.57 mmol) was combined with pyrrolidine (0.052 mL, 0.63 mmol) in N,N-dimethylformamide (2.0 mL) with cesium carbonate (0.19 g, 0.57 mmol) and heated to 120° C. in a sealed tube. After heating for 18 hrs the reaction was allowed to cool, taken up in ethyl acetate, washed with water, brine, dried over magnesium sulfate and concentrated to give the crude product as a dark oil. The product was purified by FCC on silica gel eluting with hexane: ethyl acetate gradient to give 4-acetyl-6-chloro-3-ethoxy-2-pyrrolidin-1-ylbenzonitrile as an oil (0.045 g, 27%). LCMS calculated for $C_{15}H_{18}ClN_2O_2(M+H)^+$: m/z=293.1. found 293.1.

Step 3. 6-chloro-3-ethoxy-4-(1-hydroxyethyl)-2-pyrrolidin-1-ylbenzonitrile

The 4-acetyl-6-chloro-3-ethoxy-2-pyrrolidin-1-ylbenzonitrile (0.045 g, 0.15 mmol) was dissolved in methanol (3 mL) and cooled in an ice bath. The sodium tetrahydroborate (0.0058 g, 0.15 mmol) was added and the reaction was monitored by LC/MS. After stirring for 1 h, the reaction was taken up in ethyl acetate and washed with water, sodium bicarbonate, brine and dried over magnesium sulfate to give crude 6-chloro-3-ethoxy-4-(1-hydroxyethyl)-2-pyrrolidin-1-ylbenzonitrile as a clear oil (0.045 g, 100%). LCMS calculated for $C_{15}H_{20}ClN_2O_2(M+H)^+$: m/z=295.1. found 295.1.

Step 4. 6-chloro-4-(1-chloroethyl)-3-ethoxy-2-pyrrolidin-1-ylbenzonitrile

The 6-chloro-3-ethoxy-4-(1-hydroxyethyl)-2-pyrrolidin-1-ylbenzonitrile (0.045 g, 0.15 mmol) was taken up in methylene chloride (3.0 mL) and N,N-dimethylformamide (0.002 mL, 0.03 mmol) and cooled in an ice bath. The thionyl chloride (0.017 mL, 0.23 mmol) was added and the reaction was monitored by LC/MS. After stirring for 2 hrs the reaction was complete. The reaction was then taken up in ethyl acetate, washed with sodium bicarbonate, brine, dried over magnesium sulfate and concentrated to give crude 6-chloro-4-(1-chloroethyl)-3-ethoxy-2-pyrrolidin-1-ylbenzonitrile as a yellow oil (0.048 g, 100%). LCMS calculated for $C_{15}H_{19}Cl_2N_2O$ $(M+H)^+$: m/z=313.1. found 313.1.

Step 5. 4-[1-(4-amino-3-methyl-1H-pyrazolo[3,4-d]pyrimidin-1-yl)ethyl]-6-chloro-3-ethoxy-2-pyrrolidin-1-ylbenzonitrile The 6-chloro-4-(1-chloroethyl)-3-ethoxy-2-pyrrolidin-1-ylbenzonitrile (0.048 g, 0.15 mmol, racemic mixture) was combined with 3-methyl-1H-pyrazolo[3,4-d]pyrimidin-4-amine (0.034 g, 0.23 mmol) and cesium carbonate (0.10 g, 0.31 mmol) in N,N-dimethylformamide (3.0 mL) and heated in an oil bath to 85° C. After heating for 18 hrs the reaction was complete. The crude reaction was purified with out work up by prep HPLC on a C-18 column eluting water: acetonitrile gradient buffered pH 10 to give the title compound as a white amorphous solid (0.012 g, 18%). The product was isolated as a racemic mixture. LCMS calculated for $C_{21}H_{25}ClN_7O$ $(M+H)^+$: m/z=426.1. found 426.1. $^1H$ NMR (300 MHz, DMSO-$d_6$) δ 8.11 (s, 1H), 6.91 (s, 1H), 6.25 (q, J=7.1 Hz, 1H), 3.71 (dp, J=15.7, 8.1, 7.2 Hz, 4H), 3.49-3.35 (m, 2H), 2.55 (s, 3H), 2.00-1.76 (m, 4H), 1.70 (d, J=7.1 Hz, 3H), 1.34 (t, J=7.0 Hz, 3H).

Example 319

4-[1-(4-amino-3-methyl-1H-pyrazolo[3,4-d]pyrimidin-1-yl)ethyl]-6-chloro-3-ethoxy-2-(3-methoxyazetidin-1-yl)benzonitrile

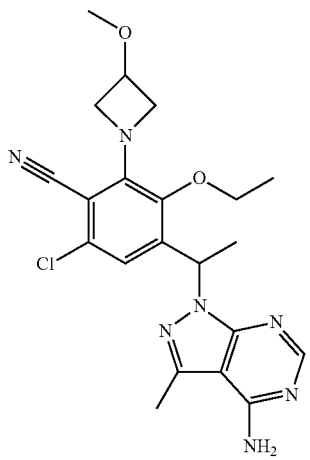 [SMILES: CCOc1c(C(C)n2nc(C)c3c(N)ncnc32)cc(Cl)c(C#N)c1N1CC(OC)C1]

Step 1. 4-acetyl-6-chloro-3-ethoxy-2-(3-methoxyazetidin-1-yl)benzonitrile

To a mixture of 4-acetyl-6-chloro-3-ethoxy-2-iodobenzonitrile (50 mg, 0.1 mmol, Example 318, Step 1), 3-methoxyazetidine hydrochloride (21 mg, 0.17 mmol Chem-Impex catalog#20140) and cesium carbonate (70. mg, 0.21 mmol) in 1,4-dioxane (4 mL) was added (9,9-dimethyl-9H-xanthene-4,5-diyl)bis(diphenylphosphine) (40 mg, 0.07 mmol) and tris(dibenzylideneacetone)dipalladium (0) (60 mg, 0.07 mmol). The reaction mixture was degassed with $N_2$. The reaction was heated at 80° C. for 2 hrs and was monitored by LC/MS. The reaction was allowed to cool to room temperature, was diluted with water and extracted with EtOAc. The combined organic layers were washed with brine, dried over $MgSO_4$, filtered and concentrated to give the crude product. The product was purified by FCC on silica gel eluting (hexanes: EtOAc 0-70%) gradient to give to 4-acetyl-6-chloro-3-ethoxy-2-(3-methoxyazetidin-1-yl)benzonitrile as clear oil (0.030 g, 70%). LCMS calculated for $C_{15}H_{18}ClN_2O_3(M+H)^+$: m/z=309.1. found: 309.1.

Step 2. 6-chloro-3-ethoxy-4-(1-hydroxyethyl)-2-(3-methoxyazetidin-1-yl)benzonitrile 4-Acetyl-6-chloro-3-ethoxy-2-(3-methoxyazetidin-1-yl)benzonitrile (30 mg, 0.1 mmol was dissolved in methanol (5 mL) cooled to 0° C. and sodium tetrahydroborate (5.5 mg, 0.14 mmol) was added. Reaction was stirred for 1 h at 0° C. The reaction was partitioned between EtOAc and water. The combined organic layer was washed with water and saturated $NaHCO_3$, brine, dried over $Na_2SO_4$, filtered and concentrated to give crude 6-chloro-3-ethoxy-4-(1-hydroxyethyl)-2-(3-methoxyazetidin-1-yl)benzonitrile (0.030 g, 100%). LCMS calculated for $C_{15}H_{20}ClN_2O_3(M+H)^+$: m/z=311.1. found: 311.1.

Step 3. 6-chloro-4-(1-chloroethyl)-3-ethoxy-2-(3-methoxyazetidin-1-yl)benzonitrile 6-chloro-3-ethoxy-4-(1-hydroxyethyl)-2-(3-methoxyazetidin-1-yl)benzonitrile (30 mg, 0.1 mmol) (racemic mixture)

was dissolved in methylene chloride (5 mL) and N,N-dimethylformamide (100 μL, 1 mmol). Thionyl chloride (18 μL, 0.24 mmol) was added dropwise at room temperature and the reaction was stirred for 2 hrs. The reaction was diluted with EtOAc, washed with water and saturated NaHCO$_3$, brine, dried over Na$_2$SO$_4$, filtered and concentrated to give the crude 6-chloro-4-(1-chloroethyl)-3-ethoxy-2-(3-methoxyazetidin-1-yl)benzonitrile (0.030 g, 100%). LCMS calculated for $C_{15}H_{19}Cl_2N_2O_3(M+H)^+$: m/z=329.1. found: 329.1.

Step 4. 4-[1-(4-amino-3-methyl-1H-pyrazolo[3,4-d]pyrimidin-1-yl)ethyl]-6-chloro-3-ethoxy-2-(3-methoxyazetidin-1-yl)benzonitrile Cesium carbonate (50 mg, 0.2 mmol) was added to a mixture of 3-methyl-1H-pyrazolo[3,4-d]pyrimidin-4-amine (16 mg, 0.10 mmol) and 6-chloro-4-(1-chloroethyl)-3-ethoxy-2-(3-methoxyazetidin-1-yl)benzonitrile (30 mg, 0.09 mmol) in N,N-dimethylformamide (3 mL, 40 mmol) and the reaction was stirred at 80° C. overnight. The mixture was diluted with EtOAc, washed with water, brine, dried over Na$_2$SO$_4$, filtered and concentrated the crude product. The product was purified was purified by prep HPLC on a C-18 column eluting water: acetonitrile gradient buffered pH 10 to give the title compound as a white amorphous solid (0.007 g, 20%). The product was isolated as a racemic mixture. LCMS calculated for $C_{21}H_{25}ClN_7O_2(M+H)^+$: m/z=442.1. found: 442.1. $^1$H NMR (400 MHz, DMSO-d$_6$) δ 8.11 (s, 1H), 6.80 (s, 1H), 6.18 (d, J=7.1 Hz, 1H), 4.58-4.44 (m, 2H), 4.18 (m, 1H), 4.13-4.01 (m, 2H), 3.81-3.62 (m, 2H), 3.23 (s, 3H), 2.55 (s, 3H), 1.69 (d, J=7.1 Hz, 3H), 1.35 (t, J=7.0 Hz, 3H).

Example 320

4-[1-(4-amino-3-methyl-1H-pyrazolo[3,4-d]pyrimidin-1-yl)ethyl]-3-ethoxy-2-(1-isopropylazetidin-3-yl)-6-methylbenzonitrile

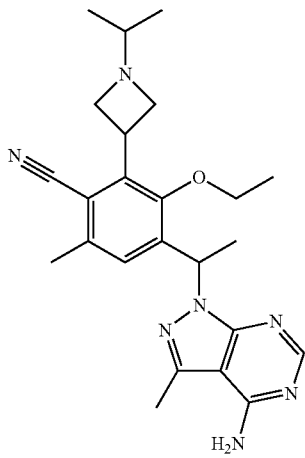 [SMILES: CCOc1c(C(C)n2nc(C)c3c(N)ncnc32)cc(C)c(C#N)c1C1CN(C(C)C)C1]

Step 1: 4-[1-(4-amino-3-methyl-1H-pyrazolo[3,4-d]pyrimidin-1-yl)ethyl]-2-azetidin-3-yl-3-ethoxy-6-methylbenzonitrile bis(trifluoroacetate)

Using methods described in Example 315 but using ethyl iodide in Step 3, instead of methyl iodide, the intermediate 4-[1-(4-amino-3-methyl-1H-pyrazolo[3,4-d]pyrimidin-1-yl)ethyl]-2-azetidin-3-yl-3-ethoxy-6-methylbenzonitrile bis(trifluoroacetate) was prepared. LCMS calculated for $C_{21}H_{26}N_7O$ (M+H)$^+$: m/z=392.2. found: 392.2.

Step 2. 4-[1-(4-amino-3-methyl-1H-pyrazolo[3,4-d]pyrimidin-1-yl)ethyl]-3-ethoxy-2-(1-isopropylazetidin-3-yl)-6-methylbenzonitrile To a mixture of 4-[1-(4-amino-3-methyl-1H-pyrazolo[3,4-d]pyrimidin-1-yl)ethyl]-2-azetidin-3-yl-3-ethoxy-6-methylbenzonitrile (70 mg, 0.2 mmol) in methanol (50 mL) was added acetone (0.1 mL, 2 mmol) and sodium cyanoborohydride (17 mg, 0.27 mmol). The reaction was stirred at room temperature for 1 h, and was complete by LC/MS. The reaction was quenched with water and was extracted with EtOAc. The combined organic layer was washed with brine, dried over MgSO$_4$, filtered and concentrated to give the crude product. The product was purified by prep HPLC on a C-18 column eluting water: acetonitrile gradient buffered pH 10 to give the title compound as a white amorphous solid (0.030 g, 40%). The product was isolated as a racemic mixture. LCMS calculated for $C_{24}H_{32}N_7O$ (M+H)$^+$: m/z=434.2. found: 434.3. $^1$H NMR (300 MHz, CD$_3$OD) δ 8.17 (s, 1H), 7.35 (s, 1H), 6.37 (q, J=7.1 Hz, 1H), 4.17-3.98 (m, 4H), 3.90-3.71 (m, 3H), 2.65 (s, 3H), 2.46 (s, 4H), 1.84 (d, J=7.1 Hz, 3H), 1.42 (t, J=7.0 Hz, 3H), 1.03 (dd, J=6.2, 1.4 Hz, 6H).

Example 321

4-[1-(4-amino-3-methyl-1H-pyrazolo[3,4-d]pyrimidin-1-yl)ethyl]-3-ethoxy-2-[1-(2-hydroxy-2-methylpropyl)azetidin-3-yl]-6-methylbenzonitrile

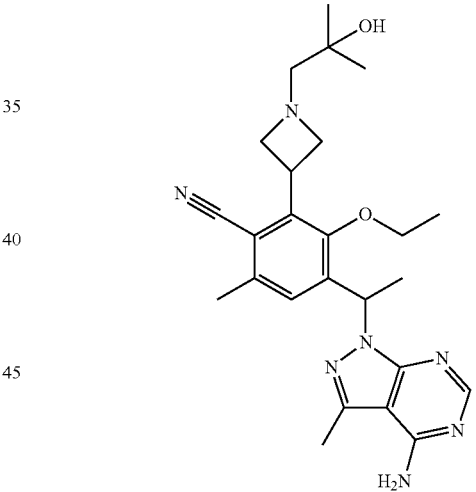

The 4-[1-(4-amino-3-methyl-1H-pyrazolo[3,4-d]pyrimidin-1-yl)ethyl]-2-azetidin-3-yl-3-ethoxy-6-methylbenzonitrile (0.055 g, 0.14 mmol, chiral intermediate from Example 320, Step 1) was combined with tetrahydrofuran (22 mL), DIPEA (0.049 mL, 0.28 mmol) and oxirane, 2,2-dimethyl- (0.018 mL, 0.21 mmol) at room temperature. The reaction was heated to 95° C. and allowed to stir overnight. The reaction was allowed to cool to room temperature and was purified without workup by prep HPLC on a C-18 column eluting water: acetonitrile gradient buffered pH 10 to give the title compound as a white amorphous solid (0.035 g, 50%). The product was isolated as a single enantiomer. LCMS calculated for $C_{25}H_{34}N_7O_2(M+H)^+$: m/z=464.3. found: 464.3. $^1$H NMR (300 MHz, DMSO-d$_6$) δ 8.09 (s, 1H), 7.23 (s, 1H), 6.21 (q, J=6.8 Hz, 1H), 4.00 (m, 4H), 3.81-3.54 (m, 2H), 3.15 (m, 2H), 2.53 (s, 3H), 2.33 (s, 3H), 2.27 (bs, 2H), 1.70 (d, J=7.1 Hz, 3H), 1.30 (t, J=6.9 Hz, 3H), 1.04 (s, 6H).

Example 322

4-[1-(4-amino-3-methyl-1H-pyrazolo[3,4-d]pyrimidin-1-yl)ethyl]-3-ethoxy-2-[1-(2-hydroxy-2-methylpropanoyl)azetidin-3-yl]-6-methylbenzonitrile

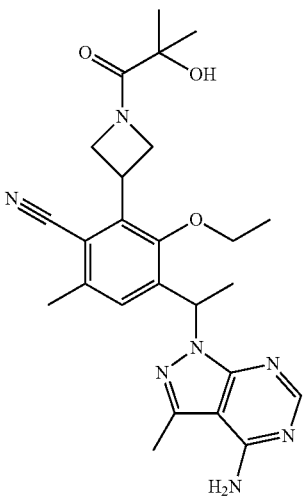 [SMILES: CCOc1c(C(C)n2nc(C)c3c(N)ncnc32)cc(C)c(C#N)c1C1CN(C(=O)C(C)(C)O)C1]

The 4-[1-(4-amino-3-methyl-1H-pyrazolo[3,4-d]pyrimidin-1-yl)ethyl]-2-azetidin-3-yl-3-ethoxy-6-methylbenzonitrile (0.075 g, 0.10 mmol, chiral intermediate from Example 320, Step 1) was dissolved in N,N-dimethylformamide (3.0 mL) and DIPEA (0.089 mL, 0.51 mmol) and the propanoic acid, 2-hydroxy-2-methyl- (0.013 g, 0.12 mmol) and N,N,N',N'-tetramethyl-O-(7-azabenzotriazol-1-yl)uronium hexafluorophosphate (0.058 g, 0.15 mmol) were added. The reaction was stirred at room temperature for 18 hrs and was complete by LC/MS. The product was purified without workup by prep HPLC on a C-18 column eluting water: acetonitrile gradient buffered to pH 10 to give the title compound as a white amorphous solid (0.025 g, 51%). The product was isolated as a single enantiomer. LCMS calculated for $C_{25}H_{32}N_7O_3(M+H)^+$: m/z=478.2. found: 478.2. $^1$H NMR (300 MHz, DMSO-$d_6$) δ 8.10 (s, 1H), 7.29 (s, 1H), 6.24 (q, J=6.8 Hz, 1H), 5.07 (s, 1H), 4.90-4.75 (m, 1H), 4.73-4.58 (m, 1H), 4.39 (p, J=8.5 Hz, 1H), 4.30-4.05 (m, 2H), 3.75 (d, J=7.1 Hz, 2H), 2.54 (s, 3H), 2.38 (s, 3H), 1.72 (d, J=6.9 Hz, 3H), 1.35 (t, J=6.1 Hz, 3H), 1.26 (s, 3H), 1.23 (s, 3H).

Compounds Synthesized

Experimental procedures for compound Examples 326-344 are summarized in Tables 7 and 8.

TABLE 7

| Ex. No. | Name | $R^2$ | $R^4$ | $R^5$ | $R^6$ | Salt | Proc.[1] |
|---|---|---|---|---|---|---|---|
| 326 | 4-[1-(4-amino-3-methyl-1H-pyrazolo[3,4-d]pyrimidin-1-yl)ethyl]-3-ethoxy-2-{1-[(2S)-2-hydroxypropyl]azetidin-3-yl}-6-methylbenzonitrile[3] | Et | CN | $CH_3$ | -CH$_2$-CH(OH)-CH$_3$ | | 321 |
| 327 | 4-[-1-(4-amino-3-methyl-1H-pyrazolo[3,4-d]pyrimidin-1-yl)ethyl]-3-ethoxy-2-[1-(2-hydroxyethyl)azetidin-3-yl]-6-methylbenzonitrile[3] | Et | CN | $CH_3$ | -CH$_2$-CH$_2$-OH | | 320 |
| 328 | 4-[-1-(4-amino-3-methyl-1H-pyrazolo[3,4-d]pyrimidin-1-yl)ethyl]-2-[1-(2-hydroxy-2-methylpropyl)azetidin-3-yl]-3-methoxy-6-methylbenzonitrile[3] | $CH_3$ | CN | $CH_3$ | -CH$_2$-C(CH$_3$)$_2$-OH | | 315 |

[1]Synthesized according to the experimental procedure of compound listed;
[2]Compound isolated as a racemic mixture;
[3]Compound isolated as a single enantiomer.

TABLE 8

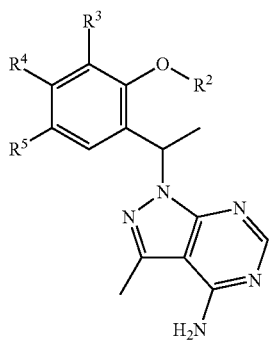

| Ex. No. | Name | R² | R⁴ | R⁵ | R³ | Salt | Proc.¹ |
|---|---|---|---|---|---|---|---|
| 329 | 4[1-(4-amino-3-methyl-1H-pyrazolo[3,4-d]pyrimidin-1-yl)ethyl]-6-chloro-3-ethoxy-2-pyrimidin-5-ylbenzonitrile² | Et | CN | Cl | 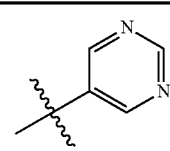 | TFA | 43 |
| 330 | 5-{3[1-(4-amino-3-methyl-1H-pyrazolo[3,4-d]pyrimidin-1-yl)ethyl]-5-chloro-6-cyano-2-ethoxyphenyl}nicotinonitrile³ | Et | CN | Cl | 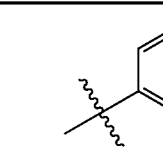 | TFA | 43 |
| 331 | 5-{3-[1-(4-amino-3-methyl-1H-pyrazolo[3,4-d]pyrimidin-1-yl)ethyl]-5-chloro-6-cyano-2-ethoxyphenyl}-N,N-dimethylnicotinamide³ | Et | CN | Cl | 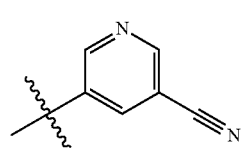 [SMILES: *c1cncc(C#N)c1] | | 43 |
| 332 | 4-[1-(4-amino-3-methyl-1H-pyrazolo[3,4-d]pyrimidin-1-yl)ethyl]-6-chloro-3-methoxy-2-[5-(methylsulfonyl)pyridin-3-yl]benzonitrile³ | Me | CN | Cl | 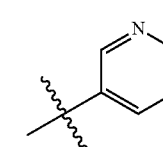 | | 313 |
| 333 | 5-{3-[1-(4-amino-3-methyl-1H-pyrazolo[3,4-d]pyrimidin-1-yl)ethyl]-5-chloro-6-cyano-2-ethoxyphenyl}-N-methylpyridine-2-carboxamide² | Et | CN | Cl | 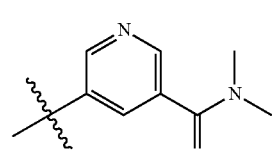 | | 43 |
| 334 | 4-{3-[1-(4-amino-3-methyl-1H-pyrazolo[3,4-d]pyrimidin-1-yl)ethyl]-5-chloro-6-cyano-2-ethoxyphenyl}-N,N-dimethylpyridine-2-carboxamide³ | Et | CN | Cl | 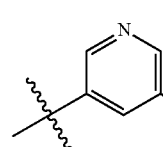 | | 43 |
| 335 | 4-[1-(4-amino-3-methyl-1H-pyrazolo[3,4-d]pyrimidin-1-yl)ethyl]-3-ethoxy-6-methyl-2-[5-(methylsulfonyl)pyridin-3-yl]benzonitrile³ | Et | CN | CH₃ | 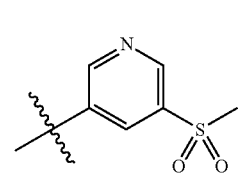 [SMILES: *c1cncc(S(C)(=O)=O)c1] | | 314 |

TABLE 8-continued

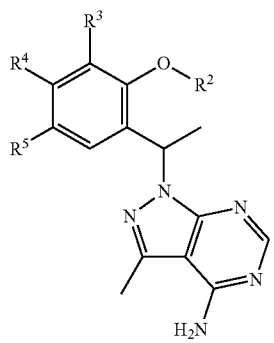

| Ex. No. | Name | R² | R⁴ | R⁵ | R³ | Salt | Proc.¹ |
|---|---|---|---|---|---|---|---|
| 336 | 4-[1-(4-amino-3-methyl-1H-pyrazolo[3,4-d]pyrimidin-1-yl)ethyl]-6-chloro-3-ethoxy-2-[6-(2-methyl-2H-tetrazol-5-yl)pyridin-3-yl]benzonitrile² | Et | CN | Cl | 5-(2-methyl-2H-tetrazol-5-yl)pyridin-2-yl | | 43 |
| 337 | 4-[1-(4-amino-3-methyl-1H-pyrazolo[3,4-d]pyrimidin-1-yl)ethyl]-6-chloro-3-ethoxy-2-[6-(2-methyl-2H-1,2,3-triazol-4-yl)pyridin-3-yl]benzonitrile² | Et | CN | Cl | 5-(2-methyl-2H-1,2,3-triazol-4-yl)pyridin-2-yl | | 43 |
| 338 | 4-[1-(4-amino-3-methyl-1H-pyrazolo[3,4-d]pyrimidin-1-yl)ethyl]-6-chloro-3-ethoxy-2-[6-(5-methyl-1,3,4-oxadiazol-2-yl)pyridin-3-yl]benzonitrile² | Et | CN | Cl | 5-(5-methyl-1,3,4-oxadiazol-2-yl)pyridin-2-yl | | 43 |
| 339 | 4-[1-(4-amino-3-methyl-1H-pyrazolo[3,4-d]pyrimidin-1-yl)ethyl]-6-chloro-3-ethoxy-2-[5-(1,3-oxazol-2-yl)pyridin-3-yl]benzonitrile² | Et | CN | Cl | 5-(1,3-oxazol-2-yl)pyridin-3-yl | | 43 |
| 340 | 4-{3-[1-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide³ | Et | CN | CH₃ | N,N-dimethylpyridine-2-carboxamid-4-yl | | 314 |
| 341 | 4-[1-(4-amino-3-methyl-1H-pyrazolo[3,4-d]pyrimidin-1-yl)ethyl]-6-chloro-3-ethoxy-2-[3-(methoxymethyl)azetidin-1-yl]benzonitrile² | Et | CN | Cl | 3-(methoxymethyl)azetidin-1-yl | | 321 |

TABLE 8-continued

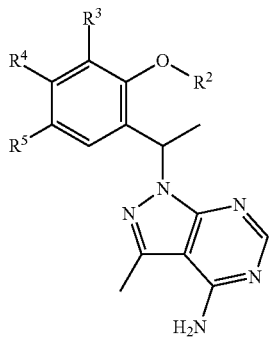

| Ex. No. | Name | R² | R⁴ | R⁵ | R³ | Salt | Proc.[1] |
|---|---|---|---|---|---|---|---|
| 342 | 1-{3-[1-(4-amino-3-methyl-1H-pyrazolo[3,4-d]pyrimidin-1-yl)ethyl]-5-chloro-6-cyano-2-ethoxyphenyl}azetidine-3-carbonitrile[2] | Et | CN | Cl | azetidine-CN | | 319 |
| 343 | 4-[1-(4-amino-3-methyl-1H-pyrazolo[3,4-d]pyrimidin-1-yl)ethyl]-3-ethoxy-6-methyl-2-(1-methyl-1H-pyrazol-4-yl)benzonitrile[2] | Et | CN | CH₃ | 1-methylpyrazol-4-yl | | 314 |
| 344 | 5-{3-[1-(4-amino-3-methyl-1H-pyrazolo[3,4-d]pyrimidin-1-yl)ethyl]-6-cyano-2-methoxy-5-methylphenyl}-N,N-dimethylpyridine-2-carboxamide[3] | Me | CN | CH₃ | N,N-dimethylpyridine-2-carboxamide | | 317 |

[1]Synthesized according to the experimental procedure of compound listed;
[2]Compound isolated as a racemic mixture;
[3]Compound isolated as a single enantiomer.

Analytical Data

¹H NMR data (Varian Inova 500 spectrometer, a Mercury 400 spectrometer, or a Varian (or Mercury) 300 spectrometer) and LCMS mass spectral data (MS) for the compounds of Examples 326-344 is provided in Table 9

TABLE 9

| Ex. No. | MS [M + H]⁺ | Solvent | MHz | ¹H NMR Spectra |
|---|---|---|---|---|
| 329 | 435.1 | DMSO-d₆ | 500 | ¹H NMR (500 MHz, DMSO) δ 9.33 (s, 1H), 9.04 (s, 2H), 8.18 (s, 1H), 7.81 (s, 1H), 6.36 (q, J = 7.0 Hz, 1H), 3.56 (td, J = 14.1, 7.0 Hz, 1H), 3.39 (dq, J = 14.1, 6.9 Hz, 1H), 2.59 (s, 3H), 1.81 (d, J = 7.0 Hz, 3H), 0.94 (t, J = 7.0 Hz, 3H). |
| 330 | 459.1 | DMSO-d₆ | 500 | ¹H NMR (500 MHz, DMSO) δ 9.18 (d, J = 1.9 Hz, 1H), 9.03 (d, J = 2.0 Hz, 1H), 8.63 (t, J = 2.0 Hz, 1H), 8.33 (s, 1H), 7.82 (s, 1H), 6.38 (q, J = 7.0 Hz, 1H), 3.56-3.44 (m, 1H), 3.43-3.33 (m, 1H), 2.61 (s, 3H), 1.83 (d, J = 7.0 Hz, 3H), 0.92 (t, J = 7.0 Hz, 3H). |
| 331 | 505.2 | DMSO-d₆ | 300 | ¹H NMR (300 MHz, dmso) δ 8.77 (d, J = 2.2 Hz, 1H), 8.73 (d, J = 1.9 Hz, 1H), 8.10 (d, J = 3.9 Hz, 2H), 7.74 (s, 1H), 6.33 (d, J = 7.4 Hz, 1H), 3.52 (m, 1H), 3.39 (m, 1H), 3.00 (s, 3H), 2.94 (s, 3H), 2.56 (s, 3H), 1.79 (d, J = 7.0 Hz, 3H), 0.91 (t, J = 7.0 Hz, 3H). |
| 332 | 498.1 | DMSO-d₆ | 500 | ¹H NMR (500 MHz, DMSO) δ 9.21 (d, J = 2.2 Hz, 1H), 9.11 (d, J = 1.9 Hz, 1H), 8.58 (t, J = 2.0 Hz, 1H), 8.12 (s, 1H), 7.77 (s, 1H), 6.34 (q, J = 7.0 Hz, 1H), 3.37 (s, 3H), 3.30 (s, 3H), 2.58 (s, 3H), 1.81 (d, J = 7.1 Hz, 3H). |

TABLE 9-continued

| Ex. No. | MS [M + H]+ | Solvent | MHz | 1H NMR Spectra |
|---|---|---|---|---|
| 333 | 491.1 | CD3OD | 300 | 1H NMR (300 MHz, CD3OD) δ 8.80 (d, J = 1.9 Hz, 1H), 8.27 (d, J = 8.1 Hz, 1H), 8.19 (d, J = 10.3 Hz, 2H), 7.80 (s, 1H), 6.47 (q, J = 7.2 Hz, 1H), 3.64-3.38 (m, 2H), 3.04 (s, 3H), 2.68 (s, 3H), 1.93 (d, J = 7.1 Hz, 3H), 1.01 (t, J = 7.0 Hz, 3H). |
| 334 | 505.2 | CD3OD | 300 | 1H NMR (300 MHz, CD3OD) δ 8.80 (d, J = 5.0 Hz, 1H), 8.17 (s, 1H), 7.80 (d, J = 3.4 Hz, 2H), 7.71 (d, J = 4.9 Hz, 1H), 6.47 (m, J = 7.1 Hz, 1H), 3.69-3.42 (m, 2H), 3.19 (s, 3H), 3.08 (s, 3H), 2.67 (s, 3H), 1.92 (d, J = 7.1 Hz, 3H), 1.07 (t, J = 6.9 Hz, 3H). |
| 335 | 492.2 | DMSO-d6 | 300 | 1H NMR (300 MHz, dmso) δ 9.16 (d, J = 2.2 Hz, 1H), 9.07 (d, J = 2.0 Hz, 1H), 8.54 (t, J = 2.1 Hz, 1H), 8.10 (s, 1H), 7.56 (s, 1H), 6.34 (q, J = 7.1 Hz, 1H), 3.57-3.42 (m, 1H), 3.38 (s, 3H), 3.30-3.19 (m, 1H), 2.56 (s, 3H), 2.47 (s, 3H), 1.79 (d, J = 7.1 Hz, 3H), 0.90 (t, J = 6.9 Hz, 3H). |
| 336 | 516.1 | DMSO-d6 | 300 | 1H NMR (300 MHz, dmso) δ 8.99 (d, J = 1.5 Hz, 1H), 8.42 (d, J = 8.2 Hz, 1H), 8.31 (dd, J = 8.2, 2.2 Hz, 1H), 8.11 (s, 1H), 7.77 (s, 1H), 6.35 (q, J = 6.8 Hz, 1H), 4.45 (s, 3H), 3.64-3.47 (m, 1H), 3.44-3.33 (m, 1H), 2.57 (s, 3H), 1.80 (d, J = 7.1 Hz, 3H), 0.94 (t, J = 6.9 Hz, 3H). |
| 337 | 515.2 | DMSO-d6 | 400 | 1H NMR (400 MHz, dmso) δ 8.78 (dd, J = 2.2, 0.9 Hz, 1H), 8.32 (s, 1H), 8.12-8.08 (m, 2H), 8.04 (dd, J = 8.2, 0.8 Hz, 1H), 7.73 (s, 1H), 6.35 (q, J = 7.1 Hz, 1H), 4.25 (s, 3H), 3.44 (ddd, J = 57.4, 9.1, 7.0 Hz, 2H), 2.57 (s, 3H), 1.80 (d, J = 7.1 Hz, 3H), 0.93 (t, J = 7.0 Hz, 3H). |
| 338 | 516.2 | CD3OD | 300 | 1H NMR (300 MHz, CD3OD) δ 8.93 (d, J = 1.3 Hz, 1H), 8.39 (d, J = 8.2 Hz, 1H), 8.29 (dd, J = 8.2, 2.2 Hz, 1H), 8.17 (s, 1H), 7.83 (s, 1H), 6.49 (q, J = 7.0 Hz, 1H), 3.72-3.55 (m, 1H), 3.55-3.40 (m, 1H), 2.73 (s, 3H), 2.68 (s, 3H), 1.94 (d, J = 7.1 Hz, 3H), 1.04 (t, J = 7.0 Hz, 3H). |
| 339 | 501.2 | DMSO-d6 | 400 | 1H NMR (400 MHz, dmso) δ 9.27 (d, J = 2.1 Hz, 1H), 8.88 (d, J = 2.1 Hz, 1H), 8.56 (t, J = 2.1 Hz, 1H), 8.36 (d, J = 0.7 Hz, 1H), 8.12 (s, 1H), 7.77 (s, 1H), 7.49 (d, J = 0.7 Hz, 1H), 6.36 (q, J = 7.0 Hz, 1H), 3.55 (dd, J = 9.1, 7.0 Hz, 1H), 3.47-3.33 (m, 1H), 2.58 (s, 3H), 1.80 (d, J = 7.1 Hz, 3H), 0.91 (t, J = 7.0 Hz, 3H). |
| 340 | 485.2 | CD3OD | 300 | 1H NMR (300 MHz, CD3OD) δ 8.77 (dd, J = 5.1, 0.8 Hz, 1H), 8.16 (s, 1H), 7.76 (d, J = 1.6, 0.8 Hz, 1H), 7.69 (dd, J = 5.1, 1.7 Hz, 1H), 7.59 (s, 1H), 6.46 (q, J = 7.1 Hz, 1H), 3.63-3.39 (m, 2H), 3.19 (s, 3H), 3.08 (s, 3H), 2.66 (s, 3H), 2.56 (s, 3H), 1.92 (d, J = 7.1 Hz, 3H), 1.04 (t, J = 7.0 Hz, 3H). |
| 341 | 456.2 | DMSO-d6 | 500 | 1H NMR (500 MHz, DMSO) δ 8.11 (s, 1H), 6.79 (s, 1H), 6.18 (q, J = 6.9 Hz, 1H), 4.37 (q, J = 8.4 Hz, 2H), 4.08-3.97 (m, 2H), 3.82-3.62 (m, 2H), 3.51 (d, J = 6.5 Hz, 2H), 3.27 (s, 3H), 2.90-2.77 (m, 1H), 2.55 (s, 3H), 1.69 (d, J = 7.0 Hz, 3H), 1.34 (t, J = 7.0 Hz, 3H). |
| 342 | 437.1 | CD3OD | 300 | 1H NMR (300 MHz, CD3OD) δ 8.13 (s, 1H), 6.95 (s, 1H), 6.30 (q, J = 7.2 Hz, 1H), 4.63 (t, J = 8.6 Hz, 2H), 4.46 (ddd, J = 8.3, 6.0, 1.9 Hz, 2H), 3.94-3.56 (m, 3H), 2.61 (s, 3H), 1.78 (d, J = 7.1 Hz, 3H), 1.41 (t, J = 7.0 Hz, 3H). |
| 326 | 450.3 | DMSO-d6 | 300 | 1H NMR (300 MHz, dmso) δ 8.09 (s, 1H), 7.24 (s, 1H), 6.21 (q, J = 6.8 Hz, 1H), 4.41 (bs, 1H), 4.02 (m, J = 20.9 Hz, 3H), 3.81-3.47 (m, 3H), 3.14 (m, 2H), 2.54 (s, 3H), 2.34 (s, 5H), 1.70 (d, J = 7.1 Hz, 3H), 1.31 (t, J = 6.9 Hz, 3H), 1.00 (d, J = 6.2 Hz, 3H). |
| 343 | 417.3 | CD3OD | 300 | 1H NMR (300 MHz, CD3OD) δ 8.12 (s, 1H), 8.00 (s, 1H), 7.82 (s, 1H), 7.34 (s, 1H), 6.39 (q, J = 7.1 Hz, 1H), 3.97 (s, 3H), 3.60-3.41 (m, 2H), 2.61 (s, 3H), 2.46 (s, 3H), 1.84 (d, J = 7.0 Hz, 3H), 1.14 (t, J = 7.0 Hz, 3H). |
| 327 | 436.2 | DMSO-d6 | 300 | 1H NMR (300 MHz, dmso) δ 8.09 (s, 1H), 7.23 (s, 1H), 6.21 (d, J = 7.0 Hz, 1H), 4.39 (t, J = 5.4 Hz, 1H), 4.10-3.81 (m, 3H), 3.69 (dt, J = 15.5, 7.8 Hz, 2H), 3.36 (m, 2H), 3.12-2.97 (m, 2H), 2.54 (s, 3H), 2.45-2.38 (m, 2H), 2.34 (s, 3H), 1.70 (d, J = 7.1 Hz, 3H), 1.31 (t, J = 6.9 Hz, 3H). |

TABLE 9-continued

| Ex. No. | MS [M + H]+ | Solvent | MHz | $^1$H NMR Spectra |
|---|---|---|---|---|
| 344 | 471.2 | DMSO-$d_6$ | 300 | $^1$H NMR (300 MHz, dmso) δ 8.67 (d, J = 1.5 Hz, 1H), 8.10 (s, 1H), 8.06 (dd, J = 8.0, 2.2 Hz, 1H), 7.69 (d, J = 8.0 Hz, 1H), 7.48 (s, 1H), 6.32 (q, J = 7.0 Hz, 1H), 3.26 (s, 3H), 3.03 (s, 3H), 2.96 (s, 3H), 2.57 (s, 3H), 2.45 (s, 3H), 1.79 (d, J = 7.0 Hz, 3H). |
| 328 | 450.2 | DMSO-$d_6$ | 300 | $^1$H NMR (300 MHz, dmso) δ 8.08 (s, 1H), 7.20 (s, 1H), 6.21 (q, J = 6.9 Hz, 1H), 4.04 (s, 1H), 4.03-3.91 (m, 3H), 3.58 (s, 3H), 3.15-3.02 (m, 2H), 2.54 (s, 3H), 2.32 (s, 3H), 2.25 (s, 2H), 1.70 (d, J = 7.1 Hz, 3H), 1.03 (s, 6H). |

Examples 310 and 311

Diastereoisomers of 4-{3-[1-(4-amino-3-methyl-1H-pyrazolo[3,4-d]pyrimidin-1-yl)ethyl]-5-chloro-2-ethoxy-6-methylphenyl}pyrrolidin-2-one

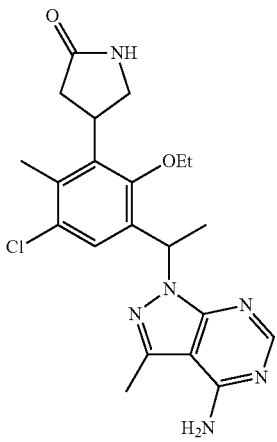

Step 1.
1-(5-Chloro-2-ethoxy-3-iodo-4-methylphenyl)ethanol

The desired compound was prepared according to the procedure of Example 212, step 4 (racemic mixture), using 1-(5-chloro-2-ethoxy-3-iodo-4-methylphenyl)ethanone instead of tert-butyl 3-(3-acetyl-5-chloro-6-cyano-2-ethoxyphenyl)azetidine-1-carboxylate as the starting material in 94% yield as a 96:4 mixture of enantiomers (RT=3.56 min and 4.28 min; Chiral Technologies ChiralPak AD-H column, 20×250 mm, 5 micron particle size, eluting with 5% ethanol in hexanes at 1 ml/min). LCMS for $C_{11}H_{13}ClIO$ (M-(OH))+: m/z=323.0. Found: 322.9.

Step 2. 1-[1-(5-Chloro-2-ethoxy-3-iodo-4-methylphenyl)ethyl]-3-methyl-1H-pyrazolo[3,4-d]pyrimidin-4-amine The desired compound was prepared according to the procedure of Example 212, step 5, using 1-(5-Chloro-2-ethoxy-3-iodo-4-methylphenyl)ethanol (96:4 mixture from step 1) instead of tert-butyl 3-[3-chloro-2-cyano-6-ethoxy-5-(1-hydroxyethyl)phenyl]azetidine-1-carboxylate as the starting material in 32% yield as a single enantiomer (peak 1 desired, retention time=3.39 min; ChiralPak IA column, 20×250 mm, 5 micron particle size, eluting with 3% ethanol in hexanes at 18 ml/min). LCMS for $C_{17}H_{20}ClIN_5O$ (M+H)+: m/z=472.0. Found: 472.0.

Step 3. Methyl (2E)-3-{3-[1-(4-amino-3-methyl-1H-pyrazolo[3,4-d]pyrimidin-1-yl)ethyl]-5-chloro-2-ethoxy-6-methylphenyl}acrylate A suspension of 1-[1-(5-chloro-2-ethoxy-3-iodo-4-methylphenyl)ethyl]-3-methyl-1H-pyrazolo[3, 4-d]pyrimidin-4-amine (peak 1 single isomer from step 2) (0.61 g, 1.3 mmol) in acetonitrile (7.4 mL) in a sealed tube was degassed with nitrogen and treated with triphenylphosphine (0.048 g, 0.18 mmol), methyl acrylate (0.41 mL, 4.5 mmol), and palladium acetate (0.029 g, 0.13 mmol) followed by triethylamine (0.54 mL, 3.9 mmol) and heated at 100° C. for 16 h. The reaction mixture was cooled to room temperature, filtered, and the solids washed with acetonitrile. The filtrate was concentrated to a residue. The crude material was purified by flash column chromatography using ethyl acetate (containing 3% methanol) in hexanes (0%-100%) to give the desired product (0.40 g, 72%). LCMS for $C_{21}H_{25}ClN_5O_3$ (M+H)+: m/z=430.2. Found: 430.2.

Step 4. Diastereoisomers of methyl 3-{3-[1-(4-amino-3-methyl-1H-pyrazolo[3,4-d]pyrimidin-1-yl)ethyl]-5-chloro-2-ethoxy-6-methylphenyl}-4-nitrobutanoate A solution of methyl (2E)-3-{3-[1-(4-amino-3-methyl-1H-pyrazolo[3,4-d]pyrimidin-1-yl)ethyl]-5-chloro-2-ethoxy-6-methylphenyl}acrylate (0.40 g, 0.93 mmol) in nitromethane (6.3 mL) was treated with 1,8-diazabicyclo [5.4.0]undec-7-ene (0.14 mL, 0.93 mmol) and stirred at 90° C. for 22 h. The reaction mixture was concentrated, diluted with methanol, and purified by preparative LCMS (XBridge C18 Column, eluting with a gradient of acetonitrile in water with 0.1% trifluoroacetic acid, at flow rate of 60 mL/min) The LCMS fractions were concentrated to remove acetonitrile, treated with solid sodium bicarbonate, and extracted into ethyl acetate. The ethyl acetate was concentrated to give the desired product (0.22 g, 48%) as a mixture of diastereoisomers. LCMS for $C_{22}H_{28}ClN_6O_5$ (M+H)+: m/z=491.2. Found: 491.2.

Step 5. Diastereoisomers of 4-{3-[1-(4-amino-3-methyl-1H-pyrazolo[3,4-d]pyrimidin-1-yl)ethyl]-5-chloro-2-ethoxy-6-methylphenyl}pyrrolidin-2-on A solution of methyl 3-{3-[1-(4-amino-3-methyl-1H-pyrazolo[3,4-d]pyrimidin-1-yl)ethyl]-5-chloro-2-ethoxy-6-methylphenyl}-4-nitrobutanoate (0.089 g, 0.18 mmol) in methanol (1.3 mL) was treated with nickel chloride hexahydrate (0.087 g, 0.36 mmol) was and stirred for 5 min. The reaction mixture was cooled to 0° C., treated with sodium tetrahydroborate (0.073 g, 1.9 mmol) in four portions, and stirred at room temperature for 30 min. The reaction mixture was heated at 60° C. for 1.5 h, cooled to room temperature, diluted with saturated sodium bicarbonate solution (10 mL) and dichloromethane (25 mL), and filtered through Celite. The Celite was washed with dichloromethane and the filtrate was transferred to a separatory funnel. The organic layer was separated, washed with brine, dried over sodium sulfate, filtered, and concentrated to residue. The crude residue was diluted with methanol and purified by preparative LCMS (XBridge C18 column, eluting with a gradient of acetonitrile/water containing 0.1% ammonium hydroxide, at flow rate of 60 mL/min) to give the desired peak 1 diastereoisomer (16 mg, 21%) and peak 2 diastereoisomer (19 mg, 24%). Peak 1 (compound 310): $^1$H NMR (300 MHz, DMSO-$d_6$) δ 8.10 (s, 1H), 7.89 (s, 1H), 7.34 (s, 1H), 6.21 (q, J=7.1 Hz, 1H), 4.38-4.22 (m, 1H), 3.93-3.80 (m, 1H), 3.79-3.67 (m, 1H), 3.65-3.55 (m, 1H), 3.28-3.20 (m, 1H), 2.54 (s, 3H), 2.29 (dd, J=17.5, 8.3 Hz, 1H), 2.21 (s, 3H), 1.70 (d, J=7.0 Hz, 3H), 1.40 (t, J=6.9 Hz, 3H). LCMS for $C_{21}H_{26}ClN_6O_2$ (M+H)$^+$: m/z=429.2. Found: 429.2. Peak 2 (compound 311): $^1$H NMR (300 MHz, DMSO-$d_6$) δ 8.11 (s, 1H), 7.89 (s, 1H), 7.33 (s, 1H), 6.20 (q, J=7.1 Hz, 1H), 4.38-4.22 (m, 1H), 3.90-3.68 (m, 2H), 3.65-3.56 (m, 1H), 3.28-3.17 (m, 1H), 2.54 (s, 3H), 2.32 (dd, J=17.3, 8.5 Hz, 1H), 2.21 (s, 3H), 1.69 (d, J=7.0 Hz, 3H), 1.39 (t, J=6.9 Hz, 3H). LCMS for $C_{21}H_{26}ClN_6O_2$ (M+H)$^+$: m/z=429.2. Found: 429.2.

Example 323

4-[1-(4-amino-3-methyl-1H-pyrazolo[3,4-d]pyrimidin-1-yl)ethyl]-6-chloro-3-ethoxy-2-(2-oxo-1,3-oxazolidin-5-yl)benzonitrile

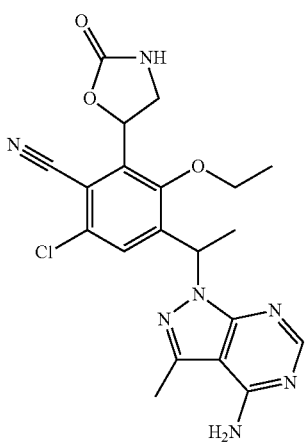 [SMILES: CCOc1c(C(C)n2nc(C)c3c(N)ncnc32)cc(Cl)c(C#N)c1C1CNC(=O)O1]

Step 1.
4-Acetyl-6-chloro-3-ethoxy-2-vinylbenzonitrile

A mixture of 4-acetyl-6-chloro-3-ethoxy-2-iodobenzonitrile (1.3 g, 3.6 mmol), 4,4,5,5-tetramethyl-2-vinyl-1,3,2-dioxaborolane (740 μL, 4.3 mmol), [1,1'-bis(diphenylphosphino)ferrocene]dichloropalladium(II), complex with dichloromethane (1:1) (100 mg, 0.20 mmol) and potassium carbonate (1.5 g, 11 mmol) in 1,4-dioxane (20 mL) and water (10 mL) was heated at 80° C. overnight. The mixture was cooled to room temperature and extracted with ethyl acetate. The extracts were washed with brine, dried over sodium sulfate, filtered and concentrated. Purification on silica gel using ethyl acetate in hexanes (0-20%) gave the desired compound, 780 mg, 87%. LCMS calculated for $C_{13}H_{13}ClNO_2$ (M+H)$^+$: m/z=250.1. found: 250.1. $^1$H NMR (400 MHz, DMSO-$d_6$): δ 7.78 (s, 1H), 6.83 (m, 1H), 6.10 (m, 1H), 5.83 (m, 1H), 3.84 (m, 2H), 2.58 (s, 3H), 1.22 (m, 3H).

Step 2. tert-Butyl [2-(3-acetyl-5-chloro-6-cyano-2-ethoxyphenyl)-2-hydroxyethyl]carbamate 0.2 M Osmium tetraoxide in water (0.5 mL) was added to a solution of tert-butyl [(4-chlorobenzoyl)oxy]carbamate (Ref Lawrence Harris, J. Org. Chem, 2011, 76, 358-372). (0.91 g, 3.3 mmol) in acetonitrile (10 mL) and stirred for 10 minutes. 4-Acetyl-6-chloro-3-ethoxy-2-vinylbenzonitrile (0.56 g, 2.2 mmol) as a solution in acetonitrile (10 mL) was added to the carbamate solution followed by the addition of water (2 mL) and the reaction was stirred for 3 hours at room temperature. The reaction was quenched with saturated 10 M dipotassium disulfite in water (12 mL) and stirred for 5 minutes. Water was added and the reaction mixture was extracted with ethyl acetate. The extracts were washed with saturated sodium bicarbonate solution, brine and dried over sodium sulfate, filtered and evaporated. Purification on silica gel using ethyl acetate in hexane (0-100%) gave the desired compound as a racemic mixture, 610 mg, 72%. LCMS calculated for $C_{18}H_{24}ClN_2O_5$ (M+H)$^+$: m/z=383.1. found: 383.1. $^1$H NMR (400 MHz, DMSO-$d_6$): δ 7.62 (s, 1H), 7.03 (br s, 1H), 5.68 (br s, 1H), 3.96 (m, 1H), 3.69 (m, 1H), 3.31 (m, 1H), 3.19 (m, 1H), 2.60 (s, 3H), 1.30 (m, 12H).

Step 3. 4-Acetyl-6-chloro-3-ethoxy-2-(2-oxo-1,3-oxazolidin-5-yl)benzonitrile tert-Butyl [2-(3-acetyl-5-chloro-6-cyano-2-ethoxyphenyl)-2-hydroxyethyl]carbamate (290 mg, 0.76 mmol) (racemic mixture from step 2) was treated with 4.0 M hydrogen chloride in 1,4-dioxane (6.1 mL) for 15 minutes and the mixture was evaporated. The residue was dissolved in tetrahydrofuran (2.3 mL) and N,N-diisopropylethylamine (0.66 mL, 3.8 mmol). N,N-carbonyldiimidazole (250 mg, 1.5 mmol) was added and the reaction mixture was refluxed at 70° C. overnight. The reaction mixture was evaporated. Purification on silica gel using ethyl acetate in hexane (0-100%) gave the desired compound as a racemic mixture, 110 mg, 47%. LCMS calculated for $C_{14}H_{14}ClN_2O_4$ (M+H)$^+$: m/z=309.1. found: 309.1. $^1$H NMR (400 MHz, DMSO-$d_6$): δ 8.00 (br s, 1H), 7.93 (s, 1H), 5.99 (m, 1H), 3.89 (m, 1H), 3.81 (m, 2H), 3.52 (m, 1H), 2.58 (s, 3H), 1.23 (m, 3H).

Step 4. 6-Chloro-3-ethoxy-4-(1-hydroxyethyl)-2-(2-oxo-1,3-oxazolidin-5-yl)benzonitrile Sodium tetrahydroborate (19 mg, 0.50 mmol) was added to a mixture of 4-acetyl-6-chloro-3-ethoxy-2-(2-oxo-1,3-oxazolidin-5-yl)benzonitrile (100 mg, 0.34 mmol) (racemic mixture from step 3) in methanol (1.6 mL, 38 mmol) at 0° C. and the reaction mixture was stirred at room temperature for 10 minutes and evaporated. The residue was diluted with ethyl acetate, washed with 1 N HCl, brine, dried over sodium sulfate, filtered and concentrated to give the desired compound as a mixture of four diastereomers, 58 mg, 55%. LCMS calculated for $C_{14}H_{16}ClN_2O_4$ (M+H)$^+$: m/z=311.1. found: 311.1.

Step 5. 6-Chloro-4-(1-chloroethyl)-3-ethoxy-2-(2-oxo-1,3-oxazolidin-5-yl)benzonitrile To a mixture of 6-chloro-3-ethoxy-4-(1-hydroxyethyl)-2-(2-oxo-1,3-oxazolidin-5-yl)benzonitrile (58 mg, 0.19 mmol) (mixture of four diastereomers from step 4), N,N-dimethylformamide (36 μL) in methylene chloride (1 mL), thionyl chloride (40. μL, 0.56 mmol) was added and the mixture was stirred at room temperature for 20 minutes. The mixture was diluted with methylene chloride, washed with saturated sodium bicarbonate, water, brine, dried over sodium sulfate, filtered and concentrated to give the desired compound as a mixture of four diastereomers, 55 mg, 91%. LCMS calculated for $C_{14}H_{15}Cl_2N_2O_3$ (M+H)$^+$: m/z=329.0. found: 329.1.

Step 6. 4-[1-(4-Amino-3-methyl-1H-pyrazolo[3,4-d]pyrimidin-1-yl)ethyl]-6-chloro-3-ethoxy-2-(2-oxo-1,3-oxazolidin-5-yl)benzonitrile Cesium Carbonate (0.11 g, 0.34 mmol) was added to a mixture of 3-methyl-1H-pyrazolo[3,4-d]pyrimidin-4-amine (30 mg, 0.20 mmol) (mixture of four diastereomers from step 5) in N,N-dimethylformamide (0.91 mL) and stirred for 10 minutes. To the mixture was added 6-chloro-4-(1-chloroethyl)-3-ethoxy-2-(2-oxo-1,3-oxazolidin-5-yl)benzonitrile (56 mg, 0.17 mmol) in N,N-dimethylformamide (1.0 mL) and the reaction was stirred at 90° C. for 1 hour. Purification by preparative LCMS (pH 10) using RP-HPLC (XBridge C18 column, eluting with a gradient of acetonitrile/water containing 0.1% ammonium hydroxide, at flow rate of 30 mL/min) gave the desired compounds as Peak 1 (racemic mixture of two diastereomers) LCMS calculated for $C_{20}H_{21}ClN_7O_3$ (M+H)$^+$: m/z=442.1. found: 442.1. $^1$H NMR (400 MHz, DMSO-d$_6$): δ 8.17 (s, 1H), 8.00 (br s, 1H), 7.79 (s, 1H), 6.25 (m, 1H), 5.92 (m, 1H), 3.90 (m, 3H), 3.57 (m, 1H), 2.58 (s, 3H), 1.75 (m, 3H), 1.40 (m, 3H); Peak 2 (racemic mixture of 2 diastereomers):

LCMS calculated for $C_{20}H_{21}ClN_7O_3$ (M+H)$^+$: m/z=442.1. found: 442.1. $^1$H NMR (400 MHz, DMSO-d$_6$): δ 8.12 (s, 1H), 8.00 (br s, 1H), 7.71 (s, 1H), 6.23 (m, 1H), 5.96 (m, 1H), 3.85 (m, 3H), 3.58 (m, 1H), 2.58 (s, 3H), 1.75 (m, 3H), 1.40 (m, 3H).

Chiral purification of Peak 2 (racemic mixture of two diastereomers) on Phenomenex Lux Cellulose-1, 21.2×250 mm, 5 micron particle size at 18 mL/min using 20% ethanol in hexanes gave Peak 3 and Peak 4. Peak 3, retention time=12.22 minutes (single enantiomer): LCMS calculated for $C_{20}H_{21}ClN_7O_3$ (M+H)$^+$: m/z=442.1. found: 442.1. $^1$H NMR (400 MHz, DMSO-d$_6$): δ 8.12 (s, 1H), 7.98 (br s, 1H), 7.71 (s, 1H), 6.23 (m, 1H), 5.96 (m, 1H), 3.85 (m, 3H), 3.58 (m, 1H), 2.58 (s, 3H), 1.75 (m, 3H), 1.40 (m, 3H). Peak 4, retention time=16.25 minutes (single enantiomer). LCMS calculated for $C_{20}H_{21}ClN_7O_3$ (M+H)$^+$: m/z=442.1. found: 442.1. $^1$H NMR (400 MHz, DMSO-d$_6$): δ 8.12 (s, 1H), 7.98 (br s, 1H), 7.71 (s, 1H), 6.23 (m, 1H), 5.96 (m, 1H), 3.85 (m, 3H), 3.58 (m, 1H), 2.58 (s, 3H), 1.75 (m, 3H), 1.40 (m, 3H).

Example 324

6-{3-[1-(4-Amino-3-methyl-1H-pyrazolo[3,4-d]pyrimidin-1-yl)ethyl]-5-chloro-2-methoxy-6-methylphenyl}morpholin-3-one

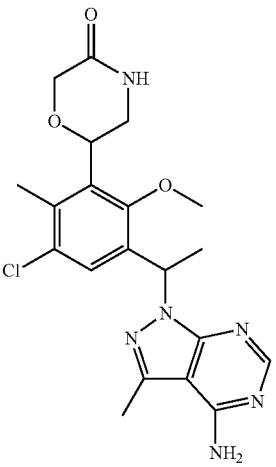 [SMILES: COc1c(C(C)n2nc(C)c3c(N)ncnc32)cc(Cl)c(C)c1C1CNC(=O)CO1]

Step 1. 1-(5-Chloro-2-methoxy-4-methyl-3-vinylphenyl)ethanone

A mixture of 1-(3-bromo-5-chloro-2-methoxy-4-methylphenyl)ethanone (2.6 g, 9.5 mmol), 4,4,5,5-tetramethyl-2-vinyl-1,3,2-dioxaborolane (1.9 mL, 11 mmol), [1,1'-bis(diphenylphosphino)ferrocene]dichloropalladium(II), complex with dichloromethane (1:1) (400 mg, 0.5 mmol) and potassium carbonate (4.0 g, 29 mmol) in 1,4-dioxane (60 mL), and water (30 mL). The resulting mixture was heated at 80° C. for 3 hours. The mixture was cooled to room temperature and extracted with ethyl acetate. Purification on a silica gel using ethyl acetate in hexanes (0-20%) gave the desired compound, 2.0 g, 94%. LCMS calculated for $C_{12}H_{14}ClO_2$ (M+H)$^+$: m/z=225.1. found: 225.1.

Step 2. tert-Butyl[2-(3-acetyl-5-chloro-2-methoxy-6-methylphenyl)-2-hydroxyethyl]carbamate 0.2 M Osmium tetraoxide in water (1 mL) was added to a solution of tert-butyl [(4-chlorobenzoyl)oxy]carbamate (2.0 g, 7.2 mmol) (Ref Lawrence Harris, J. Org. Chem, 2011, 76, 358-372) in acetonitrile (22 mL) and stirred for 10 minutes. 1-(5-Chloro-2-methoxy-4-methyl-3-vinylphenyl)ethanone (1.1 g, 4.8 mmol) as a solution in acetonitrile (22 mL) was added to the carbamate solution followed by the addition of water (5 mL). The reaction was stirred for 3 hours at room temperature. The reaction was quenched with saturated 10 M dipotassium disulfite in water (25 mL) and stirred for 5 minutes. Water was added to the reaction and the mixture was extracted with ethyl acetate. The organic extracts were washed with saturated sodium bicarbonate solution, brine, dried over sodium sulfate and evaporated under reduced pressure. Purification on silica gel using ethyl acetate in hexane (0-100%) gave the desired compound as a racemic mixture, 1.2 g, 69%. LCMS calculated for $C_{17}H_{24}ClNO_5Na$ (M+Na)$^+$: m/z=380.1. found: 380.1. $^1$H NMR (500 MHz, DMSO-d$_6$): δ 7.48 (s, 1H), 6.80 (m, 1H), 5.50 (br s, 1H), 5.20 (br s, 1H), 3.83 (s, 3H), 3.32 (m, 1H), 3.22 (m, 1H), 2.59 (s, 3H), 2.55 (s, 3H), 1.32 (s, 9H).

Chiral purification on ChiralPak AD-H, 20×250 mm (Chiral Technologies), 5 micron particle size, at flow rate of 18 mL/min using 8% ethanol in hexanes gave the Peak 1 (single enantiomer) (retention time=9.86 minutes) and Peak 2 (single enantiomer) (retention time=11.47 minutes).

Step 3. N-[2-(3-Acetyl-5-chloro-2-methoxy-6-methylphenyl)-2-hydroxyethyl]-2-chloroacetamide tert-Butyl[2-(3-acetyl-5-chloro-2-methoxy-6-methylphenyl)-2-hydroxyethyl]carbamate (170 mg, 0.47 mmol) (Peak 1 from step 2) was treated with 4.0 M hydrogen chloride in 1,4-dioxane (12 mL) for 15 minutes. The solvents were evaporated, methylene chloride (6 mL) and triethylamine (200 μL, 1.4 mmol) were added and the mixture cooled to 0° C. Chloroacetyl chloride (45 μL, 0.56 mmol) was added slowly and was stirred for 10 minutes at 0° C. The solvents were evaporated to dryness. Water was added and the mixture was extracted with ethyl acetate. The combined extracts were washed with brine, dried over sodium sulfate, and concentrated to give the crude residue as a single enantiomer. LCMS calculated for $C_{14}H_{17}Cl_2NO_4Na$ (M+Na)$^+$: m/z=356.1. found: 356.1.

Step 4. 6-(3-Acetyl-5-chloro-2-methoxy-6-methylphenyl)morpholin-3-one

To a solution of N-[2-(3-acetyl-5-chloro-2-methoxy-6-methylphenyl)-2-hydroxyethyl]-2-chloroacetamide (170 mg, 0.50 mmol) (single enantiomer from step 3) in tetrahydrofuran (4 mL) cooled at 0° C., a mixture of sodium hydride (60% dispersion in mineral oil; 39 mg, 1.0 mmol) was added and stirred for 1 hour. The reaction was quenched with water and extracted with ethyl acetate. The combined extracts were washed with brine, dried over sodium sulfate, and concentrated to give the crude residue as a single enantiomer, 61 mg, 41%. LCMS calculated for $C_{14}H_{17}ClNO_4$ (M+H)$^+$: m/z=298.1. found: 298.1.

Step 5. 6-[3-Chloro-5-(1-hydroxyethyl)-6-methoxy-2-methylphenyl]morpholin-3-one

To a solution of 6-(3-acetyl-5-chloro-2-methoxy-6-methylphenyl)morpholin-3-one (27 mg, 0.090 mmol) (single enantiomer from step 4) in methanol (2 mL) was added sodium tetrahydroborate (6.8 mg, 0.18 mmol) at 0° C. and stirred for 1 hour. Purification by preparative LCMS (pH 10) gave the desired compound as a racemic mixture of two diastereomers, 20 mg, 76%. LCMS calculated for $C_{14}H_{17}ClNO_3$ (M-OH)$^+$: m/z=282.1. found: 282.1.

Step 6. 6-[3-Chloro-5-(1-chloroethyl)-6-methoxy-2-methylphenyl]morpholin-3-one

A mixture of thionyl chloride (15 μL, 0.21 mmol) and N,N-dimethylformamide (10.0 μL) was stirred at room temperature for 10 minutes. A solution of 6-[3-chloro-5-(1-hydroxyethyl)-6-methoxy-2-methylphenyl]morpholin-3-one (19.0 mg, 0.0634 mmol) (racemic mixture of two diastereomers from step 5) in methylene chloride (1.0 mL) was added and the mixture was stirred at room temperature overnight. The mixture was diluted with methylene chloride, washed with saturated sodium bicarbonate, water, brine, dried over sodium sulfate, filtered and concentrated to give the desired compound as a racemic mixture of two diastereomers, 19 mg, 94%. LCMS calculated for $C_{14}H_{17}ClNO_3$ (M-Cl)$^+$: m/z=282.1. found: 282.1.

Step 7. 6-{3-[1-(4-Amino-3-methyl-1H-pyrazolo[3,4-d]pyrimidin-1-yl)ethyl]-5-chloro-2-methoxy-6-methylphenyl}morpholin-3-one A mix of 6-[3-chloro-5-(1-chloroethyl)-6-methoxy-2-methylphenyl]morpholin-3-one (19.0 mg, 0.0597 mmol) (racemic mixture of two diastereomers from step 6) 3-methyl-1H-pyrazolo[3,4-d]pyrimidin-4-amine (11 mg, 0.072 mmol), cesium carbonate (29 mg, 0.090 mmol) and potassium iodide (0.99 mg, 0.006 mmol) in N,N-dimethylformamide (0.19 mL) was heated at 140° C. for 1 hour. The mixture was diluted with ether, washed with water, concentrated and purified by preparative LCMS (pH 10) using RP-HPLC (XBridge C18 column, eluting with a gradient of acetonitrile/water containing 0.1% ammonium hydroxide, at flow rate of 30 mL/min) to give 2.5 mg, 10% of Peak 1 (single enantiomer, retention time 10.15 min) LCMS calculated for $C_{20}H_{24}ClN_6O_3$ (M+H)$^+$: m/z=431.2. found: 431.1, and 2.7 mg, 10% of Peak 2 (single enantiomer, retention time 10.76 min): LCMS calculated for $C_{20}H_{24}ClN_6O_3$ (M+H)$^+$: m/z=431.2. found: 431.1.

Example 325

5-{3-[1-(4-Amino-3-methyl-1H-pyrazolo[3,4-d]pyrimidin-1-yl)ethyl]-5-chloro-2-methoxy-6-methylphenyl}-1,3-oxazolidin-2-one

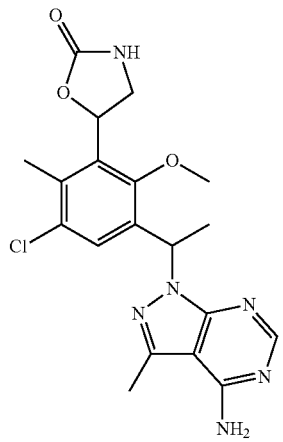 [SMILES: COc1c(C(C)n2nc(C)c3c(N)ncnc32)cc(Cl)c(C)c1C1CNC(=O)O1]

Step 1. 5-(3-Acetyl-5-chloro-2-methoxy-6-methylphenyl)-1,3-oxazolidin-2-one

To a solution of tert-butyl[2-(3-acetyl-5-chloro-2-methoxy-6-methylphenyl)-2-hydroxyethyl]carbamate (140 mg, 0.40 mmol) (Peak 1, single enantiomer from step 2, Example 324) in tetrahydrofuran (2.5 mL), N,N-diisopropylethylamine (0.35 mL, 2.0 mmol) and N,N-carbonyldiimidazole (130 mg, 0.80 mmol). The reaction was refluxed at 70° C. for 10 minutes. The reaction was evaporated to dryness. Purification on silica gel using (0-50%) ethyl acetate in hexane gave the desired compound as a single enantiomer, 78 mg, 69%. LCMS calculated for $C_{13}H_{15}ClNO_4$ (M+H)$^+$: m/z=284.1. found: 284.1.

Step 2. 5-[3-Chloro-5-(1-hydroxyethyl)-6-methoxy-2-methylphenyl]-1,3-oxazolidin-2-one To a solution of 5-(3-acetyl-5-chloro-2-methoxy-6-methylphenyl)-1,3-oxazolidin-2-one (21 mg, 0.072 mmol) (single enantiomer from step 1) in methanol (1 mL) was added sodium tetrahydroborate (5.5 mg, 0.14 mmol) at 0° C. The mixture was stirred at 0° C. for 1 hour. It was diluted with methanol and purified on preparative LCMS using pH 10 buffer to give the desired compound as a racemic mixture of two diastereomers, 17 mg, 83%. LCMS calculated for $C_{13}H_{15}ClNO_3$ (M-OH)⁺: m/z=268.1. found: 268.1.

Step 3. 5-[3-Chloro-5-(1-chloroethyl)-6-methoxy-2-methylphenyl]-1,3-oxazolidin-2-one A mixture of cyanuric chloride (16 mg, 0.084 mmol) and N,N-dimethylformamide (15 μL) was stirred at room temperature for 10 minutes. A solution of 5-[3-chloro-5-(1-hydroxyethyl)-6-methoxy-2-methylphenyl]-1,3-oxazolidin-2-one (16 mg, 0.056 mmol) (racemic mixture of two diastereomers from step 2) in methylene chloride (0.3 mL) was added and the reaction was stirred at room temperature overnight. Thionyl chloride (12 μL, 0.17 mmol) was added and stirred for 10 min. The mixture was diluted with methylene chloride, washed with saturated sodium bicarbonate, water, brine, dried over sodium sulfate, filtered and concentrated to give the desired compound as a racemic mixture of two diastereomers, 17 mg, 100%. LCMS calculated for $C_{13}H_{16}Cl_2NO_3$ (M+H)⁺: m/z=304.0. found: 304.1.

Step 4. 5-{3-[1-(4-amino-3-methyl-1H-pyrazolo[3,4-d]pyrimidin-1-yl)ethyl]-5-chloro-2-methoxy-6-methylphenyl}-1,3-oxazolidin-2-one A mixture of 5-[3-chloro-5-(1-chloroethyl)-6-methoxy-2-methylphenyl]-1,3-oxazolidin-2-one (17 mg, 0.056 mmol) (racemic mixture of two diastereomers from step 3) 3-methyl-1H-pyrazolo[3,4-d]pyrimidin-4-amine (10 mg, 0.067 mmol), cesium carbonate (27 mg, 0.084 mmol) and potassium iodide (0.93 mg, 0.0056 mmol) in N,N-dimethylformamide (0.18 mL) was heated at 140° C. for 1 hour. The mixture was diluted with ether, washed with water, concentrated and purified by preparative LCMS (pH 10) to give the desired compound as a racemic mixture of two diastereomers, 2.2 mg, 9%; LCMS calculated for $C_{19}H_{22}ClN_6O_3$ (M+H)⁺: m/z=417.1. found: 417.1.

Examples 345-348

Diastereoisomers of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one

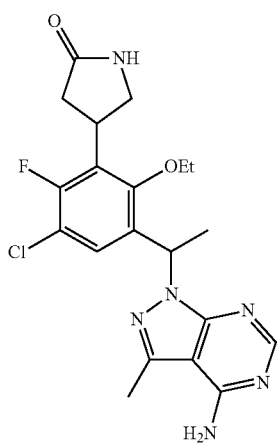 [SMILES: CCOc1c(C(C)n2nc(C)c3c(N)ncnc32)cc(Cl)c(F)c1C1CNC(=O)C1]

Step 1. 1-(5-Chloro-2-ethoxy-3-iodo-4-methylphenyl)ethanol

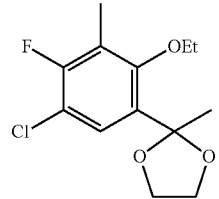 [SMILES: CCOc1c(C2(C)OCCO2)cc(Cl)c(F)c1C]

A solution of 1-(5-chloro-2-ethoxy-4-fluoro-3-iodophenyl)ethanone (20.0 g, 58.4 mmol; Example 212, step 1) and 1,2-ethanediol (6.5 mL, 120 mmol) in toluene (190 mL) was treated with p-toluenesulfonic acid monohydrate (1.1 g, 5.8 mmol). The flask was fitted with a Dean-Stark trap that was filled with sieves, and refluxed for 3 h. The reaction mixture was cooled and added to ice cooled saturated sodium bicarbonate solution (250 mL) and extracted with ethyl acetate. The organic layer was washed with brine, dried over sodium sulfate, filtered, and concentrated to a crude orange oil. The crude material was purified by flash column chromatography using ethyl acetate in hexanes (0%-20%) to give the desired product (22 g, 99%). LCMS for $C_{12}H_{14}ClF_1O_3$ (M+H)⁺: m/z=387.0. Found: 386.9.

Step 2. Ethyl (2E)-3-[3-chloro-6-ethoxy-2-fluoro-5-(2-methyl-1,3-dioxolan-2-yl)phenyl]acrylate

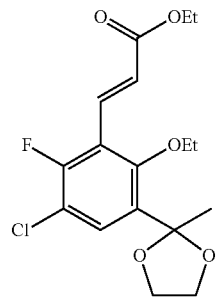 [SMILES: CCOC(=O)/C=C/c1c(F)c(Cl)cc(C2(C)OCCO2)c1OCC]

A mixture of 2-(5-chloro-2-ethoxy-4-fluoro-3-iodophenyl)-2-methyl-1,3-dioxolane (22 g, 58 mmol) (from Step 1), ethyl (2E)-3-(4,4,5,5-tetramethyl-1,3,2-dioxaborolan-2-yl)acrylate (16 mL, 70 mmol), and potassium carbonate (24 g, 170 mmol) in 1,4-dioxane (230 mL) and water (110 mL) was degassed with nitrogen for 10 min. The reaction mixture was treated with [1,1'-bis(diphenylphosphino\)ferrocene]dichloropalladium(II), complex with dichloromethane (1:1) (2.4 g, 2.9 mmol), degassed with nitrogen for another 10 min, and heated at 80° C. for 2 h. The reaction mixture was filtered through Celite and washed with ethyl acetate (300 mL). The filtrate was poured into water (400 mL). The aqueous layer was separated and extracted with additional ethyl acetate (300 mL). The combined organic extracts were washed with brine, dried over sodium sulfate, filtered, and concentrated to a crude brown solid. The crude material was purified by flash column chromatography using ethyl acetate in hexanes (0%-30%) to give the desired product (20 g, 96%). ¹H NMR (400 MHz, CDCl₃) δ 7.74 (d, J=16.5 Hz, 1H), 7.56 (d, J=8.6 Hz, 1H), 6.70 (dd, J=16.5, 0.9 Hz, 1H), 4.26 (q, J=7.1 Hz, 2H), 4.10-3.99 (m, 2H), 3.91 (q, J=7.0 Hz, 2H), 3.87-3.76

(m, 2H), 1.73 (s, 3H), 1.44 (t, J=7.0 Hz, 3H), 1.33 (t, J=7.1 Hz, 3H). LCMS for $C_{17}H_{21}ClFO_5$ (M+H)+: m/z=359.1. Found: 359.1.

Step 3. Ethyl 3-[3-chloro-6-ethoxy-2-fluoro-5-(2-methyl-1,3-dioxolan-2-yl)phenyl]-4-nitrobutanoate

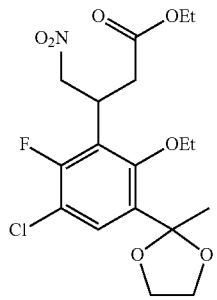 [SMILES: CCOC(=O)CC(C[N+](=O)[O-])c1c(F)c(Cl)cc(C2(C)OCCO2)c1OCC]

A solution ethyl (2E)-3-[3-chloro-6-ethoxy-2-fluoro-5-(2-methyl-1,3-dioxolan-2-yl\)phenyl]acrylate (10 g, 28 mmol) (from Step 2) in nitromethane (100 mL) was treated with 1,8-diazabicyclo[5.4.0]undec-7-ene (4.6 mL, 31 mmol) and stirred at 60° C. for 15 h. The reaction mixture was poured into water (400 mL) and extracted with ethyl acetate (2×300 mL). The combined organic extracts were washed with brine, dried over sodium sulfate, filtered, and concentrated to a crude orange oil. The crude material was purified by flash column chromatography using ethyl acetate in hexanes (0%-30%) to give the desired product as a mixture of enantiomers (10.4 g, 89%). $^1$H NMR (400 MHz, CDCl$_3$) δ 7.52 (d, J=9.1 Hz, 1H), 4.82 (ddd, J=12.5, 7.6, 1.4 Hz, 1H), 4.68 (dd, J=12.5, 7.2 Hz, 1H), 4.54-4.40 (m, 1H), 4.15-3.90 (m, 6H), 3.89-3.75 (m, 2H), 2.85 (ddd, J=16.0, 8.6, 1.4 Hz, 1H), 2.73 (dd, J=16.1, 6.2 Hz, 1H), 1.70 (s, 3H), 1.47 (t, J=7.0 Hz, 3H), 1.21 (t, J=7.1 Hz, 3H). LCMS for $C_{18}H_{24}ClFNO_7$ (M+H)+: m/z=420.1. Found: 420.1.

Step 4. Enantiomers 4-[3-chloro-6-ethoxy-2-fluoro-5-(2-methyl-1,3-dioxolan-2-yl)phenyl]pyrrolidin-2-one

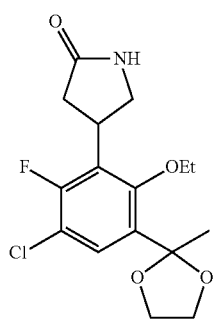 [SMILES: CCOc1c(C2(C)OCCO2)cc(Cl)c(F)c1C1CNC(=O)C1]

A suspension of ethyl 3-[3-chloro-6-ethoxy-2-fluoro-5-(2-methyl-1,3-dioxolan-2-yl)phenyl]-4-nitrobutanoate (1.0 g, 2.4 mmol) (from Step 3) in ethanol (16 mL) was warmed to dissolve the solid. The solution was cooled back to ambient temperature, degassed with nitrogen, and treated with a slurry of 2800 Raney Nickel in water (1.5 mL). The reaction mixture was degassed again with nitrogen and hydrogenated with a balloon of hydrogen for 3 h. The reaction mixture was filtered through Celite and concentrated to give the intermediate amino ester (0.93 g, 100%). The intermediate amino ester was dissolved in toluene (12 mL) and heated at 110° C. for 12 h. The reaction mixture was cooled to ambient temperature, at which point a solid precipitated from solution. This mixture was cooled to 0° C., stirred for 30 min, filtered, washed with cold toluene, and dried to give the desired product as a mixture of enantiomers (0.61 g, 75%). LCMS for $C_{16}H_{20}ClFNO_4$ (M+H)+: m/z=344.1. Found: 344.1. The mixture of enantiomers was separated by chiral HPLC to give the individual enantiomers as peak 1 and peak 2 (RT=5.39 min and 7.01 min, respectively; Phenomenex Lux Cellulose C-1, 21.2×250 mm, 5 micron particle size, eluting with 20% ethanol in hexanes at 18 mL/min).

Step 5. Enantiomers of 4-(3-acetyl-5-chloro-2-ethoxy-6-fluorophenyl)pyrrolidin-2-one

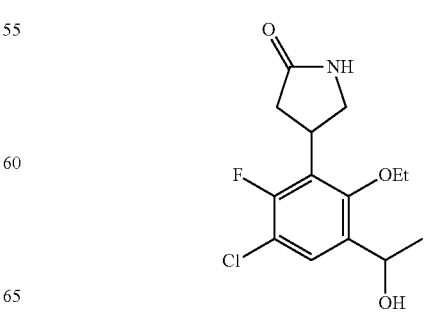

The separated enantiomers from step 4 were each processed individually to the final compounds. A solution of 4-[3-chloro-6-ethoxy-2-fluoro-5-(2-methyl-1,3-dioxolan-2-yl)phenyl]pyrrolidin-2-one (1.7 g, 5.0 mmol) (from Step 4) in methanol (17 mL) was treated with 6.0 M hydrogen chloride in water (11 mL, 69 mmol) dropwise and stirred 20° C. for 30 min. The reaction mixture was added dropwise to ice cooled saturated sodium bicarbonate solution (75 ml) and extracted with ethyl acetate (2×100 ml). The combined organic extracts were washed with brine, dried over sodium sulfate, filtered, and concentrated to give the desired products [from peak 1 (1.5 g, 99%); from peak 2 (1.5 g, 99%)] that were used without further purification. From peak 1: $^1$H NMR (400 MHz, DMSO-d$_6$) δ 7.84 (s, 1H), 7.70 (d, J=8.6 Hz, 1H), 4.16-3.99 (m, 1H), 3.83 (q, J=7.0 Hz, 2H), 3.65-3.54 (m, 1H), 3.30-3.23 (m, 1H), 2.55 (s, 3H), 2.33 (dd, J=16.8, 8.4 Hz, 1H), 1.30 (t, J=7.0 Hz, 3H). LCMS for $C_{14}H_{16}ClFNO_3$ (M+H)+: m/z=300.1. Found: 300.0. From peak 2: $^1$H NMR (400 MHz, DMSO-d$_6$) δ 7.84 (s, 1H), 7.70 (d, J=8.6 Hz, 1H), 4.13-4.00 (m, 1H), 3.87-3.77 (m, 2H), 3.65-3.55 (m, 1H), 3.31-3.23 (m, 1H), 2.55 (s, 3H), 2.32 (ddd, J=16.9, 8.4, 1.6 Hz, 1H), 1.30 (t, J=7.0 Hz, 3H). LCMS for $C_{14}H_{16}ClFNO_3$ (M+H)+: m/z=300.1. Found: 300.1.

Step 6. Diastereoisomers of 4-[3-chloro-6-ethoxy-2-fluoro-5-(1-hydroxyethyl)phenyl]pyrrolidin-2-one The enantiomers from step 5 were each processed individually to the final products. A solution of 4-(3-acetyl-5-chloro-2-ethoxy-6-fluorophenyl)pyrrolidin-2-one (0.402 g, 1.34 mmol) (from Step 5) in anhydrous methanol (6.7 mL) under an atmosphere of nitrogen at 0° C. was treated with sodium tetrahydroborate (0.10 g, 2.7 mmol) and stirred at 0° C. for 30 min. The reaction mixture was quenched with water at 0° C. and poured into water (50 mL)/ethyl acetate (100 mL) while stirring. The mixture was warmed to ambient temperature and the aqueous layer was separated and extracted with additional ethyl acetate (50 mL). The combined organic extracts were washed with brine, dried over sodium sulfate, filtered, and concentrated to give white foams. The crude material were purified by flash column chromatography using acetonitrile (containing 7% methanol) in dichloromethane (0%-100%) to give the desired products as mixtures of diastereoisomers [from peak 1 (0.40 g, 99%); from peak 2 (0.40 g, 99%)]. From peak 1: LCMS for $C_{14}H_{18}ClFNO_3$ $(M+H)^+$: m/z=302.1. Found: 302.0. From peak 2: LCMS for $C_{14}H_{18}ClFNO_3$ $(M+H)^+$: m/z=302.1. Found: 302.1.

Step 7. Diastereoisomers of 4-[3-chloro-5-(1-chloroethyl)-6-ethoxy-2-fluorophenyl]pyrrolidin-2-one

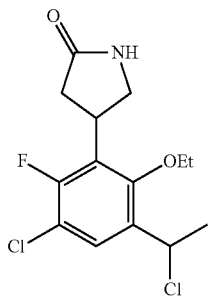 [SMILES: CCOc1c(C(C)Cl)cc(Cl)c(F)c1C1CNC(=O)C1]

The mixture of diastereoisomers from step 6 were each processed individually to the final products. A solution of 4-[3-chloro-6-ethoxy-2-fluoro-5-(1-hydroxyethyl)phenyl]pyrrolidin-2-one (0.41 g, 1.4 mmol) (from Step 6) in methylene chloride (12 mL) was treated with N,N-dimethylformamide (0.011 mL, 0.14 mmol) followed by thionyl chloride (0.21 mL, 2.9 mmol) dropwise and stirred at 20° C. for 30 min. The reaction mixture was added dropwise to ice cooled saturated sodium bicarbonate solution and extracted with dichloromethane. The organic layer was separated and washed with brine, dried over sodium sulfate, filtered, and concentrated to give the desired products [from peak 1 (0.38 g, 87%); from peak 2 (0.39 g, 89%)] along with 17-18% of the styrene that formed from chloride elimination. These mixtures were used without further purification. From peak 1: LCMS for $C_{14}H_{17}Cl_2FNO_2$ $(M+H)^+$: m/z=320.1. Found: 320.0. From peak 2: LCMS for $C_{14}H_{17}Cl_2FNO_2$ $(M+H)^+$: m/z=320.1. Found: 320.0.

Step 8. Diastereoisomers of 4-{3-[1-(4-amino-3-methyl-1H-pyrazolo[3,4-d]pyrimidin-1-yl)ethyl]-5-chloro-2-ethoxy-6-fluorophenyl}pyrrolidin-2-one

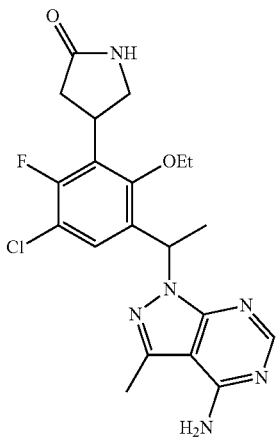 [SMILES: CCOc1c(C(C)n2nc(C)c3c(N)ncnc32)cc(Cl)c(F)c1C1CNC(=O)C1]

The mixture of diastereoisomers from step 7 were each processed individually to the final products. A mixture of 4-[3-chloro-5-(1-chloroethyl)-6-ethoxy-2-fluorophenyl]pyrrolidin-2-one (0.36 g, 1.1 mmol) (from Step 7), 3-methyl-1H-pyrazolo[3,4-d]pyrimidin-4-amine (0.19 g, 1.3 mmol), cesium carbonate (0.54 g, 1.7 mmol) and potassium iodide (18 mg, 0.11 mmol) in N,N-dimethylformamide (7.4 mL) was heated at 100° C. for 4.5 h. The reaction mixture was poured into water (30 ml) and extracted with ethyl acetate (3×50 mL) to give a mixture of diastereoisomer ((S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one; (R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one; (S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one; and (R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one). The mixture of diastereoisomers were purified by preparative LCMS (XBridge C18 column, eluting with a gradient of acetonitrile/water containing 0.1% ammonium hydroxide, at flow rate of 60 mL/min) to give the desired products [from peak 1 were isolated peak A (compound 345) (0.13 g, 54%) and peak B (compound 346) (0.11 g, 46%); from peak 2 were isolated peak A (compound 347) (0.15 g, 63%) and peak B (compound 348) (0.14 g, 55%)]. Compound 346: $^1$H NMR (300 MHz, DMSO-$d_6$) δ 8.12 (s, 1H), 7.82 (s, 1H), 7.52 (d, J=8.5 Hz, 1H), 7.30 (br s, 1H), 6.23 (q, J=7.0 Hz, 1H), 4.05-3.90 (m, 1H), 3.88-3.78 (m, 2H), 3.63-3.53 (m, 1H), 3.29-3.20 (m, 1H), 2.54 (s, 3H), 2.38-2.21 (m, 1H), 1.70 (d, J=7.1 Hz, 3H), 1.39 (t, J=6.9 Hz, 3H). LCMS for $C_{20}H_{23}ClFN_6O_2$ $(M+H)^+$: m/z=433.2. Found: 433.1. Compound 347: $^1$H NMR (500 MHz, DMSO-$d_6$) δ 8.12 (s, 1H), 7.77 (s, 1H), 7.53 (d, J=8.5 Hz, 1H), 7.26 (br s, 2H), 6.24 (q, J=7.0 Hz, 1H), 4.04-3.94 (m, 1H), 3.93-3.85 (m, 1H), 3.84-3.77 (m, 1H), 3.61-3.53 (m, 1H), 3.27-3.22 (m, 1H), 2.54 (s, 3H), 2.30 (dd, J=18.1, 8.6 Hz, 1H), 1.71 (d, J=7.1 Hz, 3H), 1.40 (t, J=6.9 Hz, 3H). LCMS for $C_{20}H_{23}ClFN_6O_2$ $(M+H)^+$: m/z=433.2. Found: 433.1.

Examples 349-352

Diastereoisomers of 4-[1-(4-amino-3-methyl-1H-pyrazolo[3,4-d]pyrimidin-1-yl)ethyl]-6-chloro-3-ethoxy-2-(5-oxopyrrolidin-3-yl)benzonitrile

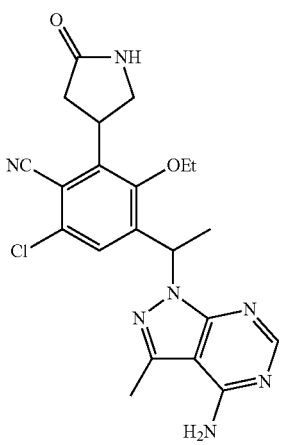

Step 1. Enantiomers of 4-acetyl-6-chloro-3-ethoxy-2-(5-oxopyrrolidin-3-yl)benzonitrile

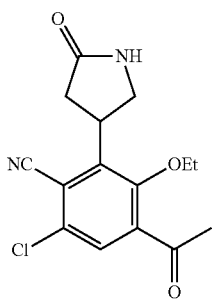 [SMILES: CCOc1c(C(C)=O)cc(Cl)c(C#N)c1C1CNC(=O)C1]

A racemic mixture of 4-(3-acetyl-5-chloro-2-ethoxy-6-fluorophenyl)pyrrolidin-2-one (0.20 g, 0.67 mmol) (from Example 345, Step 5) and sodium cyanide (0.057 g, 1.2 mmol) in dimethyl sulfoxide (1.5 mL) was stirred at 80° C. for 3 h. The reaction mixture was poured into water (35 mL) and extracted with ethyl acetate (2×50 mL). The combined organic extracts were washed with brine, dried over sodium sulfate, filtered, and concentrated to give a crude residue. The crude material was purified by flash column chromatography using ether (containing 10% methanol) in hexanes (0%-100%) to give the desired product (0.15 g, 71%) as a mixture of enantiomers. LCMS for $C_{15}H_{16}ClN_2O_3$ (M+H)$^+$: m/z=307.1. Found: 307.0. The mixture of enantiomers was separated by chiral HPLC to give the individual enantiomers as peak 1 and peak 2 (RT=5.00 min and 10.4 min; Phenomenex Lux Cellulose C-2, 21.2×250 mm, 5 micron particle size, eluting with 60% ethanol in hexanes at 18 mL/min).

Step 2. Diastereoisomers of 6-chloro-3-ethoxy-4-(1-hydroxyethyl)-2-(5-oxopyrrolidin-3-yl)benzonitrile

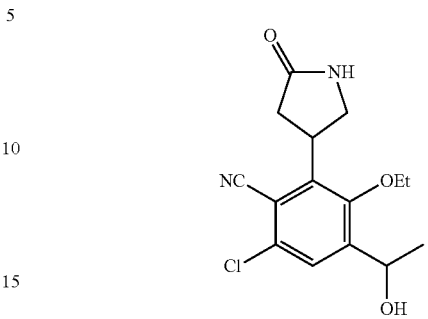

The enantiomers from step 1 were each processed individually to the final products. A solution of 4-acetyl-6-chloro-3-ethoxy-2-(5-oxopyrrolidin-3-yl)benzonitrile (from peak 1: 0.83 g, 2.7 mmol; from peak 2: 0.86 g, 2.8 mmol) in anhydrous methanol (14 mL) under an atmosphere of nitrogen at 0° C. was treated with sodium tetrahydroborate (0.20 g, 5.4 mmol) and stirred at 0° C. for 30 min. The reaction mixture was quenched with water at 0° C. and poured into water (50 mL)/ethyl acetate (100 mL) while stirring. The mixture was warmed to ambient temperature and the aqueous layer was separated and extracted with additional ethyl acetate (50 mL). The combined organic extracts were washed with brine, dried over sodium sulfate, filtered, and concentrated to give the desired products as mixtures of diastereoisomers [from peak 1 (0.83 g, 99%); from peak 2 (0.87 g, 99%)]. From peak 1: LCMS for $C_{15}H_{18}ClN_2O_3$ (M+H)$^+$: m/z=309.1. Found: 309.1. From peak 2: LCMS for $C_{15}H_{18}ClN_2O_3$ (M+H)$^+$: m/z=309.1. Found: 309.1.

Step 3. Diastereoisomers of 6-chloro-4-(1-chloroethyl)-3-ethoxy-2-(5-oxopyrrolidin-3-yl)benzonitrile

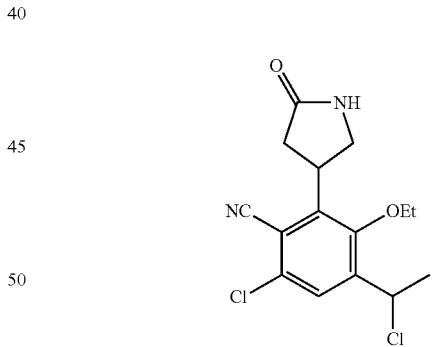

The mixture of diastereoisomers from step 2 were each processed individually to the final products. A solution of 6-chloro-3-ethoxy-4-(1-hydroxyethyl)-2-(5-oxopyrrolidin-3-yl)benzonitrile (from peak 1: 0.83 g, 2.7 mmol; from peak 2: 0.87 g, 2.8 mmol) in methylene chloride (23 mL) was treated with N,N-dimethylformamide (0.021 mL, 0.27 mmol) followed by thionyl chloride (0.490 mL, 6.72 mmol) dropwise and stirred at 20° C. for 2 h. The reaction mixture was added dropwise to ice cooled saturated sodium bicarbonate solution and extracted with dichloromethane. The organic layer was separated and washed with brine, dried over sodium sulfate, filtered, and concentrated to give the desired products as mixtures of diastereoisomers [from peak 1 (0.85 g, 97%); from peak 2 (0.90 g, 98%)]. These mixtures were used without further purification. From peak 1: LCMS for $C_{15}H_{17}Cl_2N_2O_2$ (M+H)+: m/z=327.1. Found: 327.1. From peak 2: LCMS for $C_{15}H_{17}Cl_2N_2O_2$ (M+H)+: m/z=327.1. Found: 327.1.

Step 4. Diastereoisomers of 4-[1-(4-amino-3-methyl-1H-pyrazolo[3,4-d]pyrimidin-1-yl)ethyl]-6-chloro-3-ethoxy-2-(5-oxopyrrolidin-3-yl)benzonitrile

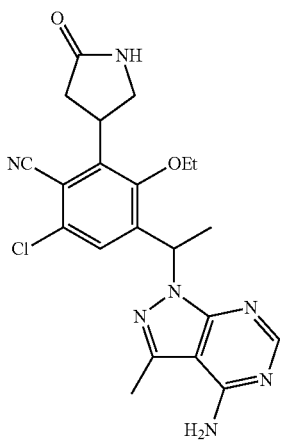 [SMILES: CCOc1c(C(C)n2nc(C)c3c(N)ncnc32)cc(Cl)c(C#N)c1C1CNC(=O)C1]

The mixture of diastereoisomers from step 3 were each processed individually. A mixture of 6-chloro-4-(1-chloroethyl)-3-ethoxy-2-(5-oxopyrrolidin-3-yl)benzonitrile (from peak 1: 0.85 g, 2.6 mmol; from peak 2: 0.89 g, 2.7 mmol), 3-methyl-1H-pyrazolo[3,4-d]pyrimidin-4-amine (0.46 g, 3.1 mmol), cesium carbonate (1.3 g, 3.9 mmol) and potassium iodide (43 mg, 0.26 mmol) in N,N-dimethylformamide (17 mL, 220 mmol) was heated at 90° C. for 3 h.

The reaction mixture was poured into water (100 mL)/ethyl acetate (100 mL) and filtered through Celite to remove black solids. The aqueous layer was separated and extracted with ethyl acetate (2×100 mL). The combined organic extracts were washed with brine, dried over sodium sulfate, filtered, and concentrated to give white foams. The crude material were purified by flash column chromatography using methanol in dichloromethane (0%-20%) to give the desired products as mixtures of diastereoisomers [from peak 1 (0.49 g, 43%); from peak 2 (0.53 g, 44%)]. Analytical chiral HPLC analysis of the diastereoisomers from peak 1 revealed a mixture of four peaks instead of the desired two due to epimerization. Analysis of the diastereoisomers from peak 2 also revealed four peaks. Both sets of mixtures were combined and purified via chiral HPLC to give four individual peaks (RT=6.41 min, 8.13 min, 9.93 min, 14.4 min; Phenomenex Lux Cellulose C-2, 21.2×250 mm, 5 micron particle size, eluting with 60% ethanol in hexanes at 18 mL/min) The compounds of peak 1 (compound 351), peak 2 (compound 349), peak 3 (compound 352), and peak 4 (compound 350) were then tested in the assays of Example A3 and B2. Compound 349: ¹H NMR (500 MHz, DMSO-$d_6$) δ 8.12 (s, 1H), 7.88 (s, 1H), 7.58 (s, 1H), 7.30 (br s, 2H), 6.26 (q, J=7.0 Hz, 1H), 4.32-4.20 (m, 1H), 4.00-3.91 (m, 1H), 3.90-3.81 (m, 1H), 3.65-3.59 (m, 1H), 3.49-3.42 (m, 1H), 2.55 (s, 3H), 1.74 (d, J=7.0 Hz, 3H), 1.43 (t, J=6.9 Hz, 3H). LCMS for $C_{21}H_{23}ClN_7O_2$ (M+H)+: m/z=440.2. Found: 440.2. Compound 352: ¹H NMR (500 MHz, DMSO-$d_6$) δ 8.12 (s, 1H), 7.88 (s, 1H), 7.56 (s, 1H), 7.30 (br s, 2H), 6.26 (q, J=7.0 Hz, 1H), 4.32-4.19 (m, 1H), 3.97-3.82 (m, 2H), 3.67-3.59 (m, 1H), 3.49-3.40 (m, 1H), 2.59-2.52 (m, 3H), 1.73 (d, J=7.0 Hz, 3H), 1.42 (t, J=6.9 Hz, 3H). LCMS for $C_{21}H_{23}ClN_7O_2$ (M+H)+: m/z=440.2. Found: 440.2.

Examples 353 and 354

Diastereomers of 4-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one

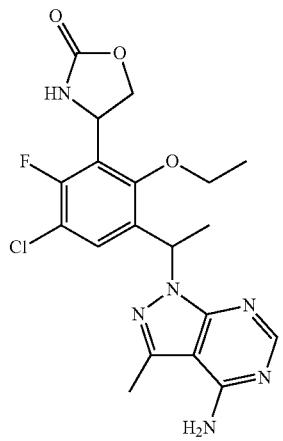 [SMILES: CCOc1c(C(C)n2nc(C)c3c(N)ncnc32)cc(Cl)c(F)c1C1COC(=O)N1]

Step 1: 1-(5-Chloro-2-ethoxy-4-fluoro-3-vinylphenyl)ethanone

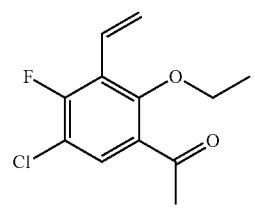 [SMILES: C=Cc1c(F)c(Cl)cc(C(C)=O)c1OCC]

A mixture of 1-(5-chloro-2-ethoxy-4-fluoro-3-iodophenyl)ethanone (13.3 g, 38.8 mmol) (from Example 139, Step 1), 4,4,5,5-tetramethyl-2-vinyl-1,3,2-dioxaborolane (7.9 mL, 46 mmol), [1,1'-bis(diphenylphosphino)ferrocene]dichloropalladium(II), complex with dichloromethane (1:1) (1.0 g, 1.0 mmol) and potassium carbonate (16 g, 120 mmol) in 1,4-dioxane (200 mL) and water (100 mL) was heated at 80° C. for 2 hours. The mixture was cooled to rt and extracted with ethyl acetate. The extracts were washed with brine, dried over sodium sulfate, filtered and concentrated. Purification on silica gel using ethyl acetate in hexanes (0-30%) gave the desired compound, 7.0 g, 74%. LCMS calculated for $C_{12}H_{13}ClFO_2$ (M+H)+: m/z=243.0. found: 243.1.

Step 2: 1-[5-Chloro-3-(1,2-dihydroxyethyl)-2-ethoxy-4-fluorophenyl]ethanone

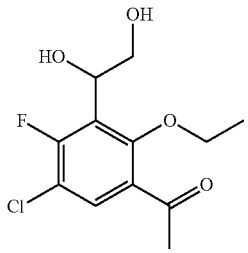 [SMILES: CCOc1c(C(C)=O)cc(Cl)c(F)c1C(O)CO]

AD-mix-alpha (5.8 g, 7.3 mmol) (Aldrich #392758) was stirred in tert-butyl alcohol (21 mL) with water (21 mL) for 15 minutes. 1-(5-chloro-2-ethoxy-4-fluoro-3-vinylphenyl)ethanone (1.0 g, 4.1 mmol) (from Step 1) was added and the suspension was stirred for 16 hours. Sodium sulfite (6.2 g, 49 mmol) was added and the suspension was stirred for 15 minutes. The reaction mixture was extracted with ethyl acetate. The extracts were washed with brine and dried over sodium sulfate, filtered and evaporated. Purification on silica gel using ethyl acetate in hexanes (0-80%) gave the desired compound as a racemic mixture, 900 mg, 80%. Chiral purification on Phenomenex Lux Cellulose C-2, 21.2×250 mm (Chiral Technologies), 5 micron particle size, at flow rate of 18 mL/min using 20% ethanol in hexanes gave peak 1 (single enantiomer) (retention time=7.88 minutes) and peak 2 (single enantiomer) (retention time=11 minutes); the desired enantiomer was peak 2. LCMS calculated for $C_{12}H_{13}ClFO_3$ (M-OH)$^+$: m/z=259.1. found: 259.1.

Step 3: 1-[3-(2-{[tert-Butyl(dimethyl)silyl]oxy}-1-hydroxyethyl)-5-chloro-2-ethoxy-4-fluorophenyl]ethanone

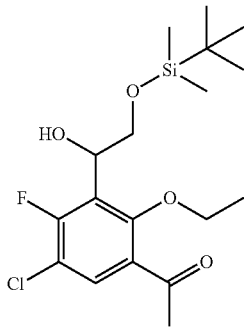 [SMILES: CCOc1c(C(C)=O)cc(Cl)c(F)c1C(O)CO[Si](C)(C)C(C)(C)C]

1-[5-Chloro-3-(1,2-dihydroxyethyl)-2-ethoxy-4-fluorophenyl]ethanone (700 mg, 2 mmol) (from Step 2, peak 2) was stirred in 1,2-dichloroethane (6 mL) with N,N-diisopropylethylamine (4.0 mL, 23 mmol) and a 1.0 M solution of tert-butyldimethylsilyl chloride in 1,2-dichloroethane (7.6 mL) was added. The mixture was heated to 80° C. for 3 hours and cooled to rt. Evaporation and purification on silica gel using ethyl acetate in hexanes (0-50%) gave the desired compound 800 mg, 80%. LCMS calculated for $C_{18}H_{28}ClFO_4SiNa$ (M+Na)$^+$: m/z=413.1. found: 413.1.

Step 4: 1-(3-Acetyl-5-chloro-2-ethoxy-6-fluorophenyl)-2-{[tert-butyl(dimethyl)silyl]oxy}ethyl methanesulfonate

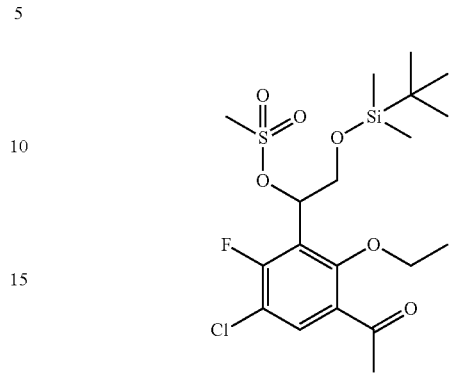

1-[3-(2-{[tert-Butyl(dimethyl)silyl]oxy}-1-hydroxyethyl)-5-chloro-2-ethoxy-4-fluorophenyl]ethanone (700 mg, 2.0 mmol) (from Step 3) was stirred in 1,2-dichloroethane (15 mL) with triethylamine (2.0 mL, 14 mmol) and methanesulfonic anhydride (670 mg, 3.8 mmol) at rt for 1.5 hours. The mixture was poured into brine and extracted with dichloromethane. The extracts were dried over sodium sulfate, filtered and evaporated to give the desired compound 830 mg, 100%. LCMS calculated for $C_{18}H_{27}ClFO_3Si$ (M-OMs)$^+$: m/z=373.1. found: 373.1.

Step 5: 1-[3-(1-Azido-2-{[tert-butyl(dimethyl)silyl]oxy}ethyl)-5-chloro-2-ethoxy-4-fluorophenyl]ethanone

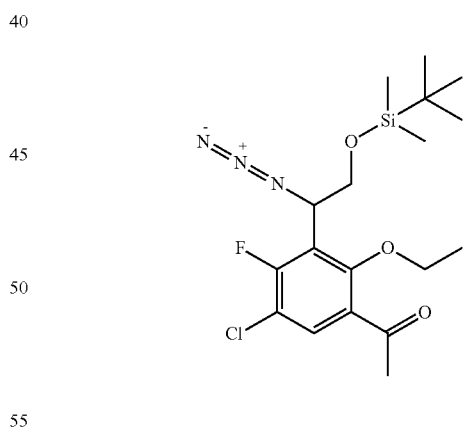

1-(3-Acetyl-5-chloro-2-ethoxy-6-fluorophenyl)-2-{[tert-butyl(dimethyl)silyl]oxy}ethyl methanesulfonate (0.83 g, 1.77 mmol) (from Step 4) was stirred in dimethyl sulfoxide (10 mL) and sodium azide (0.12 g, 1.8 mmol) was added. The mixture was heated to 50° C. for 1 hour and cooled to rt. The mixture was poured into brine and extracted with ethyl acetate. The extracts were dried over sodium sulfate, filtered and evaporated to give the desired compound 736 mg, 100%. LCMS calculated for $C_{18}H_{27}ClFN_3O_3SiNa$ (M+Na)$^+$: m/z=438.1. found: 438.1.

Step 6: 1-[3-(1-Amino-2-{[tert-butyl(dimethyl)silyl]oxy}ethyl)-5-chloro-2-ethoxy-4-fluorophenyl]ethanone

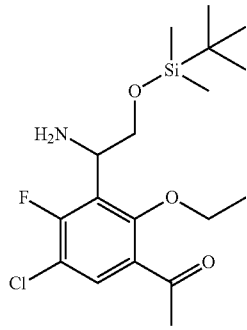 [SMILES: CCOc1c(C(C)=O)cc(Cl)c(F)c1C(N)CO[Si](C)(C)C(C)(C)C]

1-[3-(1-Azido-2-{[tert-butyl(dimethyl)silyl]oxy}ethyl)-5-chloro-2-ethoxy-4-fluorophenyl]ethanone (750 mg, 1.8 mmol) (from Step 5) was stirred in tetrahydrofuran (10 mL) with water (0.33 mL) and triphenylphosphine was added. The mixture was heated to 60° C. for 2 hours and cooled to rt. Brine was added and the mixture was extracted with ethyl acetate. The extracts were dried over sodium sulfate, filtered and evaporated to give the desired compound 700 mg, 100%. LCMS calculated for $C_{18}H_{30}ClFNO_3Si$ (M+H)$^+$: m/z=390.2. found: 390.2.

Step 7: tert-Butyl (1-(3-acetyl-5-chloro-2-ethoxy-6-fluorophenyl)-2-{[tert-butyl(dimethyl)silyl]oxy}ethyl)carbamate

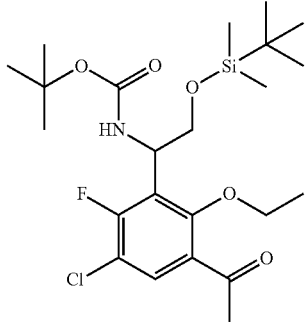 [SMILES: CCOc1c(C(C)=O)cc(Cl)c(F)c1C(CO[Si](C)(C)C(C)(C)C)NC(=O)OC(C)(C)C]

1-[3-(1-Amino-2-{[tert-butyl(dimethyl)silyl]oxy}ethyl)-5-chloro-2-ethoxy-4-fluorophenyl]ethanone (700 mg, 2.0 mmol) (from Step 6) was stirred in tetrahydrofuran (30 mL) with di-tert-butyldicarbonate (780 mg, 3.6 mmol) and N,N-diisopropylethylamine (0.94 mL, 5.4 mmol) was added. The mixture was stirred at rt for 30 minutes. Brine was added and the mixture was extracted with ethyl acetate. The extracts were dried over sodium sulfate, filtered and evaporated. Purification on silica gel using ethyl acetate in hexanes (0-30%) gave the desired compound 550 mg, 60%. LCMS calculated for $C_{23}H_{37}ClFNO_5SiNa$ (M+Na)$^+$: m/z=512.2. found: 512.2.

Step 8: tert-Butyl [7-(3-acetyl-5-chloro-2-ethoxy-6-fluorophenyl)-2-hydroxyethyl]carbamate

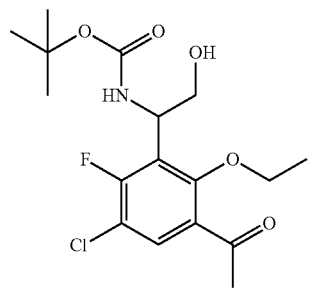 [SMILES: CCOc1c(C(C)=O)cc(Cl)c(F)c1C(CO)NC(=O)OC(C)(C)C]

Tert-Butyl (1-(3-acetyl-5-chloro-2-ethoxy-6-fluorophenyl)-2-{[tert-butyl(dimethyl)silyl]oxy}ethyl)carbamate (500 mg, 1.0 mmol) (from Step 7) was stirred in tetrahydrofuran (10 mL) and a 1.0 M solution of tetra-n-butylammonium fluoride in tetrahydrofuran (1.5 mL) was added. The mixture was stirred at rt for 30 minutes and evaporated. Purification on silica gel using ethyl acetate in hexanes (0-50%) gave the desired compound 238 mg, 60%. LCMS calculated for $C_{17}H_{23}ClFNO_5Na$ (M+Na)$^+$: m/z=398.1. found: 398.1.

Step 9: 4-(3-Acetyl-5-chloro-2-ethoxy-6-fluorophenyl)-1,3-oxazolidin-2-one

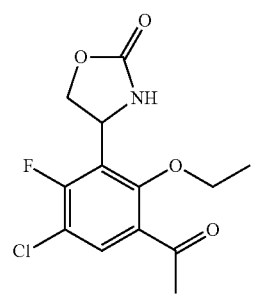 [SMILES: CCOc1c(C(C)=O)cc(Cl)c(F)c1C1COC(=O)N1]

tert-Butyl [1-(3-acetyl-5-chloro-2-ethoxy-6-fluorophenyl)-2-hydroxyethyl]carbamate (234 mg, 0.62 mmol) (from Step 8) was dissolved in 1,2-dichloroethane (12 mL) and a solution of 2.0 M phosgene in toluene (0.93 mL) was added. The mixture was heated to 80° C. for 1.5 hours. Evaporation and purification on silica gel using ethyl acetate in hexanes (0-85%) gave the desired compound, 175 mg, 93%. LCMS calculated for $C_{13}H_{14}ClFNO_4$ (M+H)$^+$: m/z=302.1. found: 302.1.

Step 10: 4-[3-chloro-6-ethoxy-2-fluoro-5-(1-hydroxyethyl)phenyl]-1,3-oxazolidin-2-one Step 12: 4-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one

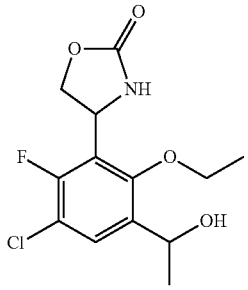 [SMILES: CCOc1c(C(C)O)cc(Cl)c(F)c1C1COC(=O)N1]

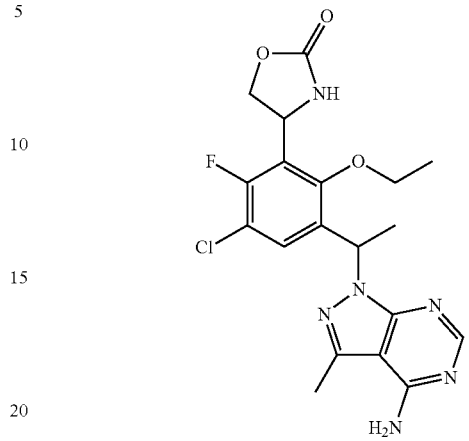

4-(3-Acetyl-5-chloro-2-ethoxy-6-fluorophenyl)-1,3-oxazolidin-2-one (175 mg, 0.58 mmol) was stirred in methanol (10 mL) at 0° C. and sodium tetrahydroborate (33 mg, 0.87 mmol) was added. The mixture was stirred at rt for 1 hour and evaporated. Water was added and the mixture was extracted with ethyl acetate. The extracts were washed with brine, dried over sodium sulfate, filtered and evaporated to give an approximate 1:1 mixture of diastereomers, 175 mg, 99%. LCMS calculated for $C_{13}H_{15}ClFNO_4Na$ (M+Na)$^+$: m/z=326.1. found: 326.1.

Step 11: 4-[3-chloro-5-(chloroethyl)-6-ethoxy-2-fluorophenyl]-1,3-oxazolidin-2-one 4-[3-chloro-5-(chloroethyl)-6-ethoxy-2-fluorophenyl]-1,3-oxazolidin-2-one (160 mg, 0.50 mmol) (from Step 11) was stirred in N,N-dimethylformamide (21 mL) with cesium carbonate (324 mg, 0.99 mmol) and 3-methyl-1H-pyrazolo[3,4-d]pyrimidin-4-amine (89 mg, 0.60 mmol) was added. The mixture was heated to 80° C. for 1.5 hours and cooled to rt. The mixture was diluted with water and extracted with ethyl acetate. The extracts were washed with brine, dried over sodium sulfate, filtered and evaporated. Purification by preparative LCMS (pH 10) using RP-HPLC (XBridge C18 column, eluting with a gradient of acetonitrile/water containing 0.1% ammonium hydroxide, at flow rate of 30 mL/min) separated the two diastereomers (peak 1 [compound 353] Rt=4.9 min. and peak 2 [compound 354] Rt=5.6 min); providing compound 354 as the desired single enantiomer, 28 mg, 13%. peak 2: LCMS calculated for $C_{19}H_{21}ClFN_6O_3$ (M+H)$^+$: m/z=435.1. found: 435.1. $^1$H NMR (300 MHz, CD$_3$OD): δ 8.15 (s, 1H), 7.62 (m, 1H), 6.31 (m, 1H), 5.39 (m, 1H), 4.79 (m, 1H), 4.40 (m, 1H), 3.95 (m, 1H), 3.80 (m, 1H), 2.60 (s, 3H), 1.80 (m, 3H), 1.40 (m, 3H).

Examples 355-358

Diastereomers of 5-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one

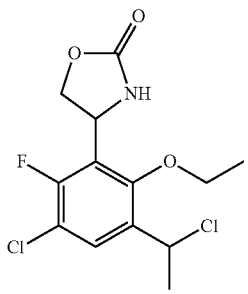 [SMILES: CCOc1c(C(C)Cl)cc(Cl)c(F)c1C1COC(=O)N1]

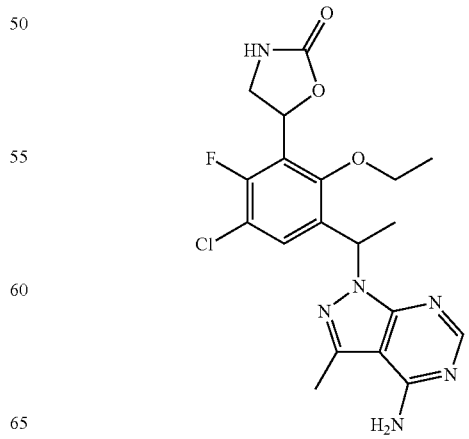

4-[3-chloro-6-ethoxy-2-fluoro-5-(1-hydroxyethyl)phenyl]-1,3-oxazolidin-2-one (150 mg, 0.49 mmol) (from Step 10) was stirred in dichloromethane (4 mL) with N,N-dimethylformamide (96 μL) and thionyl chloride (110 μL, 1.5 mmol) was added. The mixture was evaporated. Water was added and the mixture was extracted with ethyl acetate. The extracts were washed with brine, dried over sodium sulfate, filtered and evaporated to give the desired compound, 159 mg, 100%.

Step 1: tert-Butyl [2-(3-acetyl-5-chloro-2-ethoxy-6-fluorophenyl)-2-hydroxyethyl]carbamate

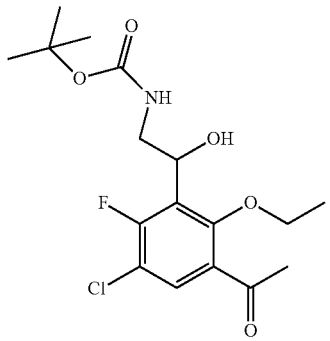 [SMILES: CCOc1c(C(C)=O)cc(Cl)c(F)c1C(O)CNC(=O)OC(C)(C)C]

0.2 M Osmium tetraoxide in water (10 mL) was added to a solution of tert-butyl [(4-chlorobenzoyl)oxy]carbamate (Lawrence Harris, *J. Org. Chem*, 2011, 76, 358-372). (19 g, 70 mmol) in acetonitrile (210 mL) and stirred for 10 minutes. 1-(5-chloro-2-ethoxy-4-fluoro-3-vinylphenyl)ethanone (11.2 g, 46 mmol) (from Example 353, Step 1) as a solution in acetonitrile (210 mL) was added to the carbamate solution followed by the addition of water (50 mL) and the reaction was stirred for 3 hours at room temperature. The reaction was quenched with saturated 10 M dipotassium disulfite in water (240 mL) and stirred for 5 minutes. Water was added and the reaction mixture was extracted with ethyl acetate. The extracts were washed with saturated sodium bicarbonate solution, brine and dried over sodium sulfate, filtered and evaporated. Purification on silica gel using ethyl acetate in hexanes (0-100%) gave the desired compound as a racemic mixture, 16.6 g, 95%. LCMS calculated for $C_{17}H_{23}ClFNO_5Na$ (M+Na)$^+$: m/z=398.1. found: 398.0.

Step 2: 5-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one

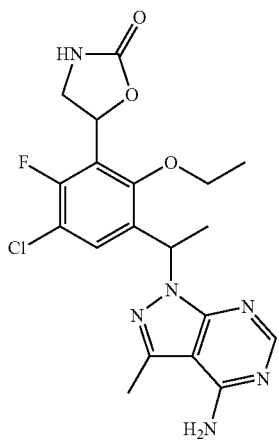 [SMILES: CCOc1c(C(C)n2nc(C)c3c(N)ncnc32)cc(Cl)c(F)c1C1CNC(=O)O1]

The desired single enantiomer (peak 3) was prepared using the same procedure as Example 353 (steps 8-12), except that the intermediate from step 1 in this example was racemic and thus the final separation of the four diastereomers occurred in step 12. Chiral purification on Phenomenex Lux Cellulose C-4, 21×250 mm (Chiral Technologies), 5 micron particle size, at flow rate of 18 mL/min using 30% ethanol in hexanes gave the peak 1: compound 355 (single enantiomer) (retention time=12.7 minutes), peak 2: compound 356 (single enantiomer) (retention time=14.2 minutes), peak 3: compound 357 (single enantiomer) (retention time=20.3 minutes), and peak 4: compound 358 (single enantiomer) (retention time=28.9 minutes); the most active enantiomer was peak 3. LCMS calculated for $C_{19}H_{21}ClFN_6O_3$ (M+H)$^+$: m/z=435.1. found: 435.1. $^1$H NMR (500 MHz, DMSO-d$_6$): δ 8.15 (s, 1H), 7.81 (s, 1H), 7.71 (d, 1H), 7.26 (bs, 1H), 6.23 (m, 1H), 5.84 (t, 1H), 3.92 (m, 1H), 3.83 (m, 1H), 2.52 (s, 3H), 1.75 (d, 3H), 1.40 (m, 3H).

Example 359

5-(3-{1-[4-Amino-5-oxo-6-(1H-pyrazol-4-yl)pyrido[2,3-d]pyrimidin-8(5H)-yl]ethyl}-5-chloro-2-methoxy-6-methylphenyl)-N,N-dimethylpyridine-2-carboxamide

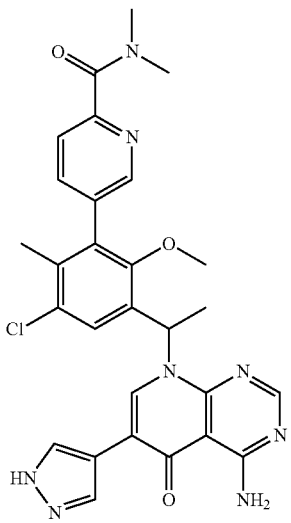 [SMILES: COc1c(C(C)n2cc(-c3cn[nH]c3)c(=O)c3c(N)ncnc32)cc(Cl)c(C)c1-c1ccc(C(=O)N(C)C)nc1]

Step 1.
4-Amino-6-iodopyrido[2,3-d]pyrimidin-5(8H)-one

To a suspension of 4-aminopyrido[2,3-d]pyrimidin-5(8H)-one (from VWR, 0.48 g, 3.0 mmol) in DMF (8 mL) was added N-iodosuccinimide (0.80 g, 3.6 mmol). The resulting mixture was stirred at ambient temperature overnight. The reaction mixture was filtered and washed with ethyl acetate to give the desired product as yellow solid (0.81 g, 95%). LCMS calculated for $C_7H_6IN_4O$ (M+H)$^+$: m/z=289.0. Found: 289.0.

Step 2. 5-{3-[1-(4-Amino-6-iodo-5-oxopyrido[2,3-d]pyrimidin-8(5H)-yl)ethyl]-5-chloro-2-methoxy-6-methylphenyl}-N,N-dimethylpyridine-2-carboxamide

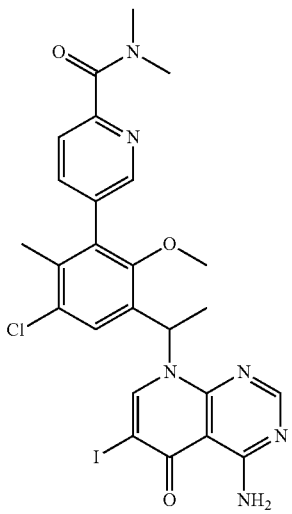 [SMILES: COc1c(C(C)n2cc(I)c(=O)c3c(N)ncnc32)cc(Cl)c(C)c1-c1ccc(C(=O)N(C)C)nc1]

To a mixture of 4-amino-6-iodopyrido[2,3-d]pyrimidin-5 (8H)-one (255 mg, 0.885 mmol), cesium carbonate (0.43 g, 1.3 mmol) and potassium iodide (14.7 mg, 0.0885 mmol) in DMF (9.4 mL) was added 5-[3-chloro-5-(1-chloroethyl)-6-methoxy-2-methylphenyl]-N,N-dimethylpyridine-2-carboxamide (325 mg, 0.885 mmol) (from example 25 step 1) and the mixture was stirred at 140° C. for 1 h. The mixture was diluted with methanol and purified on RP-HPLC (XBridge C18 column, eluting with a gradient of acetonitrile/water containing 0.1% ammonium hydroxide, at flow rate of 30 mL/min) to give the desired compound (221 mg, 40%). LCMS calculated for $C_{25}H_{25}Cl_{1}N_6O_3$ (M+H)$^+$: m/z=619.1. Found: 619.0.

Step 3. 5-(3-{1-[4-Amino-5-oxo-6-(1H-pyrazol-4-yl)pyrido[2,3-d]pyrimidin-8(5H)-yl]ethyl}-5-chloro-2-methoxy-6-methylphenyl)-N,N-dimethylpyridine-2-carboxamide

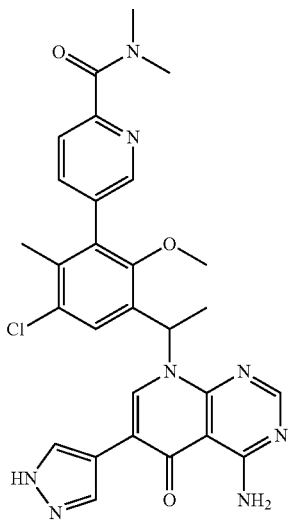 [SMILES: COc1c(C(C)n2cc(-c3cn[nH]c3)c(=O)c3c(N)ncnc32)cc(Cl)c(C)c1-c1ccc(C(=O)N(C)C)nc1]

A mixture of 5-{3-[1-(4-amino-6-iodo-5-oxopyrido[2,3-d]pyrimidin-8(5H)-yl)ethyl]-5-chloro-2-methoxy-6-methylphenyl}-N,N-dimethylpyridine-2-carboxamide (10.3 mg, 0.0166 mmol), 4-(4,4,5,5-tetramethyl-1,3,2-dioxaborolan-2-yl)-1H-pyrazole (3.5 mg, 0.018 mmol), sodium carbonate (3.5 mg, 0.033 mmol) and [1,1'-bis(diphenylphosphino) ferrocene]-dichloropalladium(II), complex with dichloromethane (1:1) (1.6 mg, 0.0020 mmol) in acetonitrile (0.1 mL)/water (0.03 mL) was degassed with $N_2$ and the stirred at 90° C. for 2.0 h. The mixture was diluted with methanol and purified on RP-HPLC (XBridge C18 column, eluting with a gradient of acetonitrile/water containing 0.1% ammonium hydroxide, at flow rate of 30 mL/min) to give the desired product (2.7 mg, 30%). LCMS calculated for $C_{28}H_{28}ClN_8O_3$ (M+H)$^+$: m/z=559.2. Found: 559.2.

Example 360

5-{3-[1-(4-Amino-6-methyl-5-oxopyrido[2,3-d]pyrimidin-8(5H)-yl)ethyl]-5-chloro-2-methoxy-6-methylphenyl}-N,N-dimethylpyridine-2-carboxamide bis(trifluoroacetate)

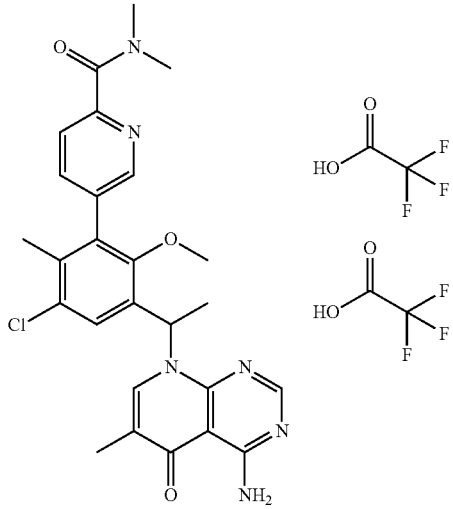

To a microwave vial was charged with 5-{3-[1-(4-amino-6-iodo-5-oxopyrido[2,3-d]pyrimidin-8(5H)-yl)ethyl]-5-chloro-2-methoxy-6-methylphenyl}-N,N-dimethylpyridine-2-carboxamide (24.0 mg, 0.0388 mmol), potassium trifluoro (methyl)borate (9.4 mg, 0.078 mmol), palladium acetate (2.1 mg, 0.0094 mmol), dicyclohexyl(2',6'-diisopropoxybiphenyl-2-yl)phosphine (8.7 mg, 0.019 mmol) and cesium carbonate (38 mg, 0.12 mmol) in toluene (0.5 mL) and water (0.06 mL). The reaction vial was evacuated under high vacuum and backfilled with $N_2$. The reaction mixture was heated at 100° C. overnight. The mixture was diluted with methanol, filtered and purified on RP-HPLC (XBridge C18 column, eluting with a gradient of acetonitrile/water containing 0.05% trifluoroacetic acid, at flow rate of 30 mL/min) to give the desired product as bis-TFA salt (3.0 mg, 15%). LCMS calculated for $C_{26}H_{28}ClN_6O_3$ (M+H)$^+$: m/z=507.2. Found: 507.0.

Examples 361-363

Diastereomers of 4-(1-(4-amino-3-methyl-1H-pyrazolo[3,4-d]pyrimidin-1-yl)ethyl)-6-chloro-2-(1-(2-hydroxypropyl)azetidin-3-yl)-3-methoxybenzonitrile Based on the stereochemistry of Example 269, the stereochemistry of each diastereomer is believed to be 4-((R)-

1-(4-amino-3-methyl-1H-pyrazolo[3,4-d]pyrimidin-1-yl)ethyl)-6-chloro-2-(1-((S)-2-hydroxypropyl)azetidin-3-yl)-3-methoxybenzonitrile (Example 361), 4-((5)-1-(4-amino-3-methyl-1H-pyrazolo[3,4-d]pyrimidin-1-yl)ethyl)-6-chloro-2-(1-((R)-2-hydroxypropyl)azetidin-3-yl)-3-methoxybenzonitrile (Example 362), and 4-((R)-1-(4-amino-3-methyl-1H-pyrazolo[3,4-d]pyrimidin-1-yl)ethyl)-6-chloro-2-(1-((R)-2-hydroxypropyl)azetidin-3-yl)-3-methoxybenzonitrile (Example 363) (structures shown below)

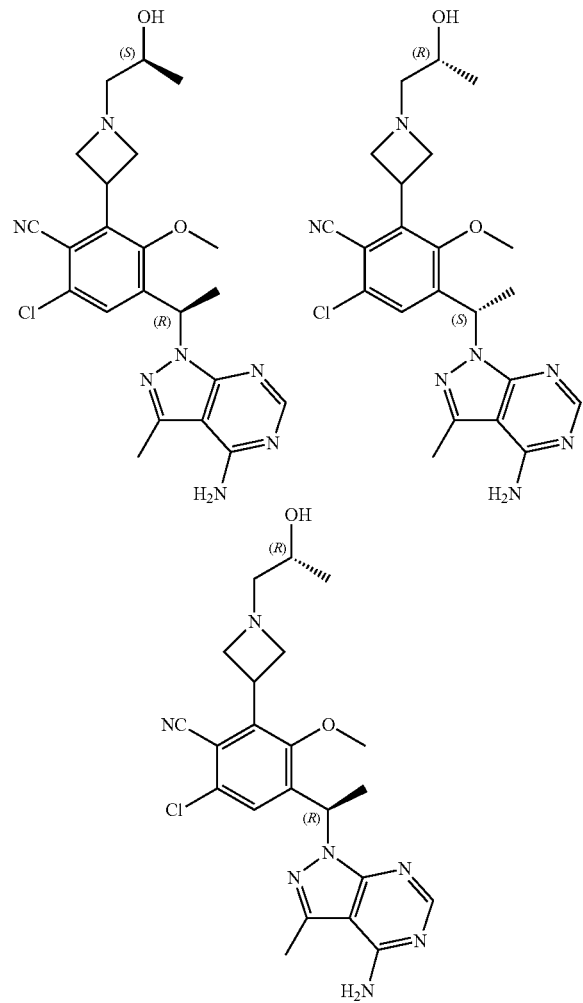

Synthesis of Example 361

To (R)-4-(1-(4-amino-3-methyl-1H-pyrazolo[3,4-d]pyrimidin-1-yl)ethyl)-2-(azetidin-3-yl)-6-chloro-3-methoxybenzonitrile (6.00 g, 14.3 mmol) was added methanol (72 mL). To the resulting suspension was added (S)-(−)-methyloxirane (2.01 mL, 28.6 mmol) at room temperature and the mixture was stirred at room temperature for 19 h. Additional (S)-(−)-methyloxirane (0.50 mL, 7.2 mmol) was added and the stirring was continued for an additional hour. To the reaction mixture was added water (280 mL) and the cloudy solution was stirred. The mixture was extracted with methylene chloride (300 mL×4). The organic layer was combined and washed with brine (50 mL) and concentrated. The crude product was purified by silica column chromatography eluted with MeOH (contained about 0.5% ammonium hydroxide) in methylene chloride. The fractions contained product were collected and evaporated to dryness. This residue was further purified by preparative HPLC to give the title compound. A sample of the title compound was analyzed by NMR spectroscopy and mass spectrometry and gave the following data. $^1$H NMR (500 MHz, DMSO) δ 8.11 (s, 1H), 7.47 (s, 1H), 7.30 (br s, 2H), 6.24 (q, J=7.0 Hz, 1H), 4.32 (br s, 1H), 4.07 (m, 1H), 3.94 (m, 2H), 3.65 (s, 3H), 3.59 (m, 1H), 3.08 (m, 2H), 2.56 (s, 3H), 2.38-2.19 (m, 2H), 1.73 (d, J=7.1 Hz, 3H), 1.00 (d, J=6.2 Hz, 3H) ppm. LCMS for $C_{22}H_{27}ClN_7O_2$ (M+H)$^+$: m/z=456.2. found: 456.2.

Synthesis of Example 362

To (S)-4-(1-(4-amino-3-methyl-1H-pyrazolo[3,4-d]pyrimidin-1-yl)ethyl)-2-(azetidin-3-yl)-6-chloro-3-methoxybenzonitrile (293.0 mg, 0.73 mmol) was added methanol (3.7 mL). To the resulting suspension was added (R)-(+)-methyloxirane 103 μL, 1.46 mmol) at room temperature and the mixture was stirred at room temperature for 19 h. Additional (R)-(+)-methyloxirane (51.3 μL, 0.73 mmol) was added and the stirring was continued for additional 2.5 hours. To the reaction mixture was added water (14 mL) and the cloudy solution was stirred. The mixture was extracted with methylene chloride (4×16 mL). The organic layer was combined and washed with brine (50 mL) and concentrated. The crude product was purified by silica column chromatography, eluted with MeOH (contained about 0.5% ammonium hydroxide) in methylene chloride. The fractions contained product were collected and evaporated to dryness. This residue was further purified by preparative HPLC to give the title compound. A sample of the title compound was analyzed by NMR spectroscopy and mass spectrometry and gave the following data. $^1$H NMR (500 MHz, DMSO) δ 8.11 (s, 1H), 7.47 (s, 1H), 7.30 (br s, 2H), 6.24 (q, J=7.0 Hz, 1H), 4.37 (br s, 1H), 4.09 (m, 2H), 3.93 (m, 2H), 3.65 (s, 3H), 3.59 (m, 1H), 3.12 (m, 2H), 2.56 (s, 3H), 2.39-2.26 (m, 2H), 1.73 (d, J=7.1 Hz, 3H), 1.00 (d, J=6.2 Hz, 3H) ppm. LCMS for $C_{22}H_{27}ClN_7O_2$ (M+H)$^+$: m/z=456.2. found: 456.2.

Synthesis of Example 363

To (R)-4-(1-(4-amino-3-methyl-1H-pyrazolo[3,4-d]pyrimidin-1-yl)ethyl)-2-(azetidin-3-yl)-6-chloro-3-methoxybenzonitrile (6.0 g, 14.3 mmol) was added methanol (72 mL). To the resulting suspension was added (R)-(+)-methyloxirane (2.01 mL, 28.6 mmol) at room temperature and the mixture was stirred at room temperature for 18 h. To the reaction mixture was added water (280 mL) and the cloudy solution was stirred. The mixture was extracted with methylene chloride (300 mL×4). The organic layer was combined and washed with brine (50 mL) and concentrated. The crude product was purified by silica column chromatography, eluted with MeOH (contained about 0.5% ammonium hydroxide) in methylene chloride. The fractions contained product were collected and evaporated to dryness. This residue was further purified by preparative HPLC to give the title compound. A sample of the title compound was analyzed by NMR spectroscopy and mass spectrometry and gave the following data. $^1$H NMR (500 MHz, DMSO) δ 8.11 (s, 1H), 7.46 (s, 1H), 7.29 (br s, 2H), 6.24 (q, J=7.0 Hz, 1H), 4.31 (d, J=4.2 Hz, 1H), 4.11-4.00 (m, 1H), 3.98-3.90 (m, 1H), 3.65 (s, 3H), 3.61-3.53 (m, 2H), 3.07 (m, 2H), 2.56 (s, 3H), 2.28 (d, J=5.9 Hz, 2H), 1.73 (d, J=7.1 Hz, 3H), 1.00 (d, J=6.2 Hz, 3H) ppm.

Three HPLC methods were developed to separate the stereoisomers from the compound of Example 269. Method A was developed to separate the diastereomer Example 361 from Example 269. The retention times of Example 361 from Example 269 are 15.7 min and 11.5 min respectively. Chromatographic conditions are described in Table B1.

TABLE B1

| | |
|---|---|
| Column | Phenomenex Cellulose 3 (250 mm, 4.6 mm, 5 micron) |
| Mobile Phase | 89.9% hexane/10% ethanol/0.1% diethylamine (pre-mixed) |
| Flow Rate | 1 mL/min |
| Run Time | 30 min |
| Detection Wavelength | 247 nm |
| Quantitation | Peak area ratio |

Method B was developed to separate the diastereomer Example 362 from Example 269. The retention times of Example 362 from Example 269 are 26.4 min and 21.7 min respectively. Chromatographic conditions are described in Table B2.

TABLE B2

| | |
|---|---|
| Column | Phenomenex Cellulose 4 (250 mm, 4.6 mm, 5 micron) |
| Mobile Phase | 84.9% hexane/15% ethanol/0.1% diethylamine (pre-mixed) |
| Flow Rate | 1 mL/min |
| Run Time | 40 min |
| Detection Wavelength | 247 nm |
| Quantitation | Peak area ratio |

Method C was developed to separate the three stereoisomers Example 361, Example 362 and Example 363 from Example 269. The stereoisomers Example 361, Example 362 and Example 363 elute at retention time 12.9 min as a broad band while Example 269 elutes at retention time 14.3 min. An estimation of the level of the enantiomer, Example 363 can be made by a combination of data from Methods A, B, and C. Chromatographic conditions are described in Table B3.

TABLE B3

| | |
|---|---|
| Column | Phenomenex Cellulose 1 (250 mm, 4.6 mm, 5 micron) |
| Mobile Phase | 88% hexanes, 12% ethanol (conatins 0.1% diethylamine) |
| Flow Rate | 1 mL/min |
| Run Time | 25 min |
| Detection Wavelength | 247 nm |
| Quantitation | Peak area ratio |

Example A1

PI3K Enzyme Assay

PI3-Kinase luminescent assay kit including lipid kinase substrate, D-myo-phosphatidylinositol 4,5-bisphosphate (PtdIns(4,5)P2)D (+)-sn-1,2-di-O-octanoylglyceryl, 3-O-phospho linked (PIP2), biotinylated I(1,3,4,5)P4, PI(3,4,5)P3 Detector Protein is purchased from Echelon Biosciences (Salt Lake City, Utah). AlphaScreen™ GST Detection Kit including donor and acceptor beads was purchased from PerkinElmer Life Sciences (Waltham, Mass.). PI3Kδ (p110δ/p85α) is purchased from Millipore (Bedford, Mass.). ATP, $MgCl_2$, DTT, EDTA, HEPES and CHAPS are purchased from SigmaAldrich (St. Louis, Mo.).

AlphaScreen™ Assay for PI3Kδ

The kinase reaction are conducted in 384-well REMP plate from Thermo Fisher Scientific in a final volume of 40 μL Inhibitors are first diluted serially in DMSO and added to the plate wells before the addition of other reaction components. The final concentration of DMSO in the assay is 2%. The PI3K assays are carried out at room temperature in 50 mM HEPES, pH 7.4, 5 mM $MgCl_2$, 50 mM NaCl, 5 mM DTT and CHAPS 0.04%. Reactions are initiated by the addition of ATP, the final reaction mixture consisted of 20 μM PIP2, 20 μM ATP, 1.2 nM PI3Kδ are incubated for 20 minutes. 10 μL of reaction mixture are then transferred to 5 μL 50 nM biotinylated I(1,3,4,5)P4 in quench buffer: 50 mM HEPES pH 7.4, 150 mM NaCl, 10 mM EDTA, 5 mM DTT, 0.1% Tween-20, followed with the addition of 10 μL AlphaScreen™ donor and acceptor beads suspended in quench buffer containing 25 nM PI(3,4,5)P3 detector protein. The final concentration of both donor and acceptor beads is 20 mg/ml. After plate sealing, the plate are incubated in a dark location at room temperature for 2 hours. The activity of the product is determined on Fusion-alpha microplate reader (PerkinElmer). $IC_{50}$ determination is performed by fitting the curve of percent control activity versus the log of the inhibitor concentration using the GraphPad Prism 3.0 software.

Example A2

PI3K Enzyme Assay

Materials:

Lipid kinase substrate, phosphoinositol-4,5-bisphosphate (PIP2), are purchased from Echelon Biosciences (Salt Lake City, Utah). PI3K isoforms α, β, δ and γ are purchased from Millipore (Bedford, Mass.). ATP, $MgCl_2$, DTT, EDTA, MOPS and CHAPS are purchased from SigmaAldrich (St. Louis, Mo.).

The kinase reaction are conducted in clear-bottom 96-well plate from Thermo Fisher Scientific in a final volume of 24 μL Inhibitors are first diluted serially in DMSO and added to the plate wells before the addition of other reaction components. The final concentration of DMSO in the assay is 0.5%. The PI3K assays are carried out at room temperature in 20 mM MOPS, pH 6.7, 10 mM $MgCl_2$, 5 mM DTT and CHAPS 0.03%. The reaction mixture is prepared containing 50 μM PIP2, kinase and varying concentration of inhibitors. Reactions are initiated by the addition of ATP containing 2.2 μCi [γ-$^{33}$P]ATP to a final concentration of 1000 μM. The final concentration of PI3K isoforms α, β, δ and γ in the assay were 1.3, 9.4, 2.9 and 10.8 nM, respectively. Reactions are incubated for 180 minutes and terminated by the addition of 100 μL of 1 M potassium phosphate pH 8.0, 30 mM EDTA quench buffer. A 100 μL aliquot of the reaction solution are then transferred to 96-well Millipore MultiScreen IP 0.45 μm PVDF filter plate (The filter plate is prewetted with 200 μL 100% ethanol, distilled water, and 1 M potassium phosphate pH 8.0, respectively). The filter plate is aspirated on a Millipore Manifold under vacuum and washed with 18×200 μL wash buffer containing 1 M potassium phosphate pH 8.0 and 1 mM ATP. After drying by aspiration and blotting, the plate is air dried in an incubator at 37° C. overnight. Packard TopCount adapter (Millipore) is then attached to the plate followed with addition of 120 μL Microscint 20 scintillation cocktail (Perkin Elmer) in each well. After the plate sealing, the radioactivity of the product is determined by scintillation counting on Topcount (PerkinElmer). $IC_{50}$ determination is performed by fitting the curve of percent control activity versus the log of the inhibitor concentration using the GraphPad Prism 3.0 software.

Example A3

PI3Kδ Scintillation Proximity Assay

Materials

[γ-$^{33}$P]ATP (10 mCi/mL) was purchased from PerkinElmer (Waltham, Mass.). Lipid kinase substrate, D-myo-Phosphatidylinositol 4,5-bisphosphate (PtdIns(4,5)P2)D (+)-sn-1,2-di-O-octanoylglyceryl, 3-O-phospho linked (PIP2), CAS 204858-53-7, was purchased from Echelon Biosciences (Salt Lake City, Utah). PI3Kδ (p110δ/p85α) was purchased from Millipore (Bedford, Mass.). ATP, $MgCl_2$, DTT, EDTA, MOPS and CHAPS were purchased from SigmaAldrich (St. Louis, Mo.). Wheat Germ Agglutinin (WGA) YSi SPA Scintillation Beads was purchased from GE healthcare life sciences (Piscataway, N.J.).

The kinase reaction was conducted in polystyrene 384-well matrix white plate from Thermo Fisher Scientific in a final volume of 25 μL Inhibitors were first diluted serially in DMSO and added to the plate wells before the addition of other reaction components. The final concentration of DMSO in the assay was 0.5%. The PI3K assays were carried out at room temperature in 20 mM MOPS, pH 6.7, 10 mM $MgCl_2$, 5 mM DTT and CHAPS 0.03%. Reactions were initiated by the addition of ATP, the final reaction mixture consisted of 20 μM PIP2, 20 μM ATP, 0.2 μCi [γ-$^{33}$P] ATP, 4 nM PI3I(6. Reactions were incubated for 210 min and terminated by the addition of 40 μL SPA beads suspended in quench buffer: 150 mM potassium phosphate pH 8.0, 20% glycerol. 25 mM EDTA, 400 μM ATP. The final concentration of SPA beads was 1.0 mg/mL. After the plate sealing, plates were shaken overnight at room temperature and centrifuged at 1800 rpm for 10 minutes, the radioactivity of the product was determined by scintillation counting on Topcount (PerkinElmer). $IC_{50}$ determination was performed by fitting the curve of percent control activity versus the log of the inhibitor concentration using the GraphPad Prism 3.0 software. $IC_{50}$ data for the Examples is presented in Table 10 as determined by Assay A3. $IC_{50}$ data for Examples 361 and 363 is shown in Table 10a as determined by Assay A2.

TABLE 10

| Example # | PI3Kδ SPA $IC_{50}$ (nM)* |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | ++++ |
| 13 | + |
| 14 | + |
| 15 | + |
| 16 | + |
| 17 | + |
| 18 | + |
| 19 | + |
| 20 (1$^{st}$ peak) | + |
| 20 (2$^{nd}$ peak) | +++ |
| 21 | + |
| 22 | + |
| 23 | + |
| 24 | + |
| 25 (1$^{st}$ peak) | ++++ |
| 25 (2$^{nd}$ peak) | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | ++ |
| 39 | +++ |
| 40 | ++ |
| 41 | +++ |
| 42 | + |
| 43 | + |
| 44 | + |
| 45 | + |
| 46 | + |
| 47 | + |
| 48 | + |
| 49 | + |
| 50 | + |
| 51 | + |
| 52 | + |
| 53 | + |
| 54 | ++ |
| 55 | ++ |
| 56 | ++ |
| 57 | + |
| 58 | + |
| 59 | + |
| 60 | + |
| 61 | + |
| 62 | + |
| 63 | + |
| 64 | + |
| 65 | + |
| 66 | + |
| 67 (1$^{st}$ peak) | + |
| 68 (1$^{st}$ peak) | + |
| 69 | + |
| 70 | + |
| 71 | + |
| 72 | + |
| 73 | + |
| 74 (1$^{st}$ peak) | + |
| 75 | + |
| 76 | + |
| 77 | + |
| 78 | + |
| 79 | + |
| 80 | + |
| 81 | +++ |
| 82 | + |
| 83 | + |
| 84 | +++ |
| 85 | +++ |
| 86 | + |
| 87 | + |
| 88 | + |
| 89 | + |
| 90 | + |
| 91 | + |
| 92 | + |

TABLE 10-continued

| Example # | PI3Kδ SPA IC$_{50}$ (nM)* |
|---|---|
| 93 | + |
| 94 | + |
| 95 | + |
| 96 | + |
| 97 | + |
| 98 | + |
| 99 | + |
| 100 | + |
| 101 | + |
| 102 | + |
| 103 | + |
| 104 | + |
| 105 | + |
| 106 | + |
| 107 | + |
| 108 | + |
| 109 | + |
| 110 | + |
| 111 | + |
| 112 | + |
| 113 | + |
| 114 | + |
| 115 | + |
| 116 | + |
| 117 | + |
| 118 | + |
| 119 | + |
| 120 | + |
| 121 | + |
| 122 | + |
| 123 | + |
| 124 | + |
| 125 | + |
| 126 | + |
| 127 | + |
| 128 | + |
| 129 | + |
| 130 | + |
| 131 | + |
| 132 | + |
| 133 | + |
| 134 | + |
| 135 | + |
| 136 | + |
| 137 | + |
| 138 | + |
| 139 (1$^{st}$ peak) | + |
| 140 | + |
| 141 | + |
| 142 | + |
| 143 | + |
| 144 | + |
| 145 | + |
| 146 | + |
| 147 | + |
| 148 | + |
| 149 | + |
| 150 | + |
| 151 | + |
| 152 | + |
| 153 | + |
| 154 | + |
| 155 | + |
| 156 | + |
| 157 | + |
| 158 | + |
| 159 | + |
| 160 | + |
| 161 | + |
| 162 | + |
| 163 | + |
| 164 | + |
| 165 | + |
| 166 | + |
| 167 | + |
| 168 | + |
| 169 | + |
| 170 | + |

TABLE 10-continued

| Example # | PI3Kδ SPA IC$_{50}$ (nM)* |
|---|---|
| 171 | + |
| 172 | + |
| 173 | + |
| 174 | + |
| 175 | + |
| 176 | + |
| 177 | + |
| 178 | + |
| 179 | + |
| 180 | + |
| 181 | + |
| 182 | + |
| 183 | + |
| 184 | + |
| 185 | + |
| 186 | + |
| 187 | + |
| 188 | + |
| 189 | + |
| 190 | + |
| 191 | + |
| 192 | ++ |
| 193 | +++ |
| 194 | + |
| 195 | + |
| 196 | + |
| 197 | + |
| 198 | + |
| 199 | + |
| 200 | + |
| 201 | + |
| 202 | + |
| 203 | + |
| 204 | + |
| 205 | + |
| 206 | + |
| 207 | + |
| 208 | + |
| 209 | ++ |
| 210 | + |
| 211 | + |
| 212 | + |
| 213 | + |
| 214 | + |
| 215 | + |
| 216 | + |
| 217 | + |
| 218 | + |
| 219 | + |
| 220 | + |
| 221 | + |
| 222 | + |
| 223 | + |
| 224 | + |
| 225 | + |
| 226 | + |
| 227 | + |
| 228 | + |
| 229 | + |
| 230 | + |
| 231 | + |
| 232 | + |
| 233 | + |
| 234 | + |
| 235 | + |
| 236 | + |
| 237 | + |
| 238 | + |
| 239 | + |
| 240 | + |
| 241 | + |
| 242 | + |
| 243 | + |
| 244 | + |
| 245 | + |
| 246 | + |
| 247 | + |
| 248 | + |

TABLE 10-continued

| Example # | PI3Kδ SPA IC$_{50}$ (nM)* |
|---|---|
| 249 | + |
| 250 | + |
| 251 | + |
| 252 | + |
| 253 | + |
| 254 | + |
| 255 | + |
| 256 | + |
| 257 | + |
| 258 | + |
| 259 | + |
| 260 | + |
| 261 | + |
| 262 | + |
| 263 | + |
| 264 | + |
| 265 | + |
| 266 | + |
| 267 | + |
| 268 | + |
| 269 | + |
| 270 | + |
| 271 | + |
| 272 | + |
| 273 | + |
| 274 | + |
| 275 | + |
| 276 | + |
| 277 | + |
| 278 | + |
| 279 | + |
| 280 | + |
| 281 | + |
| 282 | + |
| 283 | + |
| 284 | + |
| 285 | + |
| 286 | + |
| 287 | + |
| 288 | + |
| 289 | + |
| 290 | + |
| 291 | + |
| 292 | + |
| 293 | + |
| 294 | + |
| 295 | + |
| 296 | + |
| 297 | + |
| 298 (1$^{st}$ peak) | + |
| 299 | + |
| 300 | + |
| 301 | + |
| 302 | + |
| 303 | + |
| 304 | + |
| 305 | + |
| 306 | + |
| 307 | + |
| 308 | + |
| 309 | + |
| 313 (2$^{nd}$ peak) | + |
| 314 (2$^{nd}$ peak) | + |
| 315 | + |
| 316 | + |
| 317 | + |
| 318 | + |
| 319 | + |
| 320 | + |
| 321 (1$^{st}$ peak) | + |
| 322 (1$^{st}$ peak) | + |
| 326 | + |
| 327 | + |
| 328 | + |
| 329 | + |
| 330 | + |
| 331 | + |
| 332 | + |
| 333 | + |
| 334 | + |
| 335 | + |
| 336 | + |
| 337 | + |
| 338 | + |
| 339 | + |
| 340 | + |
| 341 | + |
| 342 | + |
| 343 | + |
| 344 | + |
| 310 | + |
| 311 | + |
| 323 (1$^{st}$ peak) | + |
| 323 (2$^{nd}$ peak) | + |
| 323 (3$^{rd}$ peak) | +++ |
| 323 (4$^{th}$ peak) | + |
| 324 (1$^{st}$ peak) | +++ |
| 324 (2$^{nd}$ peak) | + |
| 325 | + |
| 345 | +++ |
| 346 | + |
| 347 | + |
| 348 | +++ |
| 349 | + |
| 350 | +++++ |
| 351 | +++ |
| 352 | + |
| 353 | +++++ |
| 354 | + |
| 355 | +++ |
| 356 | +++ |
| 357 | + |
| 358 | +++++ |
| 359 | + |
| 360 | + |
| 362 | + |

*column symbols:
+ refers to ≤10 nM
++ refers to >10 nM to 50 nM
+++ refers to >50 nM to 200 nM
++++ refers to >200 nM to 500 nM
+++++ refers to >500 nM

TABLE 10a

| Example # | PI3Kδ IC$_{50}$ (nM)* |
|---|---|
| 361 | +++++ |
| 363 | +++ |

*column symbols:
+ refers to ≤10 nM
++ refers to >10 nM to 50 nM
+++ refers to >50 nM to 200 nM
++++ refers to >200 nM to 500 nM
+++++ refers to >500 nM Example B1

B Cell Proliferation Assay

To acquire B cells, human PBMC are isolated from the peripheral blood of normal, drug free donors by standard density gradient centrifugation on Ficoll-Hypague (GE Healthcare, Piscataway, N.J.) and incubated with anti-CD19 microbeads (Miltenyi Biotech, Auburn, Calif.). The B cells are then purified by positive immunosorting using an autoMacs (Miltenyi Biotech) according to the manufacture's instruction.

The purified B cells ($2 \times 10^5$/well/200 μL) are cultured in 96-well ultra-low binding plates (Corning, Corning, N.Y.) in RPMI1640, 10% FBS and goat F(ab')2 anti-human IgM (10 µg/ml) (Invitrogen, Carlsbad, Calif.) in the presence of different amount of test compounds for three days. [$^3$H]-thymidine (1 µCi/well) (PerkinElmer, Boston, Mass.) in PBS is then added to the B cell cultures for an additional 12 hours before the incorporated radioactivity is separated by filtration with water through GF/B filters (Packard Bioscience, Meriden, Conn.) and measured by liquid scintillation counting with a TopCount (Packard Bioscience).

Example B2

Pfeiffer Cell Proliferation Assay

Pfeiffer cell line (diffuse large B cell lymphoma) are purchased from ATCC (Manassas, Va.) and maintained in the culture medium recommended (RPMI and 10% FBS). To measure the anti-proliferation activity of the compounds, the Pfeiffer cells are plated with the culture medium ($2 \times 10^3$ cells/well/per 200 µl) into 96-well ultra-low binding plates (Corning, Corning, N.Y.), in the presence or absence of a concentration range of test compounds. After 3-4 days, [$^3$H]-thymidine (1 µCi/well) (PerkinElmer, Boston, Mass.) in PBS is then added to the cell culture for an additional 12 hours before the incorporated radioactivity is separated by filtration with water through GF/B filters (Packard Bioscience, Meridenj, CT) and measured by liquid scintillation counting with a TopCount (Packard Bioscience). IC50 data for select compounds is presented in Table 11.

TABLE 11

| Example # | Pfeiffer IC$_{50}$ (nM)* |
|---|---|
| 67 (1$^{st}$ peak) | + |
| 68 (1$^{st}$ peak) | + |
| 75 | + |
| 96 | + |
| 102 | + |
| 103 | ++ |
| 104 | ++ |
| 111 | + |
| 114 | + |
| 121 | ++ |
| 139 (1$^{st}$ peak) | + |
| 140 | + |
| 142 | + |
| 144 | + |
| 148 | + |
| 149 | + |
| 152 | + |
| 154 | + |
| 157 | ++ |
| 163 | ++ |
| 167 | + |
| 177 | + |
| 191 | + |
| 195 | + |
| 196 | + |
| 198 | + |
| 200 | + |
| 213 | + |
| 214 | + |
| 215 | + |
| 219 | + |
| 220 | + |
| 221 | + |
| 222 | + |
| 248 | + |
| 257 | + |
| 262 | + |
| 264 | + |
| 268 | + |
| 269 | + |
| 270 | + |
| 271 | + |

TABLE 11-continued

| Example # | Pfeiffer IC$_{50}$ (nM)* |
|---|---|
| 300 | + |
| 303 | + |
| 313 (2$^{nd}$ peak) | + |
| 314 (2$^{nd}$ peak) | + |
| 315 | + |
| 354 | + |
| 357 | + |
| 346 | + |
| 347 | + |
| 349 | + |

*column symbols:
+ refers to ≤10 nM
++ refers to >10 nM to 50 nM

Example C

Akt Phosphorylation Assay

Ramos cells (B lymphocyte from Burkitts lymphoma) are obtained from ATCC (Manassas, Va.) and maintained in RPMI1640 and 10% FBS. The cells ($3 \times 10^7$ cells/tube/3 mL in RPMI) are incubated with different amounts of test compounds for 2 hrs at 37° C. and then stimulated with goat F(ab')2 anti-human IgM (5 µg/mL) (Invitrogen) for 17 minutes in a 37° C. water bath. The stimulated cells are spun down at 4° C. with centrifugation and whole cell extracts are prepared using 300 µL lysis buffer (Cell Signaling Technology, Danvers, Mass.). The resulting lysates are sonicated and supernatants are collected. The phosphorylation level of Akt in the supernatants are analyzed by using PathScan phospho-Akt1 (Ser473) sandwich ELISA kits (Cell Signaling Technology) according to the manufacturer's instruction.

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A compound of Formula VIIa:

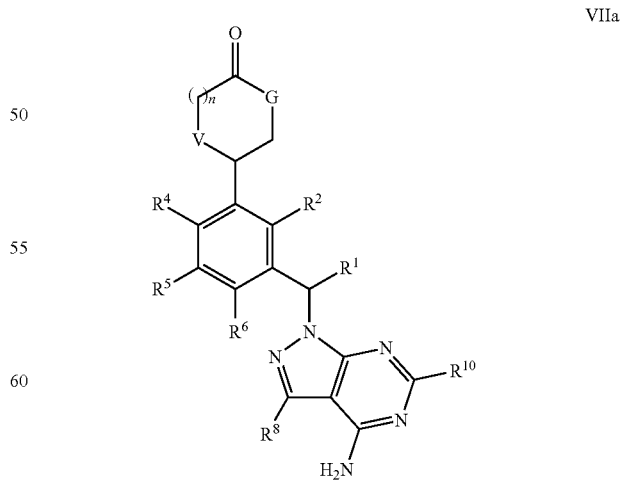

or a pharmaceutically acceptable salt thereof, wherein:
G is NH, n is 1, and V is O; or
G is NH, n is 0, and V is is CH$_2$; or G is O, n is 0 and V is NH;

$R^1$ is $C_{1-3}$ alkyl;

$R^2$ is halo, $C_{1-6}$ alkyl, $C_{1-6}$ alkoxy, $C_{1-6}$ haloalkyl, $C_{1-6}$ haloalkoxy, phenyl, or 5-6 membered heteroaryl; wherein said phenyl and 5-6 membered heteroaryl are each optionally substituted by 1, 2, 3, or 4 substituents independently selected from halo, OH, CN, $C_{1-4}$ alkyl, $C_{1-4}$ alkoxy, and $C_{1-4}$ haloalkoxy;

$R^4$ is H, halo, OH, CN, $C_{1-4}$ alkyl, $C_{1-4}$ haloalkyl, $C_{1-4}$ alkoxy, or $C_{1-4}$ haloalkoxy;

$R^5$ is halo, OH, CN, $C_{1-4}$ alkyl, $C_{1-4}$ haloalkyl, $C_{1-4}$ alkoxy, $C_{1-4}$ haloalkoxy, or cyclopropyl;

$R^6$ is H, halo, OH, CN, $C_{1-4}$ alkyl, $C_{1-4}$ haloalkyl, $C_{1-4}$ alkoxy, or $C_{1-4}$ haloalkoxy;

$R^8$ is H, halo, —OH, —CN, $C_{1-6}$ alkyl, $C_{2-6}$ alkenyl, $C_{2-6}$ alkynyl, $C_{1-6}$ haloalkyl, $Cy^2$, —($C_{1-3}$ alkylene)-$Cy^2$, $OR^{a2}$, $SR^{a2}$, $C(=O)R^{b2}$, $C(=O)NR^{c2}R^{d2}$, $C(=O)OR^{a2}$, $OC(=O)R^{b2}$, $OC(=C)NR^{c2}R^{d2}$, $NR^{c2}R^{d2}$, $NR^{c2}C(=O)R^{b2}$, $NR^{c2}C(=O)OR^{b2}$, $NR^{c2}C(=O)NR^{c2}R^{d2}$, $C(=NR^e)NR^{c2}R^{d2}$, $NR^{c2}C(=NR^e)NR^{c2}R^{d2}$, $NR^{c2}S(=O)R^{b2}$, $NR^{c2}S(=O)_2NR^{c2}R^{d2}$, $S(=O)R^{b2}$, $S(=O)_2R^{b2}$, or $S(=O)_2NR^{c2}R^{d2}$; wherein said $C_{1-6}$ alkyl, $C_{2-6}$ alkenyl, $C_{2-6}$ alkynyl are each optionally substituted by 1, 2, 3, or 4 independently selected $R^{11}$ groups;

$R^{10}$ is H or $C_{1-4}$ alkyl;

each $R^e$ is independently selected from H, CN, OH, $C_{1-4}$ alkyl, and $C_{1-4}$ alkoxy;

each $Cy^2$ is independently selected from $C_{3-7}$ cycloalkyl, 4-7 membered heterocycloalkyl, phenyl, 5-6 membered heteroaryl, or 9-10-membered bicyclic heteroaryl, each of which is optionally substituted with 1, 2, 3, or 4 independently selected $R^{11}$ groups;

each $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{3-7}$ cycloalkyl, 4-7 membered heterocycloalkyl, phenyl, and 5-6 membered heteroaryl; wherein said $C_{1-6}$ alkyl, $C_{2-6}$ alkenyl, $C_{2-6}$ alkynyl, $C_{3-7}$ cycloalkyl, 4-7 membered heterocycloalkyl, phenyl and 5-6 membered heteroaryl are each optionally substituted with 1, 2, or 3 independently selected $R^{11}$ groups;

or $R^{c2}$ and $R^{d2}$ together with the N atom to which they are attached form a 4-, 5-, 6-, or 7 membered heterocycloalkyl group, which is optionally substituted with —OH or $C_{1-3}$ alkyl; and each $R^{11}$ is independently selected from OH, $NO_2$, CN, halo, $C_{1-3}$ alkyl, $C_{2-3}$ alkenyl, $C_{2-3}$ alkynyl, $C_{1-3}$ haloalkyl, cyano-$C_{1-3}$ alkyl, HO—$C_{1-3}$ alkyl, $C_{1-3}$ alkoxy-$C_{1-3}$ alkyl, $C_{3-7}$ cycloalkyl, $C_{1-3}$ alkoxy, $C_{1-3}$ haloalkoxy, amino, $C_{1-3}$ alkylamino, di($C_{1-3}$ alkyl)amino, thio, $C_{1-3}$ alkylthio, $C_{1-3}$ alkylsulfinyl, $C_{1-3}$ alkylsulfonyl, carbamyl, $C_{1-3}$ alkylcarbamyl, di($C_{1-3}$ alkyl)carbamyl, carboxy, $C_{1-3}$ alkylcarbonyl, $C_{1-4}$ alkoxycarbonyl, $C_{1-3}$ alkylcarbonylamino, $C_{1-3}$ alkylsulfonylamino, aminosulfonyl, $C_{1-3}$ alkylaminosulfonyl, di($C_{1-3}$ alkyl)aminosulfonyl, aminosulfonylamino, $C_{1-3}$ alkylaminosulfonylamino, di($C_{1-3}$ alkyl)aminosulfonylamino, aminocarbonylamino, $C_{1-3}$ alkylaminocarbonylamino, and di($C_{1-3}$ alkyl)aminocarbonylamino.

2. The compound of claim 1, having Formula VIIb:

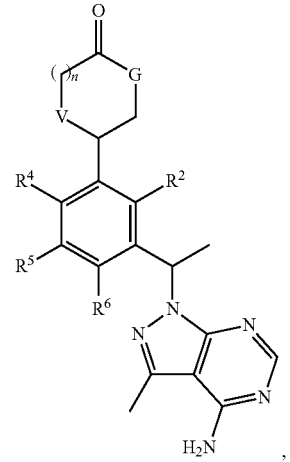

or a pharmaceutically acceptable salt thereof.

3. The compound of claim 1, or a pharmaceutically acceptable salt thereof, wherein:
G is NH;
n is 0;
V is $CH_2$;
$R^2$ is $C_{1-3}$alkoxy;
$R^4$ is halo, CN, or $C_{1-4}$ alkyl;
$R^5$ is halo; and
$R^6$ is H.

4. The compound of claim 1, or a pharmaceutically acceptable salt thereof, wherein:
G is NH;
n is 1;
V is O;
$R^2$ is $C_{1-3}$alkoxy;
$R^4$ is halo, CN, or $C_{1-4}$ alkyl;
$R^5$ is halo; and
$R^6$ is H.

5. The compound of claim 1, or a pharmaceutically acceptable salt thereof, wherein:
G is O;
n is 0;
V is NH;
$R^2$ is $C_{1-3}$alkoxy;
$R^4$ is halo;
$R^5$ is halo; and
$R^6$ is H.

6. The compound of claim 1, selected from:
4-{3-[1-(4-amino-3-methyl-1H-pyrazolo[3,4-d]pyrimidin-1-yl)ethyl]-5-chloro-2-ethoxy-6-methylphenyl}pyrrolidin-2-one;
6-{3-[1-(4-Amino-3-methyl-1H-pyrazolo[3,4-d]pyrimidin-1-yl)ethyl]-5-chloro-2-methoxy-6-methylphenyl}morpholin-3-one;
4-{3-[1-(4-amino-3-methyl-1H-pyrazolo[3,4-d]pyrimidin-1-yl)ethyl]-5-chloro-2-ethoxy-6-fluorophenyl}pyrrolidin-2-one;
4-[1-(4-amino-3-methyl-1H-pyrazolo[3,4-d]pyrimidin-1-yl)ethyl]-6-chloro-3-ethoxy-2-(5-oxopyrrolidin-3-yl)benzonitrile; and
4-{3-[1-(4-amino-3-methyl-1H-pyrazolo[3,4-d]pyrimidin-1-yl)ethyl]-5-chloro-2-ethoxy-6-fluorophenyl}-1,3-oxazolidin-2-one;
or a pharmaceutically acceptable salt thereof of any of the aforementioned.

7. A pharmaceutical composition comprising a compound of claim 1, or a pharmaceutically acceptable salt thereof, and at least one pharmaceutically acceptable carrier.

* * * * *

UNITED STATES PATENT AND TRADEMARK OFFICE
CERTIFICATE OF CORRECTION

PATENT NO. : 9,730,939 B2  
APPLICATION NO. : 14/872881  
DATED : August 15, 2017  
INVENTOR(S) : Yun-Long Li et al.

Page 1 of 1

It is certified that error appears in the above-identified patent and that said Letters Patent is hereby corrected as shown below:

In the Claims

Column 390, Line 67, Claim 1, delete "is is" and insert -- is --;

Column 391, Line 20, Claim 1, delete "(=C)" and insert -- (=O) --;

Column 391, Line 22, Claim 1, delete "C(=NR$^e$)NR$^{c2}$R$^{d2}$," and insert -- C(=NR$^e$)R$^{b2}$, C(=NR$^e$)NR$^{c2}$R$^{d2.}$ --;

Column 392, Line 38, Claim 4, delete "Vis 0;" and insert -- V is O --.

Signed and Sealed this  
Third Day of December, 2019

Andrei Iancu  
*Director of the United States Patent and Trademark Office*